US008618290B2

(12) United States Patent
Lawson et al.

(10) Patent No.: US 8,618,290 B2
(45) Date of Patent: Dec. 31, 2013

(54) HSP90 INHIBITORS

(75) Inventors: John D. Lawson, Carlsbad, CA (US); Erick Wang Co, San Diego, CA (US); Jeffrey A. Stafford, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/271,134

(22) Filed: Oct. 11, 2011

(65) Prior Publication Data

US 2012/0264770 A1 Oct. 18, 2012

Related U.S. Application Data

(62) Division of application No. 12/363,640, filed on Jan. 30, 2009, now Pat. No. 8,071,766.

(60) Provisional application No. 61/025,725, filed on Feb. 1, 2008, provisional application No. 61/101,595, filed on Sep. 30, 2008.

(51) Int. Cl.

| | |
|---|---|
| *C07D 401/10* | (2006.01) |
| *C07D 401/14* | (2006.01) |
| *C07D 239/84* | (2006.01) |
| *C07D 213/64* | (2006.01) |
| *C07D 213/50* | (2006.01) |

(52) U.S. Cl.

CPC ............ *C07D 401/10* (2013.01); *C07D 401/14* (2013.01); *C07D 239/84* (2013.01)

USPC .......................................... 544/279; 544/253

(58) Field of Classification Search

None

See application file for complete search history.

(56) References Cited

U.S. PATENT DOCUMENTS

| | | | |
|---|---|---|---|
| 5,654,307 A | 8/1997 | Bridges et al. | |
| 6,534,510 B2 | 3/2003 | Barrow et al. | |
| 7,345,048 B2 | 3/2008 | Ala et al. | |
| 7,671,059 B2 | 3/2010 | Machajewski et al. | |
| 2004/0102458 A1 | 5/2004 | Chiosis et al. | |
| 2005/0020534 A1 | 1/2005 | Johnson et al. | |
| 2006/0079493 A1 | 4/2006 | Fritz et al. | |
| 2007/0004674 A1 | 1/2007 | Shiotsu et al. | |
| 2008/0160520 A1 | 7/2008 | Amon et al. | |
| 2011/0053873 A1 * | 3/2011 | Chen et al. | 514/27 |

FOREIGN PATENT DOCUMENTS

| | | |
|---|---|---|
| EP | 0404355 | 12/1990 |
| GB | 1028405 | 5/1966 |
| GB | 1033384 | 6/1966 |
| JP | 2000038350 | 2/2000 |
| WO | WO 99/61444 | 12/1999 |
| WO | WO/99/61444 | 12/1999 |
| WO | WO00/12497 | 3/2000 |
| WO | WO/00/12497 | 3/2000 |
| WO | WO 01/70269 | 9/2001 |
| WO | WO/01/70269 | 9/2001 |
| WO | WO02/09696 | 2/2002 |
| WO | WO/02/09696 | 2/2002 |
| WO | WO/02/15925 | 2/2002 |
| WO | WO02/15925 | 2/2002 |
| WO | WO02/36075 | 5/2002 |
| WO | WO/02/36075 | 5/2002 |
| WO | WO 02/069900 | 9/2002 |
| WO | WO/02/069900 | 9/2002 |
| WO | WO/02/094169 | 11/2002 |
| WO | WO 02/094169 | 11/2002 |
| WO | WO/03/051844 | 6/2003 |
| WO | WO03/051844 | 6/2003 |
| WO | WO/03/068776 | 8/2003 |
| WO | WO03/068776 | 8/2003 |
| WO | WO03/097615 | 11/2003 |
| WO | WO/03/097615 | 11/2003 |
| WO | WO2004/037978 | 5/2004 |
| WO | WO/2004/037978 | 5/2004 |
| WO | WO/2004/081037 | 9/2004 |
| WO | WO2004/081037 | 9/2004 |
| WO | WO2004/103274 | 12/2004 |
| WO | WO/2004/103274 | 12/2004 |

(Continued)

OTHER PUBLICATIONS

Ikuina, et al., "Synthesis and Antitumor Activity of Novel O-Carbamoylmethyloxime Derivatives of Radicicol," Journal of Medicinal Chemistry, 2003, vol. 46, pp. 2534-2541 (XP-002975841).

(Continued)

*Primary Examiner* — Eric S Olson

(74) *Attorney, Agent, or Firm* — David M. Stemerick; C. Amy Smith

(57) ABSTRACT

The invention relates to HSP90 inhibiting compounds consisting of the formula:

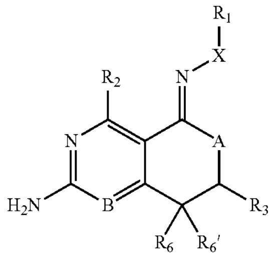

wherein the variables are as defined herein. The invention also relates to pharmaceutical compositions, kits and articles of manufacture comprising such compounds; methods and intermediates useful for making the compounds; and methods of using said compounds.

6 Claims, 3 Drawing Sheets

(56) References Cited

FOREIGN PATENT DOCUMENTS

| | | | |
|---|---|---|---|
| WO | WO2005/028478 | | 3/2005 |
| WO | WO/2005/028478 | | 3/2005 |
| WO | WO2005/070929 | | 8/2005 |
| WO | WO/2005/070929 | | 8/2005 |
| WO | WO2005/080377 | | 9/2005 |
| WO | WO/2005/080377 | | 9/2005 |
| WO | WO2006/021448 | | 3/2006 |
| WO | WO/2006/021448 | | 3/2006 |
| WO | WO2006/050333 | | 5/2006 |
| WO | WO/2006/050333 | | 5/2006 |
| WO | WO/2006/050457 | | 5/2006 |
| WO | WO2006/050457 | | 5/2006 |
| WO | WO/2006/052795 | | 5/2006 |
| WO | WO2006/052795 | | 5/2006 |
| WO | WO2006/078891 | | 7/2006 |
| WO | WO/2006/078891 | | 7/2006 |
| WO | WO2006/083979 | | 8/2006 |
| WO | WO/2006/083979 | | 8/2006 |
| WO | WO/2006/108107 | | 10/2006 |
| WO | WO2006/108107 | | 10/2006 |
| WO | WO/2006/113498 | | 10/2006 |
| WO | WO2006/113498 | * | 10/2006 |
| WO | WO2006/119504 | | 11/2006 |
| WO | WO/2006/119504 | | 11/2006 |
| WO | WO2006/124904 | | 11/2006 |
| WO | WO/2006/124904 | | 11/2006 |
| WO | WO/2006/138265 | | 12/2006 |
| WO | WO2006/138265 | | 12/2006 |
| WO | WO/2007/035963 | | 3/2007 |
| WO | WO2007/035963 | | 3/2007 |
| WO | WO2007/041362 | | 4/2007 |
| WO | WO/2007/041362 | | 4/2007 |
| WO | WO2007/082131 | | 7/2007 |
| WO | WO/2007/082131 | | 7/2007 |
| WO | WO2007/136603 | | 11/2007 |
| WO | WO2007/139951 | | 12/2007 |
| WO | WO/2007/139951 | | 12/2007 |
| WO | WO2007/143630 | | 12/2007 |
| WO | WO/2007/143630 | | 12/2007 |
| WO | WO/2007/147217 | | 12/2007 |
| WO | WO2007/147217 | | 12/2007 |
| WO | WO/2008/021981 | | 2/2008 |
| WO | WO2008/021981 | | 2/2008 |
| WO | WO2008/045529 | | 4/2008 |
| WO | WO/2008/045529 | | 4/2008 |
| WO | WO/2008/061208 | | 5/2008 |
| WO | WO2008/061208 | | 5/2008 |
| WO | WO/2008/063232 | | 5/2008 |
| WO | WO2008/063232 | | 5/2008 |
| WO | WO2008/116216 | | 9/2008 |
| WO | WO/2008/116216 | | 11/2008 |
| WO | WO/2008/142720 | | 11/2008 |
| WO | WO2008/142720 | | 11/2008 |
| WO | WO/2008/154221 | | 12/2008 |

OTHER PUBLICATIONS

Ikuina et al. "Synthesis and Antitumor Activity of Novel O-Carbamoylmethyloxime Derivatives of Radicicoi" J. Med. Chem. 2003, 46, 2534-2541.

Barker et al. "Fragment-based Identification of HSP90 Inhibitors" ChemMedChem, 2009, vol. 4, p. 963-66.

* cited by examiner

FIGURE 1

Human cDNA sequence encoding residues 9-236 of human HSP90α

(including a start and a stop codon)

[SEQ. ID NO: 1]

```
ATGGACCAAC CGATGGAGGA GGAGGAGGTT GAGACGTTCG CCTTTCAGGC AGAAATTGCC      60
CAGTTGATGT CATTGATCAT CAATACTTTC TACTCGAACA AAGAGATCTT TCTGAGAGAG     120
CTCATTTCAA ATTCATCAGA TGCATTGGAC AAAATCCGGT ATGAAAGCTT GACAGATCCC     180
AGTAAATTAG ACTCTGGGAA AGAGCTGCAT ATTAACCTTA TACCGAACAA ACAAGATCGA     240
ACTCTCACTA TTGTGGATAC TGGAATTGGA ATGACCAAGG CTGACTTGGT CAATAACCTT     300
GGTACTATCG CCAAGTCTGG GACCAAAGCG TTCATGGAAG CTTTGCAGGC TGGTGCAGAT     360
ATCTCTATGA TTGGCCAGTT CGGTGTTGGT TTTTATTCTG CTTATTTGGT TGCTGAGAAA     420
GTAACTGTGA TCACCAAACA TAACGATGAT GAGCAGTACG CTTGGGAGTC CTCAGCAGGG     480
GGATCATTCA CAGTGAGGAC AGACACAGGT GAACCTATGG GTCGTGGAAC AAAAGTTATC     540
CTACACCTGA AAGAAGACCA AACTGAGTAC TTGGAGGAAC GAAGAATAAA GGAGATTGTG     600
AAGAAACATT CTCAGTTTAT TGGATATCCC ATTACTCTTT TTGTGGAGAA GGAACGTGAT     660
AAAGAAGTAA GCGATGATGA GGCTGAATAA                                      690
```

Amino acid sequence for residues 9-236 of human HSP90α with an N-terminal 6x-histidine tag and cleavage site (underline)

[SEQ. ID NO: 2]

```
MGSSHHHHHH SSGLVPRGSH MDQPMEEEEV ETFAFQAEIA QLMSLIINTF YSNKEIFLRE      60
LISNSSDALD KIRYESLTDP SKLDSGKELH INLIPNKQDR TLTIVDTGIG MTKADLVNNL     120
GTIAKSGTKA FMEALQAGAD ISMIGQFGVG FYSAYLVAEK VTVITKHNDD EQYAWESSAG     180
GSFTVRTDTG EPMGRGTKVI LHLKEDQTEY LEERRIKEIV KKHSQFIGYP ITLFVEKERD     240
KEVSDDEAE
```

HSP90 INHIBITORS

RELATED APPLICATIONS

This application is a Divisional of U.S. application Ser. No. 12/363,640, filed Jan. 30, 2009, which claims priority to U.S. Provisional Application No. 61/025,725, filed Feb. 1, 2008, and U.S. Provisional Application No. 61/101,595, filed Sep. 30, 2008, both of which are incorporated herein by reference.

FIELD OF THE INVENTION

The present invention relates to compounds that may be used to inhibit heat shock protein 90 (HSP90) as well as compositions of matter, kits and articles of manufacture comprising these compounds. The invention also relates to methods for inhibiting HSP90 and treatment methods using compounds according to the present invention. In addition, the invention relates to methods of making the compounds of the present invention, as well as intermediates useful in such methods. In particular, the present invention relates to HSP90 inhibitors, compositions of matter, kits and articles of manufacture comprising these compounds, methods for inhibiting HSP90, and methods and intermediates useful for making the inhibitors.

BACKGROUND OF THE INVENTION

Molecular chaperones maintain the appropriate folding and conformation of nascent polypeptides. This activity is crucial in regulating the balance between protein synthesis and degradation. When a protein is damaged, molecular chaperones may also facilitate their re-folding or, in the case of irreparably impaired proteins, their removal by the protein degradation machinery of the cell[1]

Heat shock proteins (HSPs) were originally defined according to their increased expression in response to diverse cellular insults such as elevated temperature as well as exposure to heavy metals and oxidative stress[1]. Most, but not all HSPs are molecular chaperones that are organized into families according to their molecular size or function, including HSP100, HSP90, HSP70, HSP60, HSP40 and small HSPs. The rapid induction of HSP gene expression is referred to as the heat shock response (HSR) which confers cytoprotection to repeat exposure of the initial insult which would otherwise cause lethal molecular damage[2]. Cytoprotection is an example of increased molecular chaperone expression associated with the functioning of normal cells within an organism. However, aberrant expression of this family of proteins can also be associated with several disease states.

A large body of evidence exists supporting the role of molecular chaperones in maintaining the cancer phenotype. In addition, increasing evidence associating molecular chaperone expression with other disease including but not limited to: neurodegenerative disorders including Parkinson's, Alzheimer's, Huntington's and prion-related disease, inflammation and inflammation related disorders such as pain, headaches, fever, arthritis, asthma, bronchitis, tendonitis, eczema, inflammatory bowel disease, and the like, and diseases dependent on angiogenesis such as, cancer, arthritis, diabetic retinopathy, age associated macular degeneration (AMD) and infectious diseases in particular fungal infections, viral diseases including but not limited to diseases caused by hepatitis B virus (HBV), hepatitis C virus (HCV) and herpes simplex virus type-1 (HSV-1), cardiovascular and central nervous system diseases[3,4,5,6,7].

HSP90 is an abundant molecular chaperone which constitutes 1-2% of total cellular protein. It exerts its chaperone function to ensure the correct conformation, activity, intracellular localization and proteolytic turnover of a range of proteins that are involved in cell growth, differentiation and survival[3,5,8]. Because of the large number of important signaling proteins with which HSP90 has been shown to associate and assist in stabilizing (these are generally called HSP90 client proteins), a rationale exists for the therapeutic use of HSP90 inhibitors for the treatment of a wide range of human diseases (as discussed above)[9].

HSP90 activity is required for the stability and the function of many oncogenic client proteins, which contribute to all of the hallmark traits of malignancy, and thus, HSP90 has been widely acknowledged as an attractive therapeutic target for the treatment of cancer[3,4,5,8]. These client proteins include: BCR-ABL, AKT/PKB, C-RAF, CDK4, steroid hormone receptors (estrogen and androgen), surviving, c-Met, HER-2, and telomerases among others. Inhibition of HSP90 function leads to the destabilization and degradation of client proteins via the ubiquitin—proteasome pathway, resulting in the down-regulation of several signals being propagated via oncogenic signaling pathways and modulation of all aspects of the malignant phenotype[3,5,8]. Therefore, HSP90 inhibitors have potential to treat cancers driven by numerous diverse molecular abnormalities and their combinatorial effects could also reduce the possibility of resistance developing.

HSP90 is considered to exert its chaperone function via a cycle which utilizes the coordinated interaction of a number of co-chaperone proteins that are collectively involved in an orchestrated, mutually regulatory interplay with ATP/ADP exchange and ATP hydrolysis by the intrinsic and essential N-terminal ATPase domain. Crystallographic studies have revealed that several HSP90 inhibitors occupy the N-terminus ATP binding site[10], thereby inhibiting HSP90 ATPase activity and function.

The 14-membered macrocyclic antibiotic radicicol was first demonstrated to have anti-tumor activity in vitro and shown to reverse the malignant phenotype of v-SRC transformed cells[11]. Subsequently, radicicol was shown using X-ray crystallography to bind to the N-terminal ATP-binding pocket of HSP90 with high affinity[10], and to inhibit HSP90 ATPase activity resulting in the degradation of a number of signaling proteins[12]. Although radicicol inhibits tumor cell growth in vitro, it lacks activity in vivo, most likely due to its potentially reactive epoxide moiety and other adverse chemical features that cause instability and possible toxicity[8,13].

The benzoquinone ansamycins are a second class of naturally occurring antibiotics which have been demonstrated to inhibit the activity of HSP90. The first example is geldanamycin which also competes with ATP for binding to the N-terminal nucleotide binding site of HSP90[14]. As was the case with radicicol, despite promising anti-tumor activity in vitro (and in vivo), the development of geldanamycin into a human therapeutic was stopped due to compound instability and unacceptable hepatotoxicity at therapeutic doses[15].

Analogs of geldanamycin have been pursued with the objective of finding agents with an improved safety margin for clinical use, including the derivative 17-allylamino-17-demethoxygeldanamycin (17-AAG or tanespimycin)[16]. 17-AAG has similar cellular effects to geldanamycin, including client protein degradation, and cell cycle arrest but with improved metabolic stability and lower toxicity[5,8]. Preclinical studies using 17-AAG have shown this derivative to be highly potent in vitro and to exhibit anti-tumor activity at non-toxic doses in various human tumor xenograft models[17,18]. Based on its biological activity, 17-AAG has recently completed several phase I clinical trials with some encouraging results[9,19]. As a result, 17-AAG has now entered phase II monotherapy clinical trials in various tumor types, including melanoma and breast.

There are several possible factors which may reduce the clinical efficacy of 17-AAG. Preclinical studies have shown that hepatic metabolism of 17-AAG by cytochrome P450 leads to the formation of 17-amino-17-demethoxygeldanamycin (17-AG)[17]. Although 17-AG retains inhibitory activity, metabolism by CYP3A4 is likely to be a cause of variable pharmacokinetics. In addition, the activity of 17-AAG is enhanced by its conversion to the hydroquinone form, 17-AAG$H_2$, by the reductase enzyme NQO1 or DT-diaphorase[17,20]. The polymorphic expression of both of these metabolic enzymes may pose limitations for the clinical use of 17-AAG across the population[5,8,17]. The efficacy of 17-AAG may be further reduced by its association with the multi-drug resistance protein MDR1 or P-glycoprotein[17]. Finally, 17-AAG is limited by its poor solubility, cumbersome and complex formulation and lack of oral bioavailability. Attempts to reformulate 17-AAG have resulted in clinical trials commencing with CNF1010 and a cremaphore-based formulation (KOS-953) the latter of which has shown promising results during the phase I trial in patients with relapsed-refractory myeloma. The US National Cancer Institute and Kosan Biosciences have also developed a more water soluble and potentially orally bioavailable analog of 17-AAG, 17-dimethylaminoethylamino-17-demethoxygeldanamycin (17-DMAG or alvespimycin, which was evaluated in preclinical and clinical trials[9]. 17-AAG$H_2$, also known as IPI-504, has also entered clinical trial as a soluble derivative of 17-AAG[21].

Non-natural product HSP90 inhibitors have recently been described. One of these contains a 3,4-diarylpyrazole resorcinol scaffold. These molecules were exemplified by Compound CCT018159, and analogues CCT0129397/VER-49009 and VER-50589. Treatment of cancer cells with these HSP90 inhibitors resulted in HSP70 induction, client protein depletion, cytostasis and apoptosis[22,23,24,25].

Rational drug design was used by Chiosis et al.[26] to develop a novel class of HSP90 inhibitors with a purine-scaffold. The first compound to be identified from this series, PU3, bound to HSP90 with moderate affinity resulting in cellular effects which are characteristic of HSP90 inhibitors[26]. An important feature of PU3 is that it is more soluble than 17-AAG; however, it is also significantly less potent against cells than the ansamycins[26]. Subsequent efforts focused on improving the potency of PU3 and led to the identification of PU24FC1[27]. This compound exhibited biological effects on cells within a concentration range of 2-6 μM[27], and also demonstrated 10-50 times higher affinity for HSP90 from transformed cells compared to that from normal tissues[27]. Administration of PU24FC1 in human breast tumor xenograft models led to anti-tumor activity without significant toxicity[27]. A more recent study has identified 8-arylsulfanyl, 8-arylsulfoxyl and 8-arylsulfonyl adenine derivatives of the PU class which exhibit improved water solubility and approximately 50 nM potency in cellular models, together with therapeutic activity in human tumor xenograft models[28].

Additional non-natural product small molecule inhibitors of HSP90 have been identified including 2-amino-quinazolin-5-one compounds (WO2006113498A2), 2-amino-7,8-dihydro-6H-pyrido[4,3-d]pyrimidin-5-one compounds (WO2007041362A1) and quinazolin-oxime derivatives (WO2008142720A2) which target HSP90 for the prophylaxis or treatment of cell proliferative diseases. These molecules have reasonable potency and drug-likeness.

The preclinical proof-of-concept provide by small molecules with reasonable drug like properties coupled with the clinical proof-of-concept for the approach of inhibition of HSP90 activity achieved with 17-AAG, has generated a high level of interest in industry to develop additional HSP90 inhibitors with improved drug like properties that can provide therapeutic benefit to patients suffering from disease states related to abnormal protein folding.

The following publications are referred to in the background:

1. J. C. Young, V. R. Agashe, K. Siegers and F. U. Hartl, Pathways of chaperone-mediated protein folding in the cytosol, *Nat. Rev. Mol. Cell. Biol.* 5 (2004), pp. 781-791.
2. S. D. Westerheide and R. I. Morimoto, Heat shock response modulators as therapeutic tools for diseases of protein conformation, *J. Biol. Chem.* 280 (2005), pp. 33097-33100.
3. L. Whitesell and S. L. Lindquist, HSP90 and the chaperoning of cancer, *Nat. Rev. Cancer* 5 (2005), pp. 761-772.
4. S. K. Calderwood, M. A. Khaleque, D. B. Sawyer and D. R. Ciocca, Heat shock proteins in cancer: chaperones of tumorigenesis, *Trends Biochem. Sci.* 31 (2006), pp. 164-172.
5. M. V. Powers and P. Workman, Targeting of multiple signaling pathways by heat shock protein 90 molecular chaperone inhibitors, *Endocr. Belot. Cancer* 13 (Suppl. 1) (2006), pp. S125-S135.
6. A. J. Macario and Conway de Macario, Sick chaperones, cellular stress, and disease, *N. Engl. J. Med.* 353 (2005), pp. 1489-1501.
7. J. M. Barral, S. A. Broadley, G. Schaffar and F. U. Hartl, Roles of molecular chaperones in protein misfolding diseases, *Semin. Cell Dev. Biol.* 15 (2004), pp. 17-29.
8. S. Sharp and P. Workman, Inhibitors of the HSP90 molecular chaperone: current status, *Adv. Cancer Res.* 95 (2006), pp. 323-348.
9. S. Pacey, U. Banerji, I. Judson and P. Workman, Hsp90 inhibitors in the clinic, *Handbook Exp. Pharmacol.* 172 (2006), pp. 331-358.
10. S. M. Roe, C. Prodromou, R. O'Brien, J. E. Ladbury, P. W. Piper and L. H. Pearl, Structural basis for inhibition of the Hsp90 molecular chaperone by the antitumor antibiotics radicicol and geldanamycin, *J. Med. Chem.* 42 (1999), pp. 260-266.
11. H. J. Kwon, M. Yoshida, K. Abe, S. Horinouchi and T. Beppu, Radicicol, an agent inducing the reversal of transformed phenotypes of src-transformed fibroblasts, *Biosci. Biotechnol. Biochem.* 56 (1992), pp. 538-539.
12. T. W. Schulte, S. Akinaga, T. Murakata, T. Agatsuma, S. Sugimoto, H. Nakano, Y. S. Lee, B. B. Simen, Y. Argon, S. Felts, D. O. Toft, L. M. Neckers and S. V. Sharma, Interaction of radicicol with members of the heat shock protein 90 family of molecular chaperones, *Mol. Endocrinol.* 13 (1999), pp. 1435-1448.
13. Clarke, P. A., Powers, M., and Workman, P. (2006) Inhibition of the molecular chaperone heat shock protein 90 in cancer: consequences for the regulation of survival signaling and induction of cell death. In: Apoptosis and Cancer Therapy (Debatin, K.-M. and Fulda, S., Eds), pp. 933-959. Wiley-VCH, Weinheim, Germany
14. C. Prodromou, S. M. Roe, R. O'Brien, J. E. Ladbury, P. W. Piper and L. H. Pearl, Identification and structural characterization of the ATP/ADP-binding site in the Hsp90 molecular chaperone, *Cell* 90 (1997), pp. 65-75.
15. J. G. Supko, R. L. Hickman, M. R. Greyer and L. Malspeis, Preclinical pharmacologic evaluation of geldanamycin as an antitumor agent, *Cancer Chemother. Pharmacol.* 36 (1995), pp. 305-315.

16. R. C. Schnur, M. L. Corman, R. J. Gallaschun, B. A. Cooper, M. F. Dee, J. L. Doty, M. L. Muzzi, J. D. Moyer, C. I. DiOrio and E. G. Barbacci, Inhibition of the oncogene product p185erbB-2 in vitro and in vivo by geldanamycin and dihydrogeldanamycin derivatives, *J. Med. Chem.* 38 (1995), pp. 3806-3812.
17. L. R. Kelland, S. Y. Sharp, P. M. Rogers, T. G. Myers and P. Workman, DT-Diaphorase expression and tumor cell sensitivity to 17-allylamino, 17-demethoxygeldanamycin, an inhibitor of heat shock protein 90, *J. Natl. Cancer Inst.* 91 (1999), pp. 1940-1949.
18. U. Banerji, M. Walton, F. Raynaud, R. Grimshaw, L. Kelland, M. Valenti, I. Judson and P. Workman, Pharmacokinetic-pharmacodynamic relationships for the heat shock protein 90 molecular chaperone inhibitor 17-allylamino, 17-demethoxygeldanamycin in human ovarian cancer xenograft models, *Clin. Cancer Res.* 11 (2005), pp. 7023-7032.
19. U. Banerji, A. O'Donnell, M. Scurr, S. Pacey, S. Stapleton, Y. Asad, L. Simmons, A. Maloney, F. Raynaud, M. Campbell, M. Walton, S. Lakhani, S. Kaye, P. Workman and I. Judson, Phase I pharmacokinetic and pharmacodynamic study of 17-allylamino, 17-demethoxygeldanamycin in patients with advanced malignancies, *J. Clin. Oncol.* 23 (2005), pp. 4152-4161.
20. W. Guo, P. Reigan, D. Siegel, J. Zirrolli, D. Gustafson and D. Ross, Formation of 17-allylamino-demethoxygeldanamycin (17-AAG) hydroquinone by NAD(P)H:quinone oxidoreductase 1: role of 17-AAG hydroquinone in heat shock protein 90 inhibition, *Cancer Res.* 65 (2005), pp. 10006-10015.
21. J. R. Sydor, E. Normant, C. S. Pien, J. R. Porter, J. Ge, L. Grenier, R. H. Pak, J. A. Ali, M. S. Dembski, J. Hudak, J. Patterson, C. Penders, M. Pink, M. A. Read, J. Sang, C. Woodward, Y. Zhang, D. S. Grayzel, J. Wright, J. A. Barrett, V. J. Palombella, J. Adams and J. K. Tong, Development of 17-allylamino-17-demethoxygeldanamycin hydroquinone hydrochloride (IPI-504), an anti-cancer agent directed against Hsp90, *Proc. Natl. Acad. Sci. USA* 103 (2006), pp. 17408-17413.
22. K. M. Cheung, T. P. Matthews, K. James, M. G. Rowlands, K. J. Boxall, S. Y. Sharp, A. Maloney, S. M. Roe, C. Prodromou, L. H. Pearl, G. W. Aherne, E. McDonald and P. Workman, The identification, synthesis, protein crystal structure and in vitro biochemical evaluation of a new 3,4-diarylpyrazole class of Hsp90 inhibitors, *Bioorg. Med. Chem. Lett.* 15 (2005), pp. 3338-3343.
23. S. Y. Sharp, K. Boxall, M. Rowlands, C. Prodromou, S. M. Roe, A. Maloney, M. Powers, P. A. Clarke, G. Box, S. Sanderson, L. Patterson, T. P. Matthews, K. M. Cheung, K. Ball, A. Hayes, F. Raynaud, R. Marais, L. Pearl, S. Eccles, W. Aherne, E. McDonald and P. Workman, In vitro biological characterization of a novel, synthetic diaryl pyrazole resorcinol class of heat shock Protein 90 inhibitors, *Cancer Res.* 67 (2007), pp. 2206-2216.
24. B. W. Dymock, X. Barril, P. A. Brough, J. E. Cansfield, A. Massey, E. McDonald, R. E. Hubbard, A. Surgenor, S. D. Roughley, P. Webb, P. Workman, L. Wright and M. J. Drysdale, Novel, potent small-molecule inhibitors of the molecular chaperone Hsp90 discovered through structure-based design, *J. Med. Chem.* 48 (2005), pp. 4212-4215.
25. S. Y. Sharp, C. Prodromou, K. Boxall, M. V. Powers, J. L. Holmes, G. Box, T. P. Matthews, K. M. Cheung, A. Kalusa, K. James, A. Hayes, A. Hardcastle, B. Dymock, P. A. Brough, X. Barril, J. E. Cansfield, L. Wright, A. Surgenor, N. Foloppe, R. E. Hubbard, W. Aherne, L. Pearl, K. Jones, E. McDonald, F. Raynaud, S. Eccles, M. Drysdale and P. Workman, Inhibition of the heat shock protein 90 molecular chaperone in vitro and in vivo by novel, synthetic, potent resorcinylic pyrazole/isoxazole amide analogues, *Mol. Cancer. Ther.* 6 (2007), pp. 1198-1211.
26. G. Chiosis, M. N. Timaul, B. Lucas, P. N. Munster, F. F. Zheng, L. Sepp-Lorenzino and N. Rosen, A small molecule designed to bind to the adenine nucleotide pocket of Hsp90 causes Her2 degradation and the growth arrest and differentiation of breast cancer cells, *Chem. Biol.* 8 (2001), pp. 289-299.
27. M. Vilenchik, D. Solit, A. Basso, H. Huezo, B. Lucas, H. He, N. Rosen, C. Spampinato, P. Modrich and G. Chiosis, Targeting wide-range oncogenic transformation via PU24FC1, a specific inhibitor of tumor Hsp90, *Chem. Biol.* 11 (2004), pp. 787-797.
28. H. He, D. Zatorska, J. Kim, J. Aguirre, L. Llauger, Y. She, N. Wu, R. M. Immormino, D. T. Gewirth and G. Chiosis, Identification of potent water soluble purine-scaffold inhibitors of the heat shock protein 90, *J. Med. Chem.* 49 (2006), pp. 381-390.

SUMMARY OF THE INVENTION

The present invention relates to compounds that have activity for inhibiting HSP90. The present invention also provides compositions, articles of manufacture and kits comprising these compounds. In addition, the invention relates to methods of making the compounds of the present invention, as well as intermediates useful in such methods.

In one aspect, the invention is directed to compounds having the formula:

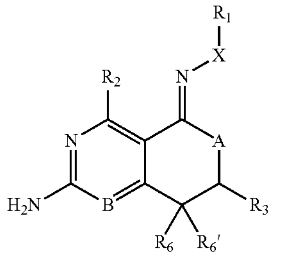

or a tautomer, stereoisomer, or pharmaceutically acceptable salt thereof, wherein A is $NR_4$ or $CR_5R_{5'}$;

B is $CR_7$ or N;

X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, and the substituents on adjacent atoms may be taken together to form a substituted or unsubstituted ring;

$R_4$ is selected from the group consisting of hydrogen, carbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_5$ and $R_{5'}$ are each independently selected from the group consisting of hydrogen, cyano, carbonyl, oxycarbonyl, aminocarbonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_7$ is selected from the group consisting of hydrogen, cyano, sulfonyl, sulfinyl, $(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and provided that when A is $CR_5R_{5'}$, B is N, X is O, $R_1$ is $(C_{1-6})$alkyl substituted with at least two hydroxyl groups.

In another aspect, the invention is directed to salts and polymorphs of the compounds. Particularly, (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A.

In another aspect, the invention is directed to pharmaceutical compositions that comprise a HSP90 inhibitor according to the present invention as an active ingredient. Pharmaceutical compositions according to the invention may optionally comprise 0.001%400% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention is directed to kits and other articles of manufacture for treating disease states associated with HSP90. In one embodiment, the kit comprises a composition comprising at least one HSP90 inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention is directed to articles of manufacture that comprise a composition comprising at least one HSP90 inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

In yet another aspect of the invention is directed to methods for preparing compounds, compositions, kits, and articles of manufacture according to the present invention. For example, several synthetic schemes are provided herein for synthesizing compounds according to the present invention.

In yet other aspect, the invention is directed to methods of using compounds, compositions, kits and articles of manufacture according to the present invention.

In one embodiment, the compounds, compositions, kits and articles of manufacture are used to inhibit HSP90.

In another embodiment, the compounds, compositions, kits and articles of manufacture are used to treat a disease state for which HSP90 possess activity that contributes to the pathology and/or symptomology of the disease state.

In another embodiment, a compound is administered to a subject wherein HSP90 activity within the subject is altered, preferably reduced.

In another embodiment, a prodrug of a compound is administered to a subject that is converted to the compound in vivo where it inhibits HSP90.

In another embodiment, a method of inhibiting HSP90 is provided that comprises contacting a HSP90 with a compound according to the present invention.

In another embodiment, a method of inhibiting HSP90 is provided that comprises causing a compound according to the present invention to be present in a subject in order to inhibit HSP90 in vivo.

In another embodiment, a method of inhibiting a HSP90 is provided that comprises administering a first compound to a subject that is converted in vivo to a second compound wherein the second compound inhibits HSP90 in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by HSP90, or which is known to be treated by HSP90 inhibitors, comprising administering to the patient a therapeutically effective amount of a compound according to the present invention.

In another embodiment, a method is provided for treating a disease state for which HSP90 possesses activity that contributes to the pathology and/or symptomology of the disease state, the method comprising: causing a compound according to the present invention to be present in a subject in a therapeutically effective amount for the disease state.

In another embodiment, a method is provided for treating a disease state for which HSP90 possesses activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which HSP90 possesses activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by HSP90, or that is known to be treated by HSP90 inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well known in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibiting HSP90 and thus may themselves be prodrugs for another compound. Such prodrugs of another compound may or may not themselves independently have HSP90 inhibitory activity.

BRIEF DESCRIPTION OF THE FIGURES

FIG. 1 illustrates SEQ ID NO:1 and SEQ ID NO: 2 referred to in this application.

DEFINITIONS

Figure 2:
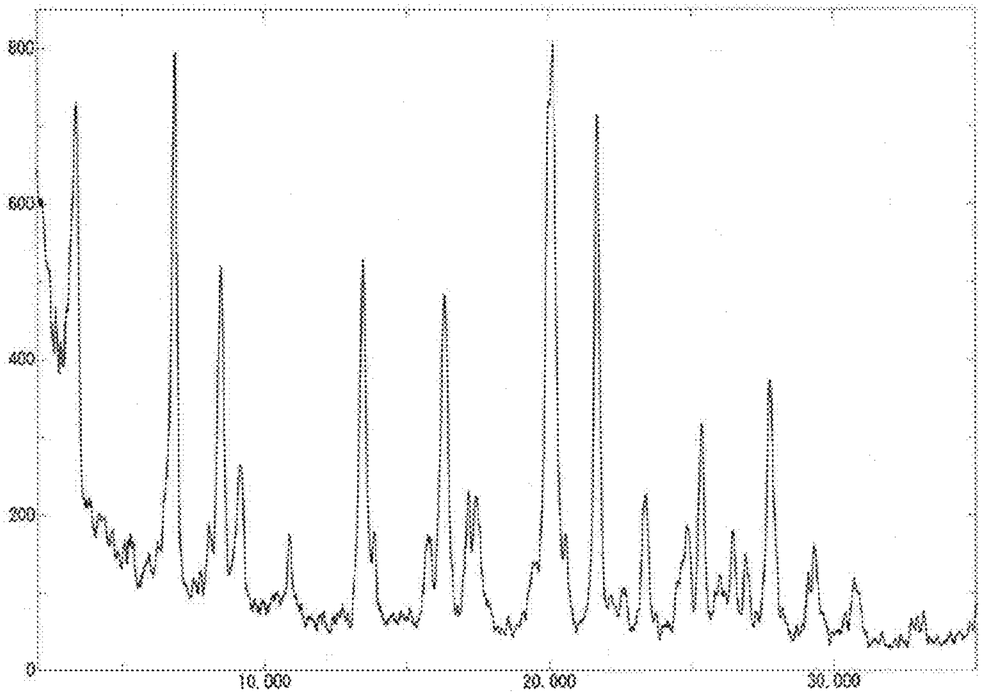
FIG. 2 illustrates the powder X-ray diffractogram of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A.

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $5^{TH}$ ED." Vols. A (2007) and B (2007), Springer Science+Business Media, New York. Also, unless otherwise indicated, conventional methods of mass spectroscopy, NMR, HPLC, protein chemistry, biochemistry, recombinant DNA techniques and pharmacology, within the skill of the art are employed.

"*" when appears in a chemical structure, particularly in radicals, indicates the point of attachment of the radical.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $(C_{3-8})$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR═CR'— or —CR═CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a $(C_{2-20})$alkenyl, a $(C_{2-15})$alkenyl, a $(C_{2-10})$alkenyl, a $(C_{2-5})$alkenyl or a $(C_{2-3})$alkenyl. Alternatively, "alkenyl," either alone or represented along with another radical, can be a $(C_2)$alkenyl, a $(C_3)$alkenyl or a $(C_4)$alkenyl.

"Alkenylene" means a straight or branched, divalent carbon chain having one or more carbon-carbon double bonds (—CR═CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a $(C_{2-20})$ alkenylene, a $(C_{2-15})$ alkenylene, a $(C_{2-10})$ alkenylene, a $(C_{2-5})$ alkenylene or a $(C_{2-3})$ alkenylene. Alternatively, "alkenylene," either alone or represented along with another radical, can be a $(C_2)$ alkenylene, a $(C_3)$ alkenylene or a $(C_4)$ alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms. $(C_X)$alkyl and $(C_{X-Y})$alkyl are typically used where X and Y indicate the number of carbon atoms in the chain. For example, $(C_{1-6})$alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a $(C_{1-20})$alkyl, a $(C_{1-15})$alkyl, a $(C_{1-10})$alkyl, a $(C_{1-5})$alkyl or a $(C_{1-3})$alkyl. Alternatively, "alkyl," either alone or represented along with another radical, can be a $(C_1)$alkyl, a $(C_2)$alkyl or a $(C_3)$alkyl.

"Alkylene", unless indicated otherwise, means a straight or branched, saturated or unsaturated, aliphatic, divalent radical. $(C_X)$alkylene and $(C_{X-Y})$alkylene are typically used where X and Y indicate the number of carbon atoms in the chain. For example, $(C_{1-6})$alkylene includes methylene ($—CH_2—$), ethylene ($—CH_2CH_2—$), trimethylene ($—CH_2CH_2CH_2—$), tetramethylene ($—CH_2CH_2CH_2CH_2—$) 2-butenylene ($—CH_2CH═CHCH_2—$), 2-methyltetramethylene ($—CH_2CH(CH_3)CH_2CH_2—$), pentamethylene ($—CH_2CH_2CH_2CH_2CH_2—$) and the like. In particular embodiments, "alkylene," either alone or represented along with another radical, can be a $(C_{1-20})$alkylene, a $(C_{1-15})$alkylene, a $(C_{1-10})$alkylene, a $(C_{1-5})$alkylene or a $(C_{1-3})$alkylene. Alternatively, "alkylene," either alone or represented along with another radical, can be a $(C_1)$alkylene, a $(C_2)$alkylene or a $(C_3)$alkylene.

"Alkylidene" means a straight or branched, saturated or unsaturated, aliphatic radical connected to the parent molecule by a double bond. $(C_X)$alkylidene and $(C_{X-Y})$alkylidene are typically used where X and Y indicate the number of carbon atoms in the chain. For example, $(C_{1-6})$alkylidene includes methylene ($═CH_2$), ethylidene ($═CHCH_3$), isopropylidene ($═C(CH_3)_2$), propylidene ($═CHCH_2CH_3$), allylidene ($═CH—CH═CH_2$), and the like. In particular embodiments, "alkylidene," either alone or represented along with another radical, can be a $(C_{1-20})$alkylidene, a $(C_{1-15})$alkylidene, a $(C_{1-10})$alkylidene, a $(C_{1-5})$alkylidene or a $(C_{1-3})$alkylidene. Alternatively, "alkylidene," either alone or represented along with another radical, can be a $(C_1)$alkylidene, a $(C_2)$alkylidene or a $(C_3)$alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a $(C_{2-20})$alkynyl, a $(C_{2-15})$alkynyl, a $(C_{2-10})$alkynyl, a $(C_{2-5})$alkynyl or a $(C_{2-3})$alkynyl. Alternatively, "alkynyl," either alone or represented along with another radical, can be a $(C_2)$alkynyl, a $(C_3)$alkynyl or a $(C_4)$alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a $(C_{2-20})$ alkynylene, a $(C_{2-15})$ alkynylene, a $(C_{2-10})$ alkynylene, a $(C_{2-5})$ alkynylene or a $(C_{2-3})$ alkynylene. Alternatively, "alkynylene," either alone or represented along with another radical, can be a $(C_2)$ alkynylene, a $(C_3)$ alkynylene or a $(C_4)$ alkynylene.

"Amido" means the radical —C(═O)—NR—, —C(═O)—NRR', —NR—C(═O)— and/or —NR—C(═O)R', wherein each R and R' are independently hydrogen or a further substituent.

"Amino" means a nitrogen moiety having two further substituents where, for example, a hydrogen or carbon atom is attached to the nitrogen. For example, representative amino groups include —$NH_2$, —$NHCH_3$, —$N(CH_3)_2$, —NH(($C_{1-10}$)alkyl), —N(($C_{1-10}$)alkyl)$_2$, —NH(aryl), —NH (heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are $sp^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. ($C_X$)aryl and ($C_{X-Y}$)aryl are typically used where X and Y indicate the number of carbon atoms in the ring. In particular embodiments, "aryl," either alone or represented along with another radical, can be a ($C_{3-14}$)aryl, a ($C_{3-10}$)aryl, a ($C_{3-7}$) aryl, a ($C_{8-10}$)aryl or a ($C_{5-7}$)aryl. Alternatively, "aryl," either alone or represented along with another radical, can be a ($C_5$)aryl, a ($C_6$)aryl, a ($C_7$)aryl, a ($C_8$)aryl, a ($C_9$)aryl or a ($C_{10}$)aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a ($C_{1-10}$)azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a ($C_{4-15}$)bicycloalkyl, a ($C_{4-10}$)bicycloalkyl, a ($C_{6-10}$)bicycloalkyl or a ($C_{8-10}$)bicycloalkyl. Alternatively, "bicycloalkyl," either alone or represented along with another radical, can be a ($C_8$)bicycloalkyl, a ($C_9$)bicycloalkyl or a ($C_{10}$)bicycloalkyl.

"Bicycloaryl" means a fused, spiro or bridged bicyclic ring assembly wherein at least one of the rings comprising the assembly is aromatic. ($C_X$)bicycloaryl and ($C_{X-Y}$)bicycloaryl are typically used where X and Y indicate the number of carbon atoms in the bicyclic ring assembly and directly attached to the ring. In particular embodiments, "bicycloaryl," either alone or represented along with another radical, can be a (a ($C_{4-15}$)bicycloaryl, a ($C_{4-10}$)bicycloaryl, a ($C_{6-10}$)bicycloaryl or a ($C_{8-10}$)bicycloaryl. Alternatively, "bicycloalkyl," either alone or represented along with another radical, can be a ($C_8$)bicycloaryl, a ($C_9$)bicycloaryl or a ($C_{10}$) bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(═O)— and/or —C(═O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(═O)—O— and/or —C(═O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. ($C_X$)cycloalkyl and ($C_{X-Y}$)cycloalkyl are typically used where X and Y indicate the number of carbon atoms in the ring assembly. For example, ($C_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a ($C_{3-14}$)cycloalkyl, a ($C_{3-10}$)cycloalkyl, a ($C_{3-7}$)cycloalkyl, a ($C_{8-10}$)cycloalkyl or a ($C_{5-7}$)cycloalkyl. Alternatively, "cycloalkyl," either alone or represented along with another radical, can be a ($C_5$)cycloalkyl, a ($C_6$)cycloalkyl, a ($C_7$)cycloalkyl, a ($C_8$)cycloalkyl, a ($C_9$)cycloalkyl or a ($C_{10}$)cycloalkyl.

"Cycloalkylene" means a divalent, saturated or partially unsaturated, monocyclic, bicyclic or polycyclic ring assembly. ($C_X$)cycloalkylene and ($C_{X-Y}$)cycloalkylene are typically used where X and Y indicate the number of carbon atoms in the ring assembly. In particular embodiments, "cycloalkylene," either alone or represented along with another radical, can be a ($C_{3-14}$)cycloalkylene, a ($C_{3-10}$)cycloalkylene, a ($C_{3-7}$)cycloalkylene, a ($C_{8-10}$)cycloalkylene or a ($C_{5-7}$)cycloalkylene. Alternatively, "cycloalkylene," either alone or represented along with another radical, can be a ($C_5$)cycloalkylene, a ($C_6$)cycloalkylene, a ($C_7$)cycloalkylene, a ($C_8$) cycloalkylene, a ($C_9$)cycloalkylene or a ($C_{10}$)cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"$EC_{50}$" means the molar concentration of an agonist that produces 50% of the maximal possible effect of that agonist. The action of the agonist may be stimulatory or inhibitory.

"Fused ring" as used herein refers to a ring that is bonded to another ring to form a compound having a bicyclic structure where the ring atoms that are common to both rings are directly bound to each other. Non-exclusive examples of common fused rings include decaling, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means an alkyl, as defined in this Application, provided that one or more of the atoms within the alkyl chain is a heteroatom or a carbonyl group. "Heteroalkyl" as defined herein includes alkyl chain containing oxygen (See "oxaalkyl"), a carbonyl group (See "oxoalkyl"), sulfur (See "thioalkyl"), and nitrogen (See "azaalkyl"). Hetero($C_X$)alkyl and hetero($C_{X-Y}$)alkyl are typically used where X and Y indicate the number of carbon atoms in the chain. In particular embodiments, "heteroalkyl," either alone or represented along with another radical, can be a hetero($C_{1-20}$)alkyl, a hetero($C_{1-15}$)alkyl, a hetero($C_{1-10}$)alkyl, a hetero($C_{1-5}$)alkyl, a hetero($C_{1-3}$)alkyl or a hetero($C_{1-2}$)alkyl. Alternatively, "heteroalkyl," either alone or represented along with another radical, can be a hetero($C_1$)alkyl, a hetero($C_2$)alkyl or a hetero ($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c] pyridine, pyrrolo[3,2-b]pyridine, pyrrolo[2,3-d]pyrimidine, pyrrolo[3,2-d]pyrimidine, pyrrolo[2,3-b]pyrazine, pyrazolo [1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo [3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero ($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —$N^+$ ($O^-$)=, —O—, —S— or —$S(O)_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo [3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero ($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-14}$)bicycloaryl, a hetero($C_{4-14}$) bicycloaryl, a hetero($C_{4-9}$)bicycloarylor a hetero($C_{5-9}$)bicycloaryl. Alternatively, "heterobicycloaryl," either alone or represented along with another radical, can be a hetero($C_5$) bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero ($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-43}$) cycloalkylene, a hetero($C_{1-9}$)cycloalkylene, a hetero($C_{1-6}$) cycloalkylene, a hetero($C_{5-9}$)cycloalkylene or a hetero($C_{2-6}$) cycloalkylene. Alternatively, "heterocycloalkylene," either alone or represented along with another radical, can be a hetero($C_2$)cycloalkylene, a hetero($C_3$)cycloalkylene, a hetero ($C_4$)cycloalkylene, a hetero($C_5$)cycloalkylene, a hetero($C_6$) cycloalkylene, hetero($C_7$)cycloalkylene, hetero($C_8$)cycloalkylene or a hetero($C_9$)cycloalkylene.

"Hydroxy" means the radical —OH.

"$IC_{50}$" means the molar concentration of an inhibitor that produces 50% inhibition of the target enzyme.

"Imino" means the radical —CR(═NR') and/or —C(═NR')—, wherein R and R' are each independently hydrogen or a further substituent.

"Iminoketone derivative" means a derivative comprising the moiety —C(NR)—, wherein R is hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 5th edition, March, Jerry, John Wiley & Sons, New York, 2001).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Linker" refers to a divalent radical which links together two moieties. A "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-$(L)_X$-R' where each L is independently selected from the group consisting of CR"R'", NR"", O, S, CO, CS, C═NR"", SO, $SO_2$, and the like, where any two or more of R", R'", R"" and R"" can be taken together to form a substituted or unsubstituted ring.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(═O)— or —C(═O)—R, wherein R is hydrogen or a further substituent). The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in P. G. M. Wuts and T. W. Greene, "*Greene's Protecting Groups in Organic Synthesis,* 4th edition, John Wiley & Sons, Inc. 2007.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, $(C_{1-10})$alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, $(C_{1-10})$alkoxy, $(C_{4-12})$aryloxy, hetero $(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$bicycloaryl and hetero$(C_{4-12})$bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —$SO_2$— and/or —$SO_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and ═S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio$(C_{1-10})$alkyl refers to a chain comprising between 1 and 10 carbons and one or more sulfur atoms.

"Thiocarbonyl" means the radical —C(═S)— and/or —C(═S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $(C_1)$alkyl comprises methyl (i.e., —$CH_3$) as well as —CRR'R" where R, R', and R" may each independently be hydrogen or a further substituent where the atom attached to the carbon is a heteroatom or cyano. Hence, $CF_3$, $CH_2OH$ and $CH_2CN$, for example, are all $(C_1)$alkyls. Similarly, terms such as alkylamino and the like comprise dialkylamino and the like.

A compound having a formula that is represented with a dashed bond is intended to include the formulae optionally having zero, one or more double bonds, as exemplified and shown below:

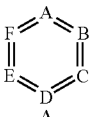
represents
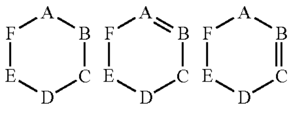
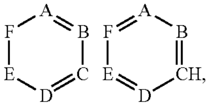
, etc.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

DETAILED DESCRIPTION OF THE INVENTION

The present invention relates to compounds that may be used to inhibit HSP90. The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

It is noted that the compounds of the present invention may also possess inhibitory activity for other HSP family members and thus may be used to address disease states associated with these other family members.

Compound of the Invention

In one of its aspects, the present invention relates to compounds that are useful as HSP90 inhibitors. In one embodiment, HSP90 inhibitors of the present invention is of a formula selected from the group consisting of:

I

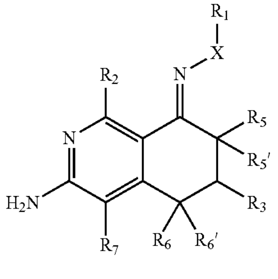

II

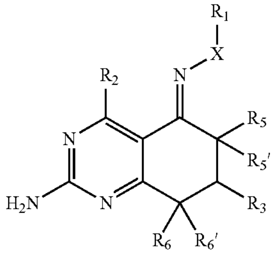

-continued

III

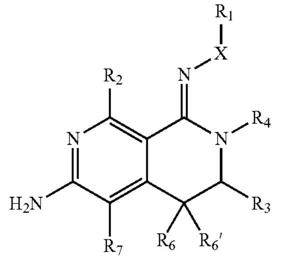

IV

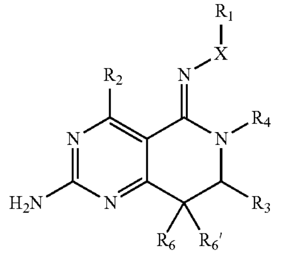

or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, and the substituents on adjacent atoms may be taken together to form a substituted or unsubstituted ring;

$R_4$ is selected from the group consisting of hydrogen, carbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_5$ and $R_{5'}$ are each independently selected from the group consisting of hydrogen, cyano, carbonyl, oxycarbonyl, aminocarbonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_7$ is selected from the group consisting of hydrogen, cyano, sulfonyl, sulfinyl, $(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and provided that for Formula II, when X is O, $R_1$ is a $(C_{1-6})$alkyl substituted with at least two hydroxyl group.

In another embodiment, the compounds of the invention consisting the formula:

I

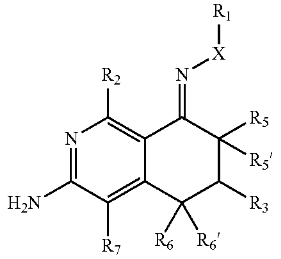

or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, hetero($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl, and hetero($C_{4-12}$)bicycloaryl, each unsubstituted or substituted with 1-3 substituents, and the substituents on adjacent atoms may be taken together to form a substituted or unsubstituted ring;

$R_5$ and $R_{5'}$ are each independently selected from the group consisting of hydrogen, cyano, carbonyl, oxycarbonyl, aminocarbonyl, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, hetero($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_6$ and $R_{6'}$ are each independently selected from the group consisting of hydrogen, halogen, cyano, ($C_{1-10}$)alkyl, sulfonyl($C_{1-10}$)alkyl, sulfinyl($C_{1-10}$)alkyl, hetero($C_{1-10}$)alkyl, ($C_{3-12}$)cycloalkyl($C_{1-5}$)alkyl, hetero($C_{3-12}$)cycloalkyl($C_{1-10}$) alkyl, aryl($C_{1-10}$)alkyl, hetero($C_{1-10}$)aryl($C_{1-5}$)alkyl, ($C_{9-12}$) bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, provided that $R_{6'}$ is absent when A is $CR_5R_5$;

$R_7$ is selected from the group consisting of hydrogen, cyano, sulfonyl, sulfinyl, ($C_{1-10}$)alkyl, sulfonyl($C_{1-10}$)alkyl, sulfinyl($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl and hetero($C_{4-12}$)bicycloaryl, each substituted or unsubstituted;

$R_8$ is selected from the group consisting of hydrogen, ($C_{1-10}$)alkyl, hetero($C_{1-10}$)alkyl, hydroxy($C_{1-10}$)alkyl, sulfonyl($C_{1-10}$)alkyl, sulfinyl($C_{1-10}$)alkyl, ($C_{3-12}$)cycloalkyl($C_{1-5}$) alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted; and $R_9$ and $R_{9'}$ are each independently selected from the group consisting of hydrogen, sulfonamido, sulfonyl, sulfinyl, ($C_{1-10}$)alkyl, hydroxy($C_{1-10}$)alkyl, sulfonyl($C_{1-10}$)alkyl, sulfinyl($C_{1-10}$)alkyl, hetero($C_{1-10}$)alkyl, ($C_{3-12}$)cycloalkyl ($C_{1-5}$)alkyl, hetero($C_{3-12}$)cycloalkyl($C_{1-10}$)alkyl, aryl($C_{1-10}$) alkyl, hetero($C_{1-10}$)aryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted.

In another embodiment, the compounds of the invention consist of the formula

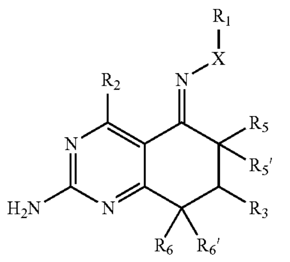

II or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, ($C_{1-10}$)alkyl, halo($C_{1-10}$)alkyl, hetero($C_{1-10}$) alkyl, ($C_{1-10}$)alkyl, hydroxy($C_{1-10}$)alkyl, alkoxy($C_{1-10}$)alkyl, amino($C_{1-10}$)alkyl, imino($C_{1-10}$)alkyl, carbonyl($C_{1-10}$)alkyl, sulfonyl($C_{1-10}$)alkyl, sulfinyl($C_{1-10}$)alkyl, carbonylamino ($C_{1-10}$)alkyl, thiocarbonyl($C_{1-10}$)alkyl, hydroxylcarbonyl ($C_{1-10}$)alkyl, aminocarbonyl($C_{1-10}$)alkyl, aminosulfonyl($C_{1-10}$)alkyl, sulfonylamino($C_{1-10}$)alkyl, ($C_{1-6}$)alkylsulfonylamino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero($C_{1-10}$) aryl($C_{1-5}$)alkyl, ($C_{9-12}$)bicycloaryl($C_{1-5}$)alkyl, hetero($C_{8-12}$) bicycloaryl($C_{1-5}$)alkyl, ($C_{3-12}$)cycloalkyl, hetero($C_{3-12}$) cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl, and hetero ($C_{4-12}$)bicycloaryl, each unsubstituted or substituted;

$R_2$ is selected from the group consisting of hydrogen, halo, cyano, thio, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, sulfonyl, sulfinyl, ($C_{1-10}$)alkyl, halo($C_{1-10}$)alkyl, hydroxy($C_{1-10}$) alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, hetero($C_{1-10}$) alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$) bicycloalkyl, ($C_{4-12}$)aryl, hetero($C_{1-10}$)aryl, ($C_{9-12}$)bicycloaryl, and hetero($C_{4-12}$)bicycloaryl, each substituted or unsubstituted;

$R_3$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, sulfonyl, sulfinyl, ($C_{1-10}$)alkyl, ($C_{1-10}$)alkenyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, hetero($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl ($C_{1-10}$)alkyl, hetero($C_{1-10}$)aryl($C_{1-5}$)alkyl, ($C_{9-12}$)bicycloaryl ($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl, and hetero($C_{4-12}$)bicycloaryl, each unsubstituted or substituted with 1-3 substituents, and the substituents on adjacent atoms may be taken together to form a substituted or unsubstituted ring;

$R_5$ and $R_{5'}$ are each independently selected from the group consisting of hydrogen, cyano, carbonyl, oxycarbonyl, aminocarbonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and provided that when X is O, $R_1$ is $(C_{1-6})$alkyl, substituted with at least two hydroxyl groups.

In one embodiment, the compounds of the invention having the formula:

III

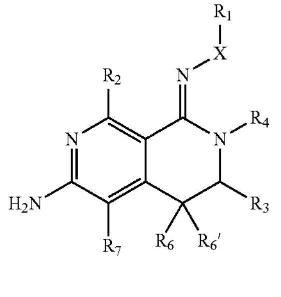

or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, and the substituents on adjacent atoms may be taken together to form a substituted or unsubstituted ring;

$R_4$ is selected from the group consisting of hydrogen, carbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_7$ is selected from the group consisting of hydrogen, cyano, sulfonyl, sulfinyl, $(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl and hetero$(C_{4-12})$bicycloaryl, each substituted or unsubstituted;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another embodiment, the compounds of the invention consisting of the formula:

IV

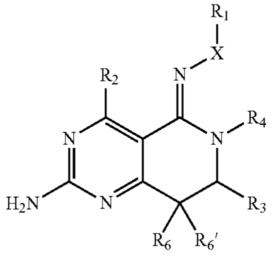

or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$ alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino $(C_{1-10})$alkyl, thiocarbonyl$(C_{1-10})$alkyl, hydroxylcarbonyl $(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero$(C_{1-10})$ aryl$(C_{1-5})$alkyl, $(C_{9-12})$bicycloaryl$(C_{1-5})$alkyl, hetero$(C_{8-12})$ bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero $(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy hetero$(C_{1-10})$ aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$ alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$ alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$ bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy hetero$(C_{1-10})$ aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl $(C_{1-10})$alkyl, hetero$(C_{1-10})$aryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl, and hetero$(C_{4-12})$bicycloaryl, each unsubstituted or substituted with 1-3 substituents, and the substituents on adjacent atoms may be taken together to form a substituted or unsubstituted ring;

$R_4$ is selected from the group consisting of hydrogen, carbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy $(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$ bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero $(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$ bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another embodiment, the compounds of the invention consisting of the formula:

IVa

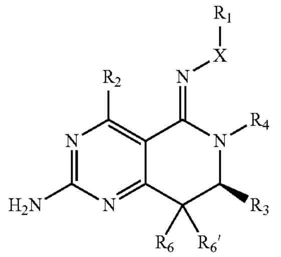

or a tautomer, stereoisomer, or pharmaceutically acceptable salt thereof, wherein X is O, $NR_8$ or $CR_9R_{9'}$;

$R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted;

$R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_3$ is selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, $(C_{1-10})$alkenyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each unsubstituted or substituted with 1-3 substituents, and the substituents on adjacent atoms may be taken together to form a substituted or unsubstituted ring;

$R_4$ is selected from the group consisting of hydrogen, carbonyl, oxycarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero$(C_{4-12})$bicycloaryl, each substituted or unsubstituted;

$R_6$ and $R_{6'}$ are each independently selected from the group consisting of hydrogen, halogen, cyano, $(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, provided that $R_{6'}$ is absent when A is $CR_5R_5$;

$R_8$ is selected from the group consisting of hydrogen, $(C_{1-10})$alkyl, hetero$(C_{1-10})$alkyl, hydroxy$(C_{1-10})$alkyl, sulfonyl$(C_{1-10})$alkyl, sulfinyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_9$ and $R_{9'}$ are each independently selected from the group consisting of hydrogen, sulfonamido, sulfonyl, sulfinyl, $(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

X

In one variation of the above embodiments of the compounds of the invention, X is O.

In another variation, X is $NR_8$, where $R_8$ is selected from the group consisting of hydrogen, $(C_{1-10})$alkyl, hydroxy$(C_{1-10})$alkyl, $(C_{3-12})$cycloalkyl$(C_{1-5})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero($C_{3-12}$)bicycloalkyl, ($C_{4-12}$)aryl, hetero($C_{1-10}$)aryl, each substituted or unsubstituted.

In yet another variation, X is $NR_8$ where $R_8$ is selected from the group consisting of hydrogen, hydroxylalkyl, alkyl, aminoalkyl, and alkoxyalkyl.

In still another variation, X is $NR_8$ where $R_8$ is selected from the group consisting of hydrogen, hydroxyl, ($C_{1-3}$)alkyl, and hydroxy($C_{1-3}$)alkyl.

In still another variation, X is NH.

In still another variation, X is $CR_9R_{9'}$ where $R_9$ and $R_{9'}$ are each individually selected from the group consisting of hydrogen, ($C_{1-10}$)alkyl, hydroxy($C_{1-10}$)alkyl, sulfonyl($C_{1-10}$)alkyl, aza($C_{1-10}$)alkyl, ($C_{1-10}$)oxaalkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{3-12}$)cycloalkyl, hetero($C_{3-12}$)cycloalkyl, ($C_{4-12}$)aryl, and hetero($C_{1-10}$)aryl, each substituted or unsubstituted.

In still another variation, X is $CR_9R_{9'}$ where $R_9$ and $R_{9'}$ are each independently selected from the group consisting of hydrogen, hydroxyl, halo, ($C_{1-3}$)alkyl, hydroxy($C_{1-3}$)alkyl, ($C_{1-3}$)alkoxy, amino, aryl and heteroaryl.

In still another variation, X is $CR_9R_{9'}$ where one of $R_9$ and $R_{9'}$ is independently hydrogen.

In still another variation, X is $CH_2$.

$R_1$

In one variation of the above embodiments and variations of the compounds of the invention, $R_1$ is selected from the group consisting of hydrogen, carbonyl, hydroxycarbonyl, oxycarbonyl, aminocarbonyl, sulfonyl, sulfinyl, ($C_{1-6}$)alkyl, halo($C_{1-6}$)alkyl, hetero($C_{1-6}$)alkyl, hydroxy($C_{1-6}$)alkyl, alkoxy($C_{1-6}$)alkyl, amino($C_{1-6}$)alkyl, imino($C_{1-6}$)alkyl, carbonyl($C_{1-6}$)alkyl, sulfonyl($C_{1-6}$)alkyl, sulfinyl($C_{1-6}$)alkyl, carbonylamino($C_{1-6}$)alkyl, thiocarbonyl($C_{1-6}$)alkyl, hydroxylcarbonyl($C_{1-6}$)alkyl, aminocarbonyl($C_{1-6}$)alkyl, aminosulfonyl($C_{1-6}$)alkyl, sulfonylamino($C_{1-6}$)alkyl, ($C_{1-6}$)alkylsulfonylamino($C_{1-6}$)alkyl, ($C_{3-6}$)cycloalkyl($C_{1-6}$)alkyl, hetero($C_{3-5}$)cycloalkyl($C_{1-6}$)alkyl, ($C_{4-6}$)aryl($C_{1-6}$)alkyl, and hetero($C_{1-5}$)aryl($C_{1-6}$)alkyl, each unsubstituted or substituted.

In another variation, $R_1$ is selected from the group consisting of hydrogen, hydroxycarbonyl, oxycarbonyl, aminocarbonyl, ($C_{1-6}$)alkyl, halo($C_{1-6}$)alkyl, hetero($C_{1-6}$)alkyl, hydroxy($C_{1-6}$)alkyl, alkoxy($C_{1-6}$)alkyl, amino($C_{1-6}$)alkyl, imino($C_{1-6}$)alkyl, carbonyl($C_{1-6}$)alkyl, carbonylamino($C_{1-6}$)alkyl, thiocarbonyl($C_{1-6}$)alkyl, hydroxylcarbonyl($C_{1-6}$)alkyl, aminocarbonyl($C_{1-6}$)alkyl, ($C_{1-6}$)alkylamino($C_{1-6}$)alkyl, ($C_{3-6}$)cycloalkyl($C_{1-6}$)alkyl, hetero($C_{3-5}$)cycloalkyl($C_{1-6}$)alkyl, ($C_{4-6}$)aryl($C_{1-6}$)alkyl, and hetero($C_{1-5}$)aryl($C_{1-6}$)alkyl, each unsubstituted or substituted.

In another variation, $R_1$ is selected from the group consisting of hydrogen, ($C_{1-6}$)alkyl, halo($C_{1-6}$)alkyl, hetero($C_{1-6}$)alkyl, hydroxy($C_{1-6}$)alkyl, alkoxy($C_{1-6}$)alkyl, amino($C_{1-6}$)alkyl, carbonylamino($C_{1-6}$)alkyl, hydroxylcarbonyl($C_{1-6}$)alkyl, aminocarbonyl($C_{1-6}$)alkyl, ($C_{1-6}$)alkylamino($C_{1-6}$)alkyl, ($C_{3-6}$)cycloalkyl($C_{1-6}$)alkyl, hetero($C_{3-5}$)cycloalkyl($C_{1-6}$)alkyl, ($C_{4-6}$)aryl($C_{1-6}$)alkyl, and hetero($C_{1-5}$)aryl($C_{1-6}$)alkyl, each unsubstituted or substituted.

In one particular variation of the above embodiments and variations of the compounds of the invention, $R_1$ is -L-$R_{45}$, where L is absent or is a linker of one to five atoms, wherein the atoms in L are each independently selected from the group consisting of N, O, and S, and are independently unsubstituted or substituted with 1-2 substituents selected from the group consisting of nitro, cyano, thio, oxy, hydroxy, carbonyloxy, ($C_{1-10}$)alkoxy, ($C_{4-12}$)aryloxy, hetero($C_{1-10}$)aryloxy, oxo, carbonyl, oxycarbonyl, aminocarbonyl, amino, alkylcarbonylamino, ($C_{1-10}$)alkylamino, sulfonylamino, aminosulfonyl, sulfonyl, sulfinyl, imino, ($C_{1-10}$)alkyl, hetero($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, ($C_{3-12}$)cycloalkyl($C_{1-6}$)alkyl, hetero($C_{3-12}$)cycloalkyl($C_{1-10}$)alkyl, aryl($C_{1-10}$)alkyl, heteraryl($C_{1-10}$)alkyl, ($C_{3-12}$)cycloalkyl, hetero($C_{3-12}$)cycloalkyl, aryl and heteroaryl, each unsubstituted or further substituted; or any two substituents on adjacent atoms of L are taken to form a 3, 4 and 5 membered ring, each unsubstituted or substituted; and $R_{45}$ is independently selected from the group consisting of hydrogen, hydroxyl, halo, ($C_{1-3}$)alkyl, hydroxy($C_{1-3}$)alkyl, ($C_{1-3}$)alkoxy, amino, carbonylamino, aminocarbonyl, carbonyl, hydroxylcarbonyl, aryl, heteroaryl, cycloalkyl, and heterocycloalkyl, each unsubstituted or further substituted.

In some variations L is absent.

In some variations of the above particular variation, L is an alkyl or heteroalkyl of one to five atoms where each atom is independently selected from the group consisting of N and O, and each atoms is independently unsubstituted or substituted with 1-2 substituents selected from the group consisting of hydroxy, oxo, carbonyloxy, ($C_{1-6}$)alkoxy, ($C_{4-6}$)aryloxy, hetero($C_{1-5}$)aryloxy, carbonyl, oxycarbonyl, aminocarbonyl, amino, alkylcarbonylamino, ($C_{1-10}$)alkylamino, imino, ($C_{1-6}$)alkyl, hetero($C_{1-6}$)alkyl, hydroxy($C_{1-6}$)alkyl, carbonyl($C_{1-6}$)alkyl, thiocarbonyl($C_{1-6}$)alkyl, sulfonyl($C_{1-6}$)alkyl, ($C_{3-6}$)cycloalkyl($C_{1-6}$)alkyl, hetero($C_{3-6}$)cycloalkyl($C_{1-6}$)alkyl, aryl($C_{1-6}$)alkyl, heteroaryl($C_{1-6}$)alkyl, ($C_{3-6}$)cycloalkyl, hetero($C_{3-6}$)cycloalkyl, aryl and heteroaryl, each unsubstituted or further substituted.

In other variation, L is (—$CR_{46}R_{47}$—)$_n$, where n is 1, 2, 3, 4, or 5. In yet other variations, L is (—$CR_{46}R_{47}$—)$_5$. In still other variations, L is (—$CR_{46}R_{47}$—)$_4$. In still other variations, L is (—$CR_{46}R_{47}$—)$_3$. In still other variations, L is (—$CR_{46}R_{47}$—)$_2$. In still other variations, L is —($CR_{46}R_{47}$)—.

In the above variations where L is (—$CR_{46}R_{47}$—)$_n$, $R_{46}$ and $R_{47}$ are each independently selected from the group consisting of hydrogen, hydroxy, oxo, carbonyloxy, ($C_{1-6}$)alkoxy, ($C_{4-6}$)aryloxy, hetero($C_{1-5}$)aryloxy, carbonyl, oxycarbonyl, aminocarbonyl, amino, alkylcarbonylamino, ($C_{1-10}$)alkylamino, imino, ($C_{1-6}$)alkyl, hetero($C_{1-6}$)alkyl, hydroxy($C_{1-6}$)alkyl, carbonyl($C_{1-6}$)alkyl, thiocarbonyl($C_{1-6}$)alkyl, sulfonyl($C_{1-6}$)alkyl, ($C_{3-6}$)cycloalkyl($C_{1-6}$)alkyl, hetero($C_{3-6}$)cycloalkyl($C_{1-6}$)alkyl, aryl($C_{1-6}$)alkyl, heteroaryl($C_{1-6}$)alkyl, ($C_{3-6}$)cycloalkyl, hetero($C_{3-6}$)cycloalkyl, aryl and heteroaryl, each unsubstituted or further substituted.

In other variations, $R_{46}$ and $R_{47}$ are each independently selected from the group consisting of hydrogen, hydroxyl, hydroxy($C_{1-6}$)alkyl, ($C_{1-6}$)alkoxy, oxo, amino, imino, ($C_{1-6}$)alkyl, ($C_{4-6}$)aryl($C_{1-6}$)alkyl, hetero($C_{1-5}$)aryl($C_{1-6}$)alkyl, ($C_{3-6}$)cycloalkyl($C_{1-6}$)alkyl, hetero($C_{1-5}$)cycloalkyl($C_{1-6}$)alkyl, ($C_{4-6}$)aryl, hetero($C_{1-5}$)aryl, ($C_{3-6}$)cycloalkyl, and hetero($C_{1-5}$)cycloalkyl, each unsubstituted or substituted. In other variations, $R_{46}$ and $R_{47}$ are each independently selected from the group consisting of hydrogen, hydroxyl, oxo, ($C_{1-6}$)alkyl, hydroxy($C_{1-6}$)alkyl, ($C_{1-6}$)alkoxy, amino and aminocarbonyl, each substituted or unsubstituted. In other variations, $R_{46}$ and $R_{47}$ are both hydrogen.

In one variation of the above embodiment and variations, $R_1$ is selected from the group consisting of hydrogen, and

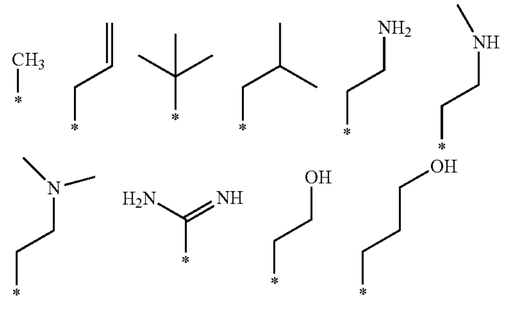

-continued
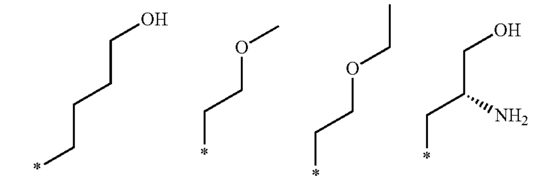
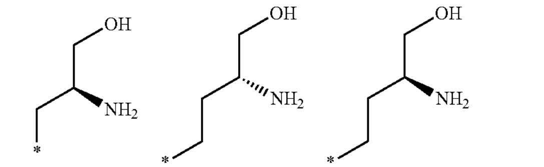
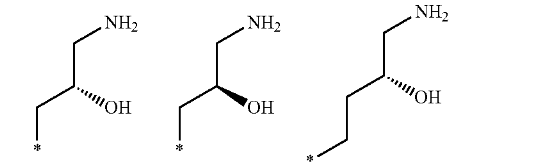
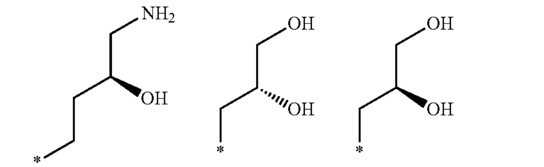
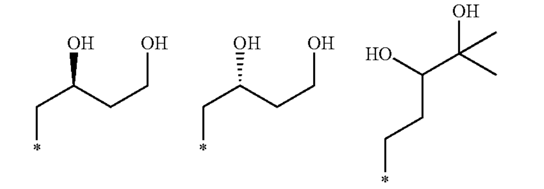
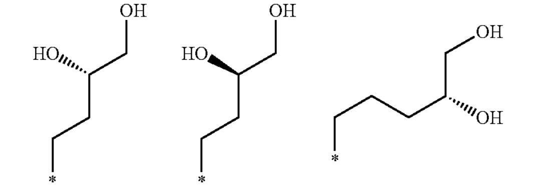
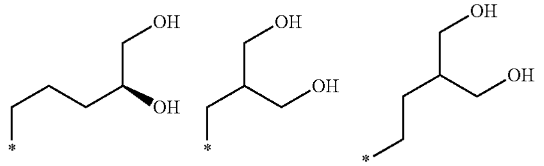
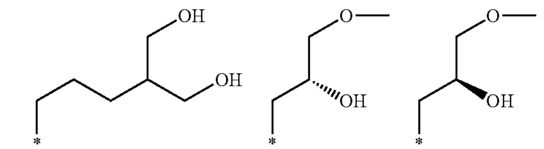
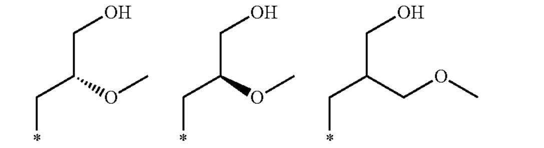
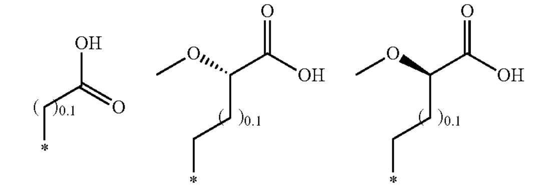
-continued
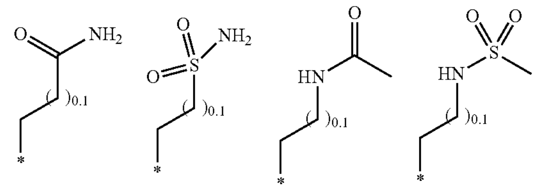
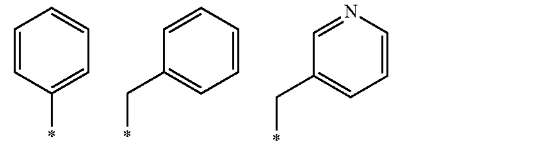
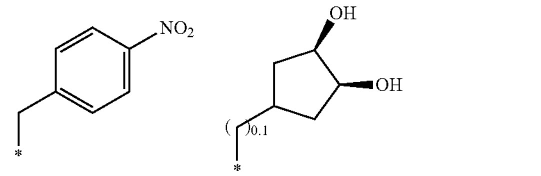
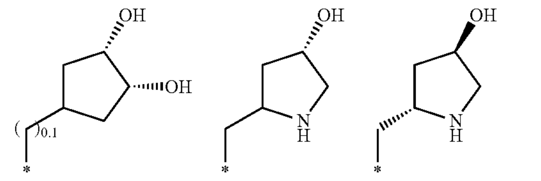
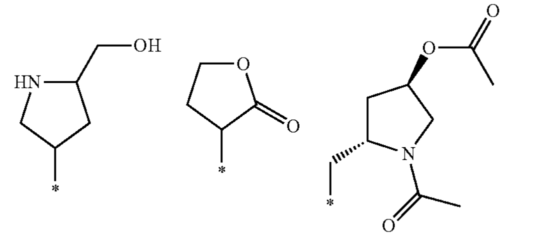
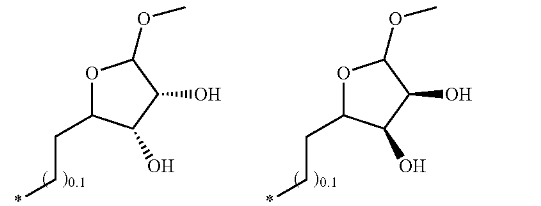
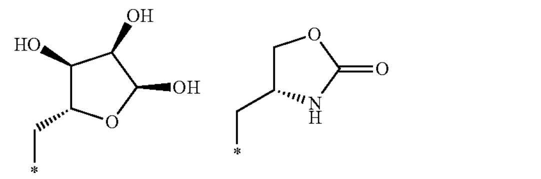
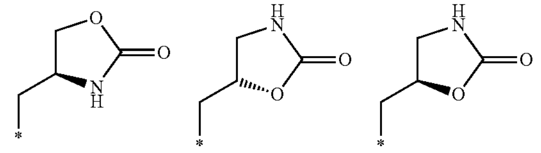
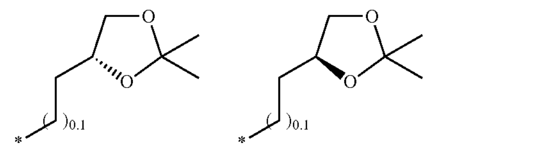

-continued
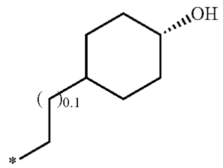
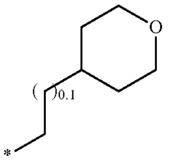
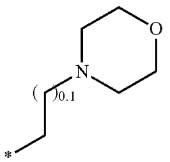
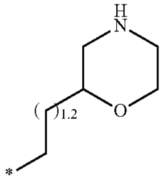
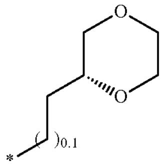
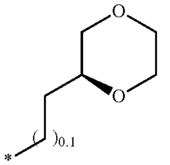
In another variation, $R_1$ is selected from the group consisting of hydrogen,
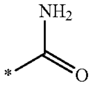
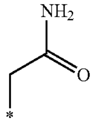
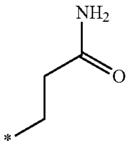
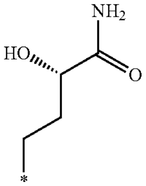
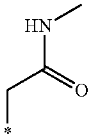
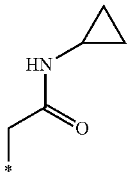
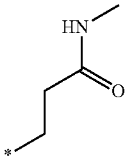
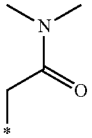
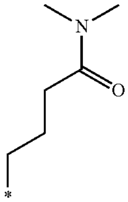
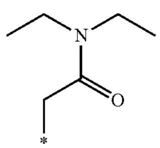
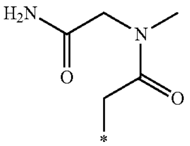
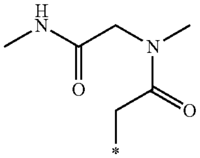
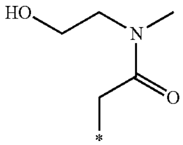
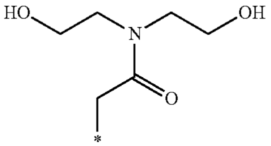
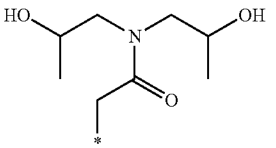
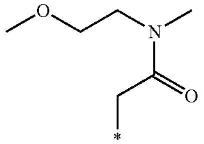
-continued
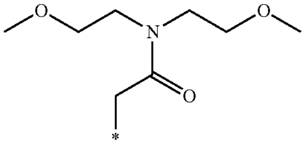
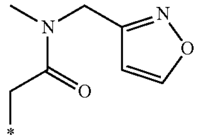
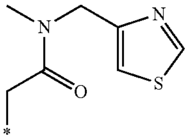
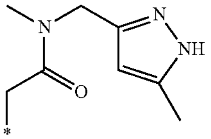
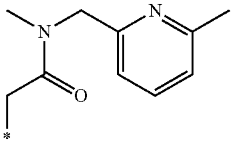
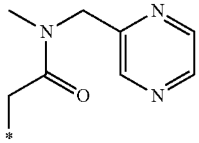
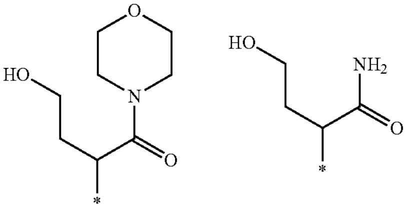
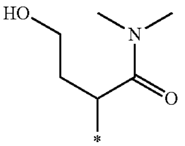
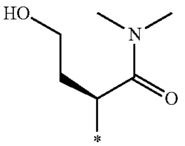
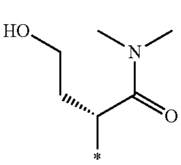
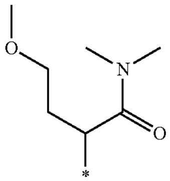
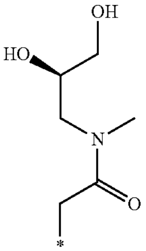
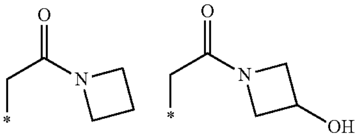
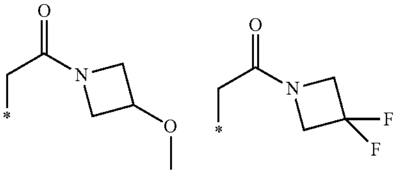
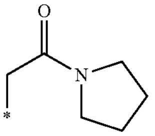
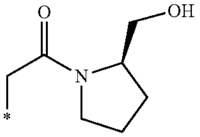
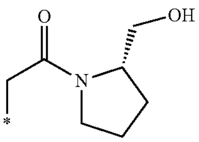
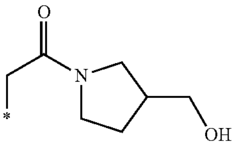

-continued
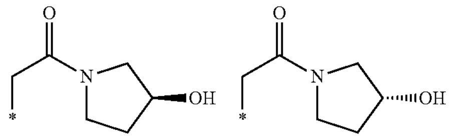
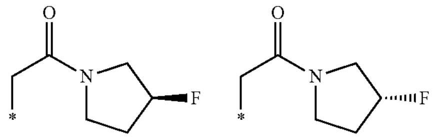
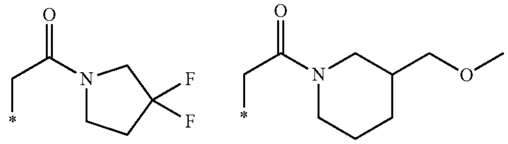
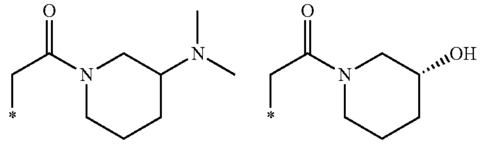
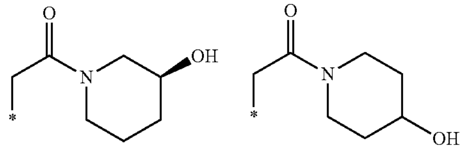
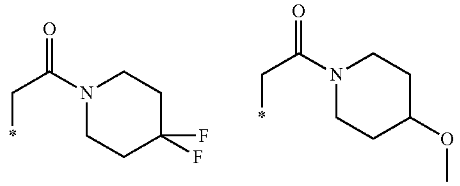
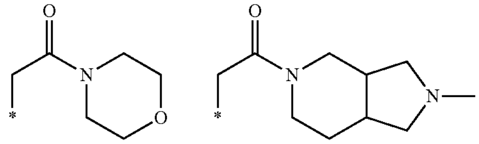
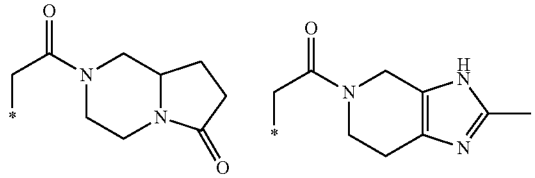
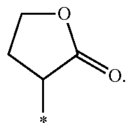
In still another variation, $R_1$ is selected from the group consisting of hydrogen,
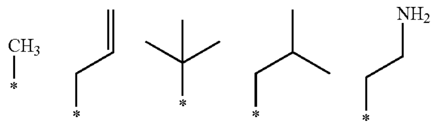
-continued
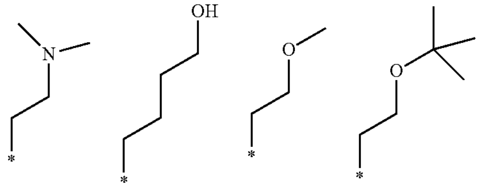
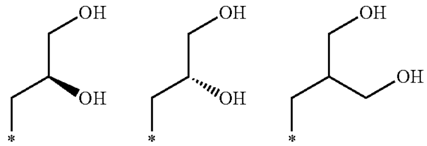
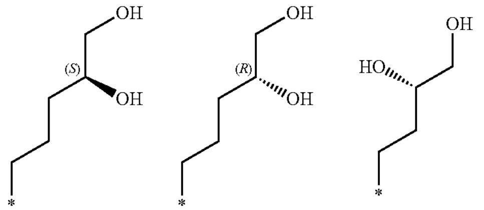
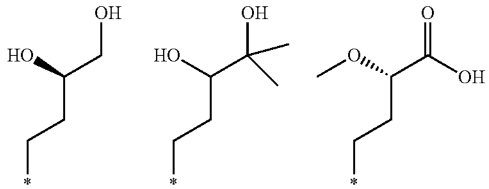
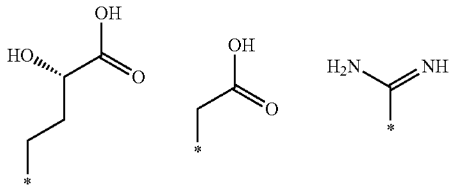
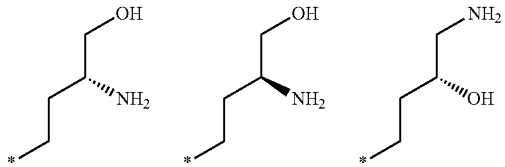
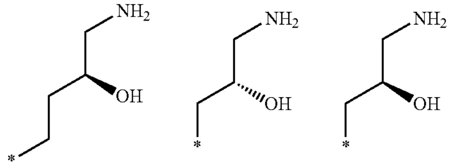
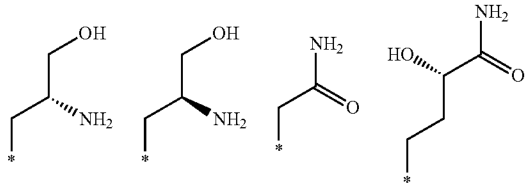
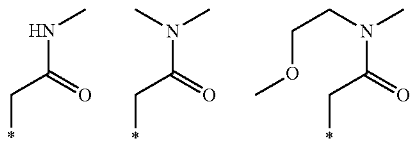
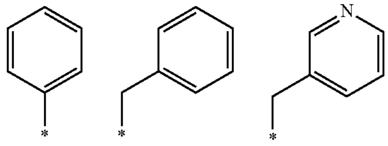

-continued
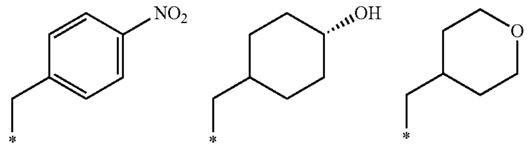
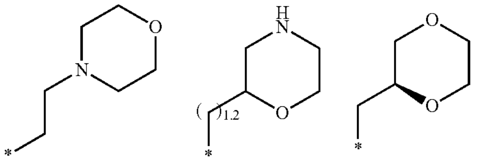
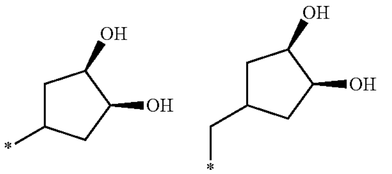
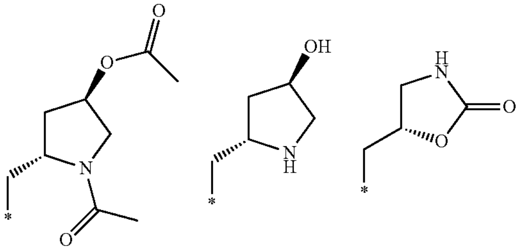
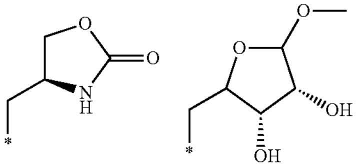
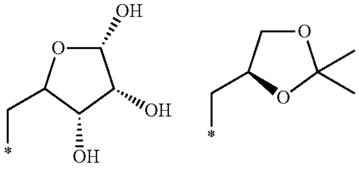
In still another variation, $R_1$ is selected from the group consisting of hydrogen,
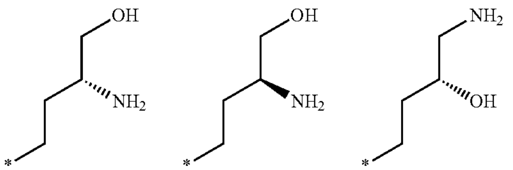
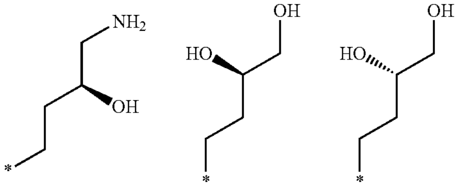
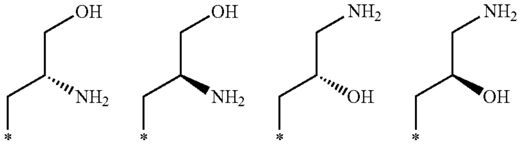
-continued
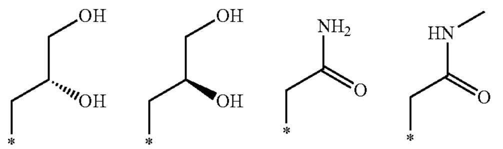
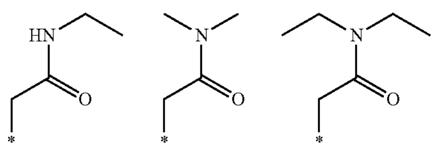
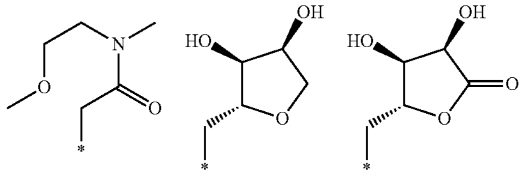
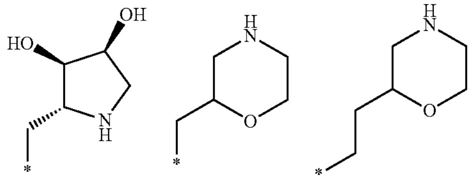
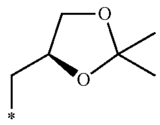
In still another variation, $R_1$ is selected from the group consisting of hydrogen,
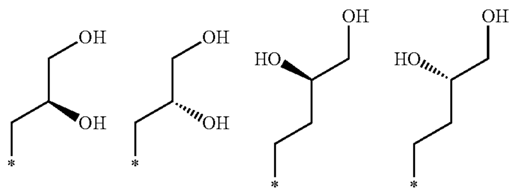
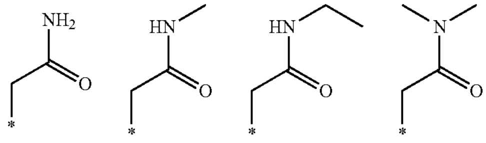
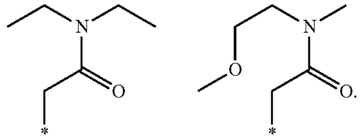
In still other variations, $R_1$ is selected from the group consisting of hydrogen,
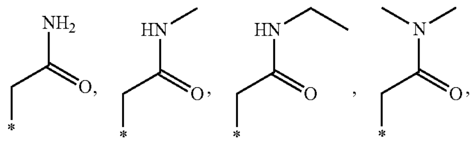

-continued

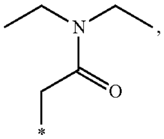

, and

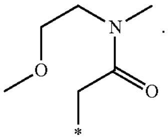

.

In yet other variations, $R_1$ is

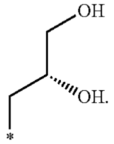

In yet other variations, $R_1$ is

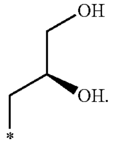 [SMILES: *C[C@H](O)CO]

In yet other variations, $R_1$ is

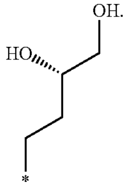

In yet other variations, $R_1$ is

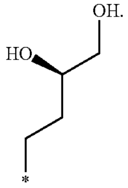

In still further variations, $R_1$ is

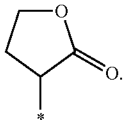 [SMILES: *C1CCOC1=O]

In yet further variations, $R_1$ is

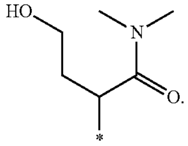

In yet further variations, $R_1$ is

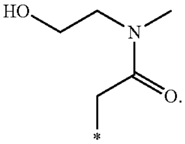 [SMILES: *CC(=O)N(C)CCO]

In still yet further variations, $R_1$ is hydrogen

X—$R_1$

In one variation of the above embodiments and variations of the compounds of the invention, —X—$R_1$ is selected from the group consisting of

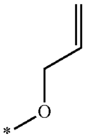
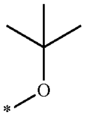
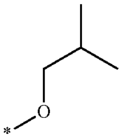
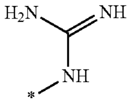
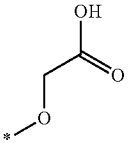
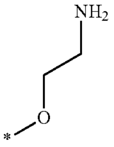
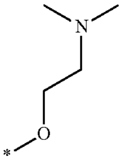
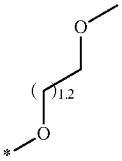
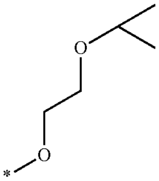
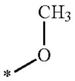
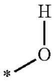
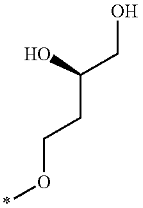
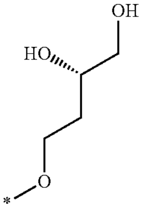
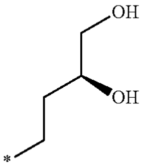
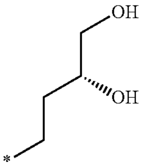
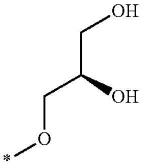
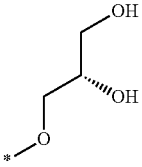
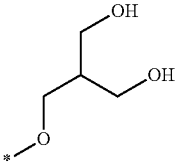
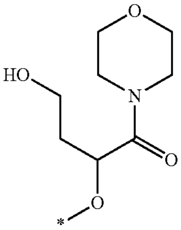
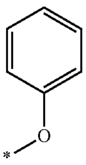
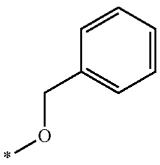
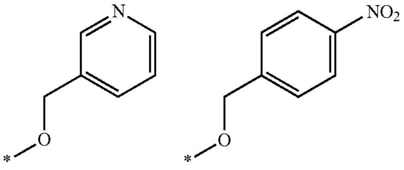

-continued
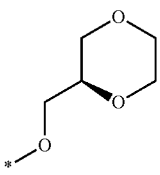
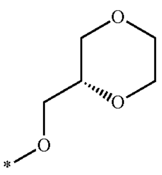
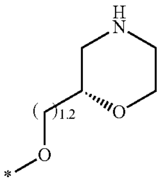
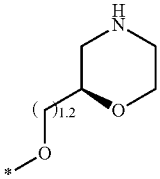
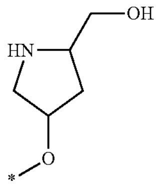
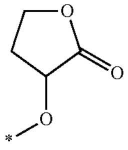
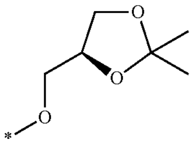
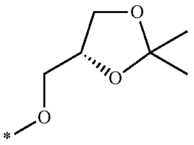
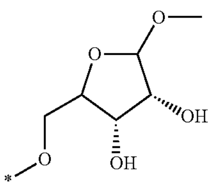
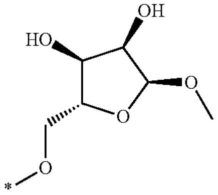
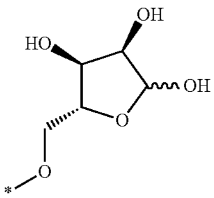
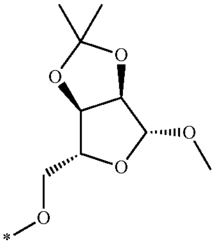
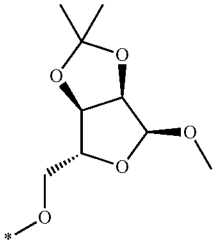
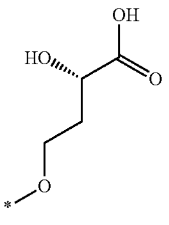
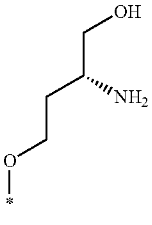
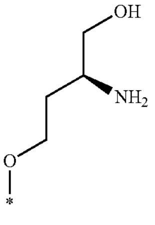
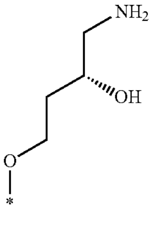
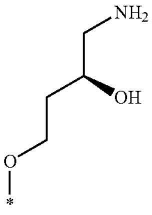
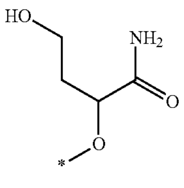
-continued
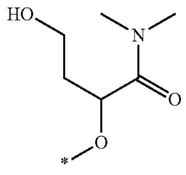
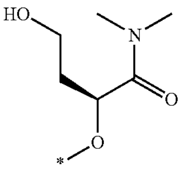
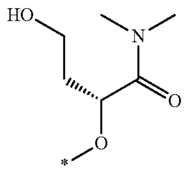
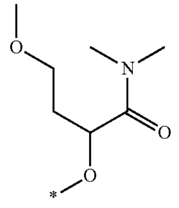
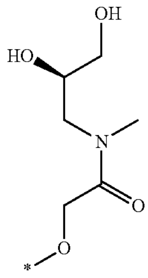
In another variation, —X—$R_1$ is selected from the group consisting of
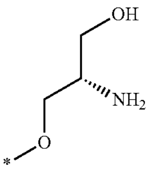
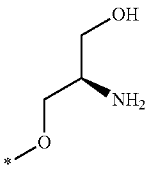
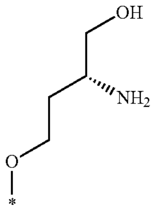
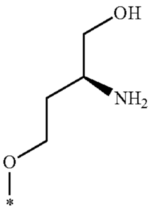
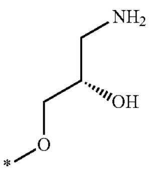
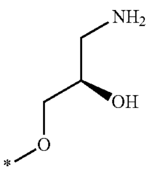
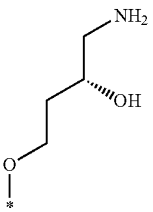
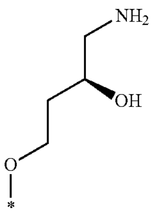
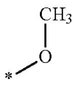
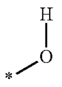
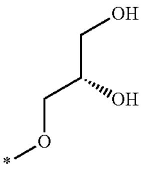
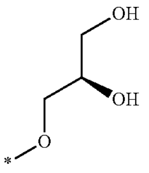
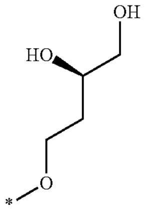

-continued
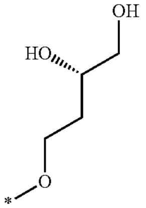 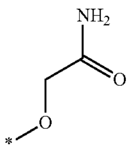 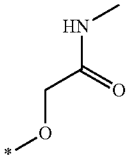
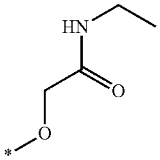 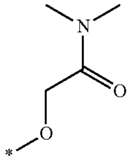 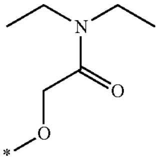
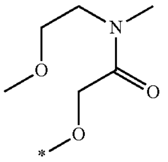 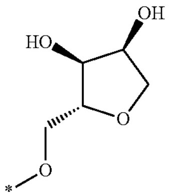
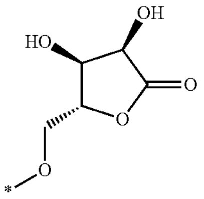 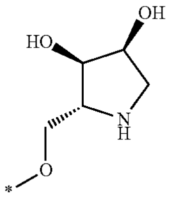
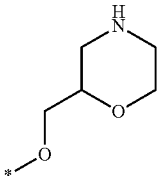 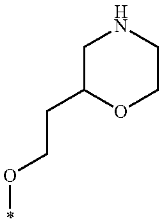
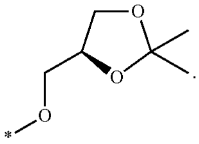 [SMILES: *OC[C@H]1COC(C)(C)O1]
In another variation, —X—$R_1$ is selected from the group consisting of
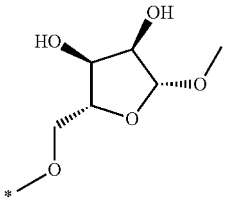 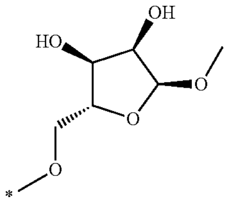
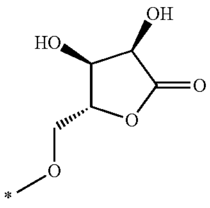 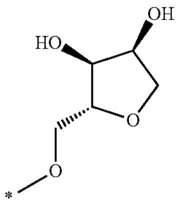
-continued
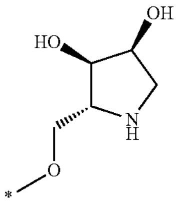 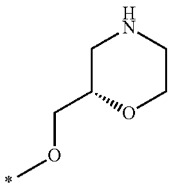
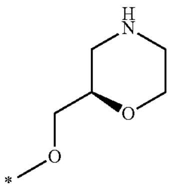 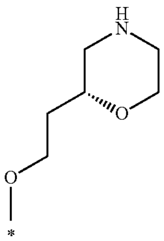 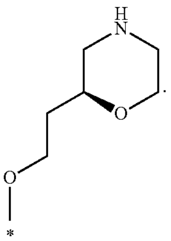
In another variation, —X—$R_1$ is selected from the group consisting of hydroxyl, methoxy,
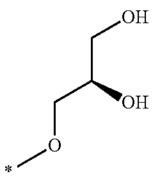 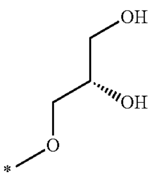 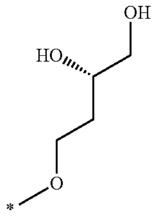
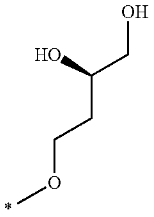 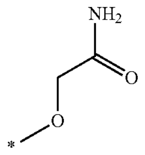 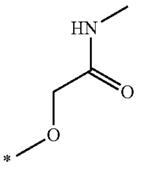
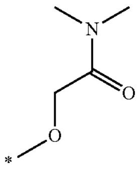 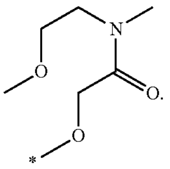
In still other variations, —X—$R_1$ is —OH. In still other variations, —X—$R_1$ is —$OCH_3$. In still other variations, —X—$R_1$ is
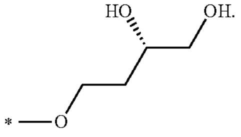
In still other variations, —X—$R_1$ is
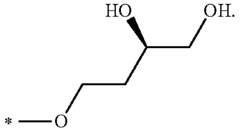

In still further variations, —X—$R_1$ is

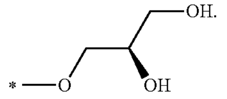

In still further variations, —X—$R_1$ is

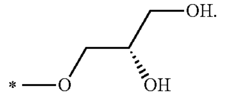

In other further variations, —X—$R_1$ is

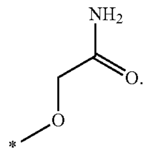

In yet other further variations, —X—$R_1$ is

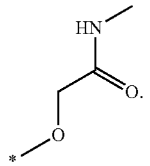

In other further variations, —X—$R_1$ is

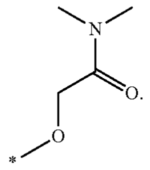

In yet other further variations, —X—$R_1$ is

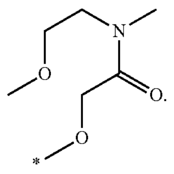

$R_2$

In another variation of the embodiments and variations of the compounds of the invention, $R_2$ is selected from the group consisting of hydrogen, halo, hydroxy, $(C_{1-10})$alkoxy, $(C_{4-12})$ aryloxy, hetero$(C_{1-10})$aryloxy, amino, $(C_{1-10})$alkylamino, sulfonamido, sulfonyl, sulfinyl, $(C_{1-10})$alkyl, halo$(C_{1-10})$ alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$ bicycloaryl, and hetero$(C_{4-12})$bicycloaryl, each substituted or unsubstituted.

In another variation, $R_2$ is selected from the group consisting of hydrogen, of hydrogen, hydroxyl, halo, cyano, thiol, $(C_{1-6})$alkoxy, $(C_{1-6})$alkylthiol, $(C_{1-6})$alkyl, hetero$(C_{1-6})$alkyl, aryl$(C_{1-6})$alkyl, heteroaryl$(C_{1-6})$alkyl, $(C_{1-5})$cycloalkyl$(C_{1-6})$ alkyl, hetero$(C_{1-5})$cycloalkyl$(C_{1-6})$alkyl, $(C_{4-6})$ aryl, $(C_{1-5})$ heteroaryl, $(C_{1-6})$cycloalkyl, and hetero$(C_{1-5})$cycloalkyl, each unsubstituted and substituted.

In yet another variation, $R_2$ is selected from the group consisting of hydrogen, hydroxyl, halo, cyano, thiol, $(C_{1-6})$ alkoxy, $(C_{1-6})$alkylthiol, $(C_{1-6})$alkyl, hetero$(C_{1-6})$alkyl, aryl $(C_{1-6})$alkyl, heteroaryl$(C_{1-6})$alkyl, $(C_{1-5})$cycloalkyl$(C_{1-6})$ alkyl, hetero$(C_{1-5})$cycloalkyl$(C_{1-6})$alkyl, $(C_{4-6})$ aryl, $(C_{1-5})$ heteroaryl, $(C_{1-6})$cycloalkyl, and hetero$(C_{1-5})$cycloalkyl, each unsubstituted and substituted.

In yet another variation, $R_2$ is selected from the group consisting of hydrogen, hydroxyl, methyl, ethyl, methoxymethyl, trifluoromethyl, phenylethyl, and substituted benzyl where the substituents are each independently selected from the group consisting of methoxy, halo, nitro, amino, and acetamide.

In still another variation, $R_2$ is selected from the group consisting of hydrogen, $(C_{1-6})$alkyl or halo$(C_{1-6})$alkyl, aza $(C_{1-6})$alkyl, $(C_{1-6})$oxaalkyl, each unsubstituted or substituted.

In yet another variation, $R_2$ is selected from the group consisting of unsubstituted or substituted $(C_{1-6})$alkyl.

In yet another variation, $R_2$ is hydrogen.

In yet another variation, $R_2$ is methyl.

$R_4$

In one variation of the above embodiments and variations of the compounds of the invention, when present, $R_4$ is selected from the group consisting of hydrogen, $(C_{1-6})$alkyl, $(C_{2-6})$alkenyl, $(C_{2-6})$alkynyl, hydroxy$(C_{1-6})$alkyl, amino$(C_{1-6})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{4-12})$aryl, hetero$(C_{1-10})$aryl, $(C_{3-7})$ cycloalkyl, $(C_{5-7})$cycloalkenyl, and hetero$(C_{3-12})$cycloalkyl, each unsubstituted or substituted.

In another variation, when present, $R_4$ is selected from the group consisting of hydrogen, methyl, ethyl, allyl, 3-methyl-butyl, isobutyl, 2-hydroxyethyl, 3-aminopropyl, 1-(4-methoxyphenyl)ethyl, (2-methyl-2-morpholin-4-yl)propyl, pyridin-4-ylmethyl, tetrahydropyran-4-ylmethyl, benzyl, 2,4-dimethoxy-benzyl, 3-chloro-benzyl, 2-chloro-benzyl, 2-fluoro-benzyl, 4-fluoro-benzyl, 3-trifluoromethyl-benzyl, pyrazin-2-yl, and—$(CH_2)_3NHC(O)O$—$C(CH_3)_3$.

In yet another variation, when present, $R_4$ is selected from the group consisting of hydrogen, unsubstituted $(C_{1-6})$alkyl, and substituted $(C_{1-6})$alkyl.

In yet another variation, when present, $R_4$ is selected from the group consisting of methyl, ethyl, allyl, 3-methyl-butyl, and isobutyl.

In still another variation, when present, $R_4$ is selected from the group consisting of hydrogen, benzyl, 1-(4-methoxyphenyl)ethyl, 1-methyl-(4-methoxyphenyl)methyl, methyl, 3-aminopropyl, and 2-methyl-2-morpholinopropyl.

In still another variation, when present, wherein $R_4$ is hydrogen.

$R_5$ and $R_{5'}$

In one variation of the embodiments and variations of the compounds of the invention, when present, $R_5$ and $R_{5'}$ are each independently selected from the group consisting of hydrogen, halo, cyano, carbonyl, aminocarbonyl, sulfonyl, $(C_{1-10})$alkyl, halo$(C_{1-10})$alkyl, hydroxy$(C_{1-10})$alkyl, carbonyl $(C_{1-10})$alkyl, and hetero$(C_{1-10})$alkyl, each substituted or unsubstituted.

In another variation, when present, $R_5$ and $R_{5'}$ are each independently selected from the group consisting of hydrogen, halogen, $(C_{1-6})$alkyl, —$OR_{42}$, —$SR_{42}$, —$N(R_{42})_2$, —$OC(O)R_{42}$, —$NR_{42}C(O)R_{42}$, and —$N(R_{42})S(O)_2R_{42}$, where $R_{42}$ is selected from the group consisting of hydrogen, $(C_{1-6})$alkyl, $(C_{2-6})$alkenyl, $(C_{2-6})$alkynyl, $(C_{3-7})$cycloalkyl, $(C_{5-7})$cycloalkenyl, aryl, heteroaryl, and $(C_{3-7})$heterocycloalkyl, each unsubstituted or substituted.

In another variation, when present, $R_5$ and $R_{5'}$ are each independently selected from the group consisting of hydrogen, unsubstituted $(C_{1-6})$alkyl, and substituted $(C_{1-6})$alkyl.

In still another variation, when present, $R_5$ and $R_{5'}$ is hydrogen.

In yet another variation, when present, both $R_5$ and $R_{5'}$ are hydrogen.

$R_6$

In one variation of the embodiments and variations of the compounds of the invention, when present, $R_6$ and $R_{6'}$ are each independently selected from the group consisting of hydrogen, halogen, cyano, $(C_{1-10})$alkyl, and hetero$(C_{1-10})$alkyl, each substituted or unsubstituted.

In another variation, when present, $R_6$ and $R_{6'}$ are each independently selected from the group consisting of hydrogen, halogen, cyano, $(C_{1-6})$alkyl, —$OR_{43}$, —$SR_{43}$, —$N(R_{43})_2$, —$OC(O)R_{43}$, —$NR_{43}C(O)R_{43}$, and —$N(R_{43})S(O)_2R_{43}$, where $R_{43}$ is selected from the group consisting of hydrogen, halogen, cyano, nitro, amino, $(C_{1-6})$alkyl, $(C_{2-6})$alkenyl, $(C_{2-6})$alkynyl, $(C_{3-7})$cycloalkyl, $(C_{5-7})$cycloalkenyl, aryl, heteroaryl, and $(C_{3-7})$heterocycloalkyl, each unsubstituted or substituted.

In still another variation, when present, $R_6$ and $R_{6'}$ are each independently selected from the group consisting of hydrogen, halogen, unsubstituted or substituted $(C_{1-6})$alkyl.

In still another variation, when present, $R_6$ and $R_{6'}$ are both halogen.

In still another variation, when present, one of $R_6$ and $R_{6'}$ is halogen, and the other one of $R_6$ and $R_{6'}$ is hydrogen.

In one variation, the halogen of the $R_6$ and $R_{6'}$ definition is fluoro.

In yet still other variations, when present, $R_6$ and $R_{6'}$ are both hydrogen.

In yet still other variations, when present, $R_6$ is fluoro. In yet still other variations, when present, $R_6$ is cyano. In yet another variation, when present, $R_6$ is hydrogen.

$R_7$

In one variation of the embodiments and variations of the compounds of the invention, when present, $R_7$ is selected from the group consisting of hydrogen, cyano, sulfonyl, sulfinyl, $(C_{1-10})$alkyl, hetero$(C_{1-10})$alkyl, amino$(C_{1-10})$alkyl, hydroxy$(C_{1-10})$alkyl, sulfonyl$(C_{1-10})$alkyl, $(C_{1-10})$alkoxy, and $(C_{1-10})$alkoxy$(C_{1-10})$alkyl, each unsubstituted or substituted.

In another variation, when present, $R_7$ is selected from the group consisting of hydrogen, cyano, sulfonyl, sulfinyl, $(C_{1-10})$alkyl, sulfonyl$(C_{1-10})$alkyl, aza$(C_{1-10})$alkyl, and $(C_{1-10})$oxaalkyl, each substituted or unsubstituted.

In another variation, when present, $R_7$ is selected from the group consisting of hydrogen, cyano, alkoxy, hydroxylalkyl, alkyl, aminoalkyl, and alkoxyalkyl.

In yet another variation, when present, $R_7$ is hydrogen.

$R_3$

In one variation of the above embodiments and variations of the compounds of the invention, $R_3$ is selected from the group consisting of hydrogen, $(C_{1-6})$alkyl, $(C_{1-6})$alkenyl, $(C_{3-15})$cycloalkyl, hetero$(C_{1-14})$cycloalkyl cycloalkenyl, $(C_{4-15})$aryl, and hetero$(C_{1-14})$aryl, each unsubstituted or substituted with 1-4 substituents each of which is independently selected from the group consisting of hydrogen, halo, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonylamino, aminosulfonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-3 substituents, or the substituents on adjacent atom may be taken together to form a substituted or unsubstituted ring.

In one variation, $R_3$ is of the formula

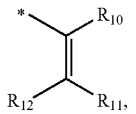

wherein $R_{10}$ and $R_{11}$ are each independently selected from the group consisting of hydrogen, $(C_{1-10})$alkyl, halo$(C_{1-10})$alkyl, hydroxy$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{10}$ and $R_{11}$ are taken together to form Ring C which is selected from a group consisting of monocyclic, bicyclic, saturated, unsaturated, aromatic, carbocyclyl and heterocyclyl, each unsubstituted or substituted with 1-3 substituents independently selected from the group consisting of hydroxy, nitro, halo, cyano, thio, oxy, carbonyloxy, $(C_{1-10})$alkoxy, aryloxy, heteroaryloxy, carbonyl, oxycarbonyl, aminocarbonyl, amino, $(C_{1-10})$alkylamino, sulfonylamino, aminosulfonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl $(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and $R_{12}$ is selected from a group consisting of $(C_{4-12})$aryl, hetero$(C_{1-10})$aryl, $(C_{9-12})$bicycloaryl, hetero$(C_{4-12})$bicycloaryl, $(C_{3-12})$cycloalkyl, and hetero$(C_{2-11})$cycloalkyl, each unsubstituted or substituted with 1-3 substituents independently selected from the group consisting of hydroxy, halo, nitro, cyano, thio, alkylthio, carbonyloxy, $(C_{1-10})$alkoxy, $(C_{1-10})$haloalkoxy, $(C_{4-12})$aryloxy, hetero$(C_{1-10})$aryloxy, carbonyl, oxycarbonyl, aminocarbonyl, alkylaminocarbonyl, amino, amido, $(C_{1-10})$alkylamino, sulfonylamino, aminosulfonyl, imino, alkoxyalkyl, alkoxycarbonylalkyl, aryloxyalkyl, heteroarylalkyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, unsubstituted or substituted; or one of said 1-3 substituents on $R_{12}$ and one of said 1-3 substituents on said Ring C are taken together to form a six or seven membered, saturated, unsaturated, or aromatic ring that is unsubstituted or substituted with 1-4 substituents.

In one variation, when present, $R_{10}$ is selected from the group consisting of hydrogen, $(C_{1-10})$alkyl, halo$(C_{1-10})$alkyl, hydroxy$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, and hetero$(C_{1-10})$aryl$(C_{1-5})$alkyl, each substituted or unsubstituted.

In another variation, when present, $R_{10}$ is selected from the group consisting of hydrogen, halo, unsubstituted or substituted alkyl, and unsubstituted or substituted heteroalkyl.

In still another variation, when present, $R_{10}$ is selected from the group consisting of hydrogen, halo, unsubstituted or substituted alkyl.

In one variation, when present, $R_{11}$ is selected from the group consisting of hydrogen, $(C_{1-10})$alkyl, halo$(C_{1-10})$alkyl, hydroxy$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, and hetero$(C_{1-10})$aryl$(C_{1-5})$alkyl, each substituted or unsubstituted.

In another variation, when present, $R_{11}$ is selected from the group consisting of hydrogen, halo, alkyl, and heteroalkyl.

In still another variation, when present, $R_{11}$ is methyl.

$R_{10}$ and $R_{11}$ are Taken Together to Form a Ring

In one specific variation of $R_3$, where $R_{10}$ and $R_{11}$ are taken together to form Ring C, $R_3$ is of the formula

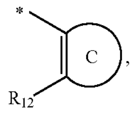

wherein Ring C is selected from the group consisting of $(C_{4-12})$aryl, $(C_{1-11})$heteroaryl, $(C_{3-12})$cycloalkyl, and hetero$(C_{1-11})$cycloalkyl, each of which is unsubstituted or substituted said 1-3 substituents independently selected from the group consisting of hydroxy, nitro, halo, cyano, thio, oxy, carbonyloxy, $(C_{1-10})$alkoxy, aryloxy, heteroaryloxy, carbonyl, oxycarbonyl, aminocarbonyl, amino, $(C_{1-10})$alkylamino, sulfonylamino, aminosulfonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another variation, Ring C is selected from the group consisting of aryl, heterocyclyl, heteroaryl, $(C_{3-7})$cycloalkyl, and $(C_{5-7})$cycloalkenyl, each of which is substituted with 1-3 substituents. In some variations, the aryl, heterocyclyl, heteroaryl, $(C_{3-7})$cycloalkyl, and $(C_{5-7})$cycloalkenyl is selected from the group consisting of pyrrolyl, phenyl, pyridyl, pyrazinyl, pyrimidinyl, pyridazinyl, pyrazolyl, imidazolyl, triazolyl, indolyl, oxadiazole, thiadiazole, furanyl, quinolinyl, isoquinolinyl, isoxazolyl, oxazolyl, thiazolyl, morpholino, piperidinyl, pyrrolidinyl, thienyl, cyclohexyl, cyclopentyl, cyclohexenyl, and cyclopentenyl, each unsubstituted or substituted with 1-3 substituents selected from the group consisting of halo, alkoxy, alkyl, amino, alkylamino, haloalkyl, and haloalkoxy.

In another variation, Ring C is selected from the group consisting of $(C_{4-6})$aryl or $(C_{1-5})$heteroaryl, each unsubstituted or substituted with 1-3 substituents. In one variation, the aryl or heteroaryl is selected from the group consisting of phenyl, pyridinyl, pyrimidinyl, pyrazinyl, indolyl, thiazolyl, and thienyl, each of which is unsubstituted or substituted with 1-3 substituents.

In the above embodiments and variations, the 1-3 substituents on Ring C is, in some variations, independently selected from the group consisting of hydroxy, nitro, halo, cyano, thio, oxy, carbonyloxy, $(C_{1-10})$alkoxy, aryloxy, heteroaryloxy, carbonyl, oxycarbonyl, aminocarbonyl, amino, $(C_{1-10})$alkylamino, sulfonylamino, aminosulfonyl, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted. In some other variations, the 1-3 substituents are each independently selected from the group consisting of substituted or unsubstituted aryl, substituted or unsubstituted heteroaryl, halo, alkyl, haloalkyl, alkoxy, and haloalkoxy. In some other variations, at least one of the 1-3 substituents on Ring C is selected from the group consisting of fluoro, methyl, and methoxy. In other variations, the 1-3 substituents on Ring C are each independently selected from the group consisting of halo. In other variations, the substituents are fluoro. In still other variations, the substituents are methyl. In yet still other variations, the substituents are methoxy.

In one particular variation, $R_3$ is of the formula:

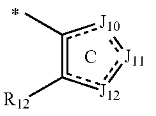

wherein $J_{10}$ is selected from the group consisting of O, S, $NR_{26}$, and $CR_{27}R_{27'}$, $J_{11}$ is selected from the group consisting of O, S, $NR_{28}$, and $CR_{29}R_{29'}$, $J_{12}$ is selected from the group consisting of O, S, $NR_{30}$, and $CR_{31}R_{31'}$, where $R_{26}$, $R_{28}$ and $R_{30}$ are each independently selected from the group consisting of hydrogen, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{26}$, $R_{28}$, and $R_{30}$ are each independently absent when the nitrogen atom to which it is bound forms parts of a double bond, and $R_{27}$, $R_{27'}$, $R_{29}$, $R_{29'}$, $R_{31}$, and $R_{31'}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, (Cl_10) alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{27'}$, $R_{29'}$, $R_{31'}$ are each independently absent when the carbon atom to which it is bound forms parts of a double bond.

In one variation of the above variation of Ring C, $R_{26}$, $R_{28}$ and $R_{30}$, are each individually selected from the group consisting of hydrogen, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, and hetero$(C_{1-10})$aryl$(C_{1-5})$alkyl, each substituted or unsubstituted, or $R_{26}$, $R_{28}$, and $R_{30}$ are each independently absent when the nitrogen to which it is bound forms parts of a double bond; and $R_{27}$, $R_{27'}$, $R_{29}$, $R_{29'}$, $R_{31}$, and $R_{31'}$ are each individually selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, each substituted or unsubstituted, or $R_{27'}$, $R_{29'}$, $R_{31'}$ are each independently absent when the carbon atom to which it is bound forms parts of a double bond.

In yet another variation of the above embodiment of Ring C, $R_{26}$, $R_{28}$ and $R_{30}$, are each individually selected from the group consisting of hydrogen, $(C_{1-10})$alkylamino, $(C_{1-10})$alkyl, halo$(C_{1-10})$alkyl, hydroxy$(C_{1-10})$alkyl, carbonyl$(C_{1-10})$alkyl, and aza$(C_{1-10})$alkyl, each substituted or unsubstituted, or $R_{26}$, $R_{28}$, and $R_{30}$ each is independently absent when the nitrogen atom to which it is bound forms parts of a double bond; and $R_{27}$, $R_{27'}$, $R_{29}$, $R_{29'}$, $R_{31}$, and $R_{31'}$ are each individually selected from the group consisting of hydrogen, halo, nitro, cyano, oxy, hydroxy, carbonyloxy, $(C_{1-10})$alkoxy, carbonyl, aminocarbonyl, amino, $(C_{1-10})$alkylamino, hydroxy$(C_{1-10})$alkyl, aza$(C_{1-10})$alkyl, and $(C_{1-10})$oxaalkyl, each substituted or unsubstituted, or $R_{27'}$, $R_{29'}$, $R_{31'}$ are each independently absent when the carbon atom to which it is bound forms parts of a double bond.

In still another variation, $R_{26}$, $R_{28}$ and $R_{30}$, are each individually selected from the group consisting of hydrogen, $(C_{1-6})$alkylamino, $(C_{1-6})$alkyl, halo$(C_{1-6})$alkyl, hydroxy$(C_{1-6})$alkyl, carbonyl$(C_{1-6})$alkyl, aza$(C_{1-6})$alkyl, each substituted or unsubstituted, or $R_{26}$, $R_{28}$, and $R_{30}$ each is independently absent when the nitrogen atom to which it is bound forms part of a double bond; and $R_{27}$, $R_{27'}$, $R_{29}$, $R_{29'}$, $R_{31}$, and $R_{31'}$ are each individually selected from the group consisting of hydrogen, halo, nitro, cyano, oxy, hydroxy, carbonyloxy, $(C_{1-6})$alkoxy, carbonyl, aminocarbonyl, amino, $(C_{1-10})$alkylamino, hydroxy$(C_{1-10})$alkyl, aza$(C_{1-6})$alkyl, $(C_{1-6})$oxaalkyl, each substituted or unsubstituted, or $R_{27'}$, $R_{29'}$, $R_{31'}$ are each independently absent when the carbon atom to which it is bound forms part of a double bond.

In another particular variation, $R_3$ is of the formula:

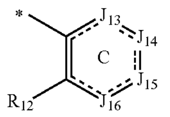

where $J_{13}$ is selected from the group consisting of O, S, $NR_{32}$, and $CR_{33}R_{33'}$, $J_{14}$ is selected from the group consisting of O, S, $NR_{34}$, and $CR_{35}R_{35'}$, $J_{15}$ is selected from the group consisting of O, S, $NR_{36}$, and $CR_{32}R_{37'}$, $J_{16}$ is selected from the group consisting of O, S, $NR_{38}$, and $CR_{39}R_{39'}$, where $R_{32}$, $R_{34}$, $R_{36}$, and $R_{38}$ are each independently selected from the group consisting of hydrogen, oxy, hydroxy, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl, and hetero $(C_{4-12})$bicycloaryl, each substituted or unsubstituted, or $R_{32}$, $R_{34}$, $R_{36}$, and $R_{38}$ are each independently absent when the nitrogen atom to which it is bound forms parts of a double bond, and $R_{33}$, $R_{33'}$, $R_{35}$, $R_{35'}$, $R_{37}$, $R_{37'}$, $R_{38}$, and $R_{38}$, are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, $(C_{3-12})$cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$ cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$ bicycloaryl, and hetero$(C_{4-12})$bicycloaryl, each substituted or unsubstituted, or $R_{33'}$, $R_{35'}$, $R_{37'}$, and $R_{39'}$ are each independently absent when the carbon atom to which it is bound forms parts of a double bond, and $R_{12}$ is as previously defined.

In one variation of the above embodiment of Ring C, $R_{32}$, $R_{34}$, $R_{36}$, and $R_{38}$ are each independently selected from the group consisting of hydrogen, oxy, hydroxy, $(C_{1-10})$alkylamino, $(C_{1-10})$alkyl, hydroxy$(C_{1-10})$alkyl, aza$(C_{1-10})$alkyl, $(C_{3-12})$cycloalkyl$(C_{1-5})$alkyl, hetero$(C_{3-12})$cycloalkyl$(C_{1-10})$ alkyl, aryl$(C_{1-10})$alkyl, hetero$(C_{1-10})$aryl$(C_{1-5})$alkyl, each substituted or unsubstituted, or $R_{32}$, $R_{34}$, $R_{36}$, and $R_{38}$ are each independently absent when the nitrogen atom to which it is bound forms parts of a double bond, and $R_{33}$, $R_{33'}$, $R_{35}$, $R_{35'}$, $R_{37}$, $R_{37'}$, $R_{39}$, and $R_{39'}$ are each independently selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, oxycarbonyl, aminocarbonyl, amino, $(C_{1-10})$alkylamino, $(C_{1-10})$alkyl, halo$(C_{1-10})$alkyl, hydroxy $(C_{1-10})$alkyl, carbonyl$(C_{1-10})$alkyl, hetero$(C_{1-10})$alkyl, each substituted or unsubstituted, or $R_{33'}$, $R_{35'}$, $R_{37'}$, and $R_{39'}$ are each independently absent when the carbon atom to which it is bound forms parts of a double bond.

In still another variation, $R_{32}$, $R_{34}$, $R_{36}$, and $R_{38}$ are each independently selected from the group consisting of hydrogen, oxy, hydroxy, $(C_{1-10})$alkylamino, $(C_{1-10})$alkyl, hydroxy $(C_{1-10})$alkyl, aza$(C_{1-10})$alkyl, each substituted or unsubstituted, or $R_{32}$, $R_{34}$, $R_{36}$, and $R_{38}$ are each independently absent when the nitrogen atom to which it is bound forms parts of a double bond, and $R_{33}$, $R_{33'}$, $R_{35}$, $R_{35'}$, $R_{37}$, $R_{37'}$, $R_{39}$, and $R_{39'}$ are each independently selected from the group consisting of hydrogen, halo, nitro, cyano, oxy, hydroxy, carbonyloxy, $(C_{1-10})$alkoxy, aminocarbonyl, amino, $(C_{1-10})$alkylamino, $(C_{1-10})$alkyl, hydroxy$(C_{1-10})$alkyl, carbonyl$(C_{1-10})$alkyl, aza $(C_{1-10})$alkyl, $(C_{1-10})$oxaalkyl, each substituted or unsubstituted, or $R_{33'}$, $R_{35'}$, $R_{37'}$, and $R_{39'}$ are each independently absent when the carbon atom to which it is bound forms parts of a double bond.

In still another variation, $R_3$ is selected from the group consisting of

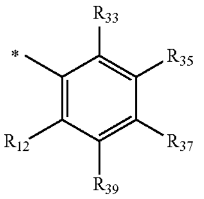

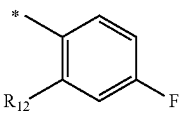

-continued

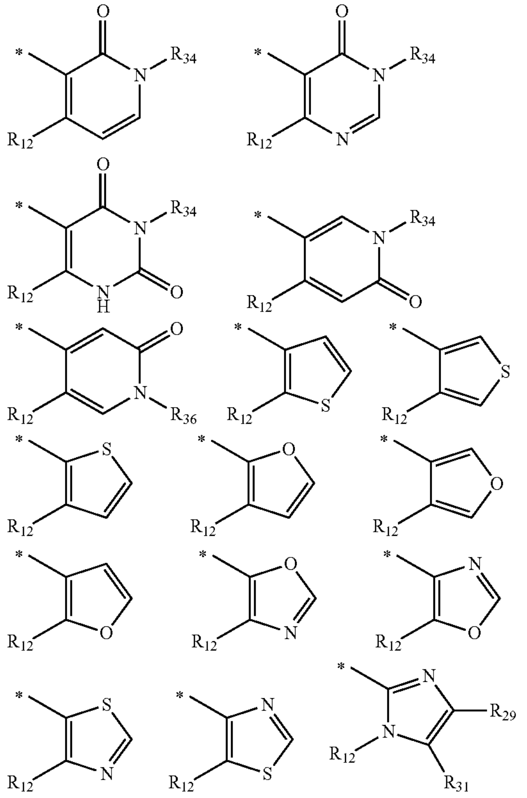

where $R_{29}$ and $R_{31}$ are each independently selected from the group consisting of hydrogen, halo, cyano, hydroxy, carbonyloxy, $(C_{1-10})$alkoxy, $(C_{4-12})$aryloxy, hetero$(C_{1-10})$aryloxy, aminocarbonyl, amino, $(C_{1-10})$alkylamino, sulfonamido, $(C_{1-10})$alkyl, halo$(C_{1-10})$alkyl, hydroxy$(C_{1-10})$alkyl, sulfonyl $(C_{1-10})$alkyl, sulfinyl$(C_{1-10})$alkyl, hetero$(C_{1-10})$alkyl, each substituted or unsubstituted;

$R_{33}$, $R_{35}$, $R_{37}$, and $R_{39}$ are each independently selected from the group consisting of hydrogen, halo, $(C_{1-10})$alkoxy, $(C_{1-10})$alkyl; and $R_{34}$ and $R_{36}$ are each independently selected from selected from the group consisting of alkyl, aza$(C_{1-10})$alkyl, and hydroxyl$(C_{1-10})$alkyl.

In still another variation, wherein $R_3$ is of the formula

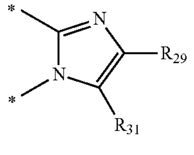

where $R_{29}$ and $R_{31}$ are each independently selected from the group consisting of hydrogen, halogen, cyano, nitro, $(C_{1-6})$ alkyl, $(C_{2-6})$alkenyl, $(C_{2-6})$alkynyl, amino or substituted amino, aryl, heteroaryl, $(C_{3-7})$cycloalkyl, $(C_{5-7})$cycloalkenyl, $(C_{3-7})$heterocycloalkyl, —$OR_{40}$, —$SR_{40}$, —$C(O)R_{40}$, —$C(O)OR_{40}$, —$C(O)N(R_{40})_2$, —$S(O)R_{40}$, —$S(O)_2R_{40}$, —$S(O)_2N(R_{40})_2$, —$OC(O)R_{40}$, —$NR_{40}C(O)R_{40}$, and —$N(R_{40})S(O)_2R_{40}$;

where $R_{40}$ is selected from the group consisting of methyl, ethyl, isopropyl, cyclopentyl, cyclohexyl, unsubstituted or substituted phenyl, unsubstituted or substituted thiazolyl, unsubstituted or substituted pyridyl, unsubstituted or substituted pyrazinyl, and unsubstituted or substituted pyrimindinyl, 2-aminoethyl, 2-piperidinylethyl, 2-piperazinylethyl, 2-morpholinylethyl, and 2-(N-methylpiperazinyl)ethyl.

In one variation of the immediately above variation, $R_{40}$ is selected from the group consisting of methyl, ethyl, isopropyl, cyclopentyl, and 2-aminoethyl. In another variation, $R_{40}$ is methyl. In another variation, $R_{40}$ is ethyl. In another variation, $R_{40}$ is isopropyl. In another variation, $R_{40}$ is cylcopentyl. In another variation, $R_{40}$ is 2-aminoethyl.

In still another variation, $R_3$ is of the formula

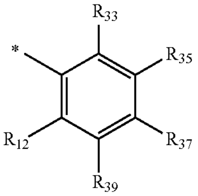

where $R_{33}$, $R_{35}$, $R_{37}$, and $R_{39}$ are each independently selected from the group consisting of hydrogen, alkyl, alkoxy, halo, unsubstituted or substituted aryl, and substituted heteroaryl.

In still another variation, $R_3$ is selected is selected from the group consisting of

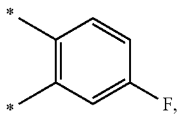, 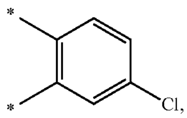, and

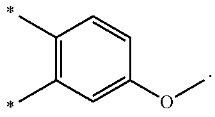.

$R_{12}$

Of the above embodiments and variations of the present invention, in some variations, $R_{12}$ is selected from the group consisting of $(C_{4-12})$aryl, hetero$(C_{1-10})$aryl, $(C_{9-12})$bicycloaryl, hetero$(C_{4-12})$bicycloaryl, $(C_{3-12})$cycloalkyl, and hetero$(C_{2-11})$cycloalkyl, each unsubstituted or substituted with 1-3 substituents. In other variations $R_{12}$ is selected from the group consisting of furanyl, thienyl, pyrrolyl, oxazolyl, thiazolyl, imidazolyl, pyrazolyl, triazolyl, isoxazolyl, oxadiazolyl, thiadiazolyl, phenyl, pyridyl, pyrazinyl, pyrimidinyl, pyridazinyl, triazinyl, indolyl, isoindolyl, indolizinyl, benzimidazolyl, purinyl, naphthalenyl, quinolinyl, isoquinolinyl, cinnolinyl, phthalazinlyl, quinazolinyl, quinoxalinyl, naphthyridinyl, pteridinyl, pyridone, and pyrimidone, each of which is unsubstituted or substituted with 1-3 substituents.

In some variations of the above embodiments and variations, the 1-3 substituents of $R_{12}$ are each independently selected from the group consisting of halo, nitro, cyano, thio, oxy, oxo, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, amido, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or further substituted.

In other variations, the 1-3 substituents on $R_{12}$ are each independently selected from the group consisting of halo, cyano, oxy, oxo, $(C_{1-6})$alkoxy, $(C_{4-12})$aryloxy, hetero$(C_{1-10})$aryloxy, carbonyl, amino, amido, sulfonyl, $(C_{1-6})$alkyl, sulfonyl$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, and hetero$(C_{1-10})$aryl, each unsubstituted or substituted.

In still other variations, the 1-3 substituents on $R_{12}$ are each independently selected from the group consisting of halo, cyano, $(C_{1-6})$alkyl, $(C_{1-6})$alkoxy, amino, acetamido, carbonyl, aryl, heteroaryl, cycloalkyl, and heterocycloalkyl, each unsubstituted or substituted. In still other variations, the 1-3 substituents on $R_{12}$ are each independently selected from the group consisting of fluoro, difluoro, chloro, bromo, cyano, amino, methylamino, ethylamino dimethylamino, hydroxyethylamino, methyl, ethyl, ethynyl, trifluoromethyl, aminomethyl, methoxy, ethoxy, dimethoxy, 2,2,2-trifluoroethoxy, trifluoromethoxy, phenoxy, acetamido, ethoxyacetamido, acetyl, substituted methoxycarbonyl, ethoxyaminocarbonyl, methanesulfonylamino, 4-trifluoromethoxyphenoxymethyl, 3-trifluoromethoxyphenoxymethyl, and isothiazolidine 1,1 dioxide. In still other variations, the 1-3 substituents on $R_{12}$ are each independently selected from the group consisting of fluoro, chloro, methoxy, ethoxy, and amino In still another variation, the 1-3 substituents on $R_{12}$ are each independently selected from the group consisting of fluoro, chloromethoxy, ethoxy, and amino In still another variation, $R_{12}$ is selected from the group consisting of (2-hydroxy-ethylamino)-pyrazin-2-yl, 1H-pyrazol-4-yl, 1-methyl-1H-pyrazol-4-yl, 1-methyl-1H-pyrazol-4-yl, 2-(5-methyl-pyridin-2-yl)-phenyl, 2,3-difluoro-phenyl, 2,3-dimethoxy-phenyl, 2,4-difluoro-phenyl, 2,4-dimethoxy-phenyl, 2,4-dimethoxy-pyrimidin-5-yl, 2,5-difluoro-phenyl, 2,6-difluoro-phenyl, 2,6-dimethyl-pyridin-3-yl, 2-acetamidophenyl, 2-aminocarbonylphenyl, 2-amino-pyrimidin-5-yl, 2-chloro-4-methoxy-pyrimidin-5-yl, 2-chloro-5-fluoro-pyridin-3-yl, 2-chloro-phenyl, 2-chloro-pyridin-3-yl, 2-chloro-pyridin-4-yl, 2-difluoro-3-methoxyphenyl, 2-ethyl-phenyl, 2-ethoxy-thiazol-4-yl, 2-fluoro-3-methoxy-phenyl, 2-fluoro-3-methylphenyl, 2-fluoro-4-methyl-phenyl, 2-fluoro-5-methoxy-phenyl, 2-fluoro-5-methylphenyl, 2-fluorophenyl, 2-fluoro-pyridin-3-yl, 2-hydroxymethyl-3-methoxyphenyl, 2-hydroxymethylphenyl, 2-isoquinolin-4-yl, 2-methoxy-5-trifluoromethyl-phenyl, 2-methoxy-phenyl, 2-methoxy-pyridin-3-yl, 2-methoxy-pyrimidin-4-yl, 2-methoxy-thiazol-4-yl, 2-methyl-phenyl, 2-methyl-pyridin-3-yl, 2-oxo-1,2-dihydro-pyridin-3-yl, 2-phenoxyphenyl, 2-pyridin-3-yl, 2-pyrimidin-5-yl, 2-trifluoromethoxyphenyl, 2-trifluoromethoxy-phenyl, 3,4-dimethoxy-phenyl, 3,5-dimethyl-isoxazol-4-yl, 3,6-dimethyl-pyrazin-2-yl, 3-acetamidophenyl, 3-aminocarbonylphenyl, 3-bromo-phenyl, 3-chloro-pyrazin-2-yl, 3-cyanophenyl, 3-dimethylaminophenyl, 3-ethoxy-phenyl, 3-ethyl-4-methyl-phenyl, 3-ethynyl-phenyl, 3-fluoro-6- methoxy-pyridin-2-yl, 3-fluorophenyl, 3-fluoro-pyrazin-2-yl, 3-methanesulfonamidophenyl, 3-methoxycarbonylphenyl, 3-methoxyphenyl, 3-methoxy-pyrazin-2-yl, 3-methyl-3H-imidazo[4,5-b]pyrazin-5-yl, 3-methylphenyl, 3-methyl-pyridin-2-yl, 3-trifluoromethoxyphenyl, 3-trifluoromethylphenyl, 4,5-dimethoxy-pyrimidin-2-yl, 4-amino-5-fluoro-pyrimidin-2-yl, 4-chloro-2,5-dimethoxy-phenyl, 4-chloro-2-fluoro-phenyl, 4-chloro-2-methoxy-5-methyl-phenyl, 4-chloro-pyridin-3-yl, 4-difluoro-2-methyl-phenyl, 4-ethoxy-5-fluoro-pyrimidin-2-yl, 4-ethoxy-pyrimidin-2-yl, 4-ethoxy-pyrimidin-5-yl, 4-ethyl-1H-pyrazol-3-yl, 4-fluoro-2-methoxy-phenyl, 4-fluoro-2-methyl-phenyl, 4-fluorophenyl, 4-methoxy-5-methyl-pyrimidin-2-yl, 4-methoxy-pyridin-3-yl, 4-methoxy-pyrimidin-2-yl, 4-methoxy-pyrimidin-5-yl, 4-methyl-phenyl, 4-methyl-pyridin-2-yl, 4-methyl-pyridin-3-yl, 4-pyrrolidin-1-yl-pyrimidin-2-yl, 5,6-dimethoxy-pyrazin-2-yl, 5-acetyl-thiophen-2-yl, 5-amino-6-ethoxy-pyrazin-2-yl, 5-amino-6-methoxy-3-methyl-pyrazin-2-yl, 5-amino-6-methoxy-pyridin-2-yl, 5-chloro-4-methoxy-pyrimidin-2-yl, 5-chloro-6-methoxy-pyrazin-2-yl, 5-dimethylamino-6-methoxy-pyrazin-2-yl, 5-fluoro-2-methoxyphenyl, 5-fluoro-4-methoxy-pyrimidin-2-yl, 5-fluoro-6-methoxy-pyrazin-2-yl, 5-fluoro-pyridin-2-yl, 5-methoxy-pyridin-3-yl, 5-methoxy-thiophen-2-yl, 5-trifluoromethyl-pyrimidin-2-yl, 6-acetyl-pyridin-2-yl, 6-chloro-pyrazin-2-yl, 6-ethoxy-pyrazin-2-yl, 6-ethoxy-pyridin-2-yl, 6-fluoro-pyridin-2-yl, 6-fluoro-pyridin-3-yl, 6-hydroxy-pyridin-2-yl, 6-methoxy-5-methylamino-pyrazin-2-yl, 6-methoxy-5-methyl-pyrazin-2-yl, 6-methoxy-pyrazin-2-yl, 6-methoxy-pyridin-2-yl, 6-methoxy-pyridin-3-yl, 6-methylamino-pyrazin-2-yl, 6-methyl-pyridin-2-yl, 5-amino-6-(2,2,2-trifluoroethoxy)pyrazin-2-yl, and 6-trifluoromethyl-pyridin-2-yl.

In other variations of the above embodiments and variations of the invention, $R_{12}$, when present, is a five membered aryl or heteroaryl of the formula

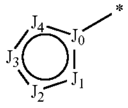

wherein $J_0$ is selected from the group consisting of N and C;

$J_1$ is selected from the group consisting of O, S, N, $NR_{13}$ and $CR_{14}$;

$J_2$ is selected from the group consisting of O, S, N, $NR_{15}$ and $CR_{16}$;

$J_3$ is selected from the group consisting of O, S, N, $NR_{17}$ and $CR_{18}$;

$J_4$ is selected from the group consisting of O, S, N, $NR_{19}$ and $CR_{20}$;

where $R_{13}$, $R_{15}$, $R_{17}$, and $R_{19}$ are each individually selected from the group consisting of hydrogen, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_{14}$, $R_{16}$, $R_{18}$, and $R_{20}$ are each individually selected from the group consisting of hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted; and one of $R_{13}$, $R_{14}$, $R_{19}$ and $R_{20}$ may be taken together with $R_u$ to form a 6 or 7 membered, saturated, unsaturated or aromatic ring, each unsubstituted or further substituted with 1-3 substitutents, and one of $R_{13}$, $R_{14}$, $R_{19}$ and $R_{20}$ may be taken together with a substituent on the ring formed by taking $R_{10}$ and $R_{11}$ together to form a 6 or 7 membered, saturated, unsaturated or aromatic ring, each unsubstituted or further substituted with 1-3 substituents.

In another variation, $R_{12}$, when present, is a six membered aryl or heteroaryl of the

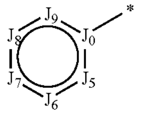

wherein $J_0$ is selected from the group consisting of N and C;

$J_5$ is selected from the group consisting of $NR_{21'}$, $CR_{21}$ and C(O);

$J_6$ is selected from the group consisting of $NR_{22'}$, $CR_{22}$ and C(O);

$J_7$ is selected from the group consisting of $NR_{23'}$, $CR_{23}$ and C(O);

$J_8$ is selected from the group consisting of $NR_{24'}$, $CR_{24}$ and C(O);

$J_9$ is selected from the group consisting of $NR_{25'}$, $CR_{25}$ and C(O);

where $R_{21}$, $R_{21'}$, $R_{22}$, $R_{22'}$, $R_{23}$, $R_{23'}$, $R_{24}$, $R_{24'}$, $R_{25}$ and $R_{25'}$ are each individually selected from the group consisting of hydrogen, halo, nitro, cyano, thio, alkylthio, hydroxy, oxy, $(C_{1-10})$alkoxy, $(C_{1-10})$haloalkoxy, aryloxy, heteroaryloxy, carbonyloxy, carbonyl, alkoxycarbonyl, alkoxyaminocarbonyl, alkylaminocarbonyl, amino, $(C_{1-10})$alkylamino, hydroxy$(C_{1-10})$alkylamino, $(C_{1-10})$alkylcarbonylamino, sulfonylamino, alkylsulfonylamino, arylsulfonylamino, sulfonyl, aminosulfonyl, sulfinyl, $(C_{1-10})$alkyl, halo$(C_{1-10})$alkyl, hydroxy$(C_{1-10})$alkyl, alkoxyalkyl, aryloxyalkyl, carbonyl$(C_{1-10})$alkyl, alkoxycarbonylalkyl, aryloxycarbonylalkyl, thiocarbonyl$(C_{1-10})$alkyl, sulfonyl$(C_{1-10})$alkyl, cycloalkylsulfonylalkyl, sulfinyl$(C_{1-10})$alkyl, hetero$(C_{1-10})$alkyl, alkoxycarbonylalkyl, aryloxyalkyl, heteroaryloxyalkyl, $(C_{3-12})$cycloalkyl$(C_{1-5})$alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$ alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted with 1-4 substituents, and $R_{21'}$, $R_{22'}$, $R_{23'}$, $R_{24'}$, and $R_{25'}$ may be individually absent when the nitrogen atom to which it is bonded forms part of a double bond; and one of $R_{21}$ and $R_{25}$ may be taken together with $R_{11}$ to form a 6 or 7 membered, saturated, unsaturated or aromatic ring, each unsubstituted or further substituted with 1-3 substituents; and one of $R_{21}$ and $R_{25}$ may be taken together with a substituent on the ring formed by taking $R_{10}$ and $R_{11}$ together to form a 6 or 7 membered, saturated, unsaturated or aromatic ring, each unsubstituted or further substituted with 1-3 substituents.

In one variation of the immediately above embodiments and variations, where $R_{12}$, when present, is a six membered aryl or heteroaryl of the formula

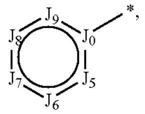

$J_0$ is selected from the group consisting of N and C; $J_5$ is N or $CR_{21}$ where $R_{21}$ is hydrogen or fluoro; $J_6$ is N or $CR_{22}$ where $R_{22}$ is selected from the group consisting of hydrogen, hydroxy, fluoro, methyl, ethyl, methoxy, and ethoxy; $J_7$ is N or $CR_{23}$ where $R_{23}$ is hydrogen or fluoro; $J_8$ is N or $CR_{24}$ where $R_{24}$ is hydrogen or fluoro; and $J_9$ is N or $CR_{25}$ where $R_{25}$ is hydrogen or fluoro. In another variation, $J_0$ is selected from the group consisting of N and C; $J_5$ is N; $J_6$ is N or $C(OCH_3)$; $J_7$ is CH; $J_8$ is CH; and $J_9$ is N or CH.

In yet another variation, $R_{12}$ is selected from the group consisting of:

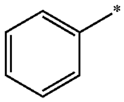
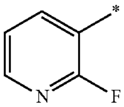
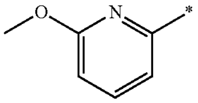
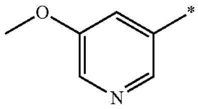
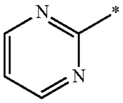
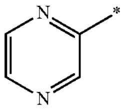
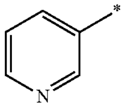
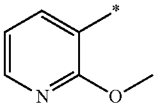
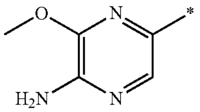
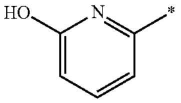
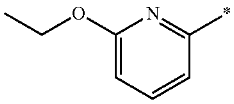
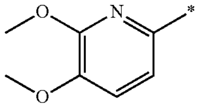
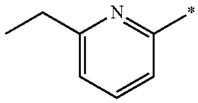

-continued

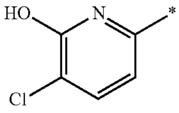
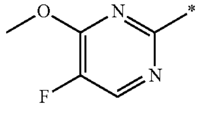
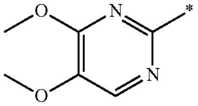
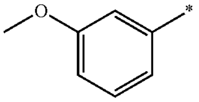
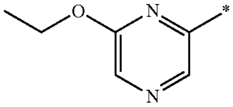
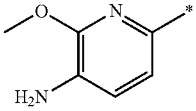
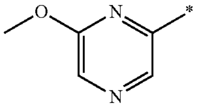
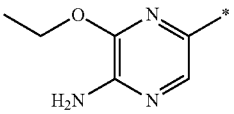
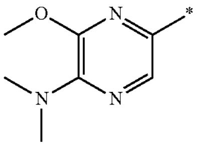
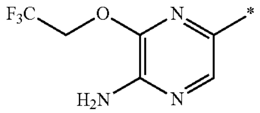
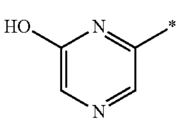
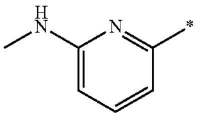
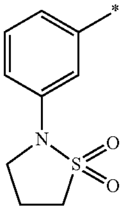
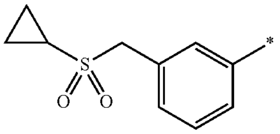
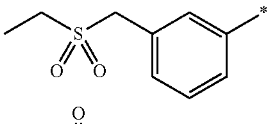
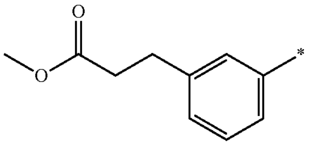
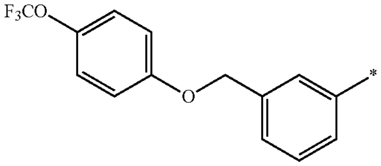
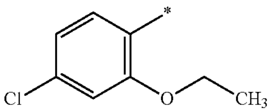
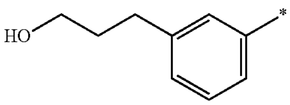
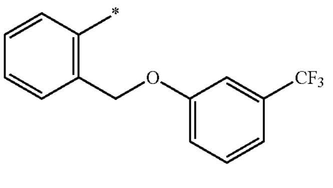

-continued
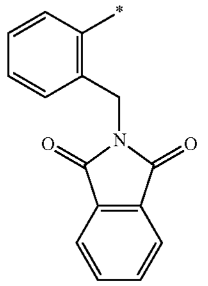
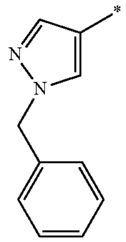
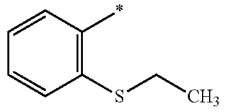
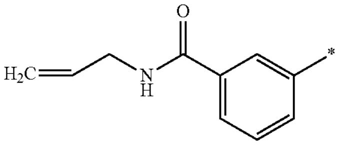
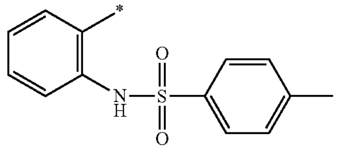
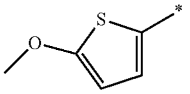
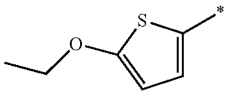
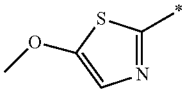
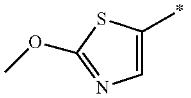
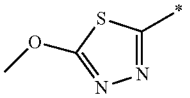
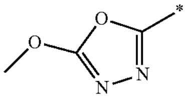
In yet other variations, $R_{12}$ is selected from the group consisting of:
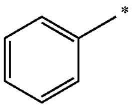
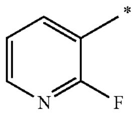
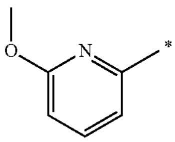
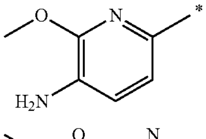
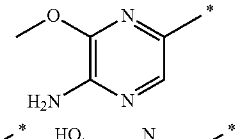
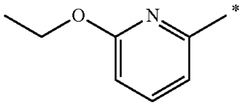
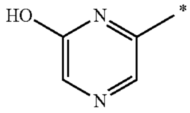
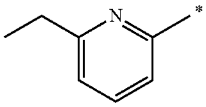
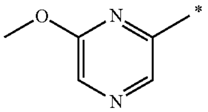
In still other variations, $R_{12}$ is of the formula
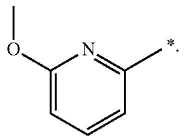
In another variation, when present, $R_3$ is selected from the group consisting of:
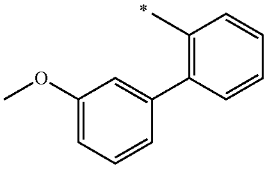
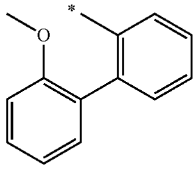
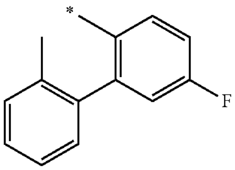
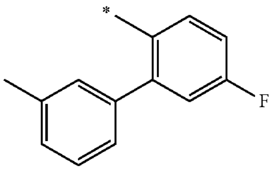
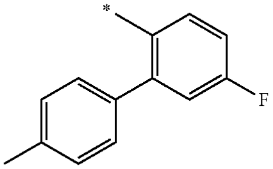
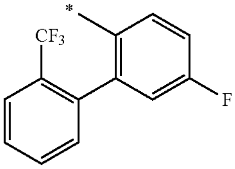
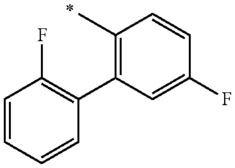
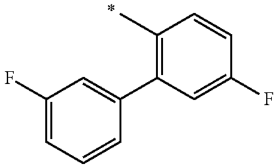
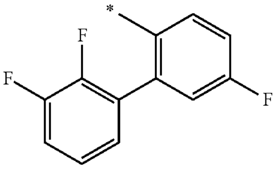
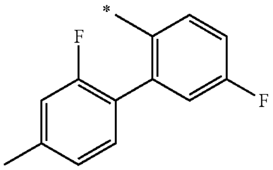
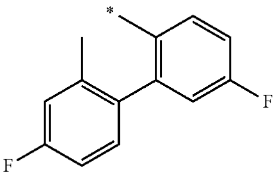
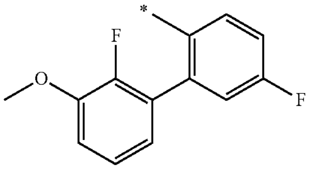

-continued
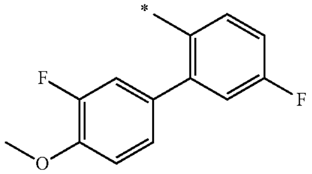
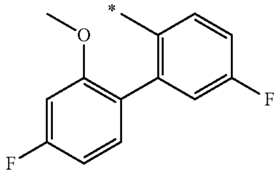
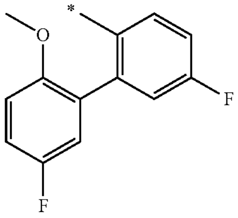
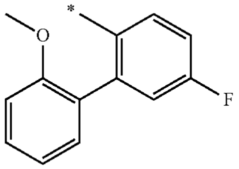
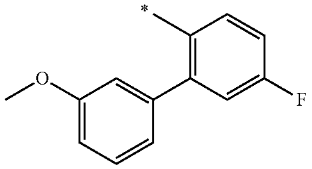
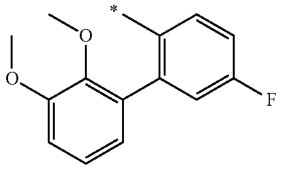
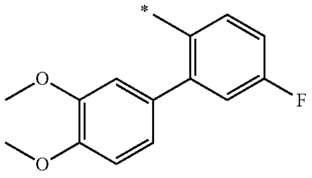
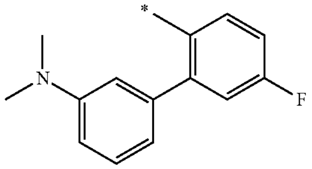
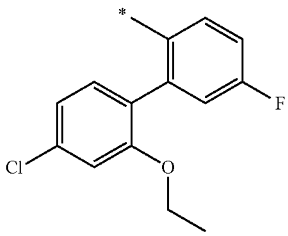
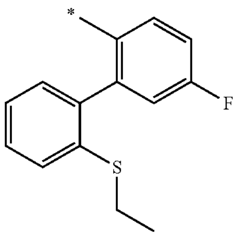
-continued
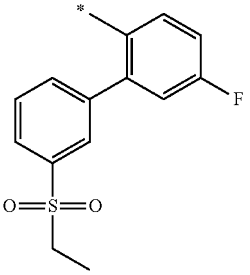
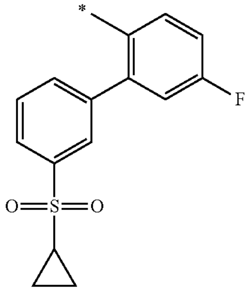
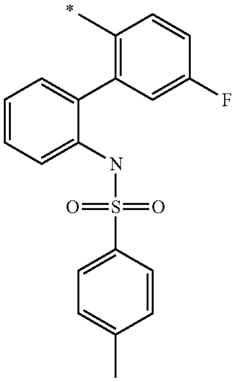
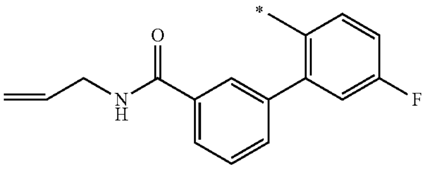
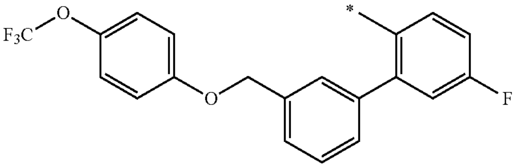
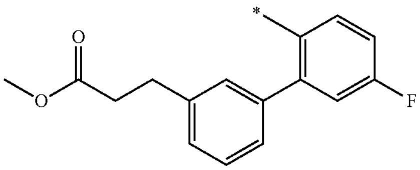
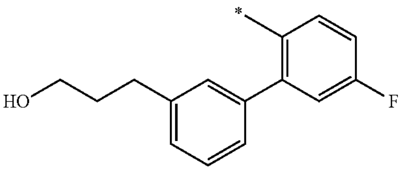
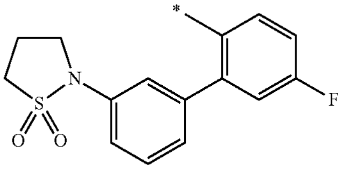

-continued
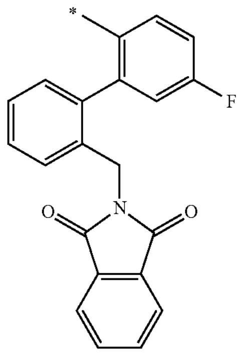 [SMILES: Cc1ccc(F)cc1-c1ccccc1CN1C(=O)c2ccccc2C1=O]
In still another variation, when present, $R_3$ is selected from the group consisting of:
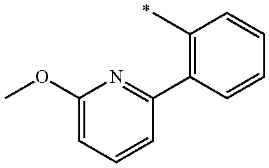
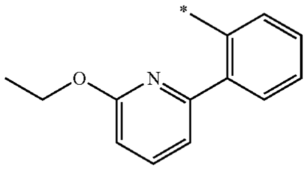
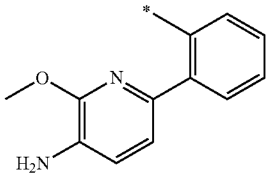
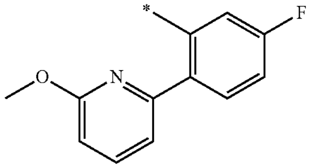
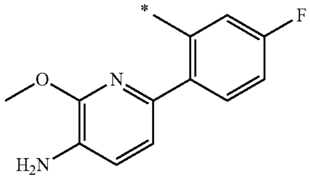
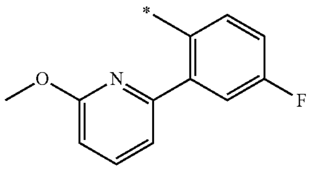
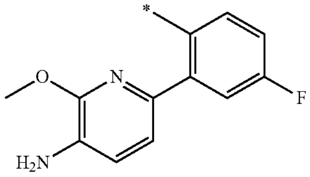
-continued
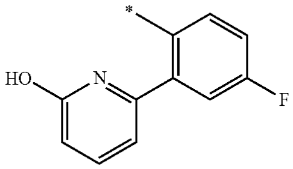
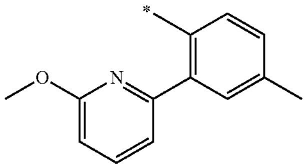
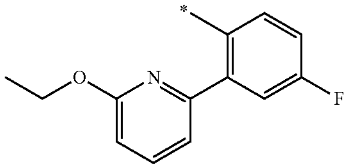
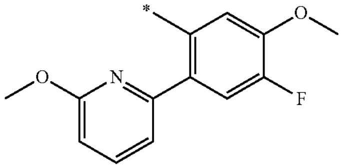
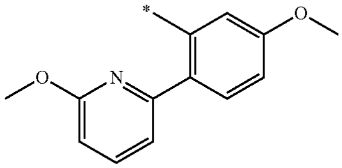
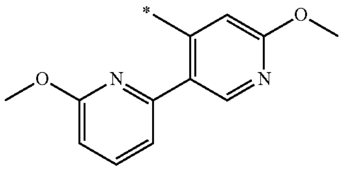
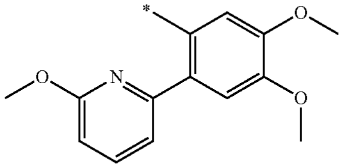
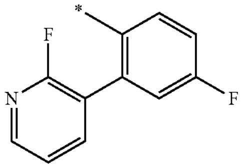
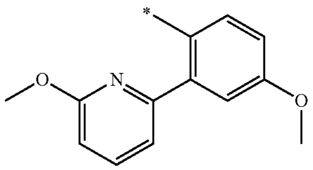
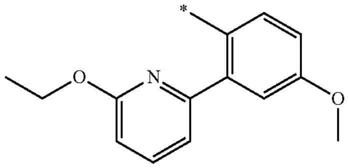

-continued
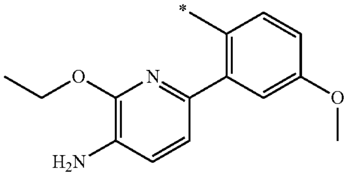
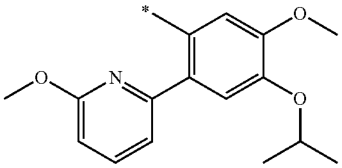
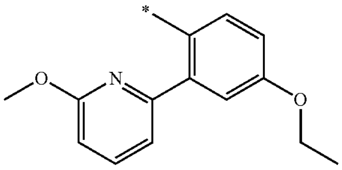
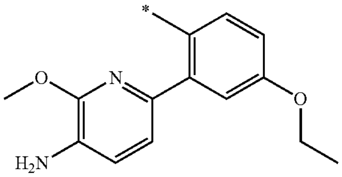
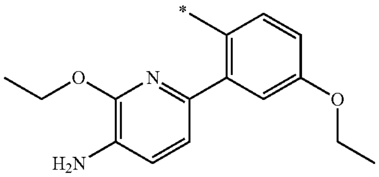
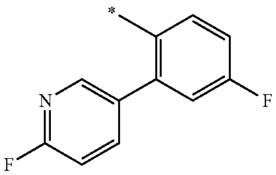
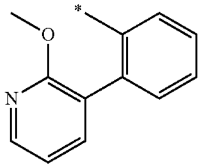
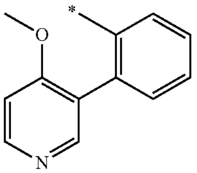
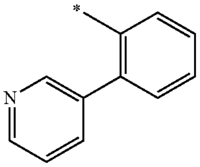
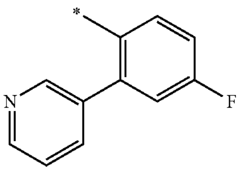
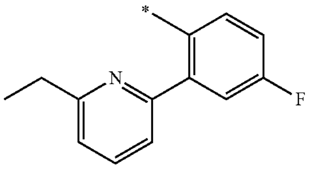
-continued
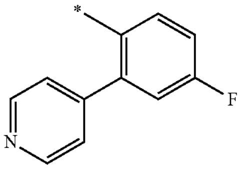
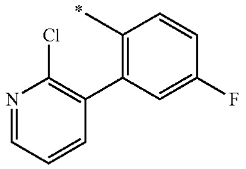
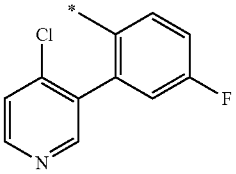
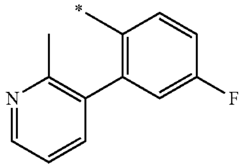
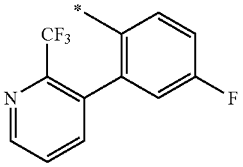
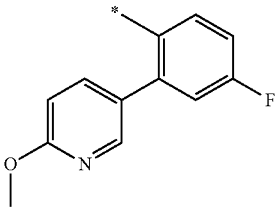
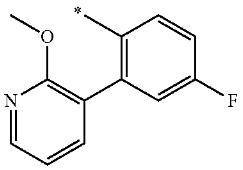
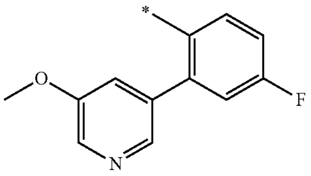
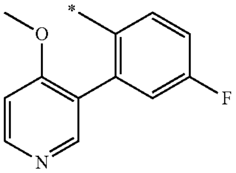
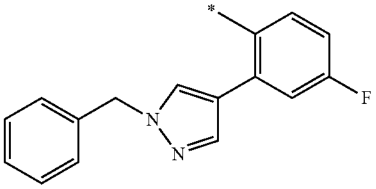
In another variation, $R_3$, when present, is selected from the group consisting of:
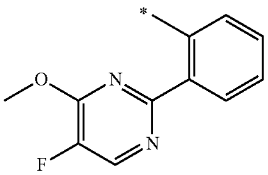

-continued
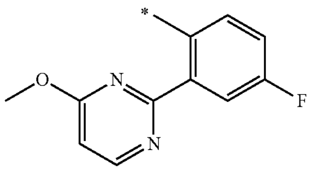
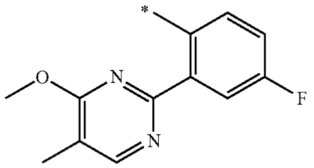
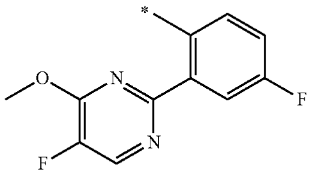
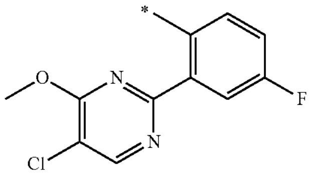
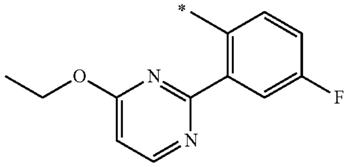
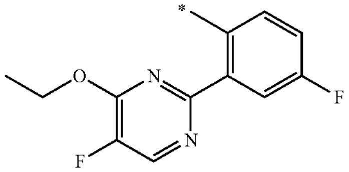
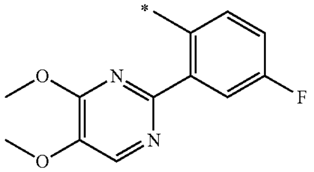
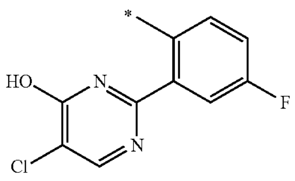
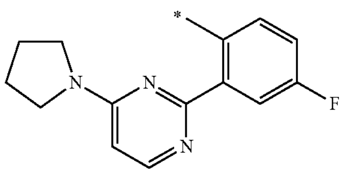 [SMILES: Cc1ccc(F)cc1-c1nccc(N2CCCC2)n1]
In another variation, $R_3$, when present, is selected from the group consisting of:
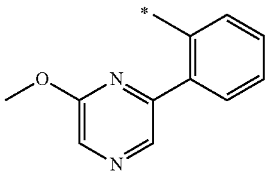
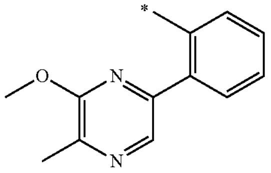
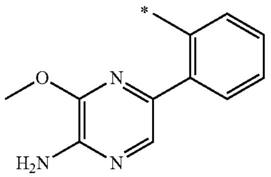
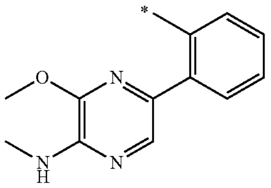
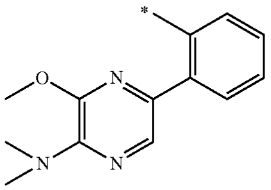
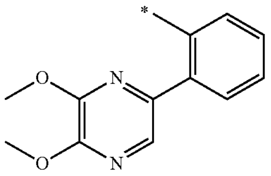
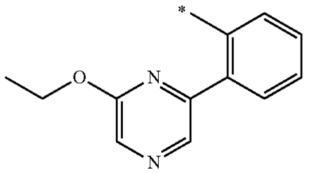
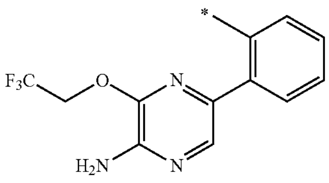
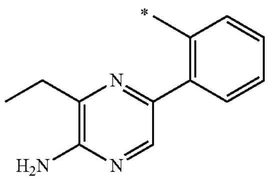

-continued
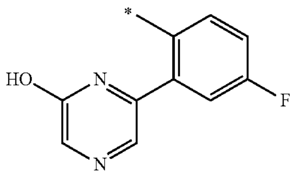
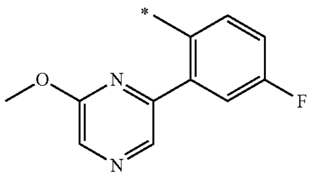
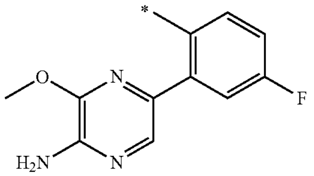
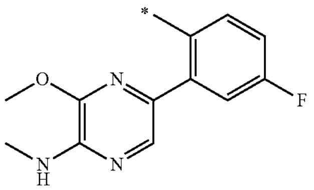
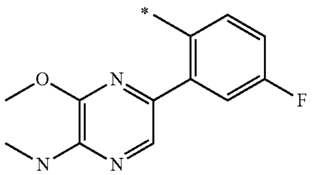
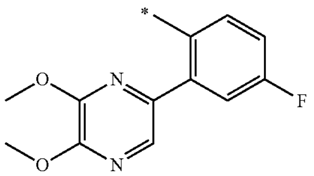
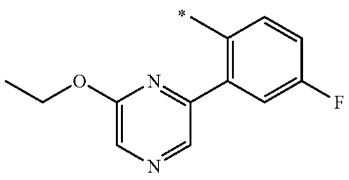
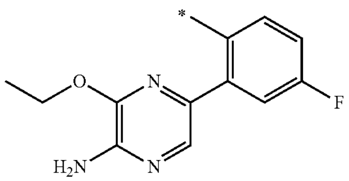
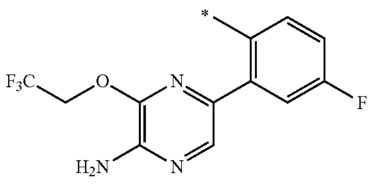
-continued
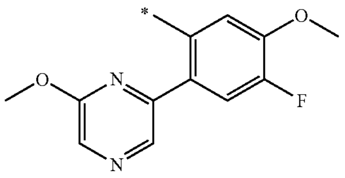
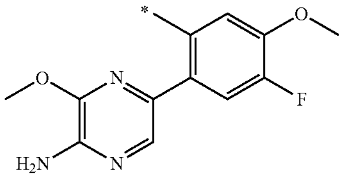
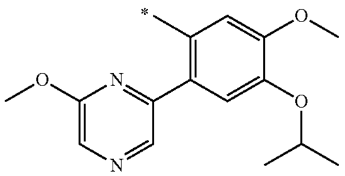
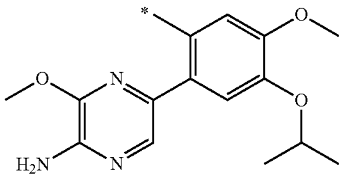
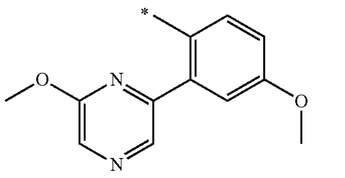
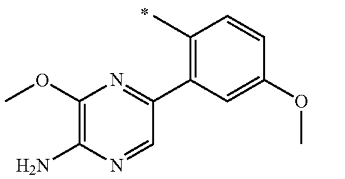
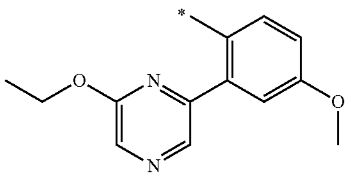
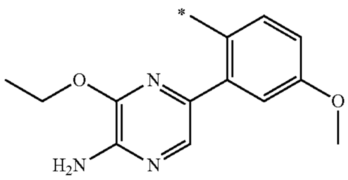
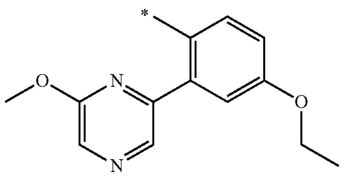

-continued
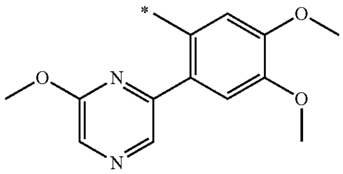
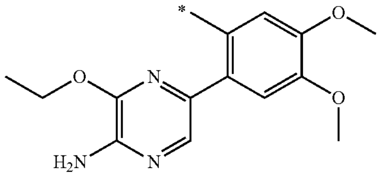
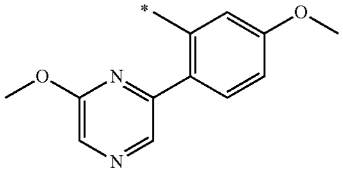
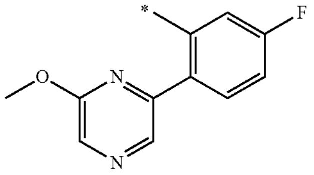
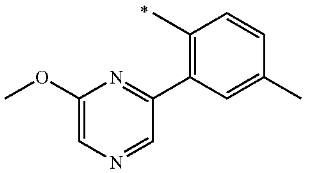
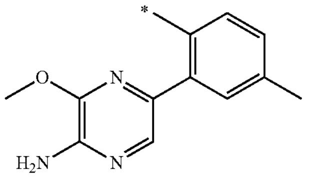
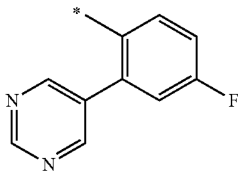
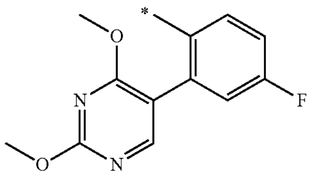
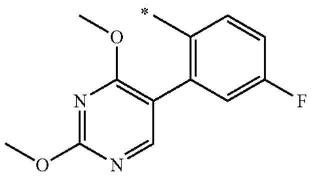
-continued
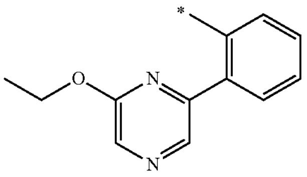
In still another variation, $R_3$, when present, is selected from the group consisting of:
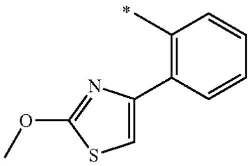
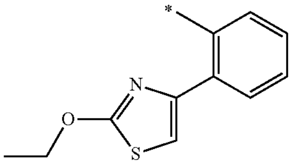
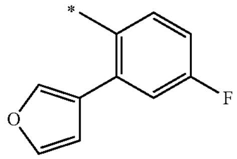
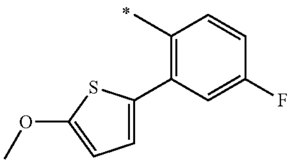
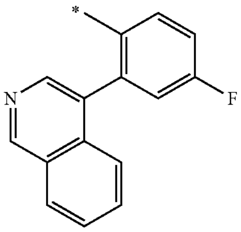
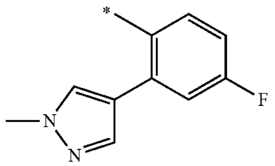
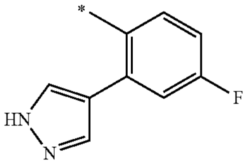
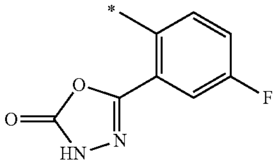
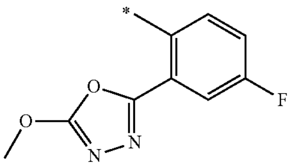
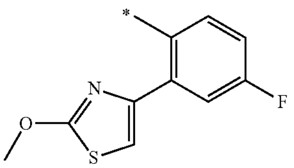
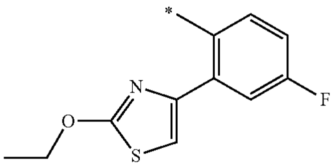

-continued
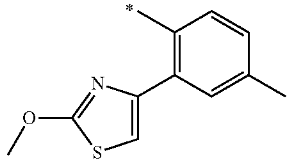
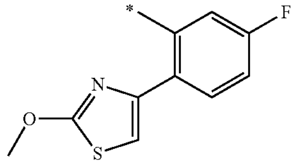
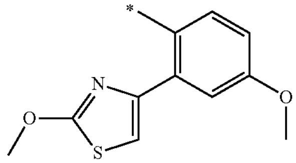
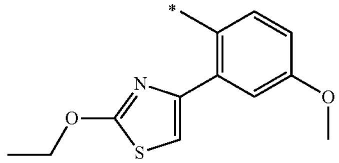
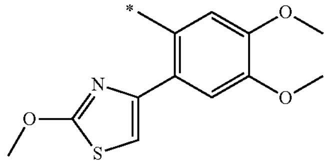
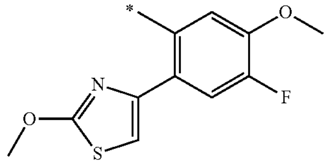
In another variation, $R_3$, when present, is selected from the group consisting of:
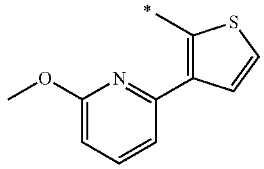
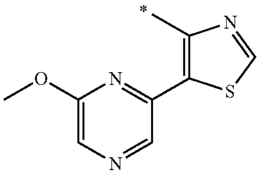
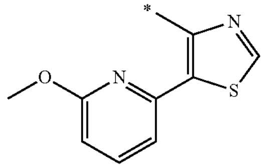
In still another variation, $R_3$, when present, is selected from the group consisting of:
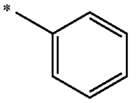
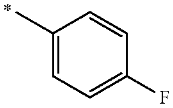
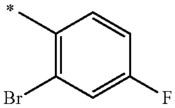
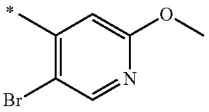
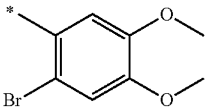
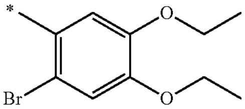
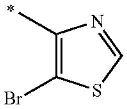
In still another variation, $R_3$, when present, is selected from the group consisting of:
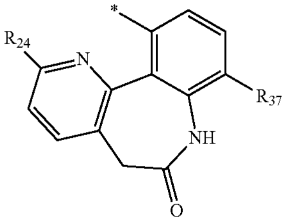
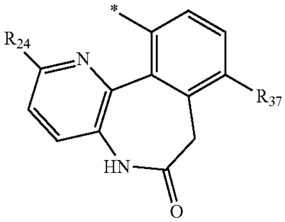
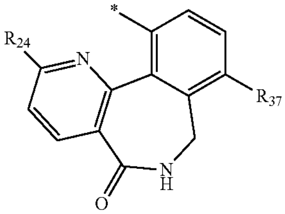
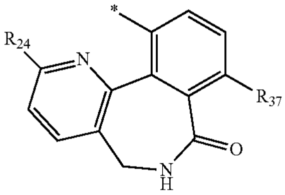
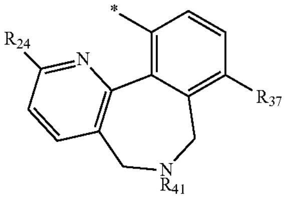

-continued

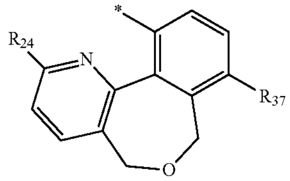

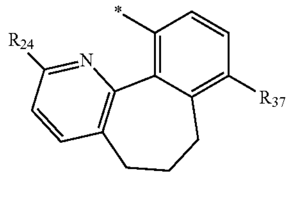

where $R_{24}$ is selected from the group consisting of methoxy and ethoxy;

$R_{37}$ is selected from the group consisting of halo, alkoxy and alkyl, each unsubstituted or substituted; and $R_{41}$ is selected from the group consisting of hydrogen, $(C_{1-6})$oxaalkyl and $(C_{1-6})$alkyl.

In still another variation, $R_3$, when present, is selected from the group consisting of

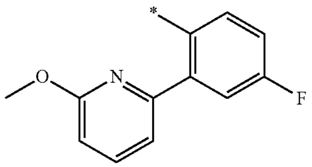 [SMILES: *c1ccc(F)cc1-c1cccc(OC)n1]

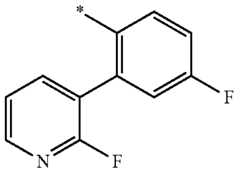

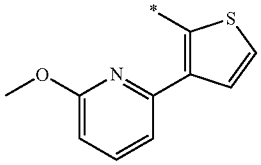

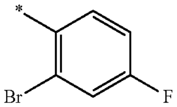

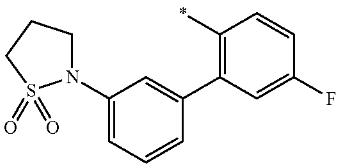

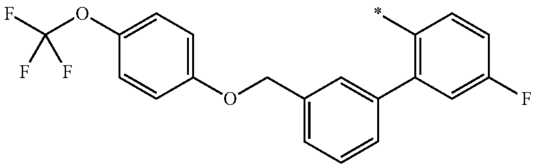

In yet still another variation, $R_3$, when present, is

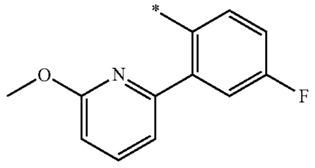

Particular examples of compounds according to the present invention include, but are not limited to:

(E)-2-amino-7-(4-fluoro-2-(2-fluoropyridin-3-yl)phenyl)-4-methyl-7,8-dihydroquinazolin-5(6H)-one O-methyl oxime;

(R,E)-2-amino-7-(4-fluoro-2-(2-fluoropyridin-3-yl)phenyl)-4-methyl-7,8-dihydroquinazolin-5(6H)-one O-methyl oxime (S,E)-2-amino-7-(4-fluoro-2-(2-fluoropyridin-3-yl)phenyl)-4-methyl-7,8-dihydroquinazolin-5(6H)-one O-methyl oxime (E)-2-amino-7-(4-fluoro-2-(2-fluoropyridin-3-yl)phenyl)-4-methyl-7,8-dihydroquinazolin-5(6H)-one O-allyl oxime;

(E)-2-amino-7-(4-fluoro-2-(2-fluoropyridin-3-yl)phenyl)-4-methyl-7,8-dihydroquinazolin-5(6H)-one O-tert-butyl oxime;

(E)-2-amino-7-(4-fluoro-2-(2-fluoropyridin-3-yl)phenyl)-4-methyl-7,8-dihydroquinazolin-5(6H)-one O-isobutyl oxime;

(E)-2-amino-7-(4-fluoro-2-(2-fluoropyridin-3-yl)phenyl)-4-methyl-7,8-dihydroquinazolin-5(6H)-one O-benzyl oxime;

(E)-2-amino-7-(4-fluoro-2-(2-fluoropyridin-3-yl)phenyl)-4-methyl-7,8-dihydroquinazolin-5(6H)-one O-phenyl oxime;

(E)-2-amino-7-(4-fluoro-2-(2-fluoropyridin-3-yl)phenyl)-4-methyl-7,8-dihydroquinazolin-5(6H)-one O-4-nitrobenzyl oxime;

(E)-2-amino-7-(4-fluoro-2-(6-methoxypyridin-2-yl)phenyl)-4-methyl-7,8-dihydroquinazolin-5(6H)-one O-2-methoxyethyl oxime;

(R,E)-2-amino-7-(4-fluoro-2-(6-methoxypyridin-2-yl)phenyl)-4-methyl-7,8-dihydroquinazolin-5(6H)-one O-2-methoxyethyl oxime (S,E)-2-amino-7-(4-fluoro-2-(6-methoxypyridin-2-yl)phenyl)-4-methyl-7,8-dihydroquinazolin-5(6H)-one O-2-methoxyethyl oxime (E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime;

(R,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime;

(S,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime;

(E)-2-amino-7-(4-fluoro-2-(6-methoxypyridin-2-yl)phenyl)-4-methyl-7,8-dihydroquinazolin-5(6H)-one O-2-tert-butoxyethyl oxime;

(E)-2-amino-7-(4-fluoro-2-(6-methoxypyridin-2-yl)phenyl)-4-methyl-7,8-dihydroquinazolin-5(6H)-one O-3-methoxypropyl oxime;

(E)-2-(2-amino-7-(4-fluoro-2-(6-methoxypyridin-2-yl)phenyl)-4-methyl-7,8-dihydroquinazolin-5(6H)-ylideneaminooxy)acetic acid;

(E)-2-amino-7-(4-fluoro-2-(6-methoxypyridin-2-yl)phenyl)-4-methyl-7,8-dihydroquinazolin-5(6H)-one O—(S)-2,3-dihydroxypropyl oxime;

(R,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime;

(S,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime;

(E)-2-amino-7-(4-fluoro-2-(6-methoxypyridin-2-yl)phenyl)-4-methyl-7,8-dihydroquinazolin-5(6H)-one O-2-aminoethyl oxime;

(R,E)-2-amino-7-(4-fluoro-2-(6-methoxypyridin-2-yl)phenyl)-4-methyl-7,8-dihydroquinazolin-5(6H)-one O-2-aminoethyl oxime;

(S,E)-2-amino-7-(4-fluoro-2-(6-methoxypyridin-2-yl)phenyl)-4-methyl-7,8-dihydroquinazolin-5(6H)-one O-2-aminoethyl oxime;

(E)-2-amino-7-(4-fluoro-2-(6-methoxypyridin-2-yl)phenyl)-4-methyl-7,8-dihydroquinazolin-5(6H)-one O-pyridin-3-ylmethyl oxime;

(Z)-2-amino-7-(4-fluoro-2-(6-methoxypyridin-2-yl)phenyl)-4-methyl-7,8-dihydroquinazolin-5(6H)-one O-pyridin-3-ylmethyl oxime;

(E)-2-amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime;

(R,E)-2-amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime;

(S,E)-2-amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime;

(E)-2-(2-amino-7-(4-fluoro-2-(6-methoxypyridin-2-yl)phenyl)-4-methyl-7,8-dihydroquinazolin-5(6H)-ylidene)hydrazinecarboximidamide;

(S,E)-2-amino-7-(4-fluoro-2-(6-methoxypyridin-2-yl)phenyl)-4-methyl-7,8-dihydroquinazolin-5(6H)-one O—(S)-3,4-dihydroxybutyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—((R)-2,2-dimethyl-1,3-dioxolan-4-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-2,3-dihydroxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-2,3-dihydroxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxy-2-(hydroxymethyl)propyl oxime;

(R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-3,4-dihydroxybutyl oxime;

(S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)amino)butane-1,2-diol;

(R,Z)-2-amino-7-(4-fluoro-2-(6-methoxypyridin-2-yl)phenyl)-4-methyl-7,8-dihydropyrido[4,3-d]pyrimidin-5(6H)-one O—((R)-1,4-dioxan-2-yl)methyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-morpholin-2-ylmethyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-morpholin-2-ylmethyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-morpholin-2-ylmethyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R)-3,4,5-trihydroxytetrahydrofuran-2-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R,5R)-3,4-dihydroxy-5-methoxytetrahydrofuran-2-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((3aR,4R,6R,6aR)-6-methoxy-2,2-dimethyltetrahydrofuro[3,4-d][1,3]dioxol-4-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R,5S)-3,4-dihydroxy-5-methoxytetrahydrofuran-2-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((3aR,4R,6S,6aR)-6-methoxy-2,2-dimethyltetrahydrofuro[3,4-d][1,3]dioxol-4-yl)methyl oxime;

(R,Z)-2-amino-7-(3'-(cyclopropylsulfonyl)-5-fluorobiphenyl-2-yl)-4-methyl-7,8-dihydropyrido[4,3-d]pyrimidin-5(6H)-one O—(S)-2,3-dihydroxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R)-3,4,5-trihydroxytetrahydrofuran-2-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4S)-3,4-dihydroxytetrahydrofuran-2-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2S,4R)-4-hydroxypyrrolidin-2-yl)methyl oxime;

(3R,5S)-1-acetyl-5-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)pyrrolidin-3-yl acetate, (2S,4R)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)pyrrolidine-2-carboxylate;

(2S,4R)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)pyrrolidine-2-carboxylic acid;

(R,Z)-2-amino-7-(4-fluoro-2-(6-methoxypyridin-2-yl)phenyl)-4-methyl-7,8-dihydropyrido[4,3-d]pyrimidin-5(6H)-one O-(3R,5S)-5-(hydroxymethyl)pyrrolidin-3-yl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3R,4S)-3,4-dihydroxypyrrolidin-2-yl)methyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-(3R,4S)-3,4-dihydroxycyclopentyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-((3R,4S)-3,4-dihydroxycyclopentyl)methyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-3,4-dihydroxy-4-methylpentyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one oxime;

(R)-4-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)oxazolidin-2-one;

(R,Z)-2-amino-7-(4-fluoro-2-(6-methoxypyridin-2-yl)phenyl)-4-methyl-7,8-dihydropyrido[4,3-d]pyrimidin-5(6H)-one O-2-morpholinoethyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-(tetrahydro-2H-pyran-4-yl)methyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-((1s,4S)-4-hydroxycyclohexyl)methyl oxime;

(S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanamide;

(7R,Z)-2-amino-7-(4-fluoro-2-(6-methoxypyridin-2-yl)phenyl)-4-methyl-7,8-dihydropyrido[4,3-d]pyrimidin-5(6H)-one O-2-(morpholin-2-yl)ethyl oxime;

(S)-4-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)-3-benzyloxazolidin-2-one;

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-2-amino-3-hydroxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-(1-methyl-1H-imidazol-4-yl)methyl oxime;

(R)-7-(4-fluoro-2-(6-methoxypyridin-2-yl)phenyl)-5-imino-4-methyl-5,6,7,8-tetrahydropyrido[4,3-d]pyrimidin-2-amine;

(R,Z)-2-amino-7-(2-(5-amino-6-methoxypyrazin-2-yl)-4-fluorophenyl)-4-methyl-7,8-dihydropyrido[4,3-d]pyrimidin-5(6H)-one O—(S)-3,4-dihydroxybutyl oxime;

(R,Z)-2-amino-7-(4-fluoro-2-(6-methoxypyrazin-2-yl)phenyl)-4-methyl-7,8-dihydropyrido[4,3-d]pyrimidin-5(6H)-one O—(S)-3,4-dihydroxybutyl oxime;

(R,Z)-2-amino-7-(4-fluoro-2-(2-methoxythiazol-4-yl)phenyl)-4-methyl-7,8-dihydropyrido[4,3-d]pyrimidin-5(6H)-one O—(S)-3,4-dihydroxybutyl oxime;

(R,Z)-2-amino-7-(4-fluoro-2-(6-methoxypyridin-2-yl)phenyl)-4-methyl-7,8-dihydropyridol[4,3-d]pyrimidin-5(6H)-one O—(S)-4,5-dihydroxypentyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3-amino-2-hydroxypropyl oxime;

(S)-5-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)oxazolidin-2-one;

(R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O-4-hydroxybutyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxy-2-methoxypropyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-4,5-dihydroxypentyl oxime;

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-(2-hydroxyethyl)-N-methylacetamide;

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-dimethylacetamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypyrrolidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-fluoropyrrolidin-1-yl)ethanone;

(S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanoic acid;

3-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)dihydrofuran-2(3H) one;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxybutanamide;

(S,Z)-2-amino-7-(4-fluoro-2-(6-methoxypyridin-2-yl)phenyl)-4-methyl-7,8-dihydropyrido[4,3-d]pyrimidin-5(6H)-one O—(R)-3,4-dihydroxybutyl oxime;

(S,Z)-2-amino-7-(4-fluoro-2-(6-methoxypyridin-2-yl)phenyl)-4-methyl-7,8-dihydropyrido[4,3-d]pyrimidin-5(6H)-one O—(R)-3,4-dihydroxybutyl oxime;

2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide;

2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide;

(S)-2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide;

(R)-2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide;

(R)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide;

(S)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-1-morpholinobutan-1-one;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-methoxy-N,N-dimethylbutanamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-N—((S)-2,3-dihydroxypropyl)-N-methylacetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N-(2-hydroxyethyl)-N-methylacetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N,N-bis(2-hydroxyethyl)acetamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-N,N-bis(2-hydroxypropyl)acetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(azetidin-1-yl)ethanone;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(pyrrolidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-2-(hydroxymethyl)pyrrolidin-1-yl)ethanone;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-1-(4-hydroxypiperidin-1-yl) ethanone;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-N-methyl-N-((6-methylpyridin-2-yl)methyl)acetamide;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-N,N-bis(2-methoxyethyl)acetamide;

(R,Z)—N-(2-amino-2-oxo ethyl)-2-(2-amino-7-(4-fluoro-2-(6-methoxy pyridin-2-yl)phenyl)-4-methyl-7,8-dihydropyrido[4,3-d]pyrimidin-5(6H)-ylideneaminooxy)-N-methylacetamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-2-(hydroxymethyl)pyrrolidin-1-yl)ethanone;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-N-(2-methoxyethyl)-N-methylacetamide;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-hydroxypyrrolidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-hydr oxy piperidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypyrrolidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypiperidin-1-yl)ethanone;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-1-(3-hydroxyazetidin-1-yl)ethanone;

(R,Z)-2-(2-amino-7-(4-fluoro-2-(6-methoxy pyridin-2-yl) phenyl)-4-methyl-7,8-dihydropyrido[4,3-d]pyrimidin-5 (6H)-ylideneaminooxy)-1-(3,3-difluoropyrrolidin-1-yl) ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-fluoropyrrolidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-fluoropyrrolidin-1-yl) ethanone;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(4-methoxypiperidin-1-yl) ethanone (R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(3,3-difluoroazetidin-1-yl) ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(methoxymethyl)piperidin-1-yl)ethanone;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N-methyl-N-(2-(methylamino)-2-oxoethyl)acetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N-(isoxazol-3-ylmethyl)-N-methylacetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N-methyl-N-(thiazol-4-ylmethyl)acetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(pyrazin-2-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(dimethylamino)piperidin-1-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(2-methyltetrahydro-1H-pyrrolo[3,4-c]pyridin-5 (6H,7H,7aH)-yl)ethanone;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-N-methyl-N-((5-methyl-1H-pyrazol-3-yl)methyl)acetamide;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(2-methyl-6,7-dihydro-3H-imidazo[4,5-c]pyridin-5(4H)-yl)ethanone;

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(hydroxymethyl)pyrrolidin-1-yl)ethanone;

2-(2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)acetyl)hexahydropyrrolo[1,2-a]pyrazin-6(7H)-one;

(R,Z)-2-(2-amino-7-(4-fluoro-2-(6-methoxypyridin-2-yl) phenyl)-4-methyl-7,8-dihydropyrido[4,3-d]pyrimidin-5 (6H)-ylideneaminooxy)-1-(3-methoxyazetidin-1-yl)ethanone;

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(4,4-difluoropiperidin-1-yl)ethanone;

(7R,Z)-2-amino-7-(4-fluoro-2-(6-methoxypyrazin-2-yl)phenyl)-4-methyl-7,8-dihydropyrido[4,3-d]pyrimidin-5(6H)-one O-3,4-dihydroxybutyl oxime;

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-3,4-dihydroxybutyl oxime;

(7R,Z)-2-amino-7-(4-fluoro-2-(6-methoxypyrazin-2-yl)phenyl)-4-methyl-7,8-dihydropyrido[4,3-d]pyrimidin-5(6H)-one O-(3,4-dihydroxy-5-methoxytetrahydrofuran-2-yl)methyl oxime;

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-(3,4-dihydroxy-5-methoxytetrahydrofuran-2-yl)methyl oxime;

5-(((Z)—((R)-2-amino-7-(4-fluoro-2-(6-methoxypyrazin-2-yl)phenyl)-4-methyl-7,8-dihydropyrido[4,3-d]pyrimidin-5(6H)-ylidene)aminooxy)methyl)-3,4-dihydroxydihydrofuran-2(3H)-one;

5-(((Z)—((R)-2-amino-7-(2-(5-amino-6-methoxypyrazin-2-yl)-4-fluorophenyl)-4-methyl-7,8-dihydropyrido[4,3-d]pyrimidin-5(6H)-ylidene)aminooxy)methyl)-3,4-dihydroxydihydrofuran-2(3H)-one;

(7R,Z)-2-amino-7-(4-fluoro-2-(6-methoxypyrazin-2-yl)phenyl)-4-methyl-7,8-dihydropyrido[4,3-d]pyrimidin-5(6H)-one O-(3,4-dihydroxytetrahydrofuran-2-yl)methyl oxime;

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-(3,4-dihydroxytetrahydrofuran-2-yl)methyl oxime;

(7R,Z)-2-amino-7-(4-fluoro-2-(6-methoxypyrazin-2-yl)phenyl)-4-methyl-7,8-dihydropyrido[4,3-d]pyrimidin-5(6H)-one O-(3,4-dihydroxypyrrolidin-2-yl)methyl oxime;

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-(3,4-dihydroxypyrrolidin-2-yl)methyl oxime;

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-3,4-dihydroxybutyl oxime;

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-3,4-dihydroxybutyl oxime;

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-(3,4-dihydroxytetrahydrofuran-2-yl)methyl oxime;

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-(3,4-dihydroxytetrahydrofuran-2-yl)methyl oxime;

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-(3,4-dihydroxypyrrolidin-2-yl)methyl oxime;

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-(3,4-dihydroxypyrrolidin-2-yl)methyl oxime;

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-3,4-dihydroxybutyl oxime;

(7S,Z)-2-amino-7-(2-(5-amino-6-methoxypyrazin-2-yl)-4-fluorophenyl)-8-fluoro-4-methyl-7,8-dihydropyrido[4,3-d]pyrimidin-5(6H)-one O-3,4-dihydroxybutyl oxime;

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-(3,4-dihydroxytetrahydrofuran-2-yl)methyl oxime;

(7S,Z)-2-amino-7-(2-(5-amino-6-methoxypyrazin-2-yl)-4-fluorophenyl)-8-fluoro-4-methyl-7,8-dihydropyrido[4,3-d]pyrimidin-5(6H)-one O-(3,4-dihydroxytetrahydrofuran-2-yl)methyl oxime;

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-(3,4-dihydroxypyrrolidin-2-yl)methyl oxime;

(7S,Z)-2-amino-7-(2-(5-amino-6-methoxypyrazin-2-yl)-4-fluorophenyl)-8-fluoro-4-methyl-7,8-dihydropyrido[4,3-d]pyrimidin-5(6H)-one O-(3,4-dihydroxypyrrolidin-2-yl)methyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-3-amino-4-hydroxybutyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-4-amino-3-hydroxybutyl oxime;

(7R,Z)-2-amino-7-(4-fluoro-2-(6-methoxypyridin-2-yl)phenyl)-4-methyl-7,8-dihydropyrido[4,3-d]pyrimidin-5(6H)-one O-2-amino-3-hydroxypropyl oxime; and (7R,Z)-2-amino-7-(4-fluoro-2-(6-methoxypyridin-2-yl)phenyl)-4-methyl-7,8-dihydropyrido[4,3-d]pyrimidin-5(6H)-one O-3-amino-2-hydroxypropyl oxime.

In another of its aspects, the present invention relates to process of making compounds that are useful as HSP90 inhibitors.

In one embodiment, the process comprising:

reacting a compound having the formula

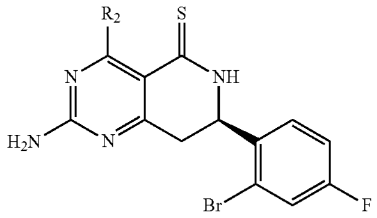

with a compound having the formula $H_2N—O—R_1$ under conditions that form a intermediate having the formula

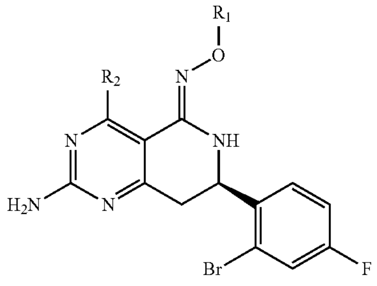

reacting the intermediate with a compound having the formula

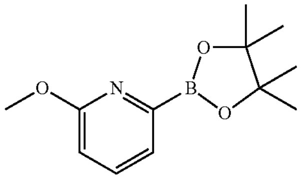

under conditions that form product having the formula

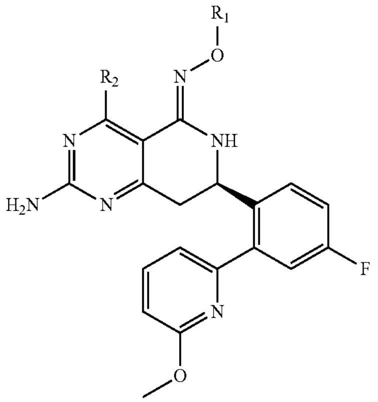

wherein $R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino $(C_{1-10})$alkyl, thiocarbonyl$(C_{1-10})$alkyl, hydroxylcarbonyl $(C_{1-10})$alkyl, aminocarbonyl$(C_{1-10})$alkyl, aminosulfonyl $(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In another embodiment of the process of making the compounds of the invention comprises reacting a compound having the formula

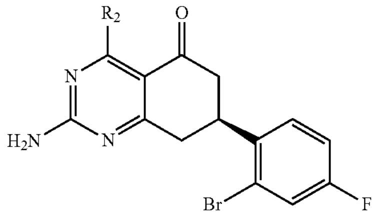

with a compound having the formula

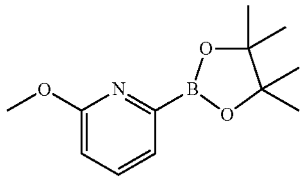

under conditions that form an intermediate having the formula

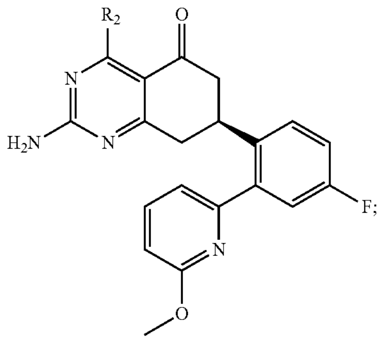

and reacting the intermediate with a compound having the formula $H_2N—O—R_1$ under conditions that form a product having the formula

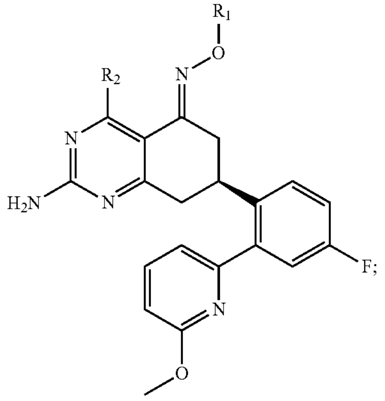

wherein $R_1$ is selected from the group consisting of hydrogen, carbonyl, hydroxycarbonyl, oxycarbonyl, aminocarbonyl, sulfonyl, sulfinyl, $(C_{1-10})$alkyl, halo$(C_{1-10})$alkyl, hetero$(C_{1-10})$alkyl, $(C_{1-10})$alkyl, hydroxy$(C_{1-10})$alkyl, alkoxy$(C_{1-10})$alkyl, amino$(C_{1-10})$alkyl, imino$(C_{1-10})$alkyl, carbonyl$(C_{1-10})$alkyl, sulfonyl$(C_{1-10})$alkyl, sulfinyl$(C_{1-10})$alkyl, carbonylamino$(C_{1-10})$alkyl, thiocarbonyl$(C_{1-10})$alkyl, hydroxylcarbonyl$(C_{1-10})$alkyl, aminocarbonyl$(C_{1-10})$alkyl, aminosulfonyl$(C_{1-10})$alkyl, sulfonylamino$(C_{1-10})$alkyl, $(C_{1-6})$alkylsulfonylamino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $R_2$ is selected from the group consisting of hydrogen, halo, cyano, thio, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

In yet another embodiment of the process of making the compounds of the invention comprising:

reacting a compound having the formula

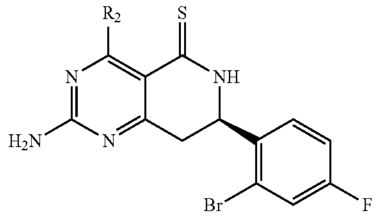

with Starting Material I having the formula

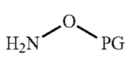

under conditions that form Intermediate F having the formula

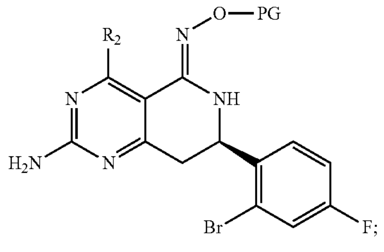

wherein

PG is a protecting group selected from the group consisting of $((C_{1-6})_3$alkyl)silyl, $(((C_{1-6})alkyl)_{3-k})$phenyl$_k$)silyl where k is 0-3, benzyl, and tetrahydropyranyl; and $R_2$ is selected from the group consisting of hydrogen, $(C_{1-6})$alkyl, halo$(C_{1-6})$alkyl, aza$(C_{1-6})$alkyl, $(C_{1-6})$oxaalkyl, each unsubstituted or substituted.

In the above embodiment of the process, preparation of the compounds of the invention may be achieved via Method A comprising:

coupling Starting Material II having the formula

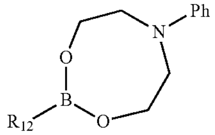

to said Intermediate F which form Intermediate G having the formula

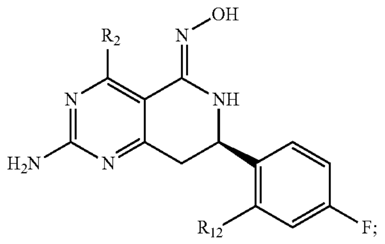

coupling Starting Material III having the formula

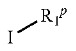

to said Intermediate G under conditions that form Intermediate H having the formula

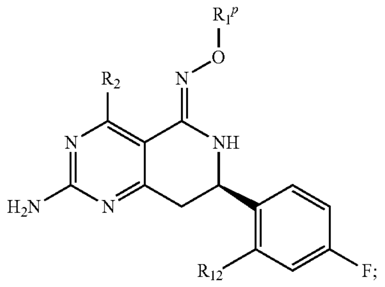

deprotecting said Intermediate H under conditions that form Product having the formula

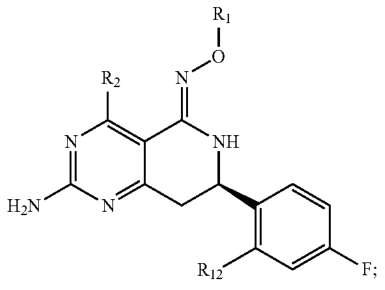

wherein $R_1^P$ is a protected form of $R_1$;

$R_1$ is selected from the group consisting of hydrogen, carbonyl, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, and hetero$(C_{1-10})$aryl, each unsubstituted or substituted with 1-3 substituents each of which is independently selected from the group consisting of hydroxyl, $(C_{1-10})$alkyl, hydroxy$(C_{1-10})$alkyl, amino, amino$(C_{1-10})$ alkyl, aminocarbonyl, $(C_{3-12})$cycloalkyl, hetero$(C_{3-12})$cycloalkyl, $(C_{4-12})$aryl, and hetero$(C_{1-10})$aryl, each is unsubstituted or further substituted; and $R_{12}$ is selected from a group consisting of $(C_{4-12})$aryl, hetero$(C_{1-10})$aryl, $(C_{9-12})$bicycloaryl, hetero$(C_{4-12})$bicycloaryl, $(C_{3-12})$cycloalkyl, and hetero$(C_{2-11})$cycloalkyl, each unsubstituted or substituted with 1-3 substituents.

In the above embodiment of the process, preparation of the compounds of the invention may be achieved via Method B comprising:

deprotecting Intermediate F under conditions which form Intermediate F' having the formula

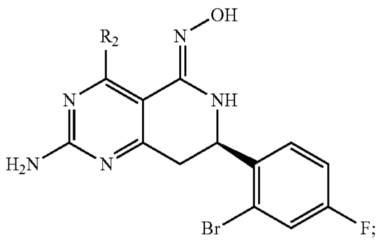

coupling Starting Material II having the formula

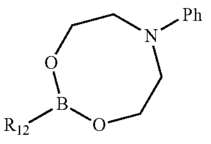

to said Intermediate F' which form Intermediate G having the formula

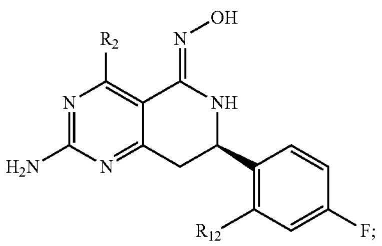

coupling Starting Material III having the formula

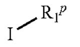

to said Intermediate G under conditions that form Intermediate H having the formula

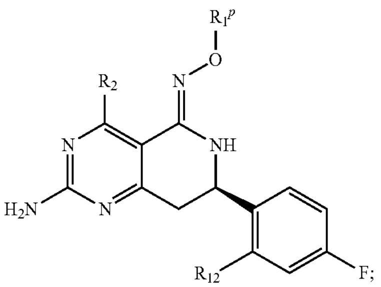

deprotecting said Intermediate H under conditions that form Product having the formula

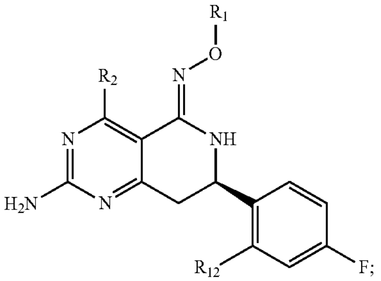

wherein $R_1^P$ is a protected form of $R_1$ is selected from the group consisting of hydrogen, carbonyl, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, and hetero$(C_{1-10})$aryl, each unsubstituted or substituted with 1-3 substituents each of which is independently selected from the group consisting of hydroxyl, $(C_{1-10})$alkyl, hydroxy$(C_{1-10})$alkyl, amino, amino$(C_{1-10})$alkyl, aminocarbonyl, $(C_{3-12})$cycloalkyl, hetero$(C_{3-12})$cycloalkyl, $(C_{4-12})$ aryl, and hetero$(C_{1-10})$aryl, each is unsubstituted or further substituted; and $R_{12}$ is selected from a group consisting of $(C_{4-12})$aryl, hetero$(C_{1-10})$aryl, $(C_{9-12})$bicycloaryl, hetero$(C_{4-12})$bicycloaryl, $(C_{3-12})$cycloalkyl, and hetero$(C_{2-11})$cycloalkyl, each unsubstituted or substituted with 1-3 substituents.

Another process which may be used to prepare the compounds of the inventions comprising:

reacting a compound having the formula

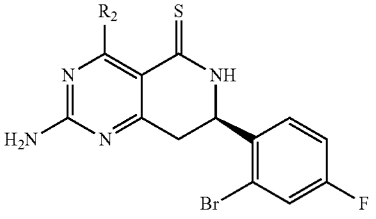

with Starting

Material I having the formula

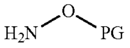

under conditions that form Intermediate F having the formula

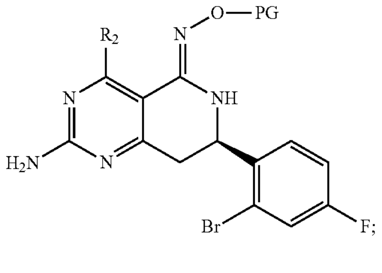

deprotecting said Intermediate F under conditions which form Intermediate F' having the formula

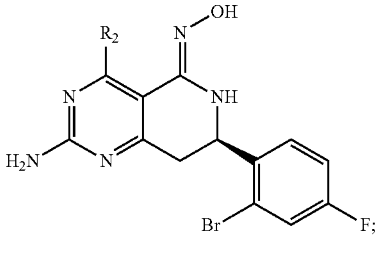

coupling Starting Material III having the formula

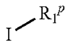

to Intermediate F' under conditions that form Intermediate J having the formula

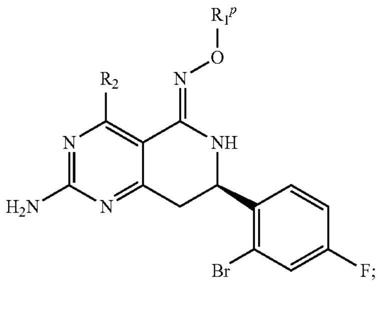

deprotecting and then coupling Starting Material II having the formula

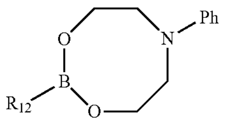

to Intermediate J under conditions which form Product having the formula

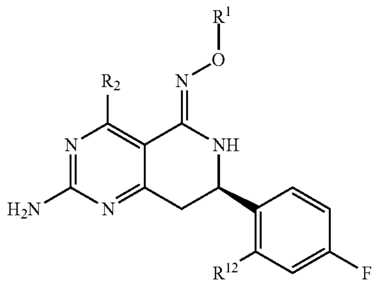

wherein $R_1^P$ is a protected form of $R_1$:

$R_1$ is selected from the group consisting of hydrogen, carbonyl, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, and hetero$(C_{1-10})$aryl, each unsubstituted or substituted with 1-3 substituents each of which is independently selected from the group consisting of hydroxyl, $(C_{1-10})$alkyl, hydroxy$(C_{1-10})$alkyl, amino, amino$(C_{1-10})$alkyl, aminocarbonyl, $(C_{3-12})$cycloalkyl, hetero$(C_{3-12})$cycloalkyl, $(C_{4-12})$aryl, and hetero$(C_{1-10})$aryl, each is unsubstituted or further substituted;

$R_2$ is selected from the group consisting of hydrogen, $(C_{1-6})$alkyl, halo$(C_{1-6})$alkyl, aza$(C_{1-6})$alkyl, $(C_{1-6})$oxaalkyl, each unsubstituted or substituted; and $R_{12}$ is selected from a group consisting of $(C_{4-12})$aryl, hetero$(C_{1-10})$aryl, $(C_{9-12})$bicycloaryl, hetero$(C_{4-12})$bicycloaryl, $(C_{3-12})$cycloalkyl, and hetero$(C_{2-11})$cycloalkyl, each unsubstituted or substituted with 1-3 substituents.

In all the above embodiments of the processes, in some variations, $R_1$ is $-L-R_{45}$, where L is $(-CR_{46}R_{47}-)-$, where n is 1, 2, 3, 4, or 5; where $R_{46}$ and $R_{47}$ are each independently selected from the group consisting of hydrogen, hydroxyl, hydroxy$(C_{1-6})$alkyl, $(C_{1-6})$alkoxy, oxo, amino, imino, $(C_{4-6})$aryl$(C_{1-6})$alkyl, hetero$(C_{1-5})$aryl$(C_{1-6})$alkyl, $(C_{3-6})$cycloalkyl$(C_{1-6})$alkyl, hetero$(C_{1-5})$cycloalkyl$(C_{1-6})$alkyl, $(C_{4-6})$aryl, hetero$(C_{1-5})$aryl, $(C_{3-6})$cycloalkyl, and hetero$(C_{1-5})$cycloalkyl, each unsubstituted or substituted; and $R_{45}$ is independently selected from the group consisting of hydrogen, hydroxyl, halo, $(C_{1-3})$alkyl, hydroxy$(C_{1-3})$alkyl, $(C_{1-3})$alkoxy, amino, carbonylamino, aminocarbonyl, carbonyl, hydroxylcarbonyl, aryl, heteroaryl, cycloalkyl, and heterocycloalkyl, each unsubstituted or further substituted.

In other variations, $R_1$ is selected from the group consisting of hydrogen,

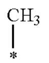
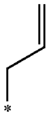
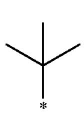
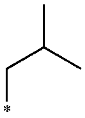
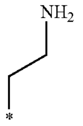

-continued
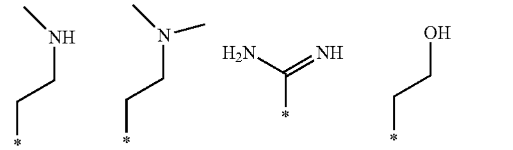
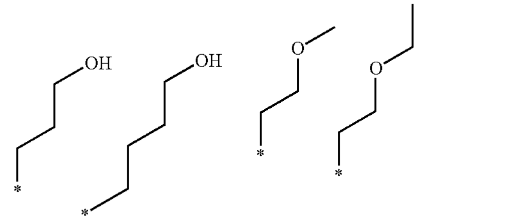
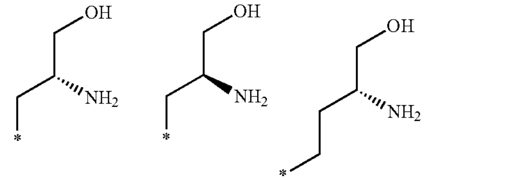
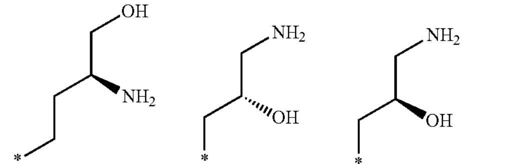
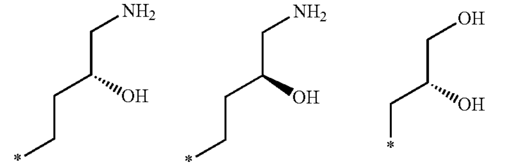
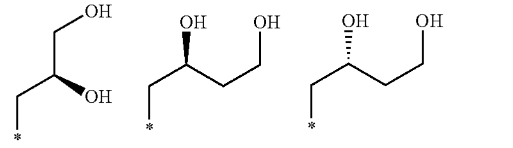
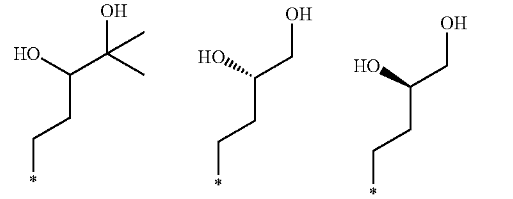
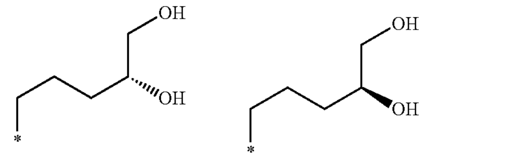
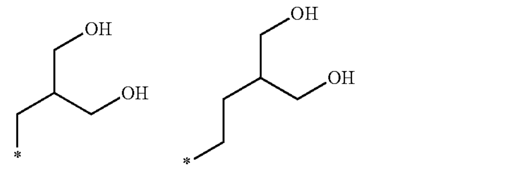
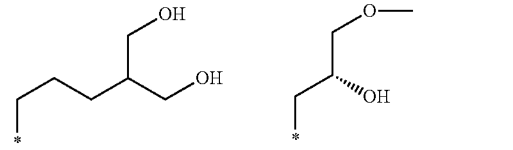
-continued
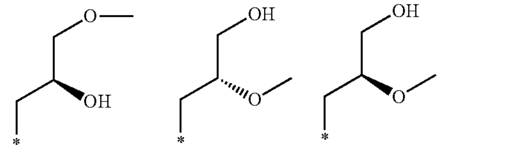
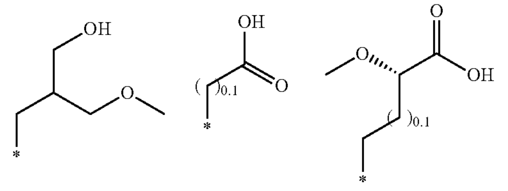
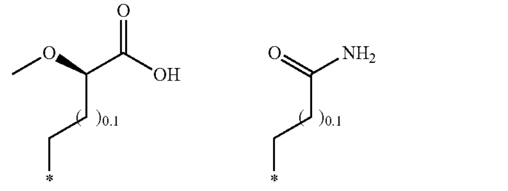
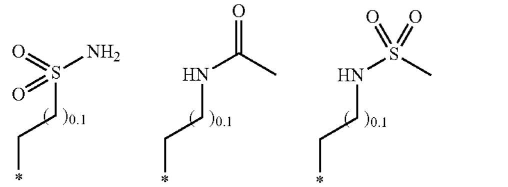
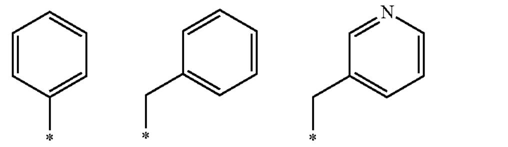
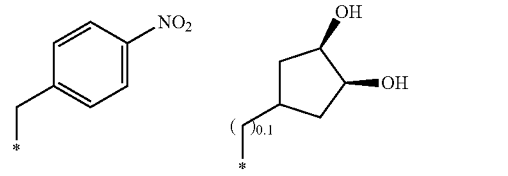
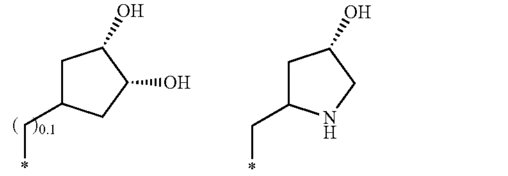
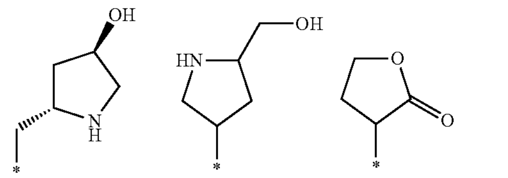
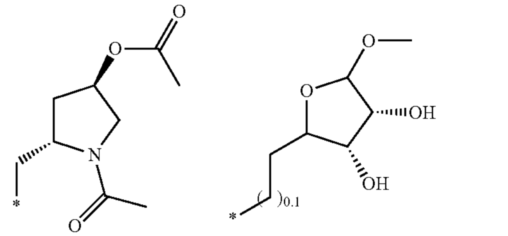

-continued
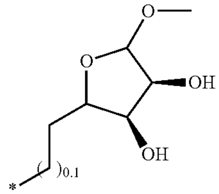
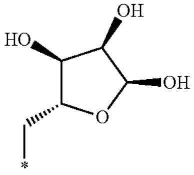
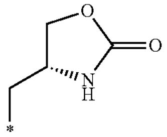
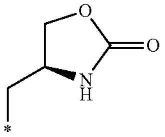
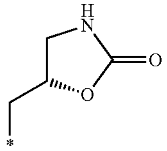
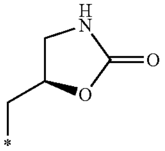
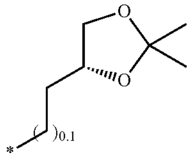
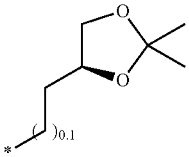
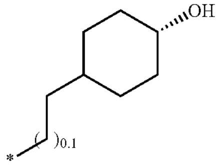
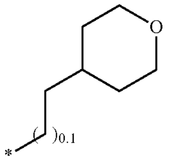
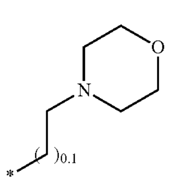
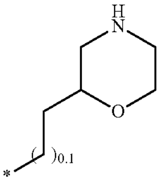
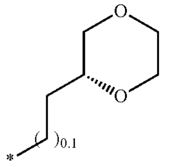
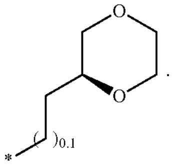
In other variations, $R_1$ is selected from the group consisting of: hydrogen,
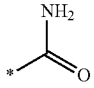
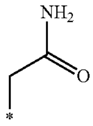
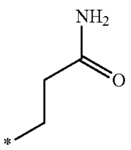
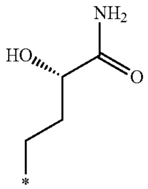
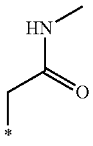
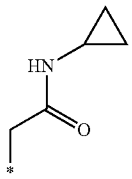
-continued
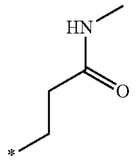
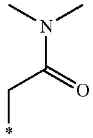
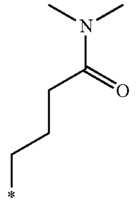
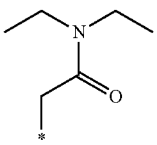
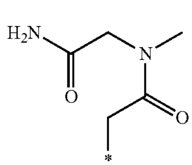
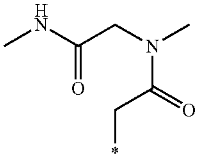
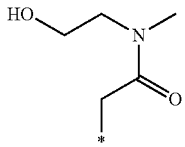
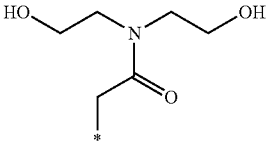
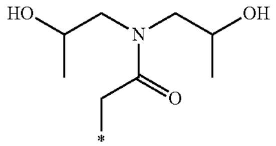
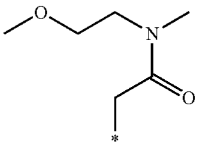
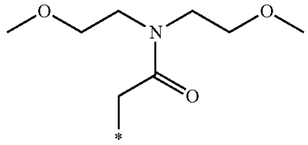
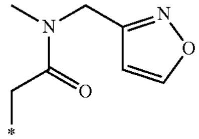
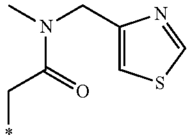
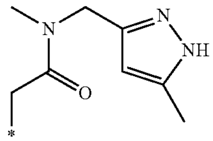
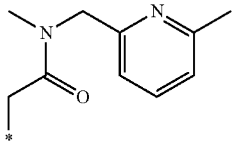
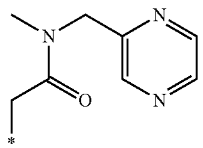
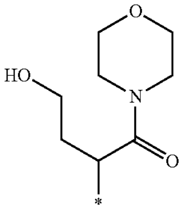
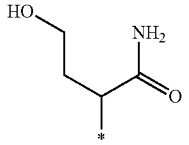
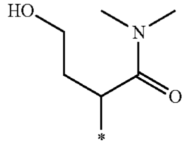

-continued
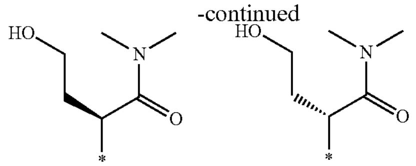
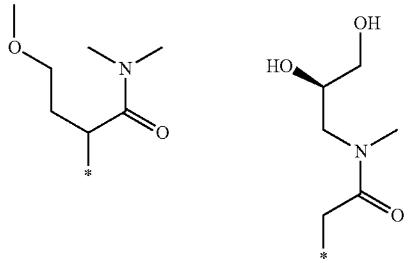
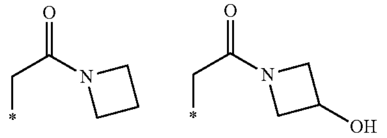
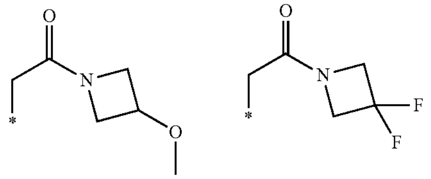
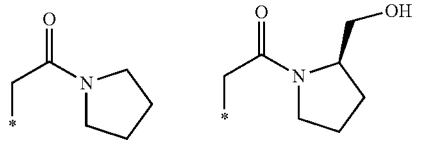
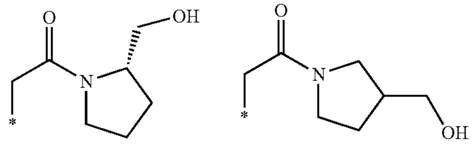
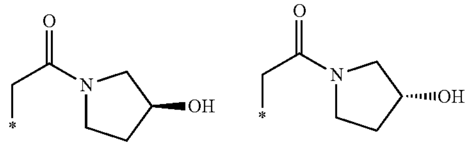
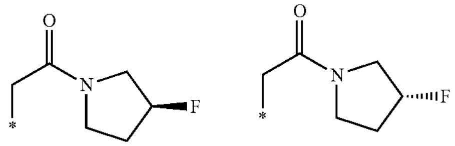
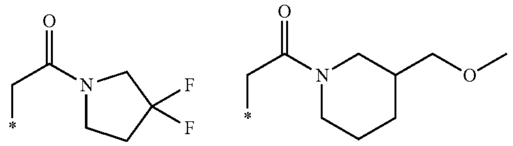
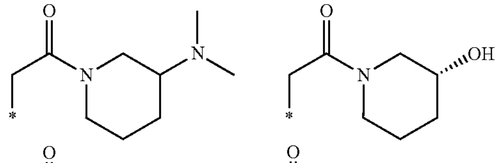
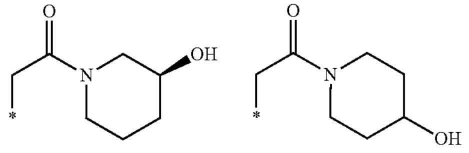
-continued
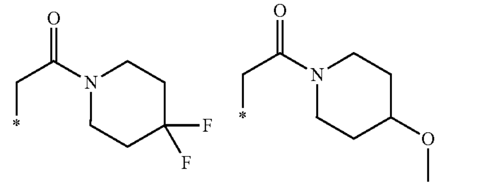
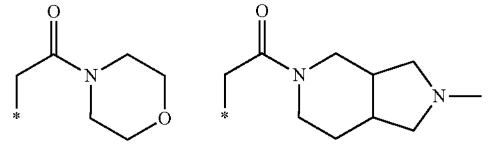
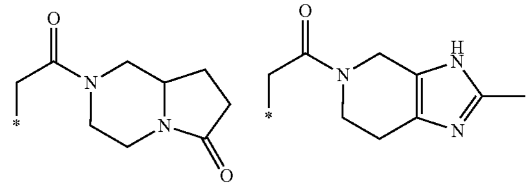
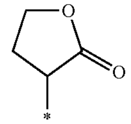
In still other variations, $R_1$ is selected from the group consisting of:
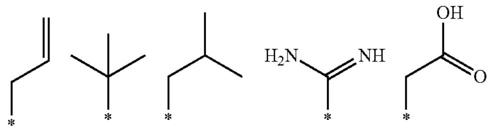
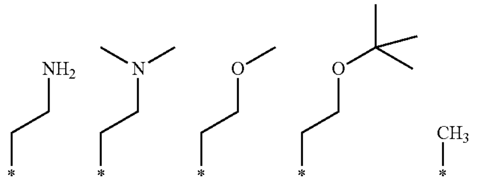
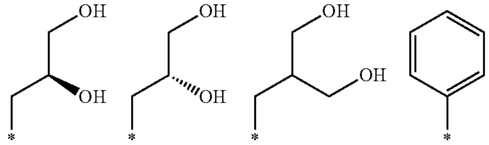
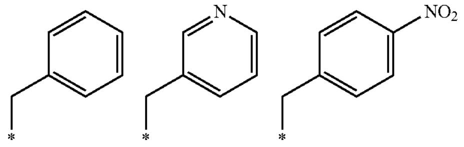
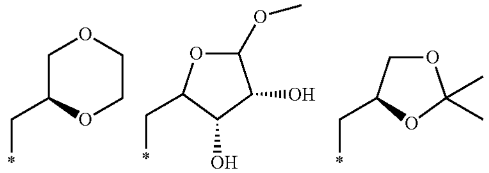

-continued

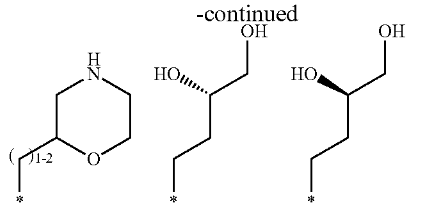

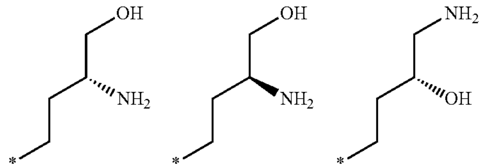

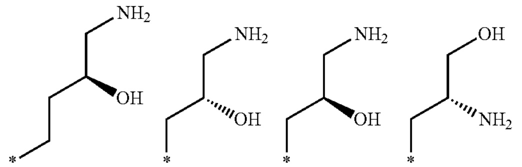

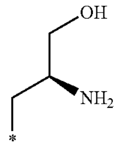

In still other variations, $R_1$ is selected from the group consisting of hydrogen,

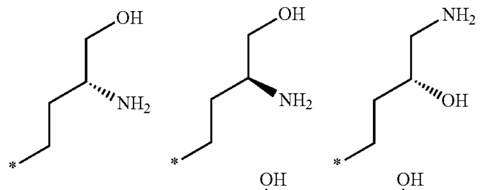

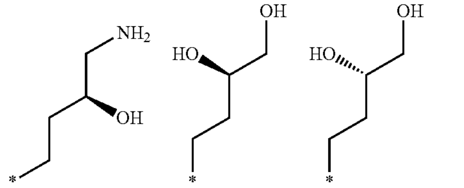

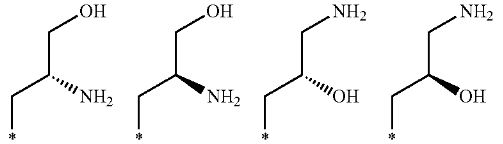

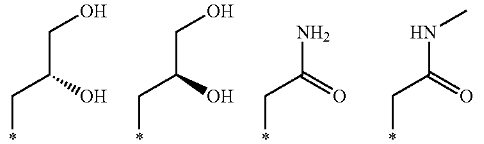

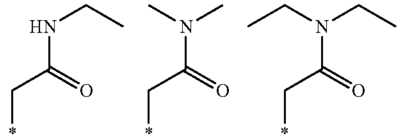

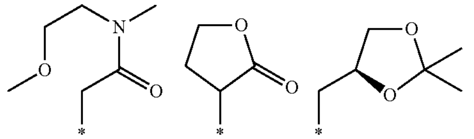

-continued

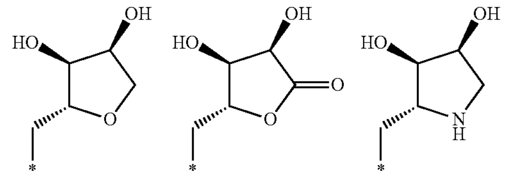

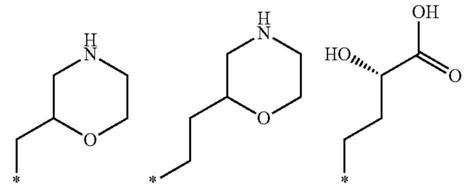

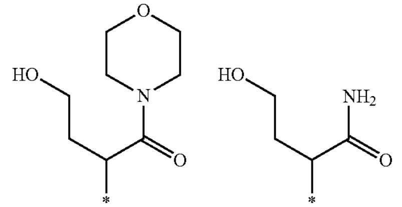

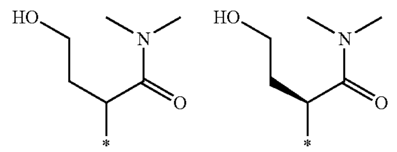

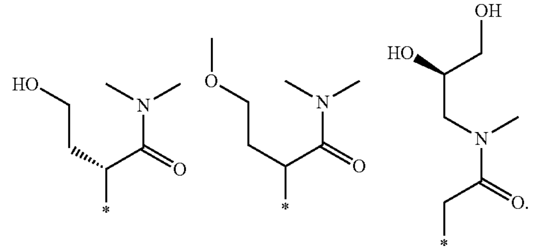

In still other variations, $R_1$ is selected from the group consisting of hydrogen,

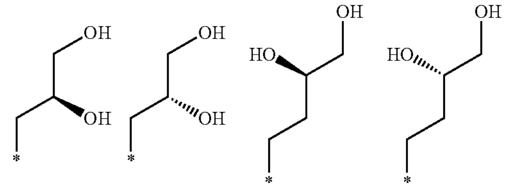

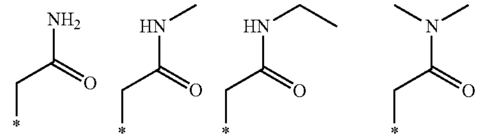

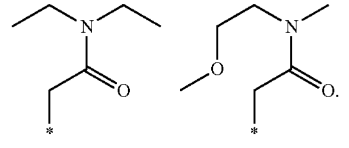

In some variation of the process of the invention, $R_2$ is selected from the group consisting of hydrogen, $(C_{1-6})$alkyl, halo$(C_{1-6})$alkyl, aza$(C_{1-6})$alkyl, $(C_{1-6})$oxaalkyl, each unsubstituted or substituted. In other variations, $R_2$ is selected from the group consisting of unsubstituted or substituted ($C_{1-6}$) alkyl. In still other variations, $R_2$ is methyl. In yet still other variations, $R_2$ is hydrogen.
In the above embodiments of the processes of the invention, in some variations, $R_{12}$ is selected from the group consisting of
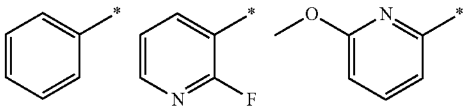
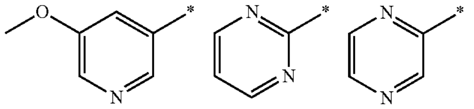
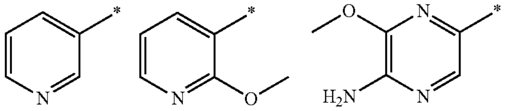
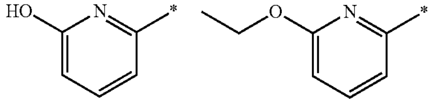
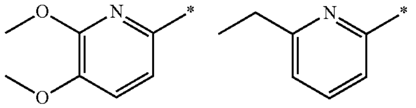
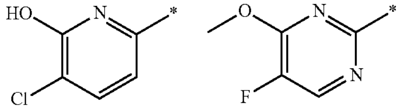
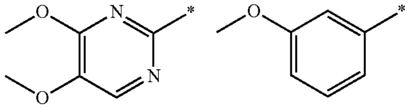
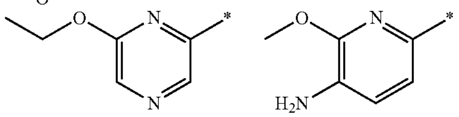
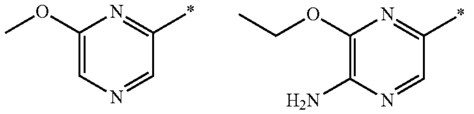
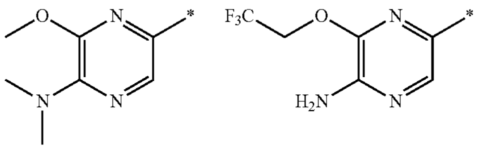
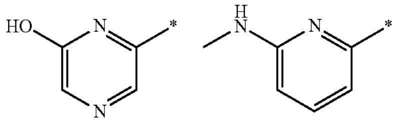
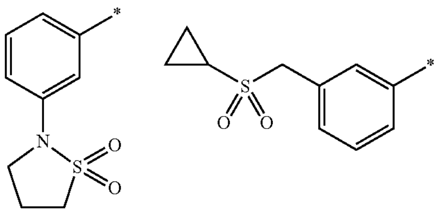
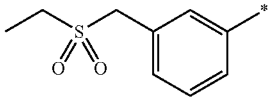
-continued
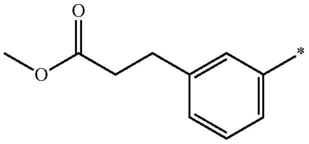
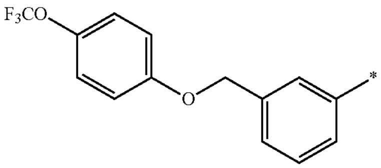
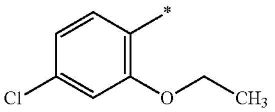
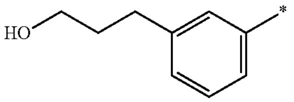
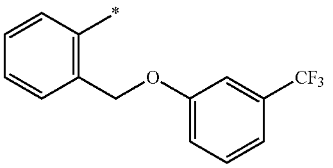
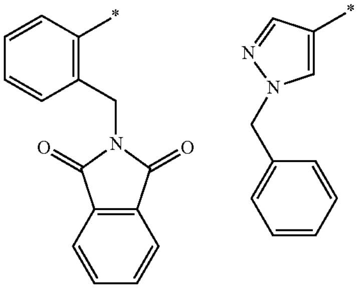
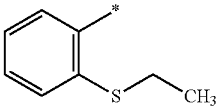
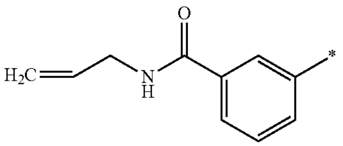
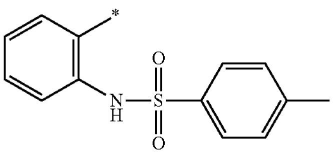
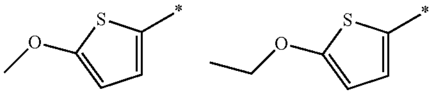
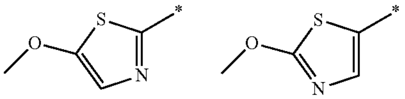
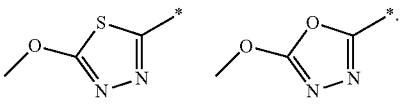

In some other variations, $R_{12}$ is selected from the group consisting of

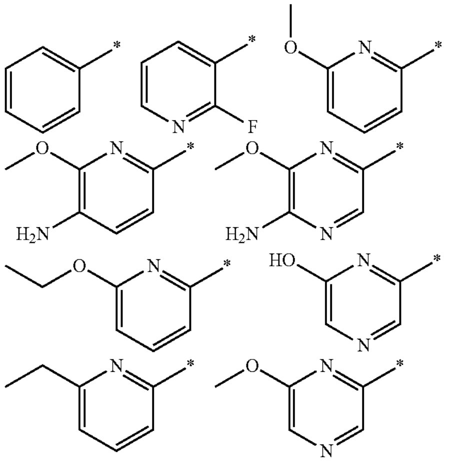

In still other variations, $R_{12}$ is of the formula

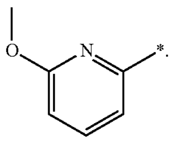

Another aspect of the invention relates to compounds that are useful for the preparation of the compounds of the invention.

In one embodiment, intermediate compounds of the invention consisting of the formula:

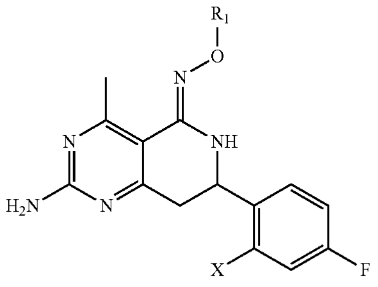

wherein $R_1$ is selected from the group consisting of hydrogen, carbonyl, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero$(C_{1-10})$ aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, and hetero$(C_{1-10})$aryl, each unsubstituted or substituted with 1-3 substituents each of which is independently selected from the group consisting of hydroxyl, $(C_{1-10})$alkyl, hydroxy $(C_{1-10})$alkyl, amino, amino$(C_{1-10})$alkyl, aminocarbonyl, $(C_{3-12})$cycloalkyl, hetero$(C_{3-12})$cycloalkyl, $(C_{4-12})$aryl, and hetero$(C_{1-10})$aryl, each is unsubstituted or further substituted; and X is a leaving group.

In yet another variation of the above embodiment of intermediate compound, wherein the intermediate compound consisting of the formula:

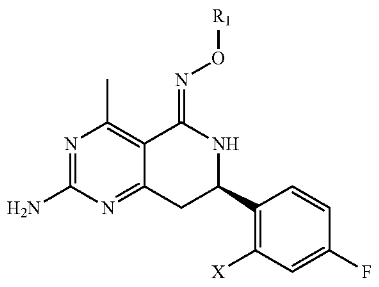

wherein $R_1$ is selected from the group consisting of hydrogen, carbonyl, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero $(C_{1-10})$aryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, and hetero$(C_{1-10})$aryl, each unsubstituted or substituted with 1-3 substituents each of which is independently selected from the group consisting of hydroxyl, $(C_{1-10})$alkyl, hydroxy$(C_{1-10})$alkyl, amino, amino$(C_{1-10})$alkyl, aminocarbonyl, $(C_{3-12})$cycloalkyl, hetero$(C_{3-12})$cycloalkyl, $(C_{4-12})$ aryl, and hetero$(C_{1-10})$aryl, each is unsubstituted or further substituted; and X is a leaving group.

In some variations of the above embodiment and variations of the intermediate compounds of the invention, $R_1$ is selected from the group consisting of hydrogen,

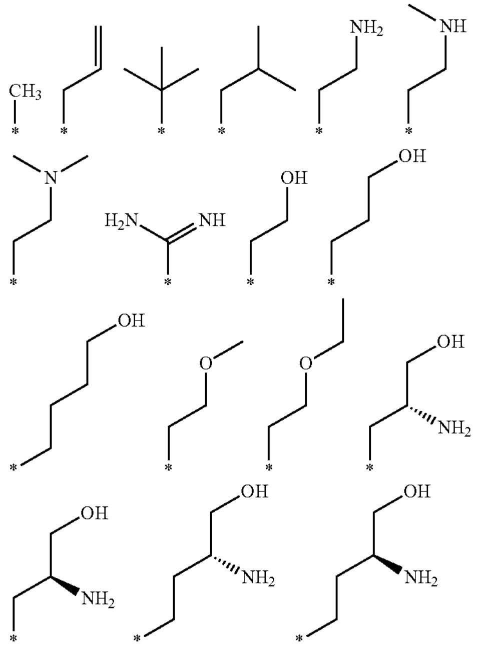

-continued
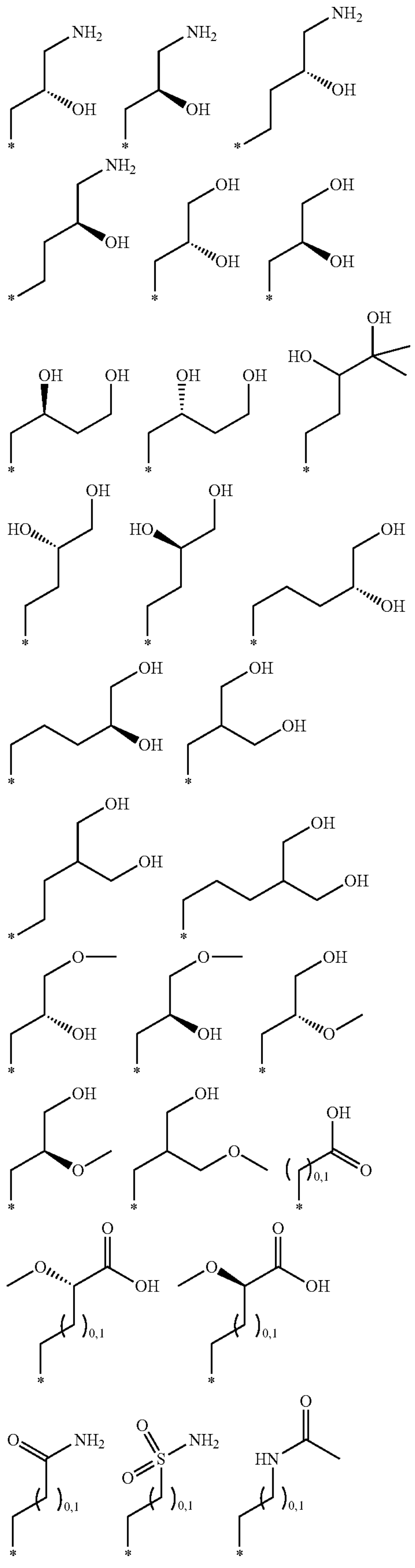
-continued
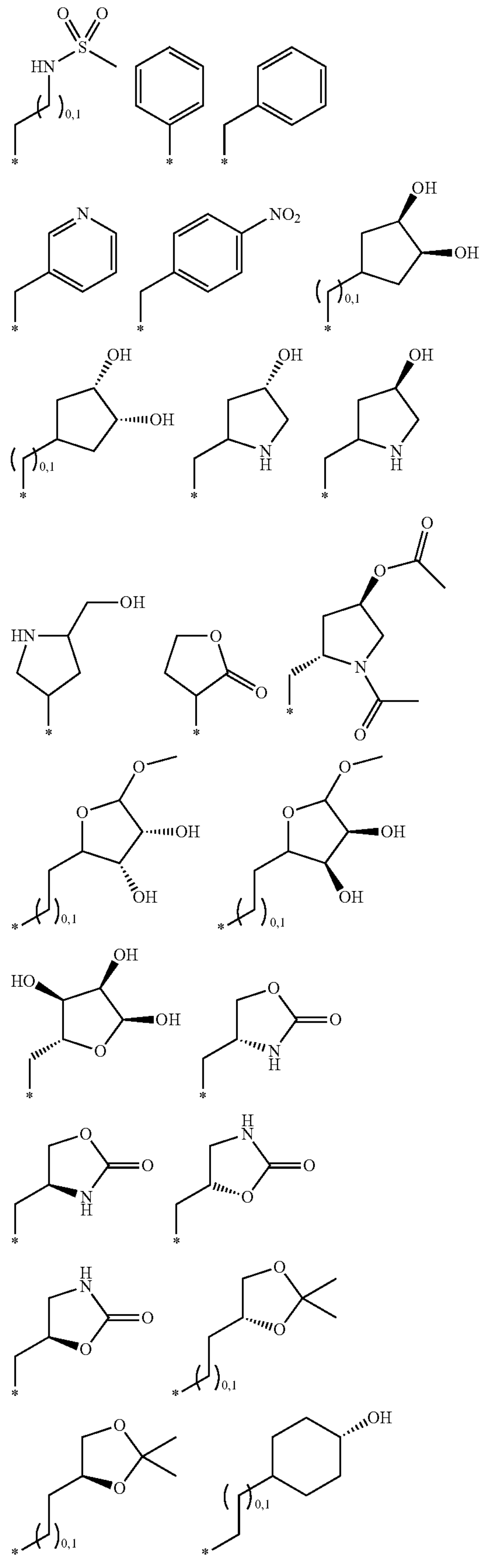

-continued
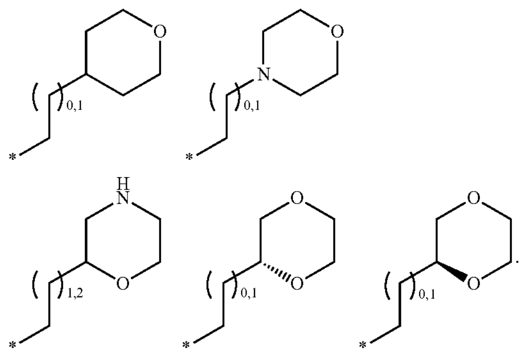
In some other variations, $R_1$ is selected from the group consisting of hydrogen,
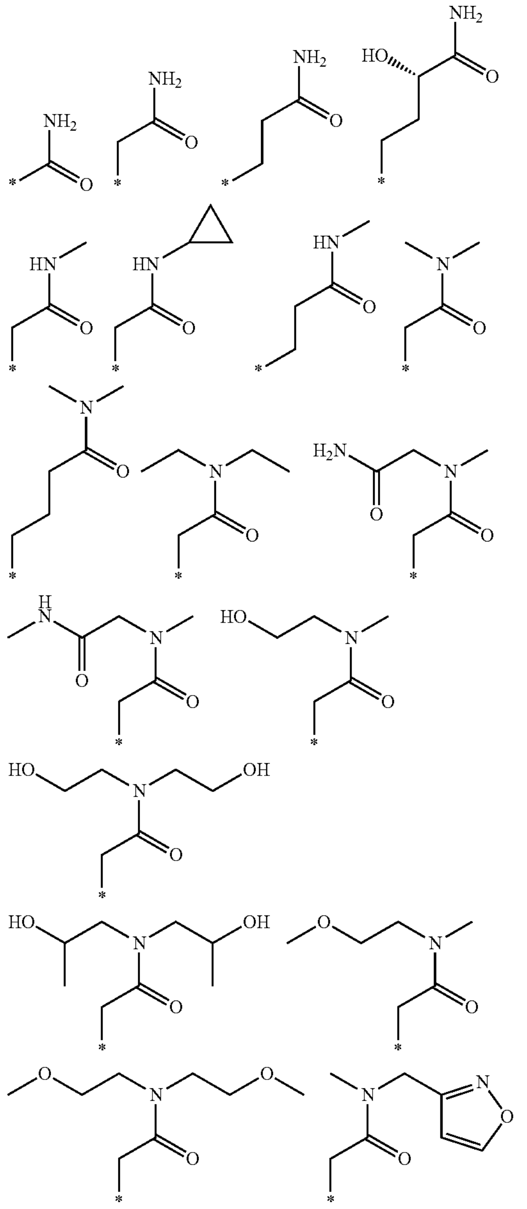
-continued
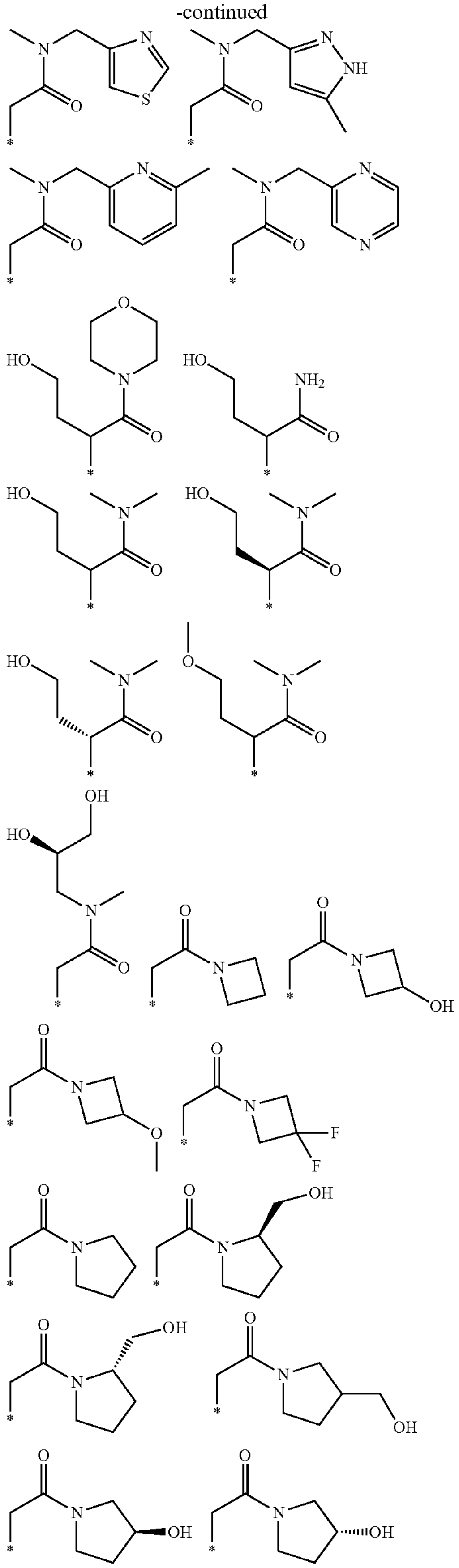

-continued
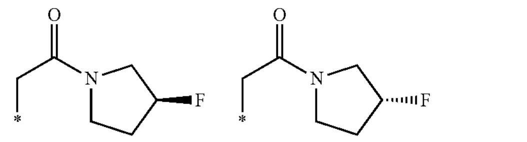
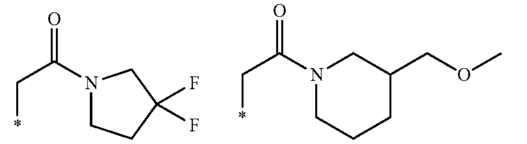
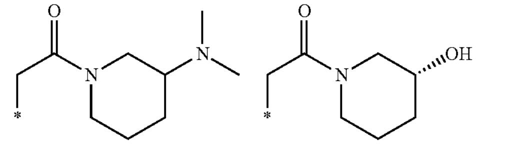
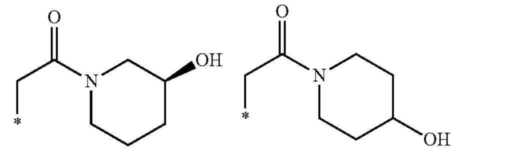
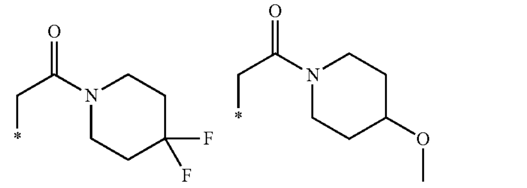
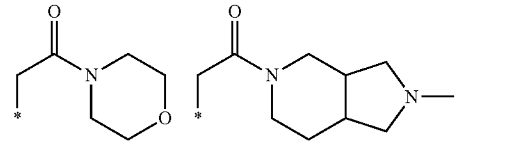
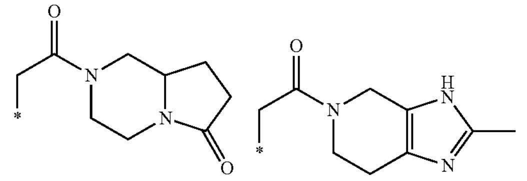
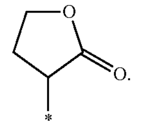
In still other variations, $R_1$ is selected from the group consisting of hydrogen,
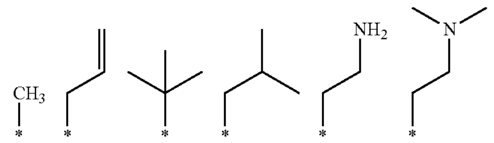
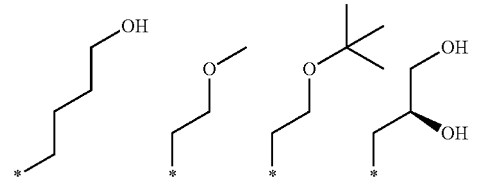
-continued
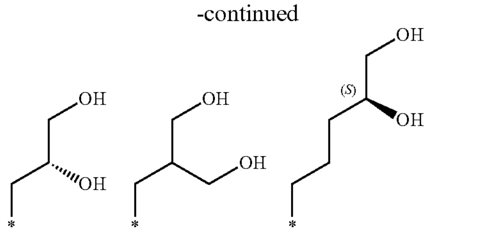
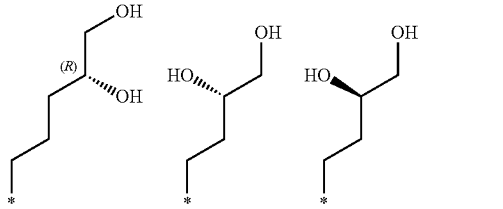
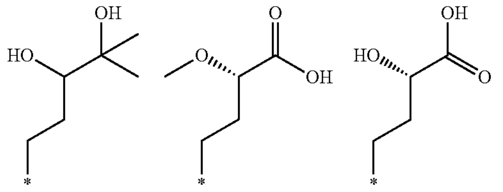
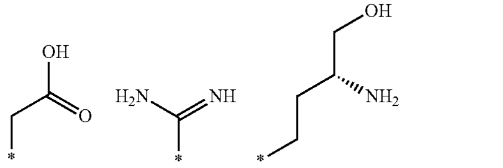
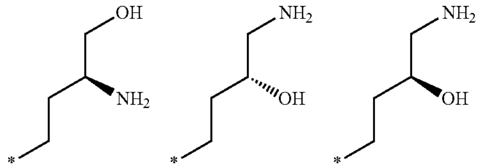
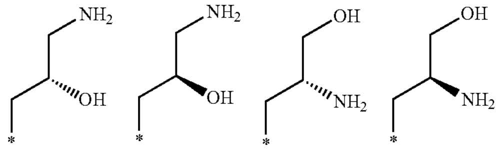
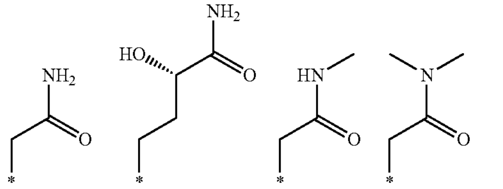
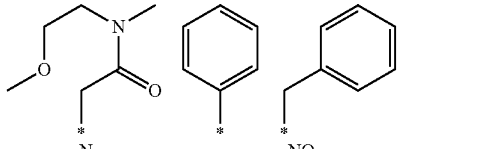
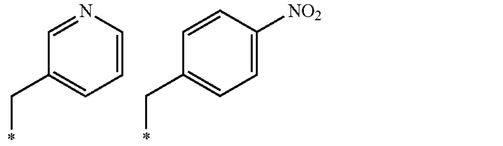
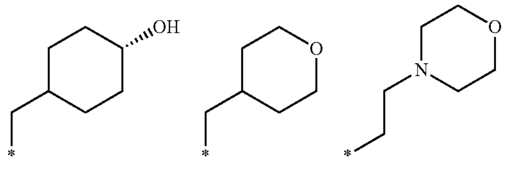

-continued
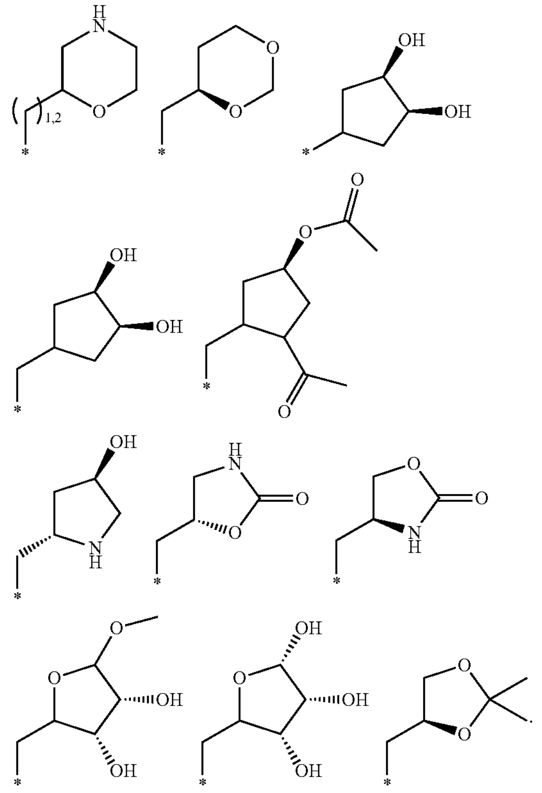
In still other variations, $R_1$ is selected from the group consisting of hydrogen,
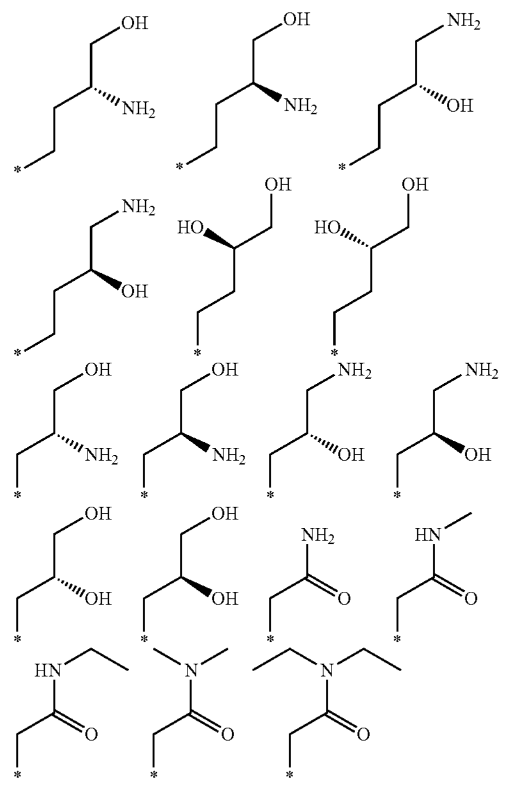
-continued
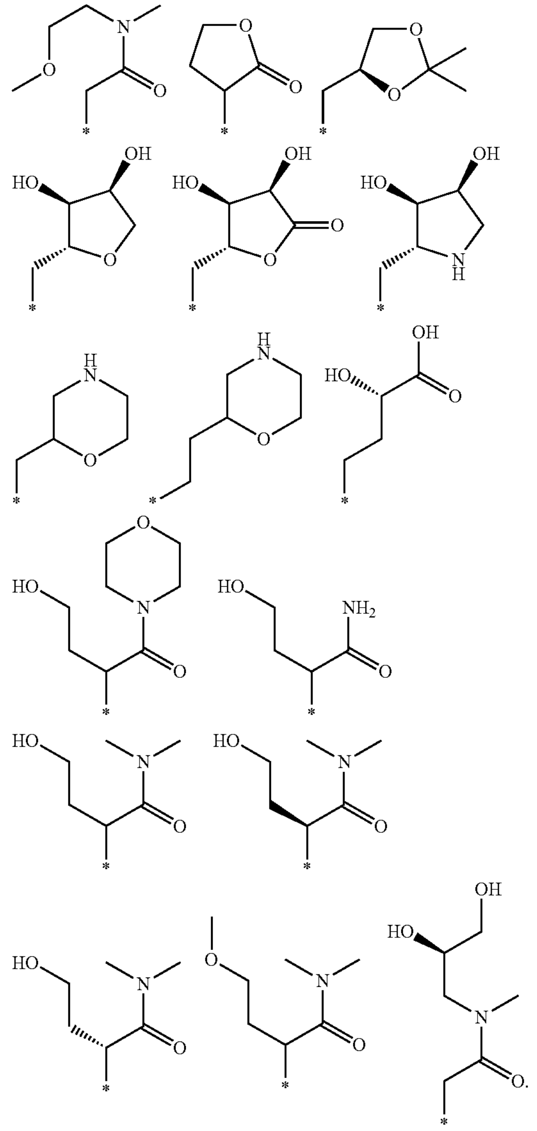
In yet other variations, $R_1$ is selected from the group consisting of
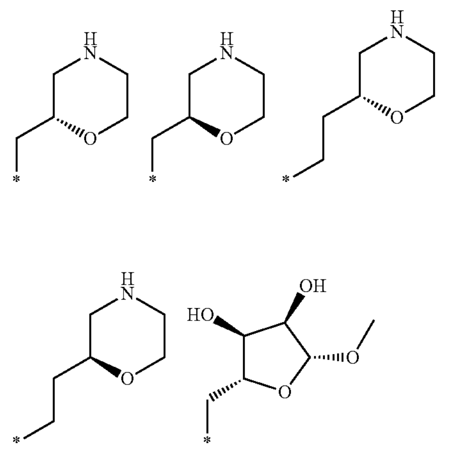

-continued

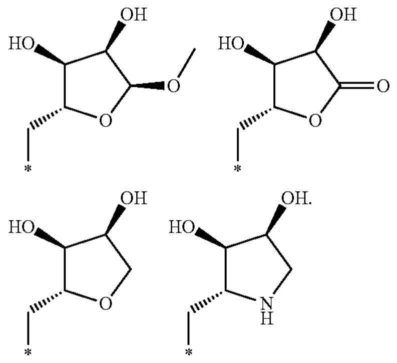

In yet still other variations, $R_1$ is selected from the group consisting of hydrogen,

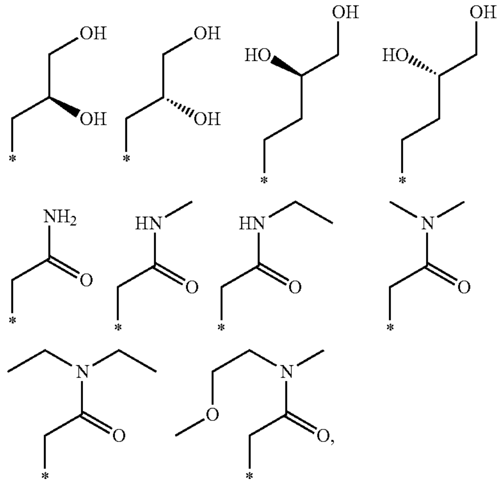

In yet still other variations, $R_1$ is selected from the group consisting of

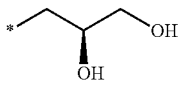 and 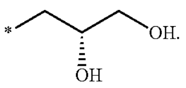

In yet still other variations, $R_1$ is selected from the group consisting of

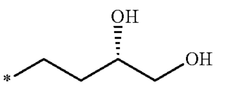 and 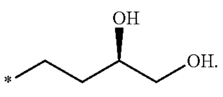

In yet still other variations, $R_1$ is

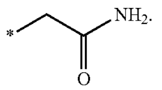

In yet still other variations, $R_1$ is

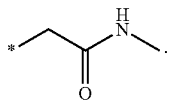 [SMILES: *CC(=O)NC]

In yet still other variations, $R_1$ is

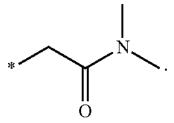 [SMILES: *CC(=O)N(C)C]

In yet still other variations, $R_1$ is

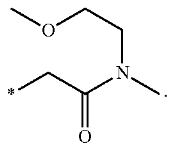 [SMILES: *CC(=O)N(C)CCOC]

In some variations of the above embodiments and variations of the compounds of the invention, $R_{12}$ is a leaving group selected from a group consisting of halo, and substituted and unsubstituted alkylsulfonate. In some variations, $R_{12}$ is bromo. In other variations, $R_{12}$ is chloro.

In still other variations, $R_{12}$ is iodo. In still other variations, $R_{12}$ is trifluoromethanesulfonate.

In another embodiment, the intermediate compound of the invention consisting of the formula:

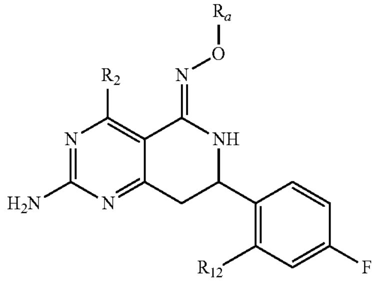

wherein $R_a$ is selected from the group consisting of hydrogen, $(C_{1-6})$alkyl, and a protecting group; and $R_{12}$ is selected from a group consisting of $(C_{4-12})$aryl and hetero$(C_{1-10})$aryl, each unsubstituted or substituted, with 1-3 substituents independently selected from the group consisting of halo, nitro, cyano, thio, alkylthio, $(C_{1-10})$alkoxy, $(C_{1-10})$haloalkoxy, hydroxy, aryloxy, heteroaryloxy, carbonyloxy, carbonyl, alkylaminocarbonyl, amino, $(C_{1-10})$alkylamino, sulfonylamino, sulfonyl, aminosulfonyl, sulfinyl, $(C_{1-10})$alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$alkyl, sulfinyl$(C_{1-10})$alkyl, hetero$(C_{1-10})$alkyl, alkoxyalkyl, alkoxycarbonylalkyl, aryloxyalkyl, heteroaryloxyalkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero($C_{3-12}$)bicycloalkyl, ($C_{4-12}$)aryl, hetero ($C_{1-10}$)aryl, ($C_{9-12}$)bicycloaryl and hetero($C_{4-12}$)bicycloaryl.

In another variation of the immediate above embodiment, the intermediate compounds of the invention are of the formula:

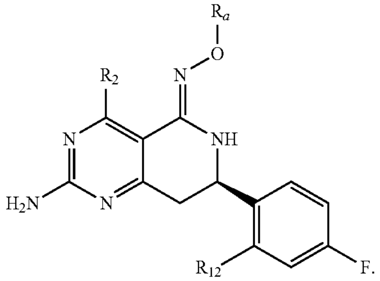

In some variations of the above embodiment and variations of the compounds of the invention, $R_a$ is hydrogen. In other variations, $R_a$ is methyl. In other variations, $R_a$ is a protecting group selected from the group consisting of (($C_{1-6}$)$_3$alkyl) silyl, ((($C_{1-6}$)alkyl)$_{3-n}$)phenyl$_n$)silyl where n is 0-3, benzyl, and tetrahydropyranyl. In still other variations, $R_a$ is selected from the group consisting trimethylsilyl, triethylsilyl, triisopropylsilyl, tert-butyldimethylsilyl, and tert-butyldiphenylsilyl. In still other variations, $R_a$ is tert-butyldimethylsilyl. In still other variations, $R_a$ is trimethylsilyl. In still other variation, $R_a$ is benzyl. In yet still other variations, $R_a$ is tetrahydropyranyl.

In some variations of the above embodiment and variations of the compounds of the invention, $R_{12}$ is phenyl or hetero ($C_{1-5}$)aryl, each unsubstituted or substituted with said 1-3 substituents. In yet still other variations, $R_{12}$ is selected from the group consisting of halo,

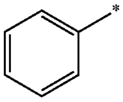 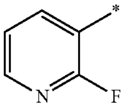 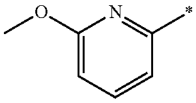
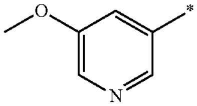 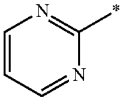 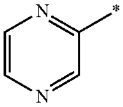
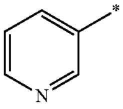 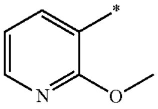 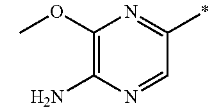
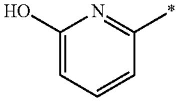 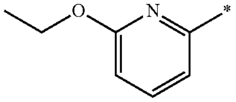
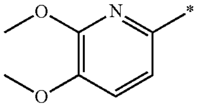 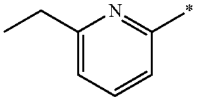
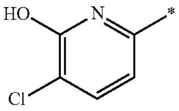 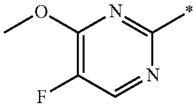
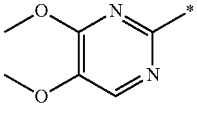 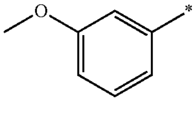

-continued

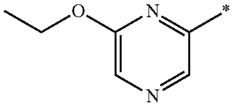 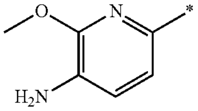
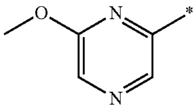 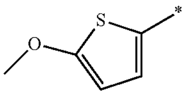
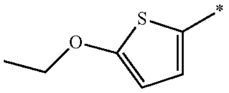 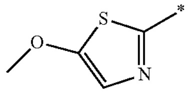
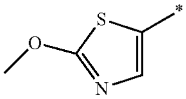 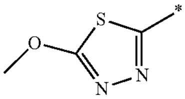
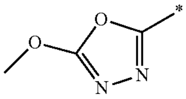 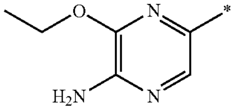
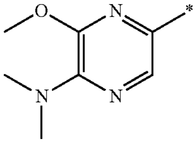 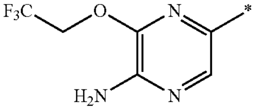
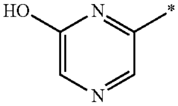 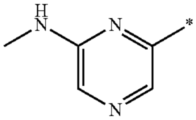
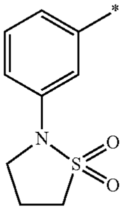 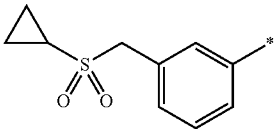
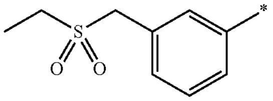
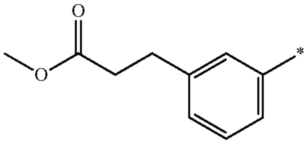
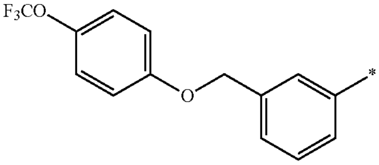
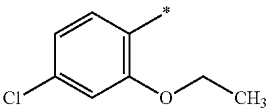
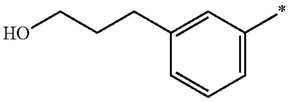

-continued

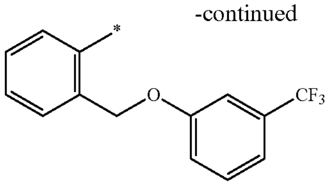

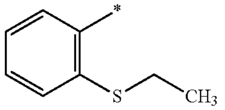

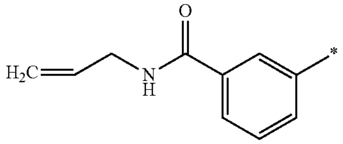

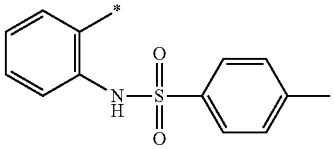

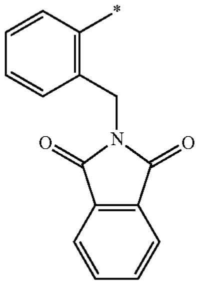

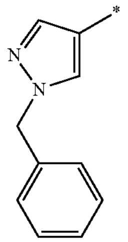

.

In still other variations, $R_{12}$ is selected from the group consisting of bromo,

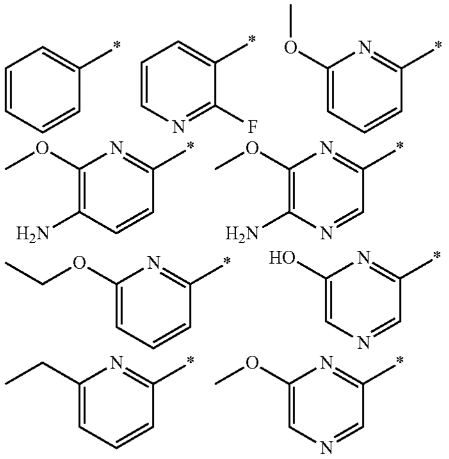

In still other variations, $R_{12}$ is

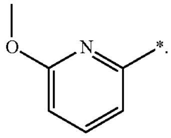

.

Particular examples of intermediate compounds according to the present invention include, but are not limited to:

(R,Z)-2-amino-7-(2-bromo-4-fluorophenyl)-4-methyl-7,8-dihydropyrido[4,3-d]pyrimidin-5(6H)-one oxime;

(R,Z)-2-amino-7-(2-bromo-4-fluorophenyl)-4-methyl-7,8-dihydropyrido[4,3-d]pyrimidin-5(6H)-one O-tert-butyldimethylsilyl oxime;

(R,Z)-2-amino-7-(4-fluoro-2-(6-methoxypyridin-2-yl)phenyl)-4-methyl-7,8-dihydropyrido[4,3-d]pyrimidin-5(6H)-one oxime;

(R,Z)-2-amino-7-(2-bromo-4-fluorophenyl)-4-methyl-7,8-dihydropyrido[4,3-d]pyrimidin-5(6H)-one O-2-((S)-2,2-dimethyl-1,3-dioxolan-4-yl)ethyl oxime;

(R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime;

(R,Z)-2-amino-7-(2-bromo-4-fluorophenyl)-4-methyl-7,8-dihydropyrido[4,3-d]pyrimidin-5(6H)-one O—((R)-2,2-dimethyl-1,3-dioxolan-4-yl)methyl oxime;

(R,Z)-2-amino-7-(2-bromo-4-fluorophenyl)-4-methyl-7,8-dihydropyrido[4,3-d]pyrimidin-5(6H)-one O—(R)-2,3-dihydroxypropyl oxime;

(R,Z)-2-(2-amino-7-(2-bromo-4-fluorophenyl)-4-methyl-7,8-dihydropyrido[4,3-d]pyrimidin-5(6H)-ylideneaminooxy)acetamide;

(R,Z)-2-(2-amino-7-(2-bromo-4-fluorophenyl)-4-methyl-7,8-dihydropyrido[4,3-d]pyrimidin-5(6H)-ylideneaminooxy)-N-methylacetamide; and (R,Z)-2-(2-amino-7-(2-bromo-4-fluorophenyl)-4-methyl-7,8-dihydropyrido[4,3-d]pyrimidin-5(6H)-ylideneaminooxy)-N,N-dimethylacetamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may present as a single stereoisomer.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting HSP90 comprising contacting HSP90 with a compound of any one of the above embodiments and variations.

In yet another of its aspects, there is provided a method of inhibiting HSP90 comprising causing a compound of any one of the above embodiments and variations to be present in a subject in order to inhibit HSP90 in vivo.

In a further of its aspects, there is provided a method of inhibiting HSP90 comprising administering a first compound to a subject that is converted in vivo to a second compound wherein the second compound inhibits HSP90 in vivo, the second compound being a compound according to any one of the above embodiments and variations.

In another of its aspects, there is provided a method of treating a disease state for which HSP90 possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which HSP90 possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which HSP90 possesses activity that contributes to the pathology and/or symptomology of the disease state, the method comprising administering a first compound to a subject that is converted in vivo to a second compound wherein the second compound inhibits HSP90 in vivo, the second compound being a compound according to any one of the above embodiments and variations.

In one variation of each of the above methods, the disease state is selected from the group consisting of cancer, inflammation, inflammatory bowel disease, psoriasis, arthritis, and transplant rejection.

In one variation of each of the above methods, the disease state is cancer. The cancer is selected from the group consisting of squamous cell carcinoma, astrocytoma, Kaposi's sarcoma, glioblastoma, non small-cell lung cancer, bladder cancer, head and neck cancer, melanoma, ovarian cancer, prostate cancer, breast cancer, small-cell lung cancer, glioma, colorectal cancer, genitourinary cancer, gastrointestinal cancer, renal cancer, hematological cancers, non-Hodgkin's lymphoma, lymphoma, multiple myeloma, leukemia (including acute myelogenous leukemia, chronic myelogenous leukemia, chronic lymphocytic leukemia), myelodysplastic syndrome, and mesothelioma.

In one variation of each of the above methods, the HSP90 is an HSP90a. In another variation, the HSP90 is an HSP9013.

Salts, Hydrates, and Prodrugs of HSP90 Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfate, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine) It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen containing groups may be quaternized with such agents as ($C_{1-4}$) alkyl halides, e.g., methyl, ethyl, iso-propyl and tert-butyl chlorides, bromides and iodides; di($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al., (1994), *Bioorganic and Medicinal Chemistry Letters*, Vol. 4, p. 1985.

Protected derivatives of compounds of the present invention can also be made. Examples of techniques applicable to the creation of protecting groups and their removal can be found in P. G. M. Wuts and T. W. Greene in "*Greene's Protective Groups in Organic Synthesis*" 4th edition, John Wiley and Sons, 2007.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Uses of the Compounds of the Invention

One set of indications that HSP90 inhibitors of the present invention may be used to treat are those involving undesirable or uncontrolled cell proliferation. Such indications include benign tumors, various types of cancers such as primary tumors and tumor metastasis, restenosis (e.g. coronary, carotid, and cerebral lesions), abnormal stimulation of endothelial cells (atherosclerosis), insults to body tissue due to surgery, abnormal wound healing, diseases that produce fibrosis of tissue, repetitive motion disorders, disorders of tissues that are not highly vascularized, proliferative responses associated with organ transplants, neurodegenerative disorders including Parkinson's, Alzheimer's, Huntington's and prion-related disease, inflammation and inflammation related disorders such as pain, headaches, fever, arthritis, asthma, bronchitis, tendonitis, eczema, inflammatory bowel disease, and the like, and diseases dependent on angiogenesis such as, cancer, arthritis, diabetic retinopathy, age associated macular degeneration (AMD) and infectious diseases in particular fungal infections, viral diseases including but not limited to diseases caused by hepatitis B virus (HBV), hepatitis C virus (HCV) and herpes simplex virus type-1 (HSV-1), cardiovascular and central nervous system diseases[3,4,5,6,7].

Generally, cells in benign tumors retain their differentiated features and do not divide in a completely uncontrolled manner. A benign tumor is usually localized and non-metastatic. Specific types of benign tumors that can be treated using HSP90 inhibitors of the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In the case of malignant tumors, cells become undifferentiated, do not respond to the body's growth control signals, and multiply in an uncontrolled manner. Malignant tumors are invasive and capable of spreading to distant sites (metastasizing). Malignant tumors are generally divided into two categories: primary and secondary. Primary tumors arise directly from the tissue in which they are found. Secondary tumors, or metastases, are tumors that originated elsewhere in the body but have now spread to distant organs. Common routes for metastasis are direct growth into adjacent structures, spread through the vascular or lymphatic systems, and tracking along tissue planes and body spaces (peritoneal fluid, cerebrospinal fluid, etc.).

Specific types of cancers or malignant tumors, either primary or secondary, that can be treated using the HSP90 inhibitors of the present invention include, but are not limited to, leukemia, breast cancer, genitourinary cancer, skin cancer, bone cancer, prostate cancer, liver cancer, lung cancer, brain cancer, cancer of the larynx, gall bladder, pancreas, rectum, parathyroid, thyroid, adrenal, neural tissue, bladder, head and neck, colon, stomach, colorectal, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, non small-cell lung cancer, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, gastrointestinal cancer, hematological cancers, myelodysplastic syndrome, mycosis fungoide, rhabdomyosarcoma, astrocytoma, non-Hodgkin's lymphoma, Kaposi's sarcoma, osteogenic and other sarcoma, malignant hypercalcemia, renal cell tumor, polycythermia vera, adenocarcinoma, glioblastoma multiforma, glioma, leukemia (including acute myelogenous leukemia, chronic myelogenous leukemia, chronic lymphocytic leukemia), lymphomas, malignant melanomas, epidermoid carcinomas, and other carcinomas and sarcomas.

The HSP90 inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue include emphysema. Repetitive motion disorders that may be treated using the present invention include carpal tunnel syndrome. An example of a cell proliferative disorder that may be treated using the invention is a bone tumor.

Proliferative responses associated with organ transplantation that may be treated using HSP90 inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, scleritis, periphigoid radial keratotomy, neovascular glaucoma and retrolental fibroplasia, syphilis, *Mycobacteria* infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using HSP90 inhibitors of the present invention. Chronic inflammation depends on continuous formation of capillary sprouts to maintain an influx of inflammatory cells. The influx and presence of the inflammatory cells produce granulomas and thus maintains the chronic inflammatory state Inhibition of angiogenesis using an HSP90 inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by HSP90 inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using HSP90 inhibitors according to the present invention to inhibit angiogenesis, such granulomas formation can be inhibited. Psoriasis, also a chronic and recurrent inflammatory disease, is characterized by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using HSP90 inhibitors according to the present invention alone or in conjunction with other anti-RA agents may prevent the formation of new blood vessels necessary to maintain the chronic inflammation and provide the RA patient relief from the symptoms.

Combination Therapy

A wide variety of therapeutic agents may have a therapeutic additive or synergistic effect with HSP90 inhibitors according to the present invention. Combination therapies that comprise one or more compounds of the present invention with one or more other therapeutic agents can be used, for example, to: 1) enhance the therapeutic effect(s) of the one or more compounds of the present invention and/or the one or more other therapeutic agents; 2) reduce the side effects exhibited by the one or more compounds of the present invention and/or the one or more other therapeutic agents; and/or 3) reduce the effective dose of the one or more compounds of the present invention and/or the one or more other therapeutic agents. It is noted that combination therapy is intended to cover when agents are administered before or after each other (sequential therapy) as well as when the agents are administered at the same time.

Examples of such therapeutic agents that may be used in combination with HSP90 inhibitors include, but are not limited to, anti-cell proliferation agents, anticancer agents, alkylating agents, antibiotic agents, antimetabolic agents, hormonal agents, plant-derived agents, and biologic agents.

Anti-cell proliferation agents are those which inhibit undesirable and uncontrolled cell proliferation. Examples of anti-cell proliferation agents that may be used in conjunction with the HSP90 inhibitors of the present invention include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline, beta-aminopropionitrile fumarate, 4-propyl-5-(4-pyridinyl)-2(3H)-oxazolone, methotrexate, mitoxantrone, heparin, interferons, 2 macroglobulin-serum, chimp-3, chymostatin, beta-cyclodextrin tetradecasulfate, eponemycin; fumagillin, gold sodium thiomalate, d-penicillamine (CDPT), beta-1-anticollagenase-serum, alpha-2-antiplasmin, bisantrene, lobenzarit disodium, n-(2-carboxyphenyl-4-chloroanthronilic acid disodium or "CCA", thalidomide, angostatic steroid, cargboxynaminolmidazole, metalloproteinase inhibitors such as BB94. Other anti-angiogenesis agents that may be used include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) *Nature Medicine* 5:1359-1364.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including an HSP90 inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including an HSP90 Inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including an HSP90 inhibitor and an antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, and flutamide), aromatase inhibitors (e.g., aminoglutethimide, anastrozole and tetrazole), ketoconazole, goserelin acetate, leuprolide, megestrol acetate and mifepristone. Combination therapy including an HSP90 inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), and taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including an HSP90 inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including an HSP90 inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with HSP90 inhibitors include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with an HSP90 inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with an HSP90 inhibitor to reduce chemotherapy-induced myelopoietic toxicity.

Other immuno-modulating agents other than cytokines may also be used in conjunction with an HSP90 inhibitor to inhibit abnormal cell growth. Examples of such immuno-modulating agents include, but are not limited to *bacillus* Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including HSP90 inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant $CD20^+$ pre-B and mature B cells. RITUXAN® is used as single agent for the treatment of patients with relapsed or refractory low-grade or follicular, $CD20^+$, B cell non-Hodgkin's lymphoma. Combination therapy including an HSP90 inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2. DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 are found in wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including an HSP90 inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancers), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, *bacillus* Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

Compositions Comprising HSP90 Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The HSP90 inhibitors and compositions comprising them may be administered or coadministered in any conventional dosage form. Co-administration in the context of this invention is intended to mean the administration of more than one therapeutic agent, one of which includes a HSP90 inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington: The Science and Practices of Pharmacy, Lippincott Williams, and Wilkins Publisher, $21^{st}$ edition, 2005. The composition or formulation to be administered will, in any event, contain a sufficient quantity of an inhibitor of the present invention to reduce HSP90 activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more HSP90 inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose, and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol, and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate, and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate, and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the HSP90 inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The HSP90 inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined C. Lyophilized Powders The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a HSP90 inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Formulation for Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The HSP90 inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the HSP90 inhibitor alone or in combination with other pharmaceutically acceptable excipients can also be administered.

E. Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Dosage, Host and Safety

The compounds of the present invention are stable and can be used safely. In particular, the compounds of the present invention are useful as HSP90 inhibitors for a variety of subjects (e.g., humans, non-human mammals and non-mammals).

The optimal dose may vary depending upon such conditions as, for example, the type of subject, the body weight of the subject, on the severity of the condition, the route of administration, and specific properties of the particular compound being used. Generally, acceptable and effective daily doses are amounts sufficient to effectively slow or eliminate the condition being treated. Typically, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Kits and Articles of Manufacture Comprising HSP90 Inhibitors

The invention is also directed to kits and other articles of manufacture for treating diseases associated with HSP90. It is noted that diseases are intended to cover all conditions for which the HSP90 possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Preparation of HSP90 Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see P. G. M. Wuts and T. W. Greene in "*Greene's Protective Groups in Organic Synthesis*" 4th edition, John Wiley and Sons, 2007.

Scheme 1: Preparation of dihydroquinazolinone oxime-ether

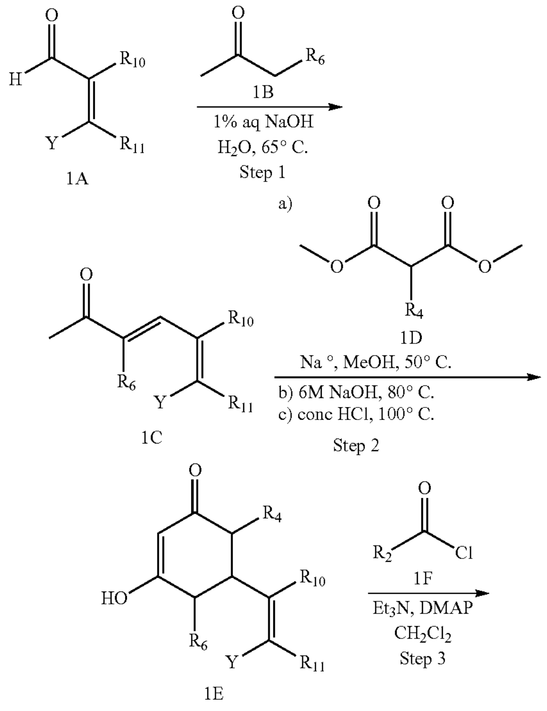

-continued

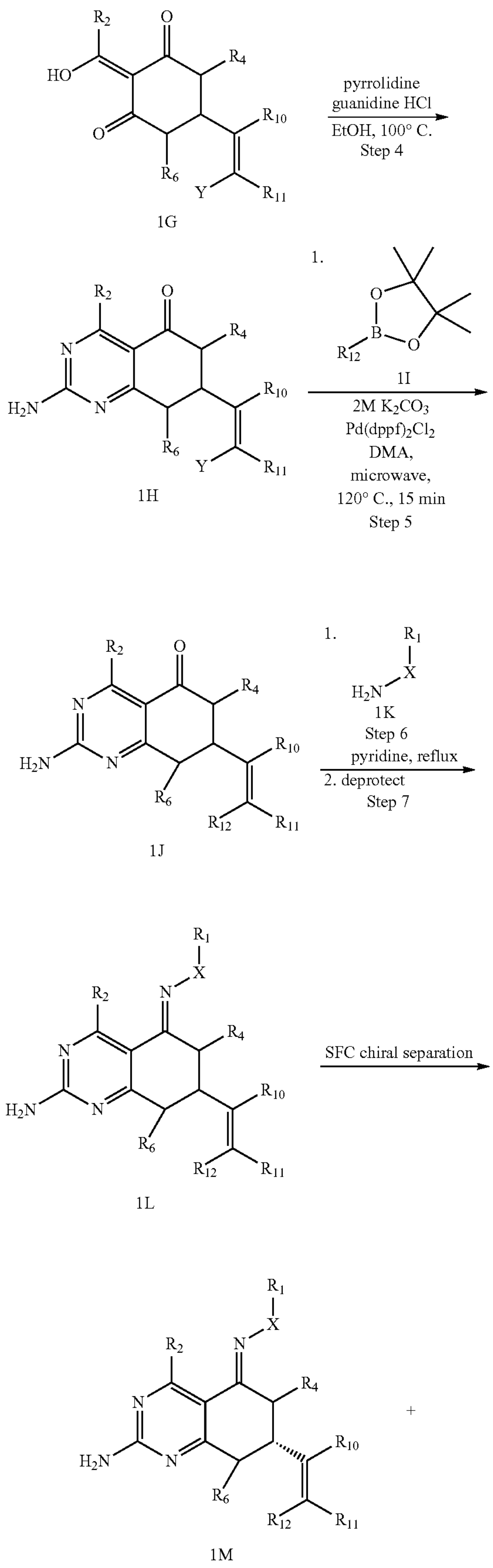

-continued

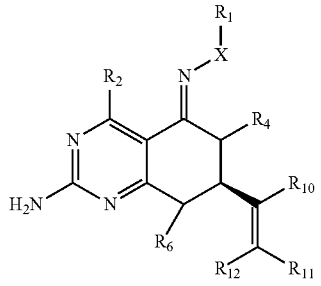

1N where Y is a halogen (Cl, Br, I)
and $R_1$ through $R_{12}$ are as defined in the application Reaction of aldehyde 1A with acetone derivative 1B gives enone 1C (Step 1). Treatment of enone 1C with malonate derivative 1D followed by saponification and decarboxylation gives vinylogous acid 1E (Step 2). C-acylation with acid chloride 1F gives trione 1G (Step 3). Treatment of 1G with guanidine in the presence of pyrrolidine gives dihydroquinazolinone 1H (Step 4). Suzuki coupling with boronic ester 11 (Step 5) gives compound 1J. Reaction with alkoxyamine 1K in refluxing pyridine (Step 6), and, if necessary, deprotection (Step 7), gives oxime ether 1L. Chiral separation via SFC gives both enantiomers, 1M and 1N.

Scheme 2. Preparation of dihydropyridopyrimidinone oxime ether

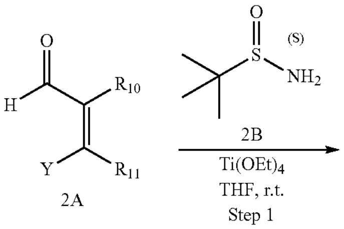

2A

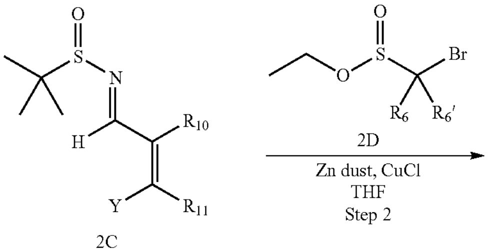

2C

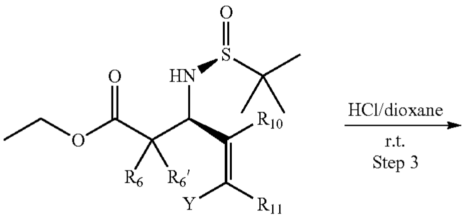

2E

-continued

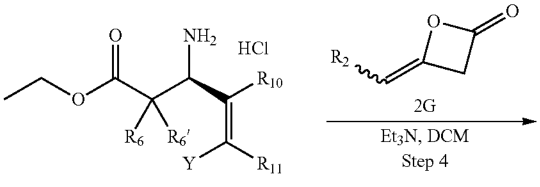

2F

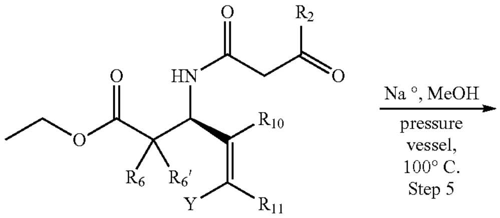

2H

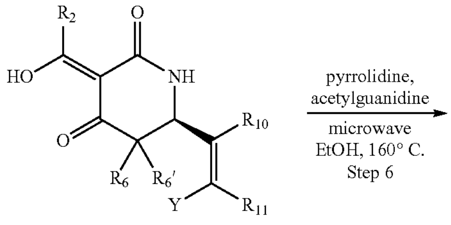

2I

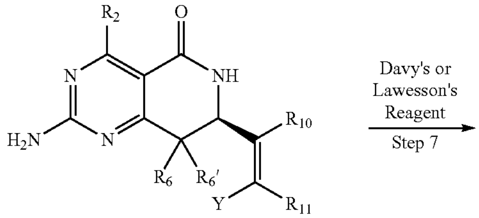

2J

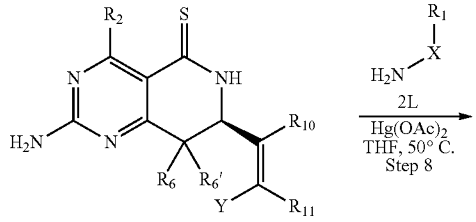

2K

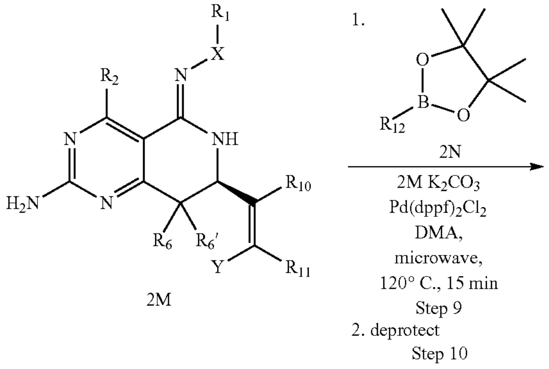

2M

-continued

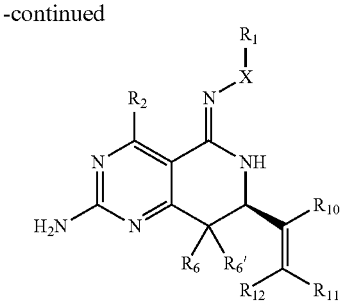

2O where Y is a halogen (Cl, Br, I)
and $R_1$ through $R_{12}$ are as defined in the application The reaction of aldehyde 2A with chiral sulfinamide 2B in the presence of titanium tetraethoxide gives imine 2C (Step 1). Treatment of the sulfinamide with the Reformatsky reagent of 2D exclusively gives chiral sulfinamide 2E (Step 2) which is followed by acid-catalyzed deprotection to give chiral beta-amino acid 2F (Step 3). Reaction of the amine with functionalized diketene 2G gives amide 2H (Step 4) which is followed by treatment with methoxide to form Dieckmann condensation product 21 (Step 5). Reaction of the vinylogous acid 21 with acetylguanidine gives condensation product 2J (Step 6). Conversion of lactam 2J to the thiolactam 2K is effected with a thiolating reagent such as Davy's or Lawesson's reagent (Step 7). Conversion of thiolactam 2K to the amidine 2M is achieved by treatment with substituted alkoxyamine 2L (Step 8). Lastly, Suzuki coupling with boronic ester 2N (Step 9) and, if necessary, deprotection (Step 10), gives final product 20.

Scheme 3: Preparation of dihydroisoquinolinone oxime ether

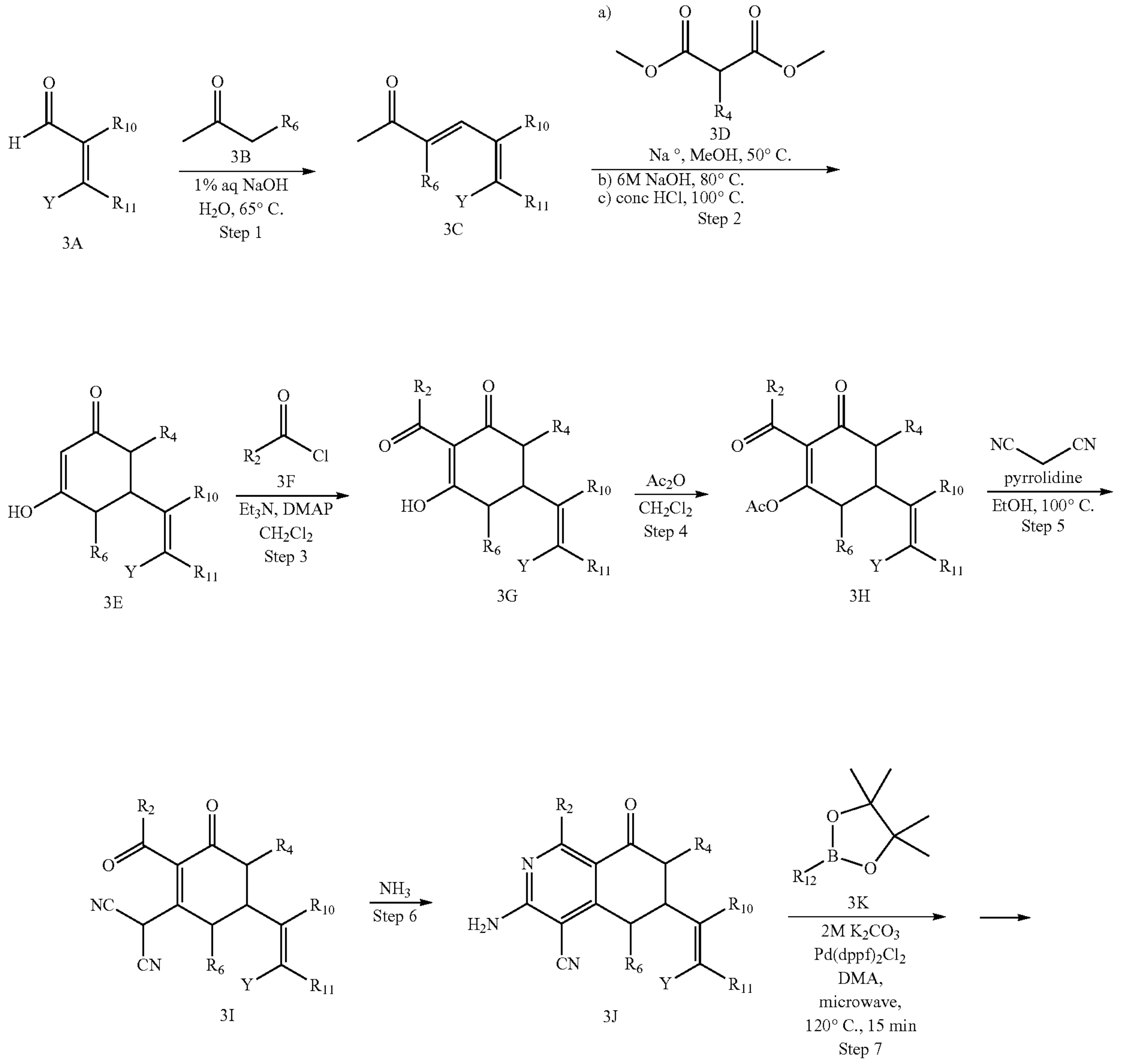

-continued
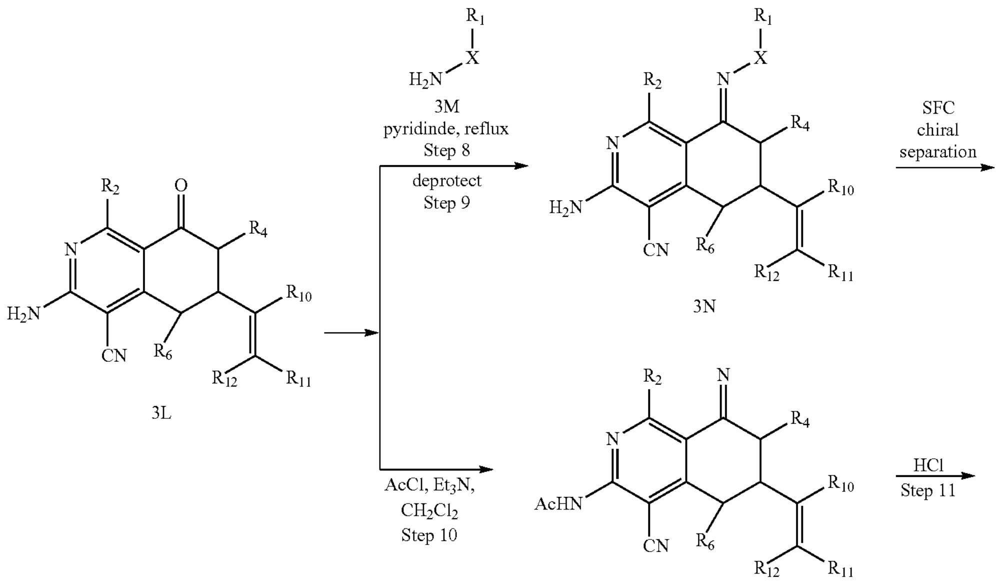
3L
3N
3Q
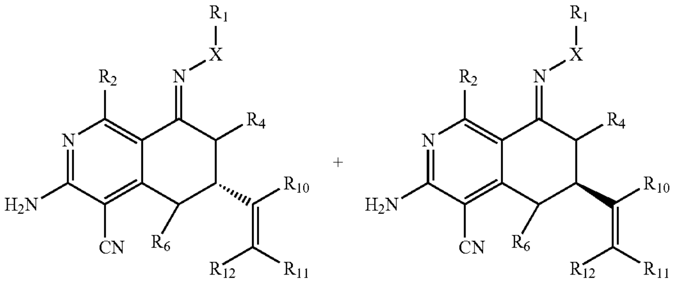
+
3O
3P
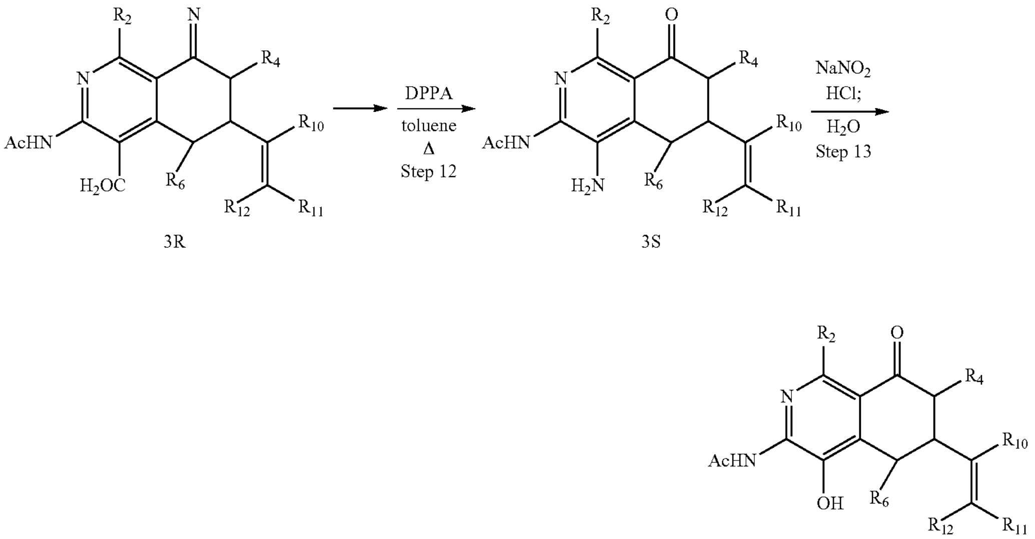
3R
3S
3T
where
Y is a halogen (Cl, Br, I); and
$R_1$ through $R_{12}$ are as defined in the application Reaction of aldehyde 3A with acetone derivative 3B gives enone 3C (Step 1). Treatment of enone 3C with malonate derivative 3D followed by saponification and decarboxylation gives vinylogous acid 3E (Step 2). C-acylation with acid chloride 3F gives trione 3G (Step 3). Acetylation of the vinylogous acid gives 3H (Step 4), which is in turn subjected to malononitrile under basic conditions to give 31 (Step 5). Treatment of bisnitrile 31 with ammonia gives aminopyridine 3J (Step 6). Suzuki coupling with boronic ester 3K (Step 7) gives compound 3L. Reaction with alkoxyamine 3M in refluxing pyridine (Step 8), and, if necessary, deprotection (Step 9), gives oxime ether 3N. Chiral separation via SFC gives both enantiomers, 3O and 3P.

Furthermore, 3L may be manipulated with the following series of transformations to access various $R_7$ moieties. Aminopyridine 3L is protected as its acetyl derivative 3Q (Step 10). Treatment of nitrile 3Q with HCl gives acid 3R (Step 11). Curtius rearrangement induced by diphenylphosphoryl azide (Step 12) gives aniline 3S. Finally aniline 3S can be converted to phenol 3T via Sandmeyer chemistry. Any of the intermediates 3Q, 3R, 3S, and 3T may be functionalized as in Steps 8 and 9 to give the corresponding oxime ethers, followed by chiral separation via SFC.

Scheme 4: Preparation of dihydro-naphthyridinone oxime ether

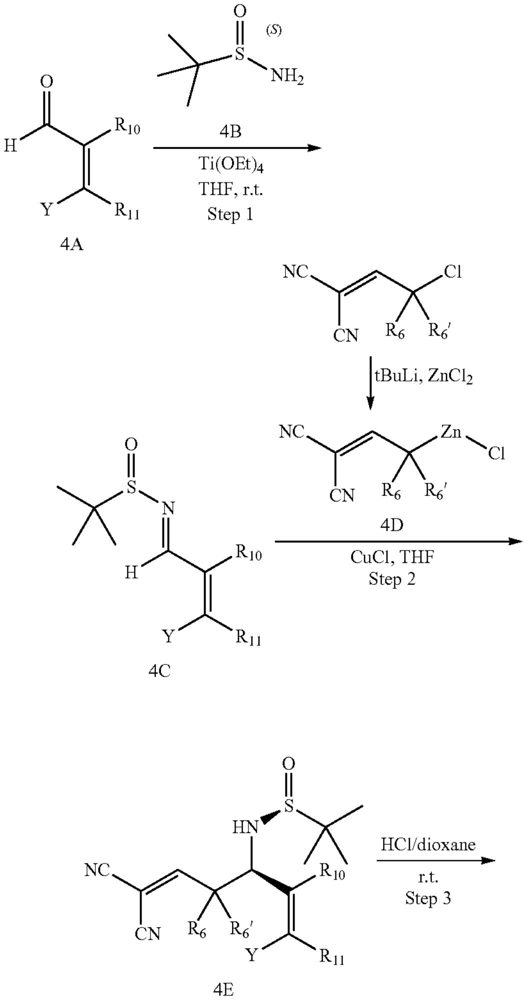

4A 4B 4C 4D 4E

-continued

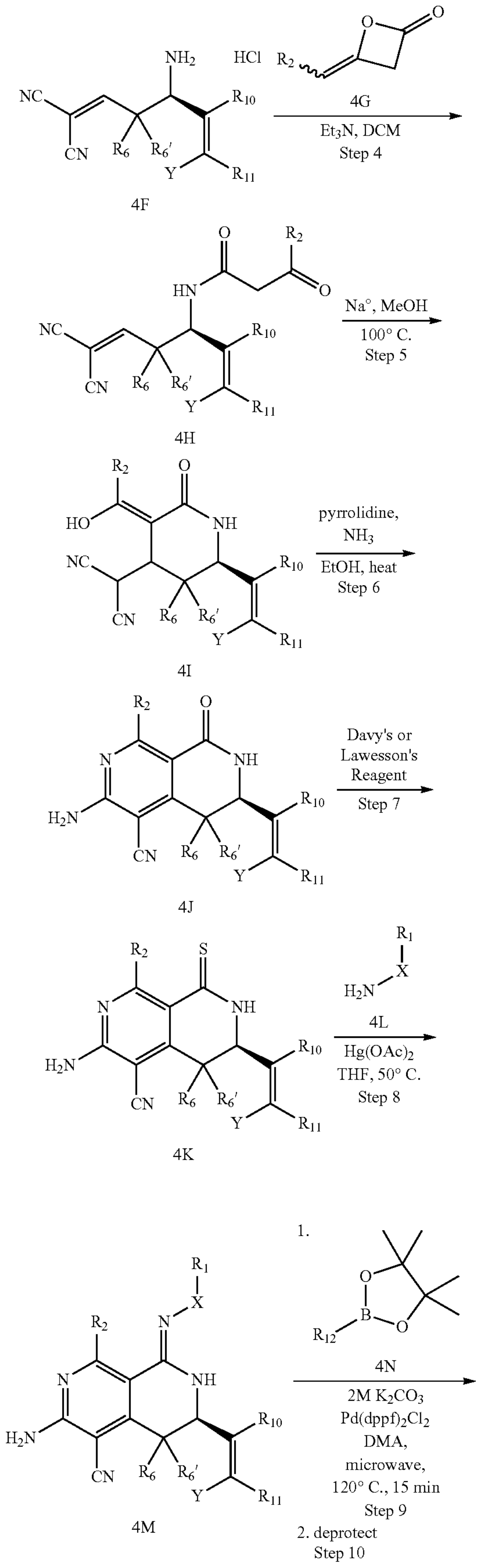

4F 4G 4H 4I 4J 4K 4L 4M 4N

-continued

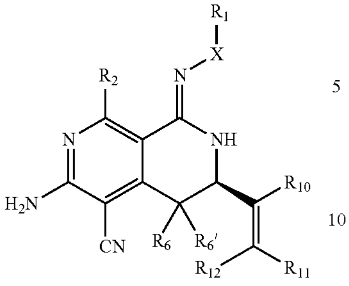

40 where Y is a halogen (Cl, Br, I)
and $R_1$ through $R_{12}$ are as defined in the application The reaction of aldehyde 4A with chiral sulfonamide 4B in the presence of titanium tetraethoxide gives imine 4C (Step 1). Treatment of the sulfinamide with the Reformatsky reagent 4D exclusively gives enantiopure sulfonamide 4E (Step 2) which is followed by acid-catalyzed deprotection to give beta-amino acid 4F (Step 3). Reaction of the amine with functionalized diketene 4G gives amide 4H (Step 4) which is followed by treatment with methoxide to give Dieckmann condensation product 4I (Step 5). After oxidation, reaction of the bisnitrile 4I with ammonia gives condensation product 4J (Step 6). Conversion of lactam 4J to the thiolactam 4K is effected with a thiolating reagent such as Davy's or Lawesson's reagent (Step 7). Conversion of thiolactam 4K to the amidine 4M is achieved by treatment with substituted alkoxyamine 4L (Step 8). Lastly, Suzuki coupling with boronic ester 4N (Step 9) and, if necessary, deprotection (Step 10), gives final product 4O.

Scheme 5: Preparation of dihydropyridopyrimidinone oxime ether

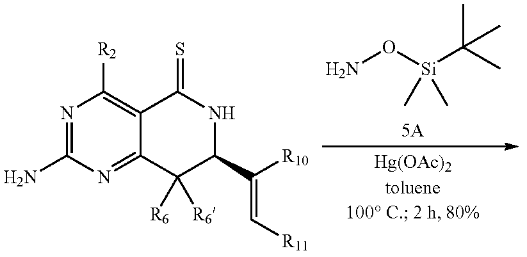

2K

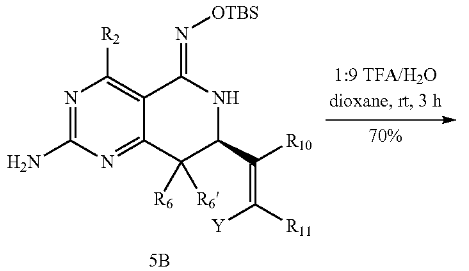

5B

-continued

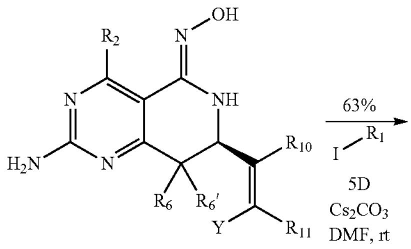

5C

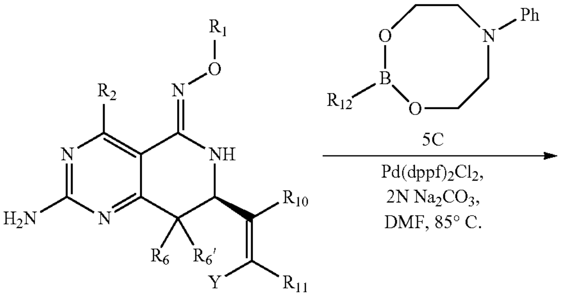

5E

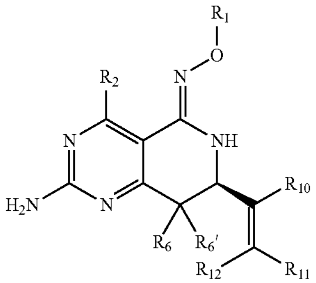

5F where Y is a halogen (Cl, Br, I)
and $R_1$ through $R_{12}$ are as defined in the application The reaction of thiolactam 2K with protected hydroxylamine 5A (e.g., TBS protected) in the presence of mercuric acetate yields amidine 5B, which is followed by acid catalyzed deprotection to give hydroxyl derivative 5C. Alkylation with the appropriate haloalkyl 5D in base, e.g., $Cs_2CO_3$, yields oxime ether 5E, followed by a coupling reaction such as Suzuki coupling with boronic acid 5C, and if necessary deprotection gives product 5F.

Scheme 6: Preparation of dihydro-naphthyridinone oxime ether

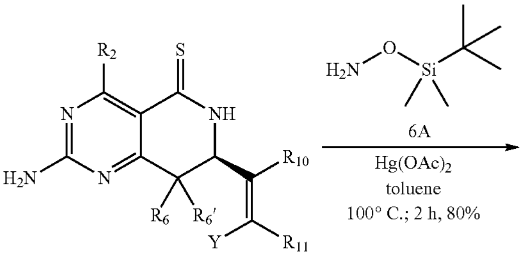

2K

-continued

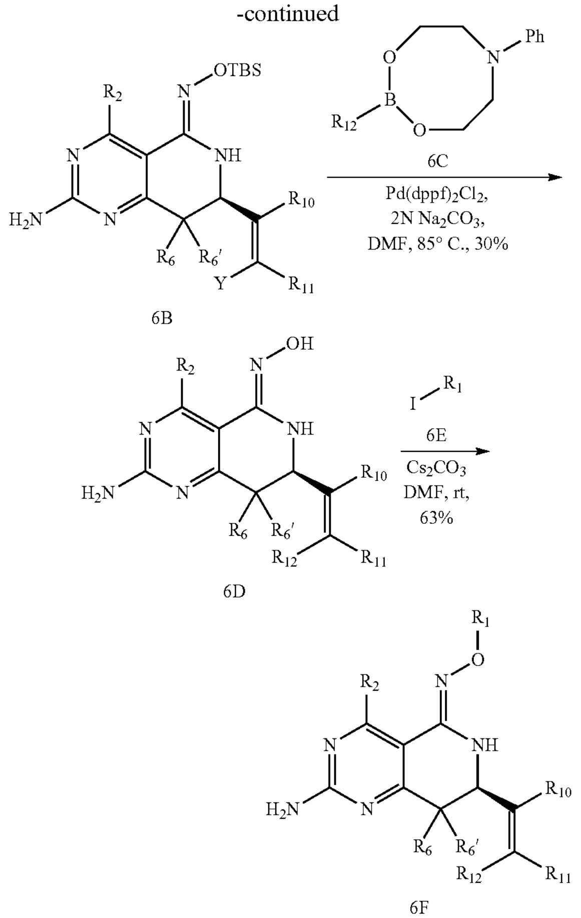

6B

6D

6F where Y is a halogen (Cl, Br, I), and
$R_1$ through $R_{12}$ are as defined in the application The reaction of thiolactam 2K with protected hydroxylamine 6A (e.g., TBS protected) in the presence of a strong thiophile (e.g., mercuric acetate) yields amidine 6B. Arylation reaction (e.g Suzuki coupling) with boronic ester 6C and deprotection to give hydroxyl derivative 6D. Alkylation with the appropriate haloalkyl 6E in base, e.g., $Cs_2CO_3$, gives product 6F.

In each of the above reaction procedures or schemes, the various substituents may be selected from among the various substituents otherwise taught herein.

General Procedures

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in P. G. M. Wuts and T. W. Greene, "*Greene's Protecting Groups in Organic Synthesis*", 4$^{th}$ edition, John Wiley & Sons, Inc. 2007.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

The present invention also provides (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A. The formation of (R,Z)-

2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A is generally carried out by crystallization from a solvent. In practice suitable solvents include chloroform, toluene, acetonitrile, and acetone. Anti-solvents, that is, a solvent or solvents in which the compound is less soluble than in the selected solvent can also be used. The volume of solvent is not critical but should be kept to a minimal amount as a matter of convenience. Optionally, the crystallization may be seeded with Form A. Such processes generally require 2 hours to seven days. It is understood that the terms "crystallize," "crystallizing," and "crystallization" to complete dissolution followed by precipitation and slurry processes that do not involve complete dissolution.

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A can be characterized by X-ray diffraction. A powder X-ray diffractogram of Form A obtained by standard powder X-ray diffraction technique is provided in FIG. 2. Standard powder diffractometers are generally equipped with a copper source, primary beam monochromator, and position sensitive detector. The incident beam is typically collimated using a divergence slit to around 1°. The source generally operated at 40 kV and 30 mA. X-ray powder diffraction data may be collected from 3 degrees to 120 degrees two theta using a step width of 0.02 to 0.04 degrees two theta. The diffractometer can be calibrated with a silicon standard or other suitable standard materials. Many modern diffractometers are also equipped with a goniometer head that can be motorized to permit spinning of the sample during data acquisition. It is recognized that the relative intensity of X-ray diffraction peaks can be dependent on preferred orientation and other factors. Therefore, a sample of Form A may require processing to mitigate such factors, such as grinding the sample in an agate mortar and pestle or other measures. It is understood that differences in relative intensity of the diffraction peaks does not preclude an acquired pattern from being consistent with (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl benzoate Form A. Further it is also understood that only a subset of the peaks shown in FIG. 2, in some instances as few as one peak, are required to identify (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl benzoate Form A.

Figure 3:
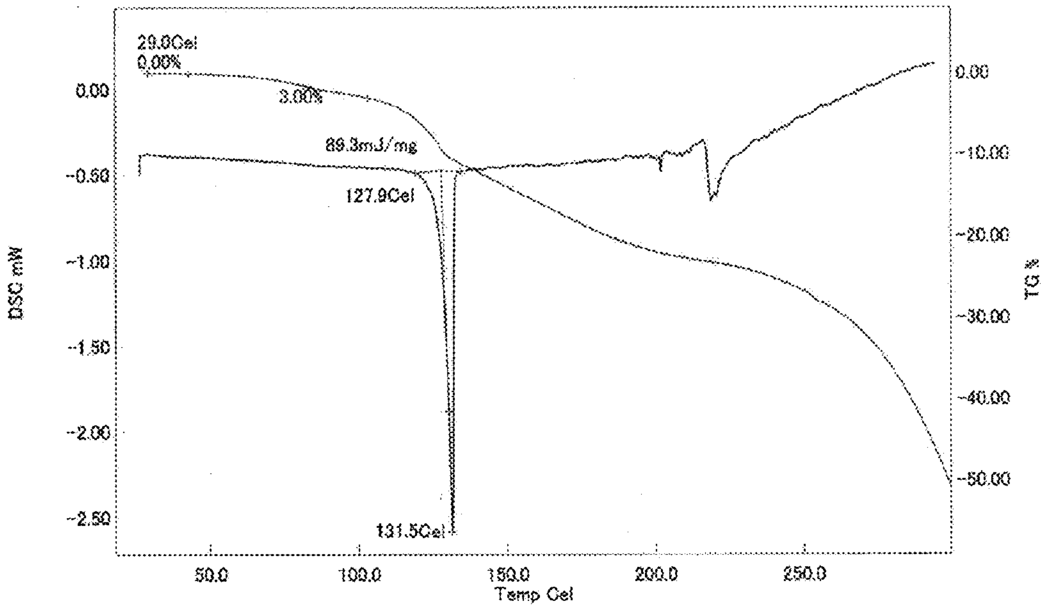
FIG. 3 shows the differential scanning calorimetry trace and the thermogravimetric trace of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A.

Form A can also be characterized by thermal analysis, typically differential scanning calorimetry (DSC) and thermogravimetry. FIG. 3 shows DSC and therogravimetry thermograms of Form A. The DSC thermogram shows a single endothermic event at 128° C. which was consistent with a melt.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| μL (microliters) | Ac (acetyl) |
| atm (atmosphere) | ATP (Adenosine Triphosphatase) |
| BOC (tert-butyloxycarbonyl) | BOP (bis(2-oxo-3-oxazolidinyl)phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| $Et_2O$ (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | r.t. (ambient temperature) |
| SPA (Scintillation Proximity Assay) | TBAF (tetra-n-butylammonium fluoride) |
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | Brij35 (polyoxyethyleneglycol dodecyl ether) |

All references to ether or $Et_2O$ are to diethyl ether; and brine refers to a saturated aqueous solution of NaCl. Unless otherwise indicated, all temperatures are expressed in ° C. (degrees Centigrade). All reactions are conducted under an inert atmosphere at r.t. unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E Merck silica gel plates (60E-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-23, John Wiley and Sons, New York, N.Y., 2006; Rodd's Chemistry of Carbon Compounds, vols. 1-5 and supps., Elsevier Science Publishers, 1998; Organic Reactions, vols. 1-68, John Wiley and Sons, New York, N.Y., 2007; March J.: Advanced Organic Chemistry, 5th ed., 2001, John Wiley and Sons, New York, N.Y.; and Larock: Comprehensive Organic Transformations, 2$^{nd}$ edition, John Wiley and Sons, New York, 1999. The entire disclosures of all documents cited throughout this application are incorporated herein by reference.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques, Andre Collet, and Samuel H. Wilen, Enantiomers, Racemates and Resolutions, John Wiley & Sons, Inc. (1981).

Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, and Samuel H. Wilen, Enantiomers, Racemates and Resolutions, John Wiley & Sons, Inc. (1981).

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 100. In particular variations, the flow rate for separation can be 70 mL/min, the injection volume up to 2 mL, and the inlet pressure set at 130 bar. Stacked injections can be applied to increase the efficiency.

Descriptions of the syntheses of particular compounds according to the present invention based on the above reaction schemes and variations thereof are set forth in the Example section.

Assaying the Biological Activity of the Compounds of the Invention

The inhibitory effect of the compound of the invention on HSP90 may be evaluated by a variety of binding assays and functional assays. It is well known that binding to the N-terminal ATP-binding domain of HSP90 inhibits ATP binding and ATP-dependent chaperone activities, Roe et al. *J. Med. Chem.* 1999 42, 260-266. A variety of in vitro and in vivo binding assays are available in the literature for assessing the affinity of the compounds of the invention on HSP90; e.g., Chiosis et al. *Chemistry & Biology* 2001 8: 289-299, Carreras et al. *Anal Biochem* 2003 317(1): 40-6; Kim et al. *J Biomol Screen* 2004 9(5): 375-81; and Zhou et al. *Anal Biochem* 2004 331(2): 349-57.

Example A-1 below provides an in vitro competition fluorescence polarization assay in which a test compound competes with a fluorescent probe for binding to the binding domain of human recombinant HSP90. The reaction can be followed kinetically using fluorescence (excitation λ=485 nm; emission λ=538 nm). The binding affinity of the test compound to HSP90 is determined by the changes in the polarized fluorescence; the intensity of the polarized fluorescence is proportional to the fraction of bound probe. A novel small molecule fluorescence probe, (S,E)-5-(2-(2-amino-7-(4-fluoro-2-(6-methoxypyridin-2-yl)phenyl)-4-methyl-7,8-dihydroquinazolin-5(6H)-ylideneaminooxy)ethylcarbamoyl)-2-(6-hydroxy-3-oxo-3H-xanthen-9-yl)benzoic acid (TSD-FP probe) was specifically developed for the assay. Inhibition constants ($IC_{50}$) may be calculated by non-linear curve fitting of the compound concentrations and fluorescence intensities to the standard $IC_{50}$ equation. As reference, the $IC_{50}$ values by this assay for the two known HSP90 inhibitors geldanamycin (GM) and 17-allylamino,17-demethoxygeldanamycin (17-AAG) after one hour incubation with the enzyme and the TSD-FP probe were 90 nM and 400 nM, respectively. Using the procedure described in Example A-1, some of the exemplified compounds were shown to have HSP90 binding affinity at an $IC_{50}$ of less than 10 μM, some others less than about 1 μM, and most others of the compounds have an $IC_{50}$ value of less than about 0.1 μM. The $IC_{50}$ values of the exemplified compounds of the present invention are given in Table 1.

The inhibitory effect of the compounds of the invention against HSP90 in live cells may be evaluated by measuring cell viability. Example A-2 described a cell viability assay where exponentially growing tumor cells were exposed to a range of drug concentrations. After the drug treatment, the viability of the cells was measured by the conversion of tetrazolium salts MTS (3-[4,5, dimethylthiazol-2-yl]-5-[3-carboxymethoxy-phenyl]-2-[4-sulfophenyl]-2H-tetrazolium, inner salt), (Promega, Madison, Wis.) by metabolically active cells. Further, the selected cancer cell panel includes BT-474, HT-29, K-562, and MKN-45 cells each of which represents a different cancer type and a well understood route of oncogenic transformation.

Downstream effects of HSP90 inhibition can be evaluated based on the induction of HSP70 and on the function and stability of various steroid receptors and signaling proteins including, e.g., HER2/ERBB2. HSP70 induction is a hallmark of HSP90 inhibition. HSP70 as an ATP dependent heat shock protein itself will be transcriptionally up-regulated in response to misfolded, denatured or aggregated proteins. As HSP90 function becomes compromised, HSP70 is induced in direct response to HSP90 client protein changes within the cell. Guo et al. *Cancer Res* 2005 65(22) 10536. Example A-3 provides a method to quantify HSP70 induction by monitoring the non-infrared luminescence of β-galactosidase, and determine the $EC_{50}$ values of the test compounds for HSP70β/β-galactosidase induction.

The depletion of HER-2/ERBB2 oncoprotein is also a hallmark of HSP90 inhibition. Sain et al. *Mol Cancer Ther* 2006 5(5) 1197; Sharp et al. *Mol Cancer Ther* 2007 6(4) 1198. HER-2 uses HSP90 for maturation; perturbations in HSP90 function lead to misfolded proteins that ultimately will be sent for ubiquitination and proteasomal degradation. Compounds of the present invention induce degradation of these molecules, which can be measured using well known antibody techniques such as immunoblotting, radioimmunoassays, Western blotting, immunoprecipitation, enzyme-linked immunosorbant assays (ELISA), and derivative techniques that make use of antibodies directed against HER2. Example A-4 provides a Western blotting procedure for the determination of the $EC_{50}$ value of the test compounds for depletion of HER2/ERBB2.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

EXAMPLE

Example 1

General Procedure for the Preparation of Oxime Ethers and Analogs

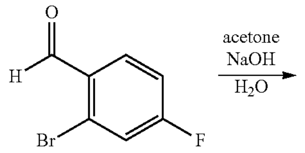

1A

-continued a)

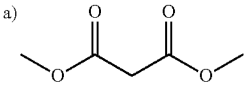

1C

NaOMe, 50° C.

b) 6M NaOH, 80° C.

c) conc HCl, 100° C.

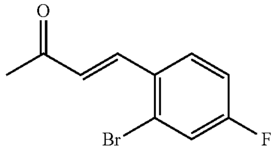

1B

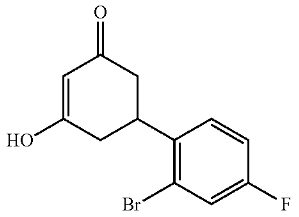

1D $Ac_2O$, $Et_3N$

DMAP, $CH_2Cl_2$

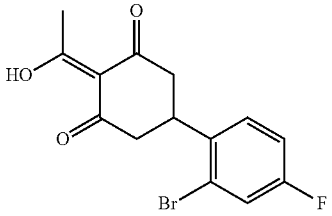

1E dimethylamine, guanidine HCl

EtOH, 100° C.

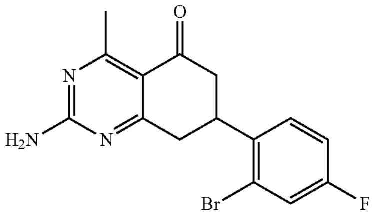

1F

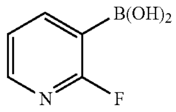

1G $Pd(Ph_3P)_4$ aq. $K_2CO_3$

DME, 100° C.

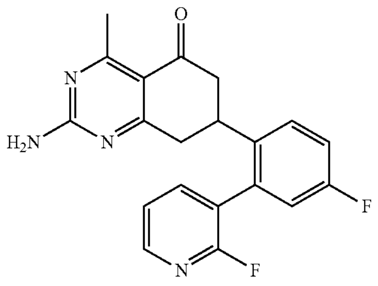

1H method A or B $NH_2—O—R_1$

1I

-continued

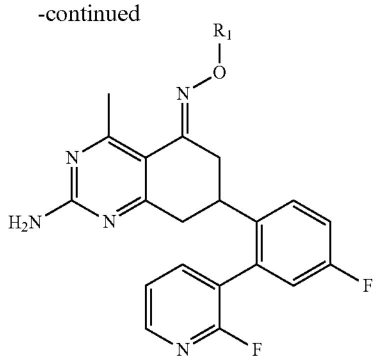

1J

A. (E)-4-(2-Bromo-4-fluorophenyl)but-3-en-2-one (1B)

To a 500 mL recovery flask was added 2-bromo-4-fluorobenzaldehyde (1A, 10.0 g, 49.3 mmol, 1.0 eq.) and acetone (22.9 g, 394 mmol, 8.0 eq.). The mixture was cooled to 0° C. in an ice bath. $H_2O$ (200 mL) was added and the mixture became a thick suspension. Solid NaOH (2.16 g, 54.2 mmol, 1.1 eq.) was added and the reaction was gradually warmed to room temperature and stirred overnight. The reaction was acidified with 1N HCl and extracted with EtOAc (3×100 mL). The organic phases were combined and washed with saturated aqueous NaCl. The organic phase was dried over anhydrous $Na_2SO_4$, filtered, and concentrated to give a dark yellow oil that was carried on to the next step without further purification (11.9 g, 99%). ESI-MS: m/z 243.2 $(M+H)^+$.

B. 5-(2-Bromo-4-fluorophenyl)-3-hydroxycyclohex-2-enone (1D)

To a 500 mL recovery flask was added (E)-4-(2-bromo-4-fluorophenyl)but-3-en-2-one (1B, 11.9 g, 49.0 mmol, 1.0 eq.) and MeOH (200 mL). Dimethyl malonate (1C, 6.47 g, 49.0 mmol, 1.0 eq.) was added, followed by NaOMe (30% wt in MeOH, 9.6 mL, 51.4 mmol, 1.05 eq.). The reaction mixture was refluxed overnight upon which it was concentrated to a brownish-red solid. The residue was taken up in 1N NaOH (150 mL) and refluxed for 1 h, during which the reaction color proceeded from cloudy-brown, to clear brown, to clear solution with brown precipitate. Concentrated HCl was carefully added until the mixture was acidic by pH paper. The reaction mixture was diluted with EtOAc (200 mL) and washed with saturated aqueous NaCl. The aqueous phase was extracted with EtOAc (lx 75 mL). The organic phase was dried over anhydrous $Na_2SO_4$, filtered, and concentrated to give a foamy orange solid that was carried on to the next step without further purification (14.3 g, 100%). ESI-MS: m/z 285.2 $(M+H)^+$.

C. 5-(2-Bromo-4-fluorophenyl)-2-(1-hydroxyethylidene)cyclohexane-1,3-dione (1E)

To a 500 mL recovery flask was added 5-(2-bromo-4-fluorophenyl)-3-hydroxycyclohex-2-enone (1D) (14.3 g, 50.1 mmol, 1.0 eq.), $CH_2Cl_2$ (200 mL), acetic anhydride (6.65 g, 65.2 mmol, 1.3 eq.), $Et_3N$ (15.22 g, 150 mmol, 3.0 eq.), and DMAP (catalytic amount). The reaction mixture was stirred overnight at room temperature. Monitoring by LC/MS judged the reaction to be complete. The reaction mixture was concentrated and purified via column chromatography (gradient 70% $CH_2Cl_2$/Hex to 100% $CH_2Cl_2$) to yield the product as light yellow foam which later became an oil (3.55 g, 22%). The crude material was used in the next step without further purification. ESI-MS: m/z 327.2 $(M+H)^+$.

D. 2-Amino-7-(2-bromo-4-fluorophenyl)-4-methyl-7,8-dihydroquinazolin-5(6H)-one (1F)

To a 150 mL pressure vessel was added 5-(2-bromo-4-fluorophenyl)-2-(1-hydroxyethylidene)cyclohexane-1,3-dione (1E, 1.12 g, 3.42 mmol, 1.0 eq.), EtOH (30 mL), guanidine hydrochloride (818 mg, 8.56 mmol, 2.5 eq.), and dimethylamine (2.0 M in THF, 10 mL, 20.5 mmol, 6.0 eq.). The vessel was sealed and heated for 72 hours at 100° C. LC/MS determined the reaction to be complete. The reaction was cooled and concentrated to give a pasty gray solid. EtOH (~10 mL) was added to the residue and sonicated to give a suspension. The solid was collected by filtration and rinsed with cold EtOH to give a light-yellow solid (288 mg, 24%). ESI-MS: m/z 350.2 $(M+H)^+$.

E. 2-Amino-7-(4-fluoro-2-(2-fluoropyridin-3-yl)phenyl)-4-methyl-7,8-dihydroquinazolin-5(6H)-one (1H)

To a 10 mL recovery flask was added 2-amino-7-(2-bromo-4-fluorophenyl)-4-methyl-7,8-dihydroquinazolin-5(6H)-one (33 mg, 0.0942 mmol, 1.0 eq.), 2-fluoropyridine-3-boronic acid (27 mg, 0.188 mmol, 2.0 eq.), DME (2 mL), potassium carbonate (2.0M aq., 94 μL, 0.188 mmol, 2.0 eq.), and palladium tetrakis triphenylphosphine (5 mg, 0.00471 mmol, 0.05 eq.). The reaction was refluxed overnight whereupon LC/MS analysis judged the reaction to be complete. The reaction mixture was filtered through Celite and concentrated to a residue. The residue was purified via preparatory-HPLC to give the product white solid (30 mg, 96%). $^1H$ NMR (400 MHz, DMSO-$d_6$) δ ppm 2.67 (dd, J=3.54, 1.77 Hz, 1H) 2.89 (br. s., 1H) 3.06 (t, J=12.51 Hz, 2H) 3.18 (br. s., 1H) 7.18 (dd, J=9.60, 2.78 Hz, 1H) 7.31-7.53 (m, 4H) 7.72 (dd, J=8.84, 5.81 Hz, 1H) 7.98 (ddd, J=9.79, 7.52, 1.89 Hz, 1H) 8.28 (d, J=4.80 Hz, 1H). ESI-MS: m/z 367.3 $(M+H)^+$. ESI-MS: m/z 367.3 $(M+H)^+$.

F. Formation of Oxime Ethers

Oxime ethers may be formed by either Method A or Method B below.

Method A, basic conditions: A solution of 2-amino-7-(4-fluoro-2-(2-fluoropyridin-3-yl)phenyl)-4-methyl-7,8-dihydroquinazolin-5(6H)-one (1H, 0.27 mmol, 1.0 eq.) and the corresponding hydroxylamine 1I (0.54 mmol, 2.0 eq.) in dry pyridine (2 mL) were stirred overnight at 75° C. The mixture was poured into ice water and the resulting precipitate was collected by filtration. The crude solid was recrystallized in hot ethanol to yield pure product 1J as a white solid in 90% yield.

Method B, acidic conditions: A solution of 2-amino-7-(4-fluoro-2-(2-fluoropyridin-3-yl)phenyl)-4-methyl-7,8-dihydroquinazolin-5(6H)-one (1H, 0.27 mmol, 1.0 eq.) in EtOH (3 mL) was stirred under nitrogen. The corresponding hydroxylamine 1I (0.35 mmol, 1.3 eq.) and aqueous HCl (5M, 0.48 mmol, 1.8 eq.) were added and the reaction was heated to reflux for 4 h. The reaction mixture was cooled to room temperature and concentrated. The resulting residue was collected and recrystallized in hot ethanol to obtain pure product 1J as a white or off-white powder in about 90% yield.

Example 2

Preparation of Hydroxylamine Reagents

A. Synthesis of O-(2-methoxyethyl)hydroxylamine (2B)

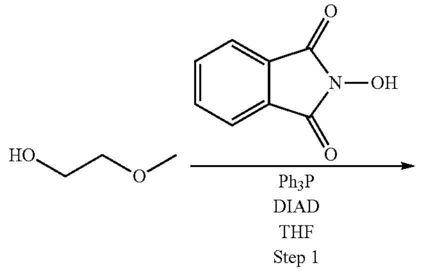

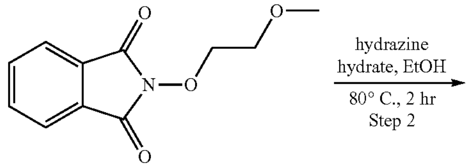

2A

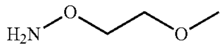

2B

Step 1: 2-methoxyethanol (2.00 g, 26.3 mmol), N-hydroxyphthalimide (4.72 g, 28.9 mmol, 1.1 eq., and triphenylphosphine (7.58 g, 28.9 mmol, 1.1 eq.) were dissolved in 85 mL of dry THF and then the mixture was cooled in an ice bath. Diisopropyl azodicarboxylate (6.91 g, 34.2 mmol, 1.3 eq.) was dissolved in 15 mL of dry THF and was added slowly to the above mixture. The reaction was stirred in the ice bath for 10 minutes and then the ice bath was removed. The reaction then was allowed to stir at room temperature under $N_2$ overnight. The reaction was done by LC/MS and was concentrated to an oil. It was then purified by flash column chromatography using hexane/ethyl acetate 70/30 to give 2-(2-methoxyethoxy)isoindoline-1,3-dione (2A, 5.19 g, 89.2% yield). ESI-MS: m/z 222.3 $(M+H)^+$.

Step 2: 2-(2-methoxyethoxy) isoindoline-1,3-dione (5.18 g, 23.4 mmol) was dissolved in 50 mL of ethanol and hydrazine hydrate (22.7 mL, 468 mmol). The solution was heated for 2 hours in a 80° C. oil bath. The reaction was then cooled to room temperature and a solid precipitated out. This solid was then filtered and the filtrate was concentrated and purified on flash column chromatography using chloroform/methanol 98/2 to give O-(2-methoxyethyl) hydroxylamine (2B, 0.866 g, 36.2% yield). $^1H$ NMR (400 MHz, MeOD) δ ppm 3.36 (s, 3H) 3.52-3.59 (m, 2H) 3.73-3.85 (m, 2H).

B. Synthesis of O-(3-methoxypropyl)hydroxylamine(2D)

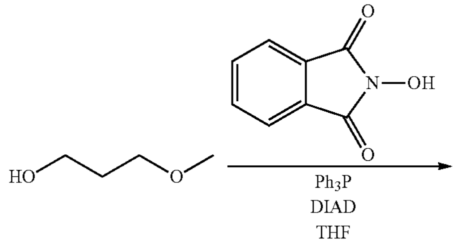

-continued

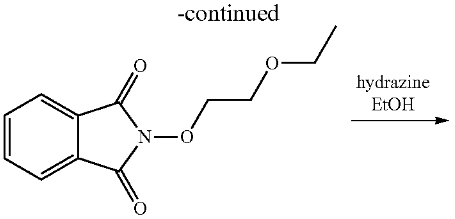

2C

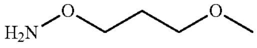

2D 2-(3-Methoxypropoxy)isoindoline-1,3-dione (2C) was prepared from 3-methoxypropan-1-ol and N-hydroxyphthalimide by a procedure analogous to Example 2A, Step 1 (3.71 g, 94.9% yield). ESI-MS: m/z 236.3 $(M+H)^+$.

2C was deprotected as described in Example 2A, Step 2 to yield O-(3-methoxypropyl)hydroxylamine (2D, 0.633 g, 38.1% yield). $^1H$ NMR (400 MHz, MeOD) δ ppm 1.81 (t, J=6.32 Hz, 2H) 3.31 (s, 3H) 3.45 (t, J=6.32 Hz, 2H) 3.70 (t, J=6.32 Hz, 2H). ESI-MS: m/z 106.4 $(M+H)^+$.

C. Synthesis of tert-butyl 2-(aminooxy)ethylcarbamate (2F)

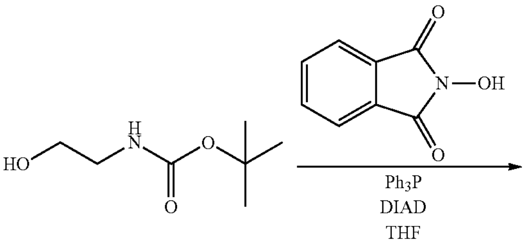

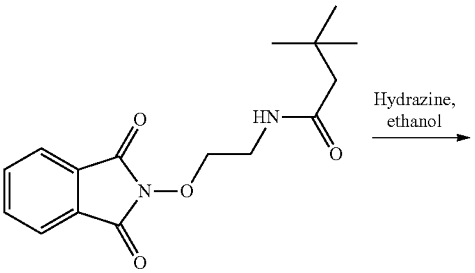

2E

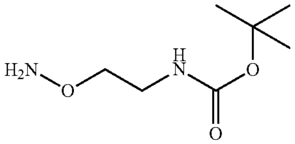

2F tert-Butyl 2-(1,3-dioxoisoindolin-2-yloxy)ethylcarbamate 2E was prepared with quantitative yield from tert-butyl 2-hydroxyethylcarbamate and N-hydroxyphthalimide by a procedure analogous to Example 2A, Step 1. ESI-MS: m/z 329.3 $(M+Na)^+$.

2E was deprotected as previously described in 2A, Step 2 to give tert-butyl 2-(aminooxy)ethylcarbamate (2F, 1.26 g, 58% yield). $^1$H NMR (400 MHz, CHLOROFORM-d) δ ppm 1.45 (s, 9H) 3.37 (q, J=5.31 Hz, 2H) 3.62-3.85 (m, 2H) 4.90 (br. s., 1H) 5.47 (br. s., 2H).

D. Synthesis of O-(pyridine-3-ylmethyl)hydroxylamine (2H)

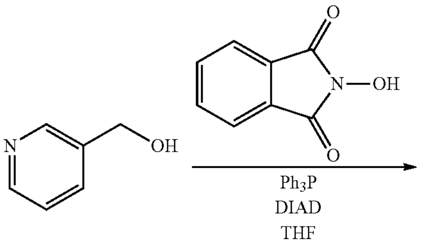

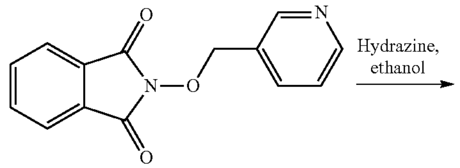

2G

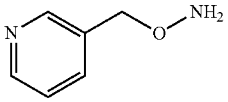

2H

Phthalimide-protected intermediate 2G was prepared from pyridin-3-ylmethanol and N-hydroxyphthalimide by a procedure analogous to Example 2A, Step 1 (3.22 g, 81.3% yield). ESI-MS: m/z 255.2 $(M+H)^+$.

2G was deprotected as previously described in Example 2A, Step 2 to give 0-(pyridine-3-ylmethyl)hydroxylamine (2H, 0.734 g, 69.2% yield). $^1$H NMR (400 MHz, DMSO-$d_6$) δ ppm 4.71 (s, 2H) 7.44 (dd, J=7.83, 5.05 Hz, 1H) 7.85 (d, J=7.83 Hz, 1H) 8.47 (dd, J=5.05, 1.26 Hz, 1H) 8.53 (d, J=2.27 Hz, 1H). ESI-MS: m/z 125.3 $(M+H)^+$.

2E. Synthesis of (R)—O-((1,4-dioxan-2-yl)methyl) hydroxylamine (2M)

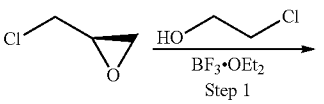

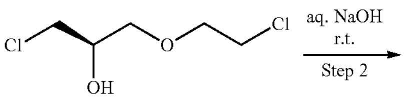

2I

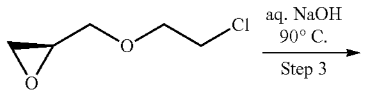

2J

-continued

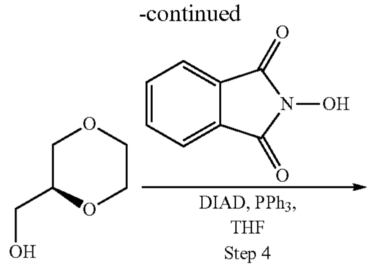

2K

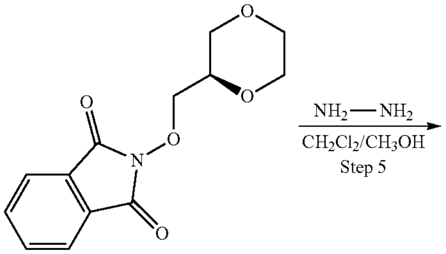

2L

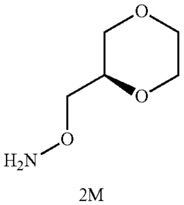

2M

Step 1: 2-chloroethanol (34.8 g, 43.2 mmol) and boron trifluoride diethyl etherate (0.136 mL, 1.08 mmol) were dissolved in 20 mL of THF and cooled in an ice bath. (R)-(−)-epichlorohydrin (10.0 g, 10.8 mmol) in 10 mL of THF was added slowly through a syringe. After the addition, the ice bath was removed and the mixture was heated in a 45° C. oil bath for 90 min at which time the reaction was complete. The reaction was concentrated in vacuo to give an oily crude product (R)-1-chloro-3-(2-chloroethoxy)propan-2-ol (2I, 16.2 g, 86.6% yield). $^1$H NMR (400 MHz, CHLOROFORM-d) δ ppm 3.56-3.71 (m, 6H) 3.85-3.92 (m, 3H).

Step 2: 2I (16.2 g, 93.6 mmol) was dissolved in 45 mL of THF and was cooled in an ice bath. Sodium hydroxide (9.36 g, 234 mmol) in 20 mL of water was added dropwise and the reaction was stirred in the ice bath for 15 min, and at room temperature for 6 h. The reaction mixture was diluted with ethyl acetate and saturated sodium chloride solution. The product was extracted into ethyl acetate layer three times. The combined organic layers was then washed with saturated sodium chloride solution, dried over sodium sulfate and concentrated to a crude oily product, (S)-2-((2-chloroethoxy) methyl)oxirane (2J, 11.1 g, 86.7% yield. $^1$H NMR (400 MHz, CHLOROFORM-d) δ ppm 2.57-2.72 (m, 2H) 2.76-2.89 (m, 2H) 3.08-3.25 (m, 2H) 3.45 (dd, J=12.25, 5.68 Hz, 1H) 3.51-3.70 (m, 2H).

Step 3: 2J (11.1 g, 81.3 mmol) was dissolved in 50 mL of THF. Sodium hydroxide (16.3 g, 406 mmol) in 50 mL of water was added and the reaction was heated in a 90° C. oil bath for one day. Despite the TLC showing the reaction to be only half completed the product was extracted from the aqueous layer with ethyl acetate/THF, dichloromethane, n-butanol. The first two extractions contained product and the starting material, which was later purified by flash column (ethyl acetate/hexane 30/70). The latter extractions contained pure (5)-(1,4-dioxan-2-yl)methanol (2K, 1.98 g, 20.8% yield). $^1$H NMR (400 MHz, CHLOROFORM-d) δ ppm 3.47 (t, J=9.98 Hz, 1H) 3.51-3.67 (m, 3H) 3.67-3.87 (m, 5H).

Step 4: 2K (1.33 g, 11.2 mmol), N-hydroxyphthalimide (2.02 g, 12.4 mmol), triphenylphosphine (3.25 g, 12.4 mmol) were dissolved in 30 mL of dry THF and the mixture was cooled in an ice bath. Diisopropyl azodicarboxylate (2.51 g, 12.4 mmol) in 5 mL of THF was added to the above mixture dropwise. After the addition was complete, the ice bath was removed and the reaction was stirred at room temp overnight. Next day, the reaction was done. It was concentrated in vacuo to an oil and then purified on flash column chromatography using ethyl acetate/hexane 20/80 to give (R)-2-((1,4-dioxan-2-yl)methoxy)isoindoline-1,3-dione (2L). $^1$H NMR (400 MHz, CHLOROFORM-d) δ ppm 3.56 (t, J=10.74 Hz, 1H) 3.60-3.85 (m, 4H) 3.92 (dd, J=11.75, 2.40 Hz, 1H) 4.05 (ddd, J=9.98, 3.03, 2.91 Hz, 1H) 4.11-4.19 (m, 1H) 4.20-4.29 (m, 1H) 7.71-7.80 (m, 2H) 7.81-7.91 (m, 2H).

Step 5: 2L (4.30 g, 12.4 mmol) was dissolved in 90 mL of methanol/dichloromethane 1/9 ratio. Hydrazine hydrate (1.67 mL, 22.4 mmol) was added and the reaction was stirred at room temperature for 2 h at which time the deprotection was done. The precipitate byproduct was filtered, and the filtrate was concentrated down to an oil and then purified by flash column chromatography, using chloroform/methanol 99/1 ratio to yield (R)—O-((1,4-dioxan-2-yl)methyl)hydroxylamine (2M, 0.915 g, 61.4% yield over 2 steps). $^1$H NMR (400 MHz, CHLOROFORM-d) δ ppm 3.41 (t, J=10.86 Hz, 1H) 3.57-3.71 (m, 4H) 3.71-3.82 (m, 3H) 3.83-3.92 (m, 1H) 5.55 (br. s., 2H).

F. Synthesis of (S)-2-(2,2-dimethyl-1,3-dioxolan-4-yl)ethanamine (2O)

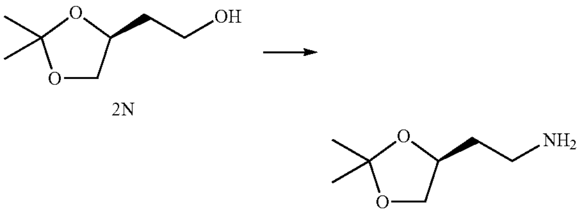

2N

2O (S)-2-(2,2-dimethyl-1,3-dioxolan-4-yl)ethanamine (2O) was prepared from (S)-2-(2,2-dimethyl-1,3-dioxolan-4-yl) ethanol (2N) using a literature procedure (*Tetrahedron Lett*, 2005, 46, 5475-5478).

G. Synthesis of (R)—O-((2,2-dimethyl-1,3-dioxolan-4-yl)methyl)hydroxylamine (2P)

2P

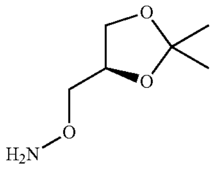

The title compound was prepared according to Bailey et al., J. Med. Chem., 1991, 34, 51-65.

2H. Synthesis of (S)—O-((2,2-dimethyl-1,3-dioxolan-4-yl)methyl)hydroxylamine (2Q)

2Q

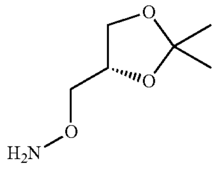

The title compound was prepared according to Bailey et al., J. Med. Chem., 1991, 34, 51-65.

2I. Synthesis of O-((2,2-dimethyl-1,3-dioxan-S-yl) methyl)hydroxylamine (2R)

2R

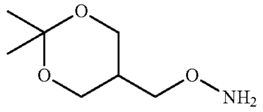

The title compound was prepared according to Harnden et al, *J. Med. Chem.*, 1990, 33, 187-196.

J. Synthesis of tert-butyl 2-(aminooxymethyl)morpholine-4-carboxylate (2T)

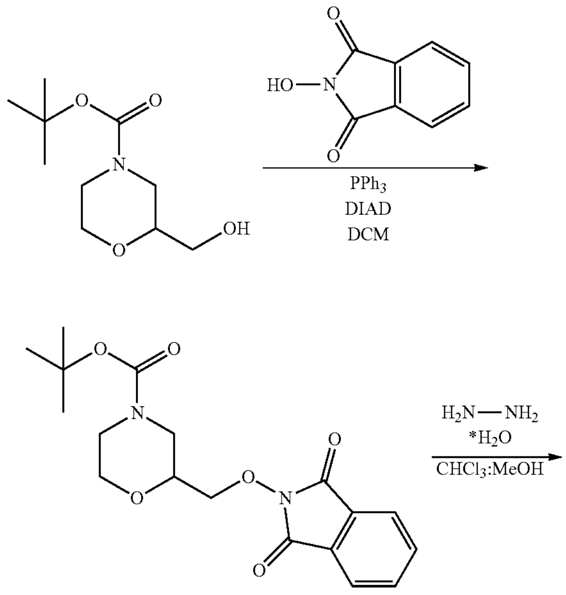

2S

-continued

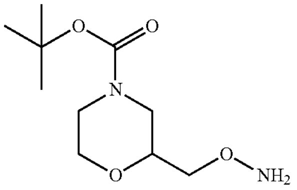

2T

To a solution of tert-butyl 2-(hydroxymethyl)morpholine-4-carboxylate (5 g, 23 mmol) in $CH_2Cl_2$ (250 mL) was added 2-hydroxyisoindoline-1,3-dione (5.6 g, 34.5 mmol) and triphenylphosphine (15 g, 57.5 mmol). The resultant mixture was cooled to 0° C. and diisopropyl azodicarboxylate (11.1 ml, 57.5 mmol) was slowly added dropwise with an addition funnel under $N_2$ atmosphere. The reaction mixture was stirred at ambient temperature for 48 h. To the reaction mixture $H_2O$ (300 mL) was added and extracted with $CH_2Cl_2$. The organic layers were washed with brine. Dried over anhydrous $MgSO_4$, filtered and concentrated to provide clear oil, which was purified by flash chromatography (50% EtOAc-Hexane). The resultant clear oily compound 2S was dissolved in $CHCl_3$:$CH_3OH$ (50 ml). Hydrazine hydrate (25 mL, 0.25 mol) was added. The reaction mixture was stirred at ambient temperature overnight. The resultant solid was filtered off and the filtrate concentrated under reduced pressure to provide a clear oil, which was purified by flash chromatography (10% $CH_3OH$—$CH_2Cl_2$) to afford 3 g (56%, over two steps) of tert-butyl 2-(aminooxymethyl)morpholine-4-carboxylate (2T) as a clear oil. $^1H$ NMR (400 MHz, CHLOROFORM-d) δ ppm 1.47 (s, 9H) 3.46-3.62 (m, 2H) 3.61-3.79 (m, 4H) 3.79-4.04 (m, 3H). [M+H] calc'd for $C_{10}H_{20}N_2O_4$, 233; found, 233.

K. Synthesis of (S)—O-(2-(2,2-dimethyl-1,3-dioxolan-4-yl)ethyl)hydroxylamine (2W)

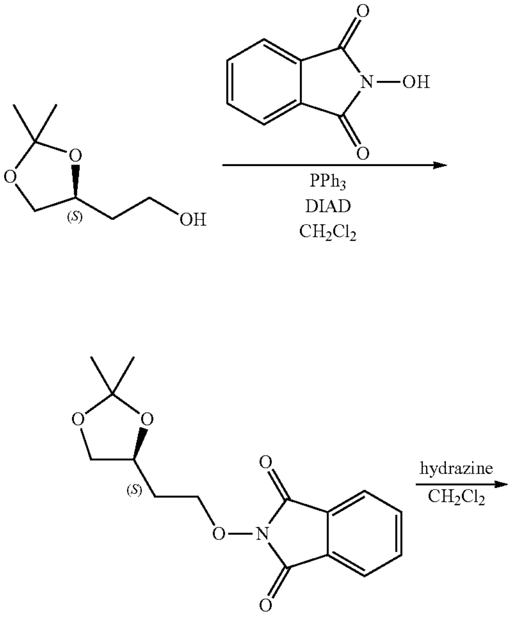

2U

-continued

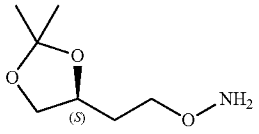

2W

To a solution of (S)-2-(2,2-dimethyl-1,3-dioxolan-4-yl) ethanol (14.2 mL, 0.1 mol) in $CH_2Cl_2$ (250 mL) was added 2-hydroxyisoindoline-1,3-dione (16.3 g, 0.1 mol) and triphenylphosphine (39.3 g, 0.15 mol). The resultant mixture was cooled to 0° C. and diisopropylazodicarboxylate (29.5 ml, 0.15 mol) was slowly added drop wise with an addition funnel under $N_2$ atmosphere. The reaction mixture was stirred at ambient temperature for 48 h. To the reaction mixture, $H_2O$ (300 mL) was added and the mixture extracted with $CH_2Cl_2$. The organic layers washed with brine. Dried over anhydrous $MgSO_4$, filtered and concentrated to provide a yellow oil, which was purified by flash chromatography (50% EtOAc-hexane) to yield 2U as a light yellow oil.

2U was dissolved in $CH_2Cl_2$ (250 ml) and cooled to 0° C. Hydrazine hydrate (25 mL, 0.25 mol) was added drop wise through an addition funnel. The reaction mixture was stirred at ambient temperature over night. The resultant solid was filtered off and the filtrate concentrated under reduced pressure to provide a yellow oil, which was purified by flash chromatography (70% EtOAc-hexane) to afford 7.2 g (45%, over two steps) of (S)—O-(2-(2,2-dimethyl-1,3-dioxolan-4-yl)ethyl)hydroxylamine (2W) as a pale yellow oil. $^1H$ NMR (400 MHz, CHLOROFORM-d) δ ppm 1.13 (s, 3H), 1.18 (s, 3H), 1.53-1.71 (m, 2H), 3.53 (q, J=6.48 Hz, 2H), 3.79-3.89 (m, 1H), 3.89-4.01 (m, 1H), 4.63-4.81 (m, 1H). MS (ES) [M+H] calculated for $C_2H_{16}NO_3$, 162.11; found 162.0.

2L. Synthesis of (R)—O-(2-(2,2-dimethyl-1,3-dioxolan-4-yl)ethyl)hydroxylamine (2X)

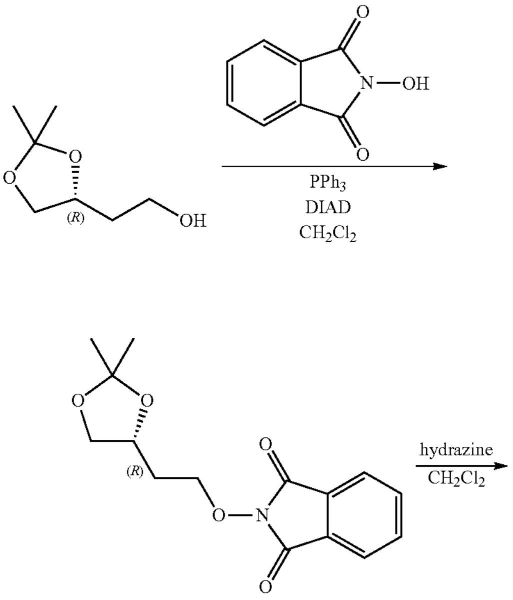

-continued

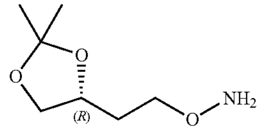

2X

The title compound was prepared using the procedure described for Example 2K by using (R)-2-(2,2-dimethyl-1,3-dioxolan-4-yl)ethanol (4.28 mL, 30 mmol), $CH_2Cl_2$ (100 mL), 2-hydroxyisoindoline-1,3-dione (4.9 g, 30 mmol), triphenylphosphine (11.8 g, 45 mmol), diisopropylazodicarboxylate (8.8 ml, 45 mmol) and hydrazine hydrate (6.0 mL, 60 mmol) to afford 2.1 g (43%, over two steps) of (R)—O-(2-(2,2-dimethyl-1,3-dioxolan-4-yl)ethyl)hydroxylamine (2X) as a pale yellow oil. $^1H$ NMR (400 MHz, CHLOROFORM-d) δ ppm 1.13 (s, 3H), 1.18 (s, 3H), 1.53-1.71 (m, 2H), 3.53 (m, 2H), 3.79-3.89 (m, 1H), 3.89-4.01 (m, 1H), 4.63-4.81 (m, 1H). MS (ES) [M+H] calculated for $C_2H_{16}NO_3$, 162.11; found 162.0.

2M. Synthesis of O-(((3aR,4R,6aR)-6-methoxy-2,2-dimethyltetrahydrofuro[3,4-d][1,3]dioxol-4-yl)methyl)hydroxylamine (2Y)

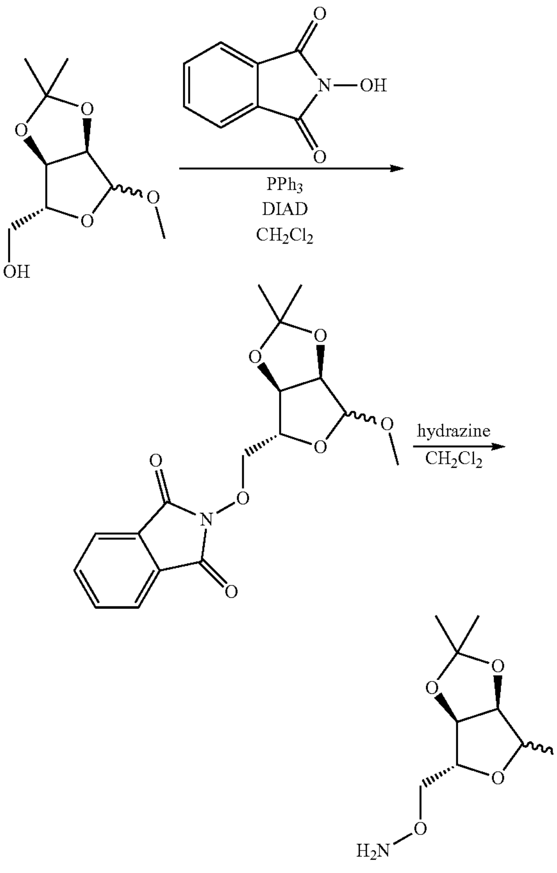

2Y

The title compound was prepared using the procedure described for Example 2K by using ((3aR,4R,6aR)-6-methoxy-2,2-dimethyltetrahydrofuro[3,4-d][1,3]dioxol-4-yl)methanol (2.04 g, 10 mmol), $CH_2Cl_2$ (25 mL), 2-hydroxyisoindoline-1,3-dione (2.0 g, 12 mmol), triphenylphosphine (4.0 g, 15 mmol), diisopropylazodicarboxylate (3.0 ml, 15 mmol) and hydrazine hydrate (2.0 mL, 20 mmol) to afford 1.12 g of 04(3aR,4R,6aR)-6-methoxy-2,2-dimethyltetrahydrofuro[3,4-d][1,3]dioxol-4-yl)methyl)hydroxylamine (2Y) (50%, over two steps) as a pale yellow oil. $^1H$ NMR (400 MHz, CHLOROFORM-d) δ ppm 1.24 (s, 3H) 1.26 (s, 3H) 3.31 (s, 3H) 3.59-3.75 (m, 2H) 4.44 (t, J=7.20 Hz, 1H) 4.56 (d, J=5.81 Hz, 1H) 4.67 (d, J=6.06 Hz, 1H) 4.92-5.00 (m, 1H). MS (ES) [M+H] calculated for $C_9H_{18}NO_5$, 220.11; found 220.10.

Example 3

Chiral Separation of Racemic Mixture of 2-Amino-7-(2-bromo-4-fluorophenyl)-4-methyl-7,8-dihydroquinazolin-5(6H)-one (1F[a] and 1F[b])

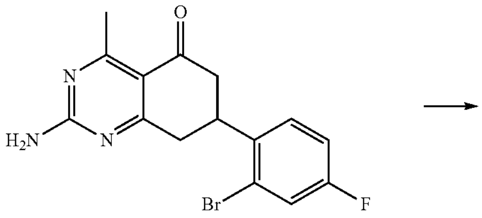

1F

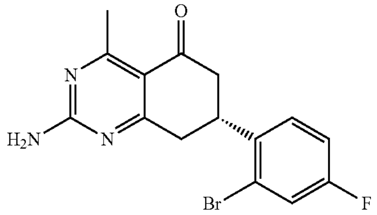

+

1F[a]

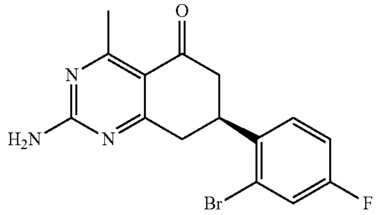

1F[b]

Dihydroquinazolinone 1F (Example 1) was separated into its enantiomers by supercritical fluid chromatography (SFC) under the following conditions:

Column: ChiralPak IA, 250×10 mm, 5 μm

Mobile Phase:

A: $CO_2$ (1)

B: MeOH

Gradient Condition: 20% MeOH

Run Time: 12 min

Flow Rate: 20 mL/min

Injection volume: 800 μL

Total yield for the two enantiomers was 82% of the original amount of the racemic mixture. The yield for (R)-2-amino-7-(2-bromo-4-fluorophenyl)-4-methyl-7,8-dihydroquinazolin-5(6H)-one (1F[a]) was 45%. The yield for (S)-2-amino-7-(2-bromo-4-fluorophenyl)-4-methyl-7,8-dihydroquinazolin-5(6H)-one (1F[b]) was 37%.

Example 4

Chiral Separation of 2-Amino-7-(4-fluoro-2-(2-fluoropyridin-3-yl)phenyl)-4-methyl-7,8-dihydroquinazolin-5(6H)-one (1H[a] and 1H[b])

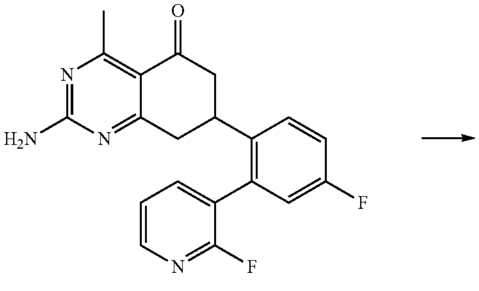

1H

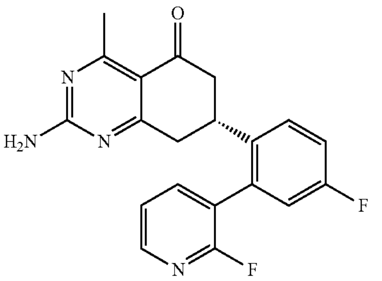

+

1H[a]

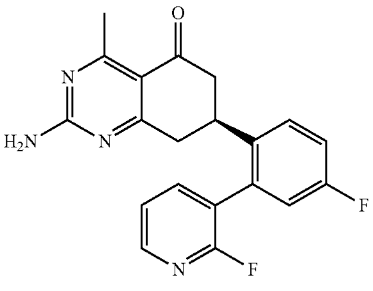

1H[b]

Dihydroquinazolinone 1H (Example 1) was separated into its enantiomers, 1H[a] and 1H[b], by supercritical fluid chromatography (SFC) under the following conditions:

Column: ChiralPak AD-H, 250×2 mm, 5 μm

Mobile Phase:

A: $CO_2$ (1)

B: MeOH

Gradient condition: 30% MeOH

Run Time: 10 min

Flow Rate: 50 mL/min

Injection volume: 1000 μL

Total yield for the two enantiomers was 68% of the original amount of the racemic mixture. The yield for (R)-2-amino-7-(4-fluoro-2-(2-fluoropyridin-3-yl)phenyl)-4-methyl-7,8-dihydroquinazolin-5(6H)-one (1H[a]) was 36%. The yield for (S)-2-amino-7-(4-fluoro-2-(2-fluoropyridin-3-yl)phenyl)-4-methyl-7,8-dihydroquinazolin-5(6H)-one (1H[b]) was 32%.

Example 5

Preparation of (E)-2-Amino-7-(4-fluoro-2-(2-fluoropyridin-3-yl)phenyl)-4-methyl-7,8-dihydroquinazolin-5(6H)-one O-methyl oxime (Compound 1)

1

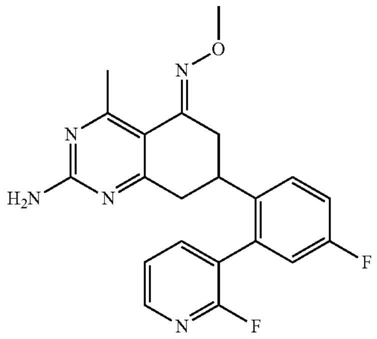

Compound 1 was prepared as a white or off-white powder (90%) according to the procedure analogous to Example 1 using O-methylhydroxylamine. $^1$H NMR (300 MHz, $CDCl_3$) δ ppm 2.58-2.68 (m, 5H), 2.78-2.88 (m, 3H), 5.02 (s, 2H), 6.92 (dd, 1H), 7.17 (td, 1H), 7.29 (m, 1H), 7.40 (dd, 1H), 7.67 (t, 1H), 8.25 (d, 1H). ESI-MS: m/z 396.1 $(M+H)^+$.

Example 6

Chiral Separation of R and S Enantiomers of (E)-2-amino-7-(4-fluoro-2-(2-fluoropyridin-3-yl)phenyl)-4-methyl-7,8-dihydroquinazolin-5(6H)-one O-methyl oxime (Compound 2 and Compound 3)

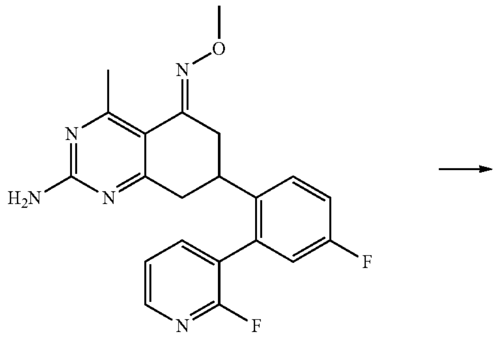

1

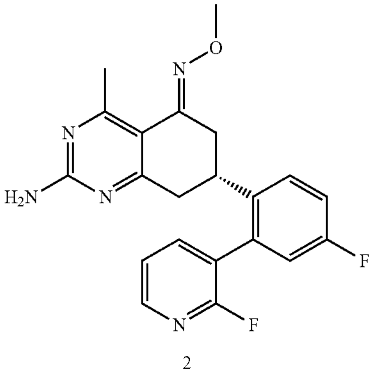

+

2

-continued

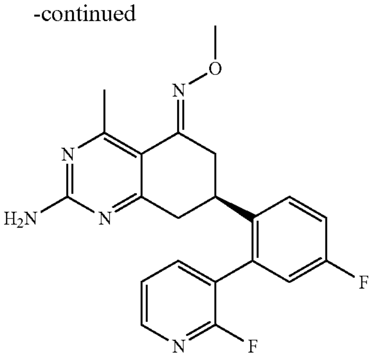

3

Racemic mixture of Compound 1 was separated into its R and S enantiomers, Compound 2 and Compound 3, by SFC under the following conditions:

Column: ChiralPak IA, 250×21 mm, 5 μm

Mobile Phase:

A: $CO_2$ (1)

B: EtOH

Gradient condition: 40% EtOH

Run time: 8 min

Flow Rate: 50 mL/min

Injection volume: 1000 μL,

Total yield for the two enantiomers was 45%. Yield for (R,E)-2-amino-7-(4-fluoro-2-(2-fluoropyridin-3-yl)phenyl)-4-methyl-7,8-dihydroquinazolin-5(6H)-one O-methyl oxime (1) was 23%. Yield for (S,E)-2-amino-7-(4-fluoro-2-(2-fluoropyridin-3-yl)phenyl)-4-methyl-7,8-dihydroquinazolin-5(6H)-one (2) was 22%.

Example 7

Preparation of (E)-2-Amino-7-(4-fluoro-2-(2-fluoropyridin-3-yl)phenyl)-4-methyl-7,8-dihydroquinazolin-5(6H)-one O-allyl oxime (Compound 4)

4

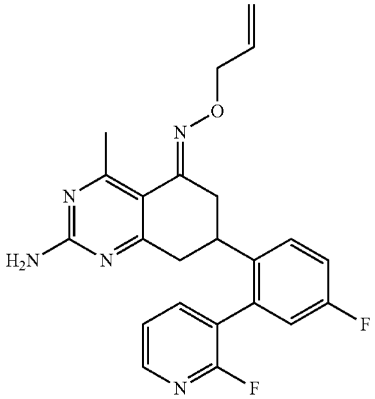

Compound 4 was prepared as a white or off-white powder (90%) according to the procedure described in Example 1 using O-allylhydroxylamine. The R and S enantiomers of Compound 4 may be obtained by SFC using a procedure analogous to Example 6. $^1H$ NMR (300 MHz, $CDCl_3$) δ ppm 2.58 (m, 5H), 2.82 (m, 3H), 4.60 (s, 2H), 4.97 (s, 2H), 5.19-5.23 (m, 2H), 5.99 (s, 1H), 6.92 (dd, 1H), 7.17 (td, 1H), 7.27 (m, 1H), 7.41 (dd, 1H), 7.69 (m, 1H), 8.23 (s, 1H). ESI-MS: m/z 422.1 $(M+H)^+$.

Example 8

Preparation of (E)-2-Amino-7-(4-fluoro-2-(2-fluoropyridin-3-yl)phenyl)-4-methyl-7,8-dihydroquinazolin-5(6H)-one O-tert-butyl oxime (Compound 5)

5

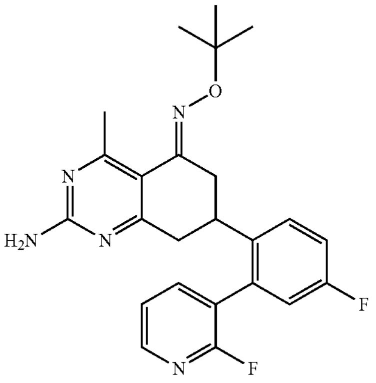

Compound 5 was prepared as a white or off-white powder (90%) according to a procedure described in Example 1 using O-tert-butylhydroxylamine The R and S enantiomers of Compound 5 may be obtained by SFC using a procedure analogous to Example 6. $^1H$ NMR (300 MHz, $CDCl_3$) δ ppm 1.29 (s, 9H), 2.61 (m, 4H), 2.82 (m, 3H), 4.96 (s, 2H), 6.94 (dd, 1H), 7.18 (td, 1H), 7.30 (m, 1H), 7.43 (dd, 1H), 7.70 (m, 1H), 8.25 (s, 1H). ESI-MS: m/z 438.2 $(M+H)^+$.

Example 9

Preparation of (E)-2-amino-7-(4-fluoro-2-(2-fluoropyridin-3-yl)phenyl)-4-methyl-7,8-dihydroquinazolin-5(6H)-one O-isobutyl oxime (Compound 6)

6

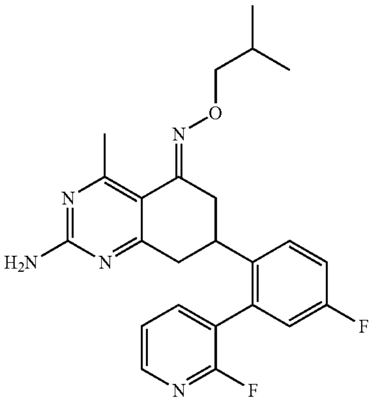

Compound 6 was prepared as a white or off-white powder (90%) according to the procedure described in Example 1 using O-isobutylhydroxylamine The R and S enantiomers of Compound 6 may be obtained by SFC using a procedure analogous to Example 6. $^1H$ NMR (300 MHz, $CDCl_3$) δ ppm 0.88 (m, 6H), 1.67 (m, 1H), 2.29 (m, 5H), 2.59 (s, 3H), 3.86 (m, 2H), 5.03 (m, 2H), 6.93 (dd, 1H), 7.19 (td, 1H), 7.27 (m, 1H), 7.41 (dd, 1H), 7.70 (m, 1H), 8.24 (s, 1H). ESI-MS: m/z 438.2 $(M+H)^+$.

Example 10

Preparation of (E)-2-amino-7-(4-fluoro-2-(2-fluoropyridin-3-yl)phenyl)-4-methyl-7,8-dihydroquinazolin-5(6H)-one O-benzyl oxime (Compound 7)

7

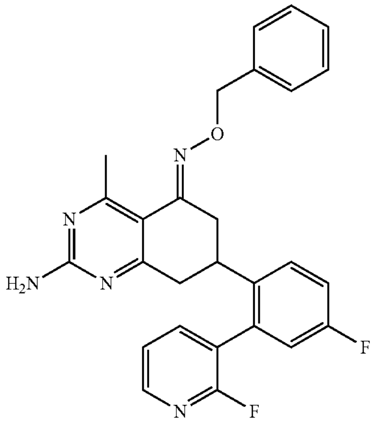

Compound 7 was prepared as a white or off-white powder (90%) according to the procedure described in Example 1 using O-benzylhydroxylamine The R and S enantiomers of Compound 7 may be obtained by SFC using a procedure analogous to Example 6. $^1$H NMR (300 MHz, $CDCl_3$) δ ppm 2.51 (s, 3H), 2.60-2.81 (m, 4H), 4.97 (m, 2H), 5.12 (m, 2H), 6.91 (dd, 1H), 7.16 (td, 1H), 7.26-7.39 (m, 7H), 7.65 (m, 1H), 8.25 (m, 1H). ESI-MS: m/z 472.1 $(M+H)^+$.

Example 11

Preparation of (E)-2-amino-7-(4-fluoro-2-(2-fluoropyridin-3-yl)phenyl)-4-methyl-7,8-dihydroquinazolin-5(6H)-one O-phenyl oxime (Compound 8)

8

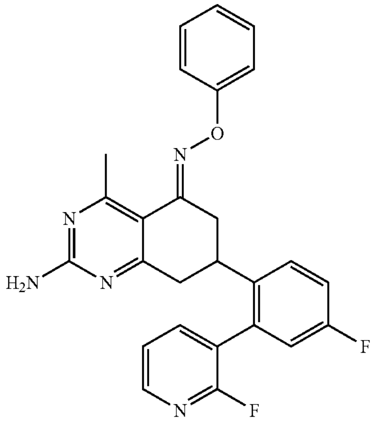

Compound 8 was prepared as a white or off-white powder (90%) according to the procedure described in Example 1 using O-phenylhydroxylamine. The R and S enantiomers of Compound 8 may be obtained by SFC using a procedure analogous to Example 6. $^1$H NMR (300 MHz, $CDCl_3$) δ ppm 2.65-3.07 (m, 7H), 6.04 (m, 2H), 6.96 (dd, 1H), 6.99 (t, 1H), 7.11-7.25 (m, 3H), 7.26-7.35 (m, 3H), 7.44 (dd, 1H), 7.72 (m, 1H), 8.25 (m, 1H). ESI-MS: m/z 458.1 $(M+H)^+$.

Example 12

Preparation of (E)-2-Amino-7-(4-fluoro-2-(2-fluoropyridin-3-yl)phenyl)-4-methyl-7,8-dihydroquinazolin-5(6H)-one O-4-nitrobenzyl oxime (Compound 9)

9

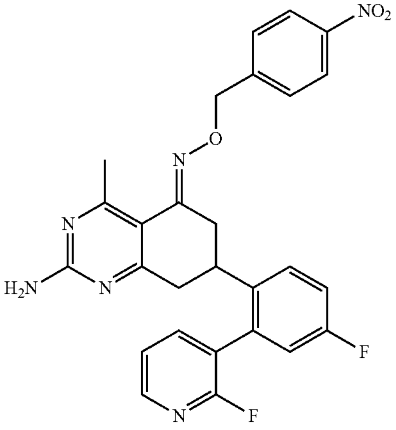

Compound 9 was prepared as a white or off-white powder (90%) according to the procedure described in Example 1 using O-4-nitrobenzylhydroxylamine The R and S enantiomers of Compound 9 may be obtained by SFC using a procedure analogous to Example 6. $^1$H NMR (300 MHz, DMSO-$d_6$) δ ppm 2.44 (s, 3H), 2.64-6.80 (m, 3H), 3.20 (m, 2H), 5.28 (s, 2H), 7.18 (dd, 1H), 7.38 (td, 1H), 7.45 (m, 1H), 7.60 (m, 2H), 7.72 (dd, 1H), 7.99 (m, 1H), 8.25 (m, 3H). ESI-MS: m/z 517.2 $(M+H)^+$.

Example 13

Preparation of 2-Amino-7-(4-fluoro-2-(6-methoxypyridin-2-yl)phenyl)-4-methyl-7,8-dihydroquinazolin-5(6H)-one (13A)

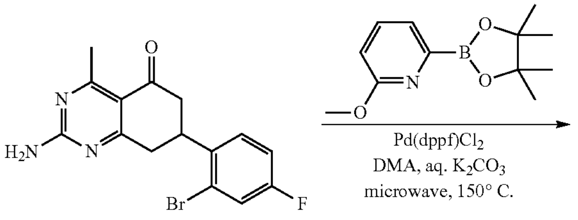

1F

-continued

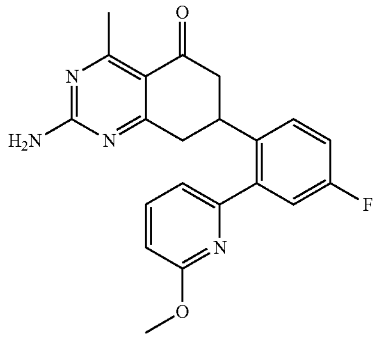

13A

To a 5 mL microwave vial was added 2-amino-7-(2-bromo-4-fluorophenyl)-4-methyl-7,8-dihydroquinazolin-5(6H)-one (1F (Example 1), 56 mg, 0.163 mmol, 1.0 eq.), 2-methoxy-6-(4,4,5,5-tetramethyl-1,3,2-dioxaborolan-2-yl)pyridine (77 mg, 0.325 mmol, 2.0 eq.), Pd(dppf)$Cl_2$ (11 mg, 0.013 mmol, 0.08 eq.), 2.0 M aqueous $K_2CO_3$ (162 μL, 0.325 mmol, 2.0 eq.), and dimethylacetamide (2 mL). The vial was sealed and heated in a microwave at 150° C. for 10 min. LC/MS analysis showed the reaction was completed. The reaction mixture was filtered through Celite and purified via preparative-HPLC to give the product 13A as a white solid (33 mg, 55%). $^1$H NMR (400 MHz, DMSO-$d_6$) δ ppm 2.54 (s, 3H) 2.62 (ddd, J=15.73, 3.03, 2.72 Hz, 1H) 2.84-3.04 (m, 2H) 3.15-3.31 (m, 1H) 3.60-3.73 (m, 1H) 3.78 (s, 3H) 6.81 (d, J=8.34 Hz, 1H) 7.15 (d, J=7.07 Hz, 1H) 7.22 (dd, J=9.60, 2.78 Hz, 1H) 7.33 (td, J=8.59, 2.78 Hz, 1H) 7.55 (br. s., 2H) 7.71 (dd, J=8.84, 5.81 Hz, 1H) 7.81 (dd, J=8.34, 7.33 Hz, 1H). ESI-MS: m/z 379.3 $(M+H)^+$.

Example 14

Chiral Separation of R and S Enantiomers of 2-Amino-7-(4-fluoro-2-(6-methoxypyridin-2-yl)phenyl)-4-methyl-7,8-dihydroquinazolin-5(6H)-one ($13A^a$ and $13A^b$)

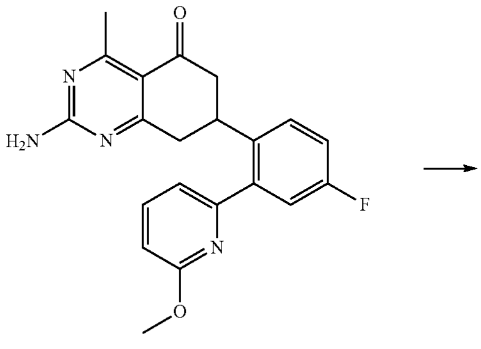

13A

-continued

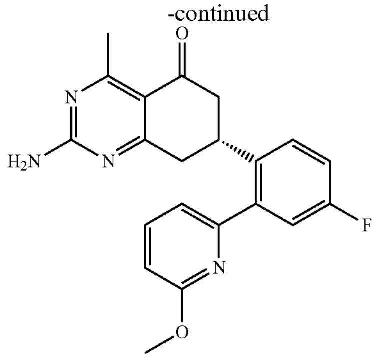

$13A^a$

+

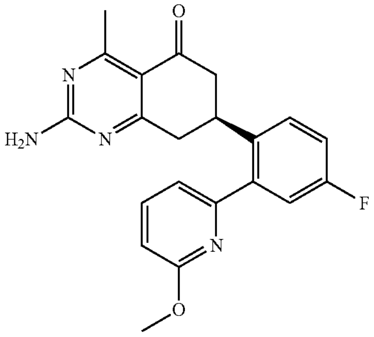

$13A^b$

Racemic mixture of Compound 13A was separated into its R and S enantiomers, Compound $13A^a$ and Compound $13A^b$, by SFC under the following conditions:

Column: ChiralPak AD-H, 150×2.1 mm, 5 μm
Mobile Phase:
A: $CO_2$ (1)
B: MeOH
Gradient condition: 30% MeOH
Run Time: 10 min
Flow Rate: 50 mL/min
Injection volume: 1000 μL Total yield for the two enantiomers was 20%. Yield for (R)-2-amino-7-(4-fluoro-2-(6-methoxypyridin-2-yl)phenyl)-4-methyl-7,8-dihydroquinazolin-5(6H)-one ($13A^a$) was 10%. Yield for (S)-2-amino-7-(4-fluoro-2-(6-methoxypyridin-2-yl)phenyl)-4-methyl-7,8-dihydroquinazolin-5(6H)-one ($13A^b$) was 10%.

Example 15

Preparation of (E)-2-Amino-7-(4-fluoro-2-(6-methoxypyridin-2-yl)phenyl)-4-methyl-7,8-dihydroquinazolin-5(6H)-one O-2-methoxyethyl oxime (Compound 10)

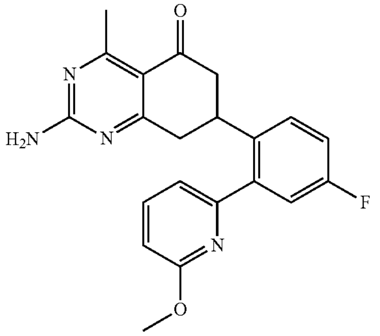

13A

+

-continued

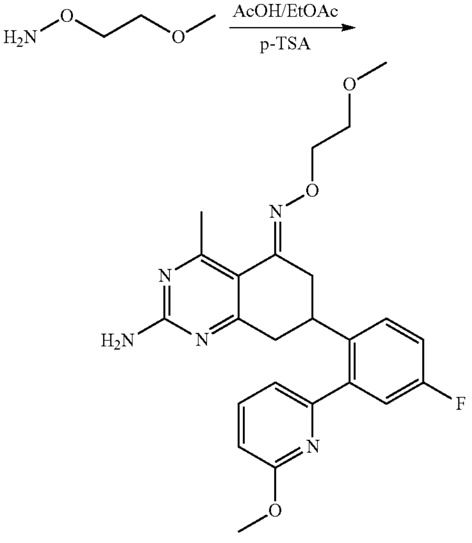

10

2-amino-7-(4-fluoro-2-(6-methoxypyridin-2-yl)phenyl)-4-methyl-7,8-dihydroquinazolin-5(6H)-one (13A (Example 13), 0.126 g, 0.33 mmol) and O-(2-methoxyethyl) hydroxylamine (0.121 g, 1.33 mmol) were dissolved in 2.2 mL of acetic acid/ethyl acetate 20/80 mol/mol ratio with a small amount of p-toluenesulfonic acid monohydrate (0.0127 g, 0.0666 mmol). The reaction was heated in a 80-85° C. oil bath overnight. The product was purified by preparatory LC/MS (35-50% $CH_3CN$ in $H_2O$ to give (E)-2-amino-7-(4-fluoro-2-(6-methoxypyridin-2-yl)phenyl)-4-methyl-7,8-dihydroquinazolin-5(6H)-one O-2-methoxyethyl oxime (10) as a TFA salt (0.067 g, 45% yield). $^1H$ NMR (400 MHz, DMSO-$d_6$) δ ppm 2.58 (s, 3H) 2.60-2.69 (m, 1H) 2.73-2.83 (m, 1H) 3.17-3.22 (m, 1H) 3.23 (s, 3H) 3.36 (dd, J=13.89, 2.02 Hz, 2H) 3.55 (t, J=4.67 Hz, 2H) 3.74 (s, 3H) 4.17 (q, J=4.29 Hz, 2H) 6.79 (d, J=8.34 Hz, 1H) 7.15 (d, J=7.33 Hz, 1H) 7.22 (dd, J=9.73, 2.65 Hz, 1H) 7.32 (td, J=8.53, 2.65 Hz, 1H) 7.69 (dd, J=8.59, 5.81 Hz, 1H) 7.78 (t, J=7.83 Hz, 1H). ESI-MS: m/z 452.2 $(M+H)^+$.

Example 16

Chiral Separation of R and S Enantiomers of (E)-2-Amino-7-(4-fluoro-2-(6-methoxypyridin-2-yl)phenyl)-4-methyl-7,8-dihydroquinazolin-5(6H)-one O-2-methoxyethyl oxime (Compound 11 and Compound 12)

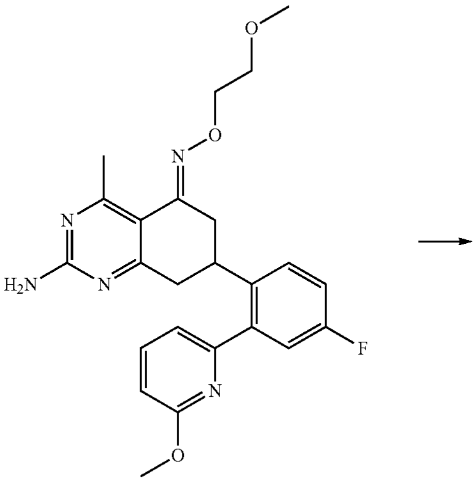

10

-continued

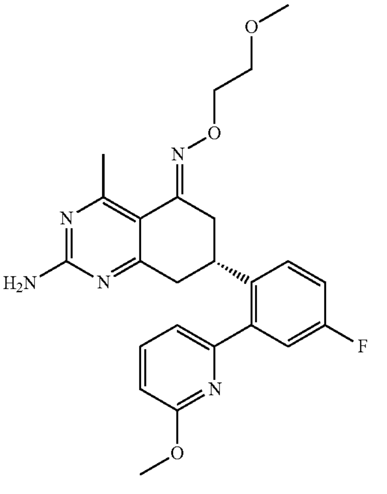

11

+

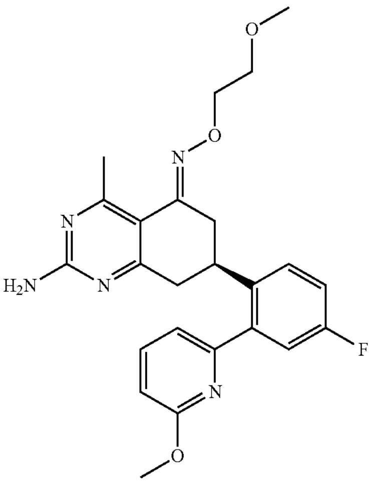

12

Racemic mixture of Compound 10 was separated into its R and S enantiomers, Compound 11 and Compound 12, by SFC under the following conditions:

Column: ChiralPak AD-H, 250×21.2 mm, 5 μm

Mobile Phase:

A: $CO_2$ (1)

B: EtOH

Gradient condition: 30% B

Run Time: 15 min

Flow Rate: 50 mL/min

Injection volume: 1000 μL,

Total yield for the two enantiomers was 68.1%. The yield for (R,E)-2-amino-7-(4-fluoro-2-(6-methoxypyridin-2-yl)phenyl)-4-methyl-7,8-dihydroquinazolin-5(6H)-one O-2-methoxyethyl oxime (11) was 33.6%. The yield for (S,E)-2-amino-7-(4-fluoro-2-(6-methoxypyridin-2-yl)phenyl)-4-methyl-7,8-dihydroquinazolin-5(6H)-one O-2-methoxyethyl oxime (12) was 34.5%.

Example 17

Preparation of (E)-2-Amino-7-(4-fluoro-2-(6-methoxypyridin-2-yl)phenyl)-4-methyl-7,8-dihydroquinazolin-5(6H)-one O—(R)-2,3-dihydroxypropyl oxime (Compound 13)

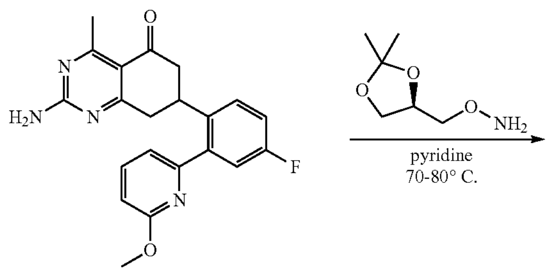

13A

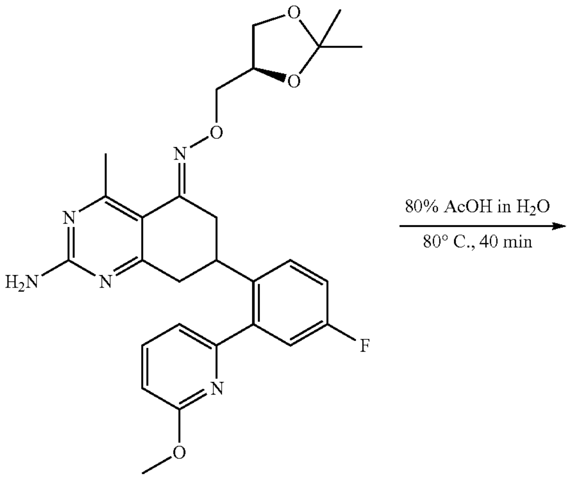

17A

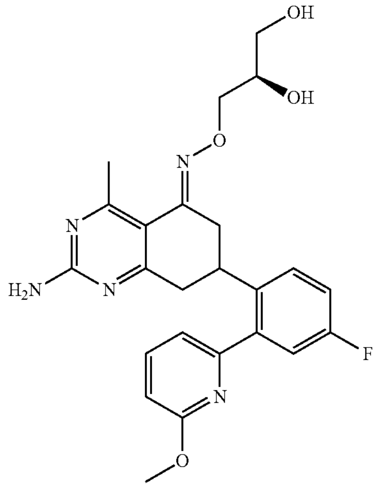

13

2-Amino-7-(4-fluoro-2-(6-methoxypyridin-2-yl)phenyl)-4-methyl-7,8-dihydroquinazolin-5(6H)-one (13A (Example 13), 0.097 g, 0.256 mmol) and R—O-(2,2-dimethyl-1,3-dioxolan-4-yl-methyl)-hydroxylamine (0.113 g, 0.769 mmol) were dissolved in 2.0 mL of dry pyridine. The reaction was heated in a 70-80° C. oil bath overnight. The reaction was poured into an ice cold water beaker and the product precipitated out. It was then filtered and rinsed with $H_2O$ to yield (E)-2-amino-7-(4-fluoro-2-(6-methoxypyridin-2-yl)phenyl)-4-methyl-7,8-dihydroquinazolin-5(6H)-one O—((R)-2,2-dimethyl-1,3-dioxolan-4-yl)methyl oxime (17A) which was taken onto the next step without further purification. ESI-MS: m/z 508.4 $(M+H)^+$.

17A was deprotected with 80% acetic acid in water for 40 min, and the product was then purified by preparatory LC/MS (30-45% $CH_3CN$ in $H_2O$ to give (E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime (13) as a TFA salt (0.108 g, 89.7% yield). $^1H$ NMR (400 MHz, MeOD) δ ppm 2.69-2.81 (m, 4H) 3.07 (br. s., 1H) 3.15-3.25 (m, 2H) 3.36-3.63 (m, 3H) 3.81-3.86 (s, 3H) 3.87-3.97 (m, 1H) 4.21 (m, 2H) 4.38 (m, 1H) 4.42-4.54 (m, 1H) 6.75 (d, J=8.34 Hz, 1H) 7.06 (d, J=7.07 Hz, 1H) 7.09-7.17 (m, 1H) 7.17-7.27 (m, 1H) 7.57 (d, J=2.27 Hz, 1H) 7.73 (t, J=7.96 Hz, 1H). ESI-MS: m/z 468.4 $(M+H)^+$.

Example 18

Chiral Separation of R and S Enantiomers of (E)-2-Amino-7-(4-fluoro-2-(6-methoxypyridin-2-yl)phenyl)-4-methyl-7,8-dihydroquinazolin-5(6H)-one O—(R)-2,3-dihydroxypropyl oxime (Compound 14 and Compound 15)

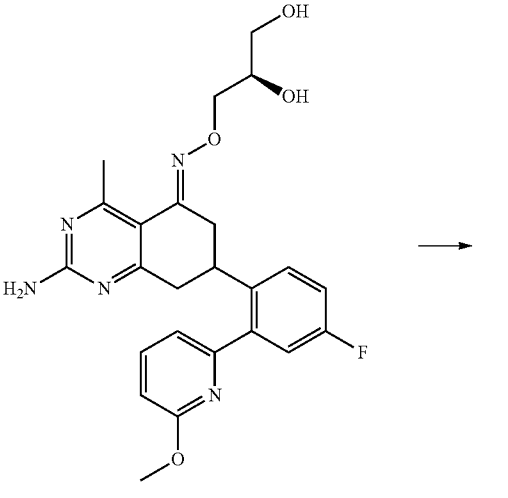

13

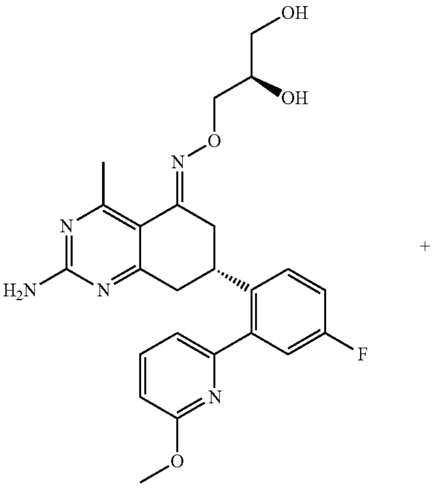

14

-continued

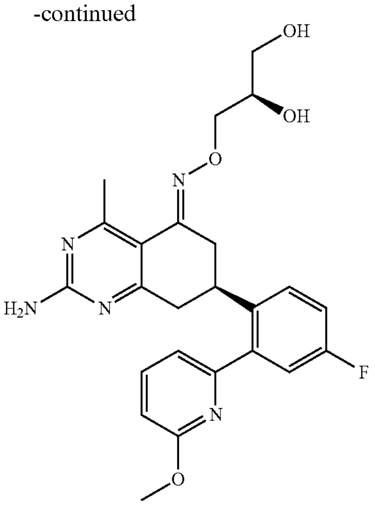

15

Racemic mixture of Compound 13 was separated into its R and S enantiomers, Compound 14 and Compound 15 by SFC under the following conditions:

Column: ChiralPak AD-H, 250×21.2 mm, 5 μm

Mobile Phase:

A: $CO_2$ (1)

B: EtOH

Gradient condition: 20% B

Run Time: 25 min

Flow Rate: 20 mL/min

Injection volume: 1000 μL

Total yield for the two enantiomers was 16.2%. Yield for (R,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime (14) was 9.0%. Yield for (S,E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime (15) was 7.2%.

Example 19

Preparation of (E)-2-Amino-7-(4-fluoro-2-(6-methoxypyridin-2-yl)phenyl)-4-methyl-7,8-dihydroquinazolin-5(6H)-one O-2-tert-butoxyethyl oxime (Compound 16)

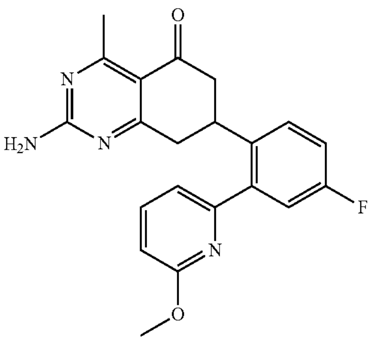

13A

+

-continued

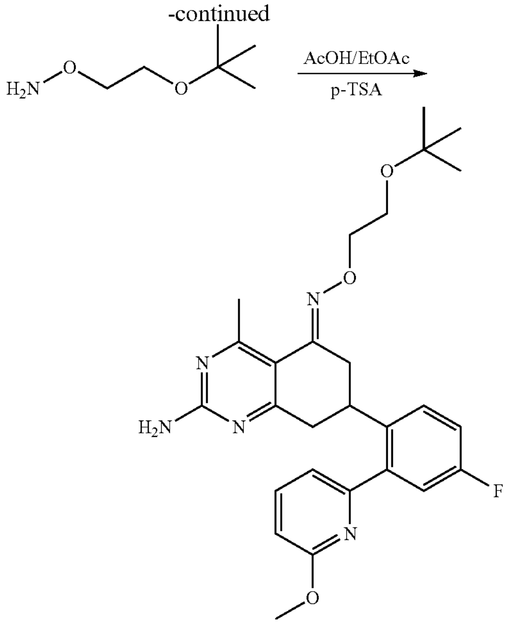

16

Compound 16 was prepared according to a procedure analogous to that described in Example 15 using O-(2-tert-butoxyethyl)hydroxylamine. The crude product was purified by preparatory LC/MS (45-55% $CH_3CN$ in $H_2O$) to give Compound 16 as a TFA salt (0.0417 g, 51% yield). The R and S enantiomers of Compound 16 may be obtained by SFC using a procedure analogous to Example 16. $^1H$ NMR (400 MHz, DMSO-$d_6$) δ ppm 1.07 (s, 9H) 2.58 (s, 3H) 2.60-2.69 (m, 1H) 2.73-2.87 (m, 1H) 3.20 (dd, J=16.04, 12.25 Hz, 1H) 3.28-3.44 (m, 2H) 3.52 (t, J=5.31 Hz, 2H) 3.75 (s, 3H) 4.02-4.17 (m, 2H) 6.79 (d, J=8.08 Hz, 1H) 7.14 (d, J=7.33 Hz, 1H) 7.22 (dd, J=9.73, 2.91 Hz, 1H) 7.32 (td, J=8.53, 2.91 Hz, 1H) 7.68 (dd, J=8.59, 5.81 Hz, 1H) 7.74-7.83 (m, 1H). ESI-MS: m/z 494.3 $(M+H)^+$.

Example 20

Preparation of (E)-2-Amino-7-(4-fluoro-2-(6-methoxypyridin-2-yl)phenyl)-4-methyl-7,8-dihydroquinazolin-5(6H)-one O-3-methoxypropyl oxime (Compound 17)

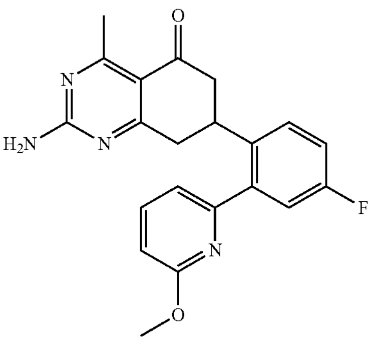

13A

+

-continued

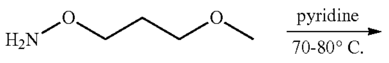

4D

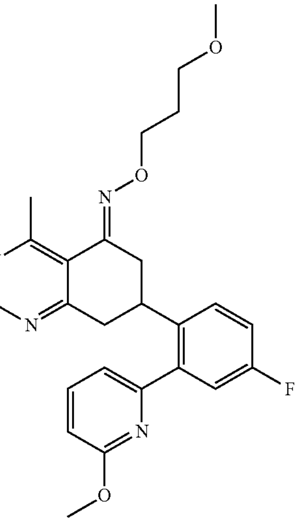

17

Compound 17 was prepared according to a procedure analogous to that described in Example 15 except O-(3-methoxy-propyl)hydroxylamine was used. The crude product was purified by preparatory LC/MS (50-65% $CH_3CN$ in $H_2O$ to give Compound 17 as a TFA salt (0.0428 g, 55.4% yield). The R and S enantiomers of Compound 17 may be obtained by SFC using a procedure analogous to Example 16. $^1H$ NMR (400 MHz, DMSO-$d_6$) δ ppm 1.83 (t, J=6.57 Hz, 2H) 2.51 (s, 3H) 2.55-2.66 (m, 1H) 2.67-2.79 (m, 1H) 3.07-3.18 (m, 1H) 3.20 (s, 3H) 3.25-3.32 (m, 2H) 3.35 (t, J=6.32 Hz, 2H) 3.74 (s, 3H) 4.08 (td, J=6.44, 1.77 Hz, 2H) 6.79 (d, J=8.08 Hz, 1H) 7.14 (d, J=7.33 Hz, 1H) 7.21 (dd, J=9.60, 2.78 Hz, 1H) 7.31 (td, J=8.65, 2.91 Hz, 1H) 7.68 (dd, J=8.84, 5.81 Hz, 1H) 7.74-7.84 (m, 1H). ESI-MS: m/z 466.4 $(M+H)^+$.

Example 21

Preparation of (E)-2-(2-Amino-7-(4-fluoro-2-(6-methoxypyridin-2-yl)phenyl)-4-methyl-7,8-dihydroquinazolin-5(6H)-ylideneaminooxy)acetic acid (Compound 18)

18

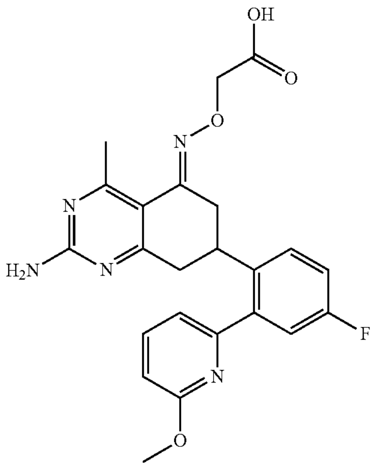

Compound 18 was prepared using an analogous procedure described for Example 15 except that 2-(aminooxy)acetic acid was used. The crude product was purified by preparatory LC/MS (40-60% $CH_3CN$ in $H_2O$ to give Compound 18 as a TFA salt (0.0413 g, 70% yield). The R and S enantiomers of Compound 18 may be obtained by SFC using a procedure analogous to Example 16. $^1H$ NMR (400 MHz, DMSO-$d_6$) δ ppm 2.42 (s, 3H) 2.66-2.79 (m, 3H) 3.08-3.12 (m, 2H) 3.75 (s, 3H) 4.56 (d, J=1.77 Hz, 2H) 6.79 (d, J=8.08 Hz, 1H) 7.14 (d, J=7.07 Hz, 1H) 7.21 (dd, J=9.73, 2.91 Hz, 1H) 7.26-7.36 (m, 1H) 7.66-7.73 (m, 1H) 7.74-7.83 (m, 1H). ESI-MS: m/z 452.3 $(M+H)^+$.

Example 22

Preparation of (E)-2-Amino-7-(4-fluoro-2-(6-methoxypyridin-2-yl)phenyl)-4-methyl-7,8-dihydroquinazolin-5(6H)-one O—(S)-2,3-dihydroxypropyl oxime (Compound 19)

19

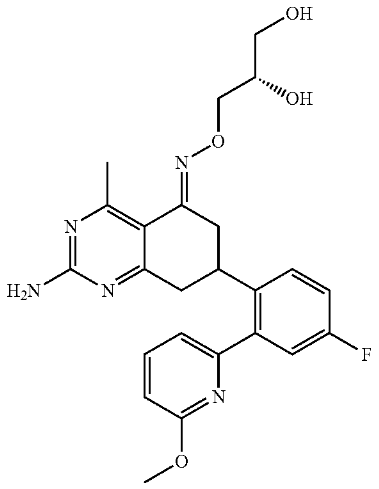

Compound 19 was prepared using an analogous procedure described for Example 17 except that S—O-(2,2-dimethyl-1,3-dioxolan-4-yl-methyl)-hydroxylamine was used. The crude product was purified by preparatory LC/MS (30-40% $CH_3CN$ in $H_2O$ to give Compound 19 as a TFA salt (0.0818 g, 70.5% yield). $^1H$ NMR (400 MHz, DMSO-$d_6$) δ ppm 2.52 (s, 3H) 2.62 (dd, J=17.94, 14.15 Hz, 1H) 2.75 (d, J=1.01 Hz, 1H) 3.07-3.19 (m, 1H) 3.27-3.38 (m, 5H) 3.68-3.73 (m, 2H) 3.75 (s, 3H) 3.89-3.99 (m, 1H) 4.06 (ddd, J=10.86, 4.67, 3.16 Hz, 1H) 6.79 (d, J=7.83 Hz, 1H) 7.14 (d, J=7.33 Hz, 1H) 7.21 (dd, J=9.60, 2.78 Hz, 1H) 7.32 (td, J=8.59, 2.78 Hz, 1H) 7.69 (dd, J=8.72, 5.94 Hz, 1H) 7.75-7.82 (m, 1H). ESI-MS: m/z 468.4 $(M+H)^+$.

Example 23

Chiral Separation of R and S Enantiomers of (E)-2-Amino-7-(4-fluoro-2-(6-methoxypyridin-2-yl)phenyl)-4-methyl-7,8-dihydroquinazolin-5(6H)-one O—(R)-2,3-dihydroxypropyl oxime (Compound 20 and Compound 21)

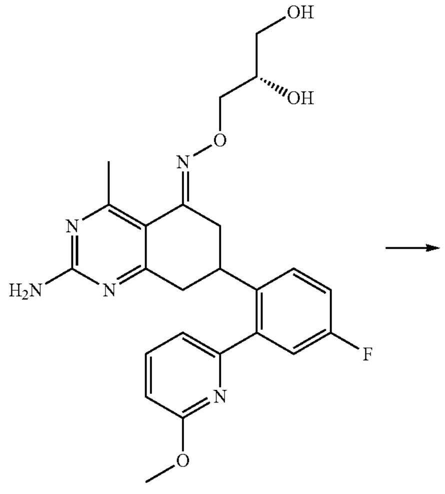

19

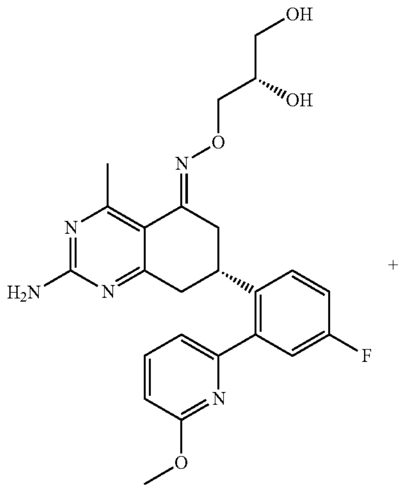

20

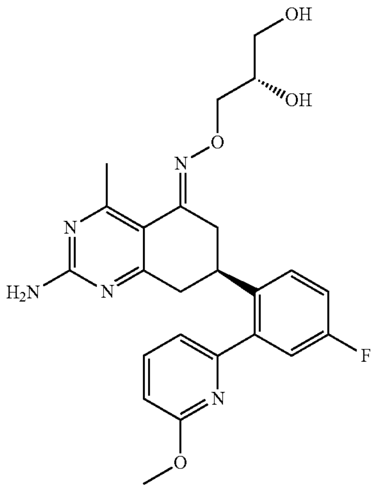

21

Racemic mixture of Compound 19 was separated into its R and S enantiomers, Compound 20 and Compound 21 by SFC under the following conditions:

Column: ChiralPak AD-H, 250×10 mm, 5 μm

Mobile Phase:

A: $CO_2$ (1)

B: MeOH

Gradient condition: 25% B

Run Time: 15 min

Flow Rate: 20 mL/min

Injection volume: 1000 μL,

Total yield for the two enantiomers was 34.7%. Yield for (R,E)-(E)-2-amino-7-(4-fluoro-2-(6-methoxypyridin-2-yl)phenyl)-4-methyl-7,8-dihydroquinazolin-5(6H)-one O—(R)-2,3-dihydroxypropyl oxime (2O) was 14.1%. Yield for (S,E)-(2-amino-7-(4-fluoro-2-(6-methoxypyridin-2-yl)phenyl)-4-methyl-7,8-dihydroquinazolin-5(6H)-one O—(R)-2,3-dihydroxypropyl oxime (21) was 20.6%.

Example 24

Preparation of (E)-2-Amino-7-(4-fluoro-2-(6-methoxypyridin-2-yl)phenyl)-4-methyl-7,8-dihydroquinazolin-5(6H)-one O-2-aminoethyl oxime (Compound 22)

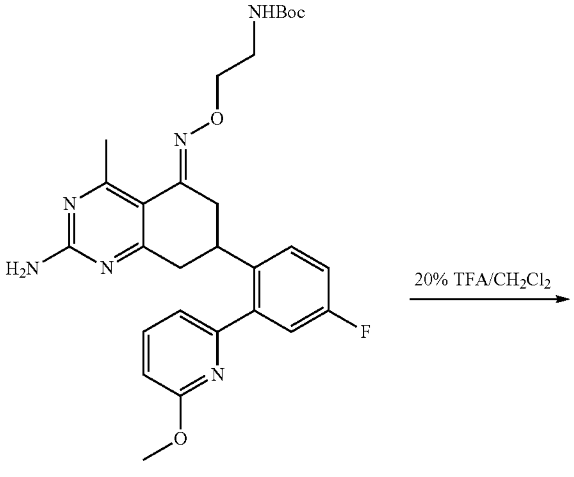

24A

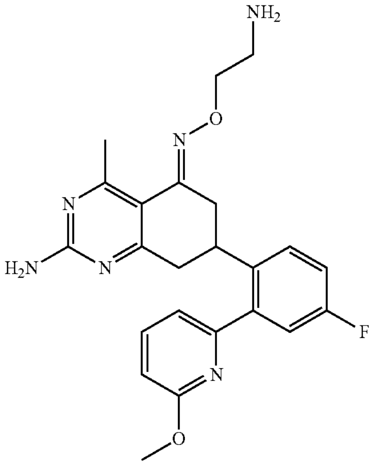

22

Compound 22 was prepared using an analogous procedure described for Example 15 except that tert-butyl 2-(aminooxy)ethylcarbamate was used. The final Boc-deprotection was effected by treatment of 24A (0.180 g, 0.019 mmol) with 20%

$TFA/CH_2Cl_2$ for 10 min. The reaction was completed as judged by LC/MS. The reaction was concentrated in vacuo and the residue was purified by preparatory LC/MS (25-35% $CH_3CN$ in $H_2O$) to give product 22 as a TFA salt (0.0625 g, 75.3% yield). $^1$H NMR (400 MHz, DMSO-$d_6$) δ ppm 2.52 (s, 3H) 2.62-2.74 (m, 1H) 2.76-2.90 (m, 1H) 2.99-3.18 (m, 3H) 3.32 (d, J=12.38 Hz, 2H) 3.75 (s, 3H) 4.20 (t, J=5.05 Hz, 2H) 6.80 (d, J=8.08 Hz, 1H) 7.14 (d, J=7.33 Hz, 1H) 7.23 (dd, J=9.73, 2.91 Hz, 1H) 7.33 (td, J=8.53, 2.91 Hz, 1H) 7.69 (dd, J=8.84, 5.81 Hz, 1H) 7.74-7.86 (m, 1H). ESI-MS: m/z 437.4 $(M+H)^+$.

Example 25

Chiral Separation of R and S Enantiomers of (E)-2-Amino-7-(4-fluoro-2-(6-methoxypyridin-2-yl)phenyl)-4-methyl-7,8-dihydroquinazolin-5(6H)-one O-2-aminoethyl oxime (Compound 23 and Compound 24)

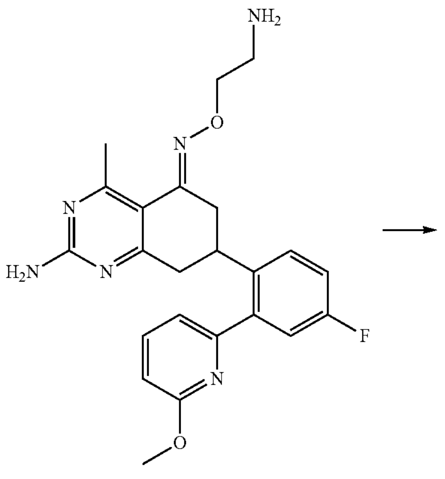

22

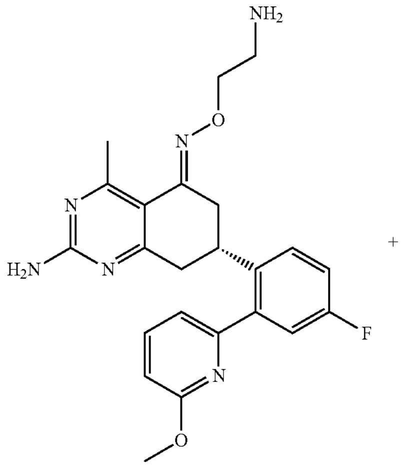

23

-continued

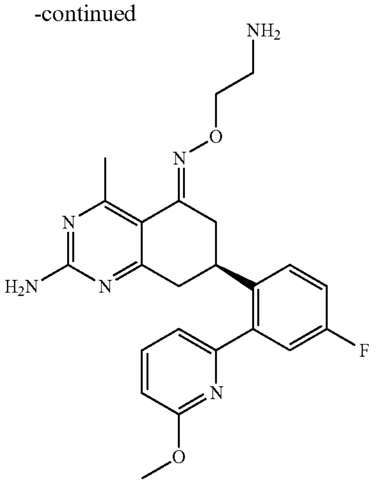

24

Racemic mixture of Compound 22 was separated into its R and S enantiomers, Compound 23 and Compound 24, by SFC under the following conditions:

Column: ChiralPak AD-H, 250×10 mm, 5 μm

Mobile Phase:

A: $CO_2$ (1)

B: MeOH+10 mM $NH_4OAc$

Gradient condition: 30% B

Run Time: 8 min

Flow Rate: 20 mL/min

Injection volume: 75 μL

Total yield for the two enantiomers was 23%. Yield for (R,E)-2-amino-7-(4-fluoro-2-(6-methoxypyridin-2-yl)phenyl)-4-methyl-7,8-dihydroquinazolin-5(6H)-one O-2-aminoethyl oxime (23) was 9.2%. Yield for (S,E)-2-amino-7-(4-fluoro-2-(6-methoxypyridin-2-yl)phenyl)-4-methyl-7,8-dihydroquinazolin-5(6H)-one O-2-aminoethyl oxime (24) was 13.9%.

Example 26

Preparation of (E) and (Z) Isomers of 2-Amino-7-(4-fluoro-2-(6-methoxypyridin-2-yl)phenyl)-4-methyl-7,8-dihydroquinazolin-5(6H)-one O-pyridin-3-ylmethyl oxime (Compound 25 and Compound 26)

25

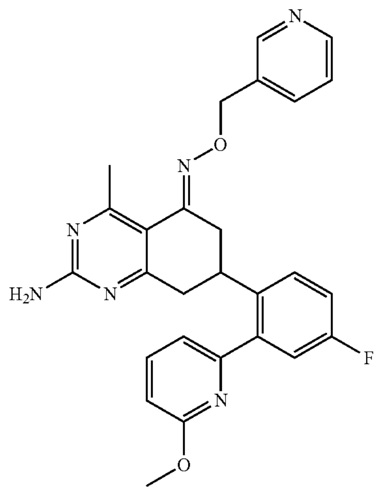

-continued

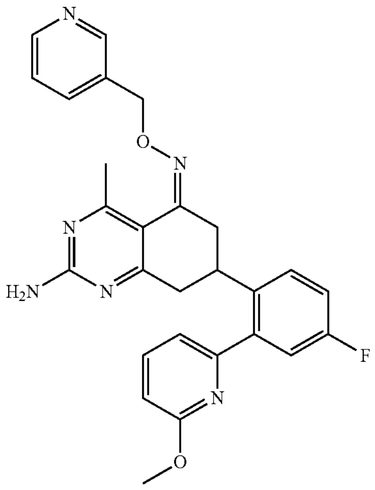

26

The racemic mixture which contained Compounds 25 and 26 was prepared by a procedure analogous to that described in Example 15 except that O-(pyridin-3-ylmethyl)hydroxylamine was used. The crude product was purified by preparatory LC/MS (25-40% $CH_3CN$ in $H_2O$ to give products as TFA salt. The E and Z isomers were separated by preparatory LC/MS (25%-40% $CH_3CN$ in $H_2O$) with a total yield of 71.6%.

Yield for (E) 2-amino-7-(4-fluoro-2-(6-methoxypyridin-2-yl)phenyl)-4-methyl-7,8-dihydroquinazolin-5(6H)-one O-pyridin-3-ylmethyl oxime (25) was 0.0398 g, 50.2%. $^1H$ NMR (400 MHz, DMSO-$d_6$) δ ppm 2.37 (s, 3H) 2.58-2.83 (m, 2H) 3.12 (dd, J=16.04, 12.25 Hz, 1H) 3.32 (dd, J=13.26, 3.92 Hz, 2H) 3.67 (s, 3H) 5.20 (d, J=3.03 Hz, 2H) 6.78 (d, J=8.34 Hz, 1H) 7.14 (d, J=7.33 Hz, 1H) 7.21 (dd, J=9.60, 2.78 Hz, 1H) 7.31 (td, J=8.53, 2.91 Hz, 1H) 7.63-7.73 (m, 2H) 7.78 (t, J=7.83 Hz, 1H) 8.11 (d, J=7.58 Hz, 1H) 8.68 (br. s., 1H) 8.74 (s, 1H). ESI-MS: m/z 485.4 $(M+H)^+$.

Yield for (Z) 2-amino-7-(4-fluoro-2-(6-methoxypyridin-2-yl)phenyl)-4-methyl-7,8-dihydroquinazolin-5(6H)-one O-pyridin-3-ylmethyl oxime (26) was 0.017 g, 21.4%. $^1H$ NMR (400 MHz, DMSO-$d_6$) δ ppm 2.12 (s, 3H) 2.63-2.71 (m, 1H) 2.72-3.00 (m, 4H) 3.80 (s, 3H) 5.11 (s, 2H) 6.83 (d, J=8.34 Hz, 1H) 7.12 (d, J=7.33 Hz, 1H) 7.18 (dd, J=9.73, 2.91 Hz, 1H) 7.26 (td, J=8.53, 2.91 Hz, 1H) 7.57 (ddd, J=13.71, 8.40, 5.43 Hz, 2H) 7.73-7.88 (m, 1H) 7.96 (d, J=7.33 Hz, 1H) 8.64 (s, 1H) 8.79 (br. s., 1H). ESI-MS: m/z 485.4 $(M+H)^+$.

Example 27

Preparation of (E)-2-Amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime (Compound 27) and Chiral Separation of Enantiomers

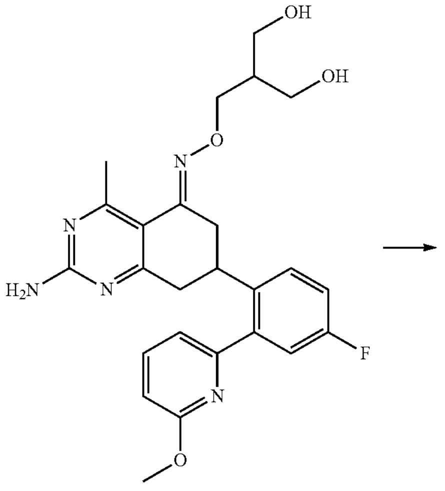

27

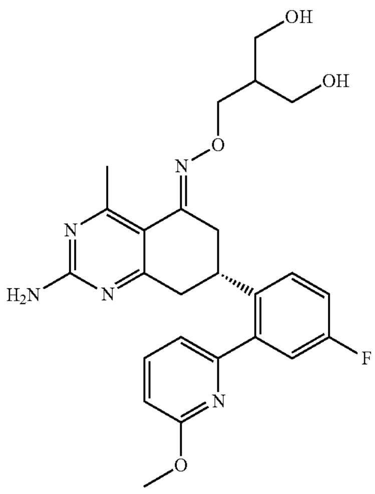

+

28

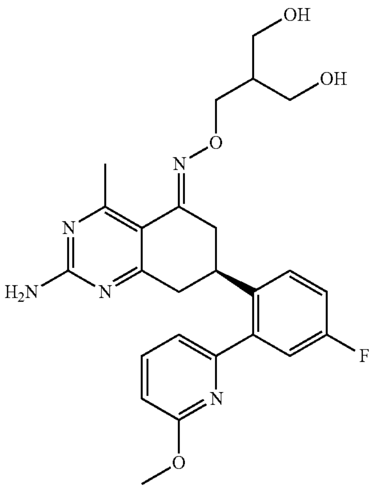

29

Compound 27 was prepared by a procedure analogous to that described in Example 17 except that O-((2,2-dimethyl-1,3-dioxan-5-yl)methyl)hydroxylamine was used. The crude product was purified by preparatory LC/MS (35-40% $CH_3CN$ in $H_2O$ to give Compound 17 as a TFA salt (0.109 g, 42.9% yield). $^1H$ NMR (400 MHz, DMSO-$d_6$) δ ppm 1.89 (m, 1H) 2.47 (s, 3H) 2.54 (m, 1H) 2.67 (br. s., 2H) 3.07 (d, J=15.66 Hz, 1H) 3.25 (m, 1H) 3.41 (q, J=5.31 Hz, 4H) 3.75 (s, 3H) 4.03 (d, J=8.00 Hz, 2H) 4.39 (q, J=4.97 Hz, 2H) 6.79 (d, J=8.34 Hz, 1H) 7.13 (d, J=7.33 Hz, 1H) 7.20 (dd, J=9.60, 2.53 Hz, 1H) 7.25-7.35 (m, 1H) 7.68 (dd, J=8.59, 5.81 Hz, 1H) 7.74-7.83 (m, 1H). ESI-MS: m/z 482.4 $(M+H)^+$.

The R and S enantiomers of Compound 27 was separated by SFC under the following conditions:

Column: ChiralPak AD, 250×10 mm, 5 μm

Mobile Phase:

A: $CO_2$ (1)

B: IPOH

Gradient condition: 40% B

Run Time: 12 min

Flow Rate: 15 mL/min

Injection volume: 500 μL

Total yield for the two enantiomers was 50.3%. Yield for (R,E)-2-amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime (28) was 27.9%. Yield for (S,E)-2-amino-7-(4-fluoro-2-(6-methoxypyridin-2-yl)phenyl)-4-methyl-7,8-dihydroquinazolin-5(6H)-one O-3-hydroxy-2-(hydroxymethyl)propyl oxime (29) was 22.4%.

Example 28

Preparation of (E)-2-(2-Amino-7-(4-fluoro-2-(6-methoxypyridin-2-yl)phenyl)-4-methyl-7,8-dihydroquinazolin-5(6H)-ylidene)hydrazinecarboximidamide (Compound 30)

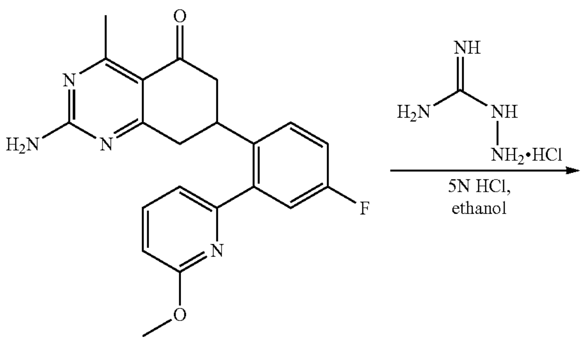

13A

-continued

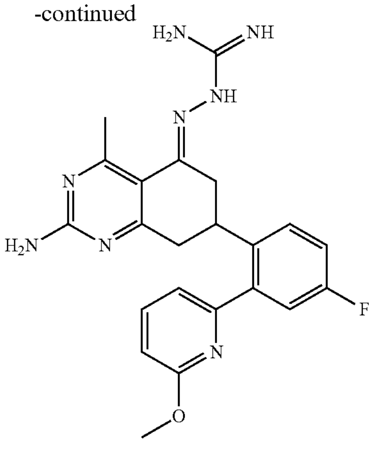

30

The ketone 13A ((Example 13) 0.100 g), aminoguanidine hydrochloride (0.0876 g, 3 eq.) and 5N HCl (5 eq.) were dissolved in ethanol and was heated in a 90° C. oil bath for 2 hours. The crude product was then purified by preparatory LC/MS (40-45% $CH_3CN$ in $H_2O$ to give (E)-2-(2-amino-7-(4-fluoro-2-(6-methoxypyridin-2-yl)phenyl)-4-methyl-7,8-dihydroquinazolin-5(6H)-ylidene)hydrazinecarboximidamide (30) as a TFA salt (0.0617 g, 53.6% yield). $^1H$ NMR (400 MHz, DMSO-$d_6$) δ ppm 2.64 (s, 3H) 2.70-2.82 (m, 2H) 3.15-3.33 (m, 2H) 3.48 (br. s., 1H) 3.73 (s, 3H) 6.80 (d, J=8.34 Hz, 1H) 7.17 (d, J=7.33 Hz, 1H) 7.25 (dd, J=9.73, 2.65 Hz, 1H) 7.33-7.40 (m, 1H) 7.74-7.86 (m, 2H) 10.74 (s, 1H). ESI-MS: m/z 435.4 $(M+H)^+$.

Example 29

Preparation of (S,E)-2-amino-7-(4-fluoro-2-(6-methoxypyridin-2-yl)phenyl)-4-methyl-7,8-dihydroquinazolin-5(6H)-one O—(S)-3,4-dihydroxybutyl oxime (Compound 31)

31

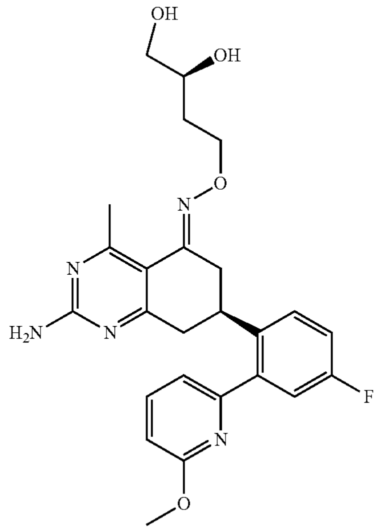

Compound 31 was prepared using an analogous procedure described for Example 17 except that (S)—O-(2-(2,2-dimethyl-1,3-dioxolan-4-yl)ethyl)hydroxylamine was used. The crude product was purified by preparatory LC/MS ($CH_3CN$ in $H_2O$ to give (S,E)-2-amino-7-(4-fluoro-2-(6-methoxypyridin-2-yl)phenyl)-4-methyl-7,8-dihydroquinazolin-5(6H)-one O—(S)-3,4-dihydroxybutyl oxime as a TFA salt (31, 4.5 mg, 7.1% yield). $^1$H NMR (400 MHz, CHLOROFORM-d) δ ppm 1.17-1.37 (m, 1H) 2.46-2.64 (m, 4H) 2.81-2.99 (m, 2H) 3.25-3.53 (m, 3H) 3.58-3.66 (m, 1H) 3.77-3.96 (m, 4H) 4.16-4.38 (m, 3H) 5.18 (br. s., 2H) 6.66-6.78 (m, 1H) 6.95 (dd, J=7.33, 4.29 Hz, 1H) 7.02-7.22 (m, 2H) 7.31-7.44 (m, 1H) 7.55-7.68 (m, 1H). [M+H] calc'd for $C_{25}H_{28}FN_5O_4$, 482; found, 482.

Example 30

Preparation of 2-Amino-7-(3-(6-methoxypyridin-2-yl)thiophen-2-yl)-4-methyl-7,8-dihydroquinazolin-5(6H)-one (30H)

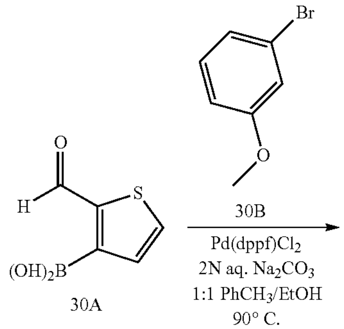

30B

30A

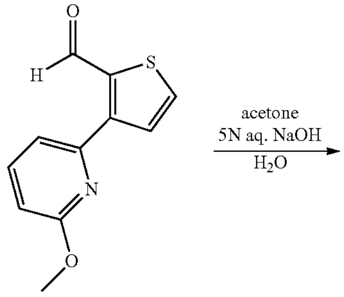

30C

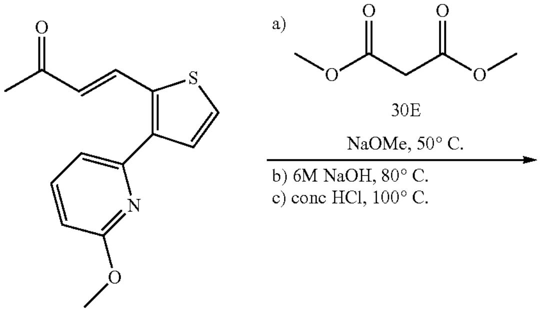

30E

30D

-continued

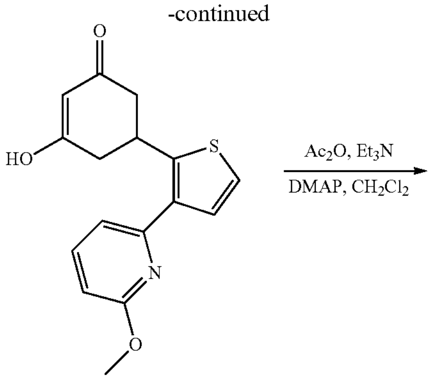

30F

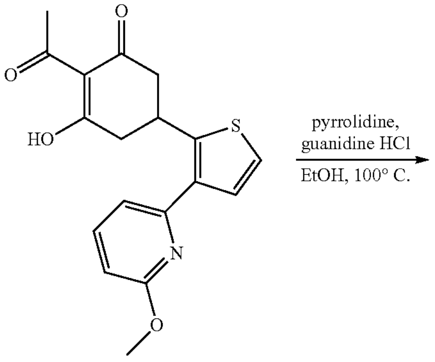

30G

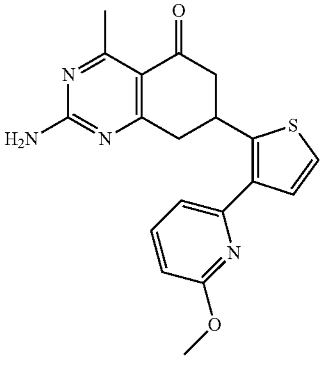

30H

A. Synthesis of 3-(6-methoxypyridin-2-yl)thiophene-2-carbaldehyde (30C)

To a 500 mL flask was added 2-formylthiophene-3-boronic acid (30A, 5.00 g, 32.1 mmol, 1.0 eq.), 2-bromo-6-methoxypyridine (30B, 6.03 g, 32.1 mmol, 1.0 eq.), toluene (100 mL), EtOH (100 mL), aqueous sodium carbonate (2N, 32 ml, 64 mmol, 2.0 eq.), and Pd(dppf)$Cl_2$ (1.17 g, 1.6 mmol, 0.05 eq.). The reaction was stirred overnight at 90° C. The reaction was cooled and saturated aqueous NaCl (100 mL) was added and the mixture was stirred for 20 min. The reaction mixture was extracted with EtOAc (2×100 mL) and the resulting organic layers were combined and passed through a Celite pad to remove residual Pd. The organic phases were washed with a succession of $H_2O$ (100 mL) and saturated aqueous NaCl (100 mL) and then dried over anhydrous $Na_2SO_4$, filtered, and concentrated to give a bubbly brown solid that was used in the next step without further purification (6.2 g, 88%). ESI-MS: m/z 220.2 $(M+H)^+$.

B. Synthesis of (E)-4-(3-(6-methoxypyridin-2-yl) thiophen-2-yl)but-3-en-2-one (30D)

To a 500 mL recovery flask was added 3-(6-methoxypyridin-2-yl)thiophene-2-carbaldehyde (30C, 6.2 g, 28.3 mmol, 1.0 eq.), acetone (16.6 mL, 226 mmol, 8.0 eq.), and $H_2O$ (130 mL). Upon cooling to 0° C. in an ice bath, aqueous NaOH (5N, 6.2 mL, 31.1 mmol, 1.1 eq.) was added. The reaction mixture was stirred overnight while warming to room temperature. LC/MS monitoring showed the reaction to be –60% complete, so additional aqueous NaOH (5N, 1 mL, 5.0 mmol, 0.18 eq.) was added. After stirring for an additional 6 h the reaction was complete by LC/MS. The reaction mixture was neutralized with 3N aqueous HCl to a pH ~8. The mixture was extracted with EtOAc (3×100 mL). The organic phases were combined and washed with saturated aqueous NaCl (100 mL). The combined aqueous phases were extracted with EtOAc (100 mL). The organic phases were combined and dried over anhydrous $Na_2SO_4$, filtered, and concentrated to give a black solid. The residue was purified via flash chromatography (60% $CH_2Cl_2$/Hex to 100% $CH_2Cl_2$) to give a yellow solid 30D (4.8 g, 67%). $^1$H NMR (400 MHz, DMSO-$d_6$) δ ppm 2.29 (s, 3H) 3.96 (s, 3H) 6.59 (d, J=15.92 Hz, 1H) 6.84 (d, J=8.34 Hz, 1H) 7.41 (d, J=7.58 Hz, 1H) 7.60 (d, J=5.31 Hz, 1H) 7.75-7.88 (m, 2H) 8.71 (d, J=15.92 Hz, 1H). ESI-MS: m/z 260.3 $(M+H)^+$.

C. Synthesis of 3-hydroxy-5-(3-(6-methoxypyridin-2-yl)thiophen-2-yl)cyclohex-2-enone (30F)

To a 200 mL recovery flask was added (E)-4-(3-(6-methoxypyridin-2-yl)thiophen-2-yl)but-3-en-2-one (30D, 4.81 g, 18.6 mmol, 1.0 eq.), MeOH (100 mL), and dimethylmalonate (30E, 2.13 mL, 18.6 mmol, 1.0 eq.). NaOMe (30% wt in MeOH, 3.66 mL, 19.5 mmol, 1.05 eq.) was added and the reaction mixture was stirred overnight at reflux. LC/MS analysis showed the desired intermediate and the mixture was concentrated and then taken up in 1N aqueous NaOH (100 mL) and refluxed for 1 h. The reaction was then cooled to 0° C. in an ice bath and acidified with 1N HCl until acidic. The reaction mixture was then stirred at 80° C. for 1 h. After cooling to room temperature, EtOAc (200 mL) was added and the organic phase was washed with saturated aqueous NaCl (100 mL). The combined aqueous phases were extracted with EtOAc (100 mL). The combined organic phases were dried over anhydrous $Na_2SO_4$, filtered, and concentrated to give a foamy brown solid 30F that was taken on to the next step without further purification. (4.9 g, 88%). $^1$H NMR (400 MHz, DMSO-$d_6$) δ ppm 2.67 (m, 3H) 3.79 (s, 3H) 4.54-4.70 (m, 1H) 5.30 (s, 1H) 6.73 (d, J=8.08 Hz, 1H) 7.31 (d, J=7.33 Hz, 1H) 7.39-7.54 (m, 2H) 7.76 (t, J=7.83 Hz, 1H). ESI-MS: m/z 302.3 $(M+H)^+$.

D. Synthesis of 2-acetyl-3-hydroxy-5-(3-(6-methoxypyridin-2-yl)thiophen-2-yl)cyclohex-2-enone (30G)

To a 200 mL recovery flask was added 3-hydroxy-5-(3-(6-methoxypyridin-2-yl)thiophen-2-yl)cyclohex-2-enone (30F, 4.9 g, 16.3 mmol, 1.0 eq.), $CH_2Cl_2$ (100 mL), acetic anhydride (2.15 g, 21.1 mmol, 1.3 eq.), $Et_3N$ (6.8 mL, 48.8 mmol, 3.0 eq.), and DMAP (catalytic). The reaction mixture was stirred overnight at room temperature whereupon LC/MS showed two signals corresponding to M+H=344. Additional acetic anhydride (0.5 mL, 5.3 mmol, 0.32 eq.) was added and the reaction mixture was heated for 6 h at 40° C. LC/MS analysis showed the reaction to be complete whereupon the mixture was concentrated to a solid and purified via flash chromatography (70% $CH_2Cl_2$/Hex to 100% $CH_2Cl_2$) to yield a dark orange solid 30G (1.72 g, 31%). $^1$H NMR (400 MHz, DMSO-$d_6$) δ ppm 2.52-2.57 (m, 3H) 2.83 (m, 2H) 3.09 (m, 2H) 3.78 (s, 3H) 4.68 (m, 1H) 6.74 (d, J=8.34 Hz, 1H) 7.32 (d, J=7.33 Hz, 1H) 7.41-7.47 (m, 1H) 7.51 (d, J=5.31 Hz, 1H) 7.76 (t, J=7.96 Hz, 1H). ESI-MS: m/z 344.3 $(M+H)^+$.

E. Synthesis of 2-amino-7-(3-(6-methoxypyridin-2-yl)thiophen-2-yl)-4-methyl-7,8-dihydroquinazolin-5 (6H)-one (30H)

To a 150 mL pressure vessel was added 2-acetyl-3-hydroxy-5-(3-(6-methoxypyridin-2-yl)thiophen-2-yl)cyclohex-2-enone (30G, 1.72 g, 5.01 mmol, 1.0 eq.), EtOH (50 mL), pyrrolidine (2.13 g, 30.1 mmol, 6.0 eq.), guanidine hydrochloride (1.44 g, 15 mmol, 3.0 eq.). The vessel was sealed and heated overnight at 100° C. LC/MS analysis showed the reaction to be complete whereupon the reaction mixture was concentrated and the residue was taken up in 20% EtOAc/$CH_2Cl_2$. An insoluble solid proving not to be product was filtered off The remaining filtrate was purified via column chromatography (20% EtOAc/$CH_2Cl_2$ to 70% EtOAc/$CH_2Cl_2$) to yield the product 30H as a light gray solid (270 mg, 15%). $^1$H NMR (400 MHz, DMSO-$d_6$) δ ppm 2.55 (s, 3H) 2.76-2.95 (m, 2H) 3.02-3.22 (m, 2H) 3.70 (s, 3H) 4.62-4.77 (m, 1H) 6.72 (d, J=8.34 Hz, 1H) 7.31 (d, J=7.58 Hz, 1H) 7.41-7.54 (m, 4H) 7.75 (t, J=7.83 Hz, 1H). ESI-MS: m/z 367.3 $(M+H)^+$.

Example 31

Preparation of (R)-2-Amino-7-(2-bromo-4-fluorophenyl)-4-methyl-7,8-dihydro-6H-pyrido[4,3-d]pyrimidine-5-thione (31I) and (R)-2-Amino-7-(4-fluoro-2-(6-methoxypyridin-2-yl)phenyl)-4-methyl-7,8-dihydropyrido[4,3-d]pyrimidin-5(6H)-one (31J)

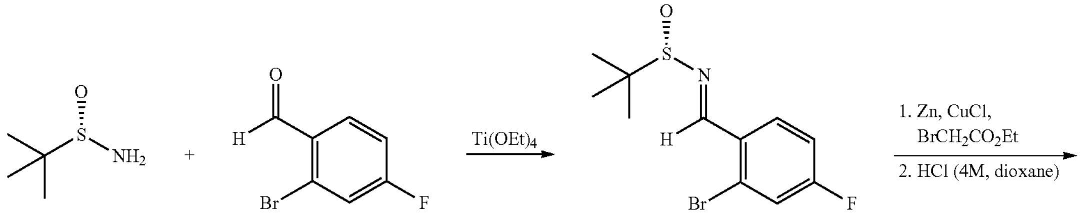

31A 31B 31C

-continued

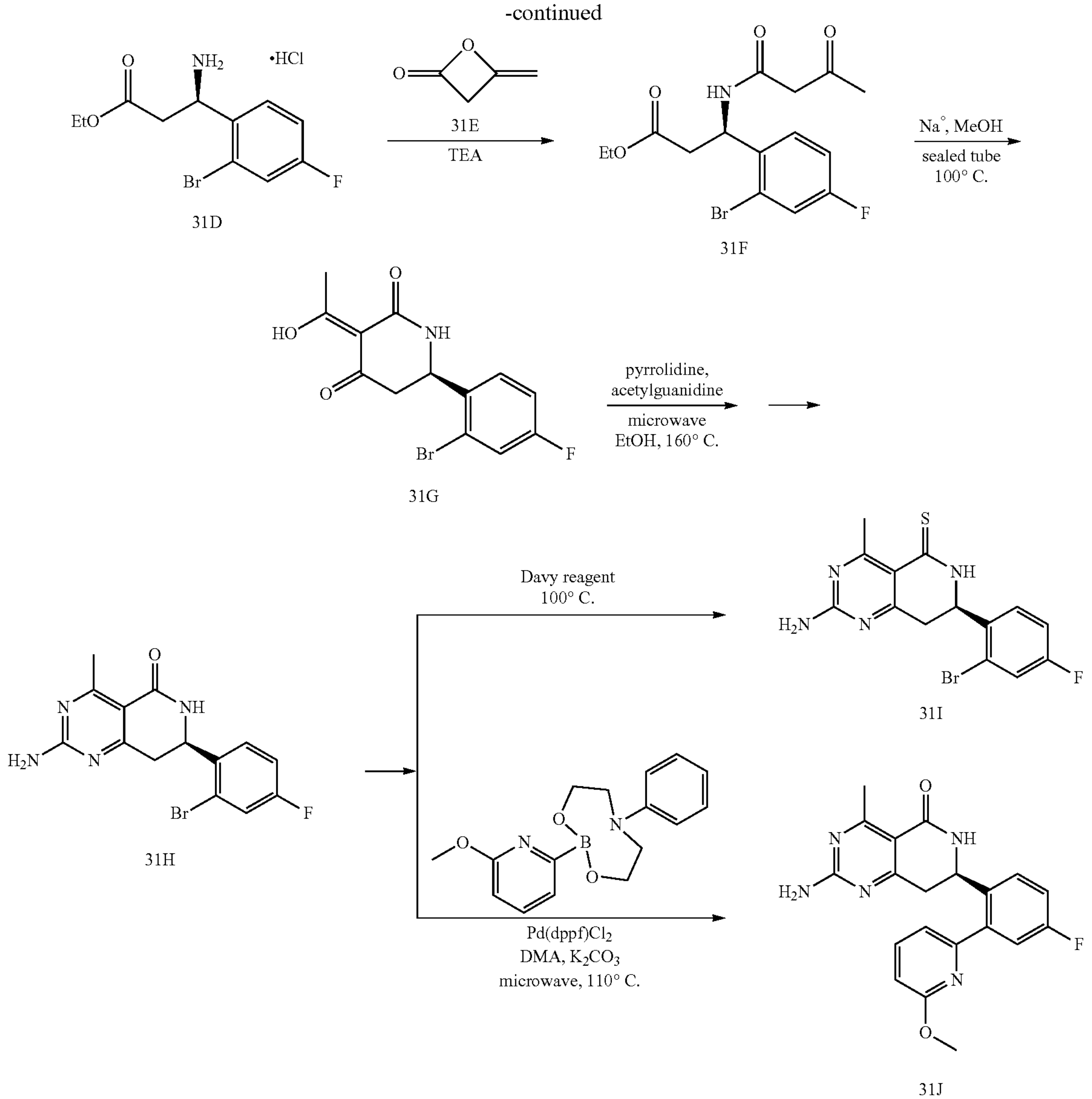

31D 31E 31F 31G 31H 31I 31J

A. Synthesis of (S)-2-methyl-propane-2-sulfinic acid 1-(2-bromo-4-fluoro-phenyl)-methyl-(E)-ylideneamide (31C)

(S)-tert-Butanesulfinimide (31A, 9.9 g, 81.6 mmol), 2-bromo-4-fluoro-benzaldehyde (31B, 15.5 g, 76 mmol), and titanium tetraethoxide (34 mL) were charged into a 500 mL round bottom flask containing THF (dry, 50 mL). The reaction was allowed to stir at ambient temperature for 2 h which was deemed complete by LCMS. EtOAc (200 mL), brine (150 mL), and celite was added and stir for 1 h. The heterogeneous mixture was filtered through a pad of celite, and washed with EtOAc. The organic layer was washed with brine and dried ($Na_2SO_4$), then concentrated in vacuo to afford the product 31C as viscous oil (23.3 g, 99% yield). 31C was used in the next step without further purification.

B. Synthesis of (R)-3-amino-3-(2-bromo-4-fluoro-phenyl)-propionic acid ethyl ester (31D)

A 500 mL 3-necked flask fitted with an overhead stirrer, a 150 mL addition funnel and a reflux condenser, was charged with THF (dry, 150 mL), Zn (74.5 g, 1.14 mol, 10 μm particle size) and CuCl (11.3 g, 114 mmol) under $N_2$ atmosphere. The heterogeneous mixture was refluxed for 1 h while stirring vigorously. After cooling to ambient temperature, ethyl bromoacetate (12.61 mL, 114 mmol) was added and the reaction was held at 50° C. for 1 h then cooled to 0° C. 31C (23.3 g, 76 mmol) in THF (dry, 80 mL) was added via the addition funnel over 10 min. The reaction was held at 0° C. for 4 h then warmed to ambient temp and stirred for 12 h. The heterogeneous mixture was filtered through a pad of celite and washed with EtOAc. The organic layer was washed with citric acid (1M), $NaHCO_3$, brine, dried over $Na_2SO_4$ and concentrated in vacuo to give 24.3 g of light yellow solid. The solid was then taken up in diethyl ether (200 mL), EtOH (5 mL), and HCl (38 mL, 4M in dioxane). After 30 min the product 31D precipitated and was filtered, the solid washed with excess diethyl ether dried under high vacuum to afford the (3-amino ester HCl salt in good yield (15.6 g, 47.7 mmol, 63%). The mother liquor contained an additional 1.9 g (6.5 mmol, 8.5%)

of freebase after neutralization and column chromatography (1-5%, MeOH in DCM). ESI-MS: m/z 290.01 (MH+).

C. Synthesis of (R)-3-(2-bromo-4-fluoro-phenyl)-3-(3-oxo-butyrylamino)-propionic acid ethyl ester (31F)

A 500 mL round-bottom flask charged with 31D (13.3 g, 41 mmol) in 200 mL of DCM and TEA (22.8 mL, 3 equiv.) was added diketene (31E, 8.81 mL, 50% in DCM). The reaction was stirred at ambient temperature until completion (2 h, determined by LCMS). The reaction mixture was washed with 1 N $NaHSO_4$, brine, dried over $Na_2SO_4$ and concentrated in vacuo to afford Compound 31F as a yellow solid (15.3 g, 99%). ESI-MS: m/z 374.0 ($MH^+$).

D. Synthesis of (R,E)-6-(2-bromo-4-fluorophenyl)-3-(1-hydroxyethylidene)piperidine-2,4-dione (31G)

To a flask containing 30 mL dry MeOH was added sodium metal (1.00 g, 43.5 mmol, 3.4 eq.). The mixture was stirred vigorously until sodium is dissolved. To a pressure vessel containing 31F (4.81 g, 12.9 mmol, 1.0 eq.) in MeOH (50 mL) was added the freshly prepared NaOMe solution. The pressure vessel was sealed and heated at 100° C. overnight. LC/MS analysis showed the product as the major signal. The reaction mixture was concentrated and then diluted with methylene chloride (500 mL) and aqueous 1 N $NH_4Cl$ (100 mL). The organic phase was further washed with aqueous 1 N $NH_4Cl$ (100 mL) and saturated aqueous NaCl (100 mL). The combined aqueous phases were extracted with methylene chloride (2×75 mL). The combined organic phases were dried over anhydrous $Na_2SO_4$, filtered, and concentrated to give a dark yellow solid 31G which was deemed pure enough to take on to the next reaction without further purification (2.05 g, 49%). ESI-MS: m/z 328.2 $(M+H)^+$ E. Synthesis of (R)-2-amino-7-(2-bromo-4-fluorophenyl)-4-methyl-7,8-dihydropyrido[4,3-d]pyrimidin-5(6H)-one (31H)

A microwave vial charged with acetylguanidine (800 mg, 7.9 mmol) was added pyrrolidine (3.25 mL, 39 mmol), 5 mL of EtOH and 31G (1.3 g, 3.9 mmol). The mixture was heated in a microwave at 160° C. for 10 min. The reaction mixture was diluted with EtOAc (50 mL) and washed with 1M $NaHSO_4$ (40 mL×2), brine, dried over $Na_2SO_4$, concentrated in vacuo. The resulting solid was purified by column chromatography (2-5% MeOH in DCM gradient) to give the product 31H as a light yellow crystalline solid (989 mg, 72%). $^1H$ NMR (400 MHz, DMSO-$d_6$) δ ppm 2.61 (s, 3H) 2.83 (dd, J=16.29, 5.94 Hz, 1H) 3.22 (dd, J=16.42, 6.06 Hz, 1H) 4.84-5.06 (m, 1H) 7.11 (br. s., 2H) 7.19-7.40 (m, 2H) 7.61 (dd, J=8.59, 2.53 Hz, 1H) 7.98 (d, J=3.28 Hz, 4H). ESI-MS: m/z 351.0 ($MH^+$).

F. Synthesis of (R)-2-Amino-7-(2-bromo-4-fluorophenyl)-4-methyl-7,8-dihydro-6H-pyrido[4,3-d]pyrimidine-5-thione (31I)

A 4 mL vial charged with 31H and 2 mL of DME was added Davy reagent (250 mg, 0.71 mmol). The mixture was heated to 100° C. for 20 min. The crude mixture was directly charged into a 12 g silica column and eluted (2-4% MeOH in DCM) to give the thiolactam 31I in modest yield (134 mg, 52%). ESI-MS: m/z 367.0 ($MH^+$).

G. Synthesis of (R)-2-amino-7-(4-fluoro-2-(6-methoxypyridin-2-yl)phenyl)-4-methyl-7,8-dihydropyrido[4,3-d]pyrimidin-5(6H)-one (31J)

To a 5 mL microwave vial was added 31H (700 mg, 1.99 mmol, 1.0 eq.), 2-(6-methoxypyridin-2-yl)-6-phenyl-1,3,6,2-dioxazaborocane (1.43 g, 4.78 mmol, 2.4 eq.), Pd(dppf)$Cl_2$ (73 mg, 0.0997 mmol, 0.05 eq.), $K_2CO_3$ (826 mg, 5.98 mmol, 3.0 eq.), and dimethylacetamide (10 mL). The vial was sealed and heated in a microwave at 110° C. for 30 min. LC/MS analysis showed the reaction was complete. The reaction mixture was diluted with methanol, filtered, and purified via preparative-HPLC to give the product 31J as a white solid (618 mg, 81.7% yield). $^1H$ NMR (400 MHz, DMSO-$d_6$) δ ppm 2.58 (s, 3H) 2.80-2.95 (m, 1H) 3.08-3.22 (m, 1H) 3.86 (s, 3H) 5.15 (br. s., 1H) 6.86 (d, J=7.58 Hz, 1H) 7.18 (d, J=6.82 Hz, 1H) 7.23-7.33 (m, 2H) 7.55 (dd, J=8.59, 5.81 Hz, 1H) 7.84 (dd, J=8.34, 7.33 Hz, 2H). ESI-MS: m/z 380.2 $(M+H)^+$.

Example 32

Preparation of (R,Z)-2-Amino-7-(4-fluoro-2-(6-methoxypyridin-2-yl)phenyl)-4-methyl-7,8-dihydropyrido[4,3-d]pyrimidin-5(6H)-one O—((R)-2,2-dimethyl-1,3-dioxolan-4-yl)methyl oxime (Compound 32) and (R,Z)-2-Amino-7-(4-fluoro-2-(6-methoxypyridin-2-yl)phenyl)-4-methyl-7,8-dihydropyrido[4,3-d]pyrimidin-5(6H)-one O—(R)-2,3-dihydroxypropyl oxime (Compound 33)

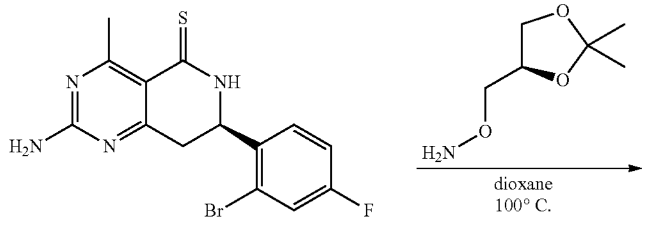

31I

-continued

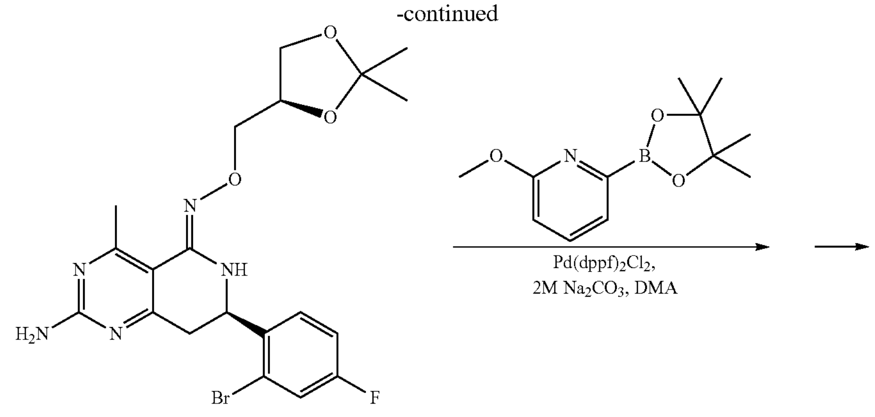

32A

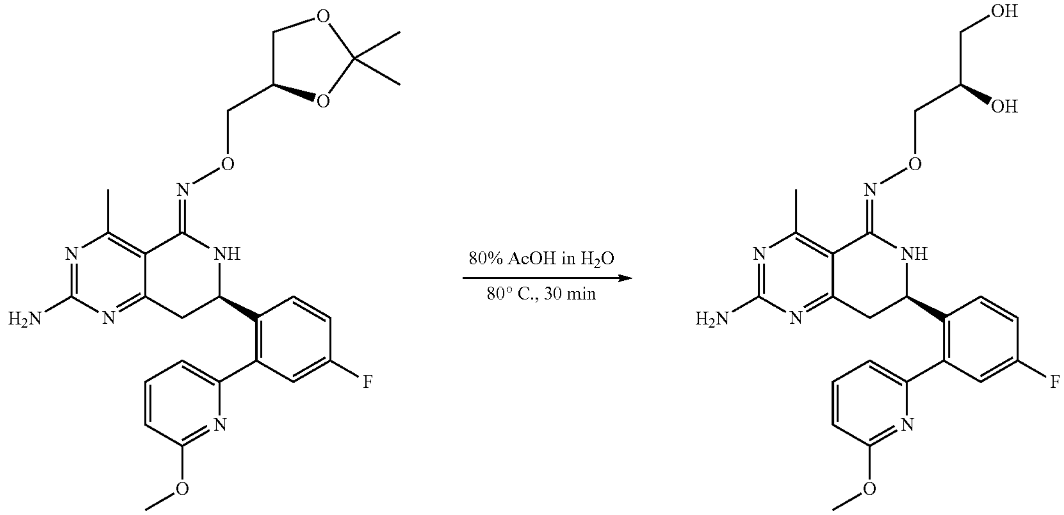

32 33

A 4 mL vial charged with (R)-2-amino-7-(2-bromo-4-fluoro-phenyl)-4-methyl-7,8-dihydro-6H-pyrido[4,3-d]pyrimidine-5-thione (31I (Example 31), 107 mg, 0.28 mmol), (R)—O-((2,2-dimethyl-1,3-dioxolan-4-yl)methyl)hydroxylamine (247 mg, 1.68 mmol), and dioxane (2 mL) was heated to 100° C. for 12 h. The crude mixture was purified by preparative reverse phase HPLC (10-70% $H_2O$—AcCN, 0.035% TFA) to afford the product (R,Z)-2-amino-7-(2-bromo-4-fluorophenyl)-4-methyl-7,8-dihydropyrido[4,3-d]pyrimidin-5(6H)-one O—((R)-2,2-dimethyl-1,3-dioxolan-4-yl) methyl oxime (32A) in modest yield (40 mg, 30% yield). ESI-MS: m/z 480.1 $(M+H)^+$.

To a vial containing 32A (40 mg, 0.083 mmol), 2-methoxy-6-(4,4,5,5-tetramethyl-1,3,2-dioxaborolan-2-yl)pyridine (58 mg, 0.25 mmol), $Na_2CO_3$ (0.5 mL, 1.0 mmol), $Pd(dppf)_2Cl_2$ (3.4 mg, 0.004 mmol) and DMA (0.5 mL) was heated to 130° C. for 20 min in the microwave. The resultant crude mixture was diluted with EtOAc, and washed with $H_2O$, brine, dried over $Na_2SO_4$, and concentrated in vacuo to yield (R,Z)-2-amino-7-(4-fluoro-2-(6-methoxypyridin-2-yl)phenyl)-4-methyl-7,8-dihydropyrido[4,3-d]pyrimidin-5(6H)-one O—((R)-2,2-dimethyl-1,3-dioxolan-4-yl)methyl oxime (32) after reverse-phase preparative HPLC (16 mg, 39% yield, 10-70% $H_2O$—AcCN, 0.035% TFA). $^1H$ NMR (400 MHz, CHLOROFORM-d) δ ppm 1.35 (s, 3H) 1.41 (s, 3H) 2.85 (s, 3H) 3.15 (dd, J=17.05, 10.48 Hz, 1H) 3.46 (dd, J=17.18, 3.79 Hz, 1H) 3.70-3.80 (m, 1H) 3.88 (s, 3H) 3.99-4.17 (m, 3H) 4.36-4.49 (m, 1H) 4.90 (dd, J=10.36, 3.54 Hz, 1H) 4.30-5.10 (br, 2H) 5.80 (br, 1H) 6.76 (d, J=8.34 Hz, 1H) 7.02 (d, J=7.33 Hz, 1H) 7.10-7.24 (m, 2H) 7.60 (dd, J=8.59, 5.56 Hz, 1H) 7.68 (t, J=7.83 Hz, 1H). ESI-MS: m/z 509.4 $(M+H)^+$.

Compound 32 was taken up in AcOH—$H_2O$ (1 mL, 5:1) and heated to 80° C. for 30 min; the excess AcOH was removed under vacuum. The crude product was then purified by reverse phase preparative HPLC to yield (R,Z)-2-amino-7-(4-fluoro-2-(6-methoxypyridin-2-yl)phenyl)-4-methyl-7,8-dihydropyrido[4,3-d]pyrimidin-5(6H)-one O—(R)-2,3-dihydroxypropyl oxime (33, 12 mg, 20-75% $H_2O$—AcCN, 10 mM $(NH_4)_2CO_2$). $^1H$ NMR (400 MHz, DMSO-$d_6$) δ ppm 2.48 (s, 3H) 2.81 (dd, J=16.17, 7.83 Hz, 1H) 3.04 (dd, J=16.17, 4.80 Hz, 1H) 3.28-3.41 (m, 2H) 3.66-3.76 (m, 1H) 3.78-3.84 (m, 1H) 3.9 (s, 3H) 3.89-3.97 (m, 1H) 4.51 (t, J=5.68 Hz, 1H) 4.64 (d, J=4.80 Hz, 1H) 4.94-5.05 (m, 1H) 6.48 (s, 1H) 6.79 (s, 2H) 6.85 (d, J=8.34 Hz, 1H) 7.18 (d, J=7.33 Hz, 1H) 7.23-7.35 (m, 2H) 7.53 (dd, J=8.59, 5.81 Hz, 1H) 7.84 (t, J=7.83 Hz, 1H). ESI-MS: m/z 469.2 $(M+H)^+$.

Example 33

Preparation of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-2,3-dihydroxypropyl oxime (Compound 34)

34

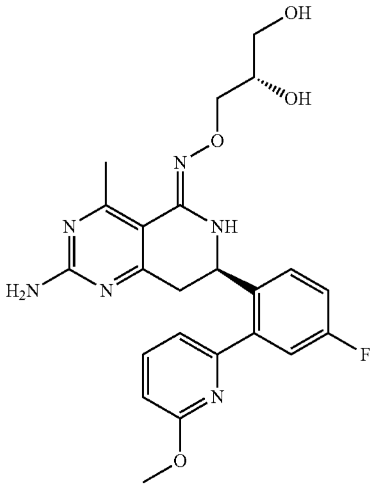

The title compound was prepared by the procedure of Example 32 except that (S)—O-((2,2-dimethyl-1,3-dioxolan-4-yl)methyl)hydroxylamine was used. $^1$H NMR (400 MHz, CHLOROFORM-d) δ ppm 2.63 (s, 3H) 2.97-3.14 (m, 1H) 3.16-3.28 (m, 1H) 3.55-3.68 (m, 1H) 3.68-3.76 (m, 3H) 3.90 (s, 3H) 3.97-4.20 (m, 3H) 4.90 (dd, J=10.23, 3.92 Hz, 1H) 5.26 (br. s., 2H) 5.83 (s, 1H) 6.74 (d, J=8.34 Hz, 1H) 7.00 (d, J=7.07 Hz, 1H) 7.07-7.22 (m, 2H) 7.52-7.76 (m, 2H). ESI-MS: m/z 469.2 $(M+H^+)$.

Example 34

Synthesis of (R,Z)-2-Amino-7-(4-fluoro-2-(6-methoxypyridin-2-yl)phenyl)-4-methyl-7,8-dihydropyrido[4,3-d]pyrimidin-5(6H)-one O-3-hydroxy-2-(hydroxymethyl)propyl oxime (Compound 35)

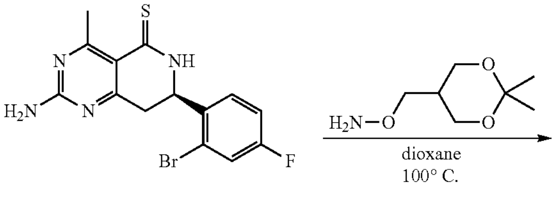

311

-continued

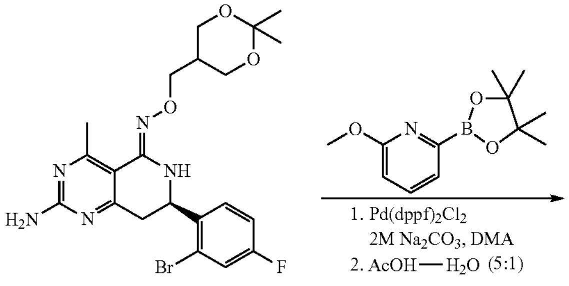

34A

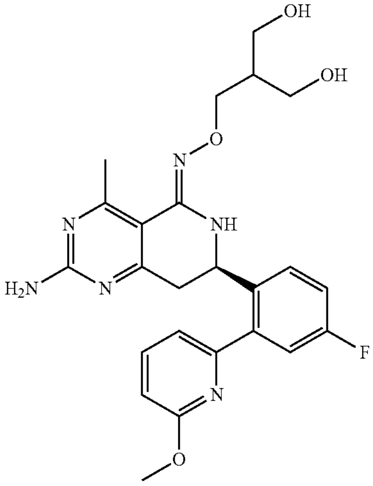

35

The title compound 35 was prepared by a procedure analogous to that disclosed in Example 32 except O-((2,2-dimethyl-1,3-dioxan-5-yl)methyl)hydroxylamine was used. The crude product was purified by reverse phase HPLC (5 mg, 20-75% $H_2O$—AcCN, 10 mM $(NH_4)_2CO_2$) to afford (R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxy-2-(hydroxymethyl)propyl oxime (33, 5 mg, 2.9% yield). $^1$H NMR (400 MHz, DMSO-d$_6$) δ ppm 1.88-2.05 (m, 1H) 2.53 (s, 3H) 2.81 (dd, J=16.17, 7.33 Hz, 1H) 3.03 (dd, J=16.04, 4.93 Hz, 1H) 3.42-3.50 (m, 4H) 3.86 (s, 3H) 3.93 (dd, J=6.32, 2.53 Hz, 2H) 4.29-4.39 (m, 2H) 5.00-5.10 (m, 1H) 6.31 (s, 1H) 6.76 (s, 2H) 6.85 (d, J=8.34 Hz, 1H) 7.19 (d, J=7.33 Hz, 1H) 7.21-7.32 (m, 2H) 7.49 (dd, J=8.59, 5.81 Hz, 1H) 7.84 (t, J=7.83 Hz, 1H). ESI-MS: m/z 483.3 $(M+H^+)$.

Example 35

Synthesis of (R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime (Compound 36) and (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime (Compound 37)

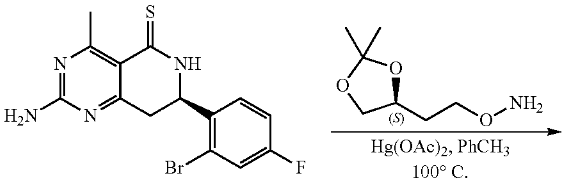

31I

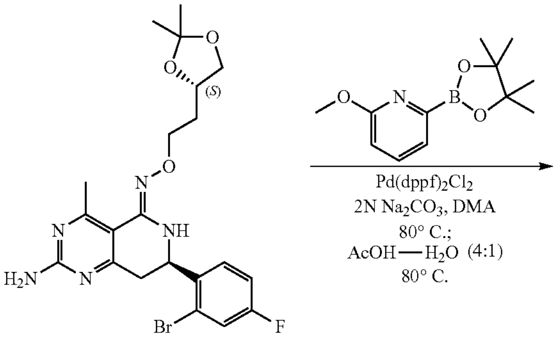

35A

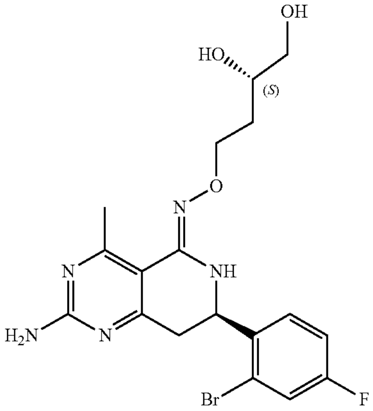

36

+

-continued

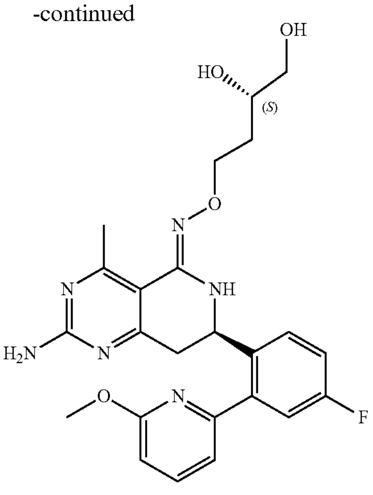

37

A mixture of (R)-2-amino-7-(2-bromo-4-fluorophenyl)-4-methyl-7,8-dihydropyrido[4,3-d]pyrimidine-5(6H)-thione (311,100 mg, 0.3 mmol), (S)—O-(2-(2,2-dimethyl-1,3-dioxolan-4-yl)ethyl)hydroxylamine (194 mg, 1.2 mmol), $Hg(OAc)_2$ (192 mg, 0.6 mmol) and anhydrous toluene (2 mL) was heated at 100° C. for 1 h. LCMS shows completion of the reaction. The mixture was cooled, filtered through celite and washed with ethyl acetate. Filtrate concentrated and the resulting oily residue was purified by preparative LCMS to afford (R,Z)-2-amino-7-(2-bromo-4-fluorophenyl)-4-methyl-7,8-dihydropyrido[4,3-d]pyrimidin-5(6H)-one O-2-((S)-2,2-dimethyl-1,3-dioxolan-4-yl)ethyl oxime (35A, 87 mg, 65%) as a pale yellow solid. $^1$H NMR (400 MHz, CHLOROFORM-d) δ 1.35 (s, 3H) 1.40 (s, 3H) 2.01 (qd, J=6.32, 3.03 Hz, 2H) 2.76 (s, 3H) 2.95 (dd, J=16.42, 8.84 Hz, 1H) 3.18 (dd, J=17.18, 5.05 Hz, 1H) 3.56-3.62 (m, 1H) 4.09 (dd, J=7.96, 5.94 Hz, 1H) 4.16-4.28 (m, 2H) 4.98 (ddd, J=8.78, 4.61, 1.52 Hz, 1H) 7.07 (td, J=8.21, 2.53 Hz, 1H) 7.34 (dd, J=8.08, 2.53 Hz, 1H) 7.68 (dd, J=12.00, 6.95 Hz, 1H). MS (ES) [M+H] calculated for $C_{2i}H_{26}BrFN_5O_3$, 494.11; found 494.00.

A mixture of the above compounds (83.0 mg, 0.17 mmol), 2-methoxy-6-(4,4,5,5-tetramethyl-1,3,2-dioxaborolan-2-yl) pyridine (80.0 mg, 0.34 mmol), $Pd(dppf)_2Cl_2$ (14 mg, 0.017 mmol), 2N $Na_2CO_3$ (0.42 mL, 0.85 mmol) in DMA (2 mL) was degassed with $N_2$ and heated at 80° C. for 2.5 h. LCMS shows 1:1 mixture of starting material and product. The reaction mixture was cooled, filtered through celite and washed with 1:1 MeOH—$CH_2Cl_2$. The filtrate was concentrated and the residue was dissolved in 4:1 mixture of AcOH—$H_2O$ and heated at 80° C. for 30 minutes. Solvent removed under reduced pressure and the residue was purified by preparative HPLC (basic mode) to afford Compounds 36 and 37.

Compound 36: (R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime (36, 8.0 mg). $^1$H NMR (400 MHz, METHANOL-$d_4$) d 1.68-1.80 (dddd, J=14.31, 8.75, 5.65, 5.65 Hz, 1H), 2.02 (dddd, J=14.24, 7.74, 6.44, 3.92 Hz, 1H), 2.85 (s, 3H), 3.18 (dd, J=16.93, 6.57 Hz, 1H), 3.37 (dd, J=16.80, 5.43 Hz, 1H), 3.43-3.55 (m, 2H), 3.72-3.82 (m, 1H), 4.18-4.31 (m, 2H), 5.14 (t, J=5.94 Hz, 1H), 7.15 (td, J=8.40, 2.65 Hz, 1H), 7.39 (dd, J=8.84, 5.81 Hz, 1H), 7.46 (dd, J=8.34, 2.78 Hz, 1H). MS (ES) [M+H] calculated for $C_{18}H_{22}BrFN_5O_3$, 454.29; found 454.20).

Compound 37: (R,Z)-2-amino-7-(4-fluoro-2-(6-methoxy-pyridin-2-yl)phenyl)-4-methyl-7,8-dihydropyrido[4,3-d]pyrimidin-5(6H)-one O—(S)-3,4-dihydroxybutyl oxime (37, 8.0 mg). $^1$H NMR (400 MHz, CHLOROFORM-d) δ 1.53-1.58 (m, 1H) 1.69-1.73 (m, 1H) 2.46 (s, 3H) 2.79-2.87 (m, 1H) 2.93-2.98 (m, 1H) 3.22-3.28 (m, 1H) 3.35-3.38 (m, 1H) 3.54-3.60 (m, 1H) 3.70 (s, 3H) 3.94-4.00 (m, 2H) 4.69 (ddd, J=10.23, 3.03, 2.91 Hz, 1H) 6.55 (dd, J=8.34, 2.53 Hz, 1H) 6.84 (dd, J=7.33, 2.53 Hz, 1H) 6.94-7.00 (m, 2H) 7.43-7.52 (m, 2H). MS (ES) [M+H] calculated for $C_{24}H_{28}FN_6O_4$, 483.50; found 483.30.

Example 36

Synthesis of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxy-butyl oxime (Compound 37)

37

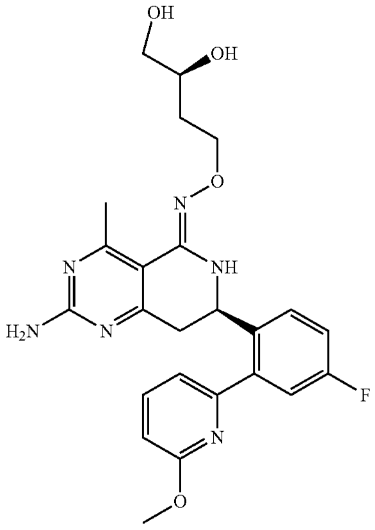

Compound 37 was synthesized using an analogous procedure described for Example 39 except that (S)—O-(2-(2,2-dimethyl-1,3-dioxolan-4-yl)ethyl)hydroxylamine was used. $^1$H NMR (400 MHz, CHLOROFORM-d) δ 1.43-1.55 (m, 1H) 1.66 (m, 1H) 2.55 (s, 3H) 2.83-2.95 (m, 2H) 3.11-3.44 (m, 1H) 3.17-3.24 (m, 1H) 3.27-3.33 (m, 1H) 3.48-3.56 (m, 1H) 3.65 (s, 3H) 3.89-4.01 (m, 2H) 4.68 (ddd, J=10.23, 3.03, 2.91 Hz, 1H) 6.53 (dd, J=8.34, 2.53 Hz, 1H) 6.81 (dd, J=7.33, 2.53 Hz, 1H) 6.90 (dt, J=9.28, 2.68 Hz, 1H) 6.96 (td, J=8.40, 2.65 Hz, 1H) 7.38-7.43 (m, 1H) 7.44-7.51 (m, 1H). MS (ES) $[M+H]^+$ calculated for $C_{24}H_{28}FN_6O_4$, 483.21; found 483.00.

Example 37

(R,Z)-2-Amino-7-(4-fluoro-2-(6-methoxypyridin-2-yl)phenyl)-4-methyl-7,8-dihydropyrido[4,3-d]pyrimidin-5(6H)-one O—(R)-3,4-dihydroxybutyl oxime (Compound 38)

38

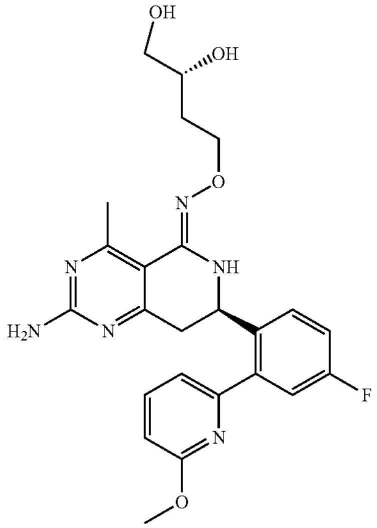

Compound 38 was synthesized using an analogous procedure described for Example 39 except that (R)—O-(2-(2,2-dimethyl-1,3-dioxolan-4-yl)ethyl)hydroxylamine was used. $^1$H NMR (400 MHz, CHLOROFORM-d) δ ppm 1.74-1.93 (m, 1H) 2.13-2.16 (m, 1H) 2.66 (s, 3H) 3.00-3.11 (m, 1H) 3.14-3.24 (m, 1H) 3.32 (d, J=3.03 Hz, 1H) 3.50 (ddd, J=11.18, 7.01, 4.55 Hz, 1H) 3.65 (ddd, J=10.74, 6.95, 3.54 Hz, 1H) 3.90 (s, 3H) 4.13-4.28 (m, 2H) 4.88 (dd, J=10.61, 4.04 Hz, 1H) 5.11 (s, 2H, OH) 5.72 (s, 1H, NH) 6.74 (d, J=8.84 Hz, 1H) 7.00 (d, J=7.83 Hz, 1H) 7.10-7.22 (m, 2H) 7.61-7.70 (m, 2H). MS (ES) [M+H] calculated for $C_{24}H_{28}FN_6O_4$, 483.21; found 483.30.

Example-38

(S)-4-((Z)—((R)-2-amino-7-(4-fluoro-2-(6-methoxy-pyridin-2-yl)phenyl)-4-methyl-7,8-dihydropyrido[4,3-d]pyrimidin-5(6H)-ylidene)amino)butane-1,2-diol (Compound 39)

39

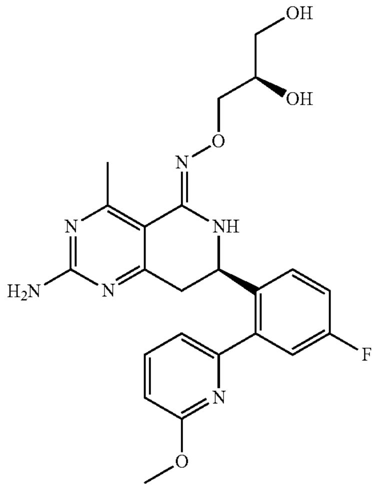

Compound 39 was synthesized using an analogous procedure described for Example 39 except that (S)-2-(2,2-dimethyl-1,3-dioxolan-4-yl)ethanamine (20, Example 2-F) was used. $^1$H NMR (400 MHz, CHLOROFORM-d) δ ppm 1.55-1.68 (m, 2H) 2.57 (s, 3H) 2.66-2.78 (m, 2H) 3.16 (dd, J=16.17, 3.54 Hz, 1H) 3.25 (ddd, J=14.08, 4.29, 4.11 Hz, 1H) 3.41-3.49 (m, 1H) 3.52-3.59 (m, 1H) 3.65-3.78 (m, 1H) 3.88 (s, 3H) 4.83 (dd, J=12.63, 3.03 Hz, 1H) 5.30 (br. s., 2H, OH) 6.70 (d, J=8.34 Hz, 1H) 7.01 (d, J=7.33 Hz, 1H) 7.10 (dd, J=9.47, 2.65 Hz, 1H) 7.17 (td, J=8.27, 2.65 Hz, 1H) 7.62 (t, J=7.83 Hz, 1H) 7.80 (dd, J=8.59, 5.81 Hz, 1H). MS (ES) [M+H] calculated for $C_{24}H_{28}FN_6O_3$, 467.21; found 467.30.

Example 39

Synthesis of (R,Z)-2-Amino-7-(4-fluoro-2-(6-methoxypyridin-2-yl)phenyl)-4-methyl-7,8-dihydropyrido[4,3-d]pyrimidin-5(6H)-one O—((R)-1,4-dioxan-2-yl)methyl oxime (Compound 40)

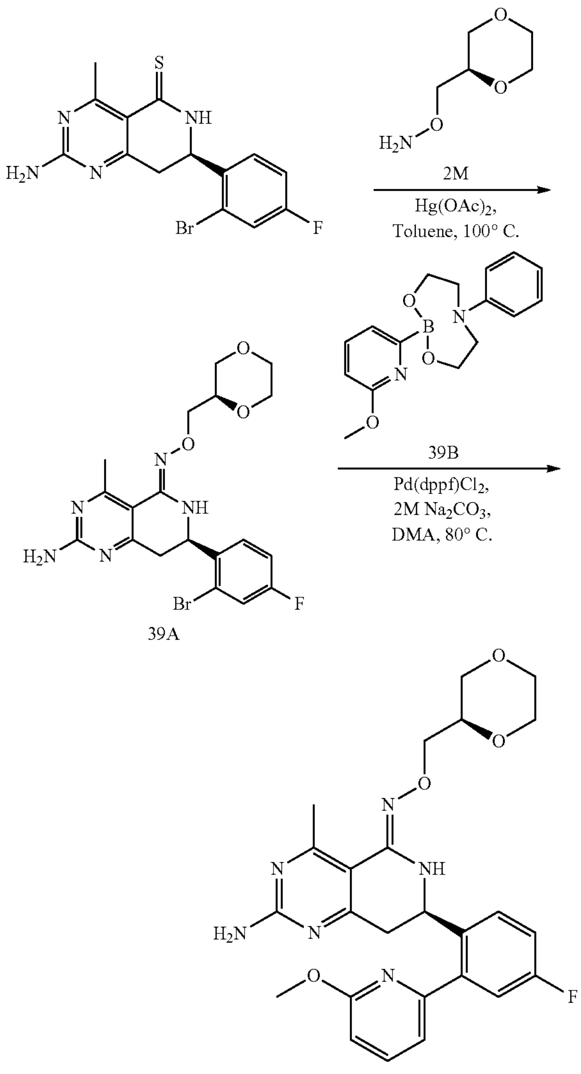

39A

40

Thiolactam (31I (Example 31), 0.087 g, 0.0272 mmol), (R)—O-((1,4-dioxan-2-yl)methyl)hydroxylamine (2M (Example 2-E), 0.145 g, 1.09 mmol), and mercury (II) acetate (0.173 g, 0.045 mmol) were dissolved in 3.5 mL of dry toluene and heated in 100° C. oil bath for 1 h. The reaction was done as judged by LC/MS. The crude mixture was filtered through Celite, rinsed with methanol and then concentrated and purified on preparatory LC/MS (25-55% $CH_3CN$ in $H_2O$) to afford (R,Z)-2-amino-7-(2-bromo-4-fluorophenyl)-4-methyl-7,8-dihydropyrido[4,3-d]pyrimidin-5(6H)-one O—((R)-1,4-dioxan-2-yl)methyl oxime (39A, 0.0405 g, 36.7% yield). $^1$H NMR (400 MHz, CHLOROFORM-d) δ ppm 2.90 (s, 3H) 3.04 (dd, J=17.05, 8.97 Hz, 2H) 3.28 (dd, J=17.56, 4.17 Hz, 1H) 3.43 (dd, J=11.62, 9.85 Hz, 1H) 3.58-3.68 (m, 1H) 3.70-3.76 (m, 2H) 3.77-3.88 (m, 2H) 3.93-4.00 (m, 1H) 4.01-4.08 (m, 1H) 4.09-4.18 (m, 1H) 5.01 (d, J=5.05 Hz, 1H) 5.78 (s, 1H) 7.11 (td, J=8.21, 2.53 Hz, 1H) 7.37 (dd, J=7.96, 2.65 Hz, 1H) 7.41 (dd, J=8.84, 5.81 Hz, 1H). ESI-MS: m/z 468.1 (M+H)$^+$.

39A was reacted with 2-(6-methoxypyridin-2-yl)-6-phenyl-1,3,6,2-dioxazaborocane (39B) according to a procedure analogous to Example 31, the step of 31H to 31J, to afford (R,Z)-2-amino-7-(4-fluoro-2-(6-methoxypyridin-2-yl)phenyl)-4-methyl-7,8-dihydropyrido[4,3-d]pyrimidin-5(6H)-one O—((R)-1,4-dioxan-2-yl)methyl oxime (40, 37.3% yield). $^1$H NMR (400 MHz, DMSO-d$_6$) δ ppm 2.55 (s, 3H) 2.85 (dd, J=16.17, 7.07 Hz, 1H) 3.10 (dd, J=16.29, 5.18 Hz, 1H) 3.24-3.35 (m, 1H) 3.45 (dd, J=10.99, 2.65 Hz, 1H) 3.50-3.59 (m, 1H) 3.59-3.74 (m, 2H) 3.76-3.84 (m, 3H) 3.86 (s, 3H) 3.89-3.96 (m, 1H) 5.10 (m, 1H) 6.54 (br. s., 1H) 6.85 (d, J=8.34 Hz, 1H) 7.19 (d, J=7.07 Hz, 1H) 7.23-7.31 (m, 2H) 7.45 (dd, J=8.46, 5.94 Hz, 1H) 7.78-7.92 (m, 1H). ESI-MS: m/z 495.3 (M+H)$^+$.

Example 40

Preparation of (7R,Z)-2-amino-7-(4-fluoro-2-(6-methoxypyridin-2-yl)phenyl)-4-methyl-7,8-dihydropyrido[4,3-d]pyrimidin-5(6H)-one O-morpholin-2-ylmethyl oxime and isomers (Compounds 41-43)

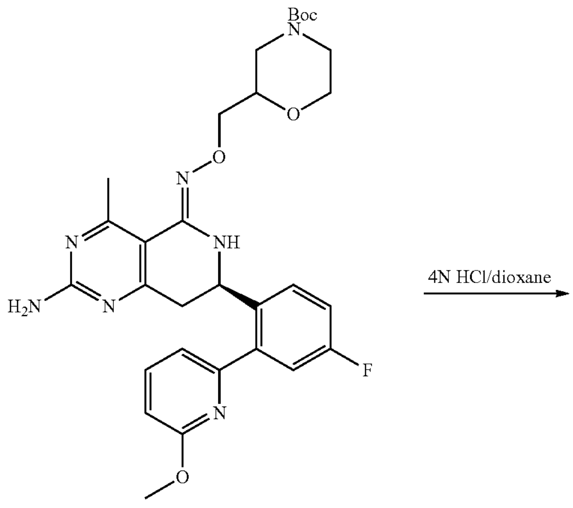

40A

-continued

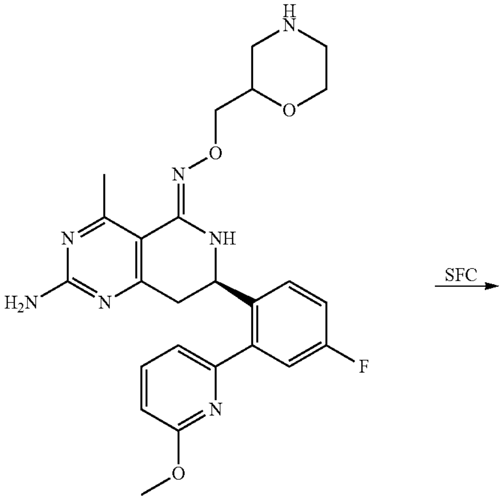

41

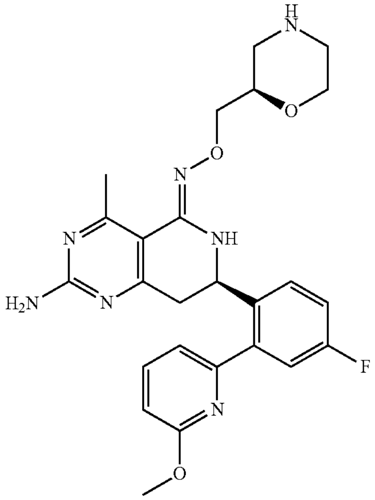

42

+

-continued

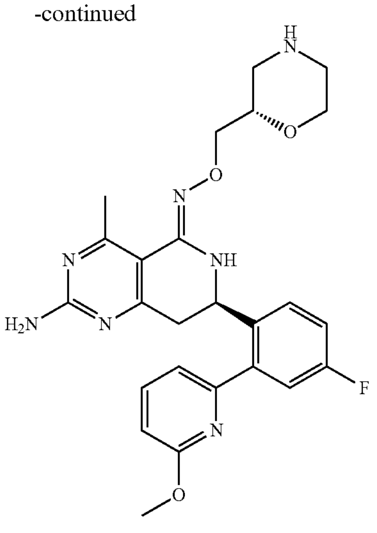

43

40A was prepared by a procedure analogous to that disclosed in Example 39 except tert-butyl 2-(aminooxymethyl) morpholine-4-carboxylate was used. The final Boc-deprotection was effected by treatment of 40A (6 mg, 0.01 mmol) with 4N HCl in dioxane (0.7 mL). The reaction was dried in vacuo to afford (7R,Z)-2-amino-7-(4-fluoro-2-(6-methoxypyridin-2-yl)phenyl)-4-methyl-7,8-dihydropyrido[4,3-d]pyrimidin-5(6H)-one O-morpholin-2-ylmethyl oxime as a tan oil (41, quantitative yield). $^1$H NMR (400 MHz, MeOD) δ ppm 2.84 (s, 3H) 3.00-3.10 (m, 1H) 3.11-3.21 (m, 1H) 3.34-3.50 (m, 2H) 3.53-3.77 (m, 2H) 3.81-3.92 (m, 1H) 4.06 (s, 3H) 4.09-4.13 (m, 2H) 4.13-4.21 (m, 2H) 4.95-4.99 (m, 1H) 7.11-7.18 (m, 1H) 7.23-7.29 (m, 1H) 7.29-7.38 (m, 2H) 7.67-7.76 (m, 1H) 8.04-8.12 (m, 1H). [M+H]$^+$ calc'd for $C_{25}H_{28}FN_7O_3$, 494; found, 494. SFC separation of 41 yields the two enantiomers.

(R,Z)-2-Amino-7-(4-fluoro-2-(6-methoxypyridin-2-yl)phenyl)-4-methyl-7,8-dihydropyrido[4,3-d]pyrimidin-5(6H)-one O—(R)-morpholin-2-ylmethyl oxime (42). $^1$H NMR (400 MHz, MeOD) δ ppm 2.82 (s, 3H) 2.95-3.28 (m, 4H) 3.33-3.45 (m, 2H) 3.83 (td, J=12.57, 2.40 Hz, 1H) 3.92 (s, 3H) 4.02-4.21 (m, 4H) 5.07 (dd, J=8.84, 4.29 Hz, 1H) 6.81 (d, J=8.34 Hz, 1H) 7.13 (d, J=7.33 Hz, 1H) 7.17-7.29 (m, 2H) 7.63 (dd, J=8.59, 5.56 Hz, 1H) 7.78 (t, J=7.83 Hz, 1H). [M+H] calc'd for $C_{25}H_{28}FN_7O_3$, 494; found, 494.

(R,Z)-2-Amino-7-(4-fluoro-2-(6-methoxypyridin-2-yl)phenyl)-4-methyl-7,8-dihydropyrido[4,3-d]pyrimidin-5(6H)-one O—(S)-morpholin-2-ylmethyl oxime (43). $^1$H NMR (400 MHz, MeOD) δ ppm 2.82 (s, 3H) 2.95-3.28 (m, 4H) 3.33-3.45 (m, 2H) 3.83 (td, J=12.57, 2.40 Hz, 1H) 3.92 (s, 3H) 4.02-4.21 (m, 4H) 5.07 (dd, J=8.84, 4.29 Hz, 1H) 6.81 (d, J=8.34 Hz, 1H) 7.13 (d, J=7.33 Hz, 1H) 7.17-7.29 (m, 2H) 7.63 (dd, J=8.59, 5.56 Hz, 1H) 7.78 (t, J=7.83 Hz, 1H). [M+H] calc'd for $C_{25}H_{28}FN_7O_3$, 494; found, 494.

Example 41

Synthesis of (R,Z)-2-amino-7-(4-fluoro-2-(6-methoxypyridin-2-yl)phenyl)-4-methyl-7,8-dihydropyrido[4,3-d]pyrimidin-5(6H)-one O—((2R,3S,4R)-3,4,5-trihydroxytetrahydrofuran-2-yl)methyl oxime (44) and its analog (Compound 44) and stereoisomers (Compounds 45, 46, 47, and 48)

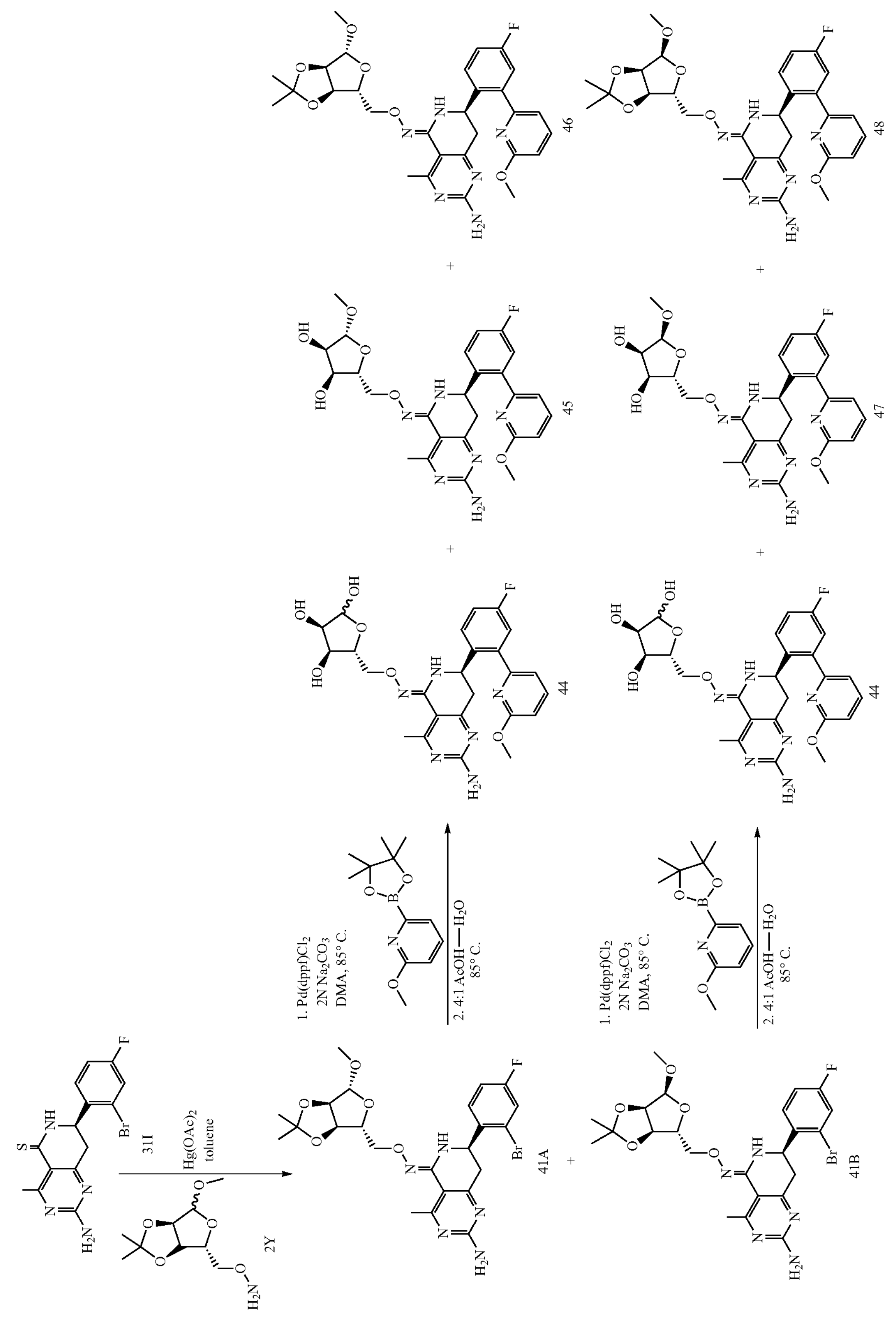
31I
2Y
Hg(OAc)2
toluene
41A
+
41B
1. Pd(dppf)Cl2
2N Na2CO3
DMA, 85° C.
2. 4:1 AcOH—H2O
85° C.
1. Pd(dppf)Cl2
2N Na2CO3
DMA, 85° C.
2. 4:1 AcOH—H2O
85° C.
44
+
45
+
46
44
+
47
+
48

Reaction of 31I and O-(((3 aR, 4R, 6aR)-6-methoxy-2,2-dimethyltetrahydrofuro[3,4-d][1,3]dioxol-4-yl)methyl)hydroxylamine (2Y) according to a procedure analogous to Example 39 yielded a racemic mixture of (R,Z)-2-amino-7-(2-bromo-4-fluorophenyl)-4-methyl-7,8-dihydropyrido[4,3-d]pyrimidin-5(6H)-one O-((3 aR, 4R, 6aR)-6-methoxy-2,2-dimethyltetrahydrofuro[3,4-d][1,3]dioxol-4-yl)methyl oxime. Prep LC/MS (40-85% $NH_4OAc$—$H_2O$—AcCN) separation yielded the diastereomers 41A and 41B.

The diastereomers, 41A and 41B, were each separately coupled to 2-methoxy-6-(4,4,5,5-tetramethyl-1,3,2-dioxaborolan-2-yl)pyridine according also according to the procedure described in Example 39. Deprotection and prep LC/MS (40-85% $NH_4OAc$—$H_2O$—AcCN) separation of each of the reaction mixtures yielded a hydroxyl analog and two stereoisomers.

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R)-3,4,5-trihydroxytetrahydrofuran-2-yl)methyl oxime (44). $^1H$ NMR (400 MHz, CHLOROFORM-d) δ ppm 2.35 (s, 3H) 2.67-2.72 (m, 1H) 2.78-2.90 (m, 1H) 3.29 (dt, J=11.94, 2.87 Hz, 1H) 3.39-3.48 (m, 1H) 3.59 (s, 3H) 3.65-3.77 (m, 1H) 3.82-3.90 (m, 1H) 3.91-4.01 (m, 1H) 4.57-4.69 (m, 1H) 4.83-4.97 (m, 1H) 6.37-6.50 (m, 1H) 6.75 (d, J=7.33 Hz, 1H) 6.79-6.91 (m, 2H) 7.32-7.44 (m, 2H). MS (ES) [M+H] calculated for $C_{25}H_{28}FN_6O_6$, 527.20; found 527.20.

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R,5R)-3,4-dihydroxy-5-methoxytetrahydrofuran-2-yl)methyl oxime (45). $^1H$ NMR (400 MHz, CHLOROFORM-d) δ ppm 2.44 (s, 3H) 2.72-2.84 (m, 1H) 2.88-2.97 (m, 1H) 3.05 (s, 3H) 3.68 (s, 3H) 3.70 (d, J=2.27 Hz, 1H) 3.81-3.94 (m, 2H) 3.95-4.03 (m, 2H) 4.56 (s, 1H) 4.69 (dd, J=9.98, 3.16 Hz, 1H) 6.53 (d, J=8.34 Hz, 1H) 6.82 (d, J=7.33 Hz, 1H) 6.88-7.00 (m, 2H) 7.39-7.52 (m, 2H). MS (ES) [M+H] calculated for $C_{26}H_{30}FN_6O_6$, 541.21; found 541.20.

(R,Z)-2-Amino-7-(4-fluoro-2-(6-methoxypyridin-2-yl)phenyl)-4-methyl-7,8-dihydropyrido[4,3-d]pyrimidin-5(6H)-one O-((3aR,4R,6R,6aR)-6-methoxy-2,2-dimethyltetrahydrofuro[3,4-d][1,3]dioxol-4-yl)methyl oxime (46). $^1H$ NMR (400 MHz, CHLOROFORM-d) δ ppm 1.10 (s, 3H) 1.27 (s, 3H) 2.46 (s, 3H) 2.79-2.88 (m, 1H) 2.92-3.01 (m, 1H) 3.08 (s, 3H) 3.69 (s, 3H) 3.78-3.91 (m, 2H) 4.32 (t, J=6.44 Hz, 1H) 4.37 (d, J=5.81 Hz, 1H) 4.57 (d, J=6.06 Hz, 1H) 4.72 (dd, J=10.74, 3.66 Hz, 1H) 4.75 (s, 1H) 6.56 (d, J=9.85 Hz, 1H) 6.84 (d, J=6.32 Hz, 1H) 6.90-7.04 (m, 2H) 7.44-7.54 (m, 2H). MS (ES) [M+H] calculated for $C_{29}H_{34}FN_6O_6$, 581.24; found 581.30.

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R,5S)-3,4-dihydroxy-5-methoxytetrahydrofuran-2-yl)methyl oxime (47). $^1H$ NMR (400 MHz, CHLOROFORM-d) δ ppm 2.51 (s, 3H) 2.81-2.91 (m, 1H) 2.96-3.04 (m, 1H) 3.12 (s, 3H) 3.74 (s, 3H) 3.77 (d, J=4.80 Hz, 1H) 3.92-4.00 (m, 2H) 4.01-4.07 (m, 2H) 4.63 (s, 1H) 4.74 (dd, J=10.36, 4.04 Hz, 1H) 6.59 (d, J=8.08 Hz, 1H) 6.88 (d, J=7.07 Hz, 1H) 6.94-7.07 (m, 2H) 7.52 (t, J=7.83 Hz, 2H). MS (ES) [M+H] calculated for $C_{26}H_{30}FN_6O_6$, 541.21; found 541.20.

(R,Z)-2-amino-7-(4-fluoro-2-(6-methoxypyridin-2-yl)phenyl)-4-methyl-7,8-dihydropyrido[4,3-d]pyrimidin-5(6H)-one O-((3aR,4R,6S,6aR)-6-methoxy-2,2-dimethyltetrahydrofuro[3,4-d][1,3]dioxol-4-yl)methyl oxime (48) $^1H$ NMR (400 MHz, CHLOROFORM-d) δ ppm 1.04 (s, 3H) 1.20 (s, 3H) 2.40 (s, 3H) 2.72-2.81 (m, 1H) 2.86-2.94 (m, 1H) 3.02 (s, 3H) 3.63 (s, 3H) 3.64-3.79 (m, 3H) 4.26 (t, J=6.69 Hz, 1H) 4.51 (d, J=4.55 Hz, 1H) 4.62-4.70 (m, 2H) 6.50 (d, J=8.59 Hz, 1H) 6.79 (d, J=7.33 Hz, 1H) 6.85-6.95 (m, 2H) 7.39-7.47 (m, 2H). MS (ES) [M+H] calculated for $C_{29}H_{34}FN_6O_6$, 581.24; found 581.30.

Example 42

General Procedure for Suzuki Coupling

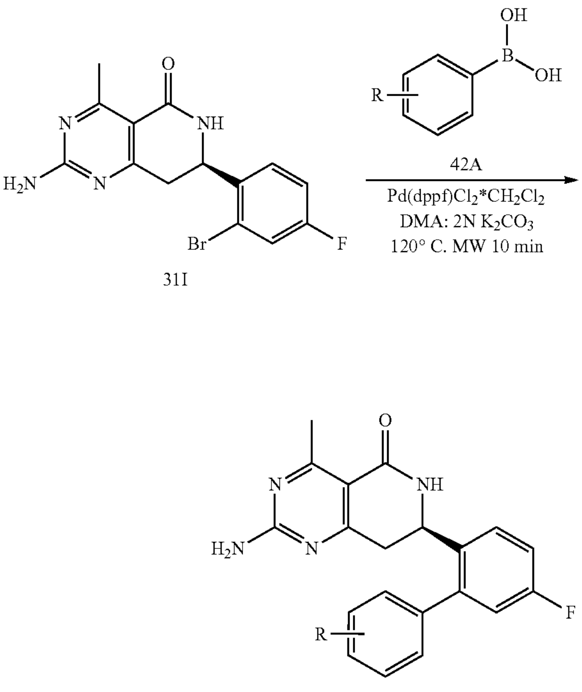

31I

42B

Into a 5 mL microwave vial was charged (R)-2-amino-7-(2-bromo-4-fluorophenyl)-4-methyl-7,8-dihydropyrido[4,3-d]pyrimidin-5(6H)-one (31H (Example 31), 100 mg, 0.28 mmol, 1 eq), boronic acid 42A (4 eq), and $Pd(dppf)Cl_2$ $CH_2Cl_2$ (93 mg, 0.11 mmol, 0.4 eq). The compounds were dissolved in a mixture of DMA (3 mL) and 2M $K_2CO_3$ (1 mL, 8 eq) and the vial was sealed. The reaction mixture was heated to 120° C. for 10 min in a microwave reactor. After cooling to RT, the reaction mixture was diluted with DCM and washed with $H_2O$ (×3) and saturated brine, then dried over anhydrous sodium sulfate, filtered, and evaporated under reduced pressure to give crude product. The crude material was purified via preparative HPLC to yield the pure TFA salt of the product 42B as an off-white solid.

Example 43

Preparation of (R)-2-amino-7-(5-fluoro-3'-((4-(trifluoromethoxy)phenoxy)methyl)biphenyl-2-yl)-4-methyl-7,8-dihydropyrido[4,3-d]pyrimidin-5(6H)-one (43A)

43A

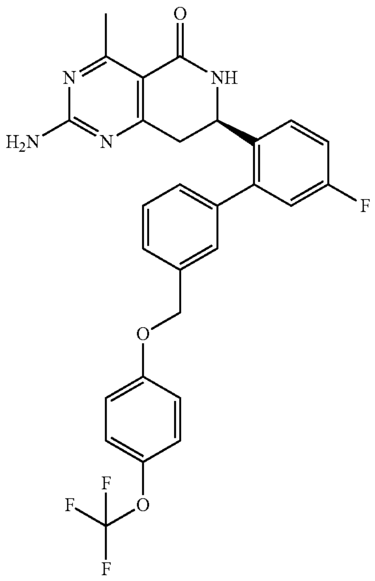

Compound 43A was prepared by the method outlined in Example 42 using 3-((4-(trifluoromethoxy)phenoxy)methyl) phenylboronic acid. $^1$H NMR (400 MHz, CHLOROFORM-d) δ ppm 2.79 (s, 3H) 2.86-2.93 (m, 1H) 3.08 (dd, J=16.80, 11.75 Hz, 1H) 4.83 (dd, J=11.49, 4.42 Hz, 1H) 5.07 (s, 2H) 6.91-6.97 (m, 3H) 6.98-7.05 (m, 2H) 7.17-7.24 (m, 2H) 7.45-7.48 (m, 1H) 7.51-7.62 (m, 2H) 7.66-7.75 (m, 1H). ESI-MS: m/z 539 ($MH^+$).

Example 44

Preparation of (R)-2-amino-7-(5-fluoro-2'-((3-(1,1-dioxidoisothiazolidin-2-yl)methyl)biphenyl-2-yl)-4-methyl-7,8-dihydropyrido[4,3-d]pyrimidin-5(6H)-on e (41A)

44A

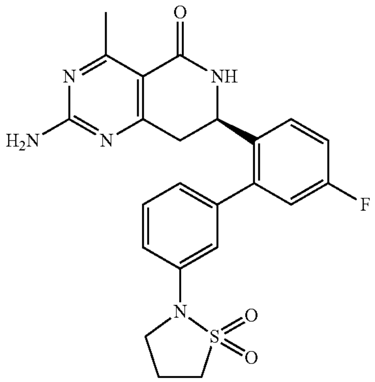

The title compound 44A was prepared by the method outlined in Example 42 using 3-(1,1-dioxidoisothiazolidin-2-yl) phenylboronic acid. $^1$H NMR (400 MHz, MeOD) δ ppm 2.50 (quin, J=6.88 Hz, 2H) 2.80 (s, 3H) 3.00 (dd, J=17.05, 4.17 Hz, 1H) 3.23-3.29 (m, 1H) 3.43 (t, J=7.45 Hz, 2H) 3.80 (t, J=6.44 Hz, 2H) 4.90-4.93 (m, 1H) 7.06 (dd, J=9.22, 2.40 Hz, 1H) 7.12 (d, J=7.58 Hz, 1H) 7.19-7.28 (m, 3H) 7.45 (t, J=7.83 Hz, 1H) 7.69 (dd, J=8.84, 5.56 Hz, 1H). ESI-MS: m/z 468 ($MH^+$).

Example 45

(R,Z)-2-Amino-7-(3'-(cyclopropylsulfonyl)-5-fluorobiphenyl-2-yl)-4-methyl-7,8-dihydropyrido[4,3-d]pyrimidin-5(6H)-one O—(S)-2,3-dihydroxypropyl oxime (Compound 49)

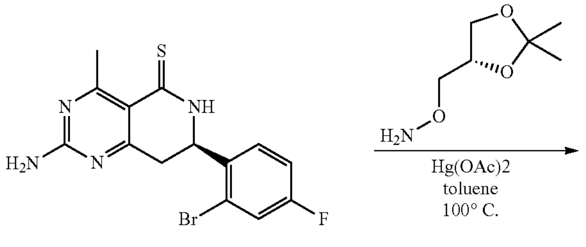

311

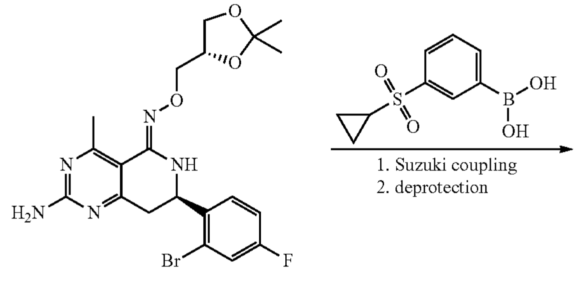

45A

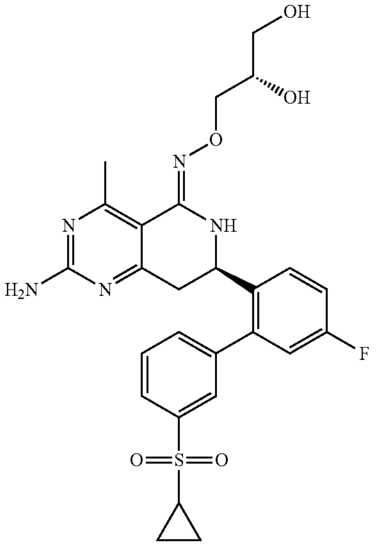

49

Compound 45A was synthesized according to the procedure of Example 39 using (S)—O-((2,2-dimethyl-1,3-dioxolan-4-yl)methyl)hydroxylamine 3-(cyclopropylsulfonyl) phenylboronic acid was then coupled to 45A according to the Suzuki coupling reaction of Example 42 yielding the title compound 49. $^1$H NMR (400 MHz, CHLOROFORM-d) δ ppm 0.76-0.88 (m, 1H) 0.99-1.11 (m, 1H) 2.29-2.38 (m, 1H) 2.45 (s, 3H) 2.60 (dd, J=16.55, 3.66 Hz, 1H) 2.81 (dd, J=16.42, 10.86 Hz, 1H) 3.28-3.43 (m, 1H) 3.70-3.76 (m, 1H) 3.77-3.85 (m, 1H) 3.85-3.92 (m, 1H) 4.21 (dd, J=10.86, 3.28 Hz, 1H) 6.78 (dd, J=9.09, 2.53 Hz, 1H) 6.98 (td, J=8.27, 2.40 Hz, 1H) 7.37-7.48 (m, 3H) 7.62 (s, 1H) 7.68 (dt, 1H). MS (ES) [M+H] calculated for $C_{26}H_{29}FN_5O_5S$, 542.18; found 542.20.

Example 46

(S)-4-((Z)—((R)-2-amino-7-(4-fluoro-2-(6-methoxy-pyridin-2-yl)phenyl)-4-methyl-7,8-dihydropyrido[4,3-d]pyrimidin-5(6H)-ylidene)aminooxy)-2-methoxybutanoic acid (Compound 50)

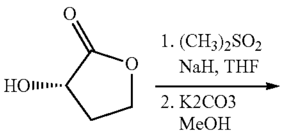

46a

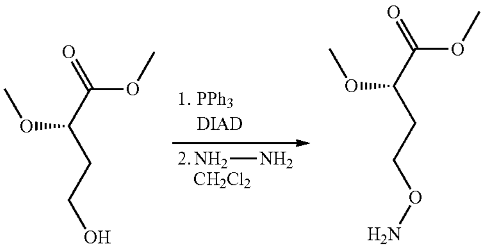

46b

46c

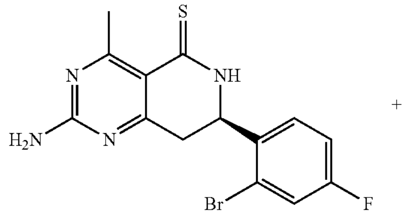

31I

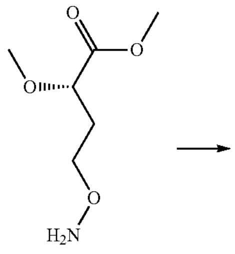

46c

-continued

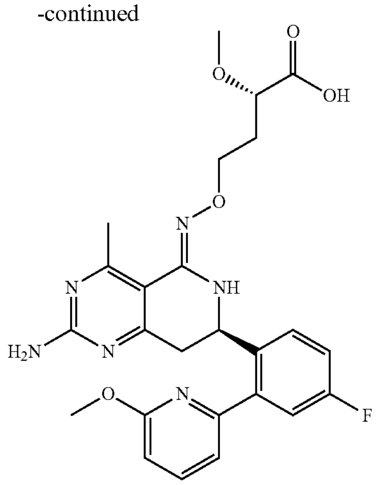

50

A. Synthesis of (S)-methyl 4-(aminooxy)-2-methoxybutanoate

To a suspension of NaH (60% in mineral oil, 552 mg, 12.0 mmol) in THF (5 mL) was added a solution of (S)-3-hydroxy-dihydrofuran-2(3H)-one (46a, 1.02 g, 10.0 mmol) in THF (5 mL) slowly drop wise at 0° C. under $N_2$ atmosphere. The reaction mixture was stirred for 30 minutes and dimethylsulphate (1.4 mL, 15.0 mmol) was added. The reaction mixture was stirred at r.t. overnight and the TLC shows completion of the reaction. Cold water (25 mL) was added to the reaction mixture and extracted with ethyl acetate. Organic layer washed with brine, dried over anhydrous $Na_2SO_4$ and filtered. Concentrated to provide (S)-3-hydr oxy dihydrofuran-2(3H)-one (46a) as yellow oil, which was dissolved in MeOH. Catalytic amount of $K_2CO_3$ (50 mg) was added at 0° C. and the reaction mixture stirred for 1 h. TLC shows completion of the reaction. Cold water (25 mL) was added to the reaction mixture and extracted with ethyl acetate. Organic layer washed with brine, dried over anhydrous $Na_2SO_4$ and filtered. Concentrated to provide (S)-methyl 4-hydroxy-2-methoxybutanoate (46b, 1.5 g, 99%) as yellow oil. $^1$H NMR (400 MHz, CHLOROFORM-d) δ ppm 2.07-2.28 (m, 1H) 2.36-2.58 (m, 1H) 3.36 (s, 3H) 3.49 (s, 3H) 3.85-4.07 (m, 1H) 4.29-4.42 (m, 2H).

To a solution of (S)-methyl 4-hydroxy-2-methoxybutanoate (46b, 1.48 g, 10.0 mmol) in $CH_2Cl_2$ (25.0 mL) was added 2-hydroxyisoindoline-1,3-dione (1.63 g, 10.0 mmol) and triphenylphosphine (3.93 g, 15.0 mmol). The resultant mixture was cooled to 0° C. and diisopropylazodicarboxylate (2.95 ml, 15.0 mmol) was slowly added drop wise under $N_2$ atmosphere. The reaction mixture was stirred at ambient temperature for 48 h. To the reaction mixture, $H_2O$ (100 mL) was added and extracted with $CH_2Cl_2$. The organic layers washed with brine. Dried over anhydrous $Na_2SO_4$, filtered and concentrated to provide yellow oil, which was purified by flash chromatography (50% EtOAc-hexane) to afford (S)-methyl 4-(1,3-dioxoisoindolin-2-yloxy)-2-methoxybutanoate (46c, 1.25 g, 42%) as light yellow oil. $^1$H NMR (400 MHz, CHLOROFORM-d) δ ppm 1.98-2.10 (m, 1H) 2.23-2.37 (m, 1H) 3.51 (s, 3H) 3.79 (s, 3H) 4.24 (dd, J=9.47, 3.66 Hz, 1H) 4.31-4.40 (m, 2H) 7.74-7.82 (m, 2H) 7.81-7.90 (m, 2H).

To a solution of (S)-methyl 4-(1,3-dioxoisoindolin-2-yloxy)-2-methoxybutanoate (1.2 g, 4.0 mmol) in $CH_2Cl_2$ (5.0 ml) was added hydrazine hydrate (0.98 mL, 10.0 mmol) was added drop wise at 0° C. The reaction mixture was stirred at ambient temperature over night. The resultant solid was filtered off and the filtrate concentrated under reduced pressure to provide a yellow oil, which was purified by flash chromatography (70% EtOAc-hexane) to afford (S)-methyl 4-(aminooxy)-2-methoxybutanoate (46c, 0.552 g, 84%) as a pale yellow oil. $^1$H NMR (400 MHz, CHLOROFORM-d) δ ppm 1.75-2.23 (m, 2H) 3.40 (s, 3H) 3.46 (s, 3H) 3.65-3.86 (m, 2H) 4.96 (dt, J=12.57, 6.22 Hz, 1H).

B. Preparation of Compound 50

A mixture of (R)-2-amino-7-(2-bromo-4-fluorophenyl)-4-methyl-7,8-dihydropyrido[4,3-d]pyrimidine-5(6H)-thione (311, 146 mg, 0.4 mmol), (S)-methyl 4-(aminooxy)-2-methoxybutanoate (46c, 260 mg, 1.6 mmol), $Hg(OAc)_2$ (257 mg, 0.8 mmol) and toluene (2 mL) was heated at 100° C. for 2 h. Cooled to rt, filtered through celite and purified to afford (S)-methyl 4-((Z)—((R)-2-amino-7-(2-bromo-4-fluorophenyl)-4-methyl-7,8-dihydropyrido[4,3-d]pyrimidin-5(6H)-ylidene)aminooxy)-2-methoxybutanoate (23 mg, 12%) as off white solid. MS (ES) [M+H] calculated for $C_{20}H_{24}BrFN_5O_4$, 496.09; found 496.20.

A mixture of the resultant compound (23 mg, 0.05 mmol), 2-(6-methoxypyridin-2-yl)-6-phenyl-1,3,6,2-dioxazaborocane (74.5 mg, 0.25 mmol), $Pd(dppf)_2Cl_2$ (4.0 mg, 0.005 mmol), 2N aq $Na_2CO_3$ (0.25 mL, 0.5 mmol) and DMA (2 mL) was degassed with $N_2$ and heated at 85° C. for 4 h. During the reaction, the methyl ester saponified in situ. Cooled to rt, filtered trough celite and purified to afford (S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-methoxybutanoic acid (4.6 mg, 20%) as off white solid. $^1$H NMR (400 MHz, CHLOROFORM-d) δ ppm 1.91-2.03 (m, 1H) 2.10-2.24 (m, 1H) 2.74 (s, 3H) 2.84-2.98 (m, 1H) 3.00-3.10 (m, 1H) 3.31 (br. s., 3H) 3.75-3.79 (m, 1H) 3.81 (s, 3H) 4.02-4.16 (m, 2H) 4.82 (ddd, J=10.23, 2.91, 2.78 Hz, 1H) 6.69 (dd, J=8.34, 2.02 Hz, 1H) 6.95 (dd, J=7.20, 1.89 Hz, 1H) 7.06 (ddd, J=9.16, 2.46, 2.27 Hz, 1H) 7.09-7.16 (m, 1H) 7.60 (dddd, J=15.73, 8.15, 7.96, 2.27 Hz, 2H). MS (ES) [M+H] calculated for $C_{25}H_{28}FN_6O_5$, 511.20; found 511.40.

Example 47

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4S)-3,4-dihydroxytetrahydrofuran-2-yl)methyl oxime (Compound 51)

51

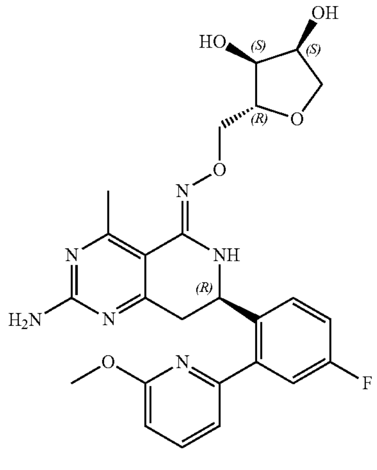

To a solution of (R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3S,4R)-3,4-dihydroxy-5-methoxytetrahydrofuran-2-yl)methyl oxime (10.5 mg, 0.02 mmol) in $CH_2Cl_2$ (1 mL) was added $Et_3SiH$ (16 μL, 0.05 mmol) and $BF_3.Et_2O$ (8.0 μL, 0.05 mmol) at 0° C. under $N_2$ atmosphere. The reaction mixture was stirred overnight at r.t. and poured on crushed ice. The resultant slurry was extracted with $CH_2Cl_2$ and washed with brine. Work-up and purification by Preparative LCMS afforded the title compound (3.0 mg, 30%) as light brown solid. $^1$H NMR (400 MHz, CHLOROFORM-d) δ ppm 2.50 (s, 3H) 2.77 (dd, J=16.04, 6.95 Hz, 1H) 3.00 (dd, J=16.04, 5.18 Hz, 1H) 3.15-3.26 (m, 2H) 3.35-3.42 (m, 2H) 3.83 (s, 3H) 3.85-3.94 (m, 2H) 4.38-4.41 (m, 1H) 4.93-5.13 (m, 1H) 6.82 (d, J=9.09 Hz, 1H) 7.16 (d, J=7.07 Hz, 1H) 7.21-7.30 (m, 2H) 7.45 (dd, J=8.46, 5.94 Hz, 1H) 7.86 (dd, J=8.34, 7.33 Hz, 1H). MS (ES) [M+H] calculated for $C_{25}H_{28}FN_6O_5$, 511.51; found 511.20.

Example 48

(2S,4R)-tert-butyl 2-(aminooxymethyl)-4-(tert-butyldimethylsilyloxy)pyrrolidine-1-carboxylate

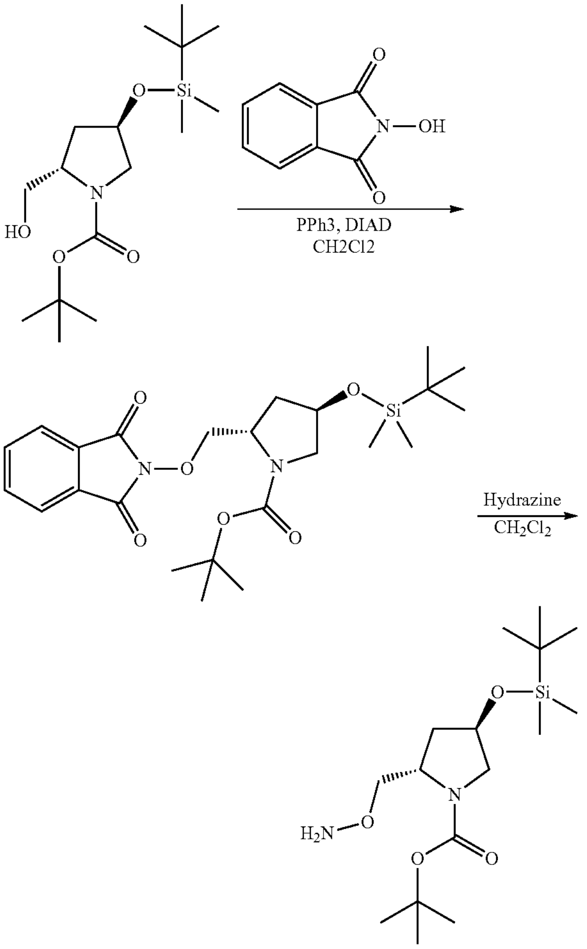

To a solution of (2S,4R)-tert-butyl 4-(tert-butyldimethylsilyloxy)-2-(hydroxymethyl)pyrrolidine-1-carboxylate (2.0 g, 6.0 mmol) in $CH_2Cl_2$ (15.0 mL) was added 2-hydroxyisoindoline-1,3-dione (978 mg, 6.0 mmol) and triphenylphosphine (2.36 g, 9.0 mmol). The resultant mixture was cooled to 0° C. and diisopropylazodicarboxylate (1.78 ml, 9.0 mmol) was slowly added drop wise under $N_2$ atmosphere.

The reaction mixture was stirred at ambient temperature for 48 h. To the reaction mixture, $H_2O$ (100 mL) was added and extracted with $CH_2Cl_2$. The organic layers washed with brine. Dried over anhydrous $Na_2SO_4$, filtered and concentrated to provide yellow oil, which was purified by flash chromatography (50% EtOAc-hexane) to yield (2S,4R)-tert-butyl 4-(tert-butyldimethylsilyloxy)-2-((1,3-dioxoisoindolin-2-yloxy)methyl)pyrrolidine-1-carboxylate as light yellow oil.

The resultant oily compound was dissolved in $CH_2Cl_2$ (250 ml) and cooled to 0° C. Hydrazine hydrate (1.2 mL, 12.0 mmol) was added dropwise. The reaction mixture was stirred at ambient temperature over night. The resultant solid was filtered off and the filtrate concentrated under reduced pressure to provide a yellow oil, which was purified by flash chromatography (70% EtOAc-hexane) to afford 1.2 g (60%, over two steps) of (2S,4R)-tert-butyl 2-(aminooxymethyl)-4-(tert-butyldimethylsilyloxy)pyrrolidine-1-carboxylate as a pale yellow oil. $^1H$ NMR (400 MHz, CHLOROFORM-d) δ ppm 0.24 (s, 3H) 0.26 (s, 3H) 0.87 (s, 9H) 1.26 (s, 9H) 1.67-1.76 (m, 1H) 1.81-1.94 (m, 1H) 3.18 (dd, J=12.25, 4.93 Hz, 1H) 3.22-3.31 (m, 1H) 3.70-3.81 (m, 1H) 3.88-3.96 (m, 1H) 3.98-4.09 (m, 1H) 4.12-4.21 (m, 1H). MS (ES) [M+H] calculated for $C_{16}H_{35}N_2O_4Si$, 347.23; found 347.22.

Example 49

(R,Z)-2-amino-7-(4-fluoro-2-(6-methoxypyridin-2-yl)phenyl)-4-methyl-7,8-dihydropyrido[4,3-d]pyrimidin-5(6H)-one O-((2S,4R)-4-hydroxypyrrolidin-2-yl)methyl oxime (Compound 52)

52

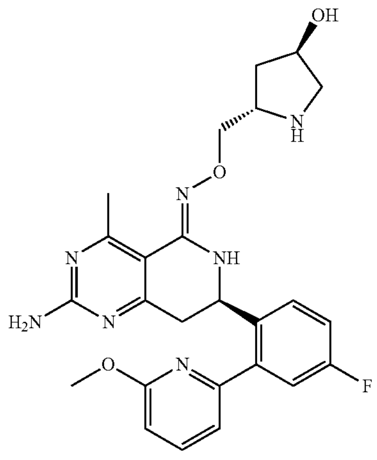

A mixture of (R)-2-amino-7-(2-bromo-4-fluorophenyl)-4-methyl-7,8-dihydropyrido[4,3-d]pyrimidine-5(6H)-thione (183 mg, 0.5 mmol), (2S,4R)-tert-butyl 2-(aminooxymethyl)-4-(tert-butyldimethylsilyloxy)pyrrolidine-1-carboxylate (692 mg, 2.0 mmol), $Hg(OAc)_2$ (320 mg, 1.0 mmol) and toluene (2 mL) was heated at 100° C. for 2 h. Cooled to r.t., filtered through celite and purified to afford (2S,4R)-tert-butyl 2-(((Z)—((R)-2-amino-7-(2-bromo-4-fluorophenyl)-4-methyl-7,8-dihydropyrido[4,3-d]pyrimidin-5-(6H)-ylidene)aminooxy)methyl)-4-(tert-butyldimethylsilyloxy)pyrrolidine-1-carboxylate (200 mg, 50%) as off white solid. MS (ES) [M+H] calculated for $C_{30}H_{45}BrFN_6O_4Si$, 679.24; found 679.20.

A mixture of the resultant compound (200 mg, 0.3 mmol), 2-(6-methoxypyridin-2-yl)-6-phenyl-1,3,6,2-dioxazaborocane (447 mg, 1.5 mmol), $Pd(dppf)_2Cl_2$ (25 mg, 0.03 mmol), 2N aq $Na_2CO_3$ (1.5 mL, 3.0 mmol) and DMA (2 mL) was degassed with $N_2$ and heated at 85° C. for 4 h. Cooled to rt, filtered trough celite and purified to afford (2S,4R)-tert-butyl 2-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)-4-hydroxypyrrolidine-1-carboxylate (94 mg, 53%) as a viscous oil. MS (ES) [M+H] calculated for $C_{30}H_{37}FN_7O_5$, 594.28; found 594.30. The resultant oily compound was dissolved in dioxane (1.0 ml) and cooled to 0° C. 4N HCl in dioxane (0.1 mL, 0.375 mmol) was added and the reaction mixture was stirred at ambient temperature for 2 h. The resultant solid was filtered off and dried to afford Compound 52 as an HCl salt (56 mg, 76%) as white solid. $^1H$ NMR (400 MHz, CHLOROFORM-d) δ ppm 1.64 (ddd, J=13.64, 8.08, 5.56 Hz, 1H) 1.88 (dd, J=13.64, 7.07 Hz, 1H) 2.65 (s, 3H) 2.90 (d, J=11.62 Hz, 1H) 3.00-3.09 (m, 2H) 3.13-3.27 (m, 1H) 3.68-3.82 (m, 1H) 3.84-3.94 (m, 4H) 3.95-4.02 (m, 1H) 4.40 (t, J=4.67 Hz, 1H) 4.87 (dd, J=10.48, 3.92 Hz, 1H) 5.18 (s, 2H) 5.72 (s, 1H) 6.73 (d, J=8.34 Hz, 1H) 7.00 (d, J=7.07 Hz, 1H) 7.07-7.24 (m, 2H) 7.57-7.77 (m, 2H). MS (ES) [M+H] calculated for $C_{25}H_{29}FN_7O_3$, 494.22; found 494.20.

Example 50

(3R,5S)-1-acetyl-5-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)pyrrolidin-3-yl acetate (Compound 53)

53

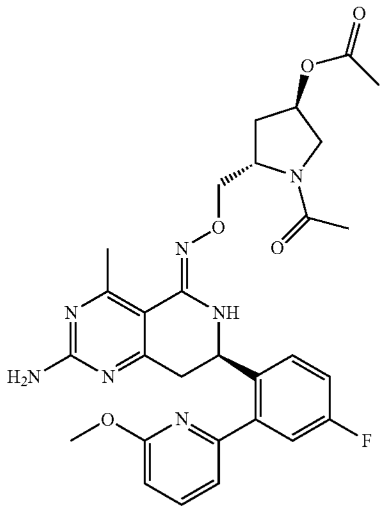

To a solution of (R,Z)-2-amino-7-(4-fluoro-2-(6-methoxypyridin-2-yl)phenyl)-4-methyl-7,8-dihydropyrido[4,3-d]pyrimidin-5(6H)-one O-((2S,4R)-4-hydroxypyrrolidin-2-yl) methyl oxime (20 mg, 0.05 mmol) in $CH_2Cl_2$ (1 mL) containing catalytic amount of DMAP was added $Et_3N$ (20.86 μL, 0.15 mmol) and acetyl chloride (10.0 μL, 0.1 mmol) at 0° C. under $N_2$ atmosphere. The reaction mixture was stirred at r.t. for 2 h. Quenched with sat $NH_4Cl$ solution and extracted with $CH_2Cl_2$. The combined organic layers washed with brine, dried over anhydrous $Na_2SO_4$. The resultant residue was purified by preparative LCMS to afford the title compound (5 mg, 25%) as a white solid. $^1$H NMR (400 MHz, CHLOROFORM-d) δ ppm 2.00 (s, 3H) 2.04 (s, 3H) 2.09-2.23 (m, 1H) 2.29-2.41 (m, 1H) 2.64 (s, 3H) 2.95-3.11 (m, 1H) 3.15-3.29 (m, 1H), 3.66 (dd, J=11.37, 5.56 Hz, 1H) 3.90 (s, 3H) 4.04 (dd, J=11.87, 5.31 Hz, 1H) 4.13-4.30 (m, 1H) 4.32-4.49 (m, 1H) 4.77-4.95 (m, 1H), 5.06-5.16 (m, 1H) 5.20-5.32 (m, 1H) 6.74 (d, J=8.34 Hz, 1H) 7.01 (d, J=8.34 Hz, 1H) 7.10-7.22 (m, 2H) 7.57-7.74 (m, 2H). MS (ES) [M+H] calculated for $C_{29}H_{33}FN_7O_5$, 578.60; found 578.30.

Example 51

(2S,4R)-1-tert-butyl 2-methyl 4-(aminooxy)pyrrolidine-1,2-dicarboxylate

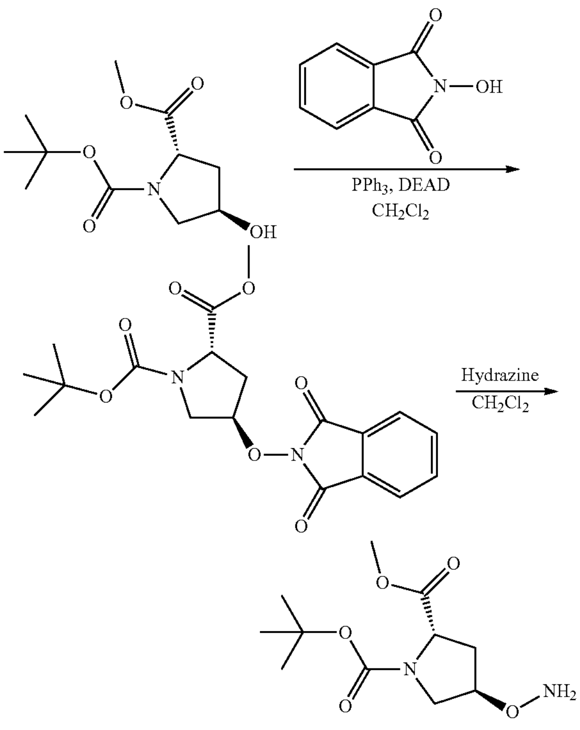

To a solution of (2S,4R)-1-tert-butyl 2-methyl 4-hydroxypyrrolidine-1,2-dicarboxylate (4.9 g, 20.0 mmol) in $CH_2Cl_2$ (50.0 mL) was added 2-hydroxyisoindoline-1,3-dione (3.26 g, 20.0 mmol) and triphenylphosphine (7.86 g, 30.0 mmol). The resultant mixture was cooled to 0° C. and diisopropylazodicarboxylate (5.90 ml, 30.0 mmol) was slowly added drop wise under $N_2$ atmosphere. The reaction mixture was stirred at ambient temperature for 48 h. Work-up and purification as described in Example 2A, Step 1 afforded (2S,4R)-1-tert-butyl 2-methyl 4-(1,3-dioxoisoindolin-2-yloxy)pyrrolidine-1,2-dicarboxylate as a viscous oil. The resultant oily compound was dissolved in $CH_2Cl_2$ (100 ml) and cooled to 0° C. Hydrazine hydrate (4.0 mL, 40.0 mmol) was added drop wise. The reaction mixture was stirred at ambient temperature over night. Work-up and purification as described in Example 2A, Step 2 afforded (2.8 g, 53%, over two steps) of (2S,4R)-1-tert-butyl 2-methyl 4-(aminooxy)pyrrolidine-1,2-dicarboxylate as a pale yellow oil. $^1$H NMR (400 MHz, CHLOROFORM-d) δ ppm 1.42 (s, 9H) 2.13-2.29 (m, 1H) 2.34-2.48 (m, 1H) 3.48-3.68 (m, 2H) 3.72 (s, 3H) 4.23-4.30 (m, 1H) 4.30-4.49 (m, 1H). MS (ES) [M+H] calculated for $C_{11}H_{21}N_2O_5$, 261.14; found 261.22.

Example 52

(2S,4R)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)pyrrolidine-2-carboxylate (Compound 54)

54

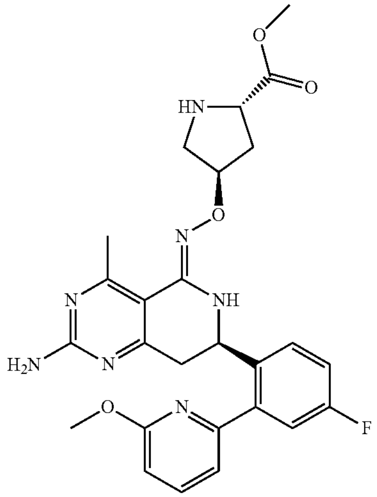

A mixture of (R)-2-amino-7-(2-bromo-4-fluorophenyl)-4-methyl-7,8-dihydropyrido[4,3-d]pyrimidine-5(6H)-thione (150 mg, 0.4 mmol), (2S,4R)-1-tert-butyl 2-methyl 4-(aminooxy)pyrrolidine-1,2-dicarboxylate (416 mg, 1.6 mmol), $Hg(OAc)_2$ (256 mg, 0.8 mmol) and toluene (2 mL) was heated at 100° C. for 2 h. Cooled to rt, filtered through celite and purified to afford (2S,4R)-1-tert-butyl 2-methyl 4-((Z)—((R)-2-amino-7-(2-bromo-4-fluorophenyl)-4-methyl-7,8-dihydropyrido[4,3-d]pyrimidin-5(6H)-ylidene)aminooxy)pyrrolidine-1,2-dicarboxylate (172 mg, 570%) as off white solid. MS (ES) [M+H] calculated for $C_{25}H_{3i}BrFN_6O_5$, 593.14; found 593.10.

A mixture of (R)-2-amino-7-(2-bromo-4-fluorophenyl)-4-methyl-7,8-dihydropyrido[4,3-d]pyrimidine-5(6H)-thione (150 mg, 0.4 mmol), (2S,4R)-1-tert-butyl 2-methyl 4-(aminooxy)pyrrolidine-1,2-dicarboxylate (416 mg, 1.6 mmol), $Hg(OAc)_2$ (256 mg, 0.8 mmol) and toluene (2 mL) was heated at 100° C. for 2 h. Cooled to rt, filtered through celite and purified to afford (2S,4R)-1-tert-butyl 2-methyl 4-((Z)—((R)-2-amino-7-(2-bromo-4-fluorophenyl)-4-methyl-7,8-dihydropyrido[4,3-d]pyrimidin-5(6H)-ylidene)aminooxy)pyrrolidine-1,2-dicarboxylate (172 mg, 570%) as off white solid. MS (ES) [M+H] calculated for $C_{25}H_{3i}BrFN_6O_5$, 593.14; found 593.10.

The resultant oily compound was dissolved in dioxane (1.0 ml) and cooled to 0° C. 4N HCl in dioxane (62.0 μL, 0.25 mmol) was added and the reaction mixture was stirred at ambient temperature for 2 h. The resultant solid was filtered off and dried to afford Compound 54 as an HCl salt (45.0 mg, 82%) as white solid. $^1$H NMR (400 MHz, CHLOROFORM-d) δ ppm 2.32-2.46 (m, 2H) 2.53 (s, 3H) 2.87 (dd, J=16.80, 10.74 Hz, 2H) 3.12 (d, J=4.04 Hz, 1H) 3.30 (dd, J=12.63, 3.54 Hz, 1H) 3.47 (s, 3H) 3.71 (s, 3H) 4.38 (dd, J=9.98, 2.65 Hz, 1H) 4.67 (t, J=3.79 Hz, 1H) 4.73 (dd, J=10.23, 3.66 Hz, 1H) 6.60 (d, J=8.34 Hz, 1H) 6.87 (d, J=7.07 Hz, 1H) 6.97 (dd, J=9.22, 2.65 Hz, 1H) 7.03 (td, J=8.46, 2.02 Hz, 1H) 7.46 (dd, J=9.09, 4.80 Hz, 1H) 7.53 (t, J=7.71 Hz, 1H). MS (ES) [M+H] calculated for $C_{26}H_{29}FN_7O_4$, 522.542; found 522.24

Example 53

(2S,4R)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy) pyrrolidine-2-carboxylic acid (Compound 55)

55

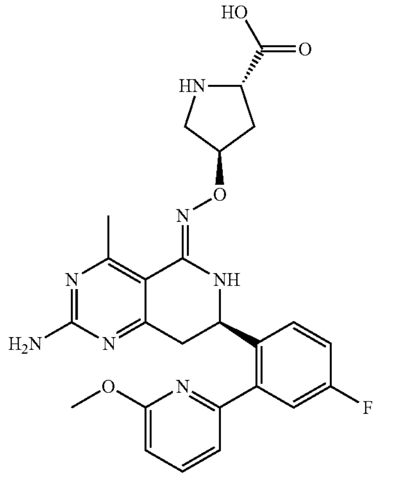

The title compound was prepared analogous to the procedure described for Example 52. $^1$H NMR (400 MHz, MeOD) δ ppm 2.23-2.36 (m, 1H) 2.39-2.49 (m, 1H) 2.69 (s, 3H) 3.14-3.26 (m, 2H) 3.43-3.54 (m, 2H) 3.76 (s, 3H) 4.14-4.26 (m, 1H) 4.53 (dd, J=9.09, 3.79 Hz, 1H) 4.60 (d, J=2.27 Hz, 1H) 6.82-6.91 (m, 1H) 6.93-7.09 (m, 2H) 7.20-7.32 (m, 1H) 7.44 (dd, J=8.84, 5.31 Hz, 1H) 7.68-7.90 (m, 1H). MS (ES) [M+H] calculated for $C_{25}H_{27}FN_7O_4$, 507.51; found 508.20.

Example 54

(R,Z)-2-amino-7-(4-fluoro-2-(6-methoxypyridin-2-yl)phenyl)-4-methyl-7,8-dihydropyrido[4,3-d]pyrimidin-5(6H)-one O-(3R,5S)-5-(hydroxymethyl)pyrrolidin-3-yl oxime (Compound 56)

56

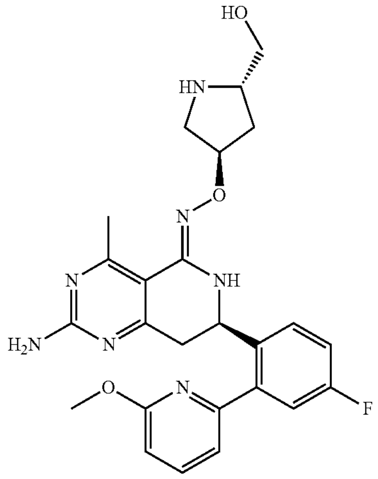

To a solution of (2S,4R)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene) aminooxy) pyrrolidine-2-carboxylate (25.0 mg, 0.04 mmol) in dry ether (1 mL) was added $LiAlH_4$ (0.1 mL, 0.01 mmol, 1M solution in ether) at 0° C. under $N_2$ atmosphere. Stirred for 1 h and quenched with 1N NaOH (0.1 mL) solution. Anhydrous $MgSO_4$ was added and filtered through celite. The filtrate was concentrated under reduced pressure and purified by preparative LCMS to afford the title compound (6.0 mg, 32%) as a white solid. $^1$H NMR (400 MHz, CHLOROFORM-d) δ ppm 1.67-1.95 (m, 2H) 2.47 (s, 3H) 2.58 (d, J=3.03 Hz, 1H) 2.71 (d, J=3.28 Hz, 1H) 2.94-3.00 (m, 2H) 3.13-3.19 (m, 1H) 3.22-3.39 (m, 2H) 3.43 (dd, J=11.12, 6.32 Hz, 1H) 3.58 (s, 3H) 4.65-4.73 (m, 1H) 6.47 (dd, J=8.46, 2.91 Hz, 1H) 6.76 (dd, J=7.20, 2.65 Hz, 1H) 6.84 (ddd, J=9.73, 2.78, 2.65 Hz, 1H) 6.87-6.93 (m, 1H) 7.29-7.36 (m, 1H) 7.41 (t, J=7.83 Hz, 1H). MS (ES) [M+H] calculated for $C_{25}H_{29}FN_7O_3$, 494.53; found 494.20.

Example 55

(3aR,4R,6aS)-tert-butyl 4-(aminooxymethyl)-2,2-dimethyldihydro-3aH-[1,3]dioxolo[4,5-c]pyrrole-5(4H)-carboxylate

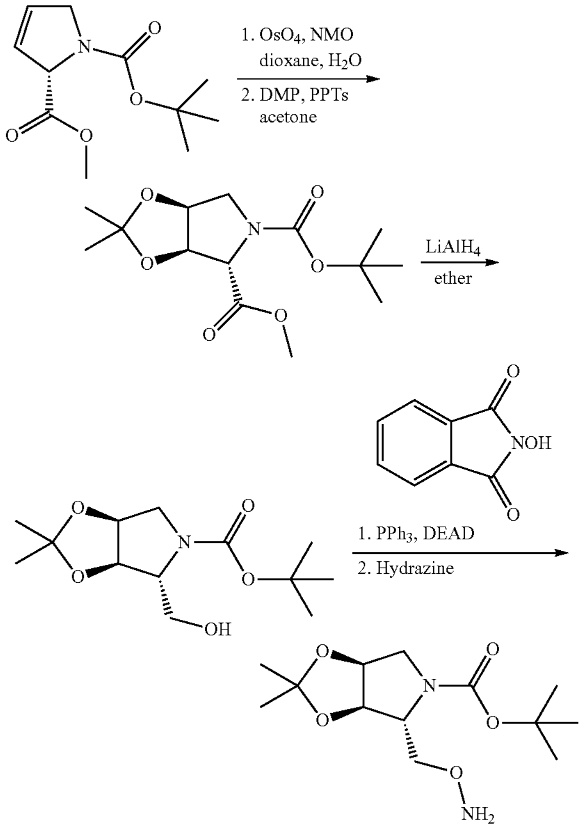

To a solution of (S)-1-tert-butyl 2-methyl 1H-pyrrole-1,2 (2H, 5H)-dicarboxylate (1.0 g, 4.5 mmol) in dioxane —$H_2O$ (4:1) was added NMO (580 mg, 4.95 mmol) and $OsO_4$ 114 mg, 0.45 mmol, 2.5 wt % in $H_2O$) and the reaction mixture was stirred for 24 h at r.t. Quenched with 10% aqueous $Na_2S_2O_3$ solution and extracted with ethyl acetate. The combined organic layers washed with brine and dried over anhydrous $Na_2SO_4$. The resultant residue was dissolved in acetone (5 mL), added catalytic amount of PPTS and dimethoxy propane (1.5 mL). The reaction mixture was stirred over night at r.t. and diluted with ethyl acetate, washed with saturated $NaHCO_3$ and brine. Dried over anhydrous $Na_2SO_4$ and concentrated under reduced pressure. The residue was dissolved in ether (5.0 mL) and $LiAlH_4$ (3.0 mL, 3.0 mmol, 1M solution in ether) was added at 0° C. under $N_2$ atmosphere. Stirred for 1 h and quenched with 1N NaOH (0.1 mL) solution. Anhydrous $MgSO_4$ was added and filtered through celite. The filtrate was concentrated under reduced pressure and purified by flash chromatography (5% MeOH—$CH_2Cl_2$) to afford (3aR,4R,6aS)-tert-butyl 4-(hydroxymethyl)-2,2-dimethyldihydro-3aH-[1,3]dioxolo[4,5-c]pyrrole-5(4H)-carboxylate (550 mg, 45%, over 3 steps). $^1$H NMR (400 MHz, CHLOROFORM-d) δ ppm 1.32 (s, 6H) 1.47 (s, 9H) 3.33-3.38 (m, 1H) 3.50 (dd, J=13.14, 6.06 Hz, 2H) 4.54 (d, J=3.79 Hz, 1H) 4.59-4.61 (m, 1H) 4.66-4.73 (m, 2H).

The resultant oily compound (550 mg, 2.0 mmol) was subjected to the Mitsunobu coupling followed by phthalimide deprotection analogous to the procedure described in Example 2 afforded (3aR,4R,6aS)-tert-butyl 4-(aminooxymethyl)-2,2-dimethyldihydro-3aH-[1,3]dioxolo[4,5-c]pyrrole-5(4H)-carboxylate (340 mg, 59%) as a viscous oil. $^1$H NMR (400 MHz, CHLOROFORM-d) δ ppm 1.31 (s, 3H) 1.45 (s, 3H) 1.47 (s, 9H) 3.26-3.47 (m, 1H) 3.59-3.80 (m, 2H) 4.07-4.38 (m, 1H) 4.51-4.67 (m, 1H) 5.41-5.71 (m, 2H). MS (ES) [M+H] calculated for $C_{13}H_{25}N_2O_5$, 289.17; found 289.20.

Example 56

(R,Z)-2-amino-7-(4-fluoro-2-(6-methoxypyridin-2-yl)phenyl)-4-methyl-7,8-dihydropyrido[4,3-d]pyrimidin-5(6H)-one O-((2R,3R,4S)-3,4-dihydroxypyrrolidin-2-yl)methyl oxime (Compound 57)

57

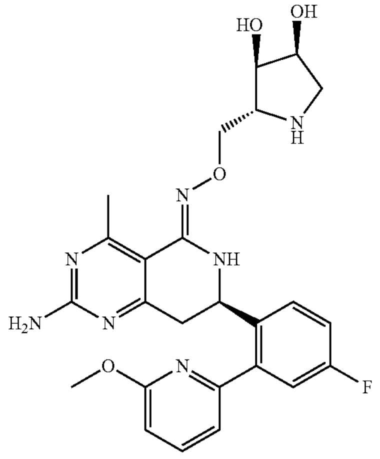

The title compound was prepared according to the procedure described for example # using (R)-2-amino-7-(2-bromo-4-fluorophenyl)-4-methyl-7,8-dihydropyrido[4,3-d]pyrimidine-5(6H)-thione (150 mg, 0.4 mmol) and (3aR,4R,6aS)-tert-butyl 4-(aminooxymethyl)-2,2-dimethyldihydro-3aH-[1,3]dioxolo[4,5-c]pyrrole-5(4H)-carboxylate (340 mg, 1.2 mmol). Suzuki coupling followed by deprotection afforded the title compound as a white solid. $^1$H NMR (400 MHz, CHLOROFORM-d) δ ppm 2.53 (s, 3H) 2.85-2.99 (m, 1H) 3.02-3.15 (m, 1H) 3.18-3.25 (m, 1H) 3.26-3.31 (m, 2H) 3.81 (s, 3H) 3.83-3.95 (m, 1H) 3.97-4.04 (m, 1H) 4.10 (brs, 1H) 4.20-4.29 (m, 1H) 4.37 (d, J=4.80 Hz, 1H) 4.60 (brs, 1H) 4.81 (dd, J=9.47, 3.41 Hz, 1H) 6.68 (d, J=8.34 Hz, 1H) 6.95 (d, J=7.07 Hz, 2H) 7.01-7.14 (m, 1H) 7.48-7.57 (m, 1H) 7.61 (t, J=7.71 Hz, 1H). MS (ES) [M+H] calculated for $C_{25}H_{29}FN_7O_4$, 510.53; found 510.40.

Example 57

(1R,2S)-4-(aminooxy)cyclopentane-1,2-diol

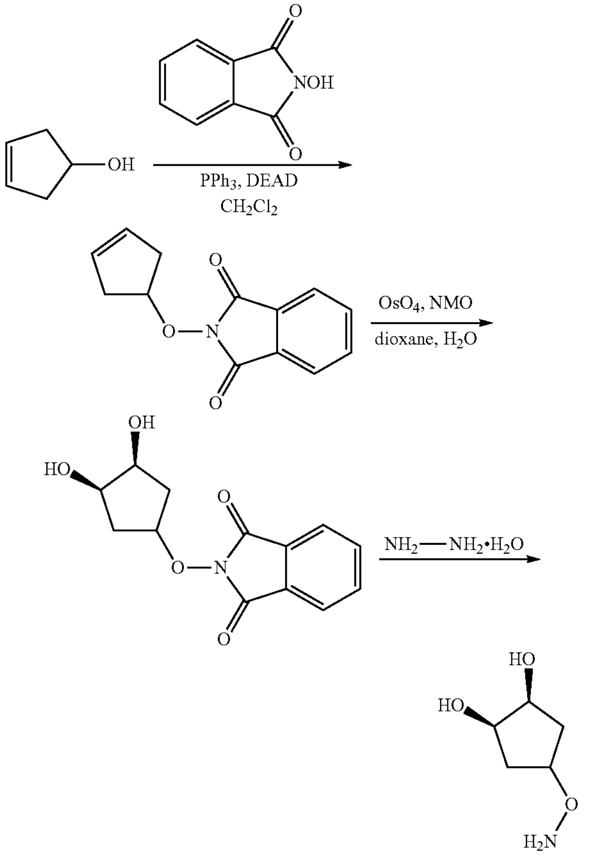

To a solution of cyclopent-3-enol (840 mg, 10.0 mmol) in $CH_2Cl_2$ (25.0 mL) was added 2-hydroxyisoindoline-1,3-dione (1.96 g, 12.0 mmol) and triphenylphosphine (3.93 g, 15.0 mmol). The resultant mixture was cooled to 0° C. and diisopropylazodicarboxylate (2.95 ml, 15.0 mmol) was slowly added drop wise under $N_2$ atmosphere. The reaction mixture was stirred at ambient temperature for 48 h. To the reaction mixture, $H_2O$ (100 mL) was added and extracted with $CH_2Cl_2$. The organic layers washed with brine. Dried over anhydrous $Na_2SO_4$, filtered and concentrated to provide yellow oil, which was purified by flash chromatography (50% EtOAc-hexane) to yield 2-(cyclopent-3-enyloxy)isoindoline-1,3-dione (740 mg, 32%) as light yellow oil. $^1$H NMR (400 MHz, CHLOROFORM-d) δ ppm 2.57-2.87 (m, 4H) 5.12 (t, J=6.19 Hz, 1H) 5.75 (s, 2H) 7.74 (dd, J=5.68, 3.16 Hz, 2H) 7.79-7.87 (m, 2H). MS (ES) [M+H] calculated for $C_{13}H_{12}NO_3$, 230.07; found 230.20.

To a solution of 2-(cyclopent-3-enyloxy)isoindoline-1,3-dione (736 mg, 3.2 mmol) in dioxane —$H_2O$ (5.0 mL, 4:1) was added NMO (421 mg, 3.60 mmol) and $OsO_4$ (1.0 mL mg, 0.32 mmol, 2.5 wt % in $H_2O$) and the reaction mixture was stirred for 24 h at rt. Quenched with 10% aqueous $Na_2S_2O_3$ solution and extracted with ethyl acetate. The combined organic layers washed with brine and dried over anhydrous $Na_2SO_4$. Filtered and concentrated to provide yellow oil, which was purified by flash chromatography (80% EtOAc-hexane) to yield 2-((3R,45)-3,4-dihydroxycyclopentyloxy) isoindoline-1,3-dione (650 mg, 77%) as light yellow oil. $^1H$ NMR (400 MHz, CHLOROFORM-d) δ ppm 1.94-2.12 (m, 2H) 2.14-2.35 (m, 2H) 4.22-4.88 (m, 2H) 4.75-5.11 (m, 1H) 7.67-7.78 (m, 2H) 7.79-7.86 (m, 2H). MS (ES) [M+H] calculated for $C_{13}H_{14}NO_5$, 264.08; found 264.20.

The resultant oily compound (650 mg, 2.47 mmol) was dissolved in $CH_2Cl_2$ (5 ml) and cooled to 0° C. Hydrazine hydrate (0.3 mL, 6.17 mmol) was added dropwise. The reaction mixture was stirred at ambient temperature over night. The resultant solid was filtered off and the filtrate concentrated under reduced pressure to afford (248 mg, 71%) of (1R,2S)-4-(aminooxy)cyclopentane-1,2-diol as a pale yellow oil. $^1H$ NMR (400 MHz, CHLOROFORM-d) δ ppm 1.67-1.87 (m, 4H) 3.86-3.96 (m, 2H) 4.00-4.21 (m, 1H). MS (ES) [M+H] calculated for $C_6H_{12}NO_3$, 134.07; found 134.21.

Example 58

(7R,Z)-2-amino-7-(4-fluoro-2-(6-methoxypyridin-2-yl)phenyl)-4-methyl-7,8-dihydropyrido[4,3-d]pyrimidin-5(6H)-one O-(3R,4S)-3,4-dihydroxycyclopentyl oxime (Compound 58)

58

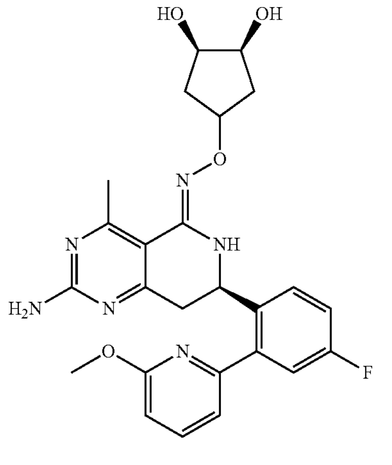

A mixture of (R)-2-amino-7-(2-bromo-4-fluorophenyl)-4-methyl-7,8-dihydropyrido[4,3-d]pyrimidine-5(6H)-thione (146 mg, 0.4 mmol), (1R,2S)-4-(aminooxy)cyclopentane-1,2-diol (212 mg, 1.6 mmol), $Hg(OAc)_2$ (256 mg, 0.8 mmol) and toluene (2 mL) was heated at 100° C. for 2 h. Cooled to rt, filtered through celite and purified to afford (7R,Z)-2-amino-7-(2-bromo-4-fluorophenyl)-4-methyl-7,8-dihydropyrido[4,3-d]pyrimidin-5(6H)-one O-(3R,4S)-3,4-dihydroxycyclopentyl oxime (78 mg, 43%) as off white solid. MS (ES) [M+H] calculated for $C_{19}H_{22}BrFN_5O_3$, 466.08; found 467.30.

A mixture of the resultant compound (75 mg, 0.16 mmol), 2-(6-methoxypyridin-2-yl)-6-phenyl-1,3,6,2-dioxazaborocane (238 mg, 0.8 mmol), $Pd(dppf)_2Cl_2$ (13 mg, 0.016 mmol), 2N aq $Na_2CO_3$ (0.4 mL, 0.8 mmol) and DMA (2 mL) was degassed with $N_2$ and heated at 85° C. for 4 h. Cooled to r.t., filtered trough celite and purified to afford (7R,Z)-2-amino-7-(4-fluoro-2-(6-methoxypyridin-2-yl)phenyl)-4-methyl-7,8-dihydropyrido[4,3-d]pyrimidin-5(6H)-one O-(3R, 4S)-3,4-dihydroxycyclopentyl oxime (8.4 mg, 12%) as white solid. $^1H$ NMR (400 MHz, CHLOROFORM-d) δ ppm 1.75-2.03 (m, 4H) 2.51 (s, 3H) 2.71-2.89 (m, 1H) 2.95-3.10 (m, 1H) 3.86 (s, 3H) 4.36 (d, J=3.28 Hz, 2H) 4.49-4.63 (m, 1H) 4.94 (m, 1H) 6.85 (d, J=7.83 Hz, 1H) 7.19 (d, J=7.33 Hz, 1H) 7.22-7.32 (m, 2H) 7.42-7.54 (m, 1H) 7.84 (t, J=7.58 Hz, 1H). MS (ES) [M+H] calculated for $C_{25}H_{28}FN_6O_4$, 495.52; found 495.40.

Example 59

(1R,2S)-4-(aminooxymethyl)cyclopentane-1,2-diol

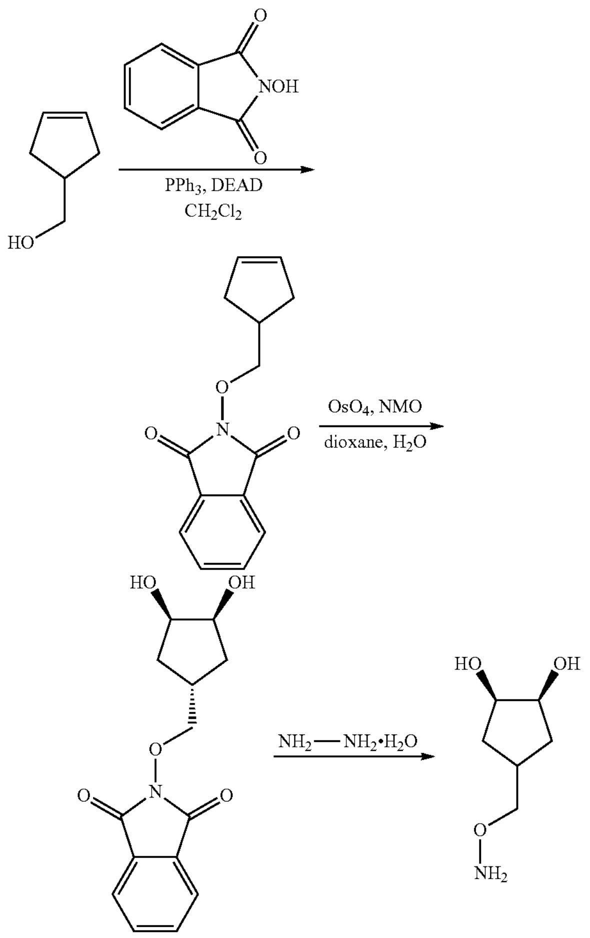

The title compound was prepared analogous to the procedure described in Example 57. $^1H$ NMR (400 MHz, CHLOROFORM-d) δ ppm 1.21-1.38 (m, 2H) 1.50-1.64 (m, 2H) 1.69-1.84 (m, 1H) 3.86-3.96 (m, 2H) 4.11 (dd, J=7.33, 1.52 Hz, 2H). MS (ES) [M+H] calculated for $C_6H_{14}NO_3$, 148.09; found 148.07.

Example 60

(7R,Z)-2-amino-7-(4-fluoro-2-(6-methoxypyridin-2-yl)phenyl)-4-methyl-7,8-dihydropyrido[4,3-d]pyrimidin-5(6H)-one O-((3R,4S)-3,4-dihydroxycyclopentyl)methyl oxime (Compound 59)

59

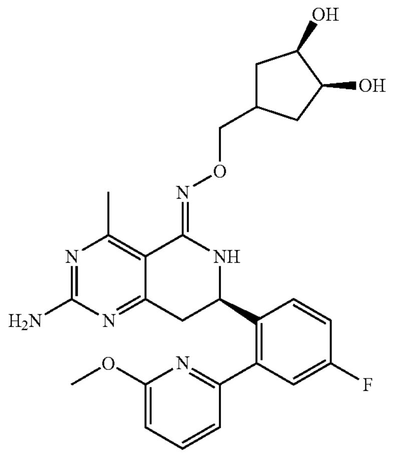

The title compound was prepared analogous to the procedure described in Example 58. $^1$H NMR (400 MHz, MeOD) δ 1.54-1.69 (m, 2H), 1.73-1.88 (m, 2H), 2.61 (s, 3H), 2.64-2.75 (m, 1H), 2.90-3.03 (m, 1H), 3.11 (dd, J=16.29, 4.42 Hz, 1H), 3.80-3.88 (m, 2H), 3.90 (s, 3H), 3.94-4.05 (m, 2H), 5.00 (dd, J=8.46, 4.42 Hz, 1H), 6.78 (d, J=8.34 Hz, 1H), 7.11 (d, J=7.33 Hz, 1H), 7.13-7.24 (m, 2H), 7.59 (dd, J=8.08, 5.81 Hz, 1H), 7.76 (t, J=7.83 Hz, 1H). MS (ES) [M+H] calc'd for $C_{26}H_{30}FN_6O_4$, 509.22; found, 509.20.

Example 61

5-(aminooxy)-2-methylpentane-2,3-diol

Route-A

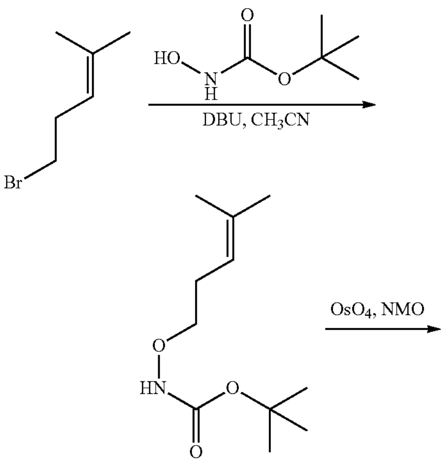

-continued

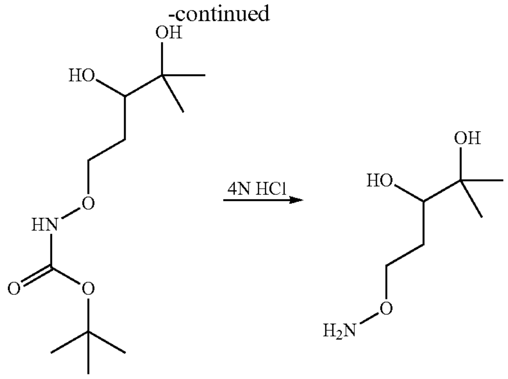

To a solution of 5-bromo-2-methylpent-2-ene (1.33 mL, 10.0 mmol) in $CH_3CN$ (25 mL) was added tert-butyl hydroxycarbamate (2.0 g, 15.0 mmol) and DBU (4.5 mL, 30 mmol) at 0° C. and the reaction mixture stirred at r.t. for overnight. Quenched with saturated $NH_4Cl$ solution and extracted with brine. Combined organic layers washed with brine and dried over anhydrous $Na_2SO_4$, filtered and concentrated to provide yellow oil, which was purified by flash chromatography (50% EtOAc-hexane) to yield tert-butyl 4-methylpent-3-enyloxycarbamate (750 mg, 70%) as a viscous oil. $^1$H NMR (400 MHz, CHLOROFORM-d) δ ppm 1.40 (s, 9H) 1.54 (s., 3H) 1.61 (s., 3H) 2.21-2.31 (m, 2H) 3.70-3.78 (m, 2H) 5.02-5.10 (m, 1H). MS (ES) [M+H] calculated for $C_{11}H_{22}NO_3$, 216.15; found 216.10.

The resultant oily compound (750 mg, 3.5 mmol) was dissolved in 4:1 dioxane-$H_2O$, NMO (409 mg, 3.85 mmol) and $OsO_4$ (0.2 mL, 0.35 mmol, 2.5 wt % in $H_2O$) was added. The reaction mixture was stirred for 24 h at rt. Work-up similar to the procedure described in Example 58 afforded tert-butyl 3,4-dihydroxy-4-methylpentyloxycarbamate (510 mg, 58%) as a viscous oil. $^1$H NMR (400 MHz, CHLOROFORM-d) δ 1.14 (s, 3H) 1.20 (s, 3H) 1.46 (s, 9H) 1.57-1.70 (m, 1H) 1.72-1.88 (m, 1H) 3.62-3.76 (m, 1H) 3.92-4.15 (m, 2H). MS (ES) [M+H] calculated for $C_{11}H_{24}NO_5$, 250.15; found 250.20.

The resultant oily compound (498 mg, 2.0 mmol) was dissolved in dioxane (2.0 ml) and cooled to 0° C. 4N HCl in dioxane (1.25 mL, 5.0 mmol) was added and the reaction mixture was stirred at ambient temperature for 2 h. The resultant solid was filtered off and dried to afford the HCl salt of the title compound (260 mg, 70%) as white solid. $^1$H NMR (400 MHz, CHLOROFORM-d) δ 1.16 (s, 3H) 1.19 (s, 3H) 1.63-1.71 (m, 1H) 1.98-2.06 (m, 1H) 3.45 (d, J=12.88 Hz, 1H) 4.14-4.33 (m, 2H). MS (ES) [M+H] calculated for $C_6H_{16}NO_3$, 150.11; found 150.10.

Route-B

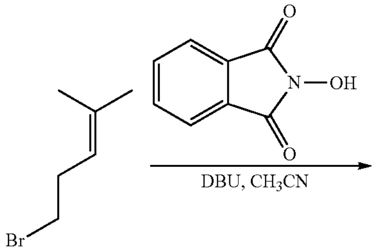

-continued

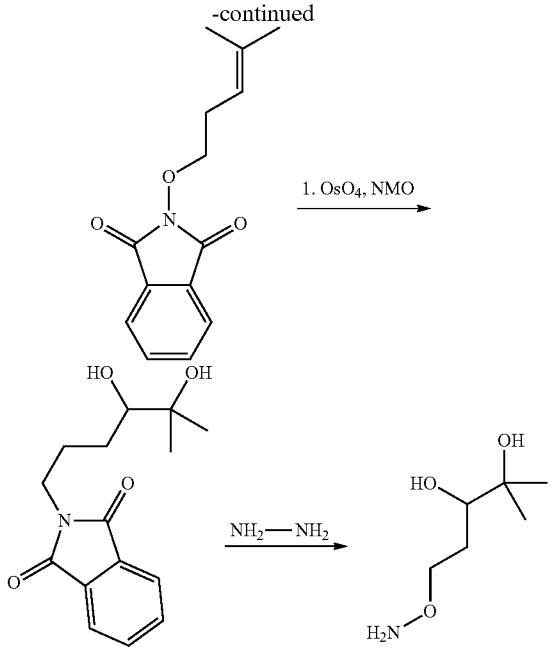

A mixture of 5-bromo-2-methylpent-2-ene (0.66 mL, 5.0 mmol) in $CH_3CN$ (15 mL) was added 2-hydroxyisoindoline-1,3-dione (3.33 g, 6.0 mmol) and DBU (4.5 mL, 30 mmol) was heated at 100° C. for 4 h. Work-up analogous to the procedure described in Example 58 afforded 2-(4-methyl-pent-3-enyloxy)isoindoline-1,3-dione (1.14 g, 90%) as a viscous oil.

The resultant compound was subjected for dihydroxylation followed by phthalimide deprotection analogous to the procedures described earlier (Example 57) afforded the title compound.

Example 62

(7R,Z)-2-amino-7-(4-fluoro-2-(6-methoxypyridin-2-yl)phenyl)-4-methyl-7,8-dihydropyrido[4,3-d]pyrimidin-5(6H)-one O-3,4-dihydroxy-4-methylpentyl oxime (Compound 60)

60

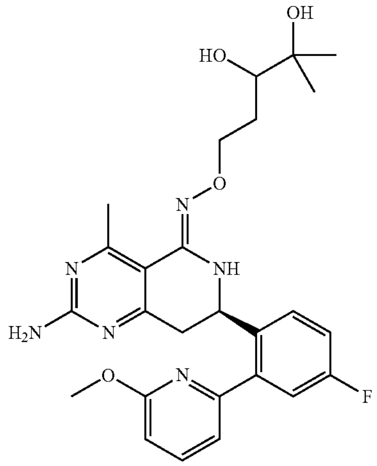

The title compound was prepared analogous to the procedure described in Example 58. $^1$H NMR (400 MHz, MeOD) δ ppm 0.99 (d, J=5.31 Hz, 3H) 1.04 (d, J=5.31 Hz, 3H) 1.34-1.51 (m, 1H) 1.92-2.07 (m, 1H) 2.53 (d, J=1.77 Hz, 3H) 2.73-2.89 (m, 1H) 3.03 (dd, J=16.17, 5.05 Hz, 1H) 3.16-3.30 (m, 1H) 3.86 (d, J=3.03 Hz, 3H) 3.95-4.06 (m, 2H) 4.93-5.13 (m, 1H) 6.86 (d, J=8.34 Hz, 1H) 7.19 (d, J=7.33 Hz, 1H) 7.22-7.34 (m, 2H) 7.41-7.56 (m, 1H) 7.78-7.91 (m, 1H). MS (ES) [M+H] calc'd for $C_{26}H_{32}FN_6O_4$, 511.56; found 511.40.

Example 63

(R,Z)-2-amino-7-(4-fluoro-2-(6-methoxypyridin-2-yl)phenyl)-4-methyl-7,8-dihydropyrido[4,3-d]pyrimidin-5(6H)-one oxime (Compound 61)

61

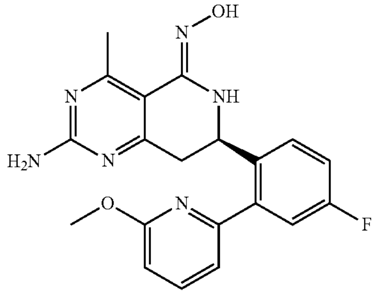

A mixture of (R)-2-amino-7-(2-bromo-4-fluorophenyl)-4-methyl-7,8-dihydropyrido[4,3-d]pyrimidine-5(6H)-thione (366 mg, 1.0 mmol), O-(tert-butyldimethylsilyl)hydroxylamine (588 mg, 4.0 mmol), $Hg(OAc)_2$ (640 mg, 2.0 mmol) and toluene (5 mL) was heated at 100° C. for 2 h. The mixture was cooled to r.t. and filtered through celite. Filtrate concentrated and the resulting oily residue was triturated with dry methanol to afford a pale yellow solid. Filtered and dried to afford ((R,Z)-2-amino-7-(2-bromo-4-fluorophenyl)-4-methyl-7,8-dihydropyrido[4,3-d]pyrimidin-5(6H)-one O-tert-butyldimethylsilyloxime (384 mg, 80%) as a pale yellow solid. $^1$H NMR (400 MHz, CHLOROFORM-d) δ ppm 0.22 (s, 3H), 0.23 (s, 3H) 0.97 (s, 9H) 2.70 (s, 3H) 2.91 (dd, J=16.42, 8.08 Hz, 1H) 3.19 (ddd, J=16.36, 4.86, 1.26 Hz, 1H) 4.99 (ddd, J=7.77, 5.12, 2.02 Hz, 1H) 7.05 (td, J=8.27, 2.65 Hz, 1H) 7.33 (dd, J=8.08, 2.78 Hz, 1H) 7.39 (dd, J=8.72, 5.94 Hz, 1H). MS (ES) [M+H] calculated for $C_{20}H_{28}BrFN_5OSi$, 480.12; found 480.30.

A mixture of the above compound (47.9 mg, 0.1 mmol), 2-(6-methoxypyridin-2-yl)-6-phenyl-1,3,6,2-dioxazaborocane (149 mg, 0.5 mmol), $Pd(dppf)_2Cl_2$ (8.12 mg, 0.01 mmol), 2N $Na_2CO_3$ (0.25 mL, 0.5 mmol) in DMA (3 mL) was degassed with $N_2$ and heated at 85° C. overnight. LCMS shows (R,Z)-2-amino-7-(4-fluoro-2-(6-methoxypyridin-2-yl)phenyl)-4-methyl-7,8-dihydropyrido[4,3-d]pyrimidin-5(6H)-one O-tert-butyldimethylsilyl oxime ([M+H] calculated for $C_{26}H_{34}BrFN_6O_2Si$, 509.24; found 509.40. The reaction mixture was diluted with ethyl acetate and filtered through celite. The filtrate was concentrated to afford brown oil which was purified by preparative LCMS to afford (R,Z)-2-amino-7-(4-fluoro-2-(6-methoxypyridin-2-yl)phenyl)-4-methyl-7,8-dihydropyrido[4,3-d]pyrimidin-5(6H)-one oxime (11.8 mg, 30%) as white solid.

Example 64

(R)-4-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)oxazolidin-2-one (Compound 62)

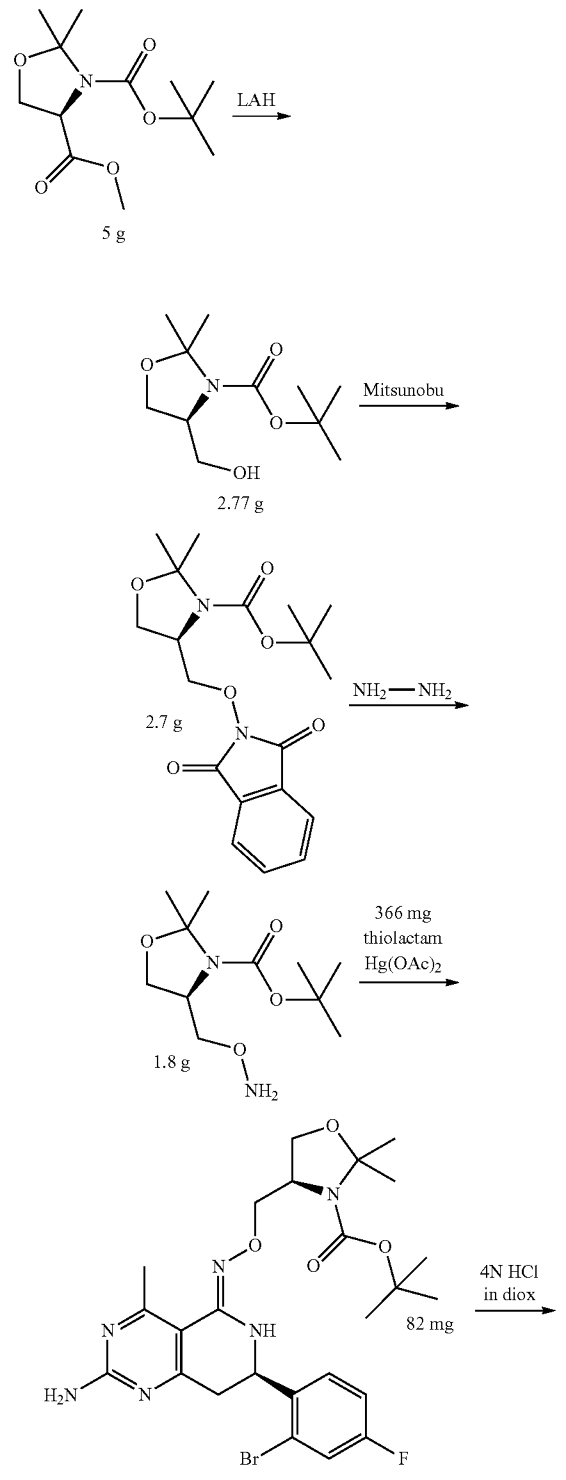

-continued

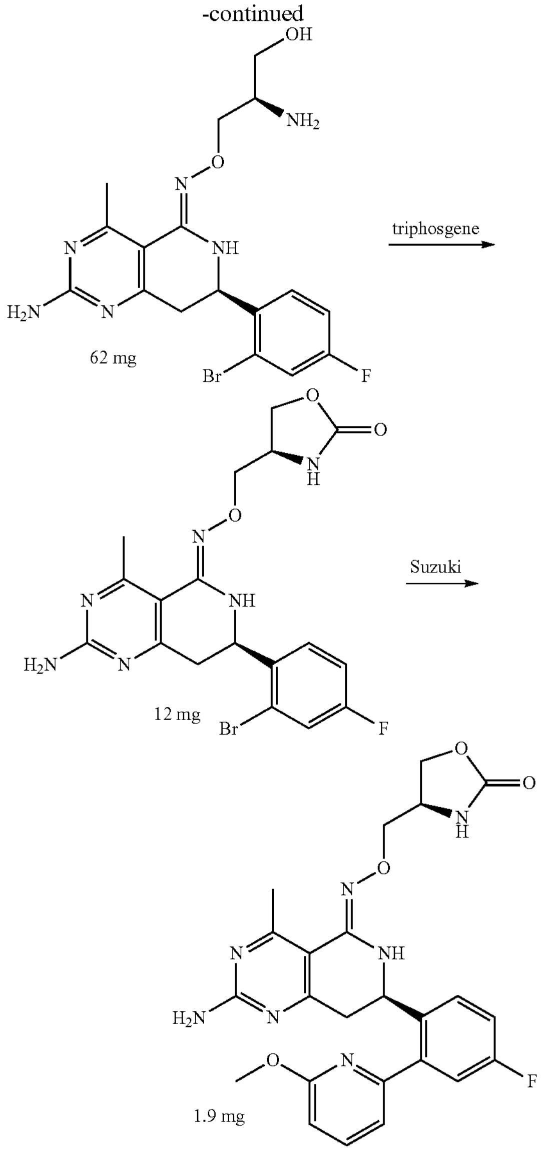

62

A solution of (R)-3-tert-butyl 4-methyl 2,2-dimethyloxazolidine-3,4-dicarboxylate (5 g, 19.3 mmol) in anhydrous diethyl ether was chilled in an ice bath and 1 M $LiAlH_4$ in diethyl ether (38 mL, 38.6 mmol) was added dropwise under an $N_2$ atmosphere. The reaction was allowed to warm to room temperature with stirring overnight. The reaction was quenched by slowly adding saturated aqueous $Na_2SO_4$ (5 mL). The slurry was filtered through a pad of Celite. The Celite pad was rinsed with EtOAc and the solution was dried in vacuo to yield (S)-tert-butyl 4-(hydroxymethyl)-2,2-dimethyloxazolidine-3-carboxylate (2.77 g, 12 mmol) as a clear oil. [M+H] calc'd for $C_{11}H_{21}NO_4$, 232; found, 232.

Standard Mitsunobu and hydrazine deprotection route to alkoxyamine was used as described in Example 2. [M+H] calc'd for $C_{11}H_{22}N_2O_4$, 247; found, 247.

Standard coupling to thiolactam scaffold via $Hg(OAc)_2$ was used as described in Example 39. [M+H] calc'd for $C_{25}H_{32}BrFN_6O_4$, 580; found, 580.

To a solution of (R)-tert-butyl 4-(((Z)—((R)-2-amino-7-(2-bromo-4-fluorophenyl)-4-methyl-7,8-dihydropyrido[4,3- d]pyrimidin-5(6H)-ylidene)aminooxy)methyl)-2,2-dimethyloxazolidine-3-carboxylate in dioxane was added 4 N HCl in dioxane. The reaction was allowed to stir under an $N_2$ atmosphere at room temperature for 90 min. The reaction was lyophilized to dryness to yield (R,Z)-2-amino-7-(2-bromo-4-fluorophenyl)-4-methyl-7,8-dihydropyrido[4,3-d]pyrimidin-5(6H)-one O—(R)-2-amino-3-hydroxypropyl oxime (65 mg, 0.13 mmol). [M+H] calc'd for $C_{17}H_{20}BrFN_6O_2$, 440; found, 440.

To a solution of (R,Z)-2-amino-7-(2-bromo-4-fluorophenyl)-4-methyl-7,8-dihydropyrido[4,3-d]pyrimidin-5(6H)-one O—(R)-2-amino-3-hydroxypropyl oxime (65 mg, 0.13 mmol) in anhydrous dichloromethane (3 mL) was added triethylamine (400 μL, 22 eq) and triphosgene (94 mg, 0.33 mmol). The reaction was stirred under an $N_2$ atmosphere at room temperature overnight. The reaction was washed with $H_2O$×1 and the organic phase dried over anhydrous $Na_2SO_4$. The solvent was removed in vacuo and the residue was purified via preparative HPLC eluting with TFA/ACN/$H_2O$ to yield (R)-4-(((Z)—((R)-2-amino-7-(2-bromo-4-fluorophenyl)-4-methyl-7,8-dihydropyrido[4,3-d]pyrimidin-5(6H)-ylidene)aminooxy)methyl)oxazolidin-2-one (12 mg, 0.026 mmol). [M+H] calc'd for $C_{18}H_{18}BrFN_6O_3$, 466; found, 466.

Standard Suzuki conditions to attach pyridyl ring were used as described in Example 39. $^1H$ NMR (400 MHz, MeOD) δ 2.76 (s, 3H), 3.03-3.19 (m, 1H), 3.33-3.53 (m, 1H), 3.91 (s, 3H), 3.97-4.08 (m, 1H), 4.07-4.24 (m, 2H), 4.29 (dd, J=8.72, 4.67 Hz, 1H), 4.42-4.55 (m, 1H), 5.05 (dd, J=8.97, 4.17 Hz, 1H), 6.79 (d, J=8.34 Hz, 1H), 7.12 (d, J=7.33 Hz, 1H), 7.14-7.29 (m, 2H), 7.66 (dd, J=8.59, 5.56 Hz, 1H), 7.77 (t, J=7.83 Hz, 1H). [M+H] calc'd for $C_{24}H_{24}FN_7O_4$, 494; found, 494.

Example 65

(R,Z)-2-amino-7-(4-fluoro-2-(6-methoxypyridin-2-yl)phenyl)-4-methyl-7,8-dihydropyrido[4,3-d]pyrimidin-5(6H)-one O-2-morpholinoethyl oxime (Compound 63)

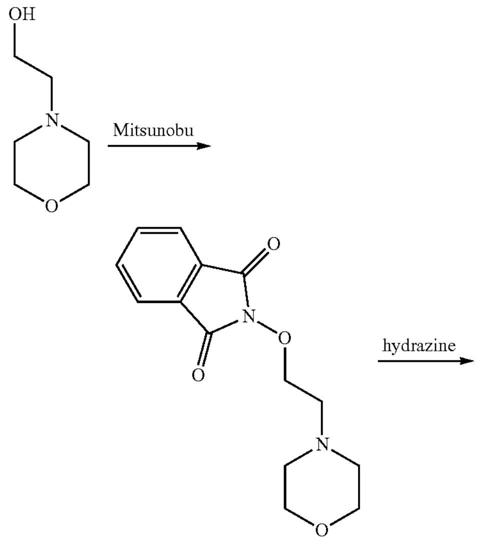

-continued

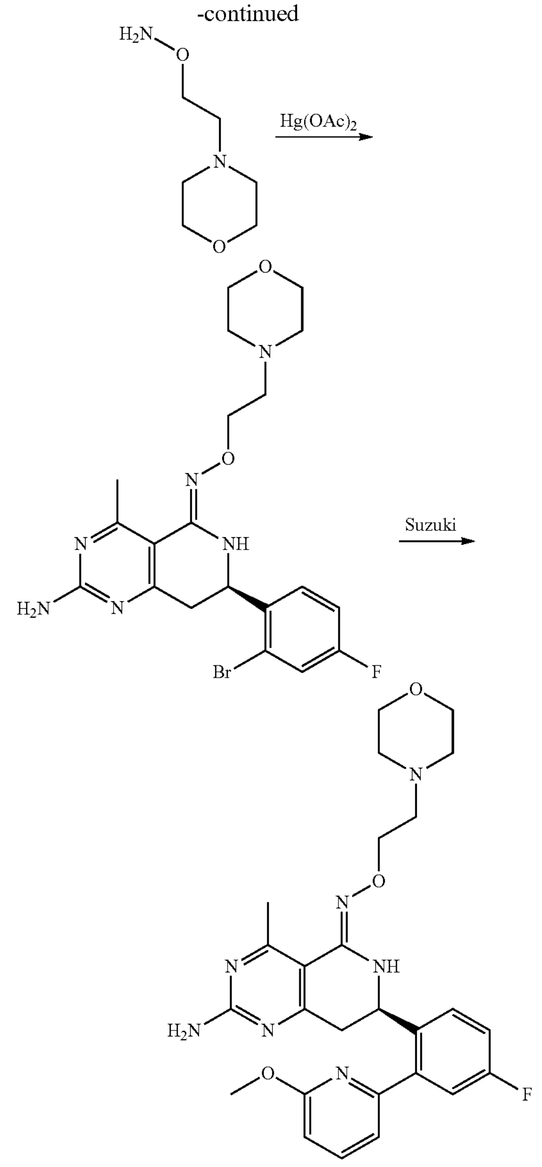

63

To a solution of 2-morpholinoethanol (5 g, 38 mmol) in $CH_2Cl_2$ (250 mL) was added 2-hydroxyisoindoline-1,3-dione (9.3 g, 57 mmol) and triphenylphosphine (15 g, 57 mmol). The resultant mixture was cooled to 0° C. and diisopropyl azodicarboxylate (11 ml, 57 mmol) was slowly added drop wise with an addition funnel under $N_2$ atmosphere. The reaction mixture was stirred at ambient temperature for 48 h. The reaction mixture was concentrated to provide clear oil, which was purified by flash chromatography (50% EtOAc—Hexane). The resultant clear oily compound was dissolved in $CH_2Cl_2$ (50 ml). Hydrazine hydrate (5.8 mL, 76 mmol) was added. The reaction mixture was stirred at ambient temperature for 8 h. The resultant solid was filtered off and the filtrate concentrated under reduced pressure to provide a clear oil of O-(2-morpholinoethyl)hydroxylamine (3.5 g, 24 mmol). [M+H] calc'd for $C_6H_{14}N_2O_2$, 147; found, 147.

To a solution of O-(2-morpholinoethyl)hydroxylamine (600 mg, 4.1 mmol) in anhydrous toluene (6 mL) was added (R)-2-amino-7-(2-bromo-4-fluorophenyl)-4-methyl-7,8-dihydropyrido[4,3-d]pyrimidine-5(6H)-thione (0.150 g, 0.41 mmol) and mercuric acetate (II) (262 mg, 0.82 mmol). The resultant mixture was heated to 100° C. for 1 h. The reaction was allowed to cool to r.t. and filtered through a pad of Celite, rinsing with EtOAc and $CH_3OH$. The filtrate was concentrated to provide a yellow-green oil, which was purified by preparative HPLC eluting with TFA/ACN/$H_2O$. The fractions were concentrated to provide (R,Z)-2-amino-7-(2-bromo-4-fluorophenyl)-4-methyl-7,8-dihydropyrido[4,3-d]pyrimidin-5(6H)-one O-2-morpholinoethyl oxime (196 mg, 0.41 mmol). [M+H] calc'd for $C_{20}H_{24}BrFN_6O_2$, 480; found, 480.

To a solution of (R,Z)-2-amino-7-(2-bromo-4-fluorophenyl)-4-methyl-7,8-dihydropyrido[4,3-d]pyrimidin-5(6H)-one O-2-morpholinoethyl oxime (100 mg, 0.21 mmol) in DMA was added 6-methoxypyridine-2-boronic acid N-phenyldiethanolamine ester (250 mg, 0.84 mmol), $Pd(dppf)_2Cl_2$ (17 mg, 0.02 mmol), and 2N $Na_2CO_3$ (522 μL, 1.05 mmol). The resultant mixture was degassed with $N_2$ for 5 min then heated in a sealed tube at 85° C. for 14 h. The reaction was allowed to cool to r.t. and filtered through a pad of Celite topped with anhydrous $Na_2SO_4$, rinsing with EtOAc and $CH_3OH$. The filtrate was concentrated to provide a brown residue which was purified by preparative HPLC eluting with TFA/ACN/$H_2O$. The solvent was removed on a rotary evaporator and the sample was dried under high vacuum to yield (R,Z)-2-amino-7-(4-fluoro-2-(6-methoxypyridin-2-yl)phenyl)-4-methyl-7,8-dihydropyrido[4,3-d]pyrimidin-5(6H)-one O-2-morpholinoethyl oxime (67.4 mg, 0.13 mmol). $^1H$ NMR (400 MHz, CHLOROFORM-d) δ 2.81 (s, 3H), 2.95 (td, J=11.87, 3.79 Hz, 2H), 3.12 (dd, J=17.18, 9.60 Hz, 1H), 3.34-3.56 (m, 3H), 3.70 (dd, J=11.75, 3.41 Hz, 2H), 3.84-4.06 (m, 7H), 4.39 (t, J=4.80 Hz, 2H), 4.94 (dd, J=9.60, 4.04 Hz, 1H), 6.81 (d, J=8.34 Hz, 1H), 7.06 (d, J=7.07 Hz, 1H), 7.08-7.21 (m, 2H), 7.50 (dd, J=8.59, 5.31 Hz, 1H), 7.68-7.81 (m, 1H). [M+H] calc'd for $C_{26}H_{30}FN7O_3$, 508; found, 508.

Example 66

(R,Z)-2-amino-7-(4-fluoro-2-(6-methoxypyridin-2-yl)phenyl)-4-methyl-7,8-dihydropyrido[4,3-d]pyrimidin-5(6H)-one O-(tetrahydro-2H-pyran-4-yl)methyl oxime (Compound 64)

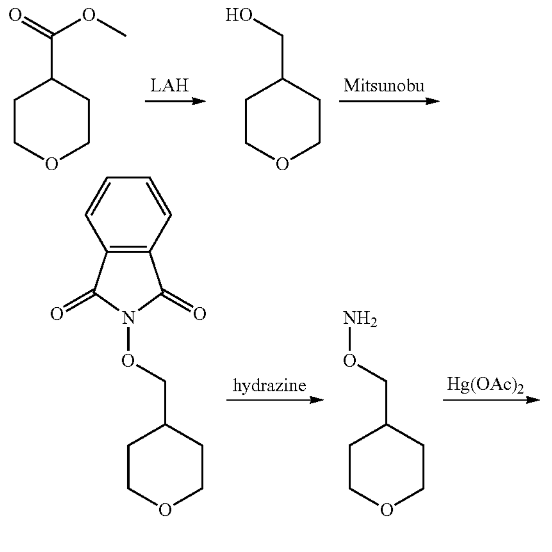

-continued

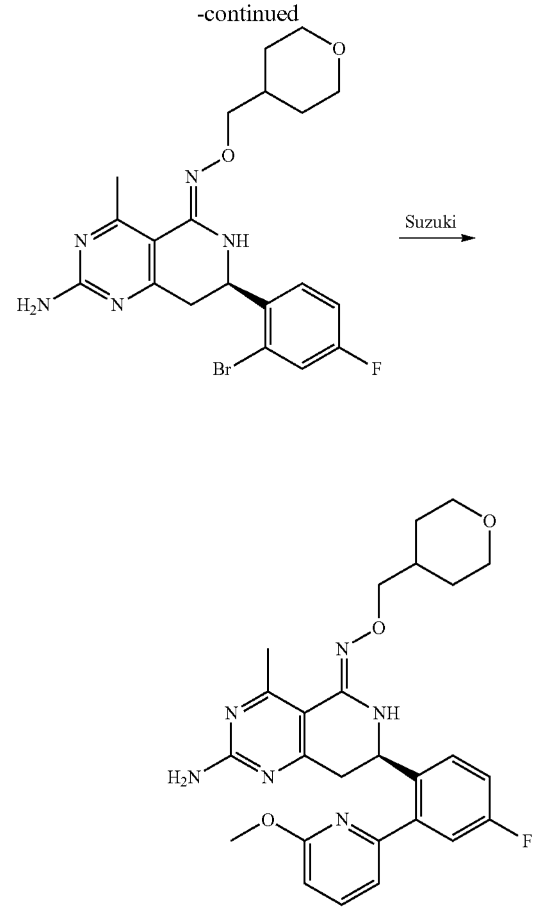

64

A solution of methyl tetrahydro-2H-pyran-4-carboxylate (5 g, 34.6 mmol) in anhydrous diethyl ether was chilled in an ice bath and 1 M $LiAlH_4$ in diethyl ether (52 mL, 51.9 mmol) was added dropwise under an $N_2$ atmosphere. The reaction was allowed to warm to room temperature with stirring overnight. The reaction was quenched by slowly adding 1 N aqueous NaOH (3 mL). The slurry was filtered through a pad of Celite. The Celite pad was rinsed with diethyl ether followed by methanol and the solution was dried in vacuo to yield (tetrahydro-2H-pyran-4-yl)methanol (4 g, 34.6 mmol) as a clear oil. [M+H] calc'd for $C_6H_{12}O_2$, 117; found, 117.

Standard Mitsunobu/hydrazine deprotection route to alkoxyamine was used as described in Example 2, [M+H] calc'd for $C_6H_{13}NO_2$, 132; found, 132.

Standard coupling to thiolactam scaffold via $Hg(OAc)_2$ was used as described in Example 39. [M+H] calc'd for $C_{20}H_{23}BrFN_5O_2$, 465; found, 465.

Standard Suzuki conditions to attach pyridyl ring were used as described in Example 39. $^1H$ NMR (400 MHz, MeOD) δ 1.19-1.41 (m, 2H), 1.64 (d, J=12.88 Hz, 2H), 1.96-2.13 (m, 1H), 2.80 (s, 3H), 3.19 (dd, J=16.93, 8.59 Hz, 1H), 3.33-3.47 (m, 3H), 3.84-4.00 (m, 7 H), 5.03-5.13 (m, 1H), 6.80 (d, J=8.34 Hz, 1H), 7.12 (d, J=7.07 Hz, 1H), 7.15-7.27

(m, 2H), 7.60 (dd, J=8.34, 5.56 Hz, 1H), 7.77 (t, J=7.83 Hz, 1H). [M+H] calc'd for $C_{26}H_{29}FN_6O_3$, 493; found, 493.

Example 67

(R,Z)-2-amino-7-(4-fluoro-2-(6-methoxypyridin-2-yl)phenyl)-4-methyl-7,8-dihydropyrido[4,3-d]pyrimidin-5(6H)-one O-((1s,4S)-4-hydroxycyclohexyl) methyl oxime (Compound 65)

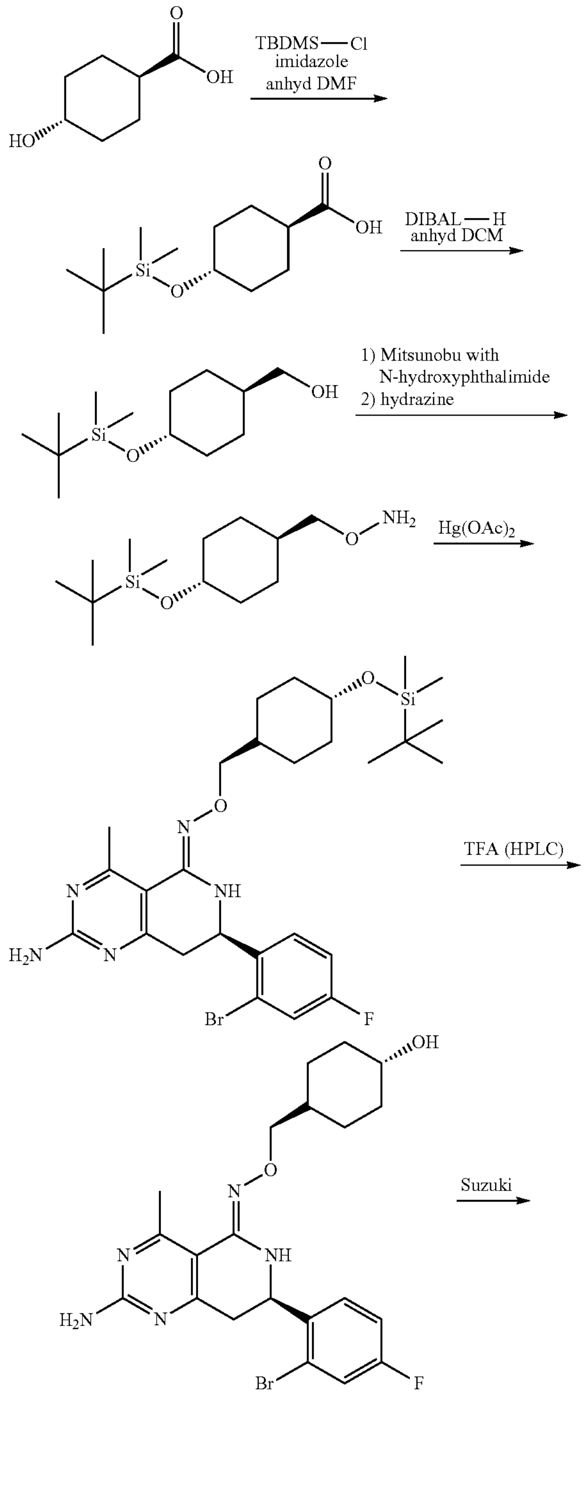

-continued

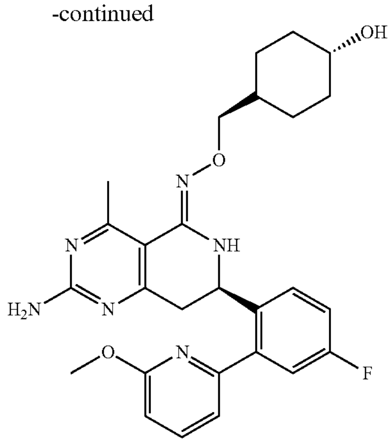

65

To a solution of (1r,4r)-4-hydroxycyclohexanecarboxylic acid (5 g, 34.7 mmol) in anhydrous DMF (35 mL) was added imidazole (4.72 g, 69.4 mmol) and TBDMS chloride (5.75 g, 38.2 mmol). The reaction was allowed to stir under an $N_2$ atmosphere at room temperature overnight. The reaction was diluted with diethyl ether and washed with 1 N aqueous HCl×2 then brine×1. The organic phase was dried over amhydrous $Na_2SO_4$ and the solvent removed in vacuo to yield (1r,4r)-4-(tert-butyldimethylsilyloxy)cyclohexanecarboxylic acid (8.9 g, 34.7 mmol) as a clear oil.

A solution of (1r,4r)-4-(tert-butyldimethylsilyloxy)cyclohexanecarboxylic acid (8.9 g, 34.7 mmol) in anhydrous dichloromethane (80 mL) was chilled in a dry ice/acetone bath and a 20 wt % solution of DIBAL-H in toluene (57 mL, 69.4 mmol) was added dropwise under an $N_2$ atmosphere. The reaction was allowed to warm to −30° C. with stirring over 1 h. The cold reaction mixture was slowly poured into chilled 1 N aqueous HCl (150 mL). The aqueous phase is washed with DCM×2 and the combined organic phases were washed with brine×1 and dried over anhydrous $Na_2SO_4$. The solvent was removed in vacuo to yield ((1r,4r)-4-(tert-butyldimethylsilyloxy)cyclohexyl)methanol (4.5 g, 18.4 mmol).

To a solution of ((1r,4r)-4-(tert-butyldimethylsilyloxy)cyclohexyl)methanol (4.5 g, 18.4 mmol) in $CH_2Cl_2$ (150 mL) was added 2-hydroxyisoindoline-1,3-dione (4.5 g, 27.6 mmol) and triphenylphosphine (7.25 g, 27.6 mmol). The resultant mixture was cooled to 0° C. and diisopropyl azodicarboxylate (5.35 ml, 27.6 mmol) was slowly added drop wise with an addition funnel under $N_2$ atmosphere. The reaction mixture was stirred at ambient temperature for 48 h. The reaction mixture was concentrated to provide clear oil, which was purified by flash chromatography (50% EtOAc—Hexane). The resultant clear oily compound was dissolved in $CH_2Cl_2$ (50 ml). Hydrazine hydrate (1.47 mL, 19.3 mmol) was added. The reaction mixture was stirred at ambient temperature for 8 h. The resultant solid was filtered off and the filtrate concentrated under reduced pressure to provide a clear oil of O-(((1r,4r)-4-(tert-butyldimethylsilyloxy)cyclohexyl)methyl)hydroxylamine (2.5 g, 9.66 mmol). [M+H] calc'd for $C_{13}H_{29}NO_2Si$, 260; found, 260.

To a solution of O-(((1r,4r)-4-(tert-butyldimethylsilyloxy)cyclohexyl)methyl)hydroxylamine (530 mg, 2.05 mmol) in anhydrous toluene (8 mL) was added (R)-2-amino-7-(2-bromo-4-fluorophenyl)-4-methyl-7,8-dihydropyrido[4,3-d]pyrimidine-5(6H)-thione (0.150 g, 0.41 mmol) and mercuric acetate (262 mg, 0.82 mmol). The resultant mixture was heated to 100° C. for 1 h. The reaction was allowed to cool to r.t. and filtered through a pad of Celite, rinsing with EtOAc and $CH_3OH$. The filtrate was concentrated to provide a yellow-green oil, which was purified by preparative HPLC eluting with TFA/ACN/$H_2O$. Upon drying down the preparative HPLC fractions at 50° C. on a rotary evaporator, the alcohol was formed cleanly to provide (R,Z)-2-amino-7-(2-bromo-4-fluorophenyl)-4-methyl-7,8-dihydropyrido[4,3-d]pyrimidin-5(6H)-one O-((1s,4S)-4-hydroxycyclohexyl)methyl oxime (63 mg, 0.13 mmol). [M+H] calc'd for $C_{21}H_{25}BrFN_5O_2$, 479; found, 479.

To a solution of (R,Z)-2-amino-7-(2-bromo-4-fluorophenyl)-4-methyl-7,8-dihydropyrido[4,3-d]pyrimidin-5(6H)-one O-((1s,4S)-4-hydroxycyclohexyl)methyl oxime (63 mg, 0.13 mmol) in DMA was added 6-methoxypyridine-2-boronic acid N-phenyldiethanolamine ester (157 mg, 0.52 mmol), $Pd(dppf)_2Cl_2$ (10.6 mg, 0.013 mmol), and 2N $Na_2CO_3$ (329 μL, 0.65 mmol). The resultant mixture was degassed with $N_2$ for 5 min then heated in a sealed tube at 85° C. for 14 h. The reaction was allowed to cool to r.t. and filtered through a pad of Celite topped with anhydrous $Na_2SO_4$, rinsing with EtOAc and $CH_3OH$. The filtrate was concentrated to provide a brown residue which was purified by preparative HPLC eluting with TFA/ACN/$H_2O$. The solvent was removed on a rotary evaporator and the sample was dried under high vacuum to yield (R,Z)-2-amino-7-(4-fluoro-2-(6-methoxypyridin-2-yl)phenyl)-4-methyl-7,8-dihydropyrido[4,3-d]pyrimidin-5(6H)-one O-((1s,4S)-4-hydroxycyclohexyl)methyl oxime (10 mg, 0.02 mmol). $^1H$ NMR (400 MHz, MeOD) δ 1.40-1.60 (m, 6H), 1.69 (dd, J=8.08, 4.55 Hz, 2H), 1.77-1.92 (m, 1H), 2.73 (s, 3H), 3.05-3.18 (m, 1H), 3.21-3.28 (m, 1H), 3.83-3.96 (m, 6H), 5.09 (dd, J=8.34, 4.55 Hz, 1H), 6.80 (d, J=8.34 Hz, 1H), 7.12 (d, J=7.07 Hz, 1H), 7.15-7.25 (m, 2H), 7.58 (dd, J=8.34, 5.81 Hz, 1H), 7.71-7.82 (m, 1H). [M+H] calc'd for $C_{27}H_{31}FN_6O_3$, 507; found, 507.

Example 68

(S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanamide (Compound 66)

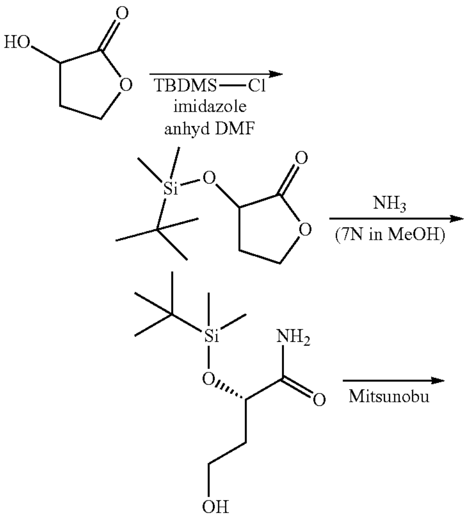

-continued

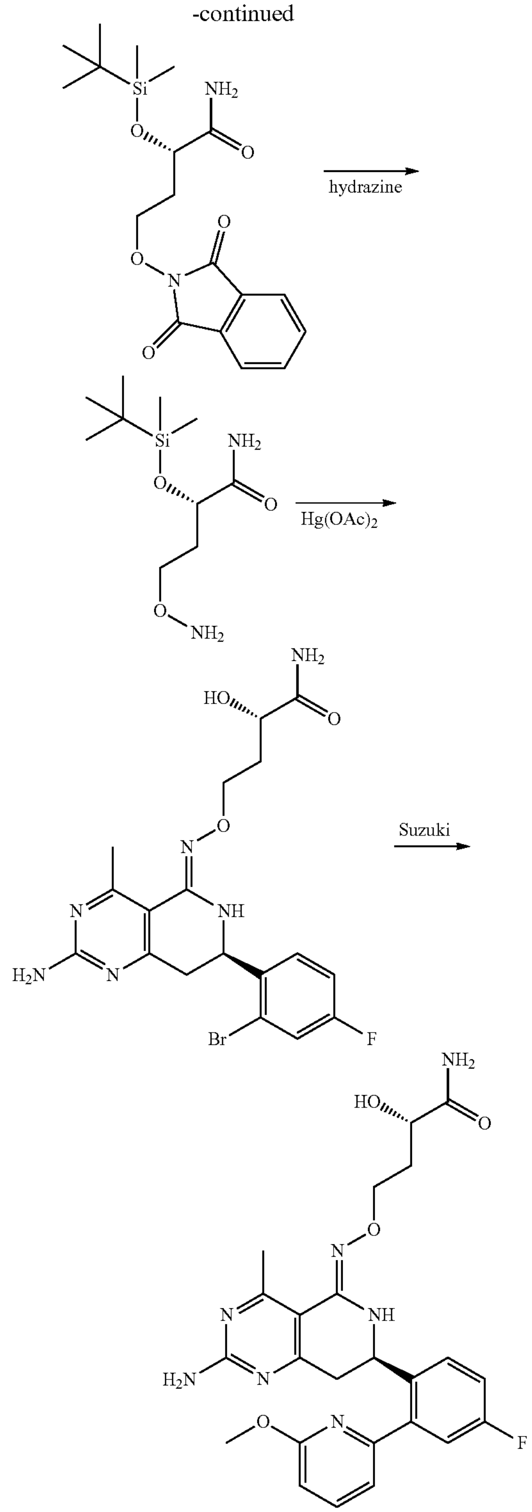

66

To a solution of 3-hydroxydihydrofuran-2(3H)-one (5 g, 49 mmol) in anhydrous DMF (50 mL) was added imidazole (6.7 g, 98 mmol) and TBDMS chloride (8.1 g, 54 mmol). The reaction was allowed to stir under an $N_2$ atmosphere at room temperature overnight. The reaction was diluted with diethyl ether and washed with 1 N aqueous HCl×2 then brine×1. The organic phase was dried over $Na_2SO_4$ and the solvent removed in vacuo to yield 3-(tert-butyldimethylsilyloxy)dihydrofuran-2(3H)-one (11 g, 49 mmol) as a clear oil. [M+H] calc'd for $C_{10}H_{20}O_3Si$, 217; found, 217.

To a solution of 3-(tert-butyldimethylsilyloxy)dihydrofuran-2(3H)-one (11 g, 49 mmol) in methanol was added 7 N ammonia in methanol (20 mL, 140 mmol). The reaction was stirred in a sealed tube for 2 days. The solvent was removed in vacuo to yield (S)-2-(tert-butyldimethylsilyloxy)-4-hydroxybutanamide (4.85 g, 20.8 mmol) as a white solid. [M+H] calc'd for $C_{10}H_{23}NO_3Si$, 234; found, 234.

To a solution of (S)-2-(tert-butyldimethylsilyloxy)-4-hydroxybutanamide (4.85 g, 20.8 mmol) in $CH_2Cl_2$ (150 mL) was added 2-hydroxyisoindoline-1,3-dione (5.1 g, 31.2 mmol) and triphenylphosphine (8.2 g, 31.2 mmol). The resultant mixture was cooled to 0° C. and diisopropyl azodicarboxylate (6.0 ml, 31.2 mmol) was slowly added dropwise with an addition funnel under $N_2$ atmosphere. The reaction mixture was stirred at ambient temperature for 48 h. The reaction mixture was concentrated to provide clear oil, which was purified by flash chromatography (60% EtOAc—Hexane). The resultant pale yellow compound was dissolved in $CH_2Cl_2$ (60 ml). Hydrazine hydrate (670 μL, 8.8 mmol) was added. The reaction mixture was stirred at ambient temperature for 8 h. The resultant solid was filtered off and the filtrate concentrated under reduced pressure to provide a clear yellow oil of (S)-4-(aminooxy)-2-(tert-butyldimethylsilyloxy)butanamide (1.1 g, 4.4 mmol). [M+H] calc'd for $C_{10}H_{24}N_2O_3Si$, 249; found, 249.

To a solution of (S)-4-(aminooxy)-2-(tert-butyldimethylsilyloxy)butanamide (1 g, 4.1 mmol) in anhydrous toluene (10 mL) was added (R)-2-amino-7-(2-bromo-4-fluorophenyl)-4-methyl-7,8-dihydropyrido[4,3-d]pyrimidine-5(6H)-thione (0.300 g, 0.82 mmol) and mercuric (II) acetate (523 mg, 1.64 mmol). The resultant mixture was heated to 100° C. for 2 h. The reaction was allowed to cool to r.t. and filtered through a pad of Celite, rinsing with EtOAc and $CH_3OH$. The filtrate was concentrated to provide a yellow-green oil, which was purified by preparative HPLC eluting with TFA/ACN/$H_2O$. Upon drying down the preparative HPLC fractions at 50° C. on a rotary evaporator, the alcohol was formed cleanly to provide (S)-4-((Z)—((R)-2-amino-7-(2-bromo-4-fluorophenyl)-4-methyl-7,8-dihydropyrido[4,3-d]pyrimidin-5(6H)-ylidene)aminooxy)-2-hydroxybutanamide (51 mg, 0.11 mmol). [M+H] calc'd for $C_{18}H_{20}BrFN_6O_3$, 477; found, 477.

To a solution of (S)-4-((Z)—((R)-2-amino-7-(2-bromo-4-fluorophenyl)-4-methyl-7,8-dihydropyrido[4,3-d]pyrimidin-5(6H)-ylidene)aminooxy)-2-hydroxybutanamide (51 mg, 0.11 mmol) in DMA was added 6-methoxypyridine-2-boronic acid N-phenyldiethanolamine ester (130 mg, 0.44 mmol), $Pd(dppf)_2Cl_2$ (9 mg, 0.011 mmol), and 2N $Na_2CO_3$ (273 μL, 0.55 mmol). The resultant mixture was degassed with $N_2$ for 5 min then heated in a sealed tube at 85° C. for 14 h. The reaction was allowed to cool to r.t. and filtered through a pad of Celite topped with anhydrous $Na_2SO_4$, rinsing with EtOAc and $CH_3OH$. The filtrate was concentrated to provide a brown residue which was purified by preparative HPLC eluting with TFA/ACN/$H_2O$. The solvent was removed on a rotary evaporator and the sample was dried under high vacuum to yield (S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanamide (12.6 mg, 0.025 mmol). $^1$H NMR (400 MHz, MeOD) δ 1.76-1.93 (m, 1H), 2.16-2.35 (m, 1H), 2.80 (s, 3H), 3.18 (dd, J=16.80, 9.22 Hz, 1H), 3.32-3.42 (m, 1H), 3.90 (s, 3H), 4.10 (dd, J=8.72, 3.16 Hz, 1H), 4.13-4.31 (m, 2H), 5.07 (dd, J=9.09, 4.04 Hz, 1H), 6.79 (d, J=8.08 Hz, 1H), 7.12 (d, J 7.33 Hz, 1H), 7.15-7.28 (m, 2H), 7.66 (dd, J=8.59, 5.56 Hz, 1H), 7.71-7.83 (m, 1H).

[M+H] calc'd for $C_{24}H_{26}FN_7O_4$, 496; found, 496.

Example 69

(7R,Z)-2-amino-7-(4-fluoro-2-(6-methoxypyridin-2-yl)phenyl)-4-methyl-7,8-dihydropyrido[4,3-d]pyrimidin-5(6H)-one O-2-(morpholin-2-yl)ethyl oxime (Compound 67)

67

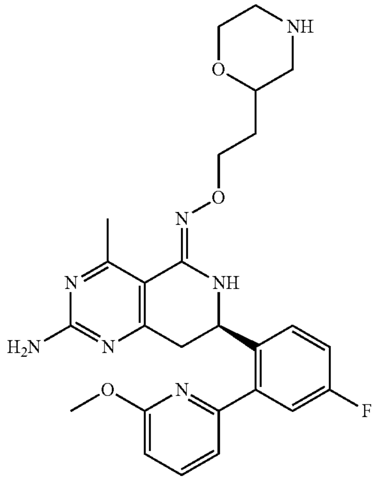

$^1$H NMR (400 MHz, MeOD) δ 1.75-1.92 (m, 1H), 1.91-2.08 (m, 1H), 2.78 (s, 3H), 2.90 (t, J=11.87 Hz, 1H), 3.03-3.18 (m, 1H), 3.18-3.28 (m, 2H), 3.32-3.42 (m, 2H), 3.68-3.85 (m, 2H), 3.91 (s, 3H), 4.02 (d, J=12.88 Hz, 1H), 4.07-4.28 (m, 2H), 5.01-5.11 (m, 1H), 6.81 (d, J=8.34 Hz, 1H), 7.13 (d, J=7.07 Hz, 1H), 7.16-7.35 (m, 2H), 7.56-7.69 (m, 1H), 7.78 (t, J=7.83 Hz, 1H). [M+H] calc'd for $C_{26}H_{30}FN_7O_3$, 508; found, 508.

Example 70

(S)-4-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)-3-benzyloxazolidin-2-one (Compound 68)

68

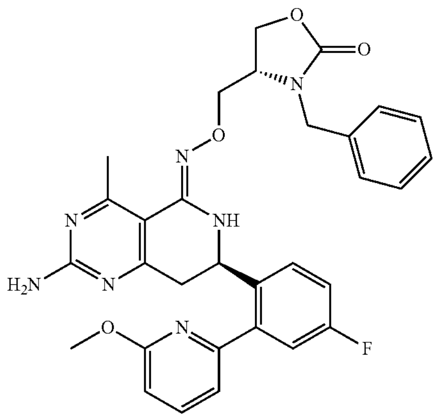

$^1$H NMR (400 MHz, CHLOROFORM-d) δ 2.48-2.65 (m, 3H), 2.97-3.16 (m, 1H), 3.19-3.35 (m, 1H), 3.88 (s, 3H), 3.90-3.99 (m, 1H), 4.00-4.16 (m, 2H), 4.15-4.27 (m, 1H), 4.26-4.39 (m, 1H), 4.72-4.86 (m, 1H), 4.90 (dd, J=10.23, 3.41 Hz, 1H), 5.47-5.63 (m, 1H), 6.74 (d, J=8.34 Hz, 1H), 6.97-7.06 (m, 1H), 7.10-7.21 (m, 2H), 7.20-7.26 (m, 5H), 7.57-7.71 (m, 2H). [M+H] calc'd for $C_{31}H_{30}FN_7O_4$, 584; found, 584.

Example 71

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-2-amino-3-hydroxypropyl oxime (Compound 69)

69

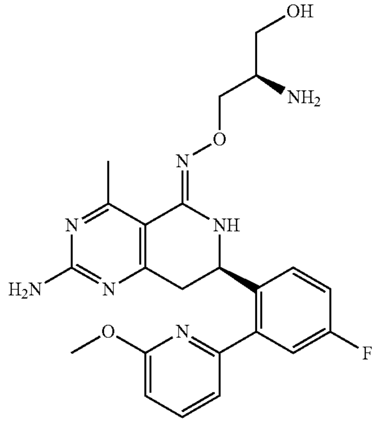

$^1$H NMR (400 MHz, MeOD) δ 2.81 (s, 3H), 2.90-3.00 (m, 1H), 3.02-3.16 (m, 1H), 3.69-3.78 (m, 1H), 3.82 (dd, J=11.37, 3.54 Hz, 2H), 3.91 (s, 3H), 4.13-4.34 (m, 2H), 5.03-5.10 (m, 1H), 6.72-6.92 (m, 1H), 7.13 (d, J=7.07 Hz, 1H), 7.16-7.34 (m, 2H), 7.63-7.75 (m, 1H), 7.79 (t, J=7.71 Hz, 1H). [M+H] calc'd for $C_{23}H_{26}FN_7O_3$, 468; found, 468.

Example 72

(R,Z)-2-amino-7-(4-fluoro-2-(6-methoxypyridin-2-yl)phenyl)-4-methyl-7,8-dihydropyrido[4,3-d]pyrimidin-5(6H)-one O-(1-methyl-1H-imidazol-4-yl)methyl oxime (Compound 70)

70

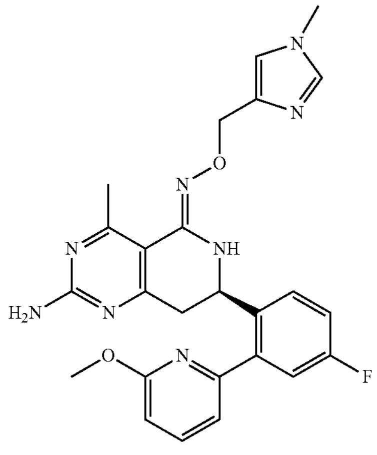

$^1$H NMR (400 MHz, MeOD) δ 2.71 (s, 3H), 3.18 (dd, J=16.80, 9.22 Hz, 1H), 3.34-3.43 (m, 1H), 3.87 (s, 3H), 3.92 (s, 3H), 5.06-5.11 (m, 3H), 6.80 (d, J=8.34 Hz, 1H), 7.12 (d, J=7.33 Hz, 1H), 7.15-7.29 (m, 2H), 7.53-7.67 (m, 2H), 7.67-7.85 (m, 1H), 8.85 (br. s., 1H). [M+H] calc'd for $C_{25}H_{25}FN_8O_2$, 489; found, 489.

Example 73

(R)-7-(4-fluoro-2-(6-methoxypyridin-2-yl)phenyl)-5-imino-4-methyl-5,6,7,8-tetrahydropyrido[4,3-d]pyrimidin-2-amine (Compound 71)

71

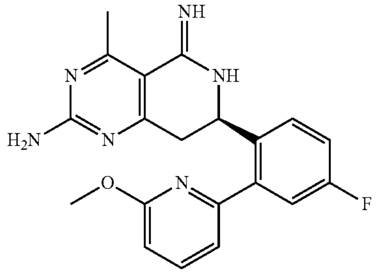

$^1$H NMR (400 MHz, MeOD) δ 2.56-2.66 (m, 3H), 3.28 (d, J=7.83 Hz, 2H), 3.88 (s, 3H), 5.32 (t, J=7.83 Hz, 1H), 6.75-6.86 (m, 1H), 7.11-7.22 (m, 1H), 7.23-7.36 (m, 2H), 7.72 (t, J=6.82 Hz, 1H), 7.74-7.84 (m, 1H). [M+H] calc'd for $C_{20}H_{19}FN_6O$, 379; found, 379.

Example 74

(R,Z)-2-amino-7-(2-(5-amino-6-methoxypyrazin-2-yl)-4-fluorophenyl)-4-methyl-7,8-dihydropyrido[4,3-d]pyrimidin-5(6H)-one O—(S)-3,4-dihydroxybutyl oxime (Compound 72)

72

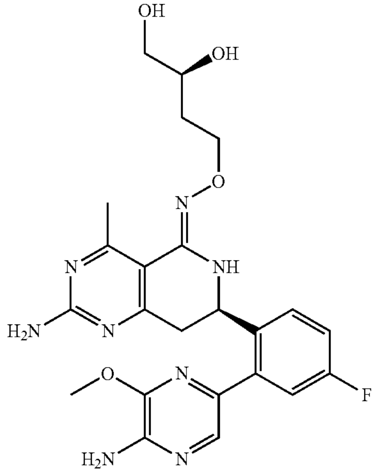

$^1$H NMR (400 MHz, DMSO-$d_6$) δ 1.44-1.61 (m, 1H), 1.78-1.95 (m, 1H), 2.53 (s, 3H), 2.86 (dd, J=16.04, 7.45 Hz, 1H), 3.08 (dd, J=15.92, 4.80 Hz, 1H), 3.20-3.30 (m, 2H), 3.47-3.58 (m, 1H), 3.89 (s, 3H), 3.96-4.07 (m, 2H), 4.40-4.51 (m, 2H), 4.95-5.06 (m, 1H), 6.22 (d, J=1.52 Hz, 1H), 6.54 (s, 2H), 6.78 (s, 2H), 7.13-7.29 (m, 2H), 7.45 (dd, J=8.46, 5.94 Hz, 1H), 7.70 (s, 1H). [M+H] calc'd for $C_{23}H_{27}FN_8O_4$, 499; found, 499.

Example 75

(R,Z)-2-amino-7-(4-fluoro-2-(6-methoxypyrazin-2-yl)phenyl)-4-methyl-7,8-dihydropyrido[4,3-d]pyrimidin-5(6H)-one O—(S)-3,4-dihydroxybutyl oxime (Compound 73)

73

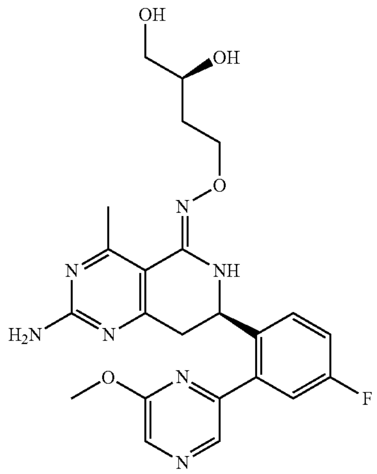

$^1$H NMR (400 MHz, MeOD) δ 1.59-1.74 (m, 1H), 1.88-2.06 (m, 1H), 2.62 (s, 3H), 3.02 (dd, J=16.29, 9.22 Hz, 1H), 3.13-3.25 (m, 1H), 3.39-3.53 (m, 2H), 3.67-3.78 (m, 1H), 3.97 (s, 3H), 4.06-4.24 (m, 2H), 4.89-4.94 (m, 1H), 7.20-7.33 (m, 2H), 7.63-7.74 (m, 1H), 8.21 (s, 1H), 8.32 (s, 1H). [M+H] calc'd for $C_{23}H_{26}FN_7O_4$, 484; found, 484.

Example 76

(R,Z)-2-amino-7-(4-fluoro-2-(2-methoxythiazol-4-yl)phenyl)-4-methyl-7,8-dihydropyrido[4,3-d]pyrimidin-5(6H)-one O—(S)-3,4-dihydroxybutyl oxime (Compound 74)

74

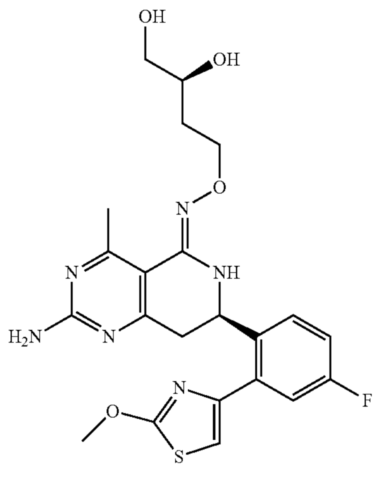

$^1$H NMR (400 MHz, MeOD) δ1.61-1.75 (m, 1H), 1.91-2.06 (m, 1H), 2.63 (s, 3H), 2.95 (dd, J=16.17, 8.08 Hz, 1H), 3.21 (dd, J=16.17, 4.80 Hz, 1H), 3.40-3.53 (m, 2H), 3.69-3.79 (m, 1H), 4.08 (s, 3H), 4.11-4.22 (m, 2H), 5.06 (dd, J=7.71, 4.93 Hz, 1H), 7.00 (s, 1H), 7.10 (td, J=8.46, 2.78 Hz, 1H), 7.22 (dd, J=9.60, 2.78 Hz, 1H), 7.48 (dd, J=8.72, 5.68 Hz, 1H). [M+H] calc'd for $C_{22}H_{25}FN_6O_4S$, 489; found, 489.

Example 77

Synthesis of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-4,5-dihydroxypentyl oxime (Compound 75)

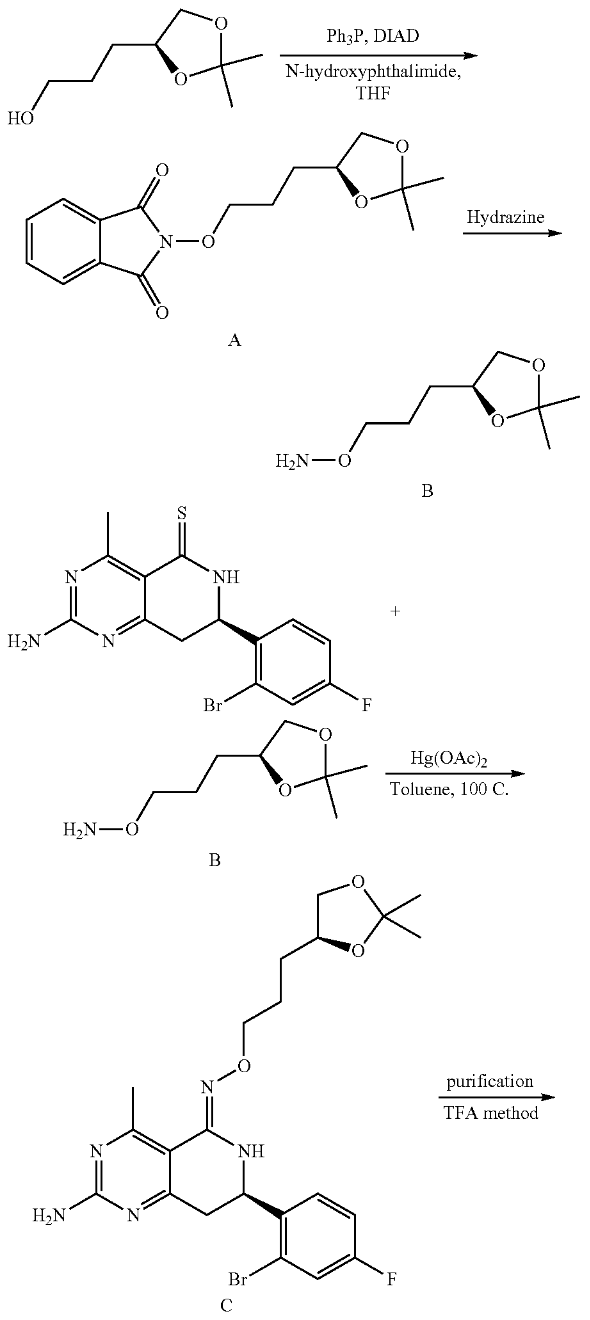

-continued

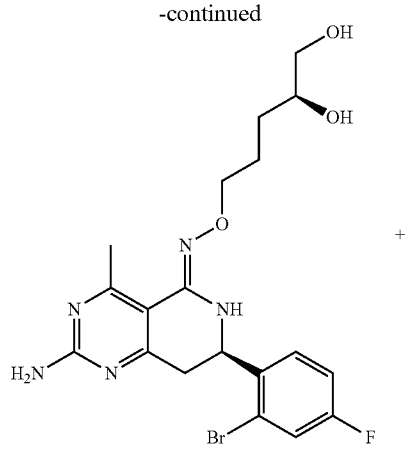

D

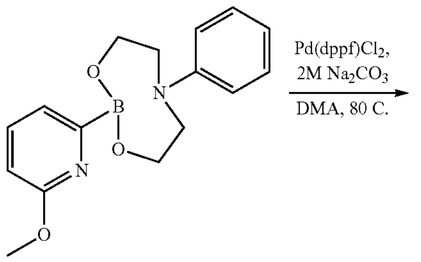

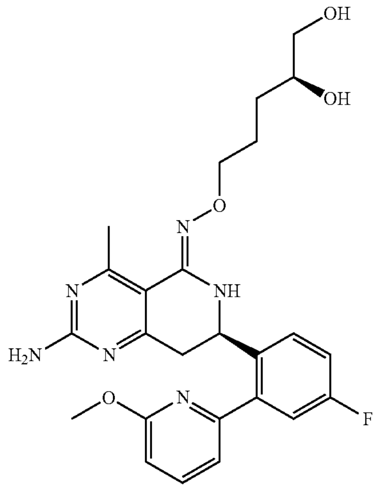

75

Compound A was synthesized as previously reported (70.7% yield) $^1H$ NMR (400 MHz, CHLOROFORM-d) δ 1.36 (s, 3H), 1.41 (s, 3H), 1.71-2.01 (m, 4H), 3.43-3.67 (m, 1H), 4.05-4.10 (m, 1H), 4.16-4.31 (m, 3H), 7.70-7.79 (m, 2H), 7.80-7.91 (m, 2H).

Compound B ((S)—O-(3-(2,2-dimethyl-1,3-dioxolan-4-yl)propyl)hydroxylamine) was synthesized as previously reported on similar chemistry, quantitative yield. $^1H$ NMR (400 MHz, CHLOROFORM-d) δ 1.36 (s, 3H), 1.41 (s, 3H), 1.57-1.76 (m, 4H), 3.50-3.55 (m, 1H), 3.69 (td, J=6.13, 2.65 Hz, 2H), 4.02-4.07 (m, 1H), 4.07-4.16 (m, 1H), 5.36 (s, 2H).

Compound C was also prepared as described before. ESI-MS: m/z 508.2 $(M+H)^+$. Purification by prep TFA method deprotected the acetonide group and gave compound D (55.1% yield). $^1H$ NMR (400 MHz, DMSO-$d_6$) δ 1.21-1.37 (m, 1H), 1.47-1.60 (m, 1H), 1.68 (ddd, J=13.01, 10.11, 5.94 Hz, 1H), 1.73-1.91 (m, 1H), 2.61 (s, 3H), 2.87 (dd, J=16.17, 4.29 Hz, 1H), 3.16-3.33 (m, 3H), 3.35-3.50 (m, 1H), 3.87-

4.07 (m, 3H), 4.89-5.00 (m, 2H), 6.91 (br. s., 1H), 7.14-7.26 (m, 3H), 7.58 (dd, J=8.46, 2.40 Hz, 1H).

Suzuki's coupling of compound D with the usual procedure provided compound 75 (19.3% yield). $^1H$ NMR (400 MHz, DMSO-$d_6$) δ 1.16-1.33 (m, 2H), 1.48 (d, J=4.55 Hz, 1H), 1.62 (br. s., 1H), 1.76 (d, J=10.36 Hz, 1H), 2.52 (s, 3H), 2.80 (dd, J=16.04, 6.95 Hz, 1H), 2.97-3.07 (m, 1H), 3.18-3.29 (m, 2H), 3.41 (br. s., 2H), 3.86 (s, 3H), 3.87-3.98 (m, 2H), 4.40 (br. s., 2H), 4.97-5.15 (m, 1H), 6.19-6.39 (m, 1H), 6.78 (s, 2H), 6.85 (d, J=8.34 Hz, 1H), 7.19 (d, J=6.57 Hz, 1H), 7.21-7.30 (m, 2H), 7.47 (dd, J=8.46, 5.94 Hz, 1H), 7.84 (dd, J=8.34, 7.33 Hz, 1H).

Example 78

(R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3-amino-2-hydroxypropyl oxime (Compound 76)

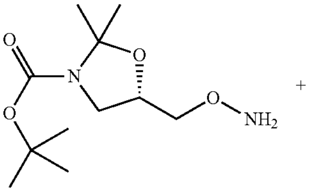

F

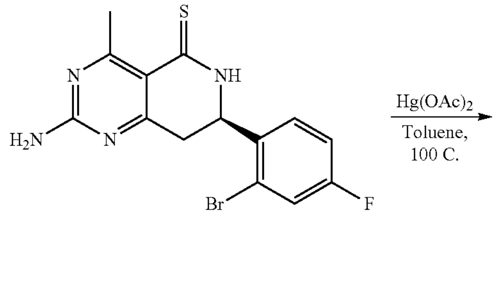

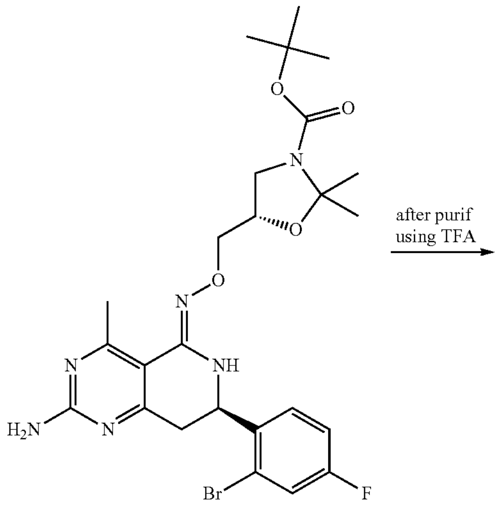

G

-continued

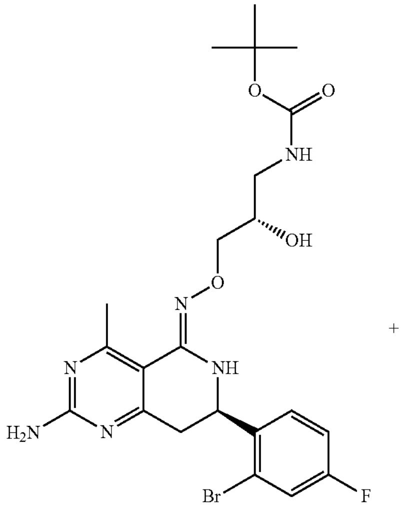

H

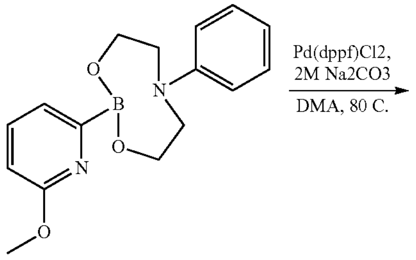

-continued

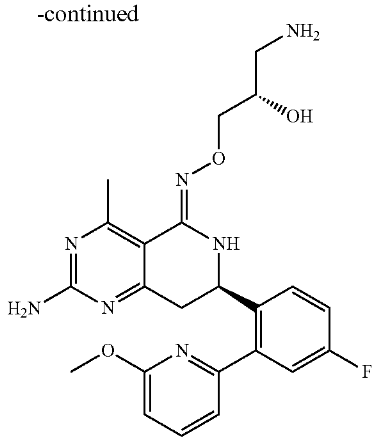

76

Compound F: $^1$H NMR (400 MHz, CHLOROFORM-d) δ 1.26 (s, 9H), 1.28 (s, 6H), 3.65-3.74 (m, 2H), 3.89-3.93 (m, 1H), 4.12 (m, 1H), 4.28-4.41 (m, 1H), 5.58 (br. s., 2H).

Compound G was synthesized as described above. ESI-MS: m/z 579.1 $(M+H)^+$.

Purification of G by LC/MS gradient 35-60% ACN in $H_2O$ with TFA system deprotected the acetonide group to give compound H after evaporation step. ESI-MS: m/z 539.2 $(M+H)^+$, 20.8% yield over 2 steps.

Suzuki's coupling of H produced compound I. ESI-MS: m/z 568.3 $(M+H)^+$, which was then deprotected with 20% TFA in dichloromethane for 45 minutes to give product Compound 76.

Compound 76 was purified by basic mode, gradient 25-50% ACN in $H_2O$, 46.1% yield. $^1$H NMR (400 MHz, DMSO-$d_6$) δ 2.52 (s, 3H), 2.69-2.86 (m, 2H), 3.05 (d, J=4.55 Hz, 2H), 3.85 (s, 3H), 3.88 (dd, J=5.81, 3.79 Hz, 2H), 3.98 (br. s., 2H), 5.02 (br. s., 1H), 5.05 (br.s., 2H), 6.59 (d, J=1.77 Hz, 1H), 6.86 (d, J=7.58 Hz, 1H), 7.18 (d, J=7.33 Hz, 1H), 7.28 (ddd, J=5.68, 2.78, 2.65 Hz, 2H), 7.52 (dd, J=8.59, 5.81 Hz, 1H), 7.75 (br. s., 2H), 7.84 (dd, J=8.34, 7.33 Hz, 1H).

Example 79

(S)-5-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)methyl)oxazolidin-2-one (Compound 77)

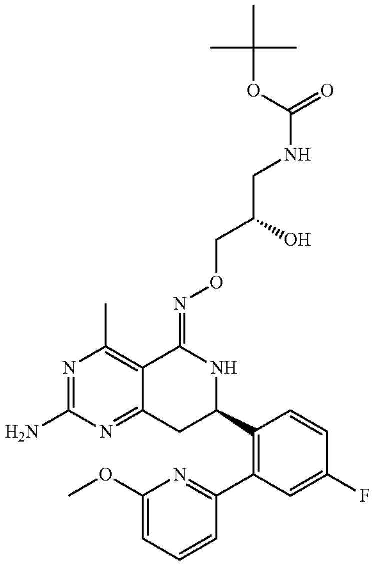

I

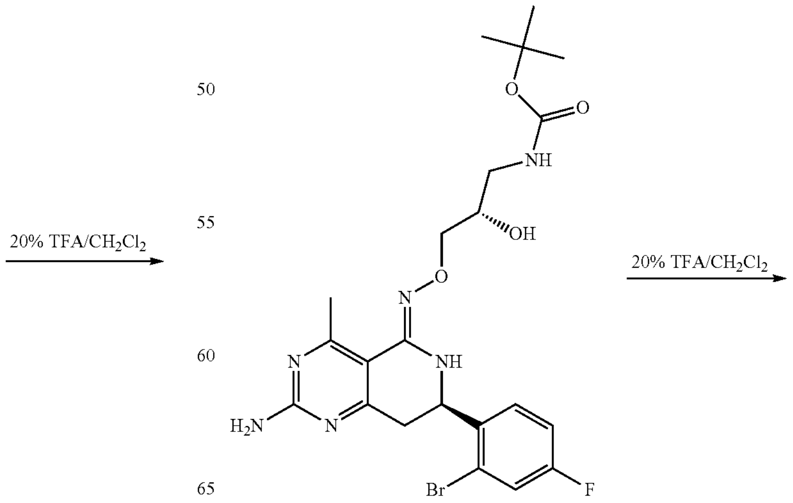

H

-continued

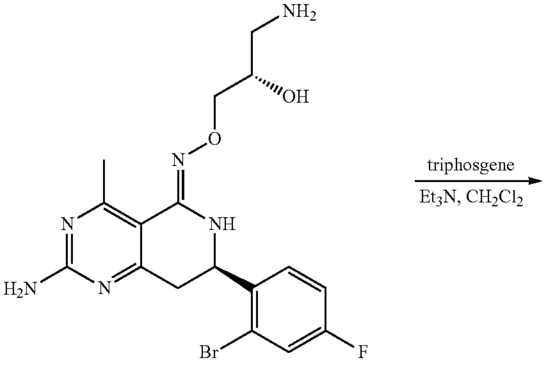

K

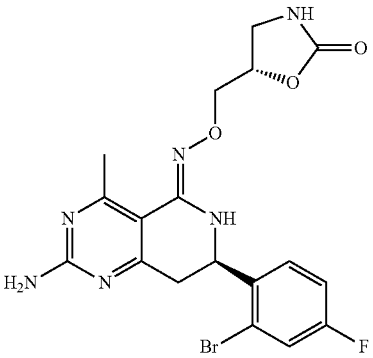

L

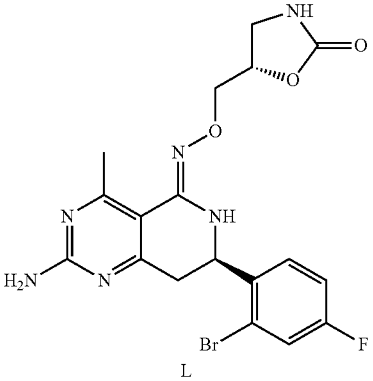

L

+

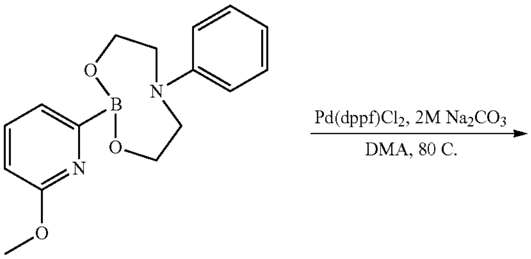

K

-continued

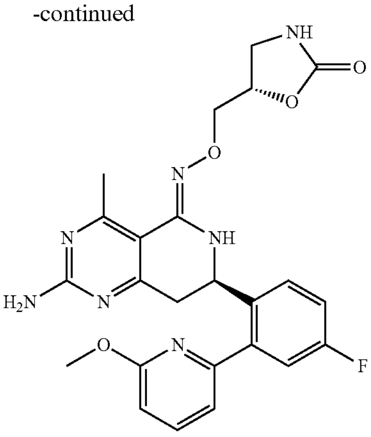

77

Compound H was deprotected with 20% TFA in dichloromethane for 10 minutes to give compound K, ESI-MS: m/z 439.1 $(M+H)^+$.

Compound K was reacted with triphosgene, triethylamine in dichloromethane as described previously to give compound L. It was purified by preparative LC/MS, gradient 25-50% ACN in $H_2O$, 10.6% yield, ESI-MS: m/z 439.2 $(M+H)^+$.

Suzuki's coupling of compound K with the normal procedure provided compound 77, 32.7% yield. $^1H$ NMR (400 MHz, MeOD) δ 2.92 (s, 3H), 3.35-3.40 (m, 1H), 3.44-3.52 (m, 1H), 3.55-3.59 (m, 1H), 3.63-3.66 (m, 1H), 3.91 (s, 3H), 4.20 (dd, J=6.44, 4.67 Hz, 2H), 4.95 (m, 1H), 5.05 (m, 1H), 6.79 (d, J=8.34 Hz, 1H), 7.11 (d, J=6.57 Hz, 1H), 7.14-7.25 (m, 2H), 7.59 (m, 1H), 7.76 (dd, J=8.46, 7.20 Hz, 1H).

Example 80

(R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxypropyl oxime (Compound 78)

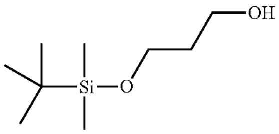

1

+

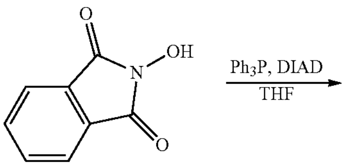

2

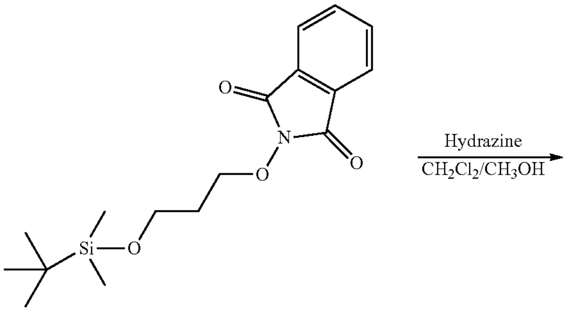

3

-continued

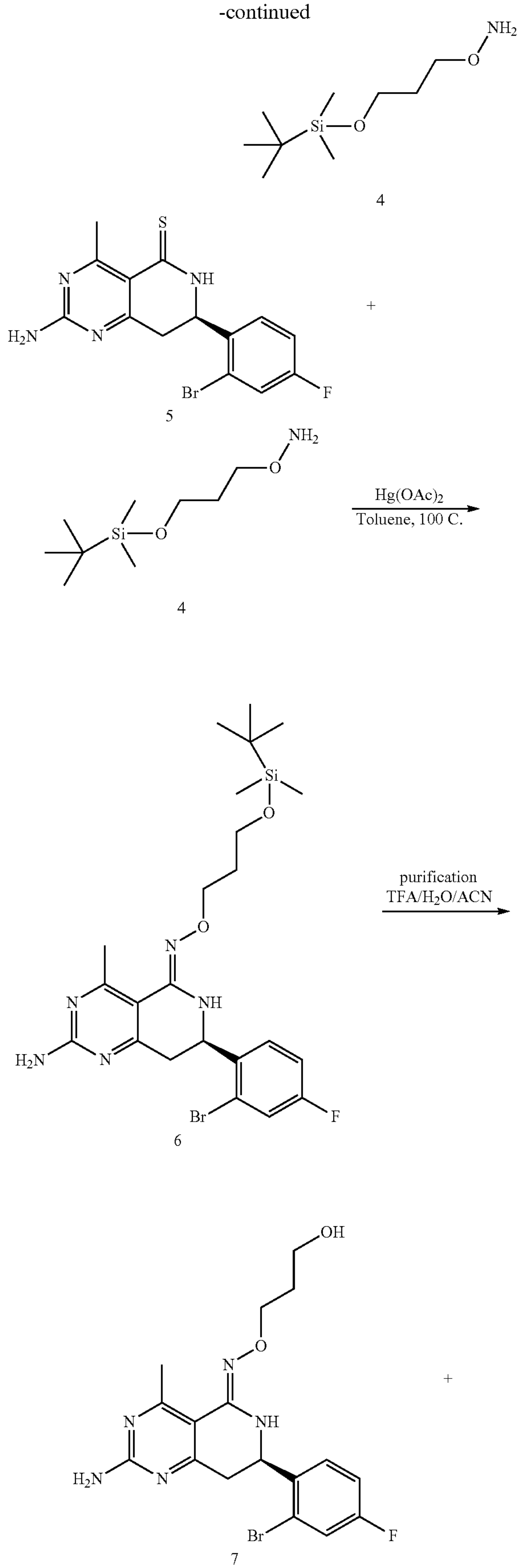

4

5

4

6

7

-continued

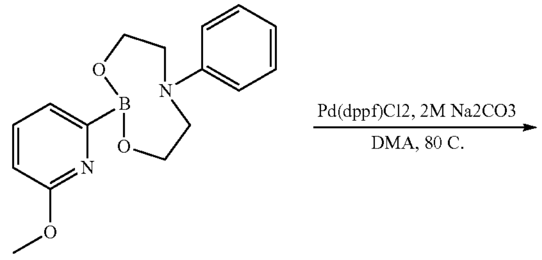

8

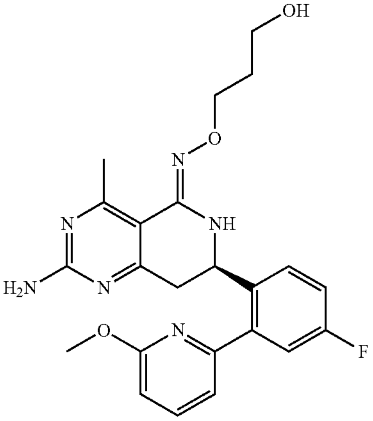

78

Compound 3 as prepared by procedure described above, 78.7% yield. $^1$H NMR (400 MHz, CHLOROFORM-d) δ 0.08 (s, 6H), 0.84-0.93 (m, 9H), 1.99 (s, 2H), 3.76-3.90 (m, 2H), 4.27-4.39 (m, 2H), 7.70-7.78 (m, 2H), 7.80-7.88 (m, 2H).

Compound 4 as prepared by procedure described above, 93.2% yield. $^1$H NMR (400 MHz, CHLOROFORM-d) δ 0.05-0.09 (m, 6H), 0.84-0.95 (m, 9H), 1.73-1.86 (m, 2H), 3.69 (t, J=6.19 Hz, 2H), 3.75 (t, J=6.32 Hz, 2H), 5.34 (s, 2H).

Compound 6: ESI-MS: m/z 538.3 $(M+H)^+$. Purification was done by preparative LC/MS, using gradient 50-85% ACN in $H_2O$ with TFA system. After evaporation compound 7 was obtained, 42.5% yield over 2 step, ESI-MS: m/z 424.2 $(M+H)^+$.

Compound 78, LC/MS purification using basic mode, gradient 40-60% ACN in $H_2O$, 45.9% yield. $^1$H NMR (400 MHz, DMSO-$d_6$) δ 1.77 (quin, J=6.44 Hz, 2H), 2.53 (s, 3H), 2.82 (dd, J=16.29, 7.20 Hz, 1H), 3.04 (dd, J=16.17, 5.05 Hz, 1H), 3.42-3.54 (m, 2H), 3.86 (s, 3H), 3.91-4.04 (m, 2H), 4.97-5.13 (m, 1H), 6.37 (br. s., 1H), 6.85 (d, J=7.58 Hz, 1H), 6.90 (br. S., 2H), 7.19 (d, J=6.82 Hz, 1H), 7.21-7.33 (m, 2H), 7.47 (dd, J=8.46, 5.94 Hz, 1H), 7.84 (dd, J=8.34, 7.33 Hz, 1H).
Example 81
(R,Z)-2-amino-7-(4-fluoro-2-(6-methoxypyridin-2-yl)phenyl)-4-methyl-7,8-dihydropyrido[4,3-d]pyrimidin-5(6H)-one O-4-hydroxybutyl oxime (Compound 79)
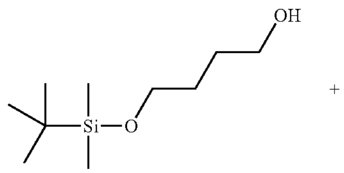
81a
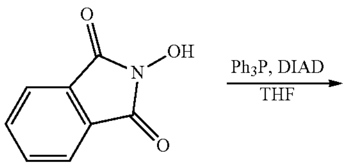
81b
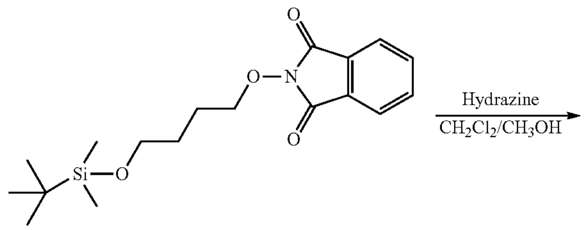
81c
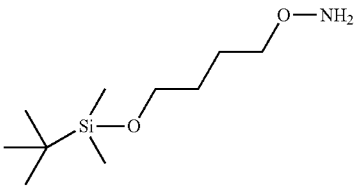
81d
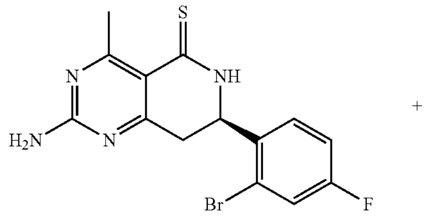
81e
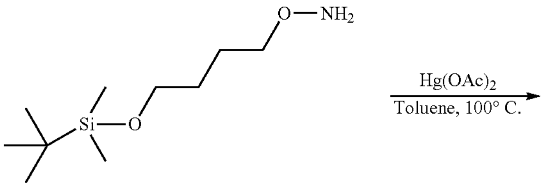
81d
-continued
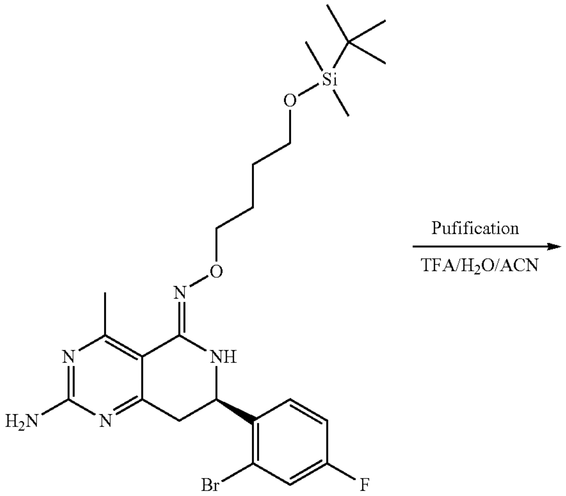
81f
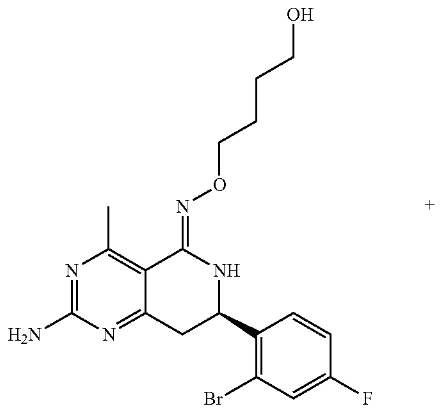
81f
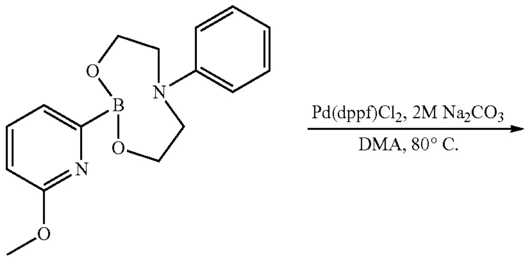
81g -continued

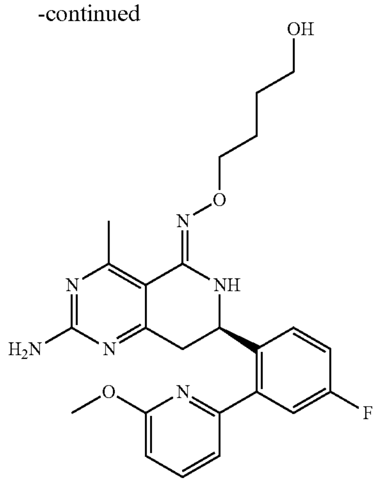

79

Compound 81c as prepared by the procedure described above, 88.0% yield. 1H NMR (400 MHz, CHLOROFORM-d) δ 0.03-0.07 (m, 6H), 0.82-0.96 (m, 9H), 1.74 (d, J=8.84 Hz, 2H), 1.86 (d, J=8.34 Hz, 2H), 3.69 (t, J=6.19 Hz, 2H), 4.24 (t, J=6.57 Hz, 2H), 7.75 (dd, J=5.56, 3.03 Hz, 2H), 7.80-7.87 (m, 2H).

Compound 81d as prepared by the procedure described above, 94.5% yield. $^{1}H$ NMR (400 MHz, CHLOROFORM-d) δ 0.060 (s, 6H), 0.85-0.94 (m, 9H), 1.51-1.59 (m, 3H), 1.59-1.69 (m, 2H), 3.63 (t, J=6.32 Hz, 2H), 3.65-3.72 (m, 2H), 5.35 (s, 2H).

Compound 81f as prepared by the procedure described above. ESI-MS: m/z 554.3 $(M+H)^+$. Purification by LC/MS using the TFA system of gradient 60-90% ACN/$H_2O$ deprotected the TBDMS group to give compound 15, 22.2% yield over 2 steps. ESI-MS: m/z 438.1 $(M+H)^+$.

Compound 79 as prepared by the procedure described above. The product was purified by the basic mode, gradient 35-65% ACN/$H_2O$, 19.2% yield. $^{1}H$ NMR (400 MHz, DMSO-$d_6$) δ 1.37-1.56 (m, 2H), 1.56-1.74 (m, 2H), 2.53 (s, 3H), 2.81 (dd, J=16.04, 7.20 Hz, 1H), 3.03 (dd, J=16.17, 5.05 Hz, 1H), 3.40 (t, J=6.44 Hz, 2H), 3.92 (s, 3H), 3.88-3.98 (m, 2H), 5.05 (br. s., 1H), 6.31 (br. s., 1H), 6.85 (d, J=8.34 Hz, 3H), 7.19 (d, J=6.57 Hz, 1H), 7.22-7.32 (m, 2H), 7.47 (dd, J=8.46, 5.94 Hz, 1H), 7.84 (dd, J=8.34, 7.33 Hz, 1H).

Example 82

(7R,Z)-2-amino-7-(4-fluoro-2-(6-methoxypyridin-2-yl)phenyl)-4-methyl-7,8-dihydropyrido[4,3-d]pyrimidin-5(6H)-one O-3-hydroxy-2-methoxypropyl oxime (Compound 80)

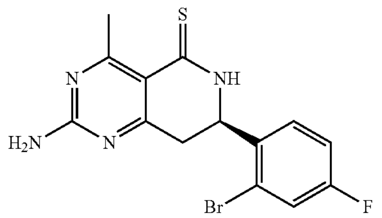

+

-continued

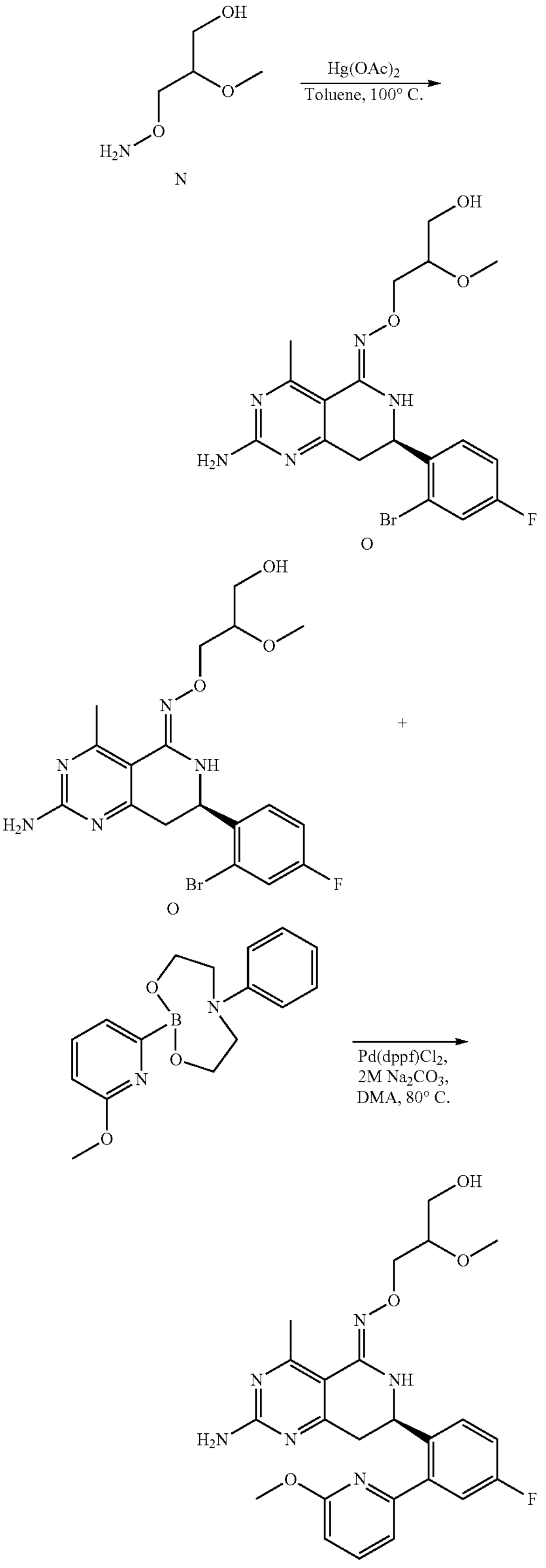

80

Compound N: ESI-MS: m/z 122.0 $(M+H)^+$. $^1H$ NMR (400 MHz, CHLOROFORM-d) δ 3.33 (s, 3H), 3.40-3.46 (m, 3H), 3.67-3.75 (m, 1H), 3.75-3.83 (m, 1H), 4.07 (m, 1H), 5.52 (br. s., 2H).

Compound O: purified by preparative LC/MS, gradient 25-55% ACN in $H_2O$, 4.9% yield, ESI-MS: m/z 454.3 $(M+H)^+$.

Compound 80: purified by preparative LC/MS, basic mode, gradient 30-70% ACN in $H_2O$, 16.1% yield. $^1H$ NMR (400 MHz, MeOD) δ 2.61 (s, 3H), 2.89-3.05 (m, 1H), 3.07-3.21 (m, 1H), 3.34 (d, J=2.02 Hz, 3H), 3.37-3.50 (m, 2H), 3.61-3.75 (m, 1H), 3.89 (s, 3H), 3.92-4.01 (m, 1H), 4.01-4.09 (m, 2H), 4.93-5.03 (m, 1H), 6.78 (d, J=8.34 Hz, 1H), 7.11 (d, J=7.07 Hz, 1H), 7.13-7.25 (m, 2H), 7.64 (dd, J=8.46, 5.68 Hz, 1H), 7.75 (t, J=7.83 Hz, 1H).

Example 83

(R,Z)-2-amino-7-(4-fluoro-2-(6-methoxypyridin-2-yl)phenyl)-4-methyl-7,8-dihydropyrido[4,3-d]pyrimidin-5(6H)-one O—(R)-4,5-dihydroxypentyl oxime (Compound 81)

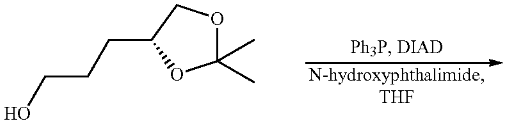

83a

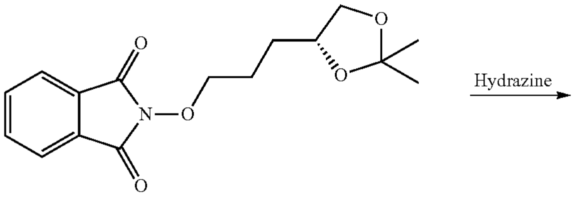

83b

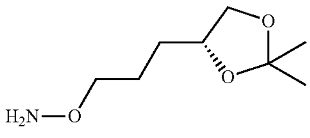

83c

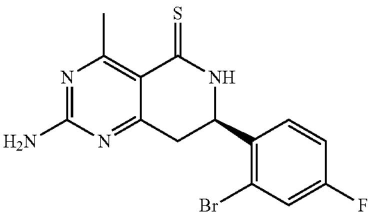

+

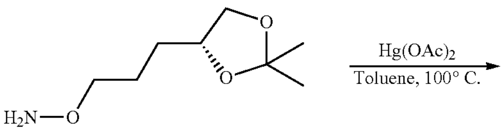

83c

-continued

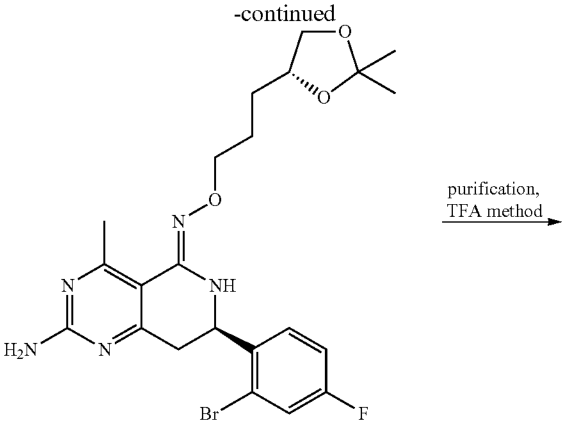

83d

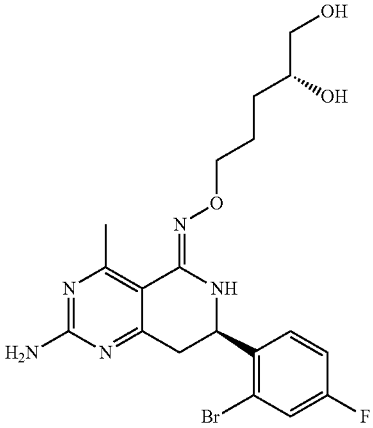

+

83e

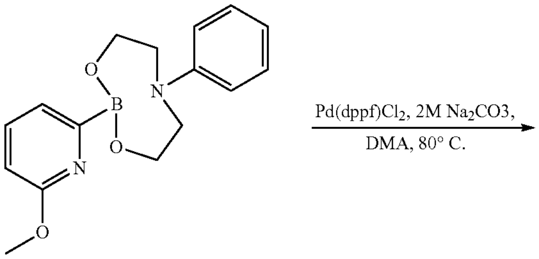

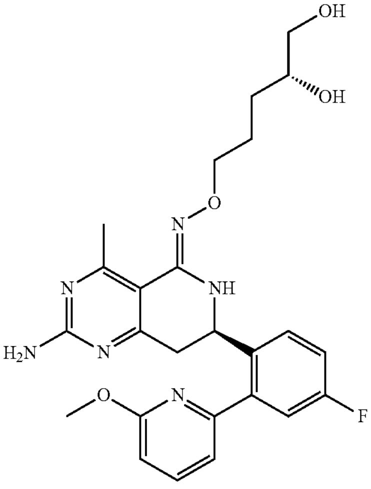

81

Compound 83b as prepared by a procedure described above. $^1H$ NMR (400 MHz, CHLOROFORM-d) δ 1.36 (s, 3H), 1.39-1.45 (s, 3H), 1.73-2.00 (m, 4H), 2.05 (s, 1H), 3.54-3.63 (m, 1H), 4.04-4.14 (m, 1H), 4.14-4.21 (m, 1H), 4.21-4.33 (m, 2H), 7.72-7.79 (m, 2H), 7.81-7.87 (m, 2H).

Compound 83c as prepared by a procedure described above, 88.2% yield over 2 steps. 1H NMR (400 MHz, CHLOROFORM-d) δ 1.36 (s, 3H), 1.41 (s, 3H), 1.59-1.78 (m, 4H), 3.50-3.55 (m, 1H), 3.69 (td, J=6.25, 2.40 Hz, 2H), 4.01-4.07 (m, 1H), 4.11 (dd, J=7.07, 5.56 Hz, 1H), 5.36 (s, 2H).

Compound 83d: ESI-MS: m/z 508.3 $(M+H)^+$. LC/MS purification using gradient 40-60% ACN in H2O (TFA method) gave compound 5, ESI-MS: m/z 468.1 $(M+H)^+$, 24.1% yield over 2 steps.

Compound 81, purification was done by both the basic mode and acidic mode, 21.6% yield, $^1$H NMR (400 MHz, MeOD) δ 1.35-1.52 (m, 1H), 1.59 (dt, J=10.04, 4.07 Hz, 1H), 1.74 (ddd, J=13.71, 10.04, 6.06 Hz, 1H), 1.82-2.08 (m, 1H), 3.14 (dd, J=16.67, 8.84 Hz, 1H), 3.28-3.35 (m, J=4.55 Hz, 1H), 3.38-3.49 (m, 2H), 3.54-3.68 (m, 1H), 3.84-3.97 (s, 3H), 4.06 (t, J=6.44 Hz, 2H), 5.08 (dd, J=8.84, 4.29 Hz, 1H), 6.79 (d, J=7.58 Hz, 1H), 7.12 (d, J=6.57 Hz, 1H), 7.15-7.24 (m, 2H), 7.62 (dd, J=8.59, 5.56 Hz, 1H), 7.76 (dd, J=8.34, 7.33 Hz, 1H).

Example 84

(S)-4-(2-iodoethyl)-2,2-dimethyl-1,3-dioxolane

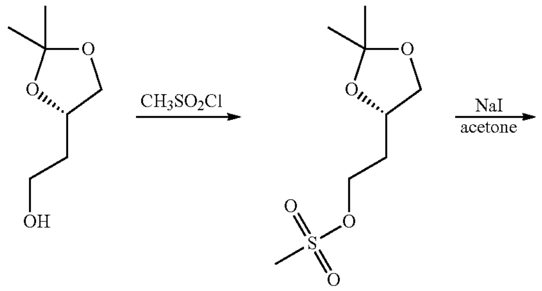

-continued

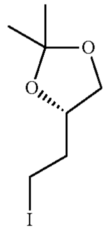

To a solution of (S)-2-(2,2-dimethyl-1,3-dioxolan-4-yl) ethanol (1.58 mL, 10.0 mmol) in $CH_2Cl_2$ (25 mL) was added DMAP (120 mg, 1.0 mmol) and triethylamine (2.08 mL, 15.0 mmol). The reaction mixture was cooled to 0° C. and methanesulfonyl chloride (12.0 mmol, 0.928 mL) was added slowly dropwise under $N_2$ atmosphere. The reaction mixture was stirred for 2 h (monitored by TLC, 1:2 EtOAc—Hexanes). Saturated $NH_4Cl$ solution (20 mL) was added and the mixture was extracted with $CH_2Cl_2$. The combined organic layers were washed with brine, dried over anhydrous $Na_2SO_4$, filtered and concentrated to provide a yellow oil, which was dissolved in dry acetone (25 ml), followed by addition of NaI (7.5 g, 50 mmol). The reaction mixture was refluxed for 2 h (monitored by TLC, 1:4 EtOAc—Hexanes), cooled to room temperature and water (50 mL) was added. Extraction with ethyl acetate, washing of the combined organic layers with brine, drying over anhydrous $Na_2SO_4$, filtration and concentration provided a yellow oil, which was purified by flash chromatography (25% EtOAC-Hexane) to afford the title compound, (S)-4-(2-iodoethyl)-2,2-dimethyl-1,3-dioxolane (0.82 g, 32% over two steps) as a clear oil. $^1$H NMR (400 MHz, CHLOROFORM-d) δ ppm 1.36 (s, 3H), 1.41 (s, 3H), 1.99-1.16 (m, 2H), 3.25 (dd, J=18.19, 8.84 Hz, 2H), 3.58 (t, J=7.20 Hz, 1H), 4.03-4.13 (m, 1H), 4.13-4.24 (m, 1H). MS (ES) [M+H] calculated for $C_2H_{14}IO_2$, 257.00; found 257.08.

Example 85

Alternative synthesis of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime (Compound 37)

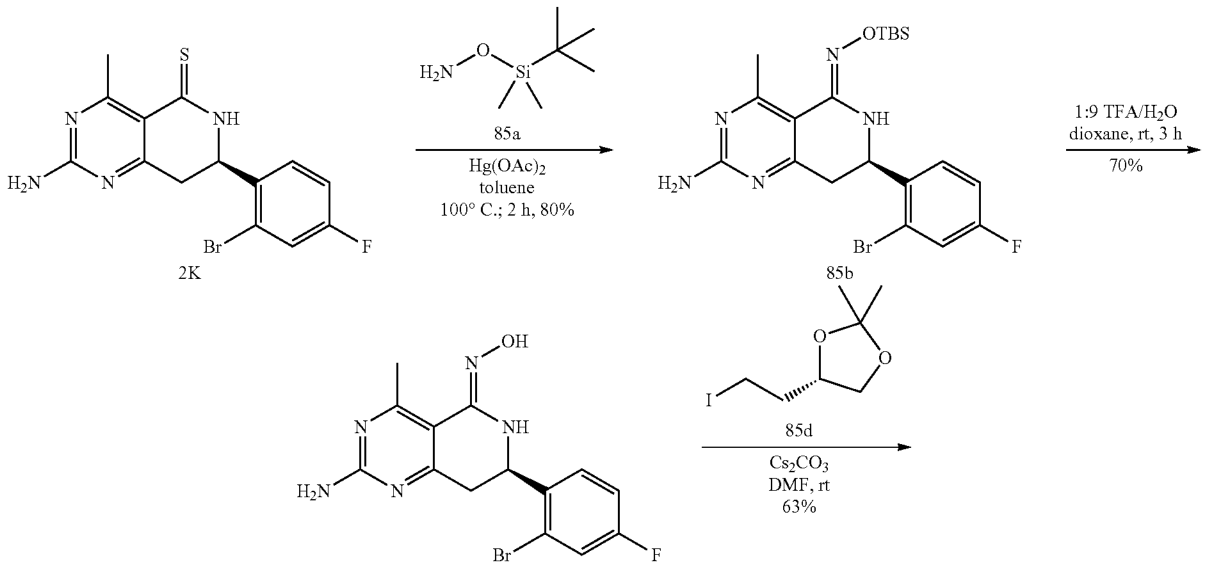

2K

85b

85c

-continued

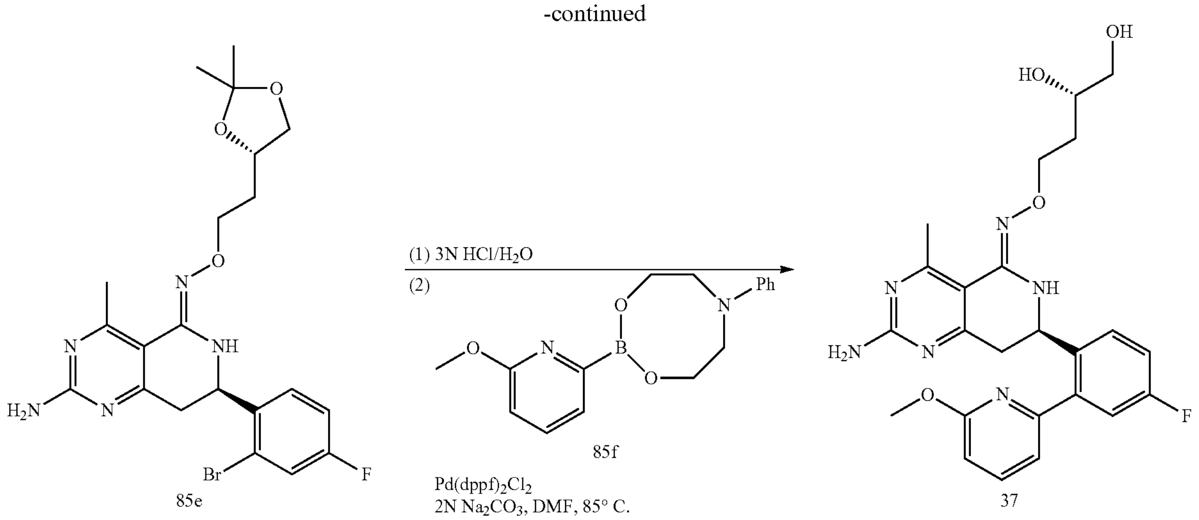

85e 37

Compound 2K was prepared as previously described. A mixture of (R)-2-amino-7-(2-bromo-4-fluorophenyl)-4-methyl-7,8-dihydropyrido[4,3-d]pyrimidine-5(6H)-thione (2K, 366 mg, 1.0 mmol), O-(tert-butyldimethylsilyl)hydroxylamine (85a, 588 mg, 4.0 mmol), $Hg(OAc)_z$ (640 mg, 2.0 mmol) and toluene (5 mL) was heated at 100° C. for 2 h. The mixture was cooled to room temperature and filtered through Celite. The filtrate was concentrated and the resulting oily residue was triturated with dry methanol to afford, after filtration and drying, (R,Z)-2-amino-7-(2-bromo-4-fluorophenyl)-4-methyl-7,8-dihydropyrido[4,3-d]pyrimidin-5(6H)-one O-tert-butyldimethylsilyloxime (384 mg, 80%) as a pale yellow solid. $^1$H NMR (400 MHz, CHLOROFORM-d) δ ppm 0.22 (s, 3H), 0.23 (s, 3H) 0.97 (s, 9H) 2.70 (s, 3H) 2.91 (dd, J=16.42, 8.08 Hz, 1H) 3.19 (ddd, J=16.36, 4.86, 1.26 Hz, 1H) 4.99 (ddd, J=7.77, 5.12, 2.02 Hz, 1H) 7.05 (td, J=8.27, 2.65 Hz, 1H) 7.33 (dd, J=8.08, 2.78 Hz, 1H) 7.39 (dd, J=8.72, 5.94 Hz, 1H). MS (ES) [M+H] calculated for $C_{20}H_{28}BrFN_5OSi$, 480.12; found 480.30.

To a solution of (R,Z)-2-amino-7-(2-bromo-4-fluorophenyl)-4-methyl-7,8-dihydropyrido[4,3-d]pyrimidin-5(6H)-one O-tert-butyldimethylsilyloxime (85b, 384 mg, 0.8 mmol) in dioxane (2 mL) was added 1:9 TFA-$H_2O$ and the reaction mixture stirred at room temperature for 2 h. The resulting solid was filtered and washed with dioxane, then dried to afford (R,Z)-2-amino-7-(2-bromo-4-fluorophenyl)-4-methyl-7,8-dihydropyrido[4,3-d]pyrimidin-5(6H)-one oxime (85c, 206 mg, 70%) as a pale yellow solid. $^1$H NMR (400 MHz, DMSO-$d_6$) δ ppm 2.56 (s, 3H) 2.83 (dd, J=15.92, 4.55 Hz, 1H) 3.17 (dd, J=16.04, 5.94 Hz, 1H) 4.90 (q, J=4.97 Hz, 1H) 7.20 (d, J=1.52 Hz, 1H) 7.21-7.23 (m, 1H) 7.57 (ddd, J=8.34, 1.64, 1.39 Hz, 1H) 9.82 (s, 1H). MS (ES) [M+H] calculated for $C_{14}H_{14}BrFN_5O$, 366.03; found 366.20.

To a solution of (R,Z)-2-amino-7-(2-bromo-4-fluorophenyl)-4-methyl-7,8-dihydropyrido[4,3-d]pyrimidin-5(6H)-one oxime (85c, 9.2 mg, 0.025 mmol) in dry DMF (1 mL) was added $Cs_2CO_3$ (12.2 mg, 0.0375 mmol) and the reaction mixture stirred at ambient temperature for 30 minutes. Then, (S)-4-(2-iodoethyl)-2,2-dimethyl-1,3-dioxolane (85d, 7.68 mg, 0.03 mmol) was added and the reaction mixture stirred overnight. LCMS showed complete consumption of the starting material. The reaction mixture was poured onto crushed ice and the resulting solid was filtered and rinsed with cold water. Drying afforded (R,Z)-2-amino-7-(2-bromo-4-fluorophenyl)-4-methyl-7,8-dihydropyrido[4,3-d]pyrimidin-5(6H)-one O-2-((S)-2,2-dimethyl-1,3-dioxolan-4-yl)ethyl oxime (7.8 mg, 63%) as a light brown solid. $^1$H NMR (400 MHz, CHLOROFORM-d) δ ppm 1.35 (s, 3H) 1.41 (s, 3H) 2.02 (qd, J=6.32, 3.03 Hz, 2H) 2.75 (s, 3H) 2.94 (dd, J=16.42, 8.84 Hz, 1H) 3.17 (dd, J=16.42, 4.55 Hz, 1H) 3.59 (dd, J=8.08, 7.07 Hz, 1H) 4.09 (dd, J=8.08, 6.06 Hz, 1H) 4.17-4.28 (m, 3H) 4.98 (ddd, J=8.72, 4.55, 1.64 Hz, 1H) 7.07 (td, J=8.27, 2.65 Hz, 1H) 7.34 (dd, J=8.08, 2.78 Hz, 1H) 7.43 (dd, J=8.72, 5.94 Hz, 1H). MS (ES) [M+H] calculated for $C_{21}H_{27}BrFN_5O_3$, 495.11; found 495.30.

To a solution of (R,Z)-2-amino-7-(2-bromo-4-fluorophenyl)-4-methyl-7,8-dihydropyrido[4,3-d]pyrimidin-5(6H)-one O-2-((S)-2,2-dimethyl-1,3-dioxolan-4-yl)ethyl oxime (85e, 1 g, 2 mmol) in 3N aq HCl (10 mL) and the reaction mixture stirred at ambient temperature for 1 h. LCMS shows complete consumption of the starting material. The resulting solid was filtered, washed with cold 1N HCl, and dried to afford (R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime (deprotected 85e, 603 mg, 65%) as an off-white solid. MS (ES) [M+H] calculated for $C_{18}H_{22}BrFN_5O_3$, 454.08; found 454.02.

A mixture of (R,Z)-2-amino-7-(2-bromo-4-fluorophenyl)-4-methyl-7,8-dihydropyrido[4,3-d]pyrimidin-5(6H)-one O—(S)-3,4-dihydroxybutyl oxime (deprotected 85e, 480 mg, 1.05 mmol), 2-(6-methoxypyridin-2-yl)-6-phenyl-1,3,6,2-dioxazaborocane (1.57 g, 5.25 mmol), $Pd(dppf)_2Cl_2$ (0.086 g, 0.1 mmol), and 2N $Na_2CO_3$ (2.64 mL, 5.25 mmol) in DMAc (5 mL) was degassed with $N_2$ and heated at 85° C. overnight. The reaction mixture was cooled to ambient temperature, diluted with ethyl acetate and filtered through Celite. The filtrate was concentrated to afford a brown oil, which was purified by preparative LCMS ($NH_4HCO_3$/ACN/$H_2O$) to afford (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime (Compound 37, 375 mg, 73%) as a light brown solid. $^1$H NMR (400 MHz, CHLOROFORM-d) δ ppm 1.43-1.55 (m, 1H) 1.66 (m, 1H) 2.55 (s, 3H) 2.83-2.95 (m, 2H) 3.11-3.44 (m, 1H) 3.17-3.24 (m, 1H) 3.27-3.33 (m, 1H) 3.48-3.56 (m, 1H) 3.65 (s, 3H) 3.89-4.01 (m, 2H) 4.68 (ddd, J=10.23, 3.03, 2.91 Hz, 1H) 6.53 (dd, J=8.34, 2.53 Hz, 1H) 6.81 (dd, J=7.33, 2.53 Hz, 1H) 6.90 (dt, J=9.28, 2.68 Hz, 1H) 6.96 (td, J=8.40, 2.65 Hz, 1H) 7.38-7.43 (m, 1H) 7.44-7.51 (m, 1H). MS (ES) [M+H] calculated for $C_{24}H_{28}FN_6O_4$, 483.21; found 483.00.

Example 86
Second alternative synthesis of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime (Compound 37)
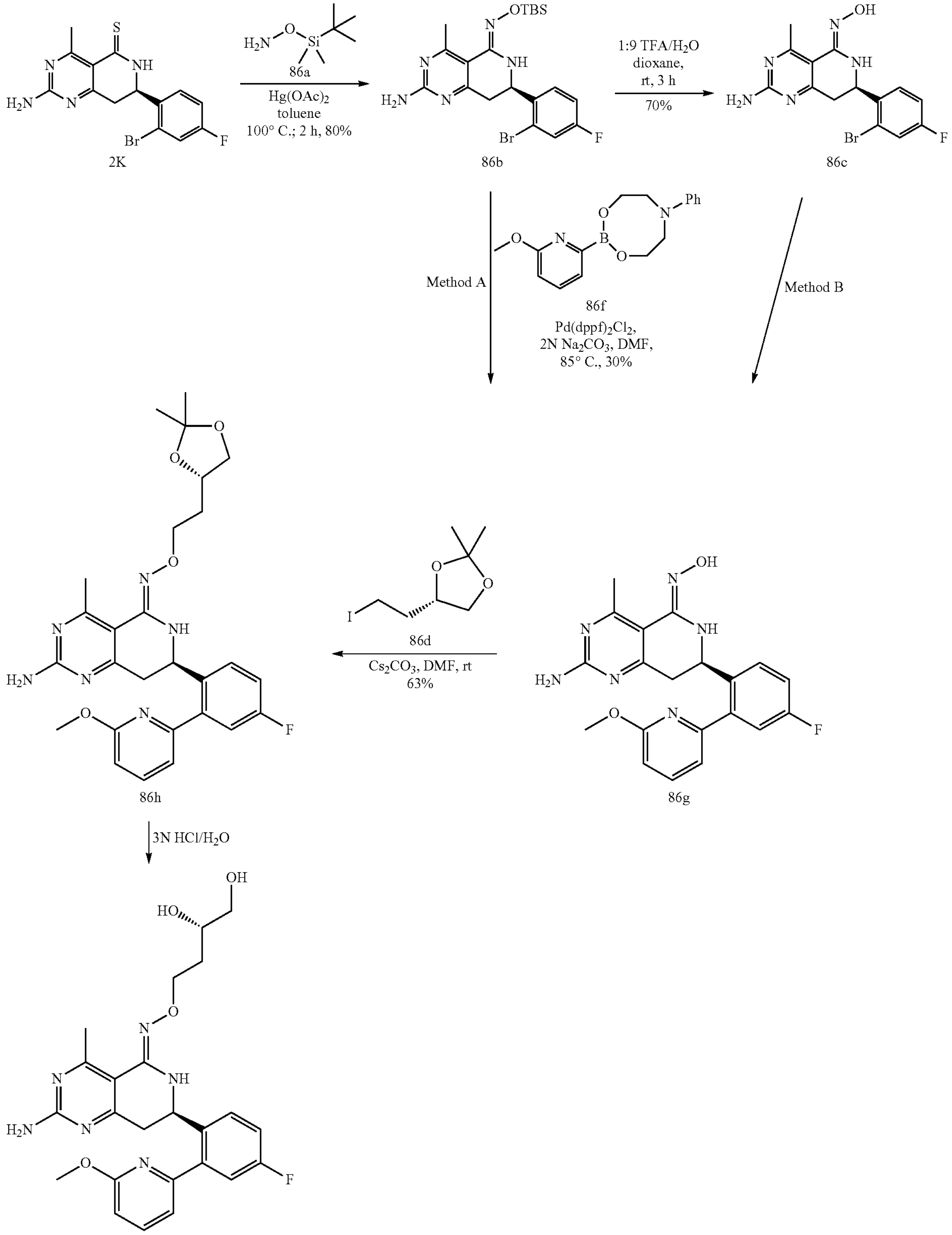
2K 86b 86c 86g 86h 37

Compound 86b was prepared as described in Example 85 above. Coupling of 86f to 86b was prepared by both Method A and Method B.

Method A: A mixture of (R,Z)-2-amino-7-(2-bromo-4-fluorophenyl)-4-methyl-7,8-dihydropyrido[4,3-d]pyrimidin-5(6H)-one O-tert-butyldimethylsilyloxime (86b, 47.9 mg, 0.1 mmol), 2-(6-methoxypyridin-2-yl)-6-phenyl-1,3,6,2-dioxazaborocane (86f, 149 mg, 0.5 mmol), Pd(dppf)$Cl_2$ (8.12 mg, 0.01 mmol), and 2N $Na_2CO_3$ (0.25 mL, 0.5 mmol) in DMA (3 mL) was degassed with $N_2$ and heated at 85° C. overnight. LCMS showed consumption of starting material and formation of (R,Z)-2-amino-7-(4-fluoro-2-(6-methoxypyridin-2-yl)phenyl)-4-methyl-7,8-dihydropyrido[4,3-d]pyrimidin-5(6H)-one O-tert-butyldimethylsilyl oxime (86g or 61). ([M+H] calculated for $C_{26}H_{34}BrFN_6O_2Si$, 509.24; found 509.40).

The reaction mixture was diluted with ethyl acetate and filtered through Celite. The filtrate was concentrated to afford a brown oil, which was purified by preparative HPLC. During this purification the tert-butyldimethylsilyl protecting group was cleaved as well, thus affording (R,Z)-2-amino-7-(4-fluoro-2-(6-methoxypyridin-2-yl)phenyl)-4-methyl-7,8-dihydropyrido[4,3-d]pyrimidin-5(6H)-one oxime (37, 11.8 mg, 30%) as a white solid. $^1H$ NMR (400 MHz, CHLOROFORM-d) δ ppm 2.78 (s, 3H) 3.14-3.31 (m, 1H) 3.43-3.46 (m, 1H) 3.89 (s, 3H) 5.08 (d, J=7.58 Hz, 1H) 6.78 (d, J=8.34 Hz, 1H) 7.05 (d, J=7.07 Hz, 2H) 7.18 (d, J=8.84, 2H) 7.70 (t, J=7.71, 1H). MS (ES) [M+H] calculated for $C_{20}H_{20}FN_6O_2$, 395.16; found 395.20.

Method B: (R,Z)-2-amino-7-(2-bromo-4-fluorophenyl)-4-methyl-7,8-dihydropyrido[4,3-d]pyrimidin-5(6H)-one oxime (Compound 86c) was prepared as described in Example 85 above. A mixture of 86c (36.5 mg, 0.1 mmol and 2-(6-methoxypyridin-2-yl)-6-phenyl-1,3,6,2-dioxazaborocane (86f, 149 mg, 0.5 mmol), Pd(dppf)$_2$$Cl_2$ (8.12 mg, 0.01 mmol), and 2N $Na_2CO_3$ (0.25 mL, 0.5 mmol) in DMA (3 mL) was degassed with $N_2$ and heated at 85° C. overnight. The reaction mixture was cooled to ambient temperature, diluted with ethyl acetate and filtered through Celite. The filtrate was concentrated to afford brown oil which was purified by preparative HPLC to afford (R,Z)-2-amino-7-(4-fluoro-2-(6-methoxypyridin-2-yl)phenyl)-4-methyl-7,8-dihydropyrido[4,3-d]pyrimidin-5(6H)-one oxime (86g or 61), 13.2 mg, 33%) as white solid. $^1H$ NMR (400 MHz, CHLOROFORM-d) δ ppm 2.78 (s, 3H) 3.14-3.31 (m, 1H) 3.43-3.46 (m, 1H) 3.89 (s, 3H) 5.08 (d, J=7.58 Hz, 1H) 6.78 (d, J=8.34 Hz, 1H) 7.05 (d, J=7.07 Hz, 2H) 7.18 (d, J=8.84, 2H) 7.70 (t, J=7.71, 1H). MS (ES) [M+H] calculated for $C_{20}H_{20}FN_6O_2$, 395.16; found 395.20.

To a solution of (R,Z)-2-amino-7-(4-fluoro-2-(6-methoxypyridin-2-yl)phenyl)-4-methyl-7,8-dihydropyrido[4,3-d]pyrimidin-5(6H)-one oxime (86g or Compound 61, 10.0 mg, 0.025 mmol) in dry DMF (1 mL) was added $Cs_2CO_3$ (12.2 mg, 0.0375 mmol) and the reaction mixture stirred at ambient temperature for 30 minutes. Then, (5)-4-(2-iodoethyl)-2,2-dimethyl-1,3-dioxolane (86d, 7.68 mg, 0.03 mmol) was added and the reaction mixture stirred overnight. LCMS showed complete consumption of starting material. The reaction mixture was poured onto crushed ice and the resulting solid was filtered, rinsed with cold water, and dried to afford (R,Z)-2-amino-7-(4-fluoro-2-(6-methoxypyridin-2-yl)phenyl)-4-methyl-7,8-dihydropyrido[4,3-d]pyrimidin-5(6H)-one O-2-((S)-2,2-dimethyl-1,3-dioxolan-4-yl)ethyl oxime (86h, 8.2 mg, 63%) as a light brown solid. $^1H$ NMR (400 MHz, CHLOROFORM-d) δ ppm 1.33 (s, 3H) 1.39 (s, 3H) 1.91-2.01 (m, 4H) 2.72 (s, 3H) 3.07 (dd, J=16.55, 10.48 Hz, 1H) 3.26 (dd, J=17.05, 4.93 Hz, 1H) 3.55 (dd, J=7.96, 7.20 Hz, 1H) 3.90 (s, 3H) 4.05 (dd, J=7.96, 5.94 Hz, 1H) 4.10-4.21 (m, 3H) 4.89 (dd, J=10.61, 3.79 Hz, 1H) 6.74 (d, J=8.84 Hz, 1H) 7.01 (d, J=8.08 Hz, 1H) 7.11-7.22 (m, 2H) 7.61-7.69 (m, 2H)MS (ES) [M+H] calculated for $C_{27}H_{32}FN_6O_4$, 523.24; found 523.50.

Deprotection of 86h was achieved by treating with diluted HCl as described in Example 85 to yield Compound 37.

Example 87

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methylacetamide (Compound 82)

82

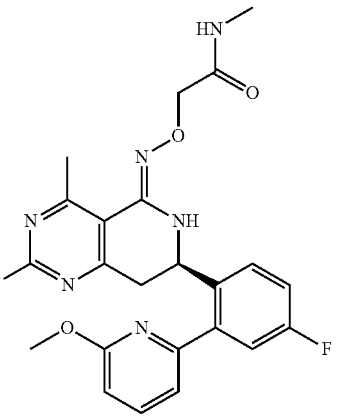

A. Synthesis of 2-(aminooxy)-N-methylacetamide (87c)

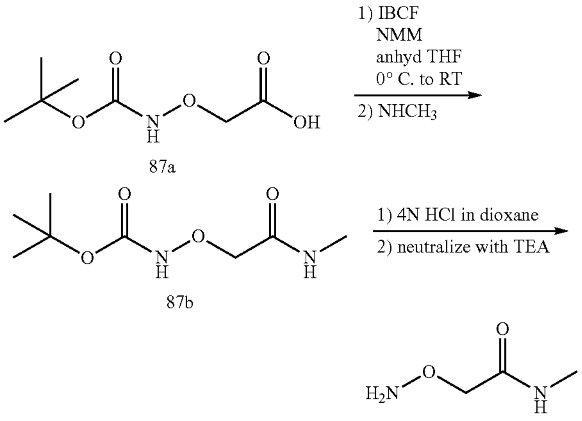

87a

87b

87c

A solution of 2-(tert-butoxycarbonylaminooxy)acetic acid (87a, 1 g, 5.23 mmol) in anhydrous THF was chilled in an ice bath and N-methylmorpholine (863 μL, 7.85 mmol) and isobutyl chloroformate (746 μL, 5.75 mmol) were added sequentially. The mixture was stirred under an $N_2$ atmosphere for 20 min. A 33 wt % solution of methanamine in ethanol (1.3 mL, 10.46 mmol) was added to the reaction which was subsequently allowed to warm to room temperature with stirring overnight. The THF was removed in vacuo and the residue was partitioned between ethyl acetate and water. The organic phase was washed with $H_2O\times2$ and dried over anhydrous $Na_2SO_4$. The ethyl acetate was removed in vacuo to yield tert-butyl 2-(methylamino)-2-oxoethoxycarbamate (87b, 775 mg, 3.80 mmol).

To a slurry of tert-butyl 2-(methylamino)-2-oxoethoxycarbamate (87c, 775 mg, 3.80 mmol) in anhydrous dioxane was added 4N HCl in dioxane (3 mL, 12 mmol). The reaction was allowed to stir at room temperature under an $N_2$ atmosphere for 5 h. The reaction was freeze-dried and the residue was taken up in 20% triethylamine in ethyl acetate to neutralize the HCl salt. The slurry was stirred for 1 h and the solvents were removed in vacuo to yield a mixture of 2-(aminooxy)-N-methylacetamide (87c) and triethylammonium chloride salt.

B. Preparation of Compound 82

The titled compound 82 was prepared by a procedure analogous to Example 68, coupling of 2-(aminooxy)-N-methylacetamide (87c) was via $Hg(OAc)_2$. $^1H$ NMR (400 MHz, MeOD) δ 2.75 (s, 3H), 2.76 (s, 3H), 3.19 (dd, J=16.67, 9.35 Hz, 1H), 3.41 (dd, J=16.80, 4.17 Hz, 1H), 3.91 (s, 3H), 4.47 (s, 2H), 5.06 (dd, J=9.35, 4.04 Hz, 1H), 6.80 (d, J=8.34 Hz, 1H), 7.13 (d, J=7.33 Hz, 1H), 7.16-7.29 (m, 2H), 7.71 (dd, J=8.84, 5.56 Hz, 1H), 7.73-7.82 (m, 1H). [M+H] calc'd for $C_{23}H_{24}FN_7O_3$, 466; found, 466.

Example 88

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-dimethylacetamide (Compound 83)

83

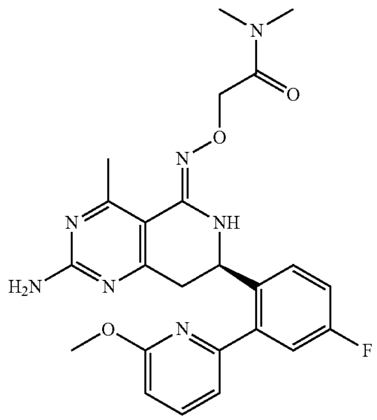

The titled compound 83 was prepared by a procedure analoguous to Example 87 except dimethylamine was used. $^1H$ NMR (400 MHz, METHANOL-$d_4$) δ 2.74 (s, 3H), 2.93 (s, 3H), 3.04 (s, 3H), 3.10-3.24 (m, 1H), 3.35-3.45 (m, 1H), 3.91 (s, 3H), 4.69-4.81 (m, 2H), 5.06 (dd, J=9.35, 4.04 Hz, 1H), 6.79 (d, J=8.08 Hz, 1H), 7.13 (d, J=7.07 Hz, 1H), 7.16-7.29 (m, 2H), 7.70 (dd, J=8.72, 5.68 Hz, 1H), 7.73-7.82 (m, 1H). [M+H] calc'd for $C_{24}H_{26}FN_7O_3$, 480; found, 480.

Example 89

(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetamide (Compound 84)

84

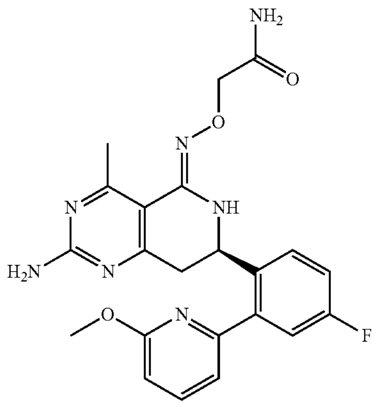

The titled compound 84 was prepared by a procedure analoguous to Example 87 except dimethylamine was used. $^1H$ NMR (400 MHz, MeOD) δ 2.73 (s, 3H), 3.09-3.23 (m, 1H), 3.34-3.43 (m, 1H), 3.91 (s, 3H), 4.46 (s, 2H), 5.01-5.12 (m, 1H), 6.80 (d, J=8.34 Hz, 1H), 7.12 (d, J=7.07 Hz, 1H), 7.16-7.28 (m, 2H), 7.64-7.73 (m, 1H), 7.73-7.82 (m, 1H). [M+H] calc'd for $C_{22}H_{22}FN_7O_3$, 452; found, 452.

Example 90

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-fluoropyrrolidin-1-yl)ethanone (Compound 85)

85

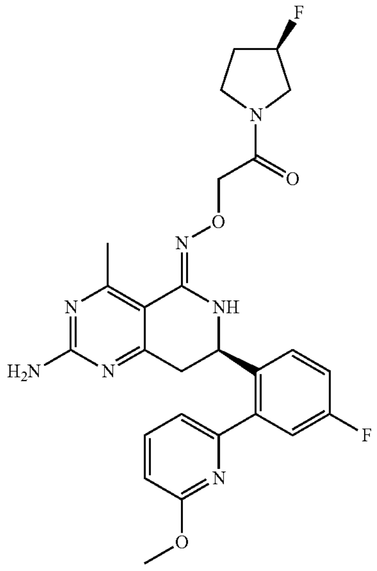

To a solution of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetic acid (0.05 mmol, 22.6 mg) in DMF (0.5 mL) was added HBTU (0.075 mmol, 28 mg), $Et_3N$ (0.125 mmol, 17 μL) and (R)-3-fluoropyrrolidine (0.06 mmol, 7.5 mg). The reaction mixture was stirred over night at r.t. and LCMS shows completion of the reaction. Purified by prep LCMS to afford the title compound (Compound 85, 13.0 mg, 50%) as light brown solid. $^1H$ NMR (400 MHz, methanol-$d_4$) δ ppm 2.05-2.40 (m, 2H) 2.72 (s, 3H) 3.06 (dd, J=16.93, 10.36 Hz, 1H) 3.27-3.38 (m, 1H) 3.39-3.62 (m, 4H) 3.63-3.78 (m, 2H) 3.82 (s, 3H) 4.47-4.67 (m, 2H) 4.87 (dd, J=10.36, 3.03 Hz, 1H) 5.11-5.36 (m, 1H) 6.69 (d, J=8.34 Hz, 1H) 6.97 (d, J=7.33 Hz, 1H) 7.06 (dd, J=9.35, 2.53 Hz, 1H) 7.13 (t, J=8.34 Hz, 1H) 7.50-7.70 (m, 2H). MS (ES) [M+H] calculated for $C_{26}H_{28}F_2N_7O_3$, 524.53; found 524.50.

Example 91

(S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanoic acid (Compound 86)

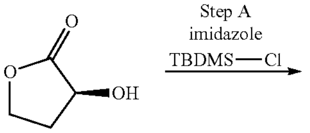

91a

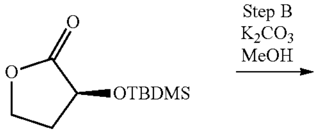

91b

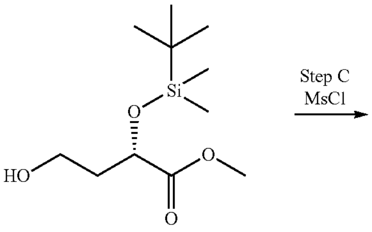

91c

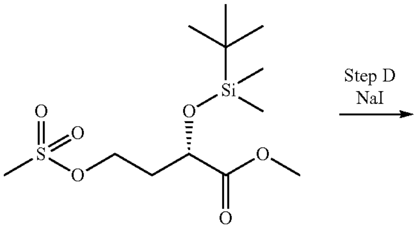

91d

-continued

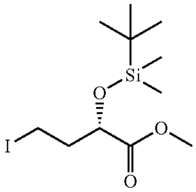

91e

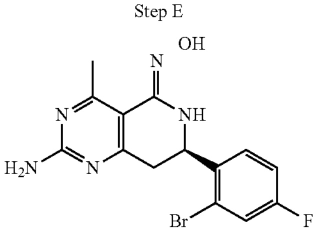

91f

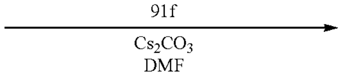

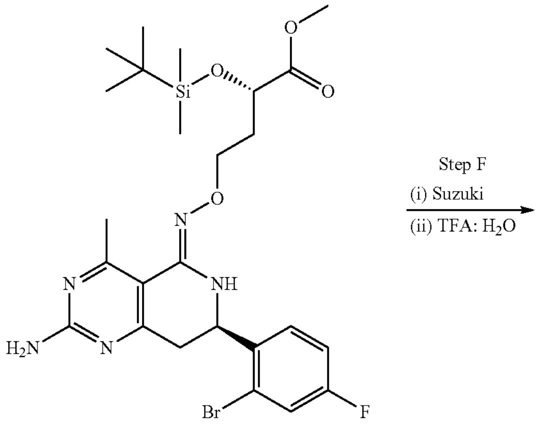

91g

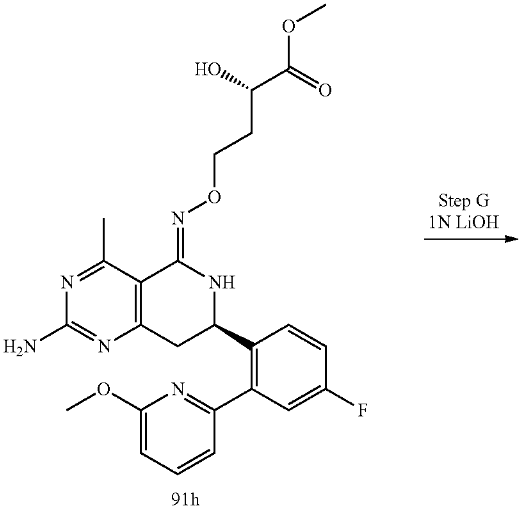

91h

-continued

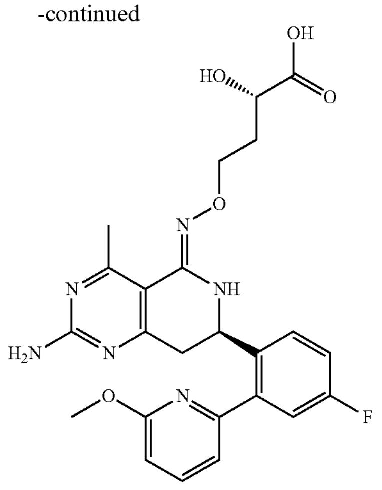

86

Step A.

To a solution of (S)-3-hydroxydihydrofuran-2(3H)-one (91a, 5 g, 49 mmol) in anhydrous DMF (40 mL) was added imidazole (6.7 g, 98 mmol) and TBDMS-chloride (8.1 g, 54 mmol) and the reaction is stirred for 3 h. The reaction was diluted with diethyl ether and washed with 1N HCl×3. The organic phase was dried over anhydrous sodium sulfate and the solvent was removed in vacuo to yield (S)-3-(tert-butyldimethylsilyloxy)dihydrofuran-2(3H)-one (91b) as a clear oil (10.6 g, 49 mmol). $^1$H NMR (400 MHz, CHLOROFORM-d) δ 0.15 (s, 3H), 0.18 (s, 3H), 0.86-0.99 (m, 9H), 2.23 (dq, J=12.63, 8.67 Hz, 1H), 2.46 (dddd, J=12.63, 7.58, 6.57, 3.28 Hz, 1H), 2.84-3.01 (m, 1H), 4.20 (td, J=9.16, 6.44 Hz, 1H), 4.33-4.47 (m, 2H).

Step B.

To a solution of (S)-3-(tert-butyldimethylsilyloxy)dihydrofuran-2(3H)-one (91b, 6 g, 27.8 mmol) in methanol (40 mL) was added potassium carbonate (500 mg, 3.6 mmol). The reaction was refluxed overnight. The methanol was removed in vacuo and the residue partitioned between ethyl acetate and water. The organic phase was washed with $H_2O$×2 and dried over anhydrous sodium sulfate. The solvent was removed in vacuo to yield (S)-methyl 2-(tert-butyldimethylsilyloxy)-4-hydroxybutanoate (91c, 3.9 g, 15.7 mmol) as a clear oil. [M+H] calc'd for $C_{11}H_{24}O_4Si$, 249; found, 249.

Step C.

To a solution of (5)-methyl 2-(tert-butyldimethylsilyloxy)-4-hydroxybutanoate (91c, 3.9 g, 15.7 mmol) in anhydrous dichloromethane was added triethylamine, DMAP, and mesyl chloride. The reaction was allowed to stir for 1.5 h. The reaction was quenched with saturated aqueous $NH_4Cl$. The aqueous phase was extracted with dicholormethane and the combine organic phases were washed with brine. The organic layer was dried over anhydrous sodium sulfate and the solvent removed in vacuo to yield (5)-methyl 2-(tert-butyldimethylsilyloxy)-4-mesylbutanoate (91d, 4.9 g, 15 mmol) as a yellow oil. [M+H] calc'd for $C_{12}H_{26}O_6SSi$, 327; found, 327.

Step D.

To a solution of (S)-methyl 2-(tert-butyldimethylsilyloxy)-4-mesylbutanoate (91d, 4.9 g, 15 mmol) in anhydrous acetone was added sodium iodide (11.5 g, 75 mmol). The reaction was heated at reflux for 1.5 h. The reaction was quenched with water and extracted into EtOAc×3. The combined organic phases were washed with brine then dried over anhydrous sodium sulfate. The solvent was removed in vacuo to yield (S)-methyl 2-(tert-butyldimethylsilyloxy)-4-iodobutanoate (91e, 4.33 g, 12 mmol) as a yellow oil. $^1$H NMR (400 MHz, CHLOROFORM-d) δ 0.07-0.13 (m, 6H), 0.82-0.99 (m, 9H), 2.09-2.32 (m, 2H), 3.17-3.36 (m, 2H), 3.74 (s, 3H), 4.29 (dd, J=8.08, 4.04 Hz, 1H).

Step E.

To a solution of (R,Z)-2-amino-7-(2-bromo-4-fluorophenyl)-4-methyl-7,8-dihydropyrido[4,3-d]pyrimidin-5(6H)-one oxime (91e, 150 mg, 0.41 mmol) in anhydrous DMF (2 mL) was added cesium carbonate (200 mg, 0.62 mmol). The reaction mixture was allowed to stir for 1 h, at which time (S)-methyl 2-(tert-butyldimethylsilyloxy)-4-mesylbutanoate (91f, 220 mg, 0.62 mmol) was added. The reaction was allowed to stir under a nitrogen atmosphere overnight. The reaction was poured onto ice to crash out (S)-methyl 4-((Z)—((R)-2-amino-7-(2-bromo-4-fluorophenyl)-4-methyl-7,8-dihydropyrido[4,3-d]pyrimidin-5(6H)-ylidene)aminooxy)-2-(tert-butyldimethylsilyloxy)butanoate (91 g, 244 mg, 0.41 mmol) as a dark yellow precipitate. [M+H] calc'd for $C_{25}H_{35}BrFN_5O_4Si$, 596; found, 596.

Step F.

To a solution of (S)-methyl 4-((Z)—((R)-2-amino-7-(2-bromo-4-fluorophenyl)-4-methyl-7,8-dihydropyrido[4,3-d]pyrimidin-5(6H)-ylidene)aminooxy)-2-(tert-butyldimethylsilyloxy)butanoate (91 g, 244 mg, 0.41 mmol) in DMA was added 6-methoxypyridine-2-boronic acid N-phenyldiethanolamine ester (488 mg, 1.64 mmol), $Pd(dppf)_2Cl_2$ (66 mg, 0.08 mmol), and 2 N $Na_2CO_3$ (2 mL, 4.1 mmol). The resultant mixture was degassed with $N_2$ for 5 min then heated in a sealed tube at 85° C. for 14 h. The reaction was allowed to cool to r.t. and filtered through a pad of Celite topped with anhydrous $Na_2SO_4$, rinsing with EtOAc and $CH_3OH$. The filtrate was concentrated to provide a black residue which was purified by preparative HPLC eluting with TFA/ACN/$H_2O$. The fractions were dried down in vacuo to yield (S)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-(tert-butyldimethylsilyloxy)butanoate. This material was directly taken up in dioxane (700 μL) and treated with 1:9 TFA:$H_2O$ (1 mL) for 3 h. The solvents were removed in vacuo to yield (S)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanoate (91h, 15 mg, 0.03 mmol). [M+H] calc'd for $C_{25}H_{27}FN_6O_5$, 511; found, 511.

Step G.

To a solution of (S)-methyl 4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanoate (91h, 15 mg, 0.03 mmol) in dioxane (500 μL) was added 1 N LiOH (74 μL, 0.08 mmol). The reaction was allowed to stir for 3 h, at which time it was diluted with 1:1 DMSO:MeOH and purified via preparative HPLC eluting with TFA/ACN/$H_2O$. The fractions were dried down in vacuo to yield (S)-4-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-2-hydroxybutanoic acid (Compound 86, 7.1 mg, 0.014 mmol) as a yellow oil. $^1$H NMR (400 MHz, METHANOL-$d_4$) δ 1.86-2.08 (m, 1H), 2.18-2.35 (m, 1H), 2.70-2.87 (m, 3H), 3.18 (dd, J=16.80, 9.22 Hz, 1H), 3.31-3.44 (m, 1H), 3.84-3.97 (m, 3H), 4.10-4.32 (m, 3H), 5.08 (dd, J=9.09, 4.04 Hz, 1H), 6.79 (d, J=8.34 Hz, 1H), 7.12 (d, J=7.33 Hz, 1H), 7.14-7.31 (m, 2H), 7.66 (dd, J=8.59, 5.56 Hz, 1H), 7.76 (t, J=7.83 Hz, 1H). [M+H] calc'd for $C_{24}H_{25}FN_6O_5$, 497; found, 497.

Example 92

3-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)dihydrofuran-2(3H) one (Compound 87)

87

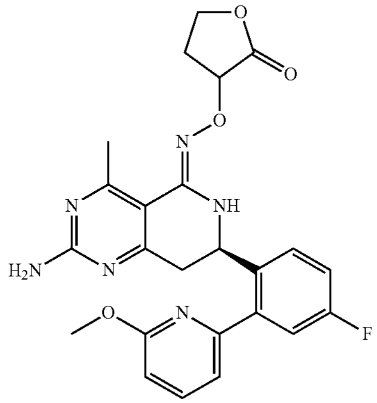

To a solution of (R,Z)-2-amino-7-(2-bromo-4-fluorophenyl)-4-methyl-7,8-dihydropyrido[4,3-d]pyrimidin-5(6H)-one oxime (0.3 mmol, 109 mg) in DMF (2.0 mL) was added $Cs_2CO_3$ (0.45 mmol, 146 mg) and 3-bromodihydrofuran-2(3H)-one (0.36 mmol, 33.6 μL). The reaction mixture was stirred overnight at r.t. and LCMS shows completion of the reaction. The reaction mixture was poured on crushed ice and the resultant solid was filtered and dried to afford 3-((Z)—((R)-2-amino-7-(2-bromo-4-fluorophenyl)-4-methyl-7,8-dihydropyrido[4,3-d]pyrimidin-5(6H)-ylidene)aminooxy)dihydrofuran-2(3H)-one (105 mg, 78%) as off white solid. MS (ES). [M+H] calculated for $C_{18}H_{18}BrFN_5O_3$, 450.05; found 450.30.

A mixture of the resultant compound (0.2 mmol, 92 mg), 2-(6-methoxypyridin-2-yl)-6-phenyl-1,3,6,2-dioxazaborocane (0.5 mmol, 150 mg), $Pd(dppf)_2Cl_2$ (0.02 mmol, 16 mg), 2N aq $Na_2CO_3$ (1.0 mmol, 0.5 mL) and DMA (2.0 mL) was degassed with $N_2$ and heated at 85° C. for 4 h. Cooled to rt, filtered trough celite and purified by prep LCMS to afford 2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxybutanoic acid (29 mg, 29%) as brown solid. MS (ES) [M+H] calculated for $C_{24}H_{26}FN_6O_5$, 497.19; found 497.00.

The resultant compound was dissolved in THF (1.0 ml) and cooled to 0° C. N-methyl morpholine (0.15 mmol, 16.5 μL) and isobutyl chloroformate (0.1 mmol, 15.5 μL) was added and the reaction mixture was stirred at ambient temperature for 2 h. Purified by prep LCMS to afford the title compound 3-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)dihydrofuran-2(3H)one (5 mg, 21%) as white solid. $^1H$ NMR (400 MHz, CHLOROFORM-d) δ 2.52 (d, J=3.54 Hz, 1H) 2.66 (br. s., 3H) 2.95-3.11 (m, 1H) 3.27 (br. s., 2H) 3.79 (s, 3H) 4.19-4.29 (m, 1H) 4.34-4.45 (m, 1H) 4.73-4.91 (m, 2H) 6.67 (d, J=8.34 Hz, 1H) 6.94 (d, J=6.57 Hz, 1H) 7.00-7.15 (m, 2H) 7.49-7.66 (m, 2H). MS (ES) [M+H] calculated for $C_{24}H_{24}FN_6O_4$, 479.47; found 479.40.

Example 93

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxybutanamide (Compound 88)

88

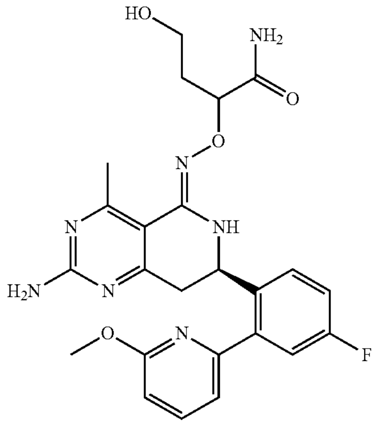

3-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)dihydrofuran-2(3H) one (14.3 mg, 0.03 mmol) was dissolved in 7N $NH_3$-MeOH solution and stirred overnight in a sealed tube. The solvent was removed and residue dried to afford the title compound 2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxybutanamide (13.2 mg, 89%) as a white solid. $^1H$ NMR (400 MHz, METHANOL-$d_4$) δ 1.83-2.16 (m, 2H) 2.58 (d, J=6.06 Hz, 3H) 2.85-3.03 (m, 1H) 3.07-3.25 (m, 1H) 3.70 (q, J=7.24 Hz, 2H) 3.90 (d, J=11.37 Hz, 3H) 4.54 (td, J=7.83, 5.05 Hz, 1H) 4.97-5.17 (m, 1H) 6.69-6.85 (m, 1H) 7.11 (dd, J=7.71, 2.40 Hz, 1H) 7.14-7.26 (m, 2H) 7.57-7.72 (m, 1H) 7.76 (dd, J=15.03, 6.69 Hz, 1H). MS (ES) [M+H] calculated for $C_{24}H_{27}FN_7O_4$, 496.50; found 496.40.

Example 94

2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide (Compound 89) and chiral separation

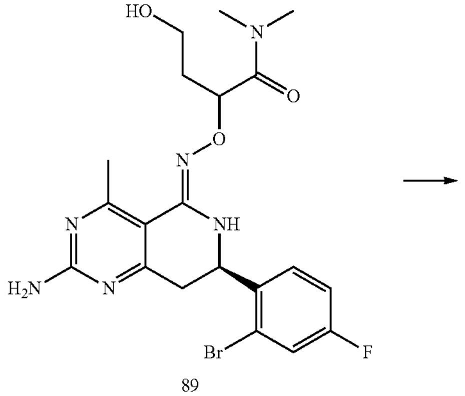

89

-continued

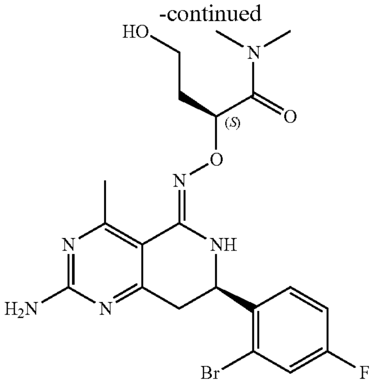

+

90

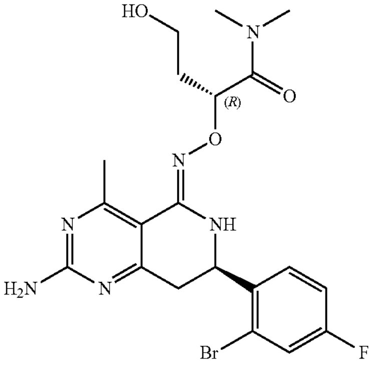

91

To a solution of 3-((Z)—((R)-2-amino-7-(2-bromo-4-fluorophenyl)-4-methyl-7,8-dihydropyrido[4,3-d]pyrimidin-5(6H)-ylidene)aminooxy)dihydrofuran-2(3H)-one (310 mg, 0.668 mg) in THF (2 mL) was added N,N-dimethylamine (2.0M solution in MeOH, 0.86 mL, 1.72 mmol) and the reaction mixture was stirred overnight at r.t. The solvent was removed and purified by LCMS to afford the title compound 2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide (89, 80 mg, 24%) as white solid. $^1$H NMR (400 MHz, METHANOL-$d_4$) 62.63 (d, J=2.78 Hz, 3H) 2.84-2.99 (m, 1H) 3.01 (d, J=3.28 Hz, 3H) 3.08-3.25 (m, 4H) 3.61-3.93 (m, 2H) 4.99 (dddd, J=15.03, 4.86, 2.59, 2.27 Hz, 1H) 5.09-5.23 (m, 3H) 5.91 (d, J=9.09 Hz, 1H) 6.98-7.14 (m, 1H) 7.33 (ddd, J=7.89, 4.99, 2.53 Hz, 1H) 7.38-7.48 (m, 1H). MS (ES) [M+H] calculated for $C_{20}H_{25}BrFN_6O_3$, 495.34; found 495.30.

2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide (89) was separated into its enantiomers by supercritical fluid chromatography (SFC) under the following conditions.

Column: ChiralPak AS-H (250×21 mm, 5 μm)

Mobile Phase:

A: $CO_2$ (1)

B: i-PrOH

Gradient Condition: 25% i-PrOH

Run Time: 8 min

Flow Rate: 50 mL/min

Injection volume: 2000 μL

Example 95

Synthesis of (R)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide (Compound 92)

92

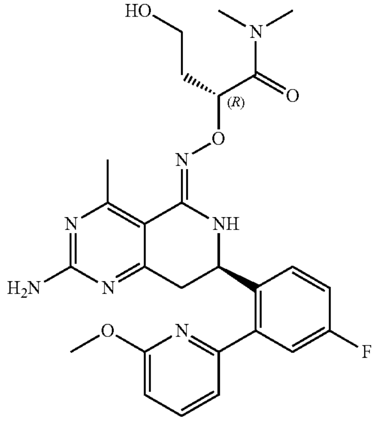

A mixture of (R)-2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide (31 mg, 0.063 mmol), 2-(6-methoxypyridin-2-yl)-6-phenyl-1,3,6,2-dioxazaborocane (93 mg, 0.313 mmol), $Pd(dppf)_2Cl_2$ (9.16 mg, 0.013 mmol), 2N aq $Na_2CO_3$ (0.156 mL, 0.313 mmol) and DMA (2.0 mL) was degassed with $N_2$ and heated at 85° C. for 4 h. Cooled to r.t., filtered trough celite and purified by prep LCMS to afford (R)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide (92, 14.4 mg, 43.9%) as off-white solid. $^1$H NMR (400 MHz, CHLOROFORM-d) δ 2.08-2.16 (m, 2H) 2.60 (s, 3H) 2.98 (s, 3H) 3.02 (d, J=9.85 Hz, 1H) 3.10 (s, 3H) 3.16-3.33 (m, 1H) 3.62-3.81 (m, 2H) 3.89 (s, 3H) 4.94 (ddd, J=10.04, 3.98, 0.88 Hz, 1H) 5.03 (t, J=6.19 Hz, 1H) 5.27 (br. s., 2H) 5.79 (s, 1H) 6.74 (dd, J=8.34, 0.76 Hz, 1H) 7.01 (dd, J=7.33, 0.76 Hz, 1H) 7.07-7.23 (m, 2H) 7.65 (dd, J=8.34, 7.33 Hz, 2H). MS (ES) [M+H] calculated for $C_{26}H_{31}FN_7O_4$, 524.56; found 524.40.

Example 96

(S)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide (Compound 93)

93

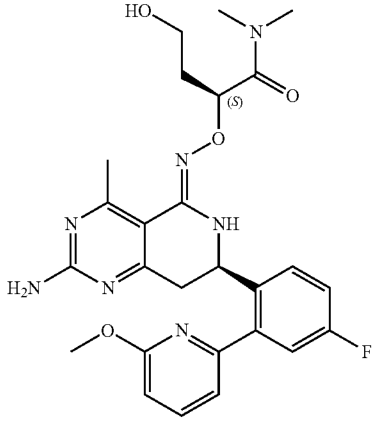

A mixture of (S)-2-((Z)—((R)-2-amino-7-(2-bromo-4-fluorophenyl)-4-methyl-7,8-dihydropyrido[4,3-d]pyrimidin-5(6H)-ylidene)aminooxy)-4-hydroxy-N,N-dimethylbutanamide (26 mg, 0.052 mmol), 2-(6-methoxypyridin-2-yl)-6-phenyl-1,3,6,2-dioxazaborocane (78 mg, 0.262 mmol), $Pd(dppf)_2Cl_2$ (7.68 mg, 0.01 mmol), 2N aq $Na_2CO_3$ (0.131 mL, 0.262 mmol) and DMA (2.0 mL) was degassed with $N_2$ and heated at 85° C. for 4 h. Cooled to r.t., filtered trough celite and purified by prep LCMS to afford (S)-2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide (93, 10.3 mg, 37%) as off-white solid. $^1$H NMR (400 MHz, CHLOROFORM-d) δ 2.04-2.15 (m, 2H) 2.60 (s, 3H) 2.97 (s, 3H) 3.01-3.07 (m, 1H) 3.13 (s, 3H) 3.30 (ddd, J=16.42, 3.79, 1.52 Hz, 1H) 3.70-3.84 (m, 2H) 3.89 (s, 3H) 4.90 (dd, J=10.74, 3.66 Hz, 1H) 5.12 (t, J=6.32 Hz, 1H) 5.26 (br. s., 1H) 5.78 (s, 1H) 6.74 (dd, J=8.34, 0.76 Hz, 1H) 7.02 (dd, J=7.20, 0.88 Hz, 1H) 7.11-7.21 (m, 2H) 7.65 (dd, J=8.34, 7.07 Hz, 2H). MS (ES) [M+H] calculated for $C_{26}H_{31}FN_7O_4$, 524.56; found 524.40.

Example 97

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-1-morpholinobutan-1-one (Compound 94)

94

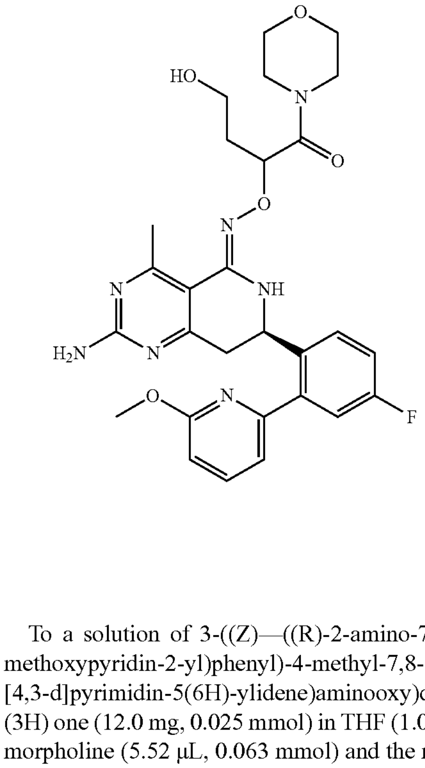

To a solution of 3-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)dihydrofuran-2(3H) one (12.0 mg, 0.025 mmol) in THF (1.0 mL) was added morpholine (5.52 μL, 0.063 mmol) and the reaction mixture was stirred overnight. Solvent was removed and purified by prep LCMS to afford the title compound 2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-1-morpholinobutan-1-one (94, 5.7 mg, 40%) as white solid. $^1$H NMR (400 MHz, METHANOL-$d_4$) δ 1.79-2.03 (m, 2H) 2.57 (d, J=7.07 Hz, 3H) 2.99 (ddd, J=16.86, 8.72, 8.53 Hz, 1H) 3.10-3.18 (m, 1H) 3.22-3.29 (m, 4H) 3.46-3.55 (m, 4H) 3.57-3.62 (m, 2H) 3.81 (d, J=5.81 Hz, 3H) 4.95 (ddd, J=19.45, 8.84, 4.80 Hz, 1H) 5.00-5.06 (m, 1H) 6.70 (dd, J=7.58, 6.06 Hz, 1H) 7.03 (d, J=6.57 Hz, 1H) 7.06-7.16 (m, 2H) 7.54 (ddd, J=19.20, 8.34, 5.81 Hz, 1H) 7.67 (td, J=7.83, 4.80 Hz, 1H). MS (ES) [M+H] calculated for $C_{28}H_{33}FN_7O_5$, 566.59; found 566.50.

Example 98

2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-methoxy-N,N-dimethylbutanamide (Compound 95)

95

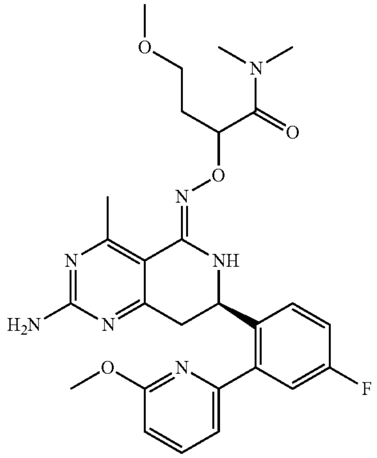

To a solution of 2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-hydroxy-N,N-dimethylbutanamide (0.03 mmol, 16 mg) in THF (2 mL) was added 50% NaH (0.034 mmol, 1.65 mg) at 0° C. under $N_2$ atmosphere. The reaction mixture was stirred for 15 minutes and dimethyl sulphate (4.08 μL, 0.043 mmol) was added. The reaction mixture was stirred at r.t. for 3 h. Quenched with MeOH (1 mL) and purified by LCMS to afford the title compound 2-((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-4-methoxy-N,N-dimethylbutanamide (95, 3.6 mg, 25%) as an off-white solid. $^1$H NMR (400 MHz, DMSO-$d_6$) δ 1.81-2.06 (m, 2H) 2.47 (s, 3H) 2.70-2.80 (m, 1H) 2.83 (d, J=10.61 Hz, 3H) 3.05 (d, J=7.58 Hz, 3H) 3.07-3.17 (m, 1H) 3.20 (d, J=4.80 Hz, 3H) 3.31-3.39 (m, 2H) 3.40-3.49 (m, 2H) 3.87 (d, J=3.79 Hz, 3H) 4.80-4.93 (m, 1H) 5.06-5.22 (m, 1H) 6.83-6.90 (m, 1H) 7.20 (d, J=8.84 Hz, 1H) 7.23-7.32 (m, 2H) 7.44 (ddd, J=14.34, 8.91, 5.81 Hz, 1H) 7.85 (td, J=7.83, 3.28 Hz, 1H). MS (ES) [M+H] calculated for $C_{27}H_{33}FN_7O_4$, 538.58; found 538.40.

Example 99

Synthesis of 2-((Z)—((R)-2-amino-7-(4-fluoro-2-(6-methoxypyridin-2-yl)phenyl)-4-methyl-7,8-dihydro-pyrido[4,3-d]pyrimidin-5(6H)-ylidene)aminooxy)-N—((S)-2,3-dihydroxypropyl)-N-methylacetamide (Compound 96)

96

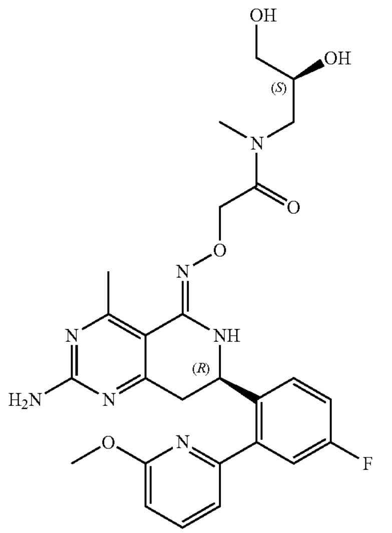

$^1$H NMR (400 MHz, METHANOL-$d_4$) δ 2.57 (d, J=5.31 Hz, 3H), 2.89-3.21 (m, 5H), 3.34-3.65 (m, 4H), 3.75-3.88 (m, 1H), 3.89 (s, 3H), 4.55-4.77 (m, 4H), 5.01 (dt, J=9.16, 4.64 Hz, 1H), 6.77 (d, J=8.34 Hz, 1H), 7.12 (d, J=7.33 Hz, 1H), 7.13-7.25 (m, 2H), 7.67 (dd, J=8.21, 5.68 Hz, 1H), 7.75 (t, J=7.83 Hz, 1H). [M+H] calc'd for $C_{26}H_{30}FN_7O_5$, 540; found, 540.

Example 100

Synthesis of (R,Z)-2-(2-amino-7-(4-fluoro-2-(6-methoxypyridin-2-yl)phenyl)-4-methyl-7,8-dihydro-pyrido[4,3-d]pyrimidin-5(6H)-ylideneaminooxy)-N-cyclopropylacetamide (Compound 97)

97

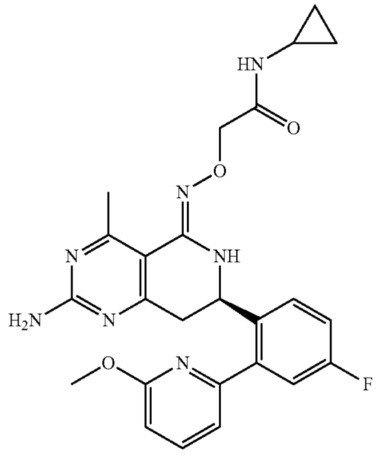

The titled compound 97 was prepared by a procedure analoguous to Example 87 except cyclopropanamine was used $^1$H NMR (400 MHz, MeOD) δ 0.43-0.53 (m, 2H), 0.68-0.79 (m, 2H), 2.67 (dt, J=7.33, 3.41 Hz, 1H), 2.71 (s, 3H), 3.09-3.21 (m, 1H), 3.37-3.52 (m, 1H), 3.91 (s, 3H), 4.43 (s, 2H), 5.06 (dd, J=9.35, 4.29 Hz, 1H), 6.80 (d, J=8.34 Hz, 1H), 7.13 (d, J=7.07 Hz, 1H), 7.15-7.29 (m, 2H), 7.69 (dd, J=8.84, 5.56 Hz, 1H), 7.72-7.83 (m, 1H). [M+H] calc'd for $C_{25}H_{26}FN_7O_3$, 492; found, 492.

Example 101

Synthesis of (R,Z)-4-(2-amino-7-(4-fluoro-2-(6-methoxypyridin-2-yl)phenyl)-4-methyl-7,8-dihydro-pyrido[4,3-d]pyrimidin-5(6H)-ylideneaminooxy)-N,N-dimethylbutanamide (Compound 98)

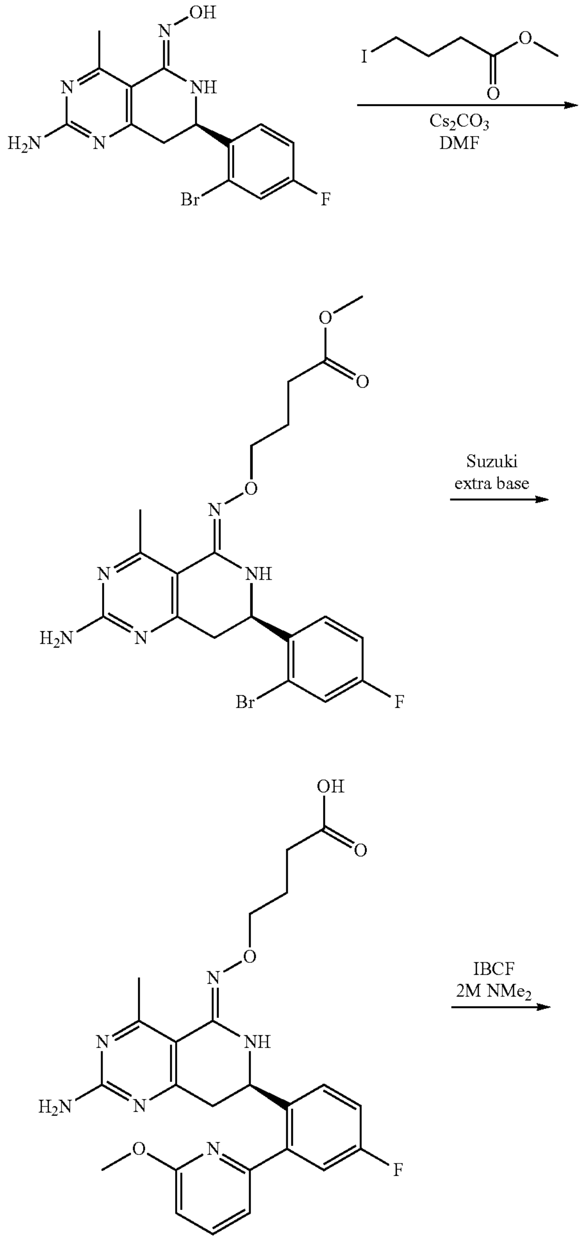

101a

-continued

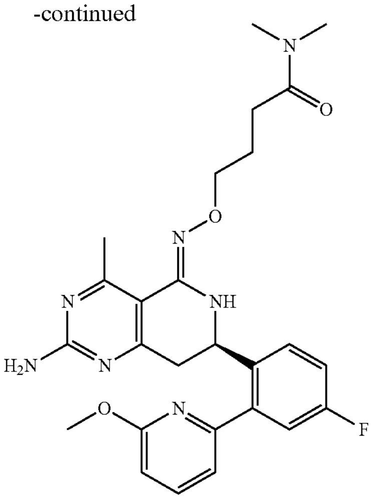

98

A solution of (R,Z)-4-(2-amino-7-(4-fluoro-2-(6-methoxypyridin-2-yl)phenyl)-4-methyl-7,8-dihydropyrido[4,3-d]pyrimidin-5(6H)-ylideneaminooxy)butanoic acid (101a, 26 mg, 0.054 mmol) in anhydrous THF was chilled in an ice bath and N-methylmorpholine (9 μL, 0.081 mmol) and isobutyl chloroformate (7.7 μL, 0.060 mmol) were added sequentially. The mixture was stirred under an $N_2$ atmosphere for 20 min. A 33 wt % solution of dimethylamine in methanol (54 μL, 0.11 mmol) was added to the reaction which was subsequently allowed to warm to room temperature with stirring overnight. The THF was removed in vacuo and the residue was partitioned between ethyl acetate and water. The organic phase was washed with $H_2O$×2 and dried over anhydrous $Na_2SO_4$. The ethyl acetate was removed in vacuo and the residue was purified via preparative HPLC to yield (R,Z)-4-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-dimethylbutanamide (98, 6.4 mg, 0.0126 mmol).

$^1$H NMR (400 MHz, MeOD) δ 1.91-2.05 (m, 2H), 2.46 (t, J=7.33 Hz, 2H), 2.70 (s, 3H), 2.87 (s, 3H), 3.00 (s, 3H), 3.02-3.16 (m, 1H), 3.25 (dd, J=16.55, 4.67 Hz, 1H), 3.91 (s, 3H), 4.00-4.12 (m, 2H), 5.05 (dd, J=8.59, 4.55 Hz, 1H), 6.79 (d, J=8.34 Hz, 1H), 7.12 (d, J=7.33 Hz, 1H), 7.15-7.25 (m, 2H), 7.59 (dd, J=8.46, 5.68 Hz, 1H), 7.71-7.82 (m, 1H). [M+H] calc'd for $C_{26}H_{30}FN_7O_3$, 508; found, 508.

Example 102

Synthesis of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-(2-hydroxyethyl)-N-methylacetamide (Compound 99)

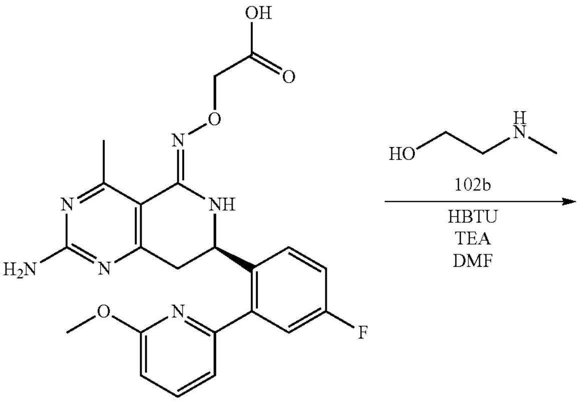

102a

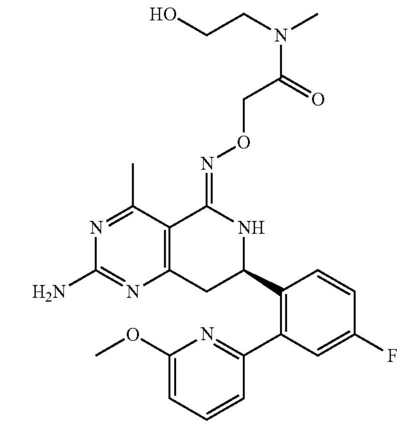

99

To a solution of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetic acid (102a, 43 mg, 0.095 mmol) in anhydrous DMF (1 mL) was added 2-(1H-benzotriazole-1-yl)-1,1,3,3-tetramethyluronium hexafluorophosphate (72 mg, 0.19 mmol), triethylamine (53 μL, 0.39 mmol), and finally 2-(methylamino)ethanol (102b, 16 μL, 0.19 mmol). The reaction was allowed to stir under a nitrogen atmosphere overnight. The reaction mixture was diluted with 1:1 DMSO:MeOH and purified via preparative HPLC eluting with $NH_4HCO_3$/ACN/$H_2O$. The titled compound (Compound 99, 11 mg, 0.022 mmol) was crashed out from the HPLC fractions as a white solid. $^1$H NMR (400 MHz, METHANOL-$d_4$) δ 2.57 (d, J=4.04 Hz, 3H), 2.86-3.21 (m, 5H), 3.44-3.55 (m, 2H), 3.66-3.73 (m, 2H), 3.89 (s, 3H), 4.69-4.82 (m, 2H), 5.01 (dt, J=9.09, 4.29 Hz, 1H), 6.77 (d, J=8.34 Hz, 1H), 7.12 (d, J=7.33 Hz, 1H), 7.14-7.24 (m, 2H), 7.60-7.70 (m, 1H), 7.70-7.80 (m, 1H). [M+H] calc'd for $C_{25}H_{28}FN_7O_4$, 510; found, 510.

Example 103

Synthesis of 2-(((Z)—((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypyrrolidin-1-yl)ethanone (Compound 100)

100

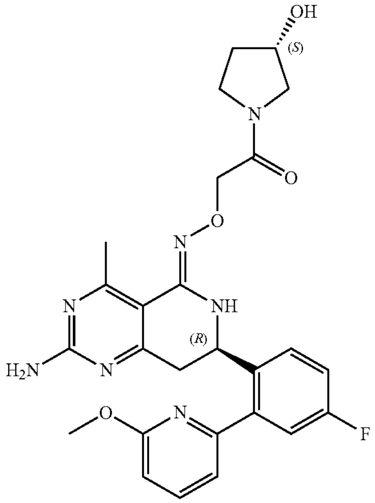

The titled compound 100 was prepared by a procedure analoguous to Example 102 except (S)-pyrrolidin-3-ol was used. $^1$H NMR (400 MHz, METHANOL-$d_4$) δ 1.82-2.13 (m, 2H), 2.57 (d, J=3.03 Hz, 3H), 2.95 (ddd, J=16.23, 8.91, 3.92 Hz, 1H), 3.09-3.22 (m, 2H), 3.38-3.54 (m, 2H), 3.54-3.74 (m, 2H), 3.90 (s, 3H), 4.41 (d, J=9.35 Hz, 1H), 4.55-4.73 (m, 2H), 4.96-5.08 (m, 1H), 6.78 (d, J=8.34 Hz, 1H), 7.12 (d, J=7.07 Hz, 1H), 7.13-7.24 (m, 2H), 7.64 (dt, J=8.53, 5.84 Hz, 1H), 7.75 (t, J=7.83 Hz, 1H). [M+H] calc'd for $C_{26}H_{28}FN_7O_4$, 522; found, 522.

Example 104

Synthesis of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-diethylacetamide (Compound 101)

101

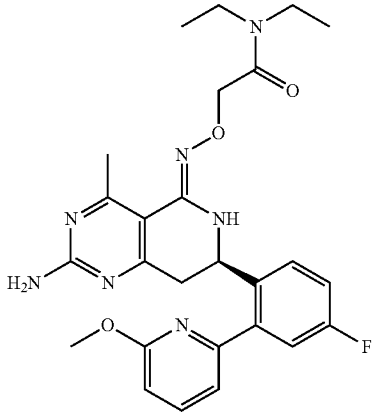

The titled compound 101 was prepared by a procedure analoguous to Example 102. $^1$H NMR (400 MHz, METHANOL-$d_4$) δ 1.12 (t, J=7.07 Hz, 3H), 1.15-1.26 (m, 3H), 2.71 (s, 3H), 3.17 (dd, J=16.80, 9.47 Hz, 1H), 3.32-3.46 (m, 5H), 3.89 (s, 3H), 4.65-4.81 (m, 2H), 5.05 (dd, J=9.47, 4.17 Hz, 1H), 6.79 (d, J=8.34 Hz, 1H), 7.13 (d, J=7.33 Hz, 1H), 7.15-7.29 (m, 2H), 7.70 (dd, J=8.59, 5.56 Hz, 1H), 7.72-7.83 (m, 1H). [M+H] calc'd for $C_{26}H_{30}FN_7O_3$, 508; found, 508.

Example 105

Synthesis of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-morpholinoethanone (Compound 102)

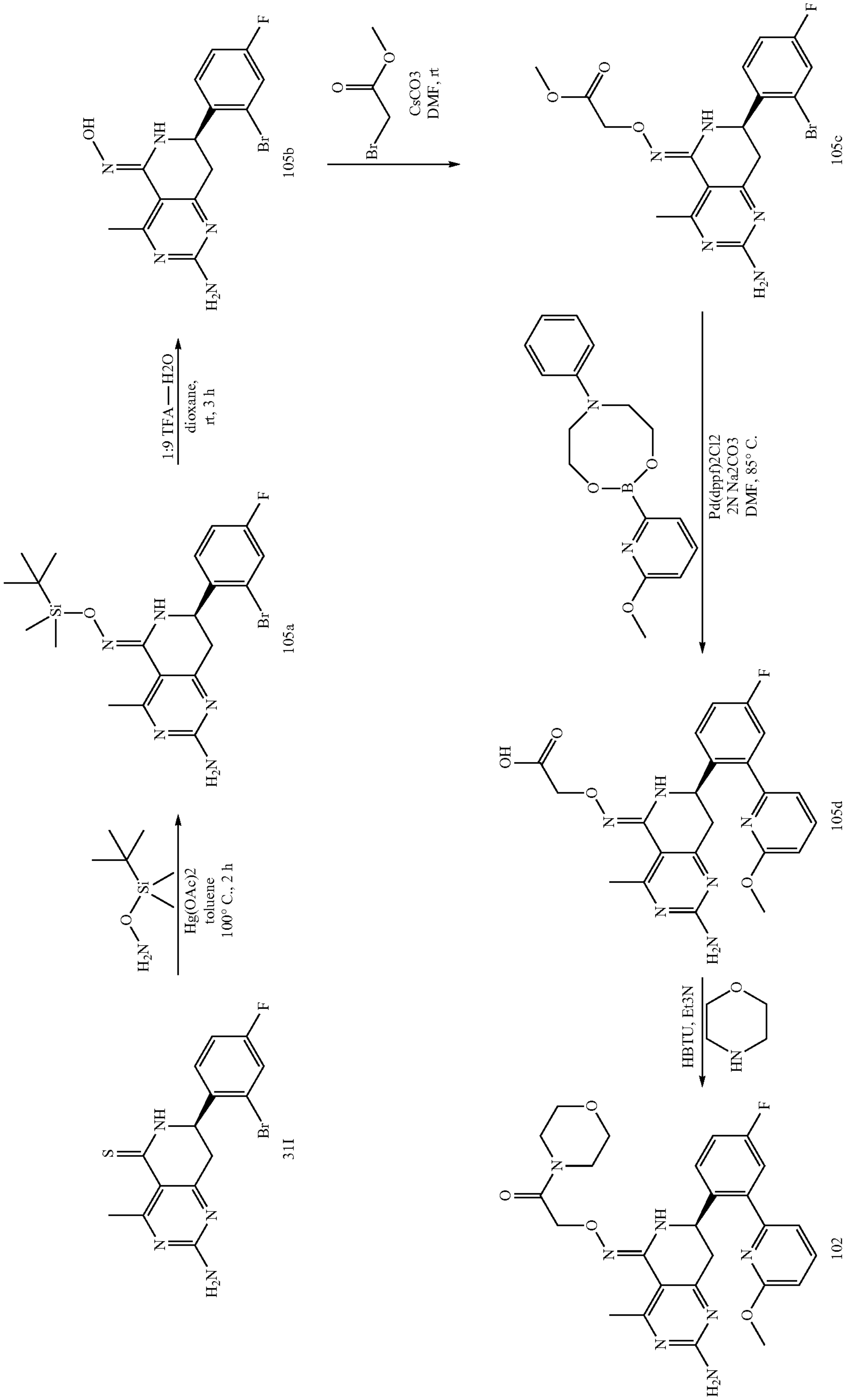
311
105a
105b
105c
105d
102

A. (R,Z)-2-amino-7-(2-bromo-4-fluorophenyl)-4-methyl-7,8-dihydropyrido[4,3-d]pyrimidin-5(6H)-one O-tert-butyldimethylsilyloxime (105a)

A mixture of (R)-2-amino-7-(2-bromo-4-fluorophenyl)-4-methyl-7,8-dihydropyrido[4,3-d]pyrimidine-5(6H)-thione (31I, 366 mg, 1.0 mmol), O-(tert-butyldimethylsilyl)hydroxylamine (588 mg, 4.0 mmol), $Hg(OAC)_2$ (640 mg, 2.0 mmol) and toluene (5 mL) was heated at 100° C. for 2 h. The mixture was cooled to r.t. and filtered through celite. Filtrate concentrated and the resulting oily residue was triturated with dry methanol to afford a pale yellow solid. Filtered and dried to afford ((R,Z)-2-amino-7-(2-bromo-4-fluorophenyl)-4-methyl-7,8-dihydropyrido[4,3-d]pyrimidin-5(6H)-one O-tert-butyldimethylsilyloxime (105a, 384 mg, 80%) as a pale yellow solid. $^1$H NMR (400 MHz, CHLOROFORM-d) δ ppm 0.22 (s, 3H), 0.23 (s, 3H) 0.97 (s, 9H) 2.70 (s, 3H) 2.91 (dd, J=16.42, 8.08 Hz, 1H) 3.19 (ddd, J=16.36, 4.86, 1.26 Hz, 1H) 4.99 (ddd, J=7.77, 5.12, 2.02 Hz, 1H) 7.05 (td, J=8.27, 2.65 Hz, 1H) 7.33 (dd, J=8.08, 2.78 Hz, 1H) 7.39 (dd, J=8.72, 5.94 Hz, 1H). MS (ES) [M+H] calculated for $C_{20}H_{28}BrFN_5OSi$, 480.12; found 480.30.

B. (R,Z)-2-amino-7-(2-bromo-4-fluorophenyl)-4-methyl-7,8-dihydro pyrido[4,3-d]pyrimidin-5(6H)-one oxime (105b)

To a solution of ((R,Z)-2-amino-7-(2-bromo-4-fluorophenyl)-4-methyl-7,8-dihydropyrido[4,3-d]pyrimidin-5(6H)-one O-tert-butyldimethylsilyloxime (105a, 384 mg, 0.8 mmol) in dioxane (2 mL) was added 1:9 TFA-$H_2O$ and the reaction mixture stirred at rt for 2 h. The resultant sold was filtered and washed with dioxane. The resultant solid was dried to afford (R,Z)-2-amino-7-(2-bromo-4-fluorophenyl)-4-methyl-7,8-dihydro pyrido[4,3-d]pyrimidin-5(6H)-one oxime (105b, 206 mg, 70%) as a pale yellow solid. $^1$H NMR (400 MHz, DMSO-$d_6$) δ ppm 2.56 (s, 3H) 2.83 (dd, J=15.92, 4.55 Hz, 1H) 3.17 (dd, J=16.04, 5.94 Hz, 1H) 4.90 (q, J=4.97 Hz, 1H) 7.20 (d, J=1.52 Hz, 1H) 7.21-7.23 (m, 1H) 7.57 (ddd, J=8.34, 1.64, 1.39 Hz, 1H) 9.82 (s, 1H). MS (ES) [M+H] calculated for $C_{14}H_{14}BrFN_5O$, 366.03; found 366.20.

C. (R,Z)-methyl 2-(2-amino-7-(2-bromo-4-fluorophenyl)-4-methyl-7,8-dihydropyrido[4,3-d]pyrimidin-5(6H)-ylideneaminooxy)acetate (105c)

To a solution of (R,Z)-2-amino-7-(2-bromo-4-fluorophenyl)-4-methyl-7,8-dihydro pyrido[4,3-d]pyrimidin-5(6H)-one oxime (105c, 150 mg, 0.4 mmol) in dry DMF (1 mL) was added $CsCO_3$ (195 mg, 0.6 mmol) and the reaction mixture stirred at ambient temperature for 30 minutes. Then methyl 2-bromoacetate (45 μL, 0.48 mmol) was added and the reaction mixture stirred for overnight. LCMS shows completion of the starting material. The reaction mixture was poured on crushed ice and the resultant sold was filtered and washed with cold water. The resultant solid was dried to afford (R,Z)-methyl 2-(2-amino-7-(2-bromo-4-fluorophenyl)-4-methyl-7,8-dihydropyrido[4,3-d]pyrimidin-5(6H)-ylideneaminooxy)acetate (105c, 172 mg, 99%) as a light brown solid. $^1$H NMR (400 MHz, CHLOROFORM-d) δ ppm 2.66 (s, 3H) 3.12-3.18 (m, 1H) 3.24-3.32 (m, 1H) 3.71 (s, 3H) 4.57 (s, 2H) 4.96 (ddd, J=8.40, 4.48, 1.77 Hz, 1H) 7.01 (td, J=8.27, 2.65 Hz, 1H) 7.23-7.29 (m, 1H) 7.39 (dd, J=8.84, 5.81 Hz, 0H). MS (ES) [M+H] calculated for $C_{12}H_{18}BrFN_5O_3$, 438.05; found 438.00.

D. (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetic acid (105d)

A mixture of (R,Z)-methyl 2-(2-amino-7-(2-bromo-4-fluorophenyl)-4-methyl-7,8-dihydropyrido[4,3-d]pyrimidin-5(6H)-ylideneaminooxy)acetate (105c, 175 mg, 0.4 mmol), 2-(6-methoxypyridin-2-yl)-6-phenyl-1,3,6,2-dioxazaborocane (298 mg, 1.0 mmol), $Pd(dppf)_2Cl_2$ (32.5 mg, 0.04 mmol), 2N $Na_2CO_3$ (1.0 mL, 2.0 mmol) in DMA (3 mL) was degassed with $N_2$ and heated at 85° C. for over night. The reaction mixture was cooled to ambient temperature, diluted with ethyl acetate and filtered through celite. The filtrate was concentrated to afford brown oil which was purified by preparative LCMS to afford (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetic acid (105d, 56 mg, 31%) as white solid. $^1$H NMR (400 MHz, CHLOROFORM-d) δ ppm 2.79 (s, 3H) 3.16 (dd, J=17.05, 10.48 Hz, 1H) 3.45 (dd, J=17.05, 3.92 Hz, 1H) 3.88 (s, 3H) 4.59 (d, J=3.03 Hz, 2H) 4.96 (dd, J=10.36, 3.79 Hz, 1H) 5.90 (brs, 1H) 6.76 (d, J=8.34 Hz, 1H) 7.02 (d, J=6.82 Hz, 1H) 7.14 (dd, J=9.09, 2.78 Hz, 1H) 7.19 (td, J=8.34, 2.78 Hz, 1H) 7.62 (dd, J=8.59, 5.56 Hz, 1H) 7.68 (dd, J=8.34, 7.33 Hz, 1H). MS (ES) [M+H] calculated for $C_{22}H_{22}FN_6O_4$, 453.16; found 453.30.

E. (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-morpholinoethanone (Compound 102)

To a solution of (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)acetic acid (105d, 0.05 mmol, 22.6 mg) in DMF (0.5 mL) was added HBTU (0.075 mmol, 28 mg), $Et_3N$ (0.125 mmol, 17 μL) and morpholine (0.1 mmol, 8.3 μL). The reaction mixture was stirred over night at r.t. and LCMS shows completion of the reaction. Purified by prep LCMS to afford the title compound (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-morpholinoethanone (102, 5.7 mg, 22%) as off white solid. $^1$H NMR (400 MHz, CHLOROFORM-d) δ ppm 2.83 (s, 3H) 3.15 (dd, J=17.31, 10.23 Hz, 2H) 3.43-3.51 (m, 2H) 3.63 (d, J=5.31 Hz, 2H) 3.65-3.71 (m, 4H) 3.89 (s, 3H) 4.71 (s, 2H) 4.97 (dd, J=10.36, 3.79 Hz, 1H) 5.96 (br. s., 1H) 6.77 (d, J=8.34 Hz, 1H) 7.03 (d, J=7.07 Hz, 1H) 7.14 (dd, J=9.35, 2.78 Hz, 1H) 7.19 (td, J=8.40, 2.65 Hz, 1H) 7.63 (dd, J=8.84, 5.56 Hz, 1H) 7.68 (dd, J=8.34, 7.33 Hz, 1H). MS (ES) [M+H] calculated for $C_{26}H_{28}FN_7O_4$, 522.22; found 522.00.

The reaction schemes disclosed in the Example above was used to prepare the compounds listed in the following table:

| Compound No. | Structure & Name | MW | M + H (observed) |
|---|---|---|---|
| 103 | 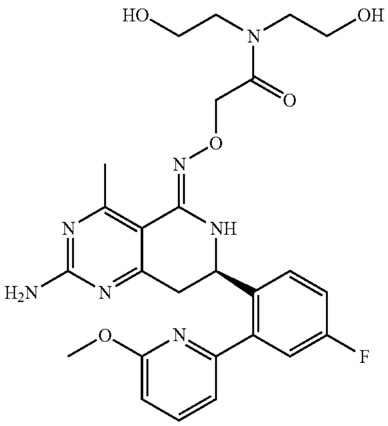 [SMILES: COc1cccc(-c2cc(F)ccc2[C@H]2Cc3nc(N)nc(C)c3/C(=N/OCC(=O)N(CCO)CCO)N2)n1]<br>(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-bis(2-hydroxyethyl)acetamide | 539.6 | 540 |
| 104 | 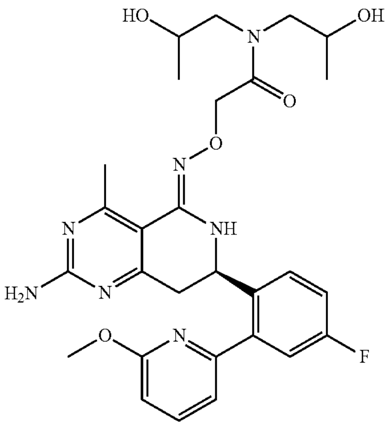 [SMILES: COc1cccc(-c2cc(F)ccc2[C@H]2Cc3nc(N)nc(C)c3/C(=N/OCC(=O)N(CC(C)O)CC(C)O)N2)n1]<br>2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-N,N-bis(2-hydroxypropyl)acetamide | 539.6<br>567.6 | 568 |

-continued
| Compound No. | Structure & Name | MW | M + H (observed) |
|---|---|---|---|
| 105 | 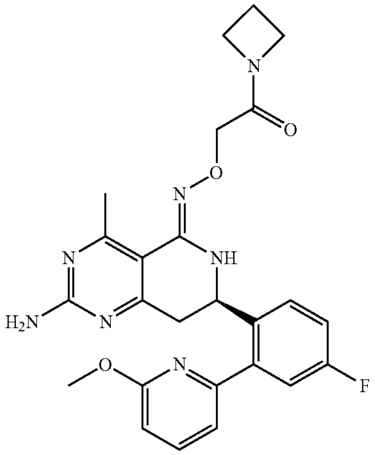 [SMILES: COc1cccc(-c2cc(F)ccc2[C@H]2Cc3nc(N)nc(C)c3/C(=N/OCC(=O)N3CCC3)N2)n1]<br>(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(azetidin-1-yl)ethanone | 491.5 | 492 |
| 106 | 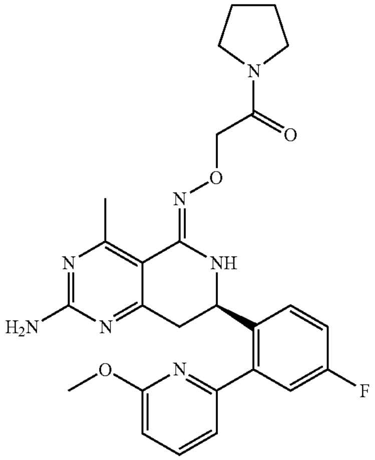 [SMILES: COc1cccc(-c2cc(F)ccc2[C@H]2Cc3nc(N)nc(C)c3/C(=N/OCC(=O)N3CCCC3)N2)n1]<br>(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(pyrrolidin-1-yl)ethanone | 505.5 | 506 |

-continued
| Compound No. | Structure & Name | MW | M + H (observed) |
|---|---|---|---|
| 107 | 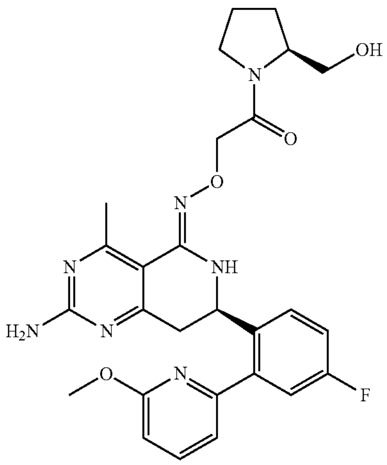 [SMILES: COc1cccc(-c2cc(F)ccc2[C@H]2Cc3nc(N)nc(C)c3/C(=N/OCC(=O)N3CCC[C@H]3CO)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-2-(hydroxymethyl)pyrrolidin-1-yl)ethanone | 535.6 | 536 |
| 108 | 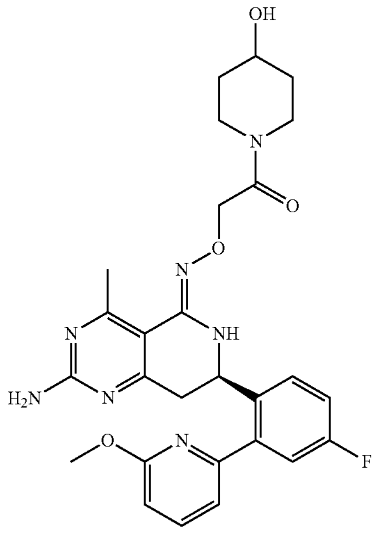 [SMILES: COc1cccc(-c2cc(F)ccc2[C@H]2Cc3nc(N)nc(C)c3/C(=N/OCC(=O)N3CCC(O)CC3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(4-hydroxypiperidin-1-yl)ethanone | 535.6 | 536 |

-continued
| Compound No. | Structure & Name | MW | M + H (observed) |
|---|---|---|---|
| 109 | 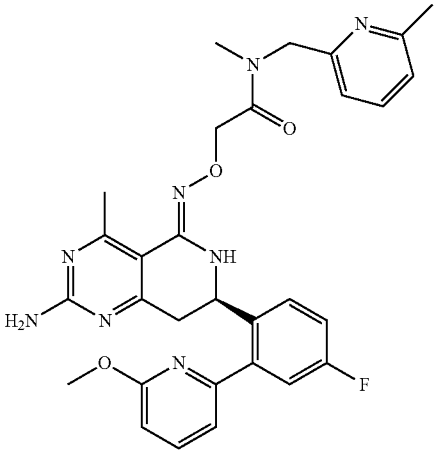 [SMILES: COc1cccc(-c2cc(F)ccc2[C@H]2Cc3nc(N)nc(C)c3/C(=N/OCC(=O)N(C)Cc3cccc(C)n3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methyl-N-((6-methylpyridin-2-yl)methyl)acetamide | 570.6 | 571 |
| 110 | 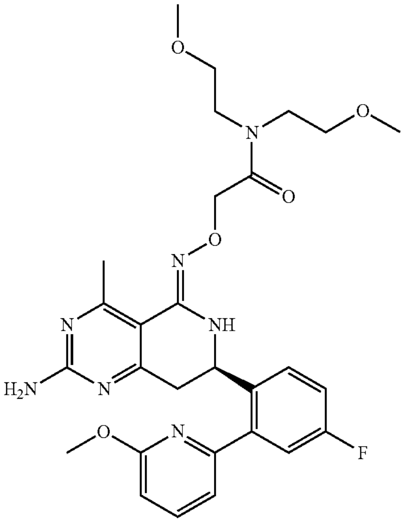 [SMILES: COCCN(CCOC)C(=O)CO/N=C1\N[C@@H](c2ccc(F)cc2-c2cccc(OC)n2)Cc2nc(N)nc(C)c21] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N,N-bis(2-methoxyethyl)acetamide | 567.6 | 568 |

-continued

| Compound No. | Structure & Name | MW | M + H (observed) |
|---|---|---|---|
| 111 | 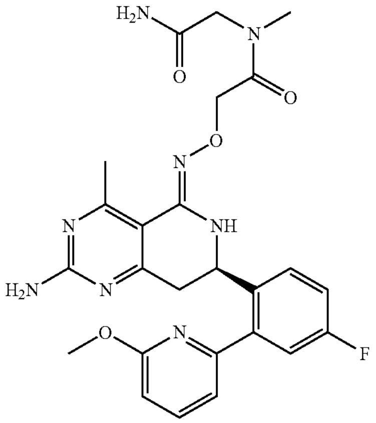 [SMILES: COc1cccc(-c2cc(F)ccc2[C@H]2Cc3nc(N)nc(C)c3/C(=N/OCC(=O)N(C)CC(N)=O)N2)n1] (R,Z)-N-(2-amino-2-oxoethyl)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methylacetamide | 522.5 | 523 |
| 112 | 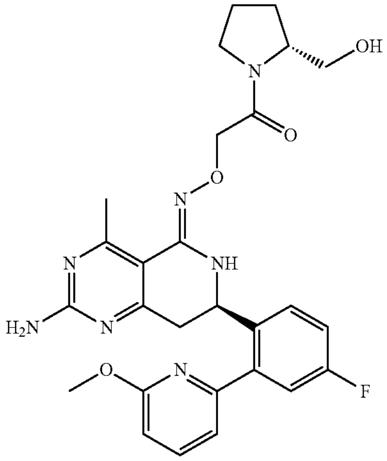 [SMILES: COc1cccc(-c2cc(F)ccc2[C@H]2Cc3nc(N)nc(C)c3/C(=N/OCC(=O)N3CCC[C@@H]3CO)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-2-(hydroxymethyl)pyrrolidin-1-yl)ethanone | 535.6 | 536 |
| 113 | 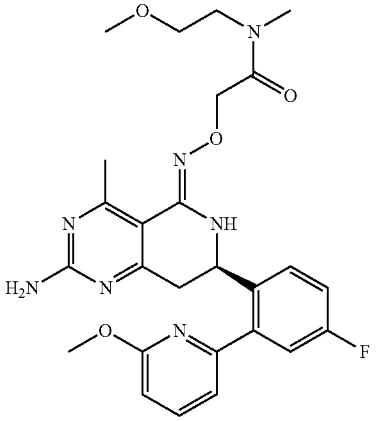 [SMILES: COCCN(C)C(=O)CO/N=C1\N[C@@H](c2ccc(F)cc2-c2cccc(OC)n2)Cc2nc(N)nc(C)c21] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-(2-methoxyethyl)-N-methylacetamide | 523.6 | 524 |

-continued
| Compound No. | Structure & Name | MW | M + H (observed) |
|---|---|---|---|
| 114 | 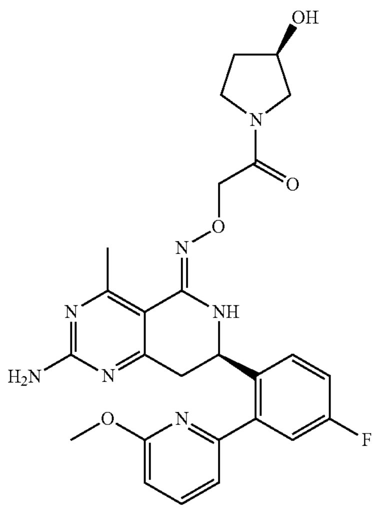 [SMILES: COc1cccc(-c2cc(F)ccc2[C@H]2Cc3nc(N)nc(C)c3/C(=N/OCC(=O)N3CC[C@@H](O)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-hydroxypyrrolidin-1-yl)ethanone | 521.5 | 522 |
| 115 | 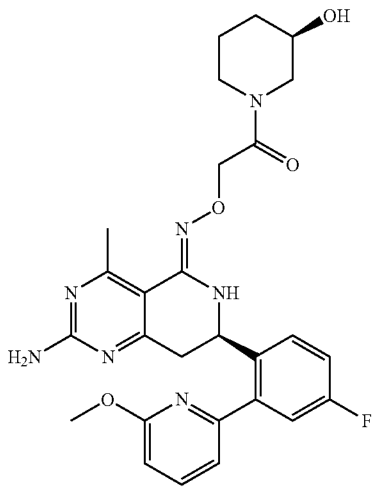 [SMILES: COc1cccc(-c2cc(F)ccc2[C@H]2Cc3nc(N)nc(C)c3/C(=N/OCC(=O)N3CCC[C@@H](O)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-hydroxypiperidin-1-yl)ethanone | 535.6 | 536 |

-continued
| Compound No. | Structure & Name | MW | M + H (observed) |
|---|---|---|---|
| 116 | 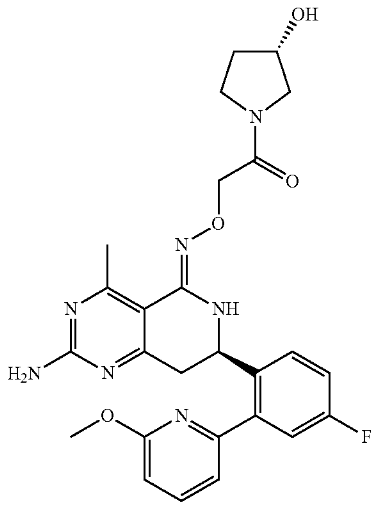 [SMILES: COc1cccc(-c2cc(F)ccc2[C@H]2Cc3nc(N)nc(C)c3/C(=N/OCC(=O)N3CC[C@H](O)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypyrrolidin-1-yl)ethanone | 521.5 | 522 |
| 117 | 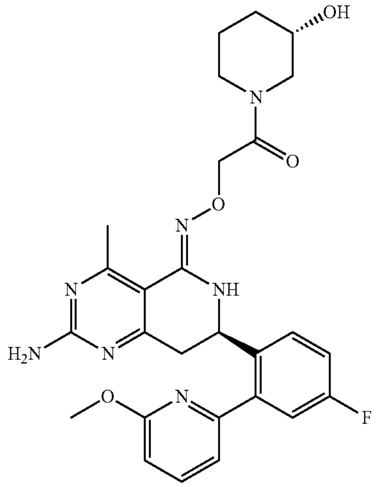 [SMILES: COc1cccc(-c2cc(F)ccc2[C@H]2Cc3nc(N)nc(C)c3/C(=N/OCC(=O)N3CCC[C@H](O)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-hydroxypiperidin-1-yl)ethanone | 535.6 | 536 |

-continued
| Compound No. | Structure & Name | MW | M + H (observed) |
|---|---|---|---|
| 118 | 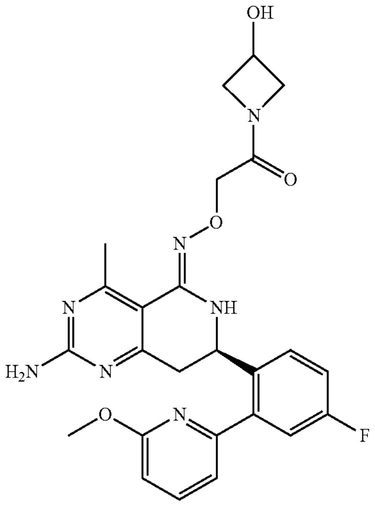 [SMILES: COc1cccc(-c2cc(F)ccc2[C@H]2Cc3nc(N)nc(C)c3/C(=N/OCC(=O)N3CC(O)C3)N2)n1]<br>(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(3-hydroxyazetidin-1-yl)ethanone | 507.5 | 508 |
| 119 | 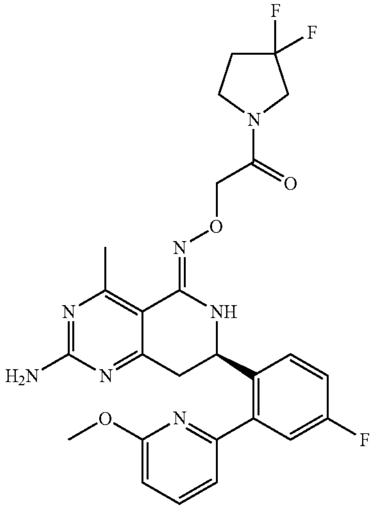 [SMILES: COc1cccc(-c2cc(F)ccc2[C@H]2Cc3nc(N)nc(C)c3/C(=N/OCC(=O)N3CCC(F)(F)C3)N2)n1]<br>(R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(3,3-difluoropyrrolidin-1-yl)ethanone | 541.5 | 542 |

-continued
| Compound No. | Structure & Name | MW | M + H (observed) |
|---|---|---|---|
| 120 | 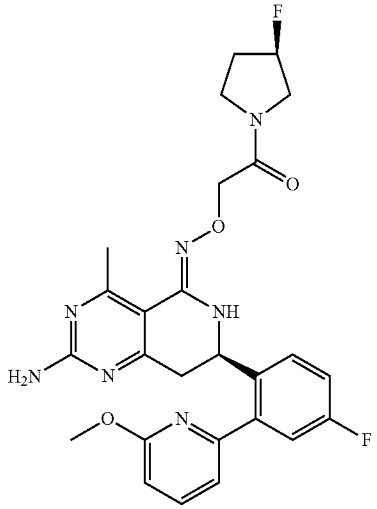 [SMILES: COc1cccc(-c2cc(F)ccc2[C@H]2Cc3nc(N)nc(C)c3/C(=N/OCC(=O)N3CC[C@@H](F)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((R)-3-fluoropyrrolidin-1-yl)ethanone | 523.5 | 524 |
| 121 | 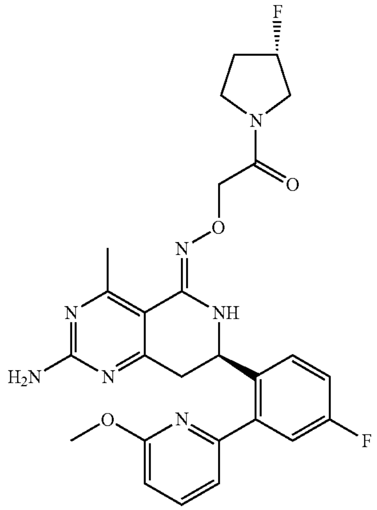 [SMILES: COc1cccc(-c2cc(F)ccc2[C@H]2Cc3nc(N)nc(C)c3/C(=N/OCC(=O)N3CC[C@H](F)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-((S)-3-fluoropyrrolidin-1-yl)ethanone | 523.5 | 524 |

-continued
| Compound No. | Structure & Name | MW | M + H (observed) |
|---|---|---|---|
| 122 | 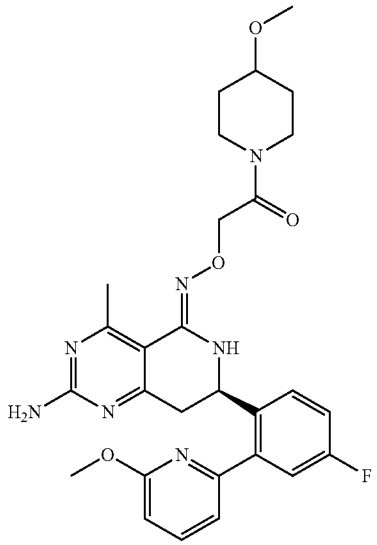 [SMILES: COc1cccc(-c2cc(F)ccc2[C@H]2Cc3nc(N)nc(C)c3/C(=N/OCC(=O)N3CCC(OC)CC3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(4-methoxypiperidin-1-yl)ethanone | 549.6 | 550 |
| 123 | 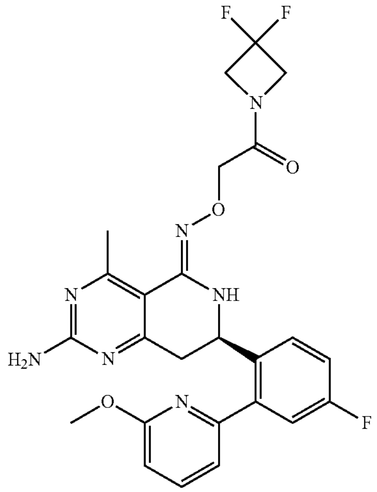 [SMILES: COc1cccc(-c2cc(F)ccc2[C@H]2Cc3nc(N)nc(C)c3/C(=N/OCC(=O)N3CC(F)(F)C3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(3,3-difluoroazetidin-1-yl)ethanone | 527.5 | 528 |

-continued
| Compound No. | Structure & Name | MW | M + H (observed) |
|---|---|---|---|
| 124 | 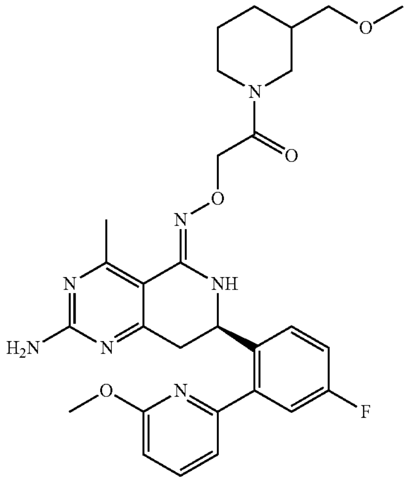 [SMILES: COCC1CCCN(C(=O)CO/N=C2\N[C@@H](c3ccc(F)cc3-c3cccc(OC)n3)Cc3nc(N)nc(C)c32)C1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(methoxymethyl)piperidin-1-yl)ethanone | 563.6 | 564 |
| 125 | 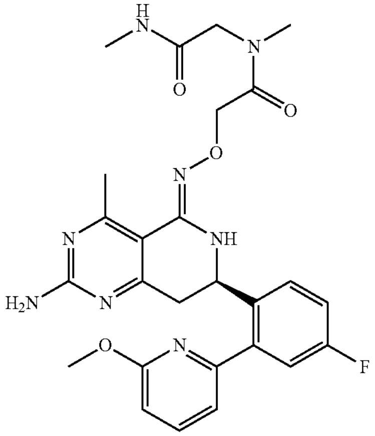 [SMILES: CNC(=O)CN(C)C(=O)CO/N=C1\N[C@@H](c2ccc(F)cc2-c2cccc(OC)n2)Cc2nc(N)nc(C)c21] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methyl-N-(2-(methylamino)-2-oxoethyl)acetamide | 536.6 | 537 |

-continued
| Compound No. | Structure & Name | MW | M + H (observed) |
|---|---|---|---|
| 126 | 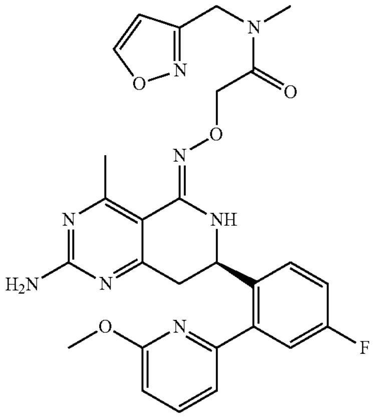 [SMILES: COc1cccc(-c2cc(F)ccc2[C@H]2Cc3nc(N)nc(C)c3/C(=N/OCC(=O)N(C)Cc3ccon3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-(isoxazol-3-ylmethyl)-N-methylacetamide | 546.6 | 547 |
| 127 | 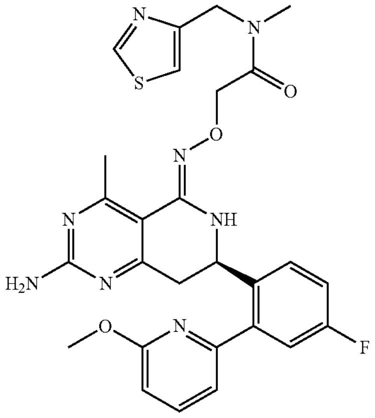 [SMILES: COc1cccc(-c2cc(F)ccc2[C@H]2Cc3nc(N)nc(C)c3/C(=N/OCC(=O)N(C)Cc3cscn3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methyl-N-(thiazol-4-ylmethyl)acetamide | 562.6 | 563 |

-continued
| Compound No. | Structure & Name | MW | M + H (observed) |
|---|---|---|---|
| 128 | 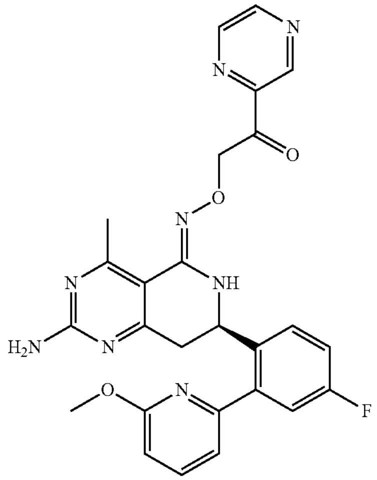 [SMILES: COc1cccc(-c2cc(F)ccc2[C@H]2Cc3nc(N)nc(C)c3/C(=N/OCC(=O)c3cnccn3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(pyrazin-2-yl)ethanone | 557.6 | 558 |
| 129 | 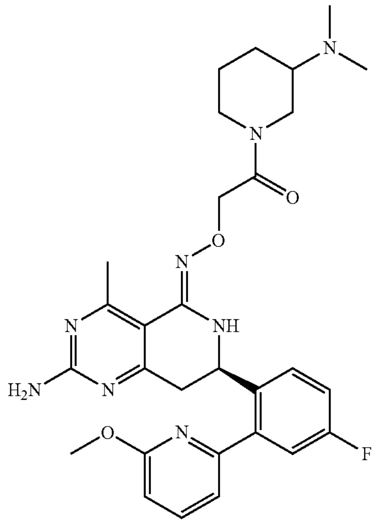 [SMILES: COc1cccc(-c2cc(F)ccc2[C@H]2Cc3nc(N)nc(C)c3/C(=N/OCC(=O)N3CCCC(N(C)C)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(dimethylamino)piperidin-1-yl)ethanone | 562.6 | 563 |

-continued
| Compound No. | Structure & Name | MW | M + H (observed) |
|---|---|---|---|
| 130 | 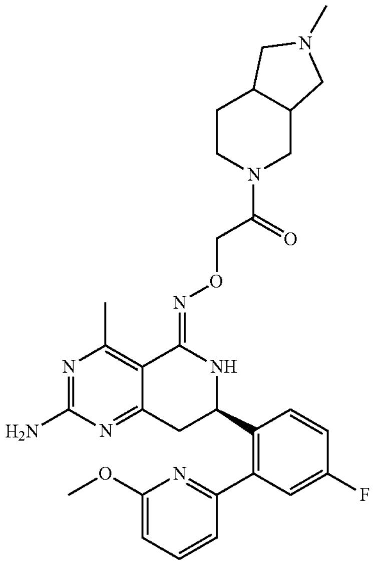 [SMILES: COc1cccc(-c2cc(F)ccc2[C@H]2Cc3nc(N)nc(C)c3/C(=N/OCC(=O)N3CCC4CN(C)CC4C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(2-methyltetrahydro-1H-pyrrolo[3,4-c]pyridin-5(6H,7H,7aH)-yl)ethanone | 574.6 | 575 |
| 131 | 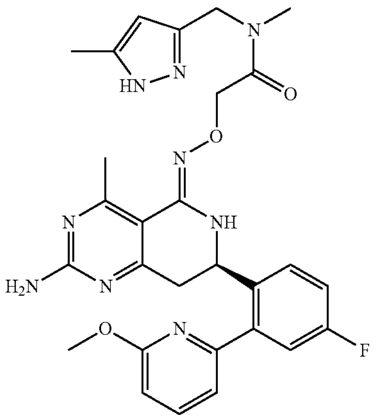 [SMILES: COc1cccc(-c2cc(F)ccc2[C@H]2Cc3nc(N)nc(C)c3/C(=N/OCC(=O)N(C)Cc3cc(C)[nH]n3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-N-methyl-N-((5-methyl-1H-pyrazol-3-yl)methyl)acetamide | 559.6 | 560 |

-continued
| Compound No. | Structure & Name | MW | M + H (observed) |
|---|---|---|---|
| 132 | 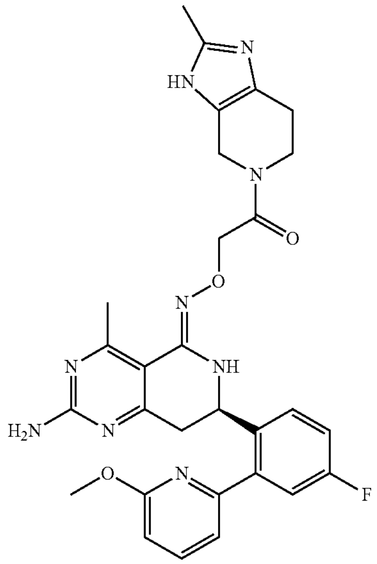 [SMILES: COc1cccc(-c2cc(F)ccc2[C@H]2Cc3nc(N)nc(C)c3/C(=N/OCC(=O)N3CCc4nc(C)[nH]c4C3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(2-methyl-6,7-dihydro-3H-imidazo[4,5-c]pyridin-5(4H)-yl)ethanone | 571.6 | 572 |
| 133 | 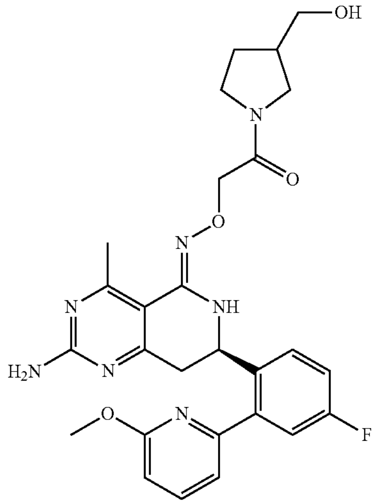 [SMILES: COc1cccc(-c2cc(F)ccc2[C@H]2Cc3nc(N)nc(C)c3/C(=N/OCC(=O)N3CCC(CO)C3)N2)n1] 2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)-1-(3-(hydroxymethyl)pyrrolidin-1-yl)ethanone | 535.6 | 536 |

-continued
| Compound No. | Structure & Name | MW | M + H (observed) |
|---|---|---|---|
| 134 | 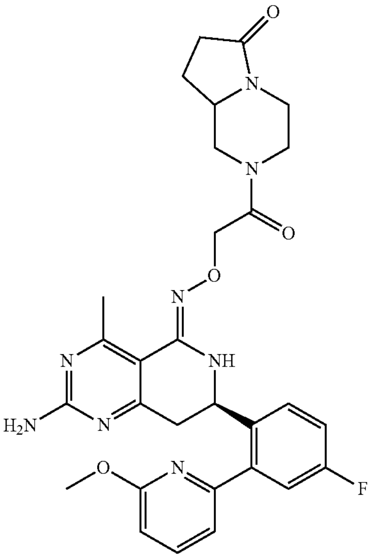 [SMILES: COc1cccc(-c2cc(F)ccc2[C@H]2Cc3nc(N)nc(C)c3/C(=N/OCC(=O)N3CCN4C(=O)CCC4C3)N2)n1] 2-(2-((Z)-((R)-2-amino-7-(4-fluoro-2-(6-methoxypyridin-2-yl)phenyl)-4-methyl-7,8-dihydropyrido[4,3-d]pyrimidin-5(6H)-ylidene)aminooxy)acetyl)hexahydropyrrolo[1,2-a]pyrazin-6(7H)-one | 574.6 | 575 |
| 135 | 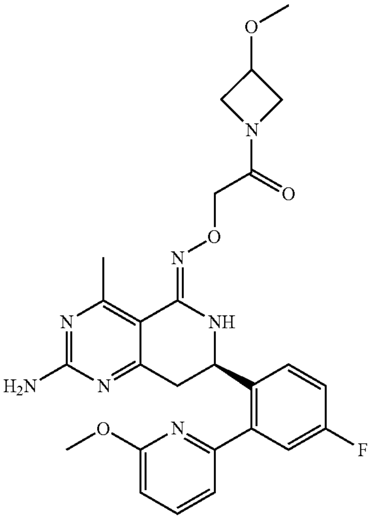 [SMILES: COc1cccc(-c2cc(F)ccc2[C@H]2Cc3nc(N)nc(C)c3/C(=N/OCC(=O)N3CC(OC)C3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(3-methoxyazetidin-1-yl)ethanone | 521.5 | 522 |

-continued
| Compound No. | Structure & Name | MW | M + H (observed) |
|---|---|---|---|
| 136 | 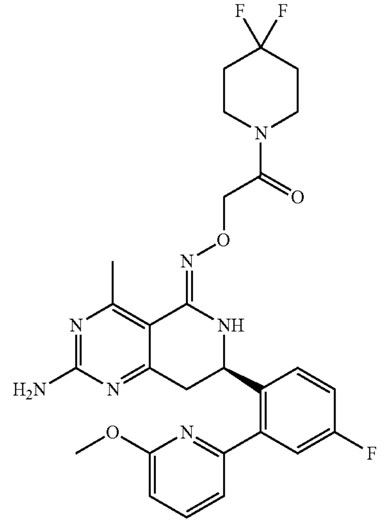 [SMILES: COc1cccc(-c2cc(F)ccc2[C@H]2Cc3nc(N)nc(C)c3/C(=N/OCC(=O)N3CCC(F)(F)CC3)N2)n1] (R,Z)-2-(2-amino-7-(4-fluoro-2-(6-methoxypyridin-2-yl)phenyl)-4-methyl-7,8-dihydropyrido[4,3-d]pyrimidin-5(6H)-ylideneaminooxy)-1-(4,4-difluoropiperidin-1-yl)ethanone | 555.6 | 556 |
Example 106
Alternative synthesis of (R,Z)-2-amino-7-(4-fluoro-2-(6-methoxypyridin-2-yl)phenyl)-4-methyl-7,8-dihydropyrido[4,3-d]pyrimidin-5(6H)-one oxime (Compound 61)
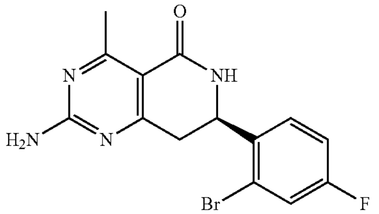
106a
+
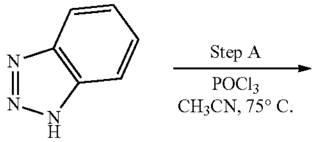
106b
-continued
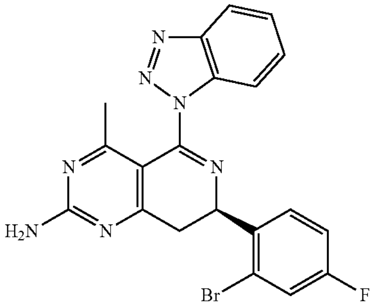
106c
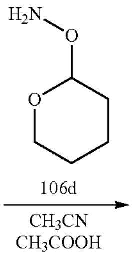
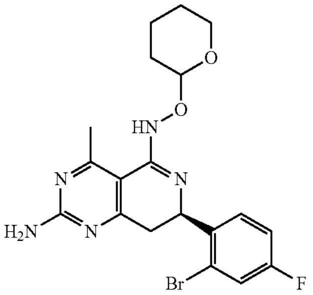
106e
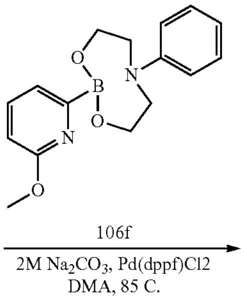

-continued

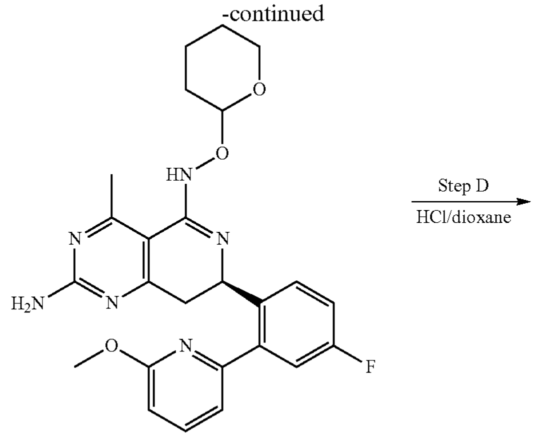

106g

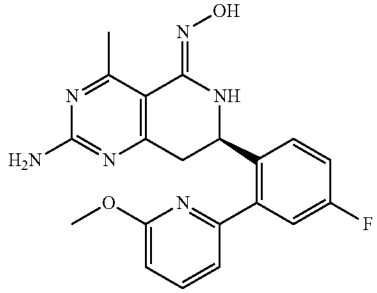

61

Step A. Synthesis of (R)-5-(1H-benzo[d][1,2,3]triazol-1-yl)-7-(2-bromo-4-fluorophenyl)-4-methyl-7,8-dihydropyrido[4,3-d]pyrimidine-2-amine (Compound 106c)

In a 2-neck round-bottomed flask, under a blanket of nitrogen was added (R)-2-amino-7-(2-bromo-4-fluorophenyl)-4-methyl-7,8-dihydropyrido[4,3-d]pyrimidin-5(6H)-one (106a, 1.00 g, 2.85 mmol), 1H-benzo[d][1,2,3]triazole (106b, 0.678 g, 5.70 mmol) and anhydrous acetonitrile (14 mL). Phosphoryl trichloride (0.796 mL, 8.54 mmol) was added slowly to the mixture and the reaction was heated in 75° C. oil bath for 18 hours. By LC/MS about 7-10% of compound 1 remained unreacted. The reaction mixture was concentrated, then diluted with 80 mL of ethyl acetate and the resulting mixture was added slowly to 40 mL of saturated sodium bicarbonate. The layers were partitioned. The aqueous layer was washed one more time with 40 mL of ethyl acetate. The organic layers combined, washed with brine, dried over sodium sulfate, and concentrated to a yellow-light brown solid, 1.72 g, contained about 0.37 g of excess benzotriazole. The crude material was taken on to the next step without purification. MS (ES) [M+H] calc'd for $C_{20}H_{15}BrFN_7$, 452; found, 452.3-454.3. $^1H$ NMR (400 MHz, CHLOROFORM-d) δ 1.96 (s, 3H), 2.74 (dd, J=16.42, 14.91 Hz, 1H), 3.13 (dd, J=16.55, 4.17 Hz, 1H), 5.20 (dd, J=14.91, 4.04 Hz, 1H), 5.69 (s, 2H), 7.03-7.12 (m, 1H), 7.38 (dd, J=8.21, 2.65 Hz, 1H), 7.47-7.52 (m, 1H), 7.56-7.63 (m, 1H), 7.74 (dd, J=8.84, 6.06 Hz, 1H), 8.16 (d, J=9.35 Hz, 2H).

Step B. Synthesis of (7R)-7-(2-bromo-4-fluorophenyl)-4-methyl-5-(tetrahydro-2H-pyran-2-yloxyamino)-7,8-dihydropyrido[4,3-d]pyrimidin-2-amine (Compound 106e)

(R)-5-(1H-benzo[d][1,2,3]triazol-1-yl)-7-(2-bromo-4-fluorophenyl)-4-methyl-7,8-dihydropyrido[4,3-d]pyrimidine-2-amine (1.13 g, 2.50 mmol) and O-(tetrahydro-2H-pyran-2-yl)hydroxylamine (0.322 g, 2.75 mmol) were combined in 15 mL of acetonitrile. Then acetic acid (0.858 mL, 15.0 mmol) was added and the reaction mixture was stirred at room temperature for 18 h. Next day, the reaction was complete and it was concentrated in vacuo and then purified by flash column chromatography, $SiO_2$, gradient 30-100% ethyl acetate/hexane. Obtained 0.838 g of compound 5, 74.5% yield. MS (ES) [M+H] calc'd for $C_{19}H_{21}BrFN_5O_2$, 450; found, 450.3-452.3. $^1H$ NMR (400 MHz, CHLOROFORM-d) δ 1.45-1.97 (m, 6H), 2.72 (s, 3H), 2.91 (ddd, J=16.17, 10.86, 7.83 Hz, 1H), 3.05-3.26 (m, 1H), 3.58-3.71 (m, 1H), 3.86-4.08 (m, 1H), 4.92-5.06 (m, 1H), 5.25 (dd, J=5.81, 2.27 Hz, 1H), 5.63 (d, J=4.04 Hz, 2H), 5.79-5.88 (d, J=36 Hz, 1H), 6.93-7.11 (m, J=16.07, 8.19, 8.19, 2.65 Hz, 1H), 7.28-7.34 (m, 1H), 7.35-7.44 (ddd, J=36 Hz, 1H).

Step C. Synthesis of (7R)-7-(4-fluoro-2-(6-methoxypyridin-2-yl)phenyl)-4-methyl-5-(tetrahydro-2H-pyran-2-yloxyamino)-7,8-dihydropyrido[4,3-d]pyrimidin-2-amine (Compound 106g)

(7R)-7-(2-bromo-4-fluorophenyl)-4-methyl-5-(tetrahydro-2H-pyran-2-yloxyamino)-7,8-dihydropyrido[4,3-d]pyrimidin-2-amine (0.838 g, 1.86 mmol), 2-(6-methoxypyridin-2-yl)-6-phenyl-1,3,6,2-dioxazaborocane (1.33 g, 4.47 mmol), sodium carbonate 2M solution (3.72 mL, 7.44 mmol) were combined in N,N-Dimethylacetamide (12 mL) and then the mixture was purged with nitrogen for 5 minutes. 1,1'-bis(diphenylphosphino)ferrocenedichloro palladium(II) dichloromethane complex (0.136 g, 0.186 mmol) was then added and the reaction was heated in 85° C. oil bath overnight. Next day, the reaction was diluted with ethyl acetate 80 mL, washed with brine (80 mL), dried over sodium sulfate, and concentrated to a crude product which was then purified by flash column chromatography, $SiO_2$, gradient 20-100% ethyl acetate/hexane to give a white solid, 1.11 g of product, contaminated with the impurity of mass 182 (byproduct from the boronic ester, compound 6). MS (ES) [M+H] calc'd for $C_{25}H_{27}FN_6O_3$, 479; found, 479.4.

Step D. Synthesis of (R,Z)-2-amino-7-(4-fluoro-2(6-methoxypyridine-2-yl)phenyl)-4-methyl-7,8-dihydropyrido[4,3-d]pyrimidin-5(6H)-one oxime (Compound 61)

(7R)-7-(4-fluoro-2-(6-methoxypyridin-2-yl)phenyl)-4-methyl-5-(tetrahydro-2H-pyran-2-yloxyamino)-7,8-dihydropyrido[4,3-d]pyrimidin-2-amine (0.891 g, 1.86 mmol) was dissolved in 10 mL of dioxane. 4M of HCl in dioxane (1.86 mL, 7.45 mmol) was then added slowly to the above stirred solution. After all the HCl was added, a yellow solid was formed at the bottom of the reaction flask. The deprotection was allowed to go for 30 minutes, then the supernatant was decanted. Dichloromethane was added to wash the solid, then it was decanted. This process was repeated a few times. No product was found in the dioxane and dichloromethane washes. The solid product was then purified on flash column chromatography, $SiO_2$, gradient 2-15% methanol/chloroform to give 0.404 g of product, 63.5% yield over 2 steps. MS (ES) [M+H] calc'd for $C_{20}H_{19}FN_6O_2$, 395; found, 395.3. $^1H$ NMR (400 MHz, METHANOL-$d_4$) δ 2.60 (s, 3H), 3.09-3.19 (m, 1H), 3.29-3.34 (m, 1H), 3.91 (s, 3H), 5.45 (br. s., 1H), 6.82 (d, J=8.34 Hz, 1H), 7.16 (d, J=6.57 Hz, 1H), 7.19-7.30 (m, 2H), 7.55 (dd, J=8.59, 5.56 Hz, 1H), 7.79 (dd, J=8.34, 7.33 Hz, 1H).

Example 107

Preparation of (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime benzoate Form A (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-3,4-dihydroxybutyl oxime (Compound 37, 20 mg, a white powder) was weighed in a reaction vessel equipped with a magnetic stirring bar. Chloroform (5 mL) and benzoic acid in 1,4-dioxane (340 mL, 0.124 mol/L) were added, and the reaction mixture was cooled at 5° C. The solvent was evaporated with a gentle stream of nitrogen, providing a paste.

Acetone (2.5 mL) was added to the residue. The mixture was sonicated at room temperature until a solution was obtained. Heptane (1 mL) was added and the reaction mixture was cooled at 5° C. The solvent was evaporated with a gentle stream of nitrogen yielding a solid.

The residual solid was characterized by powder X-ray diffraction, differential scanning calorimetry (DSC) and thermogravimetry. FIG. 2 shows the powder X-ray diffraction diffractogram, which contains distinct lines characteristic of a crystalline product. FIG. 3 shows an DSC thermogram which shows an endotherm that starts at 128° C. The solid possesses a melting point of 128° C.

In addition, the above reaction schemes and variations thereof can be used to prepare the following compounds. It is understood that recitation of a compound is intended to encompass all of the different possible stereoisomers.

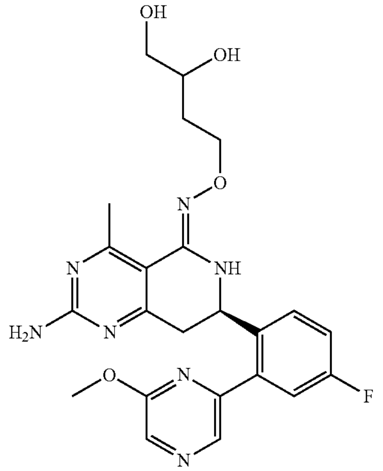

(7R,Z)-2-amino-7-(4-fluoro-2-(6-methoxypyrazin-2-yl)phenyl)-4-methyl-7,8-dihydropyrido[4,3-d]pyrimidin-5(6H)-one O-3,4-dihydroxybutyl oxime -continued

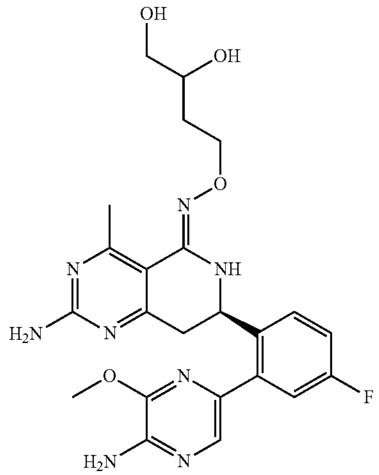

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-3,4-dihydroxybutyl oxime

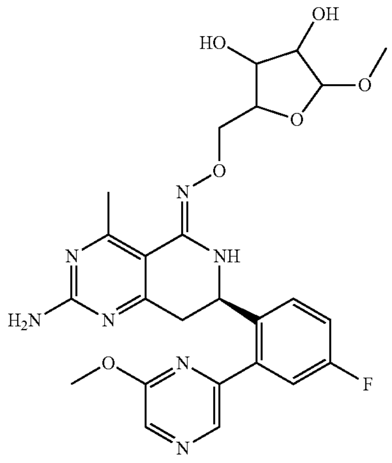

(7R,Z)-2-amino-7-(4-fluoro-2-(6-methoxypyrazin-2-yl)phenyl)-4-methyl-7,8-dihydropyrido[4,3-d]pyrimidin-5(6H)-one O-(3,4-dihydroxy-5-methoxytetrahydrofuran-2-yl)methyl oxime

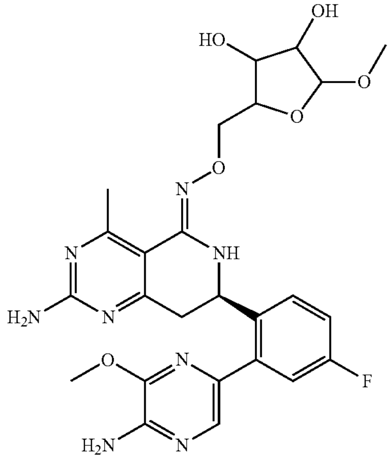

(7R,Z)-2-amino-7-(2-(5-amino-6-methoxypyrazin-2-yl)-4-fluorophenyl)-4-methyl-7,8-dihydropyrido[4,3-d]pyrimidin-5(6H)-one O-(3,4-dihydroxy-5-methoxytetrahydrofuran-2-yl)methyl oxime -continued

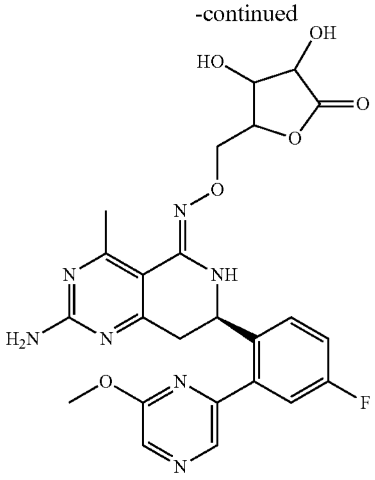

5-(((Z)-((R)-2-amino-7-(4-fluoro-2-(6-methoxypyrazin-2-yl)phenyl)-4-methyl-7,8-dihydropyrido[4,3-d]pyrimidin-5(6H)-ylidene)aminooxy)methyl)-3,4-dihydroxydigydrofuran-2(3H)-one

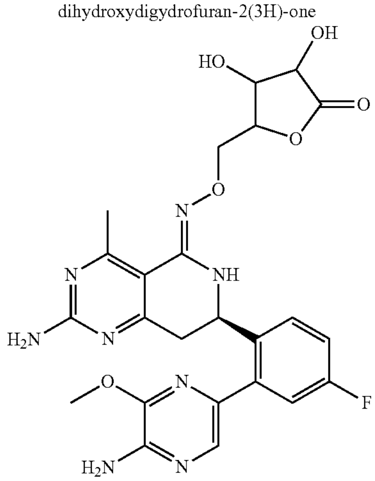

5-(((Z)-((R)-2-amino-7-(2-(5-amino-6-methoxypyrazin-2-yl)-4-fluorophenyl)-4-methyl-7,8-dihydropyrido[4,3-d]pyrimidin-5(6H)-ylidene)aminooxy)methyl)-3,4-dihydroxydihydrofuran-2(3H)-one

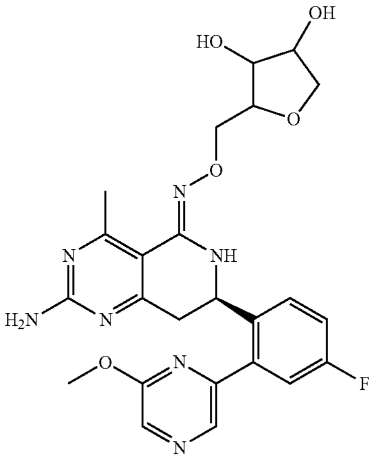

(7R,Z)-2-amino-7-(4-fluoro-2-(6-methoxypyrazin-2-yl)phenyl)-4-methyl-7,8-dihydropyrido[4,3-d]pyrimidin-5(6H)-one O-(3,4-dihydroxytetrahydrofuran-2-yl)methyl oxime -continued

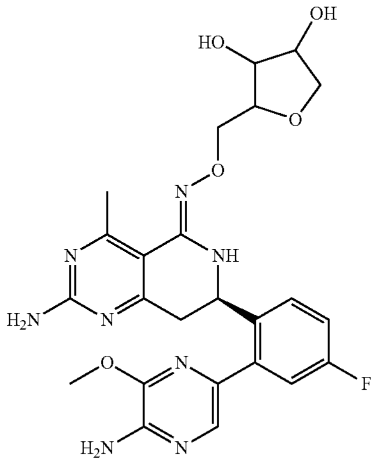

(7R,Z)-2-amino-7-(2-(5-amino-6-methoxypyrazin-2-yl)-4-fluorophenyl)-4-methyl-7,8-dihydroprido[4,3-d]pyrimidin-5(6H)-one O-(3,4-dihydroxytetrahydrofuran-2yl)methyl oxime

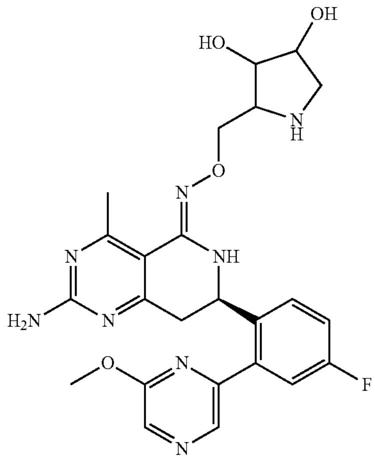

(7R,Z)-2-amino-7-(4-fluoro-2-(6-methoxypyrazin-2-yl)phenyl)-4-methyl-7,8-dihydropyrido[4,3-d]pyrimidin-5(6H)-one O-3,4-dihydroxypyrrolidin-2-yl)methyl oxime

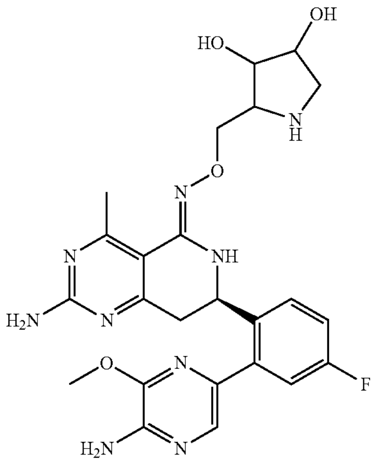

(7R,Z)-2-amino-7-(2-(5-amino-6-methoxypyrazin-2-yl)-4-fluorophenyl)-4-methyl-7,8-dihydroprido[4,3-d]pyrimidin-5(6H)-one O-(3,4-dihydroxypyrrolidin-2-yl)methyl oxime -continued

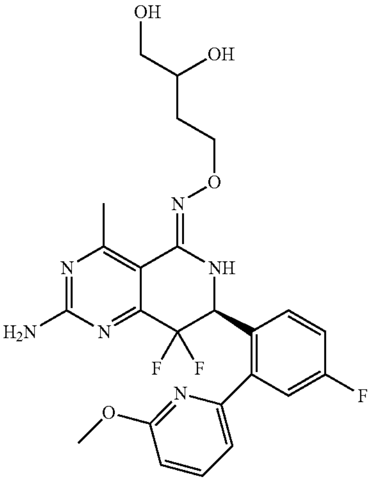

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-3,4-dihydroxybutyl oxime

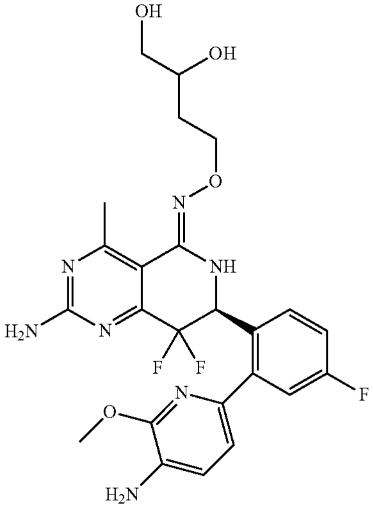

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-3,4-dihydroxybutyl oxime -continued

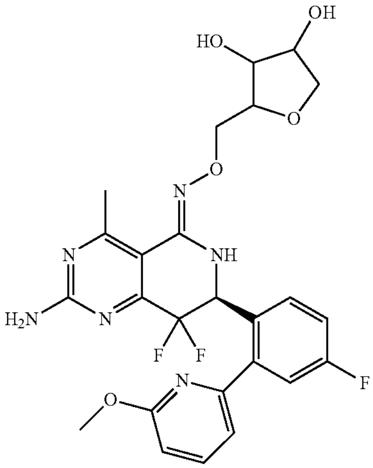

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-(3,4-dihydroxytetrahydrofuran-2-yl)methyl oxime

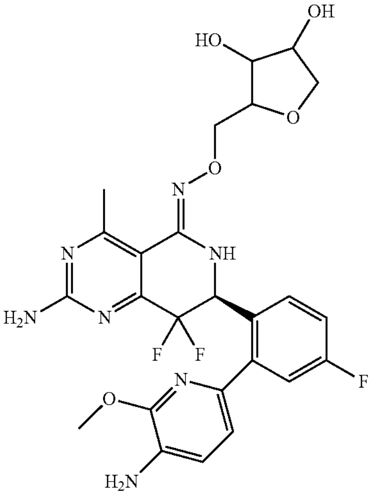

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-(3,4-dihydroxytetrahydrofuran-2-yl)methyl oxime -continued

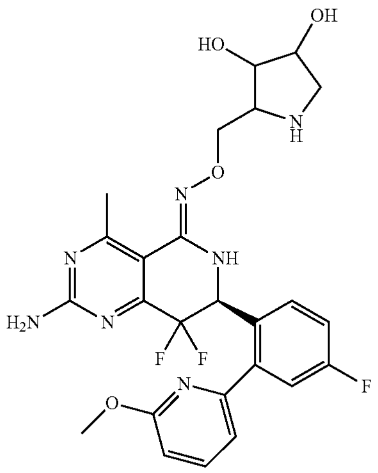

(7S,Z)-2-amino-8,8-difluoro-7-(4-fluoro-2-(6-methoxypyridin-2-yl)phenyl)-4-methyl-7,8-dihydropyrido[4,3-d]pyrimidin-5(6H)-one O-(3,4-dihydroxypyrrolidin-2-yl)methyl oxime

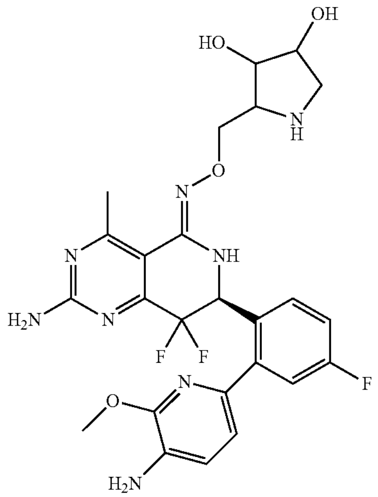

(7S,Z)-2-amino-7-(2-(5-amino-6-methoxypyrazin-2-yl)-4-fluorophenyl)-8,8-difluoro-4-methyl-7,8-dihydropyrido[4,3-d]pyrimidin-5(6H)-one O-(3,4-dihydroxypyrrolidin-2-yl)methyl oxime -continued

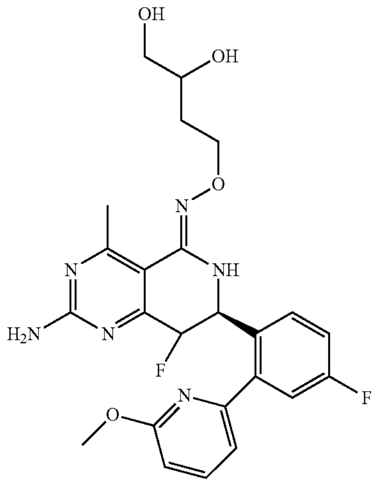

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-3,4-dihydroxybutyl oxime

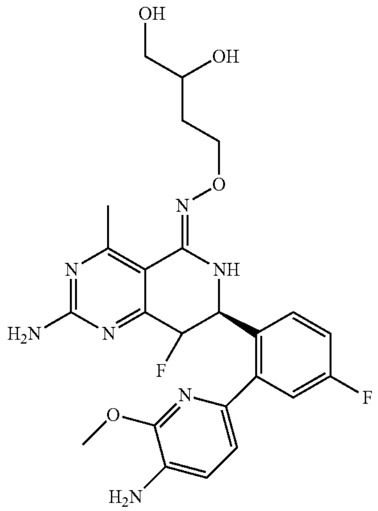

(7S,Z)-2-amino-7-(2-(5-amino-6-methoxypyrazin-2-yl)-4-fluorophenyl)-8,fluoro-4-methyl-7,8-dihydropyrido[4,3-d]pyrimidin-5(6H)-one O-3,4-dihydroxybutyl oxime -continued

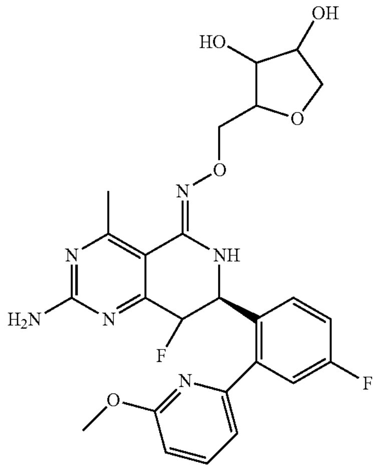

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-(3,4-dihydroxytetrahydrofuran-2-yl)methyl oxime

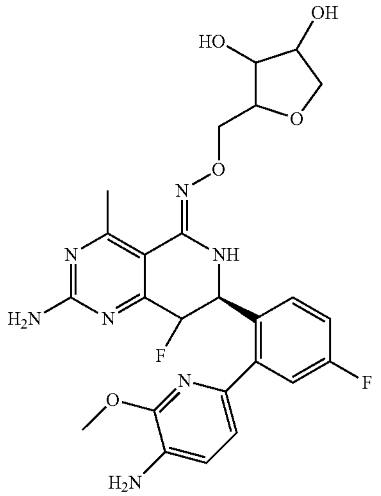

(7S,Z)-2-amino-7-(2-(5-amino-6-methoxypyrazin-2-yl)-4-fluorophenyl)-8,fluoro-4-methyl-7,8-dihydropyrido[4,3-d]pyrimidin-5(6H)-one O-(3,4-dihydroxytetrahydrofuran-2-yl)methyl oxime -continued

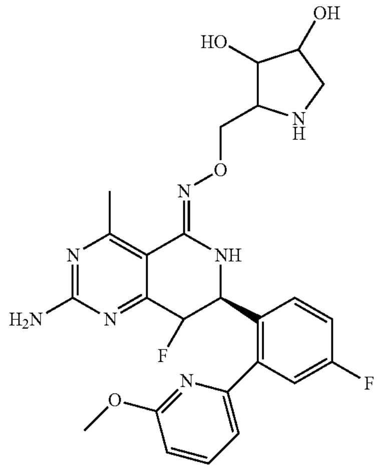

(7S,Z)-2-amino-8-fluoro-7-(4-fluoro-2-(6-methoxypyridin-2-yl)phenyl)-4-methyl-7,8-dihydropyrido[4,3-d]pyrimidin-5(6H)-one O-(3,4-dihydroxypyrrolidin-2-yl)methyl oxime

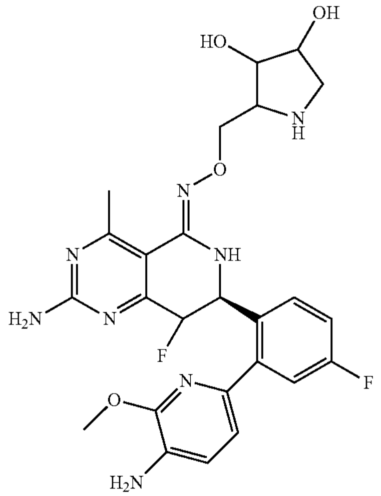

(7S,Z)-2-amino-7-(2-(5-amino-6-methoxypyrazin-2-yl)-4-fluorophenyl)-8,fluoro-4-methyl-7,8-dihydropyrido[4,3-d]pyrimidin-5(6H)-one O-(3,4-dihydroxypyrrolidin-2-yl)methyl oxime -continued

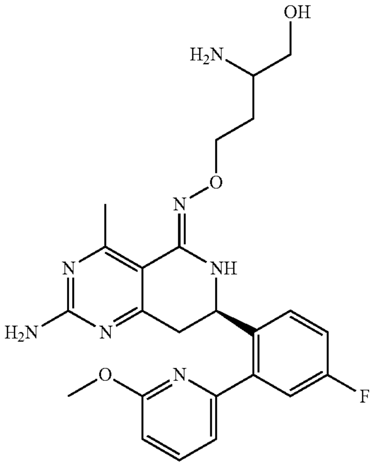

(7R,Z)-2-amino-7-(4-fluoro-2-(6-methoxypyridin-2-yl)phenyl)-4-methyl-7,8-dihydropyrido[4,3-d]pyrimidin-5(6H)-one O-3-amino-4-hydroxybutyl oxime

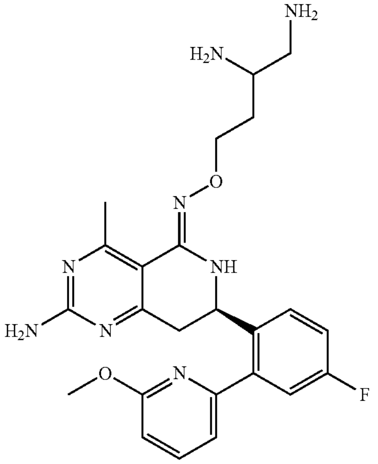

(7R,Z)-2-amino-7-(4-fluoro-2-(6-methoxypyridin-2-yl)phenyl)-4-methyl-7,8-dihydropyrido[4,3-d]pyrimidin-5(6H)-one O-4-amino-3-hydroxybutyl oxime

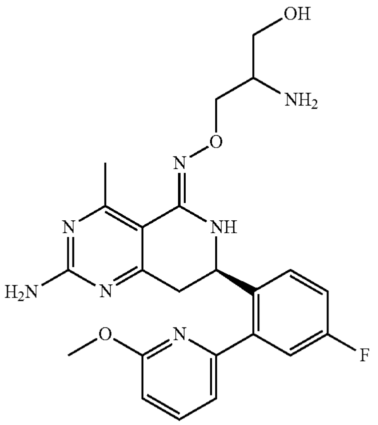

(7R,Z)-2-amino-7-(4-fluoro-2-(6-methoxypyridin-2-yl)phenyl)-4-methyl-7,8-dihydropyrido[4,3-d]pyrimidin-5(6H)-one O-2-amino-3-hydroxypropyl oxime -continued

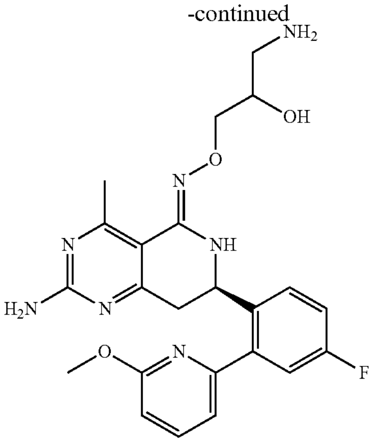

(7R,Z)-2-amino-7-(4-fluoro-2-(6-methoxypyridin-2-yl)phenyl)-4-methyl-7,8-dihydropyrido[4,3-d]pyrimidin-5(6H)-one O-3-amino-2-hydroxypropyl oxime

Example A

Biological Assays

1. Enzyme Binding (Fluorescence Polarization) Assay for HSP90 Inhibitors.

a. Preparation of HSP90a Protein

This example describes cloning, expression and purification of a protein comprising the N-terminal domain of HSP90a. It should be noted that a variety of other expression systems and hosts are also suitable for the expression of such protein, as would be readily appreciated by one of skill in the art.

The sequence of human wild-type HSP90a is well known in the art; see, Chen B. et al. *Genomics* 2005.86:627-637. The gene encoding HSP90a can be isolated from RNA, cDNA or cDNA libraries. In this case, the gene encoding residues 9-236 of image clone 5270926 of HSP90α (ATCC) was isolated. This portion of the gene encoding a section of human HSP90a that includes the N-terminal nucleotide binding domain of human HSP90a was cloned into pET28a vector (Novagen). The DNA sequence of the vector is shown in SEQ ID NO: 1. Expression from this vector produced a protein consisting of the recombinant N-terminal nucleotide binding domain of HSP90a with a cleavable 6'-histidine tag and a cleavage site at the N-terminus The amino acid sequence of this recombinant protein is shown in SEQ ID NO: 2.

Recombinant human N-terminal truncated $His_6$-HSP90a was expressed in *E. coli* (BL21) cells with IPTG induction. Cell paste from 24×60 mL tubes (grown in a multi-tube airlift fermentor) was lysed using an automated sample lyser. Briefly, the pellet in each tube was suspended in 21 mL of lysis buffer consisting of 50 mM Tris pH 7.9, 50 mM NaCl, 1 mM $MgCl_2$, 0.6 g/L Lysozyme (Sigma), 100 μL/L Benzonase (Novagen). After lysis, buffer was added; the tubes were sonicated for 75 seconds, and then incubated for 20 minutes. After incubation, 5 M NaCl was added to bring the final salt concentration to 400 mM. The tubes were sonicated for 50 seconds and then centrifuged at 3400 rpm for 50 min. The supernatants were pooled and 4 ml of ProBond Ni resin (Invitrogen) was added. After at least 30 minutes, the resin was spun down, washed with 25 mM Tris pH 7.6, 400 mM NaCl, 20 mM imidazole, poured into a column and washed with 10 column volumes of the same buffer. The protein was eluted from the column using 3 column volumes of 25 mM Tris pH 7.6, 400 mM NaCl, 400 mM imidazole. The eluate was loaded onto a Supedex 200 column (GE Healthcare) equilibrated with 25 mM Tris pH 7.6, 250 mM NaCl, 0.25 mM TCEP, 1 mM EDTA and peak fractions were pooled and concentrated to ~6 mg/mL using 10 kDA MWCO centrifugal concentrators (Millipore). Aliquots were flash frozen in liquid nitrogen and stored at −80° C. All purification was done at 4° C.

b. Preparation of the Fluorescence Polarization Probe.

A fluorescein labeled small molecule was designed and synthesized as a probe (TSD-FP probe) for the determination of the binding affinity of the test compound to HSP90 proteins. The synthesis of the small molecule, (S,E)-2-amino-7-(4-fluoro-2-(6-methoxypyridin-2-yl)phenyl)-4-methyl-7,8-dihydroquinazolin-5(6H)-one O-2-aminoethyl oxime (Compound 24) was described in Examples 24 and 25 above. The TSD-FP probe was prepared according to the following procedure:

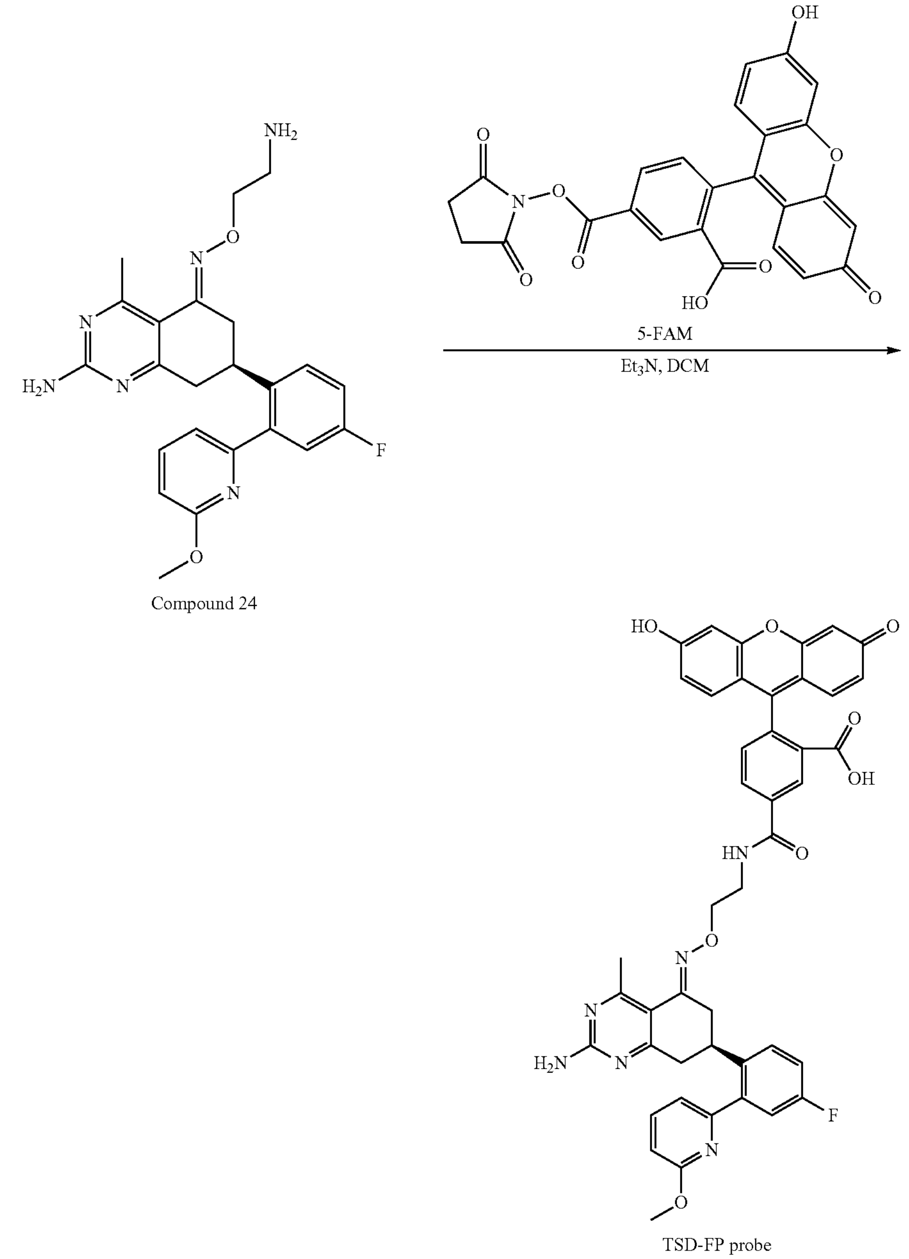

Compound 24

TSD-FP probe

To a 4 mL vial containing a solution of Compound 24 (5 mg, 0.00908 mmol, 1.0 eq.) in dichloromethane (0.6 mL) and triethylamine (6.3 μL, 0.0454 mmol) was added a solution of (5-((2,5-dioxopyrrolidin-1-yloxy)carbonyl)-2-(6-hydroxy-3-oxo-3H-xanthen-9-yl)benzoic acid (5-FAM, 4.7 mg, 0.01 mmol, 1.1 eq.) in dichloromethane (0.4 mL); the mixture was stirred at room temperature overnight. When the reaction was completed, as determined by LC/MS, the reaction mixture was diluted with MeOH and purified directly by preparative HPLC to give the TSD-FP probe as a white solid (6.8 mg, 75%). ESI-MS: m/z 795.4 $(M+H)^+$.

c. Assaying the In Vitro Enzymatic Activity of HSP90 Inhibitors.

The inhibitory effect of the compounds of the invention against HSP90a was determined by fluorescence polarization assay. The assay was run in a black 384-well-plate and in an assay buffer comprising 25 mM Hepes pH 7.3, 150 mM NaCl, 0.1 mM EDTA, 0.01% Brij35, 1 mM DTT.

To each test well, an aliquot of buffer, 2 μl of test compound in 10% DMSO, 4 μl of 6.25 nM of TSD FP probe, 4 μl of 12.5 nM of purified HSP90a protein were added. For positive control, 1 μM geldanamycin (GM) was used instead of the test compound (GM is a natural benzoquinone ansamycin that is known to bind to the N-terminal ATP-binding pocket of HSP90 and inhibits ATP binding and ATP-dependent chaperone activities). For negative control, no inhibitor was added. The assay mixtures were incubated at room temperature for 60 min and overnight (960 min) The fluorescence intensity of the assay mixtures (both 60 min and overnight incubation) was obtained using an Analyst HT (Molecular Devices) with excitation wavelength of 485 nm and emission wavelength of 535 nm.

d. Calculation of $IC_{50}$ Values $IC_{50}$ value may be calculated by non-linear curve fitting of the compound concentrations and FP signal to the standard $IC_{50}$ equation. See, J. Kim et al. "Development of a Fluorescence Polarization Assay for the Molecular Chaperone Hsp90" J. Biomolecular Screening 2004 9(5).

The percent inhibition of HSP90 at a given compound concentration is defined as:

$$100\% \times [1-(\text{FPcompound}/\text{FPblank})]$$

where FPcompound is the observed polarized fluorescence at a given concentration of test compound and FPblank is the observed polarized fluorescence in the presence of vehicle alone.

The $pIC_{50}$ value (negative log of the molar concentration of the compound that produces 50% inhibition) of a test compound is calculated by non-linear least squares curve fitting of the equation:

$$\text{Percent Inhibition}=100\%/(1+(10-pIC_{50}/10 \log [I]))$$

to percent inhibition versus compound concentration. The 50% inhibitory concentration ($IC_{50}$) of a test compound is calculated by raising 10 to the negative $pIC_{50}$ ($10-pIC_{50}$).

As reference, known HSP90 inhibitors, geldanamycin (GM) and 17 alkylamino, 17-demethoxygeldanamycin (17-AAG), were assay and the results summarized in Table 1. It is noted that these two inhibitors showed a time dependence behavior of HSP90 binding which are not common, among the small molecule inhibitors of the invention.

TABLE 1

$IC_{50}$ Values of Known HSP90 Inhibitors

| Standard Compounds | $IC_{50}$ (nM) after 1 hour incubation | $IC_{50}$ (nM) after overnight incubation |
|---|---|---|
| Geldanamycin | 90 | 10 |
| 17-AAG | 400 | 110 |

2. Cellular Viability Assay

BT-474, HT-29, K-562 and MKN-45 tumor cell lines were maintained according to the suppliers (American Type Culture Collection, Rockville, Md. or Human Science Research Resources Bank, Osaka, Japan). Cells were seeded in 96-well tissue culture microplates at 5,000-25,000 cells per well and cultured for 24 hours prior to addition of compounds or DMSO (dimethylsulfoxide) vehicle. A sample where the cells were only treated with DMSO was used a negative control and A sample where the cells were treated with 17-AAG was used a positive control. After 72 hours of test compound treatment, the conversion of tetrazolium salt MTS (Promega, Madison, Wis.) by metabolically active cells was determined through measuring the $OD_{490\ nm}$ with a Spectramax microplate reader (Molecular Devices, San Diego, Calif.). To generate concentration-response curves, cells were treated in duplicate with a range of serial compound dilutions (final DMSO concentration was 0.5%). The percentage of viable cells per well was determined by correcting for background and normalizing against DMSO-treated cells. $EC_{50}$ values for inhibition of cell viability were calculated using XLfit4 Microsoft Excel curve-fitting software.

3. HSP70β Induction Assay

The HSP70β/β-galactosidase reporter vector was purchased from Stressgen Bioreagents Corporation (Victoria, BC Canada). This vector was transiently transfected into 2 million HeLa cells per 10 $cm^2$ dish according to the protocol provided by Stressgen using the lipid based transfection reagent HeLaMONSTER (Mirus Bio Corporation, Madison, Wis.). Cells were subsequently plated in 96 well plates at 20,000 cells/well and after 24 hours of recovery dosed with test compounds for 10 hours. To generate concentration-response curves, cells were treated in duplicate with a range of serial compound dilutions (final DMSO concentration was 0.5%). To measure β-galactosidase activity, lysates were prepared using the Galacto-Star System (Applied Biosystems, Bedford, Mass.). Total non-infrared luminescence was read on an EnVision plate reader (Perkin Elmer, Turku, Finland). $EC_{50}$ values for HSP70β/β-galactosidase induction were calculated using XLfit4 Microsoft Excel curve-fitting software. A sample where the cells were treated with DMSO only was used a negative control, and a sample of 17-AAG was used as a positive control.

4. Western Blotting of the HSP90 Client Protein HER-2

1 million SKOV3 cells (American Type Culture Collection, Rockville, Md.) were seeded in 35 $mm^2$ wells in McCoy's 5A medium containing 10% fetal bovine serum. 24 hours after seeding, cells were treated with compounds serially diluted 2.5-fold in DMSO (final DMSO concentration was 0.5%). After 16 hours of test compound incubation, whole cell lysates were prepared by lysing cells in 62.5 mM Tris-HCl, pH 7, 1% SDS, 10% glycerol. Proteins were resolved by SDS-PAGE and transferred to PVDF membranes. Membranes were probed with the appropriate primary antibodies followed by incubation with secondary IRDye 680- or 800CW-conjugated antibodies (Li-Cor, Lincoln, Nebr.). HER-2/ERBB2 was analyzed using monoclonal antibodies (Cell Signaling Technologies, Danvers, Mass.). Total HSP70 levels were also analyzed using a mouse monoclonal antibody (Stressgen, Ann Arbor, Mich.). PCNA was used as a control for protein loading and was detected by a monoclonal antibody (Calbiochem, San Diego, Calif.). Blots were scanned on the Odyssey (Li-Cor, Lincoln, Nebr.) and signals corresponding to PCNA, HER-2/ERBB2, were quantified using Li-Cor software. Loss of total HER-2/ERBB2 protein $EC_{50}$s were obtained by curve-fitting the ratios of total HER-2/ERBB2 signal over PCNA protein signal using XLfit4 Microsoft Excel curve-fitting software.

Example B

In vitro HSP90 Binding Affinity of Compound of the Invention

The enzyme activities of the compounds of the present invention against HSP90 were determined using the method disclosed Example A-1. The compounds of the invention are inhibitors of HSP90; the $IC_{50}$ values of the exemplified compounds are typically less than 1 nM and more typically less than 100 nM. The $IC_{50}$ values of selected compounds are reported in Table 2.

TABLE 2

$IC_{50}$ of Exemplified Compounds Against HSP90

| Compound No | Binding Affinity $IC_{50}$(nM) |
|---|---|
| 33 | 4 |
| 35 | 13 |
| 37 | 6 |
| 40 | 10 |
| 45 | 10 |
| 58 | 5 |

TABLE 2-continued $IC_{50}$ of Exemplified Compounds Against HSP90

| Compound No | Binding Affinity $IC_{50}$(nM) |
|---|---|
| 59 | 8 |
| 61 | 3 |
| 65 | 10 |
| 75 | 10 |
| 78 | 4 |
| 79 | 6 |
| 83 | 8 |
| 85 | 4 |
| 93 | 8 |
| 96 | 13 |
| 99 | 8 |

What is claimed is:

1. The compound (R,Z)-2-amino-7-(4-fluoro-2-(6-methoxypyridin-2-yl)phenyl)-4-methyl-7,8-dihydropyrido[4,3-d]pyrimidin-5(6H)-one O—(R)-2,3-dihydroxypropyl oxime or a pharmaceutically acceptable salt thereof.

2. The compound (R,Z)-2-amino-7-(4-fluoro-2-(6-methoxypyridin-2-yl)phenyl)-4-methyl-7,8-dihydropyrido[4,3-d]pyrimidin-5(6H)-one O—(S)-2,3-dihydroxypropyl oxime or a pharmaceutically acceptable salt thereof.

3. The compound (R,Z)-2-Amino-7-(3'-(cyclopropylsulfonyl)-5-fluorobiphenyl-2-yl)-4-methyl-7,8-dihydropyrido[4,3-d]pyrimidin-5(6H)-one O—(S)-2,3-dihydroxypropyl oxime or a pharmaceutically acceptable salt thereof.

4. The compound (E)-2-Amino-7-(4-fluoro-2-(6-methoxypyridin-2-yl)phenyl)-4-methyl-7,8-dihydroquinazolin-5(6H)-one O—(R)-2,3-dihydroxypropyl oxime or a pharmaceutically acceptable salt thereof.

5. The compound (E)-2-Amino-7-(4-fluoro-2-(6-methoxypyridin-2-yl)phenyl)-4-methyl-7,8-dihydroquinazolin-5(6H)-one O—(S)-2,3-dihydroxypropyl oxime or a pharmaceutically acceptable salt thereof.

6. A pharmaceutical composition comprising as an active ingredient a compound according to any one of claims 1-5 and a pharmaceutically acceptable excipient.

* * * * *

SEQUENCE LISTING

```
<160> NUMBER OF SEQ ID NOS: 2

<210> SEQ ID NO 1
<211> LENGTH: 690
<212> TYPE: DNA
<213> ORGANISM: Artificial Sequence
<220> FEATURE:
<223> OTHER INFORMATION: Human cDNA sequence encoding residues 9-236 of
      human HSP90 (including a start and a stop codon)

<400> SEQUENCE: 1

atggaccaac cgatggagga ggaggaggtt gagacgttcg cctttcaggc agaaattgcc      60

cagttgatgt cattgatcat caatactttc tactcgaaca aagagatctt tctgagagag     120

ctcatttcaa attcatcaga tgcattggac aaaatccggt atgaaagctt gacagatccc     180

agtaaattag actctgggaa agagctgcat attaacctta taccgaacaa acaagatcga     240

actctcacta ttgtggatac tggaattgga atgaccaagg ctgacttggt caataacctt     300

ggtactatcg ccaagtctgg gaccaaagcg ttcatggaag ctttgcaggc tggtgcagat     360

atctctatga ttggccagtt cggtgttggt ttttattctg cttatttggt tgctgagaaa     420

gtaactgtga tcaccaaaca taacgatgat gagcagtacg cttgggagtc ctcagcaggg     480

ggatcattca cagtgaggac agacacaggt gaacctatgg gtcgtggaac aaaagttatc     540

ctacacctga aagaagacca aactgagtac ttggaggaac gaagaataaa ggagattgtg     600

aagaaacatt ctcagtttat tggatatccc attactcttt ttgtggagaa ggaacgtgat     660

aaagaagtaa gcgatgatga ggctgaataa                                      690


<210> SEQ ID NO 2
<211> LENGTH: 249
<212> TYPE: PRT
<213> ORGANISM: Artificial Sequence
<220> FEATURE:
<223> OTHER INFORMATION: 1- 21 = 6x-histidine tag and cleavage site and
      a methionine 22-249 = Amino acid sequence for residues 9-236 of
      human HSP90a

<400> SEQUENCE: 2

Met Gly Ser Ser His His His His His His Ser Ser Gly Leu Val Pro
1               5                   10                  15

Arg Gly Ser His Met Asp Gln Pro Met Glu Glu Glu Glu Val Glu Thr
            20                  25                  30
```

-continued

| | | | | | | | | | | | | | | | |
|---|---|---|---|---|---|---|---|---|---|---|---|---|---|---|---|
| Phe | Ala | Phe | Gln | Ala | Glu | Ile | Ala | Gln | Leu | Met | Ser | Leu | Ile | Ile | Asn |
| | | 35 | | | | | 40 | | | | | 45 | | | |
| Thr | Phe | Tyr | Ser | Asn | Lys | Glu | Ile | Phe | Leu | Arg | Glu | Leu | Ile | Ser | Asn |
| | 50 | | | | | 55 | | | | | 60 | | | | |
| Ser | Ser | Asp | Ala | Leu | Asp | Lys | Ile | Arg | Tyr | Glu | Ser | Leu | Thr | Asp | Pro |
| 65 | | | | | 70 | | | | | 75 | | | | | 80 |
| Ser | Lys | Leu | Asp | Ser | Gly | Lys | Glu | Leu | His | Ile | Asn | Leu | Ile | Pro | Asn |
| | | | | 85 | | | | | 90 | | | | | 95 | |
| Lys | Gln | Asp | Arg | Thr | Leu | Thr | Ile | Val | Asp | Thr | Gly | Ile | Gly | Met | Thr |
| | | | 100 | | | | | 105 | | | | | 110 | | |
| Lys | Ala | Asp | Leu | Val | Asn | Asn | Leu | Gly | Thr | Ile | Ala | Lys | Ser | Gly | Thr |
| | | 115 | | | | | 120 | | | | | 125 | | | |
| Lys | Ala | Phe | Met | Glu | Ala | Leu | Gln | Ala | Gly | Ala | Asp | Ile | Ser | Met | Ile |
| | 130 | | | | | 135 | | | | | 140 | | | | |
| Gly | Gln | Phe | Gly | Val | Gly | Phe | Tyr | Ser | Ala | Tyr | Leu | Val | Ala | Glu | Lys |
| 145 | | | | | 150 | | | | | 155 | | | | | 160 |
| Val | Thr | Val | Ile | Thr | Lys | His | Asn | Asp | Asp | Glu | Gln | Tyr | Ala | Trp | Glu |
| | | | | 165 | | | | | 170 | | | | | 175 | |
| Ser | Ser | Ala | Gly | Gly | Ser | Phe | Thr | Val | Arg | Thr | Asp | Thr | Gly | Glu | Pro |
| | | | 180 | | | | | 185 | | | | | 190 | | |
| Met | Gly | Arg | Gly | Thr | Lys | Val | Ile | Leu | His | Leu | Lys | Glu | Asp | Gln | Thr |
| | | 195 | | | | | 200 | | | | | 205 | | | |
| Glu | Tyr | Leu | Glu | Glu | Arg | Arg | Ile | Lys | Glu | Ile | Val | Lys | Lys | His | Ser |
| | 210 | | | | | 215 | | | | | 220 | | | | |
| Gln | Phe | Ile | Gly | Tyr | Pro | Ile | Thr | Leu | Phe | Val | Glu | Lys | Glu | Arg | Asp |
| 225 | | | | | 230 | | | | | 235 | | | | | 240 |
| Lys | Glu | Val | Ser | Asp | Asp | Glu | Ala | Glu | | | | | | | |
| | | | | 245 | | | | | | | | | | | |